US012128122B2

(12) United States Patent
Krishnan et al.

(10) Patent No.: US 12,128,122 B2
(45) Date of Patent: *Oct. 29, 2024

(54) RECOMBINANT NUCLEIC ACIDS ENCODING COSMETIC PROTEIN(S) FOR AESTHETIC

(71) Applicant: Krystal Biotech, Inc., Pittsburgh, PA (US)

(72) Inventors: Suma Krishnan, San Francisco, CA (US); Trevor Parry, San Diego, CA (US); Pooja Agarwal, Mars, PA (US)

(73) Assignee: Krystal Biotech, Inc., Pittsburgh, PA (US)

(*) Notice: Subject to any disclaimer, the term of this patent is extended or adjusted under 35 U.S.C. 154(b) by 1100 days.

This patent is subject to a terminal disclaimer.

(21) Appl. No.: 16/915,695

(22) Filed: Jun. 29, 2020

(65) Prior Publication Data

US 2021/0045988 A1 Feb. 18, 2021

Related U.S. Application Data

(63) Continuation of application No. 16/395,896, filed on Apr. 26, 2019, now Pat. No. 10,786,438.

(60) Provisional application No. 62/663,476, filed on Apr. 27, 2018.

(51) Int. Cl.

| | |
|---|---|
| ***A61K 35/763*** | (2015.01) |
| ***A61K 8/64*** | (2006.01) |
| ***A61K 8/65*** | (2006.01) |
| ***A61K 9/00*** | (2006.01) |
| ***A61Q 19/08*** | (2006.01) |

(52) U.S. Cl.

CPC .................. *A61K 8/65* (2013.01); *A61K 8/64* (2013.01); *A61Q 19/08* (2013.01); *A61K 2800/86* (2013.01); *A61K 2800/91* (2013.01); *C12N 2710/16621* (2013.01); *C12N 2710/16631* (2013.01)

(58) Field of Classification Search

None

See application file for complete search history.

(56) References Cited

U.S. PATENT DOCUMENTS

| | | | |
|---|---|---|---|
| 5,658,724 | A | 8/1997 | Deluca et al. |
| 5,672,344 | A | 9/1997 | Kelley et al. |
| 5,998,174 | A | 12/1999 | Glorioso et al. |
| 6,106,826 | A | 8/2000 | Brandt et al. |
| 6,719,982 | B1 | 4/2004 | Coffin et al. |
| 6,846,670 | B2 | 1/2005 | Schwartz et al. |
| 6,887,490 | B1 | 5/2005 | Jahoda et al. |
| 7,531,167 | B2 | 5/2009 | Glorioso et al. |
| 9,314,505 | B2 | 4/2016 | Wise et al. |
| 9,770,489 | B2 | 9/2017 | Angel et al. |
| 9,877,990 | B2 | 1/2018 | Krishnan et al. |
| 10,155,016 | B2 | 12/2018 | Krishnan et al. |
| 10,174,341 | B2 | 1/2019 | Glorioso et al. |
| 10,441,614 | B2 | 10/2019 | Krishnan et al. |
| 10,525,090 | B2 | 1/2020 | Krishnan et al. |
| 10,786,438 | B2 | 9/2020 | Krishnan et al. |
| 11,185,564 | B2 | 11/2021 | Krishnan et al. |
| 2002/0037575 | A1 | 3/2002 | Speck |
| 2003/0082142 | A1 | 5/2003 | Coffin et al. |
| 2004/0005663 | A1 | 1/2004 | Bell et al. |
| 2004/0018592 | A1 | 1/2004 | Bell et al. |
| 2004/0253606 | A1 | 12/2004 | Aziz et al. |
| 2007/0066552 | A1 | 3/2007 | Clarke et al. |
| 2008/0119433 | A1 | 5/2008 | Tabor |
| 2008/0299182 | A1 | 12/2008 | Zhang |
| 2010/0081707 | A1 | 4/2010 | Ali et al. |
| 2011/0212530 | A1 | 9/2011 | Baltimore et al. |
| 2011/0218234 | A1 | 9/2011 | Annoni et al. |
| 2011/0245592 | A1 | 10/2011 | Schoolcraft et al. |
| 2013/0259923 | A1 | 10/2013 | Bancel et al. |
| 2013/0295076 | A1 | 11/2013 | Kolattukudy et al. |
| 2013/0331547 | A1 | 12/2013 | Hall et al. |
| 2014/0256798 | A1 | 9/2014 | Osborn et al. |
| 2014/0288155 | A1 | 9/2014 | Hovnanian et al. |
| 2014/0341877 | A1 | 11/2014 | Kolattukudy |
| 2015/0038556 | A1 | 2/2015 | Heartlein et al. |
| 2015/0265688 | A1 | 9/2015 | Cigarini et al. |
| 2015/0352191 | A1 | 12/2015 | South et al. |
| 2016/0153000 | A1 | 6/2016 | Glorioso et al. |
| 2016/0158343 | A1 | 6/2016 | Jacobs et al. |
| 2016/0250267 | A1 | 9/2016 | Uchida et al. |

(Continued)

FOREIGN PATENT DOCUMENTS

| | | |
|---|---|---|
| CN | 102 212 559 | 4/2014 |
| EP | 3377637 | 9/2018 |

(Continued)

OTHER PUBLICATIONS

Non final office action U.S. Appl. No. 16/395,896 pp. 1-3; Jul. 1, 2020.*

Whitley et al. Pathogenesis and disease. In: Arvin A, Campadelli-Fiume G, Mocarski E, et al., eds. Human Herpesviruses: Biology, Therapy, and Immunoprophylaxis. Cambridge: Cambridge Univ. Press; 2007. Chapter 32. download: https://www.ncbi.nlm.nih.gov/books/NBK47449/, 19 pgs printed. (Year: 2007).*

Ain, et al (2020)"Gene Delivery to the Skin—How Far Have We Come?", Trends in Biotechnology, 39(5): 474-87. (Year: 2020).*

Perkins (2002) "Targeting apoptosis in neurological disease using the herpes simplex virus", Journal of Cellular and Molecular Medicine, 6(3): 341-56. (Year: 2002).*

(Continued)

*Primary Examiner* — Maria G Leavitt

(74) *Attorney, Agent, or Firm* — The Webb Law Firm

(57) ABSTRACT

The present disclosure provides recombinant nucleic acids comprising one or more polynucleotides encoding one or more cosmetic proteins (e.g., one or more human collagen proteins); viruses comprising the recombinant nucleic acids; compositions (e.g., cosmetic formulations) comprising the recombinant nucleic acids and/or viruses; methods of their use; and articles of manufacture or kits thereof.

14 Claims, 35 Drawing Sheets

Specification includes a Sequence Listing.

(56) References Cited

U.S. PATENT DOCUMENTS

| | | | |
|---|---|---|---|
| 2016/0324934 A1 | 11/2016 | Angel et al. |
| 2017/0096684 A1 | 4/2017 | Alton et al. |
| 2017/0290866 A1 | 10/2017 | Krishnan et al. |
| 2017/0319693 A1 | 11/2017 | Koizumi et al. |
| 2018/0353614 A1 | 12/2018 | Peters |
| 2019/0160122 A1 | 5/2019 | Krishnan et al. |
| 2019/0276845 A1 | 9/2019 | Glorioso et al. |
| 2020/0061209 A1 | 2/2020 | Bennett et al. |
| 2020/0071703 A1 | 3/2020 | Giuliano et al. |
| 2020/0093874 A1 | 3/2020 | Agarwal et al. |
| 2020/0101123 A1 | 4/2020 | Krishnan et al. |
| 2020/0199618 A1 | 6/2020 | Krisky et al. |
| 2021/0040172 A1 | 2/2021 | Cascio et al. |
| 2021/0395775 A1 | 12/2021 | Parry et al. |
| 2022/0273737 A1 | 9/2022 | Krishnan et al. |
| 2023/0149486 A1 | 5/2023 | Krishnan |

FOREIGN PATENT DOCUMENTS

| | | |
|---|---|---|
| JP | 2008-174459 | 7/2008 |
| JP | 2015-221759 | 12/2015 |
| WO | WO 1999/064094 | 12/1999 |
| WO | WO 2000/040734 | 7/2000 |
| WO | WO 2007/136428 | 11/2007 |
| WO | WO 2012/001170 | 1/2012 |
| WO | WO 2013/119880 | 8/2013 |
| WO | WO 2013/121202 | 8/2013 |
| WO | WO 2014/043189 | 3/2014 |
| WO | WO 2015/009952 | 1/2015 |
| WO | WO 2015/117021 | 8/2015 |
| WO | WO 2015/181211 | 12/2015 |
| WO | WO 2016/128374 | 8/2016 |
| WO | WO 2016/128783 | 8/2016 |
| WO | WO 2016/141315 | 9/2016 |
| WO | WO 2016/191684 | 12/2016 |
| WO | WO 2017/165806 | 9/2017 |
| WO | WO 2017/165813 | 9/2017 |
| WO | WO 2017/176336 | 10/2017 |
| WO | 2017191274 A2 | 11/2017 |
| WO | WO 2017/191315 | 11/2017 |
| WO | 2018154412 A1 | 8/2018 |
| WO | WO 2019/200163 | 10/2019 |
| WO | WO 2019/210219 | 10/2019 |
| WO | WO 2020/006486 | 1/2020 |
| WO | WO 2020/069018 | 4/2020 |

OTHER PUBLICATIONS

Unpublished U.S. Appl. No. 18/342,284, filed Jun. 27, 2023, by Krishnan et al. titled "Compositions and Methods for the Treatment of Wounds, Disorders, and Diseases of the Skin".

Acland et al., "Gene therapy restores vision in a canine model of childhood blindness," Nat Genet. (2001) 28(1):92-5.

Ali et al., "Gene therapy for inherited retinal degeneration," Br J Ophthalmol. (1997) 81(9):795-801.

Anonymous, "Public summary of opinion on orphan designation Genetically modified replication-incompetent herpes simplex virus-1 expressing collagen VII for treatment of epidermolysis bullosa", May 15, 2018 (May 15, 2018), p. 1-5, Retrieved from the Internet: URL: https://www.ema.europa.eu/en/documents/orphan-designation/eu/3/18/2012-public-summary-opinion-orphan-designation-genetically-modified-replication-incompetent-herpes_en.pdf. XP055652122 [retrieved on Dec. 12, 2019].

Anonymous, "First two patients enrolled in Phase 1/2 clinical study of KB103, a first-in-class topical gene therapy for the treatment of dystrophic epidermolysis bullosa.", Aug. 6, 2018 (Aug. 6, 2018), 2 pages. Retrieved from the Internet: URL: https://www.krystalbio.com/blog/XP055652520 [retrieved on Dec. 12, 2019].

Anonymous, "Krystal Biotech Announces FDA Clearance of IND on KB103 to Begin Enrolling Patients for the Treatment of Dystrophic Epidermolysis Bullosa", Apr. 26, 2018 (Apr. 26, 2018), p. 1-2, Retrieved from the Internet: URL: http://ir.krystalbio.com/node/6546/pdf XP055652524 [retrieved on Dec. 12, 2019].

Boehmer et al., "Herpes Virus Replication," IUBMB Life (2003) 55(1):13-22.

Choate et al., "Transglutaminase 1 delivery to lamellar ichthyosis keratinocytes," Human Gene Therapy (1996) 7:2247-2253.

Di et al., "Phase I study protocol for ex vivo lentiviral gene therapy for the inherited skin disease, Netherton syndrome," Hum Gene Ther Clin Dev. (2013) 24(4):182-190.

Farasat et al., "Novel transglutaminase-1 mutations and genotype-phenotype investigations of 104 patients with autosomal recessive congenital ichthyosis in the USA," J Med Genet (2009) 46(2):103-111.

Fraefel et al., "In vivo gene transfer to the rat retina using herpes simplex virus type 1 (HSV-1)-based amplicon vectors," Gene Ther. (2005) 12(16):1283-1288.

Liu et al., "Herpes simplex virus mediated gene transfer to primate ocular tissues," Exp Eye Res. (1999) 69(4):385-395.

Manservigi et al., "HSV Recombinant Vectors for Gene Therapy," Open Virol J. (2010) 4:123-156.

Mavilio et al., "Correction of junctional epidermolysis bullosa by transplantation of genetically modified epidermal stem cells," Nat Med. (2006) 12(12):1397-1402.

Melo et al., "Somatic correction of junctional epidermolysis bullosa by a highly recombinogenic AAV variant," Mol Ther. (2014) 22(4):725-733.

Messmer et al., "Ocular manifestations of keratitis-ichthyosis-deafness (KID) syndrome," Ophthalmology. (2005) 112(2):e1-6.

Peek et al., "Herpes simplex virus infection of the human eye induces a compartmentalized virus-specific B cell response," J Infect Dis. (2002) 186(11):1539-46.

Pepose et al., "Herpes simplex viral vectors for therapeutic gene delivery to ocular tissues. Recent breakthroughs in the molecular genetics of ocular diseases," Invest Ophthalmol Vis Sci. (1994) 35(6):2662-6.

Robbins et al., "In vivo restoration of laminin 5 beta 3 expression and function in junctional epidermolysis bullosa," Proc Natl Acad Sci USA (2001) 98(9):5193-5198.

Sabater et al., "Topical beremagene geperpavec (B-VEC) for the treatment of recurrent cicatrizing conjunctivitis in a patient with dystrophic epidermolysis bullosa," ARVO Annual Meeting, New Orleans, LA, USA, Apr. 23-27, 2023. (2023).

Spencer et al., "HSV-1 vector-delivered FGF2 to the retina is neuroprotective but does not preserve functional responses," Mol Ther. (2001) 3(5 Pt 1):746-56.

Wang et al., "Updates on Gene Therapy for Diabetic Retinopathy," Curr Diab Rep. (2020) 20(7):22.

Brehm et al., "Immunogenicity of herpes simplex virus type 1 mutants containing deletions in one or more alpha-genes: ICP4, ICP27, ICP22, and ICP0," Virology (1999) 256(2): 258-69.

Clancy et al., "Personalized Medicine in Cystic Fibrosis: Dawning of a New Era," Am J Respir Crit Care Med (2012) 186(7): 593-597.

Clancy et al., "CFTR Modulator Theratyping: Current Status, Gaps and Future Directions," J Cyst Fibros (2019) 18(1): 22-34.

Collawn et al., "CFTR and Lung Homeostasis," Am J Physiol Lung Cell Mol Physiol (2014) 307(12): L917-923.

Cooney et al., "Cystic Fibrosis Gene Therapy: Looking Back, Looking Forward," Genes (Basel) (2018) 9(11): 538.

Cutting, G. "Cystic Fibrosis Genetics: From Molecular Understanding to Clinical Application," Nat Rev Genet (2015) 16(1): 45-56.

Dekkers et al., "A Functional CFTR Assay Using Primary Cystic Fibrosis Intestinal Organoids," Nat Med (2013) 19(7): 939-945.

Derichs et al., "Hyperviscous Airway Periciliary and Mucous Liquid Layers in Cystic Fibrosis Measured by Confocal Fluorescence Photobleaching," FASEB J (2011) 25(7): 2325-2332.

Dingwell et al., "The Herpes Simplex Virus gE-gl Complex Facilitates Cell-to-Cell Spread and Binds to Components of Cell Junctions," J Virol. (1998) 72(11): 8933-8942.

Estrada-Veras et al., "Palliative Care for Patients With Cystic Fibrosis #265," J Palliat Med (2013) 16(4): 446-447.

Geller et al., "An efficient deletion mutant packaging system for defective herpes simplex virus vectors: potential applications to

(56) References Cited

OTHER PUBLICATIONS human gene therapy and neuronal physiology," Proc Natl Acad Sci U S A. (1990) 87(22): 8950-8954.
Gill et al., "Delivery of Genes Into the CF Airway," Thorax (2014) 69(10): 962-964.
Goins et al. "Generation of replication-competent and -defective HSV vectors," Cold Spring Harb Protoc. May 1, 2011;2011(5): 512; pdb.prot5615.
Gorell et al., "Gene therapy for skin diseases," Cold Spring Harb Perspect Med (2014) 4:a015149.
Hyde et al., "Repeat Administration of DNA/liposomes to the Nasal Epithelium of Patients With Cystic Fibrosis," Gene Ther (2000) 7(13): 1156-1165.
Kerem et al., "Identification of the Cystic Fibrosis Gene: Genetic Analysis," Science (1989) 245(4922): 1073-1080.
Kim et al., "Barriers to Inhaled Gene Therapy of Obstructive Lung Diseases: A Review," J Control Release (2016) 240: 465-488.
Knowles et al., "A Controlled Study of Adenoviral-Vector-Mediated Gene Transfer in the Nasal Epithelium of Patients With Cystic Fibrosis," N Engl J Med (1995) 333(13): 823-831.
Krisky et al., "Deletion of multiple immediate-early genes from herpes simplex virus reduces cytotoxicity and permits long-term gene expression in neurons," Gene Ther. (1998) 5(12):1593-603.
Krisky et al., "Development of herpes simplex virus replication-defective multigene vectors for combination gene therapy applications," Gene Ther (1998) 5(110):1517-1530.
Krystal Biotech, Inc. "Krystal Biotech Announces Settlement with PeriphaGen, Inc." Mar. 15, 2022, https://ir.krystalbio.com/node/8481/pdf. (Year: 2022).
Liou et al., "Year-to-year Changes in Lung Function in Individuals With Cystic Fibrosis," J Cyst Fibros (2010) 9(4): 250-256.
Lommatzsch et al., "The Combination of Tezacaftor and Ivacaftor in the Treatment of Patients With Cystic Fibrosis: Clinical Evidence and Future Prospects in Cystic Fibrosis Therapy," Ther Adv Respir Dis (2019) 13: 1-13. https://doi.org/10.1177/1753466619844424.
Marconi et al., "Replication-defective herpes simplex virus vectors for gene transfer in vivo," Proc Natl Acad Sci USA (1996) 93:11319-11320.
Miezeiewski et al., "Role of adherens junction proteins in differential herpes simplex virus type 2 infectivity in communication-competent and -deficient cell lines," Intervirology. (2012) 55(6): 465-474.
Miyagawa et al., "Herpes simplex viral-vector design for efficient transfuction of nonneuronal cells without cytotoxcity," Proc Natl Acad Sci USA (2015) 112(13):E1632-E1641.
Miyagawa et al., "Deletion of the Virion Host Shut-off Gene Enhances Neuronal-Selective Transgene Expression from an HSV Vector Lacking Functional IE Genes," Mol Ther Methods Clin Dev. (2017) 6: 79-90.
Periphagen, Krystal Biotech Inc., Answer and Counterclaim in *PeriphaGen* v. *Krystal Biotech*, Filed Jun. 6, 2020 in the Western District of Pennsylvania (60 pgs).
Rahn et al., "Invasion of Herpes Simplex Virus Type 1 into Murine Epidermis: An Ex Vivo Infection Study," J Invest Dermatol. (2015) 135(12): 3009-3016.
Salameh et al., "Early events in herpes simplex virus lifecycle with implications for an infection of lifetime," Open Virol J. (2012) 6:1-6.
Samaniego et al., "The herpes simplex virus immediate-early protein ICP0 affects transcription from the viral genome and infected-cell survival in the absence of ICP4 and ICP27," J Virol. (1997) 71(6): 4614-4625.
Sufiawati et al., "HIV-associated disruption of tight and adherens junctions of oral epithelial cells facilitates HSV-1 infection and spread," PLoS One. (2014) 9(2): e88803.
Sufiawati et al., "HIV-induced matrix metalloproteinase-9 activation through mitogen-activated protein kinase signalling promotes HSV-1 cell-to-cell spread in oral epithelial cells," J Gen Virol. (2018) 99(7): 937-947.
Wu et al., "Prolonged gene expression and cell survival after infection by a herpes simplex virus mutant defective in the immediate-early genes encoding ICP4, ICP27, and ICP22," J Virol. (1996) 70(9): 6358-6369.
Aldawsari et al., "Progress in Topical siRNA Delivery Approaches for Skin Disorders," Curr Pharm Des. 2015;21 (31):4594-605.
Agrawal et al., "Skin Barrier Defects in Atopic Dermatitis," Curr Allergy Asthma Rep (2014) 14:1-11.
Andtbacka et. al., "Talimogene Laherparepvec Improves Durable Response Rate in Patients With Advanced Melanoma," J Clin Oncol. Sep. 1, 2015;33(25):2780-8.
Armstrong and Gardner, "Krystal gets a flying start in epidermolysis bullosa gene therapy," Vantage, Oct. 17, 2018, 6 pages.
Armstrong, "Krystal gets more skin in the epidermolysis bullosa game," Vantage, Mar. 5, 2019, 6 pages.
Asgari et al., "In vitro fibrillogenesis of tropocollagen type III in collagen type I affects its relative fibrillar topology and mechanics," Scientific Reports (2017) 7 Article ID:1392.
Bastian et al., "Herpes simplex virus type 1 immediate-early protein ICP22 is required for VICE domain formation during productive viral infection." J Viral. Mar. 2010;84(5):2384-94. doi: 10.1128/JVI.01686-09. Epub Dec. 23, 2009.
Baumann et al., "Comparison of smooth-gel hyaluronic acid dermal fillers with cross-linked bovine collagen: a multicenter, double-masked, randomized, within-subject study," Dermatol Surg (2007) 33 Suppl 2:s128-135.
Brown et al., "Subject global evaluation and subject satisfaction using injectable poly-L-lactic acid versus human collagen for the correction of nasolabial fold wrinkles," Plast Reconstr Surg (2011) 127(4):1684-1692.
Burton EA, Fink DJ, Glorioso JC. Gene delivery using herpes simplex virus vectors. DNA Cell Biol. Dec. 2002;21(12):915-36.
Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, e307.
Cheng et al., "The content and ratio of type I and III collagen in skin differ with age and injury," African Journal of Biotechnology (2011) 10(13):2524-2529.
Christiano AM. Collagen, type VII, alpha 1 (epidermolysis bullosa, dystrophic, dominant and recessive) [*Homo sapiens*]. NCBI Reference Sequence: NP_000085.1. Dep. Mar. 19, 1999.
ClinicalTrials.gov, NCT03536143: "Topical Bercolagene Telserpavec (KB103) Gene Therapy to Restore Functional Collagen VII for the Treatment of Dystrophic Epidermolysis Bullosa (GEM-1)," May 24, 2018, 5 pages.
ClinicalTrials.gov, NCT04047732: "Topical KB105 Gene Therapy for the Treatment of TGM1-deficient Autosomal Recessive Congenital Ichthyosis (ARCI)," Aug. 7, 2019, 5 pages.
ClinicalTrials.gov, NCT04214002: "The Natural History of Wounds in Patients With Dystrophic Epidermolysis Bullosa (DEB)," Dec. 30, 2019, 5 pages.
Cole et al., "Extracellular matrix regulation of fibroblast function: redefining our perspective on skin aging," Journal of Cell Communication and Signaliing (2018) 12:35-43.
Communication pursuant to Article 94(3) EPC for EP 16826873.8, dated Apr. 17, 2019, 7 pages.
De Silva et al., "Herpes Virus Amplicon Vectors", Viruses, vol. 1, 2009, pp. 594-629.
Deluca et al., "Isolation and Characterization of Deletion Mutants of Herpes Simplex Virus Type 1 in the Gene Encoding Immediate-Early Regulatory Protein ICP4", Journal of Virology, vol. 56, No. 2, Nov. 1985, pp. 558-570.
Eming SA, Krieg T, Davidson JM. Gene therapy and wound healing. Clin Dermatol. Jan.-Feb. 2007;25(1):79-92.
European Medicines Agency, "Assessment Report on Imlygic," Published Oct. 22, 2015.
FDA Briefing Document, "Cellular, Tissue, and Gene Therapies Advisory Committee and Oncologic Drugs Advisory Committee Meeting," Dated Apr. 29, 2015.
Final Office Action received for U.S. Appl. No. 15/393,151, mailed on Aug. 31, 2017, 13 pages.

(56) References Cited

OTHER PUBLICATIONS

Fink et al., "Gene therapy for pain: Results of a Phase I clinical trial," Ann Neurol (2011) 70(2):207-212.
Fink, "Gene transfer to the peripheral nervous system: Treatments for polyneuropathy and for pain," (2011) p. 53-58.
Fisher et al., "Pathophysiology of Premature Skin Aging Induced by Ultraviolet Light," N Engl J Med (1997) 337:1419-1429.
Ganceviciene et al., "Skin anti-aging strategies," Dermato-endocrinology (2012) 4:308-319.
Georgiadis et al., "Lentiviral Engineered Fibroblasts Expressing Codon—Optimized COL7A1 Restore Anchoring Fibrils in RDEB", Journal of Investigative Dermatology, vol. 136, 2016, pp. 284-292.
Glorioso JC. Herpes simplex viral vectors: late bloomers with big potential. Hum Gene Ther. Feb. 2014;25(2):83-91.
Goins et al. "Engineering HSV-1 Vectors for Gene Therapy," Methods Mol Biol (2014) 1144: 63-79.
Gorouchi et al., "Role of topical peptides in preventing or treating aged skin," International Journal of Cosmetic Science (2009) 31:327-345.
Goto et al., "Fibroblasts Show More Potential as Target Cells than Keratinocytes in COL7A1 Gene Therapy of Dystrophic Epidermolysis Bullosa", Journal of Investigative Dermatology, vol. 126, 2006, pp. 766-772.
Grant, Kyle, "Production and Purification of Highly Replication Defective Hsv-1 Based Gene Therapy Vectors", Doctoral Dissertation, University of Pittsburgh, 2008, 137 pages.
Gurevich et al., "Successful in vivo COL7A1 gene delivery and correction of recessive dystrophic epidermolysis bullosa (RDEB) skin using an off the shelf HSV-1 vector (KB103)", J Invest Derm. vol. 138, Iss. 5 Supp. May 2018, p. S129. Available online Apr. 19, 2018.
Harrington et al., "Efficacy and safety of talimogene laherparepvec versus granulocyte-macrophage colony-stimulating factor in patients with stage IIB/C and IVMIa melanoma: subanalysis of the Phase III Optim trial," Onco Targets and Therapy (2016) 9:7081-7093.
Harrow et al., "HSV1716 injection into the brain adjacent to tumour following surgical resection of high-grade glioma: safety data and long-term survival," Gene Therapy (2004) 11:1648-1658.
Heikkinen et al., "Diremerization of human lysyl hydroxylase 3 (LH3) is mediated by the amino acids 541 547," Matrix Biology (2010) 30(1):27-33.
Hennig et al., HEK293-based production platform for y-retroviral (self-inactivating) vectors: application for safe and efficient transfer of COL7A1 cDNA. Hum Gene Ther Clin Dev. Dec. 2014;25(4):218-28.
Humbert et al., "In the shadow of the wrinkle: experimental models," Journal of Cosmetic Dermatology (2011) 11:79-83.
International Preliminary Report on Patentability received for PCT Patent Application No. PCT/US2016/068974, mailed on Oct. 18, 2018, 11 pages.
International Preliminary Report on Patentability for PCT/US2019/029422, dated Oct. 27, 2020, 5 pages.
International Search Report and Written Opinion for PCT/US2019/29422, dated Jul. 10, 2019, 13 pages.
International Search Report and Written Opinion received for PCT Patent Application No. PCT/US2016/068974, mailed on May 18, 2017, 18 pages.
Invitation to Pay Additional Fee received for PCT Patent Application No. PCT/US2016/068974, mailed on Mar. 27, 2017, 2 pages.
Kim et al., "Microneedles for Drug and Vaccine Delivery", Advanced Drug Delivery Reviews, vol. 64, 2012, pp. 1547-1568.
Kopecki and Cowin, "Commentary: New advances in the development of therapies for treating inherited skin fragility disorders," Wound Practice and Research (2015) 23(4):184-190.
Lachmann R. Herpes simplex virus-based vectors. Int J Exp Pathol. Oct. 2004; 85(4): 177-90.
Lemperle et al., "A classification of facial wrinkles," Plastic and Reconstructive Surgery (2001) 1735-1750.
Lewin et al. "Gene therapy for autosomal dominant disorders of keratin", J Investig Dermatol Symp Proc. Oct. 2005;10(1):47-61.
Liu et al., "The Use of Type I and Type III Injectable Human Collagen for Dermal Fill: 10 Years of Clinical Experience in China," Semin Plast Surg (2005) 19(3):241-250.
Liu et al., "Type III collagen is crucial for collagen I fibrillogenesis and for normal cardiovascular development," Proc Natl Acad Sci USA (1997) 94:1852-1856.
Lu et al., "Topical Application of Viral Vectors for Epidermal Gene Transfer", The Journal of Investigative Dermatology, vol. 108, No. 5, May 1997, pp. 803-808.
Ma et al., "Efficacy of Herpes Simplex Virus Vector Encoding V the Human Preproenkephalin Gene for Treatment of Facial Pain in Mice," J Oral Facial Pain Headachce (2016) 30(1):42-50.
Marconi et al., HSV as a Vector in Vaccine Development and Gene Therapy. In: Madame Curie Bioscience Database [Internet]. Austin (TX): Landes Bioscience; 2000-2013.
Markert et al., "Conditionally replicating herpes simplex virus mutant, G207 for the treatment of malignant glioma: results of a phase I trial," Gene Ther (2000) 7:867-874.
Mayr et al., "Gene Therapy for the COL7A1 Gene", Chapter 23, Intech, 2013, pp. 561-589.
Nakao et al., "Intratumoral injection of herpes simplex virus HF10 in recurrent breast cancer," Ann Oncol (2004) 15(6):988-989.
Ng et al., "Fibroblast-Derived Dermal Matrix Drives Development of Aggressive Cutaneous Squamous Cell Carcinoma in Patients with Recessive Dystrophic Epidermolysis Bullosa", Cancer Research, vol. 72, No. 14, Jul. 15, 2012, pp. 3522-3534.
Non-Final Office Action for U.S. Appl. No. 16/598,982, issued Feb. 20, 2020, 10 pages.
Non-Final Office Action received for U.S. Appl. No. 15/393,151, mailed on Apr. 14, 2017, 13 pages.
Non-Final Office Action received for U.S. Appl. No. 15/851,488, mailed on May 14, 2018, 10 pages.
Non-Final Office Action received for U.S. Appl. No. 16/177,153, mailed on May 9, 2019, 13 pages.
Notice of Allowance received for U.S. Appl. No. 15/393,151, mailed on Dec. 6, 2017, 11 pages.
Notice of Allowance received for U.S. Appl. No. 15/851,488, mailed on Oct. 29, 2018, 11 pages.
Notice of Allowance received for U.S. Appl. No. 16/177,153, mailed on Aug. 30, 2019, 10 pages.
Nuutila et al., "Recombinant human collagen Ill gel for transplantation of autologous skin cells in porcine full-thickness wounds," J Tissue Eng Regen Med (2015) 9:1386-1393.
Ortiz-Urda et al., "Injection of Genetically Engineered Fibroblasts Corrects Regenerated Human Epidermolysis Bullosa Skin Tissue", The Journal of Clinical Investigation, vol. 111, No. 2, Jan. 2003, pp. 251-255.
Papanastassiou et al., "The potential for efficacy of the modified (ICP 34.5-) herpes simplex virus HSV1716 following intratumoural injection into human malignant glioma: a proof of principle study," Gene Ther (2002) 9:398-406.
Qin et al., "Rapamycin Protects Skin Fibroblasts from Ultraviolet B-Induced Photoaging by Suppressing the Production of Reactive Oxygen Species," Cell Physiol Biochem (2018) 46:1849-1860.
Quan et al., "Role of Age-Associated Alterations of the Dermal Extracellular Matrix Microenvironment in Human Skin Aging," Gerontology (2015) 61(5):427-434.
Rampling et al., "Toxicity evaluation of replication-competent herpes simplex virus (ICP 34.5 null mutant 1716) in patients with recurrent malignant glioma," Gene Ther (2000) 7:859-866.
Rayess et al., "A Cross-sectional Analysis of Adverse Events and Litigation for Injectable Fillers," JAMA Facial Plast Surg (2018) 20(3):207-214.
Ricard-Blum, "The Collagen Family," Cold Spring Harb Perspect Biol (2011) 3:a004978.
Rittie et al., "Natural and Sun-Induced Aging of Human Skin," Cold Spring Harb Perspect Med (2015) 5:a015370.
Salam, "Krystal's KB103 splits experts' thoughts on potential for HSV-1 risk in dystrophic epidermolysis bullosa patients, but final Phase I/II efficacy assured," Biopharm. Insight. Nov. 7, 2018, 3 pages.
Salmon-Ehr et al., "Implication of Interleukin-4 in Wound Healing", Laboratory Investigation, vol. 80, No. 8, Aug. 2000, pp. 1337-1343.

(56) References Cited

OTHER PUBLICATIONS

Samaniego et al., "Persistence and Expression of the Herpes Simplex Virus Genome in the Absence of Immediate-Early Proteins", Journal of Virology, vol. 72, No. 4, Apr. 1998, pp. 3307-3320.
Sankar et al., "A novel role for keratin 17 in coordinating oncogenic transformation and cellular adhesion in eqing sarcoma," Molecular and Cellular Biology (2013) 33(22):4448-4460.
Shen et al., "Herpes simplex virus 1 (HSV-1) for cancer treatment," Cancer Gene Therapy (2006) 13: 975-992.
Siegle et al., "Intradermal Implantation of Bovine Collagen: Humoral Immune Responses Associated with Clinical Reactions," Arch Dermatol (1984) 120:183-187.
Siprashvili et al., "Long-term type VII collagen restoration to human epidermolysis bullosa skin tissue," Hum Gene Ther. Oct. 2010;21(10):1299-310.
Smith et al., "A Randomized, Bilateral, Prospective Comparison of Calcium Hydroxylapatite Microspheres versus Human-Based Collagen for the Correction of Nasolabial Folds," Dermatol Surg (2007) 33:S112-S121.
Stow et al., Isolation and characterization of a herpes simplex virus type 1 mutant containing a deletion within the gene encoding the immediate early polypeptide Vmw110. J Gen Viral. Dec. 1986;67 ( Pt 12):2571-85.
Summary of safety and effectiveness data of CosmoDerm™ 1 Human-Based collagen. Approval date to applicant Mar. 11, 2003.
Thangapazham et al., "Alteration of Skin Properties with Autologous Dermal Fibroblasts," Int J Mol Sci (2014) 15:8407-8427.
Theopold et al., "A novel replication-defective HSV-1 vector for regulatable gene delivery to wounds," Journal of the American College of Surgeons (2004) 199(3):57-58.
Uitto et al., "Progress toward Treatment and Cure of Epidermolysis Bullosa: Summary of the DEBRA International Research Symposium EB2015", Journal of Investigative Dermatology, vol. 136, 2016, pp. 352-358.
Volk et al., "Diminished Type III Collagen Promotes Myofibroblast Differentiation and Increases Scar Deposition in Cutaneous Wound Healing," Cells Tissues Organs (2011) 194:25-37.
Wang et al., "Comparative Effectiveness of Antinociceptive Gene Therapies in Animal Models of Diabetic Neuropathic Pain", Gene Therapy, vol. 20, 2013, pp. 742-750.
Wang et al., "Wound healing," J Chin Med Assoc (2018) 81:94-101.
Watanabe et al., "Properties of a Herpes Simplex Virus Multiple Immediate-early Gene-Deleted Recombinant as a Vaccine Vector", Virology, vol. 357, 2007, pp. 186-198.
Watson et al., "Autologous Fibroblasts for Treatment of Facial Rhytids and Dermal Depressions," Arch Facial Plast Surg (1999) 1:165-170.
Watt et al., "Lysyl Hydroxylase 3 Localizes to Epidermal Basement Membrane and is Reduced in Patients with Recessive Dystrophic Epidermolysis Bullosa", Plos One, 10(9):e0137639.
Weiss et al., "The Role of Interleukin 10 in the Pathogenesis and Potential Treatment of Skin Diseases", Journal of the American Academy of Dermatology, vol. 50, No. 5, May 2004, pp. 657-675.
White et al., "Evaluation and optimization of the administration of a selectively replicating herpes simplex viral vector to the brain by convection-enhanced delivery", Cancer Gene Ther. May 2011;18(5):358-69. doi: 10.1038/ cgt.2011.2. Epub Mar. 4, 2011.
Wikipedia, "Collagen, type VII, alpha 1," Edited on Apr. 17, 2020. Retrieved from https://en.wikipedia.org/wiki/Collagen,_type_VII,_alpha_1&oldid=951427836 on Jul. 22, 2020.
Wikipedia, "Collagen," p. 1-10. Retrieved Aug. 20, 2019.
Wolfe et al., "Engineering Herpes Simplex Viral Vectors for Therapeutic Gene Transfer", Chapter 6, Gene and Cell Therapy, 2004, pp. 103-129.
Woodley et al., "Normal and Gene-Corrected Dystrophic Epidermolysis Bullosa Fibroblasts Alone Can Produce Type VII Collagen at the Basement Membrane Zone" The Journal of Investigative Dermatology, vol. 121, No. 5, Nov. 2003, pp. 1021-1028.
Woodley, et al., "Intradermal Injection of Lentiviral Vectors Corrects Regenerated Human Dystrophic Epidermolysis Bullosa Skin Tissue in Vivo", Molecular Therapy, vol. 10, No. 2, Aug. 2004, pp. 318-326.
Yano et al., "Regulatory approval for autologous human cells and tissue products in the United States, the European Union, and Japan," Regenerative Therapy (2015) 1:45-56.
Yoon et al., "Anti-wrinkle effect of bone morphogenetic protein receptor 1a-extracellular domain (BMPR1a-ECD)," BMB Rep (2013) 46(9):465-470.
Yutskovskaya et al., "A Randomized, Split-Face, Histomorphological Study Comparing a Volumetric Calcium Hydroxylapatite and a Hyaluornic Acid-Based Dermal Filler," J Drugs Dermatol (2014) 13(9):47-52.
Zeng et al., "Preclinical Safety Studies on Autologous Cultured Human Skin Fibroblast Transplantation," Cell Transplant (2014) 23:39-49.
Zhao et al., "Preliminary Survival Studies on Autologous Cultured Skin Fibroblasts Transplantation by Injection," Cell Transplant (2008) 17:775-783.
Ivanov et al., "A Tobamovirus Genome That Contains an Internal Ribosome Entry Site Functional in Vitro." Virology, vol. 232, 1997, pp. 32-43.
Sadikoglou et al., "Comparative analysis of internal ribosomal entry sites as molecular tools for bicistronic expression." Journal of Biotechnology, vol. 181, 2014, pp. 31-34.
Wang et al., "Neurological Complications of herpes zoster," Zhejiang Medical Journal, Issue 6, pp. 26-28, 1985.
Office Action for related Application No. CN 201980028654.6 dated Dec. 22, 2023.
Office Action for related Application No. AE P6001497/2020 dated Dec. 4, 2023.
Saeki et al., "Improved Helper Virus-Free Packaging System for HSV Amplicon Vectors Using an ICP27-Deleted, Oversized HSV-1 DNA in a Bacterial Artificial Chromosome." Molecular Therapy. 2001. vol. 3, No. 4, pp. 591-601.
Titeux et al., "Gene therapeutics strategies for blistering skin diseases." Drug Discovery Today: Therapeutic Strategies. 2006. vol. 3, No. 1, pp. 87-92.
Office Action from related Application KR 10-2018-7030112, dated Jan. 24, 2024.
Di et al., "Ex-vivo gene therapy restores LEKT1 activity and corrects the architecture of Netherton syndromw-derived skin grafts" Mol. Ther. Feb. 2011; pp. 408-416, 19(2).
Ghazizadeh et al., "In vivo transduction of mouse epidermis with recombinant retroviral vectors: implications for cutaneous gene therapy" Gene Ther., 1999, pp. 1267-1275, vol. 6, No. 7.
Kallunki P, et al. "Laminin, gamma 2 isoform b precursor [*Homo sapiens*]," NCBI Reference Sequence: NP_061486.2; Updated Sep. 21, 2007.
Parente et al., "Collagen alpha-1 (VII) chain precursor [*Homo sapiens*]," NCBI Reference Sequence: NP_000085.1, First Dep, Mar. 24, 1999.
"Rheumatoid arthritis," May Foundation for Medical Education and Research (MFMER), 2024; Accessed Jan. 10, 2024.
Roedl et al., "rAAV2-mediated restoration of LEKTI in LEKTI-deficient cells from Netherton patients" J. Dermatol. Sci., Mar. 2011, pp. 194-198, vol. 61, No. 3.
Sybert et al., "Filaggrin [*Homo sapiens*]," NCBI Reference Sequence: NP_002007.1, Submitted Feb. 20, 2005.
Xu et al., "A loss of function mutation in the filaggrin gene associated with ichthyosis vulgaris and rheumatoid arthritis," European Journal of Inflammation, 2021; 19.
Office Action in related CA application 3,112,633 dated dated Apr. 16, 2024.
Office Action for related Application No. JP 2021-516991 dated May 13, 2024.

* cited by examiner

Adhesion to Collagen I

Adhesion to Fibronectin

Col7A1 Transcripts

Col7A1 DNA copies

LAMC2 DNA

LAMC2 transcript

RECOMBINANT NUCLEIC ACIDS ENCODING COSMETIC PROTEIN(S) FOR AESTHETIC

CROSS REFERENCE TO RELATED APPLICATIONS

This application is a continuation of U.S. application Ser. No. 16/395,896, filed Apr. 26, 2019, now issued as U.S. Pat. No. 10,786,438, which claims the priority benefit of U.S. Provisional Application Ser. No. 62/663,476, filed Apr. 27, 2018, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761342000601SeqList.txt, date recorded: Jun. 29, 2020, size: 437 KB).

FIELD OF THE INVENTION

The present disclosure relates, in part, to recombinant nucleic acids comprising one or more polynucleotides encoding one or more cosmetic proteins (e.g., one or more human collagen proteins); to viruses comprising the recombinant nucleic acids; to compositions (e.g., cosmetic formulations) comprising the recombinant nucleic acids and/or viruses; to methods of their use; and to articles of manufacture or kits thereof.

BACKGROUND

Skin, like all organs in the human body, undergoes sequential and often cumulative alterations with the passage of time. Aging of the skin occurs as the result of numerous factors, including inherent changes within the skin, the effects of gravity and facial muscles acting on the skin, soft tissue loss or shift, and loss of tissue elasticity. Interestingly, the "aged" phenotype of skin may be accelerated by environmental factors, most notably, chronic exposure to ultraviolet irradiation (e.g., from the sun). Clinically, the aged phenotype of skin may be described as wrinkled, sagging, and/or generally less elastic and resilient than its youthful counterpart, although variations within this phenotype exist between natural, chronological aging and photoaging.

The dermal extracellular matrix (ECM) comprises the bulk of skin and confers both strength and resiliency. Collagen, a major component of the connective tissue providing support to the skin, decreases as a person ages. In aged skin, collagen fibrils display high levels of degradation and fragmentation, and are replenished by dermal fibroblasts at diminishing rates. These degraded and fragmented collagen bundles become looser and lose strength (disrupting the structural organization of the dermal ECM), and inextricably leads to an "aged" manifestation of the skin.

Numerous skincare products have been developed for improving the appearance of human skin. Wrinkles and skin folds are commonly treated with dermal and subdermal injections of aesthetic facial fillers; however, such a superficial approach does not address the structural changes underlying skin aging, in particular, the damage or loss of collagen. Thus, there exists a clear need for alternative strategies to supplement, strengthen, or replace dermal ECM components (e.g., human collagen), in individuals desiring to combat or reverse the physiological effects of skin aging.

All references cited herein, including patent applications, patent publications, non-patent literature, and NCBI/UniProtKB/Swiss-Prot Accession numbers are herein incorporated by reference in their entirety, as if each individual reference were specifically and individually indicated to be incorporated by reference.

BRIEF SUMMARY

In order to meet these and other needs, provided herein are recombinant nucleic acids (e.g., recombinant herpes viral genomes) encoding one or more cosmetic proteins for use in viruses (e.g., herpes viruses), compositions, formulations, medicaments, and/or methods for aesthetic/cosmetic applications (e.g., treating wrinkles). The present inventors have shown that the recombinant, attenuated viruses described herein were capable of 1) effectively transducing human epidermal/dermal cells, and 2) successfully expressing the encoded exogenous human collagen (mRNA and protein), where the protein could then localize to the appropriate region in skin-equivalent organotypic cultures (see e.g., Example 2). Moreover, the present inventors have shown that the viruses described herein may be successfully administered either topically or intradermally without significant host cell cytotoxicity, allowing for the human collagen expressed from these viruses to localize to the appropriate region of the dermal ECM after in vivo administration without observable damage to the skin (see e.g., Examples 3 and 7). In addition, the present inventors have shown that multiple different HSV backbones can be used to construct viruses expressing human collagens (see e.g., Example 2), that multiple strategies can be employed to successfully express more than one human collagen protein from a single recombinant genome (see e.g., Example 5), and that candidate viruses can successfully express human collagen proteins in multiple relevant in vitro and in vivo models of chronological or UV-induced skin aging (see e.g., Examples 6 and 7). Furthermore, the present inventors have shown that the viruses described herein can be successfully engineered to express other cosmetic proteins (e.g., human laminins) both in vitro and in vivo, where these proteins localize to the appropriate region of the dermal ECM (see e.g., Example 8). Without wishing to be bound by theory, the data described herein provides strong evidence that the recombinant nucleic acids and/or viruses of the present disclosure may constitute a novel means for delivering cosmetic proteins (e.g., human collagen proteins, such as human Collagen 1 and human Collagen 3), and in particular, to supplement or replace natural human dermal ECM proteins in aesthetic applications (e.g., to reduce the appearance of age or photo-induced wrinkles).

Accordingly, certain aspects of the present disclosure relate to a recombinant herpes virus genome comprising a first polynucleotide encoding a first polypeptide comprising a first cosmetic protein. In some embodiments, the recombinant herpes virus genome comprises two or more copies of the first polynucleotide. In some embodiments, the recombinant herpes virus genome is replication competent. In some embodiments, the recombinant herpes virus genome is replication defective. In some embodiments that may be combined with any of the preceding embodiments, the recombinant herpes virus genome is selected from a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any derivatives thereof. In some embodiments that may be combined with any of the preceding embodiments, the recombinant herpes virus genome is a recombinant herpes simplex virus genome. In some embodiments, the recombinant herpes simplex virus genome is a recombinant type 1 herpes simplex virus (HSV-1) genome, a recombinant type 2 herpes simplex virus (HSV-2) genome, or any derivatives thereof.

In some embodiments, the recombinant herpes simplex virus genome is a recombinant type 1 herpes simplex virus (HSV-1) genome. In some embodiments that may be combined with any of the preceding embodiments, the recombinant herpes simplex virus genome comprises an inactivating mutation. In some embodiments that may be combined with any of the preceding embodiments, the inactivating mutation is in a herpes simplex virus gene. In some embodiments, the inactivating mutation is a deletion of the coding sequence of the herpes simplex virus gene. In some embodiments, the herpes simplex virus gene is selected from Infected Cell Protein (ICP) 0, ICP4, ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivating mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivating mutation in the UL41 gene. In some embodiments that may be combined with any of the preceding embodiments, the recombinant herpes simplex virus genome comprises an inactivating mutation in one or both copies of the ICP0 gene. In some embodiments that may be combined with any of the preceding embodiments, the recombinant herpes simplex virus genome comprises an inactivating mutation in the ICP27 gene. In some embodiments that may be combined with any of the preceding embodiments, the recombinant herpes simplex virus genome comprises an inactivating mutation in the UL55 gene. In some embodiments that may be combined with any of the preceding embodiments, the recombinant herpes simplex virus genome comprises an inactivating mutation in the Joint region. In some embodiments, the recombinant herpes simplex virus genome comprises a deletion of the Joint region. In some embodiments that may be combined with any of the preceding embodiments, the recombinant herpes simplex virus genome comprises the first polynucleotide within one or both of the ICP4 viral gene loci.

In some embodiments that may be combined with any of the preceding embodiments, the first cosmetic protein is selected from a first collagen protein, a first fibronectin protein, a first elastin protein, a first lumican protein, a first vitronectin protein, a first vitronectin receptor protein, a first laminin protein, a first neuromodulator protein, and a first fibrillin protein. In some embodiments that may be combined with any of the preceding embodiments, the first cosmetic protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21 and 53-64. In some embodiments, the first cosmetic protein is a structural extracellular matrix protein (e.g., a collagen protein, an elastin protein, a fibronectin protein, a laminin protein, a fibrillin protein, etc.). In some embodiments, the first cosmetic protein is a collagen protein, an elastin protein, a fibronectin protein, or a laminin protein (e.g., a human collagen protein, a human elastin protein, a human fibronectin protein, or a human laminin protein). In some embodiments that may be combined with any of the preceding embodiments, the first collagen protein is a human collagen protein. In some embodiments that may be combined with any of the preceding embodiments, the first collagen protein is selected from a Collagen alpha-1(I) chain polypeptide (COL1-1), Collagen alpha-2(I) chain polypeptide (COL1-2), a Collagen alpha-1(II) chain polypeptide (COL2), a Collagen alpha-1(III) chain polypeptide (COL3), a Collagen alpha-1(IV) chain polypeptide (COL4-1), a Collagen alpha-2(IV) chain polypeptide (COL4-2), a Collagen alpha-3(IV) chain polypeptide (COL4-3), a Collagen alpha-4(IV) chain polypeptide (COL4-4), a Collagen alpha-5(IV) chain polypeptide (COL4-5), a Collagen alpha-6(IV) chain polypeptide (COL4-6), a Collagen alpha-1(V) chain polypeptide (COL5-1), a Collagen alpha-2(V) chain polypeptide (COL5-2), a Collagen alpha-3(V) chain polypeptide (COL5-3), a Collagen alpha-1(VI) chain polypeptide (COL6-1), a Collagen alpha-2(VI) chain polypeptide (COL6-2), a Collagen alpha-3(VI) chain polypeptide (COL6-3), a Collagen alpha-4(VI) chain polypeptide (COL6-4), a Collagen alpha-5(VI) chain polypeptide (COL6-5), a Collagen alpha-6(VI) chain polypeptide (COL6-6), a Collagen alpha-1(VIII) chain polypeptide (COL8), a Collagen alpha-1(IX) chain polypeptide (COL9-1), a Collagen alpha-2(IX) chain polypeptide (COL9-2), a Collagen alpha-3(IX) chain polypeptide (COL9-3), a Collagen alpha-1(X) chain polypeptide (COL10), a Collagen alpha-1(XI) chain polypeptide (COL11-1), a Collagen alpha-2(XI) chain polypeptide (COL11-2), a Collagen alpha-1(XII) chain polypeptide (COL12), a Collagen alpha-1(XIII) chain polypeptide (COL13), a Collagen alpha-1(XIV) chain polypeptide (COL14), a Collagen alpha-1(XV) chain polypeptide (COL15), a Collagen alpha-1(XVI) chain polypeptide (COL16), a Collagen alpha-1(XVII) chain polypeptide (COL17), a Collagen alpha-1(XVIII) chain polypeptide (COL18), a Collagen alpha-1(XIX) chain polypeptide (COL19), a Collagen alpha-1(XX) chain polypeptide (COL20), a Collagen alpha-1(XXI) chain polypeptide (COL21), a Collagen alpha-1(XXII) chain polypeptide (COL22), a Collagen alpha-1(XXIII) chain polypeptide (COL23), a Collagen alpha-1(XXIV) chain polypeptide (COL24), a Collagen alpha-1(XXV) chain polypeptide (COL25), a Collagen alpha-1(XXVI) chain polypeptide (COL26), a Collagen alpha-1(XXVII) chain polypeptide (COL27), and a Collagen alpha-1(XXVIII) chain polypeptide (COL28). In some embodiments that may be combined with any of the preceding embodiments, the first collagen protein is selected from COL1-1, COL1-2, COL3, COL4-1, COL4-2, COL6-1, and COL17. In some embodiments that may be combined with any of the preceding embodiments, the first collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments that may be combined with any of the preceding embodiments, the first collagen protein is COL3. In some embodiments that may be combined with any of the preceding embodiments, the first collagen protein is human COL3. In some embodiments that may be combined with any of the preceding embodiments, the first collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 17. In some embodiments that may be combined with any of the preceding embodiments, the first cosmetic protein is not a Collagen alpha-1(VII) chain polypeptide (COL7).

In some embodiments, the first polypeptide consists essentially of the first cosmetic protein. In some embodiments, the first polypeptide consists of the first cosmetic protein. In some embodiments, the first polypeptide comprises: (a) the first cosmetic protein; (b) a further cosmetic protein; and (c) a linker polypeptide linking (a) to (b). In some embodiments, the further cosmetic protein is selected from a collagen protein, a fibronectin protein, a elastin protein, a lumican protein, a vitronectin protein, a vitronectin receptor protein, a laminin protein, a neuromodulator protein, and a fibrillin protein. In some embodiments, the further cosmetic protein is a structural extracellular matrix protein (e.g., a collagen protein, an elastin protein, a fibronectin protein, a laminin protein, a fibrillin protein, etc.). In some embodiments, the further cosmetic protein is a collagen protein, an elastin protein, a fibronectin protein, or a laminin protein (e.g., a human collagen protein, a human elastin protein, a human fibronectin protein, or a human laminin protein). In some embodiments, the further collagen protein (e.g., a further human collagen protein) is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the further collagen protein (e.g., a further human collagen protein) is selected from COL1-1, COL1-2, COL3, COL4-1, COL4-2, COL6-1, COL7, and COL17. In some embodiments, the first cosmetic protein and the further cosmetic protein are different. In some embodiments, the first cosmetic protein is COL1-1 (e.g., human COL1-1) and the further cosmetic protein is COL1-2 (e.g., human COL1-2). In some embodiments, the linker polypeptide is a cleavable linker polypeptide. In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected SEQ ID NOS: 28-31.

In some embodiments that may be combined with any of the preceding embodiments, the first polynucleotide encodes a polycistronic mRNA comprising: (a) a first open reading frame (ORF) encoding the first polypeptide; (b) a second ORF encoding an additional cosmetic protein; and (c) an internal ribosomal entry site (IRES) separating (a) and (b). In some embodiments, the additional cosmetic protein is selected from a collagen protein, a fibronectin protein, a elastin protein, a lumican protein, a vitronectin protein, a vitronectin receptor protein, a laminin protein, a neuromodulator protein, and a fibrillin protein. In some embodiments, the additional cosmetic protein is a structural extracellular matrix protein (e.g., a collagen protein, an elastin protein, a fibronectin protein, a laminin protein, a fibrillin protein, etc.). In some embodiments, the additional cosmetic protein is a collagen protein, an elastin protein, a fibronectin protein, or a laminin protein (e.g., a human collagen protein, a human elastin protein, a human fibronectin protein, or a human laminin protein). In some embodiments, the additional collagen protein (e.g., an additional human collagen protein) is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the additional collagen protein (e.g., an additional human collagen protein) is selected from COL1-1, COL1-2, COL3, COL4-1, COL4-2, COL6-1, COL7, and COL17. In some embodiments, the first cosmetic protein and the additional cosmetic protein are different. In some embodiments, the first cosmetic protein is COL1-1 (e.g., human COL1-1) and the additional cosmetic protein is COL1-2 (e.g., human COL1-2). In some embodiments, the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23.

In some embodiments that may be combined with any of the preceding embodiments, the recombinant herpes virus genome further comprises a second polynucleotide encoding a second cosmetic protein. In some embodiments, the second cosmetic protein is selected from a collagen protein, a fibronectin protein, a elastin protein, a lumican protein, a vitronectin protein, a vitronectin receptor protein, a laminin protein, a neuromodulator protein, and a fibrillin protein. In some embodiments, the second cosmetic protein is a structural extracellular matrix protein (e.g., a collagen protein, an elastin protein, a fibronectin protein, a laminin protein, a fibrillin protein, etc.). In some embodiments, the second cosmetic protein is a collagen protein, an elastin protein, a fibronectin protein, or a laminin protein (e.g., a human collagen protein, a human elastin protein, a human fibronectin protein, or a human laminin protein). In some embodiments, the second collagen protein (e.g., a second human collagen protein) is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the second collagen protein (e.g., a second human collagen protein) is selected from COL1-1, COL1-2, COL3, COL4-1, COL4-2, COL6-1, COL7, and COL17. In some embodiments, the first and second cosmetic proteins are different. In some embodiments, the first cosmetic protein is COL1-1 (e.g., human COL1-1) and the second cosmetic protein is COL1-2 (e.g., human COL1-2). In some embodiments, the first cosmetic protein is COL1-1 (e.g., human COL1-1) and the second cosmetic protein is COL3 (e.g., human COL3).

In some embodiments that may be combined with any of the preceding embodiments, the recombinant herpes virus genome has reduced cytotoxicity when introduced into a target cell, as compared to a corresponding wild-type herpes virus genome. In some embodiments, the target cell is a cell of the epidermis and/or dermis. In some embodiments, the target cell is a human cell. In some embodiments, the target cell is a fibroblast.

Other aspects of the present disclosure relate to a herpes virus comprising any of the recombinant herpes virus genomes described herein. In some embodiments, the herpes virus is replication competent. In some embodiments, the herpes virus is replication defective. In some embodiments, the herpes virus is attenuated. In some embodiments that may be combined with any of the preceding embodiments, the herpes virus has reduced cytotoxicity as compared to a corresponding wild-type herpes virus. In some embodiments that may be combined with any of the preceding embodiments, the herpes virus is selected from a herpes simplex virus, a varicella zoster virus, a human cytomegalovirus, a herpesvirus 6A, a herpesvirus 6B, a herpesvirus 7, and a Kaposi's sarcoma-associated herpesvirus. In some embodiments that may be combined with any of the preceding embodiments, the herpes virus is a herpes simplex virus. In some embodiments, the herpes simplex virus is a type 1 herpes simplex virus (HSV-1), a type 2 herpes simplex virus (HSV-2), or any derivatives thereof. In some embodiments, the herpes simplex virus is a type 1 herpes simplex virus (HSV-1).

Other aspects of the present disclosure relate to a composition comprising: (a) any of the recombinant herpes virus genomes described herein and/or any of the herpes viruses described herein; and (b) an excipient. In some embodiments, the composition is sterile. In some embodiments that may be combined with any of the preceding embodiments, the composition is suitable for topical, transdermal, subcutaneous, intradermal, oral, intranasal, intratracheal, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration. In some embodiments that may be combined with any of the preceding embodiments, the composition is suitable for intradermal administration. In some embodiments that may be combined with any of the preceding embodiments, the composition is suitable for superficial injection. In some embodiments that may be combined with any of the preceding embodiments, the composition is a cosmetic composition. In some embodiments that may be combined with any of the preceding embodiments, the composition is a skin care product.

Other aspects of the present disclosure relate to the use of any of the recombinant herpes virus genomes described herein and/or any of the herpes viruses described herein as a medicament (e.g., for an aesthetic indication).

Other aspects of the present disclosure relate to the use of any of the recombinant herpes virus genomes described herein and/or any of the herpes viruses described herein as a therapy (e.g., as an aesthetic or cosmetic therapy).

Other aspects of the present disclosure relate to the use of any of the recombinant herpes virus genomes described herein and/or any of the herpes viruses described herein in the manufacture of a medicament useful for treating one or more signs or symptoms of dermatological aging.

Other aspects of the present disclosure relate to a method of enhancing, increasing, augmenting, and/or supplementing the levels of one or more dermal extracellular matrix proteins in a subject, the method comprising administering to the subject an effective amount of any of the herpes viruses described herein and/or any of the compositions described herein.

Other aspects of the present disclosure relate to a method of enhancing, increasing, augmenting, and/or supplementing the levels of one or more collagen proteins in a subject, the method comprising administering to the subject an effective amount of any of the herpes viruses described herein and/or any of the compositions described herein. In some embodiments, the one or more collagen proteins are collagen 3. In some embodiments, the levels of endogenous collagen 3 are reduced as a result of chronological or photo-aging.

Other aspects of the present disclosure relate to a method of enhancing, increasing, augmenting, and/or supplementing the soft tissue of a subject, the method comprising administering to the subject an effective amount of any of the herpes viruses described herein and/or any of the compositions described herein. In some embodiments, the composition is injected into the soft tissue of the subject.

Other aspects of the present disclosure relate to a method of improving skin condition, quality, and/or appearance in a subject in need thereof, the method comprising administering to the subject an effective amount of any of the herpes viruses described herein and/or any of the compositions described herein. In some embodiments, the composition is administered to one or more sites of sun damage or other UV exposure, rough texture, skin sagging, wrinkles, or any combinations thereof.

Other aspects of the present disclosure relate to a method of reducing the appearance of one or more superficial depressions in the skin of a subject in need thereof, the method comprising administering to the subject an effective amount of any of the herpes viruses described herein and/or any of the compositions described herein. In some embodiments, the one or more superficial depressions in the skin are selected from the group consisting of nasolabial folds, crows' feet, frown lines, worry lines, scars, glabellar lines, brow ptosis, tear troughs, nasojugal lines, bunny lines, cheek/mid-face ptosis, marionette lines, poppy dimpling, smile lines, laugh lines, chin creases, neck lines, platysma bands, and any combinations thereof.

Other aspects of the present disclosure relate to a method of increasing and/or improving at least one of texture, smoothness, elasticity, or tension of the skin of a subject in need thereof, the method comprising administering to the subject an effective amount of any of the herpes viruses described herein and/or any of the compositions described herein.

In some embodiments that may be combined with any of the preceding embodiments, the skin of the subject is aging skin. In some embodiments that may be combined with any of the preceding embodiments, the skin of the subject has been damaged due to exposure to ultraviolet light. In some embodiments that may be combined with any of the preceding embodiments, the skin of the subject is wrinkled.

Other aspects of the present disclosure relate to a method of diminishing one or more dermatological signs of aging in a subject in need thereof, the method comprising administering to the subject an effective amount of any of the herpes viruses described herein and/or any of the compositions described herein. In some embodiments, the diminishing of one or more dermatological signs of aging is indicated by the: (a) treatment, reduction, and/or prevention of fine lines and/or wrinkles; (b) reduction of skin pore size; (c) improvement in skin thickness, plumpness, and/or tautness; (d) improvement in skin smoothness, suppleness, and/or softness; (e) improvement in skin tone, radiance, and/or clarity; (f) improvement in procollagen and/or collagen production; (g) improvement in skin texture and or promotion of retexturization; (h) improvement in appearance of skin contours; (i) restoration of skin luster and/or brightness; (j) improvement of skin appearance decreased by aging and/or menopause; (k) improvement in skin moisturization; (l) increase in skin elasticity and/or resiliency; (m) treatment, reduction, and/or prevention or skin sagging; (n) improvement in skin firmness; (o) reduction of pigment spots, mottled skin, and/or scars (such as acne scars); (p) improvement of optical properties of skin by light diffraction or reflection; or (q) any combinations thereof.

In some embodiments that may be combined with any of the preceding embodiments, the subject is a human. In some embodiments that may be combined with any of the preceding embodiments, the herpes virus or composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments that may be combined with any of the preceding embodiments, the herpes virus or composition is administered intradermally to the subject. In some embodiments that may be combined with any of the preceding embodiments, the herpes virus or composition is administered by superficial injection.

Other aspects of the present disclosure relate to a composition comprising: a herpes simplex virus (HSV) comprising a recombinant nucleic acid, wherein the recombinant nucleic acid comprises a first polynucleotide encoding a first polypeptide comprising a first human collagen protein, and an excipient. In some embodiments, the recombinant nucleic acid comprises two or more copies of the first polynucleotide. In some embodiments that may be combined with any of the preceding embodiments, the HSV is replication-defective. In some embodiments that may be combined with any of the preceding embodiments, the HSV is replication-competent. In some embodiments that may be combined with any of the preceding embodiments, the HSV is a herpes simplex type 1 virus, a herpes simplex type 2 virus, or any derivatives thereof.

In some embodiments, the recombinant nucleic acid is a herpes simplex virus amplicon. In some embodiments, the herpes simplex virus amplicon is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

In some embodiments, the recombinant nucleic acid is a recombinant herpes simplex virus genome. In some embodiments, the recombinant herpes simplex virus genome is a recombinant HSV-1 genome, a recombinant HSV-2 genome, or any derivatives thereof. In some embodiments that may be combined with any of the preceding embodiments, the recombinant herpes simplex virus genome comprises an inactivating mutation in a herpes simplex virus gene. In some embodiments, the herpes simplex virus gene is selected from the group consisting of Infected Cell Protein (ICP) 0, ICP4, ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivation mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivation mutation in the UL41 gene. In some embodiments that may be combined with any of the preceding embodiments, the recombinant herpes simplex virus genome comprises an inactivation mutation in the ICP0 gene. In some embodiments that may be combined with any of the preceding embodiments, the recombinant herpes simplex virus genome comprises an inactivation mutation in the ICP27 gene. In some embodiments that may be combined with any of the preceding embodiments, the inactivating mutation is a deletion of the coding sequence of the gene(s).

In some embodiments that may be combined with any of the preceding embodiments, the recombinant herpes simplex virus genome comprises the first polynucleotide within a viral gene locus. In some embodiments that may be combined with any of the preceding embodiments, the recombinant herpes simplex virus genome comprises the first polynucleotide within one or both copies of the ICP4 viral gene loci. In some embodiments that may be combined with any of the preceding embodiments, the recombinant herpes simplex virus genome comprises the first polynucleotide within the ICP22 viral gene locus. In some embodiments that may be combined with any of the preceding embodiments, the recombinant herpes simplex virus genome comprises the first polynucleotide within the UL41 viral gene locus. In some embodiments that may be combined with any of the preceding embodiments, the HSV has reduced cytotoxicity as compared to a wild-type herpes simplex virus.

In some embodiments that may be combined with any of the preceding embodiments, the first human collagen protein is selected from Collagen alpha-1(I) chain polypeptide (COL1-1), Collagen alpha-2(I) chain polypeptide (COL1-2), a Collagen alpha-1(II) chain polypeptide (COL2), a Collagen alpha-1(III) chain polypeptide (COL3), a Collagen alpha-1(IV) chain polypeptide (COL4-1), a Collagen alpha-2(IV) chain polypeptide (COL4-2), a Collagen alpha-3(IV) chain polypeptide (COL4-3), a Collagen alpha-4(IV) chain polypeptide (COL4-4), a Collagen alpha-5(IV) chain polypeptide (COL4-5), a Collagen alpha-6(IV) chain polypeptide (COL4-6), a Collagen alpha-1(V) chain polypeptide (COL5-1), a Collagen alpha-2(V) chain polypeptide (COL5-2), a Collagen alpha-3(V) chain polypeptide (COL5-3), a Collagen alpha-1(VI) chain polypeptide (COL6-1), a Collagen alpha-2(VI) chain polypeptide (COL6-2), a Collagen alpha-3(VI) chain polypeptide (COL6-3), a Collagen alpha-4(VI) chain polypeptide (COL6-4), a Collagen alpha-5(VI) chain polypeptide (COL6-5), a Collagen alpha-6(VI) chain polypeptide (COL6-6), a Collagen alpha-1(VII) chain polypeptide (COL7), a Collagen alpha-1(VIII) chain polypeptide (COL8), a Collagen alpha-1(IX) chain polypeptide (COL9-1), a Collagen alpha-2(IX) chain polypeptide (COL9-2), a Collagen alpha-3(IX) chain polypeptide (COL9-3), a Collagen alpha-1(X) chain polypeptide (COL10), a Collagen alpha-1(XI) chain polypeptide (COL11-1), a Collagen alpha-2(XI) chain polypeptide (COL11-2), a Collagen alpha-1(XII) chain polypeptide (COL12), a Collagen alpha-1(XIII) chain polypeptide (COL13), a Collagen alpha-1 (XIV) chain polypeptide (COL14), a Collagen alpha-1(XV) chain polypeptide (COL15), a Collagen alpha-1(XVI) chain polypeptide (COL16), a Collagen alpha-1(XVII) chain polypeptide (COL17), a Collagen alpha-1(XVIII) chain polypeptide (COL18), a Collagen alpha-1(XIX) chain polypeptide (COL19), a Collagen alpha-1(XX) chain polypeptide (COL20), a Collagen alpha-1(XXI) chain polypeptide (COL21), a Collagen alpha-1(XXII) chain polypeptide (COL22), a Collagen alpha-1(XXIII) chain polypeptide (COL23), a Collagen alpha-1(XXIV) chain polypeptide (COL24), a Collagen alpha-1(XXV) chain polypeptide (COL25), a Collagen alpha-1(XXVI) chain polypeptide (COL26), a Collagen alpha-1(XXVII) chain polypeptide (COL27), and a Collagen alpha-1(XXVIII) chain polypeptide (COL28). In some embodiments that may be combined with any of the preceding embodiments, the first human collagen protein is selected from COL1-1, COL1-2, COL3, COL4-1, COL6-1, COL7, and COL17. In some embodiments that may be combined with any of the preceding embodiments, the nucleic acid sequence encoding the first human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments that may be combined with any of the preceding embodiments, the first human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments that may be combined with any of the preceding embodiments, the first human collagen protein is not COL7.

In some embodiments that may be combined with any of the preceding embodiments, the first polypeptide comprises: (a) the first human collagen protein; (b) a further human collagen protein; and (c) a linker polypeptide linking (a) to (b). In some embodiments, the linker polypeptide is a cleavable linker polypeptide. In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 28-31. In some embodiments, the further human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the further human collagen protein is selected from COL1-1, COL1-2, COL3, COL4-1, COL6-1, COL7, and COL17. In some embodiments, the nucleic acid sequence encoding the further human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the further human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first human collagen protein and the further human collagen protein are different.

In some embodiments that may be combined with any of the preceding embodiments, the first polynucleotide encodes a polycistronic mRNA comprising: (a) a first open reading frame (ORF) encoding the first polypeptide; (b) a second ORF encoding an additional human collagen protein; and (c) an internal ribosomal entry site (IRES) separating (a) and (b). In some embodiments, the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23. In some embodiments, the additional human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the additional human collagen protein is selected from COL1-1, COL1-2, COL3, COL4-1, COL6-1, COL7, and COL17. In some embodiments, the nucleic acid sequence encoding the additional human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the additional human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first human collagen protein and the additional human collagen protein are different.

In some embodiments that may be combined with any of the preceding embodiments, the recombinant nucleic acid further comprises a second polynucleotide encoding a second human collagen protein. In some embodiments, the recombinant nucleic acid comprises two or more copies of the second polynucleotide. In some embodiments, the second human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the second human collagen protein is selected from COL1-1, COL1-2, COL3, COL4-1, COL6-1, COL7, and COL17. In some embodiments, the nucleic acid sequence encoding the second human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the second human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first and second human collagen proteins are different.

In some embodiments that may be combined with any of the preceding embodiments, the recombinant nucleic acid is a recombinant herpes simplex virus genome, and wherein the recombinant herpes simplex virus genome comprises the second polynucleotide within a viral gene locus. In some embodiments, the recombinant herpes simplex virus genome comprises the second polynucleotide within one or both copies of the ICP4 viral gene loci. In some embodiments, the recombinant herpes simplex virus genome comprises the second polynucleotide within the ICP22 viral gene locus. In some embodiments, the recombinant herpes simplex virus genome comprises the second polynucleotide within the UL41 viral gene locus. In some embodiments, the recombinant herpes simplex virus genome comprises the first polynucleotide within one or both copies of the ICP4 viral gene loci and the second polynucleotide within the ICP22 viral gene locus. In some embodiments, the recombinant herpes simplex virus genome comprises the first polynucleotide within one or both copies of the ICP4 viral gene loci and the second polynucleotide within the UL41 viral gene locus.

In some embodiments that may be combined with any of the preceding embodiments, the excipient is adapted for cutaneous (systemic or topical), transdermal, subcutaneous, and/or intradermal administration. In some embodiments that may be combined with any of the preceding embodiments, the excipient comprises a hydroxypropyl methylcellulose gel. In some embodiments that may be combined with any of the preceding embodiments, the excipient is adapted for intradermal administration. In some embodiments that may be combined with any of the preceding embodiments, the excipient comprises a phosphate buffer. In some embodiments that may be combined with any of the preceding embodiments, the excipient comprises glycerol. In some embodiments that may be combined with any of the preceding embodiments, the excipient comprises a lipid carrier. In some embodiments that may be combined with any of the preceding embodiments, the excipient comprises a nanoparticle carrier.

In some embodiments that may be combined with any of the preceding embodiments, the composition is a cosmetic composition. In some embodiments, the cosmetic composition is a skin care product.

Other aspects of the present disclosure relate to a kit comprising any of the compositions described herein and instructions for administering the composition.

Other aspects of the present disclosure relate to a method of enhancing, increasing, augmenting, and/or supplementing the levels of one or more human collagen proteins in a subject, the method comprising administering to the subject an effective amount of any of the compositions described herein.

Other aspects of the present disclosure relate to a method of enhancing, increasing, augmenting, and/or supplementing soft tissue of a subject, the method comprising administering to the subject an effective amount of any of the compositions described herein. In some embodiments, the composition is injected into a soft tissue of the subject.

Other aspects of the present disclosure relate to a method of improving skin quality, condition and/or appearance in a subject in need thereof, the method comprising administering to the subject an effective amount of any of the compositions described herein. In some embodiments, the condition is selected from sun damage, aging, UV exposure, rough texture, skin sagging, wrinkles, and any combinations thereof.

Other aspects of the present disclosure relate to a method of reducing the appearance of one or more superficial depressions in the skin of a subject in need thereof, the method comprising administering to the subject an effective amount of any of the compositions described herein. In some embodiments, administration of the composition reduces the appearance of the one or more superficial depressions in the skin of the subject for at least about three months, at least about six months, at least about nine months, or at least about 12 months. In some embodiments, the appearance of the one or more superficial depressions in the skin of the subject is reduced after administration of the composition, as compared to the appearance of the one or more superficial depression in the skin of the subject prior to administration of the composition.

Other aspects of the present disclosure relate to a method of increasing and/or improving at least one of texture, smoothness, elasticity, or tension of the skin of a subject in need thereof, the method comprising administering to the subject an effective amount of any of the compositions described herein. In some embodiments, the skin of the subject maintains at least one of an increased and/or improved texture, smoothness, elasticity, or tension for at least about three months, at least about six months, at least about nine months, or at least about 12 months after administration of the composition. In some embodiments, at least one of texture, smoothness, elasticity, or tension of the skin of the subject is increased and/or improved after administration of the composition, as compared to the texture, smoothness, elasticity, or tension of the skin of the subject prior to administration of the composition.

In some embodiments that may be combined with any of the preceding embodiments, the skin of the subject is aging skin. In some embodiments that may be combined with any of the preceding embodiments, the skin of the subject has been damaged due to exposure to ultraviolet light. In some embodiments that may be combined with any of the preceding embodiments, the skin of the subject is wrinkled.

Other aspects of the present disclosure relate to a method of diminishing one or more dermatological signs of aging in a subject in need thereof, the method comprising administering to the subject an effective amount of any of the compositions described herein. In some embodiments, the diminishing of one or more dermatological signs of aging is selected from: (a) treatment, reduction, and/or prevention of fine lines and/or wrinkles; (b) reduction of skin pore size; (c) improvement in skin thickness, plumpness, and/or tautness; (d) improvement in skin smoothness, suppleness, and/or softness; (e) improvement in skin tone, radiance, and/or clarity; (f) improvement in procollagen and/or collagen production; (g) improvement in skin texture and or promotion of retexturization; (h) improvement in appearance of skin contours; (i) restoration of skin luster and/or brightness; (j) improvement of skin appearance decreased by aging and/or menopause; (k) improvement in skin moisturization; (l) increase in skin elasticity and/or resiliency; (m) treatment, reduction, and/or prevention or skin sagging; (n) improvement in skin firmness; (o) reduction of pigment spots, mottled skin, and/or acne scars; (p) improvement of optical properties of skin by light diffraction or reflection; and (q) any combinations thereof. In some embodiments, the one or more dermatological signs of aging in the subject is diminished after administration of the composition, as compared to the one or more dermatological signs of aging in the subject prior to administration of the composition.

In some embodiments that may be combined with any of the preceding embodiments, the subject is a human. In some embodiments that may be combined with any of the preceding embodiments, the composition is administered cutaneously (systemically or topically), transdermally, subcutaneously, or intradermally to the subject. In some embodiments, the composition is administered by superficial injection. In some embodiments, the composition is administered intradermally to the subject. In some embodiments, the composition is administered once to the subject. In some embodiments, the composition is administered at least twice to the subject. In some embodiments, at least about 15, at least about 30, at least about 60, at least about 90, or at least about 120 days passes between administrations. In some embodiments that may be combined with any of the preceding embodiments, the composition is administered to one or more affected and/or unaffected areas of the subject. In some embodiments that may be combined with any of the preceding embodiments, the skin of the is abraded prior to administration.

Other aspects of the present disclosure relate to a recombinant nucleic acid comprising a first polynucleotide encoding a first polypeptide comprising a first human collagen protein, wherein the recombinant nucleic acid is a recombinant herpes simplex virus genome. In some embodiments, the recombinant nucleic acid comprises two or more copies of the first polynucleotide. In some embodiments, the recombinant herpes simplex virus genome is a recombinant HSV-1 genome, a recombinant HSV-2 genome, or any derivatives thereof.

In some embodiments that may be combined with any of the preceding embodiments, the recombinant herpes simplex virus genome comprises an inactivating mutation in a herpes simplex virus gene. In some embodiments, the herpes simplex virus gene is selected from the group consisting of Infected Cell Protein (ICP) 0, ICP4, ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivation mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivation mutation in the UL41 gene. In some embodiments that may be combined with any of the preceding embodiments, the recombinant herpes simplex virus genome comprises an inactivation mutation in the ICP0 gene. In some embodiments that may be combined with any of the preceding embodiments, the recombinant herpes simplex virus genome comprises an inactivation mutation in the ICP27 gene. In some embodiments that may be combined with any of the preceding embodiments, the inactivating mutation is a deletion of the coding sequence of the gene(s).

In some embodiments that may be combined with any of the preceding embodiments, the recombinant herpes simplex virus genome comprises the first polynucleotide within a viral gene locus. In some embodiments that may be combined with any of the preceding embodiments, the recombinant herpes simplex virus genome comprises the first polynucleotide within one or both copies of the ICP4 viral gene loci. In some embodiments that may be combined with any of the preceding embodiments, the recombinant herpes simplex virus genome comprises the first polynucleotide within the ICP22 viral gene locus. In some embodiments that may be combined with any of the preceding embodiments, the recombinant herpes simplex virus genome comprises the first polynucleotide within the UL41 viral gene locus. In some embodiments that may be combined with any of the preceding embodiments, the HSV has reduced cytotoxicity as compared to a wild-type herpes simplex virus.

In some embodiments that may be combined with any of the preceding embodiments, the first human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL2. In some embodiments that may be combined with any of the preceding embodiments, the first human collagen protein is selected from COL1-1, COL1-2, COL3, COL4-1, COL6-1, COL7, and COL17. In some embodiments that may be combined with any of the preceding embodiments, the nucleic acid sequence encoding the first human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments that may be combined with any of the preceding embodiments, the first human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments that may be combined with any of the preceding embodiments, the first human collagen protein is not COL7.

In some embodiments that may be combined with any of the preceding embodiments, the first polypeptide comprises: (a) the first human collagen protein; (b) a further human collagen protein; and (c) a linker polypeptide linking (a) to (b). In some embodiments, the linker polypeptide is a cleavable linker polypeptide. In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 28-31. In some embodiments, the further human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the further human collagen protein is selected from COL1-1, COL1-2, COL3, COL4-1, COL6-1, COL7, and COL17. In some embodiments, the nucleic acid sequence encoding the further human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the further human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first human collagen protein and the further human collagen protein are different.

In some embodiments that may be combined with any of the preceding embodiments, the first polynucleotide encodes a polycistronic mRNA comprising: (a) a first open reading frame (ORF) encoding the first polypeptide; (b) a second ORF encoding an additional human collagen protein; and (c) an internal ribosomal entry site (IRES) separating (a) and (b). In some embodiments, the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23. In some embodiments, the additional human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the additional human collagen protein is selected from COL1-1, COL1-2, COL3, COL4-1, COL6-1, COL7, and COL17. In some embodiments, the nucleic acid sequence encoding the additional human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the additional human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first human collagen protein and the additional human collagen protein are different.

In some embodiments that may be combined with any of the preceding embodiments, the recombinant nucleic acid further comprises a second polynucleotide encoding a second human collagen protein. In some embodiments, the recombinant nucleic acid comprises two or more copies of the second polynucleotide. In some embodiments, the second human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the second human collagen protein is selected from COL1-1, COL1-2, COL3, COL4-1, COL6-1, COL7, and COL17. In some embodiments, the nucleic acid sequence encoding the second human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the second human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first and second human collagen proteins are different.

In some embodiments that may be combined with any of the preceding embodiments, the recombinant herpes simplex virus genome comprises the second polynucleotide within a viral gene locus. In some embodiments, the recombinant herpes simplex virus genome comprises the second polynucleotide within one or both copies of the ICP4 viral gene loci. In some embodiments, the recombinant herpes simplex virus genome comprises the second polynucleotide within the ICP22 viral gene locus. In some embodiments, the recombinant herpes simplex virus genome comprises the second polynucleotide within the UL41 viral gene locus. In some embodiments, the recombinant herpes simplex virus genome comprises the first polynucleotide within one or both copies of the ICP4 viral gene loci and the second polynucleotide within the ICP22 viral gene locus. In some embodiments, the recombinant herpes simplex virus genome comprises the first polynucleotide within one or both copies of the ICP4 viral gene loci and the second polynucleotide within the UL41 viral gene locus.

Other aspects of the present disclosure relate to a host cell comprising any of the recombinant nucleic acids described herein. In some embodiments, the host cell is a eukaryotic cell. In some embodiments, the host cell is a mammalian cell. In some embodiments, the host cell is a human cell or a non-human primate cell. In some embodiments, the host cell is a Vero cell. In some embodiments, the host cell is a complementing host cell.

Other aspects of the present disclosure relate to a method of collecting a herpes simplex virus, the method comprising: (a) contacting a complementing host cell with any of the recombinant nucleic acids described herein; and (b) collecting the herpes simplex virus generated by the complementing host cell.

Other aspects of the present disclosure relate to a method of collecting a herpes simplex virus, the method comprising; (a) culturing a host cell comprising any of the recombinant nucleic acids described herein; and (b) collecting the herpes simplex virus generated by the host cell.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A shows a wild-type herpes simplex virus genome.

1F shows a modified herpes simplex virus genome comprising deletions of the coding sequences of ICP4 (both copies) and ICP22, with a polynucleotide containing 1) the coding sequence of a first human collagen polypeptide operably linked to a first heterologous promoter, and 2) the coding sequence of a second human collagen polypeptide operably linked to a second heterologous promoter, integrated at each of the ICP4 loci. The first and second human collagen polypeptides are encoded on opposite strands of DNA. FIG. 1N shows a modified herpes simplex virus genome comprising deletions of the coding sequences of ICP4 (both copies) and UL41, with a first polynucleotide containing the coding sequence of a first human collagen polypeptide operably linked to a heterologous promoter integrated at each of the ICP4 loci, and a second polynucleotide containing the coding sequence of a second human collagen polypeptide operably linked to a heterologous promoter integrated at the UL41 locus.

FIG. 2A shows a schematic of the virus "KCA211". FIG. 2B shows a schematic of the virus "SAR-COL7".

FIG. 3A shows human COL7 expression in HaCaT cells infected with KCA211 or SAR-COL7 at the indicated MOIs, as assessed by qPCR. Data is shown as fold change relative to SAR-COL7, after normalization to GAPDH. FIG. 3B shows human COL7 expression in uninfected HaCaT cells, or HaCaT cells infected with KCA211 or SAR-COL7 at the indicated MOIs, as assessed by western blot analysis.

FIG. 4A shows human COL7 expression in mock infected wild-type and RDEB primary human keratinocytes, or in RDEB primary human keratinocytes infected with SAR-COL7 at the indicated multiplicity of infections (MOIs). FIG. 4B shows human COL7 expression in mock infected wild-type and RDEB primary human fibroblasts, or in RDEB primary human fibroblasts infected with SAR-COL7 at the indicated MOIs.

FIG. 5A shows human COL7 expression in mock infected wild-type (N-HDK) and RDEB (EB-HDK) primary human keratinocytes, or in RDEB primary human keratinocytes infected with SAR-COL7 at the indicated MOIs. COL7 expression is shown as the relative fold change over mock infected wild-type primary human keratinocytes. FIG. 5B shows human COL7 expression in mock infected wild-type (N-HDF) and RDEB (EB-HDF) primary human fibroblasts, or in RDEB primary human fibroblasts infected with SAR-COL7 at the indicated MOIs. COL7 expression is shown as the relative fold change over mock infected wild-type primary human fibroblasts.

FIG. 6A shows cellular adhesion to untreated wells (plastic), or wells treated with increasing concentrations of rat tail Collagen 1. FIG. 6B shows cellular adhesion to untreated wells (plastic), or wells treated with increasing concentrations of human plasma fibronectin.

FIG. 8A shows human COL7A1 transcripts levels/100 ng total RNA in mouse skin at day 3 after infection. FIG. 8B shows copy number of human COL7A1 DNA/100 ng total DNA in mouse skin at day 3 after infection. FIG. 8C shows human COL7A1 transcripts levels/100 ng total RNA in mouse skin at day 6 after infection. FIG. 8D shows copy number of human COL7A1 DNA/100 ng total DNA in mouse skin at day 6 after infection.

FIG. 9A shows a representative immunofluorescent image of human COL7 expression in mouse skin after intradermal delivery of SAR-COL7. FIG. 9B shows a representative immunofluorescent image of human COL7 expression in mouse skin after topical delivery of SAR-COL7.

FIG. 10A shows human COL7A1 transcripts levels/100 ng total RNA in BALB/c mouse skin. FIG. 10B shows copy number of human COL7A1 DNA/100 ng total DNA in BALB/c mouse skin.

FIG. 11A shows human COL7A1 transcripts levels/100 ng total RNA in hypomorph mouse skin. FIG. 11B shows copy number of human COL7A1 DNA/100 ng total DNA in hypomorph mouse skin.

FIG. 12A shows control (GFP) and SAR-COL7 immunofluorescence imaging from hypomorph mouse 1 (harvested at day 3) at 10 and 20× magnification. FIG. 12B shows SAR-COL7 immunofluorescence imaging from hypomorph mouse 2 and hypomorph mouse 3 (harvested at day 7). The figure represents a tiled image of 16 fields acquired with a 10× lens, capturing the entire skin section.

FIG. 14A shows electron micrograph images of infected hypomorph mouse skin stained with an antibody specific to the NC2 domain of human COL7 (LH24). FIG. 14B shows electron micrograph images of infected hypomorph mouse skin stained with an antibody specific to the NC1 domain of human COL7 (NP185).

FIG. 15A shows human COL7A1 transcripts levels/100 ng total RNA in hypomorph mouse skin. FIG. 15B shows copy number of human COL7A1 DNA/100 ng total DNA in hypomorph mouse skin.

FIG. 17A shows the levels of human COL1A1 transcripts present in Vero cells 5 days after infection with the indicated HSV clones, as determined by qRT-PCR analysis. Data is presented for two replicates±SEM. FIG. 17B shows the levels of human COL1A2 transcripts present in Vero cells 5 days after infection with the indicated HSV clones, as determined by qRT-PCR analysis. Data is presented for two replicates±SEM. FIG. 17C shows western blot analysis of human COL1A1 and COL1A2 protein expression in Vero cells 5 days after infection with the indicated COL1A1/COL1A2 positive clones, as determined by qRT-PCR. Uninfected (mock) Vero cells were used as a negative control; GAPDH was used as a loading control.

FIG. 19A shows the levels of human COL3A1 transcripts present in immortalized human keratinocytes (HKs) after infection with C3vec01 at the indicated MOIs. Uninfected (mock) and HSV-mCherry-infected (mCherry) cells were used as negative controls. Data is presented for two replicates±SEM. FIG. 19B shows representative immunofluorescence images of human COL3 protein expression in immortalized human keratinocytes 48 hours after infection with C3vec01 at the indicated MOIs. Uninfected (mock) cells were used as negative controls.

FIG. 20A shows the levels of human COL3A1 transcripts present in immortalized human dermal fibroblasts (HDFs) after infection with C3vec01 at the indicated MOIs. Uninfected (mock) and HSV-mCherry-infected (mCherry) cells were used as negative controls. Data is presented for two replicates±SEM. FIG. 20B shows representative immunofluorescence images of human COL3 protein expression in immortalized human dermal fibroblasts 48 hours after infection with C3vec01 at the indicated MOIs. Uninfected (mock) cells were used as negative controls.

FIG. 21A shows the levels of human COL3A1 transcripts present in primary HDFs harvested from either a 65-year-old female patient or a 73-year-old male patient (vendor 1) after infection with C3vec01 at the indicated MOIs. Uninfected (mock) cells were used as a negative control. Data is presented for two replicates±SEM. FIG. 21B shows western blot analysis of human COL3A1 protein expression in primary HDFs harvested from a 73-year-old male patient (vendor 1) after infection with C3vec01 at the indicated MOIs. Uninfected (mock) cells were used as a negative control; recombinant human COL3A1 (rCOL3A1) was used as a positive control; GAPDH was used as a loading control. FIG. 21C shows the levels of human COL3A1 transcripts present in primary HDFs harvested from either a 75-year-old female patient or a 73-year-old male patient (vendor 2) after infection with C3vec01 at the indicated MOIs. Uninfected (mock) cells were used as a negative control. Data is presented for two replicates±SEM. FIG. 21D shows western blot analysis of human COL3A1 protein expression in primary HDFs harvested from a 75-year-old female patient (vendor 2) after infection with C3vec01 at the indicated MOIs. Uninfected (mock) cells were used as a negative control; recombinant human COL3A1 (rCOL3A1) was used as a positive control; GAPDH was used as a loading control.

FIG. 22A shows the concentration of COL3 secreted into the supernatant of cultured HDFs 24 hours after exposure to various dosages and times of UV light, as assessed by ELISA. Supernatant collected from non-UV exposed (−UV) HDFs cultured in parallel was used as a control. FIG. 22B shows the levels of human COL3A1 transcripts present in UV-exposed immortalized human dermal fibroblasts (HDFs) after infection with C3vec01 at the indicated MOIs. Uninfected (mock) and HSV-mCherry-infected (mCherry) cells were used as negative controls. Data is presented for two replicates±SEM.

FIG. 23A shows the levels of human COL3A1 DNA present in skin biopsies taken from young and old mice 48 hours after being intradermally administered either C3vec01 or vehicle control, as assessed by qPCR analysis. FIG. 23B shows the levels of human COL3A1 transcripts present in skin biopsies taken from young and old mice 48 hours after being intradermally administered either C3vec01 or vehicle control, as assessed by qRT-PCR analysis. For each condition in the qPCR and qRT-PCR analysis, data is presented as the average of four tissue samples (two replicates/tissue sample)±SEM. FIG. 23C shows representative immunofluorescence images of human COL3 expression in skin biopsies taken from young and old mice 48 hours after being intradermally administered C3vec01. A young mouse intradermally administered vehicle alone was used as a negative control. DAPI staining was used to visualize nuclei.

FIG. 24A shows expression of wild-type human LAMB3 in infected Vero cells, as assessed by qPCR analysis. FIG. 24B shows expression of wild-type human LamB3 protein in infected Vero cells, as assessed by western blot.

FIG. 27A shows expression of wild-type human LAMC2 in infected Vero cells, as assessed by qPCR analysis. FIG. 27B shows expression of codon-optimized human LAMC2 in infected Vero cells, as assessed by qPCR analysis. FIG. 27C shows expression of wild-type and codon-optimized human LamC2 protein in infected Vero cells, as assessed by western blot. The boxed viral isolate "LGA" expressing codon-optimized LamC2 was selected for additional experimentation.

FIG. 28A shows the viral genome copy number in primary immortalized human keratinocytes after infection with viral isolate "LGA" at the indicated MOIs. FIG. 28B shows the transcript level of codon-optimized LAMC2 expressed in primary immortalized human keratinocytes after infection with viral isolate "LGA" at the indicated MOIs. FIG. 28C shows expression of human LamC2 protein in primary immortalized human keratinocytes after infection with viral isolate "LGA" at the indicated MOIs, as assessed by western blot.

FIG. 29A shows a schematic of the intradermal injection sites on the treated animals. FIG. 29B shows the levels of human LAMC2 DNA present in skin biopsies taken from mice 72 hours after being intradermally administered either HSV isolate LGA or vehicle control, as assessed by qPCR analysis. FIG. 29C shows the levels of human LAMC2 transcripts present in skin biopsies taken from mice 72 hours after being intradermally administered either HSV isolate LGA or vehicle control, as assessed by qRT-PCR analysis. For each condition in the qPCR and qRT-PCR analysis, data is presented as the average of two replicates±SEM. FIG. 29D shows representative immunofluorescence images of human LAMC2 expression in skin biopsies taken from mice 72 hours after being intradermally administered HSV isolate LGA. A site that was intradermally administered vehicle alone was used as a negative control. DAPI staining was used to visualize nuclei; pKal staining was used to visualize mouse laminin-332.

DETAILED DESCRIPTION

Figure 1A:
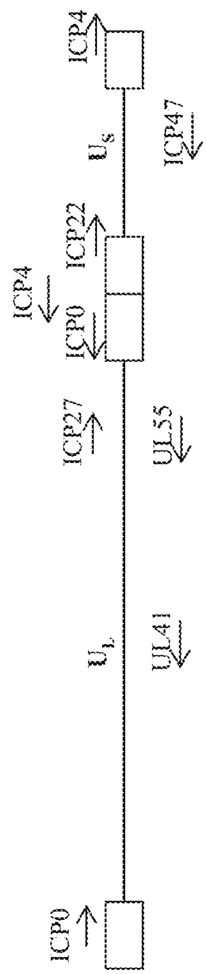
FIGS. 1A-N show schematics of wild-type and modified herpes simplex virus genomes.

In some embodiments, the present disclosure relates to recombinant nucleic acids (e.g., recombinant herpes viral genomes) encoding one or more cosmetic proteins, and to uses of these recombinant nucleic acids in viruses (e.g., in a herpes virus), compositions, formulations, medicaments, and/or methods for delivering one or more cosmetic proteins to the skin, such as onto, into, and/or through the skin (e.g., to the dermal ECM). In some embodiments, the present disclosure relates to recombinant nucleic acids (e.g., recombinant herpes viral genomes) encoding one or more cosmetic proteins, and to uses of these recombinant nucleic acids in viruses (e.g., in a herpes virus), compositions, formulations, medicaments, and/or methods in order to increase, augment, and/or supplement one or more dermal ECM proteins (e.g., one or more collagen proteins). In some embodiments, the present disclosure relates to recombinant nucleic acids (e.g., recombinant herpes viral genomes) encoding one or more cosmetic proteins, and to uses of these recombinant nucleic acids in viruses (e.g., in a herpes virus), compositions, formulations, medicaments, and/or methods in the aesthetic context (e.g., to reduce one or more dermatological signs of aging). In some embodiments, the present disclosure relates to compositions comprising a recombinant herpes viral vector and methods comprising the delivery of the recombinant herpes viral vector onto, into, and/or through the skin of a mammal, wherein the recombinant herpes viral vector comprises a promoter operable in a mammalian cell and a heterologous nucleic acid which is expressed to achieve a cosmetic effect in mammalian skin. The heterologous nucleic acid may be delivered to a mammalian target skin cell of a mammal, comprising contacting the epidermis, dermis, or subcutaneous tissue of the mammal with the composition comprising the recombinant herpes viral vector, under conditions whereby the recombinant herpes viral vector is transported onto, into, and/or through the epidermis, dermis or subcutaneous tissue and introduced into the target skin cell, where it is expressed Without wishing to be bound by theory, it is believed that administering one or more of the recombinant nucleic acids, viruses, and/or formulations described herein to an individual will allow for increased production of functional dermal ECM proteins (e.g., human collagen) in the individual. Furthermore, without wishing to be bound by theory, it is believed that increasing, augmenting, and/or supplementing the levels of cosmetic proteins in an individual by administering one or more of the recombinant nucleic acids, viruses, and/or formulations described herein will lead to at least one of: 1) the enhancement, augmentation, and/or supplementation of soft tissue; 2) the improvement of skin quality, condition, and/or appearance; 3) the reduction of one or more superficial depressions in the skin (e.g., wrinkles); 4) the improvement of texture, smoothness, elasticity, and/or tension of the skin; and/or 5) the reduction of one or more dermatological signs of aging. Ultimately, without wishing to be bound by theory, it is believed that the recombinant nucleic acids, viruses, compositions, and methods described herein provide a novel strategy for delivering functional cosmetic proteins in aesthetic settings.

The following description sets forth exemplary methods, parameters, and the like. It should be recognized, however, that such a description is not intended as a limitation on the scope of the present disclosure but is instead provided as a description of exemplary embodiments.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); *PCR: The Polymerase Chain Reaction*, (Mullis et al., eds., 1994); *Short Protocols in Molecular Biology* (Wiley and Sons, 1999).

II. Definitions

Before describing the present disclosure in detail, it is to be understood that the present disclosure is not limited to particular compositions or biological systems, which can, of course, vary. It is also to be understood that the terminology used herein is for the purpose of describing particular embodiments only and is not intended to be limiting.

As used herein, the singular forms “a”, “an” and “the” include plural referents unless the content clearly dictates otherwise. Thus, for example, reference to “a molecule” optionally includes a combination of two or more such molecules, and the like.

As used herein, the term “and/or” may include any and all combinations of one or more of the associated listed items. For example, the term “a and/or b” may refer to “a alone”, “b alone”, “a or b”, or “a and b”; the term “a, b, and/or c” may refer to “a alone”, “b alone”, “c alone”, “a or b”, “a or c”, “b or c”, “a, b, or c”, “a and b”, “a and c”, “b and c”, or “a, b, and c”; etc.

As used herein, the term “about” refers to the usual error range for the respective value readily known to the skilled person in this technical field. Reference to “about” a value or parameter herein includes (and describes) embodiments that are directed to that value or parameter per se.

It is understood that aspects and embodiments of the present disclosure include “comprising”, “consisting”, and “consisting essentially of” aspects and embodiments.

As used herein, the terms “polynucleotide”, “nucleic acid sequence”, “nucleic acid”, and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is “operatively linked” or “operably linked” when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, “operatively linked” or “operably linked” means that the DNA sequences being linked are contiguous.

As used herein, the term “vector” refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus or other vector that, upon introduction into an appropriate host cell, results in expression of the nucleic acids. Appropriate expression vectors are well known to those of skill in the art and include those that are replicable in eukaryotic cells, and those that remain episomal or those which integrate into the host cell genome.

As used herein, an "open reading frame" or "ORF" refers to a continuous stretch of nucleic acids, either DNA or RNA, that encode a protein or polypeptide. Typically, the nucleic acids comprise a translation start signal or initiation codon, such as ATG or AUG, and a termination codon.

As used herein, an "untranslated region" or "UTR" refers to untranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions, after being introduced into a cell. In some aspects, it confers a desired property to a cell into which it was introduced, or otherwise leads to a desired cosmetic, therapeutic, or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice, rats, hamsters, rabbits, and non-human primates, etc. In some embodiments, the mammal is human.

As used herein, the terms "pharmaceutical formulation" or "pharmaceutical composition" refer to a preparation which is in such a form as to permit the biological activity of the active ingredient(s) to be effective, and which contains no additional components which are unacceptably toxic to a subject to which the composition or formulation would be administered. "Pharmaceutically acceptable" excipients (e.g., vehicles, additives) are those which can reasonably be administered to a subject to provide an effective dose of the active ingredient(s) employed.

As used herein, "cutaneous administration" or "cutaneously administering" refers to the delivery of a composition to a subject by contacting, directly or otherwise, a formulation comprising the composition to all ("systemic") or a portion ("topical") of the skin of a subject. The term encompasses several routes of administration including, but not limited to, topical and transdermal. Topical administration may be used as a means to deliver a composition to the epidermis or dermis of a subject, or to specific strata thereof.

As used herein, "treatment" refers to clinical intervention designed to alter the natural course of the individual or cell being treated during the course of clinical pathology. Desirable effects of treatment include decreasing the rate of disease/disorder/defect progression, ameliorating or palliating the disease/disorder/defect state, and remission or improved prognosis. For example, an individual is successfully "treated" if one or more symptoms associated with dermatological aging are reduced, mitigated, or eliminated, including the reduction or elimination of wrinkles.

As used herein, the term "delaying progression of" a disease/disorder/defect refers to deferring, hindering, slowing, retarding, stabilizing, and/or postponing development of the disease/disorder/defect (e.g., skin wrinkles). This delay can be of varying lengths or time, depending on the history of the disease/disorder/defect and/or the individual being treated. As is evident to one of ordinary skill in the art, a sufficient or significant delay can, in effect, encompass prevention, in that the individual does not develop the disease/disorder/defect.

III. Recombinant Nucleic Acids

Certain aspects of the present disclosure relate to recombinant nucleic acids (e.g., isolated recombinant nucleic acids) comprising one or more polynucleotides (e.g., one or more, two or more, three or more, four or more, five or more, ten or more, etc.) encoding a cosmetic protein. Any suitable cosmetic protein described herein or known in the art may be encoded by the polynucleotides of the present disclosure, including, for example, collagen proteins, fibronectins, elastins, lumicans, vitronectins/vitronectin receptors, laminins, neuromodulators, fibrillins, additional dermal ECM proteins, etc. In some embodiments, the cosmetic protein is a structural extracellular matrix protein (e.g., a collagen, elastin, fibronectin, laminin, fibrillin, etc.). In some embodiments, the cosmetic protein is a collagen, elastin, fibronectin, or laminin protein (e.g., a human collagen, elastin, fibronectin, or laminin protein).

In some embodiments, the present disclosure relates to recombinant nucleic acids (e.g., isolated recombinant nucleic acids) comprising one or more polynucleotides (e.g., one or more, two or more, three or more, four or more, five or more, ten or more, etc.) encoding a collagen protein. In some embodiments, the collagen protein is a human collagen protein. In some embodiments, the present disclosure relates to recombinant nucleic acids comprising one or more polynucleotides encoding a homotrimeric collagen (e.g., a homotrimeric human collagen, such as human Collagen 3 (e.g., comprising three COL3A1 (COL3) polypeptides) or human Collagen 7 (e.g., comprising three COL7A1 (COL7) polypeptides). In some embodiments, the present disclosure relates to recombinant nucleic acids comprising one or more polynucleotides encoding a heterotrimeric collagen (e.g., a heterotrimeric human collagen, such as human Collagen 1 (e.g., comprising two COL1A1 (COL1-1) polypeptides and one COL1A2 (COL1-2) polypeptide) or human Collagen 4 (e.g., comprising two COL4A1 (COL4-1) polypeptides and one COL4A2 (COL4-2) polypeptide). In some embodiments, the present disclosure relates to recombinant nucleic acids comprising one or more polynucleotides encoding a homotrimeric collagen and a heterotrimeric collagen (e.g., a recombinant nucleic acid comprising one or more polynucleotides encoding a human Collagen 1 and a human Collagen 3). In some embodiments, the present disclosure relates to recombinant nucleic acids comprising one or more polynucleotides encoding human Collagen 1. In some embodiments, the present disclosure relates to recombinant nucleic acids comprising one or more polynucleotides encoding human Collagen 3.

In some embodiments, the present disclosure relates to recombinant nucleic acids comprising a first polynucleotide encoding a first polypeptide comprising a first cosmetic protein (e.g., a first human collagen protein). In some embodiments, the first polypeptide consists essentially of or consists of the first cosmetic protein (e.g., consists essentially of or consists of a first human collagen protein). In some embodiments, the present disclosure relates to recombinant nucleic acids comprising a first polynucleotide encoding a first polypeptide comprising: a first cosmetic protein (e.g., a first human collagen protein), a linker polypeptide, and a further cosmetic protein (e.g., a further human collagen protein). In some embodiments, the first and further cosmetic proteins (e.g., the first and further human collagen proteins) are the same. In some embodiments, the first and further cosmetic proteins (e.g., the first and further human collagen proteins) are different. In some embodiments, the linker polypeptide is a cleavable linker polypeptide.

In some embodiments, the present disclosure relates to recombinant nucleic acids comprising a first polynucleotide encoding a first polypeptide comprising a first cosmetic protein (e.g., a first human collagen protein), wherein the first polynucleotide encodes a polycistronic mRNA comprising: a first open reading frame (ORF) encoding the first polypeptide, an internal ribosomal entry site (IRES), and a second ORF encoding an additional cosmetic protein (e.g., an additional human collagen protein). In some embodiments, the first and additional cosmetic proteins (e.g., the first and additional human collagen proteins) are the same. In some embodiments, the first and additional cosmetic proteins (e.g., the first and additional human collagen proteins) are different.

In some embodiments, the present disclosure relates to recombinant nucleic acids comprising a first polynucleotide encoding a first polypeptide comprising a first cosmetic protein (e.g., a first human collagen protein), and a second polynucleotide encoding a second cosmetic protein (e.g., a second human collagen protein). In some embodiments, the first and second cosmetic proteins (e.g., the first and second human collagen proteins) are the same. In some embodiments, the first and second cosmetic proteins (e.g., the first and second human collagen proteins) are different.

In some embodiments, the recombinant nucleic acid is a vector. In some embodiments, the recombinant nucleic acid is a viral vector. In some embodiments, the recombinant nucleic acid is a herpes viral vector. In some embodiments, the recombinant nucleic acid is a herpes simplex virus amplicon. In some embodiments, the recombinant nucleic acid is a recombinant herpes virus genome. In some embodiments, the recombinant nucleic acid is a recombinant herpes simplex virus genome. In some embodiments, the recombinant herpes simplex virus genome is a recombinant type 1 herpes simplex virus (HSV-1) genome.

Polynucleotides Encoding Cosmetic Proteins

Polynucleotides Encoding Collagen Proteins

In some embodiments, the present disclosure relates to a recombinant nucleic acid comprising one or more polynucleotides comprising the coding sequence of a collagen gene. The coding sequence of any collagen gene (including any isoform thereof) from any suitable species known in the art may be encoded by a polynucleotide of the present disclosure, including, for example, human collagen genes (see e.g., NCBI Gene IDs: 1277, 1278, 1281, 1282, 1284, 1291, 1294, 1308, etc.), mouse collagen genes (see, e.g., NCBI Gene IDs: 12842, 12843, 12825, 12826, 12827, 12833, 12836, 12821, etc.), chimpanzee collagen genes (see e.g., NCBI Gene IDs: 104001053, 455117, 459815, 452689, 452661, 450204, 101056895, 101058306, etc.), rat collagen genes (see e.g., NCBI Gene IDs: 29393, 84352, 84032, 290905, 306628, 294337, 301012, 294027, etc.), rabbit collagen genes (see e.g., NCBI Gene IDs: 100347598, 100008997, 100009177, 100358256, 100358522, 100343947, 100356561, 100339335, etc.) etc. Methods of identifying collagen gene homologs/orthologs from additional species are known to one of ordinary skill in the art, including, for example, using a nucleic acid sequence alignment program such as the BLAST® blastn suite. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the collagen genes (and/or coding sequences thereof) described herein or known in the art.

In some embodiments, a polynucleotide of the present disclosure comprises a codon-optimized variant of the coding sequence of any of the collagen genes described herein or known in the art. In some embodiments, use of a codon-optimized variant of the coding sequence of a collagen gene increases stability and/or yield of heterologous expression (RNA and/or protein) of the encoded collagen protein in a target cell (such as a cell of the epidermis and/or dermis), as compared to the stability and/or yield of heterologous expression of a corresponding, non-codon-optimized, wild-type sequence. Any suitable method known in the art for performing codon optimization of a sequence for expression in one or more target cells (e.g., one or more human cells) may be used, including, for example, by the methods described by Fath et al. (PLoS One. 2011 Mar. 3; 6(3): e17596).

In some embodiments, the present disclosure relates to one or more polynucleotides (i.e., one or more first polynucleotides and/or one or more second polynucleotides) comprising the coding sequence of a human collagen gene. Any suitable human collagen gene (including any isoform thereof) known in the art may be encoded by a nucleic acid of the present disclosure, including, for example, a COL1A1 gene (see e.g., NCBI Gene ID: 1277; SEQ ID NO: 1), a COL1A2 gene (see e.g., NCBI Gene ID: 1278; SEQ ID NO: 3), a COL2A1 gene (see e.g., NCBI Gene ID: 1280), a COL3A1 gene (see e.g., NCBI Gene ID: 1281; SEQ ID NO: 5), a COL4A1 gene (see e.g., NCBI Gene ID: 1282; SEQ ID NO: 7), a COL4A2 gene (see e.g., NCBI Gene ID: 1284), a COL4A3 gene (see e.g., NCBI Gene ID: 1285), a COL4A4 gene (see e.g., NCBI Gene ID: 1286), a COL4A5 gene (see e.g., NCBI Gene ID: 1287), a COL4A6 gene (see e.g., NCBI Gene ID: 1288), a COL5A1 gene (see e.g., NCBI Gene ID: 1289), a COL5A2 gene (see e.g., NCBI Gene ID: 1290), a COL5A3 gene (see e.g., NCBI Gene ID: 50509), a COL6A1 gene (see e.g., NCBI Gene ID: 1291; SEQ ID NO: 9), a COL6A2 gene (see e.g., NCBI Gene ID: 1292), a COL6A3 gene (see e.g., NCBI Gene ID: 1293), a COL6A4 gene (see e.g., NCBI Gene ID: 344875), a COL6A5 gene (see e.g., NCBI Gene ID: 256076), a COL6A6 gene (see e.g., NCBI Gene ID: 131873), a COL7A1 gene (see e.g., NCBI Gene ID: 1294; SEQ ID NO: 10), a COL8A1 gene (see e.g., NCBI Gene ID: 1295), a COL9A1 gene (see e.g., NCBI Gene ID: 1297), a COL9A2 gene (see e.g., NCBI Gene ID: 1298), a COL9A3 gene (see e.g., NCBI Gene ID: 1299), a COL10A1 gene (see e.g., NCBI Gene ID: 1300), a COL11A1 gene (see e.g., NCBI Gene ID: 1301), a COL11A2 gene (see e.g., NCBI Gene ID: 1302), a COL12A1 gene (see e.g., NCBI Gene ID: 1303), a COL13A1 gene (see e.g., NCBI Gene ID: 1305), a COL14A1 gene (see e.g., NCBI Gene ID: 7373), a COL15A1 gene (see e.g., NCBI Gene ID: 1306), a COL16A1 gene (see e.g., NCBI Gene ID: 1307), a COL17A1 gene (see e.g., NCBI Gene ID: 1308; SEQ ID NO: 12), a COL18A1 gene (see e.g., NCBI Gene ID: 80781), a COL19A1 gene (see e.g., NCBI Gene ID: 1310), a COL20A1 gene (see e.g., NCBI Gene ID: 57642), a COL21A1 gene (see e.g., NCBI Gene ID: 81578), a COL22A1 gene (see e.g., NCBI Gene ID: 169044), a COL23A1 gene (see e.g., NCBI Gene ID: 91522), a COL24A1 gene (see e.g., NCBI Gene ID: 255631), a COL25A1 gene (see e.g., NCBI Gene ID: 84570), a COL26A1 gene (see e.g., NCBI Gene ID: 136227), a COL27A1 gene (see e.g., NCBI Gene ID: 85301), a COL28A1 gene (see e.g., NCBI Gene ID:340267), etc. In some embodiments, a polynucleotide (i.e., one or more first polynucleotides and/or one or more second polynucleotides) of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the human collagen genes (and/or coding sequences thereof) described herein or known in the art.

In some embodiments, a polynucleotide (i.e., one or more first polynucleotides and/or one or more second polynucleotides) of the present disclosure comprises a codon-optimized variant of any of the human collagen genes described herein. In some embodiments, use of a codon-optimized variant of a human collagen gene increases stability and/or yield of heterologous expression (RNA and/or protein) of the human collagen in a target cell (such as a human keratinocyte or fibroblast), as compared to the stability and/or yield of heterologous expression of a corresponding non-codon-optimized, wild-type sequence.

In some embodiments, a polynucleotide of the present disclosure comprises the coding sequence of the human COL1A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 1 or SEQ ID NO: 2. In some embodiments, a polynucleotide of the present disclosure comprises the sequence of SEQ ID NO: 1 or SEQ ID NO: 2.

In some embodiments, a polynucleotide of the present disclosure comprises a 5' truncation, a 3' truncation, or a fragment of the sequence of SEQ ID NO: 1 or SEQ ID NO: 2. In some embodiments, the 5' truncation, 3' truncation, or fragment of the sequence of SEQ ID NO: 1 or SEQ ID NO: 2 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, but fewer than 4395, consecutive nucleotides of SEQ ID NO: 1 or SEQ ID NO: 2. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4392 of SEQ ID NO: 1 or SEQ ID NO: 2. In some embodiments, a polynucleotide of the present disclosure comprises the sequence of nucleic acids 1-4392 of SEQ ID NO: 1 or SEQ ID NO: 2.

In some embodiments, a polynucleotide of the present disclosure comprises the coding sequence of the human COL1A2 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 3 or SEQ ID NO: 4. In some embodiments, a polynucleotide of the present disclosure comprises the sequence of SEQ ID NO: 3 or SEQ ID NO: 4.

In some embodiments, a polynucleotide of the present disclosure comprises a 5' truncation, a 3' truncation, or a fragment of the sequence of SEQ ID NO: 3 or SEQ ID NO: 4. In some embodiments, the 5' truncation, 3' truncation, or fragment of the sequence of SEQ ID NO: 3 or SEQ ID NO: 4 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, but fewer than 4101, consecutive nucleotides of SEQ ID NO: 3 or SEQ ID NO: 4. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4098 of SEQ ID NO: 3 or SEQ ID NO: 4. In some embodiments, a polynucleotide of the present disclosure comprises the sequence of nucleic acids 1-4098 of SEQ ID NO: 3 or SEQ ID NO: 4.

In some embodiments, a polynucleotide of the present disclosure comprises the coding sequence of the human COL3A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 5 or SEQ ID NO: 6. In some embodiments, a polynucleotide of the present disclosure comprises the sequence of SEQ ID NO: 5 or SEQ ID NO: 6.

In some embodiments, a polynucleotide of the present disclosure comprises a 5' truncation, a 3' truncation, or a fragment of the sequence of SEQ ID NO: 5 or SEQ ID NO: 6. In some embodiments, the 5' truncation, 3' truncation, or fragment of the sequence of SEQ ID NO: 5 or SEQ ID NO: 6 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, but fewer than 4401, consecutive nucleotides of SEQ ID NO: 5 or SEQ ID NO: 6. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4398 of SEQ ID NO: 5 or SEQ ID NO: 6. In some embodiments, a polynucleotide of the present disclosure comprises the sequence of nucleic acids 1-4398 of SEQ ID NO: 5 or SEQ ID NO: 6.

In some embodiments, a polynucleotide of the present disclosure comprises the coding sequence of the human COL4A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 7 or SEQ ID NO: 8. In some embodiments, a polynucleotide of the present disclosure comprises the sequence of SEQ ID NO: 7 or SEQ ID NO: 8.

In some embodiments, a polynucleotide of the present disclosure comprises a 5' truncation, a 3' truncation, or a fragment of the sequence of SEQ ID NO: 7 or SEQ ID NO: 8. In some embodiments, the 5' truncation, 3' truncation, or fragment of the sequence of SEQ ID NO: 7 or SEQ ID NO: 8 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, at least 4500, at least 5000, but fewer than 5010, consecutive nucleotides of SEQ ID NO: 7 or SEQ ID NO: 8. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-5007 of SEQ ID NO: 7 or SEQ ID NO: 8. In some embodiments, a polynucleotide of the present disclosure comprises the sequence of nucleic acids 1-5007 of SEQ ID NO: 7 or SEQ ID NO: 8.

In some embodiments, a polynucleotide of the present disclosure comprises the coding sequence of the human COL6A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 9 or SEQ ID NO: 10. In some embodiments, a polynucleotide of the present disclosure comprises the sequence of SEQ ID NO: 9 or SEQ ID NO: 10.

In some embodiments, a polynucleotide of the present disclosure comprises a 5' truncation, a 3' truncation, or a fragment of the sequence of SEQ ID NO: 9 or SEQ ID NO: 10. In some embodiments, the 5' truncation, 3' truncation, or fragment of the sequence of SEQ ID NO: 9 or SEQ ID NO: 10 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, but fewer than 3087, consecutive nucleotides of SEQ ID NO: 9 or SEQ ID NO: 10. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3084 of SEQ ID NO: 9 or SEQ ID NO: 10. In some embodiments, a polynucleotide of the present disclosure comprises the sequence of nucleic acids 1-3084 of SEQ ID NO: 9 or SEQ ID NO: 10.

In some embodiments, a polynucleotide of the present disclosure comprises the coding sequence of the human COL7A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 11 or SEQ ID NO: 12. In some embodiments, a polynucleotide of the present disclosure comprises the sequence of SEQ ID NO: 11 or SEQ ID NO: 12.

In some embodiments, a polynucleotide of the present disclosure comprises a 5' truncation, a 3' truncation, or a fragment of the sequence of SEQ ID NO: 11 or SEQ ID NO: 12. In some embodiments, the 5' truncation, 3' truncation, or fragment of the sequence of SEQ ID NO: 11 or SEQ ID NO: 12 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, at least 4500, at least 5000, at least 5500, at least 6000, at least 6500, at least 7000, at least 7500, at least 8000, at least 8500, but fewer than 8835, consecutive nucleotides of SEQ ID NO: 11 or SEQ ID NO: 12. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-8832 of SEQ ID NO: 11 or SEQ ID NO: 12. In some embodiments, a polynucleotide of the present disclosure comprises the sequence of nucleic acids 1-8832 of SEQ ID NO: 11 or SEQ ID NO: 12.

In some embodiments, a polynucleotide of the present disclosure comprises the coding sequence of the human COL17A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 13 or SEQ ID NO: 14. In some embodiments, a polynucleotide of the present disclosure comprises the sequence of SEQ ID NO: 13 or SEQ ID NO: 14.

In some embodiments, a polynucleotide of the present disclosure comprises a 5' truncation, a 3' truncation, or a fragment of the sequence of SEQ ID NO: 13 or SEQ ID NO: 14. In some embodiments, the 5' truncation, 3' truncation, or fragment of the sequence of SEQ ID NO: 13 or SEQ ID NO: 14 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, but fewer than 4494, consecutive nucleotides of SEQ ID NO: 13 or SEQ ID NO: 14. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4491 of SEQ ID NO: 13 or SEQ ID NO: 14. In some embodiments, a polynucleotide of the present disclosure comprises the sequence of nucleic acids 1-4491 of SEQ ID NO: 13 or SEQ ID NO: 14.

In some embodiments, a polynucleotide of the present disclosure encoding one or more human collagen proteins (e.g., a first human collagen protein, a further human collagen protein, an additional human collagen protein, and/or a second human collagen protein) has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, a polynucleotide of the present disclosure encoding one or more human collagen proteins (e.g., a first human collagen protein, a further human collagen protein, an additional human collagen protein, and/or a second human collagen protein) comprises a sequence selected from SEQ ID NOS: 1-14.

Polynucleotides Encoding Fibronectin Proteins

In some embodiments, the present disclosure relates to a recombinant nucleic acid comprising one or more polynucleotides comprising the coding sequence of a fibronectin gene. The coding sequence of any fibronectin gene (including any isoform thereof) from any suitable species known in the art may be encoded by a polynucleotide of the present disclosure, including, for example, a human fibronectin gene (see e.g., NCBI Gene ID: 2335), a mouse fibronectin gene (see, e.g., NCBI Gene ID: 14268), a chimpanzee fibronectin gene (see e.g., NCBI Gene ID: 459926), a rat fibronectin gene (see e.g., NCBI Gene ID: 25661), a rabbit fibronectin gene (see e.g., NCBI Gene ID: 100328589), etc. Methods of identifying fibronectin gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the fibronectin genes (and/or coding sequences thereof) described herein or known in the art. In some embodiments, a polynucleotide of the present disclosure comprises a codon-optimized variant of any of the fibronectin genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human fibronectin gene. In some embodiments, a polynucleotide of the present disclosure comprises the coding sequence of the human FN1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 35 or SEQ ID NO: 36. In some embodiments, a polynucleotide of the present disclosure comprises the sequence of SEQ ID NO: 35 or SEQ ID NO: 36.

In some embodiments, a polynucleotide of the present disclosure comprises a 5' truncation, a 3' truncation, or a fragment of the sequence of SEQ ID NO: 35 or SEQ ID NO: 36. In some embodiments, the 5' truncation, 3' truncation, or fragment of the sequence of SEQ ID NO: 35 or SEQ ID NO: 36 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, at least about 4500, at least about 5000, at least about 5500, at least about 6000, at least about 6500, at least about 7000, but fewer than 7434, consecutive nucleotides of SEQ ID NO: 35 or SEQ ID NO: 36. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-7431 of SEQ ID NO: 35 or SEQ ID NO: 36. In some embodiments, a polynucleotide of the present disclosure comprises the sequence of nucleic acids 1-7431 of SEQ ID NO: 35 or SEQ ID NO: 36.

Polynucleotides Encoding Elastin Proteins

In some embodiments, the present disclosure relates to a recombinant nucleic acid comprising one or more polynucleotides comprising the coding sequence of an elastin gene. The coding sequence of any elastin gene (including any isoform thereof) from any suitable species known in the art may be encoded by a polynucleotide of the present disclosure, including, for example, a human elastin gene (see e.g., NCBI Gene ID: 2006), a mouse elastin gene (see, e.g., NCBI Gene ID: 13717), a chimpanzee elastin gene (see e.g., NCBI Gene ID: 463943), a rat elastin gene (see e.g., NCBI Gene ID: 25043), a rabbit elastin gene (see e.g., NCBI Gene ID: 100344271), etc. Methods of identifying elastin gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the elastin genes (and/or coding sequences thereof) described herein or known in the art. In some embodiments, a polynucleotide of the present disclosure comprises a codon-optimized variant of any of the elastin genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human elastin gene. In some embodiments, a polynucleotide of the present disclosure comprises the coding sequence of the human ELN gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 37 or SEQ ID NO: 38. In some embodiments, a polynucleotide of the present disclosure comprises the sequence of SEQ ID NO: 37 or SEQ ID NO: 38.

In some embodiments, a polynucleotide of the present disclosure comprises a 5' truncation, a 3' truncation, or a fragment of the sequence of SEQ ID NO: 37 or SEQ ID NO: 38. In some embodiments, the 5' truncation, 3' truncation, or fragment of the sequence of SEQ ID NO: 37 or SEQ ID NO: 38 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, but fewer than 2361, consecutive nucleotides of SEQ ID NO: 37 or SEQ ID NO: 38. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-2358 of SEQ ID NO: 37 or SEQ ID NO: 38. In some embodiments, a polynucleotide of the present disclosure comprises the sequence of nucleic acids 1-2358 of SEQ ID NO: 37 or SEQ ID NO: 38.

Polynucleotides Encoding Lumican Proteins

In some embodiments, the present disclosure relates to a recombinant nucleic acid comprising one or more polynucleotides comprising the coding sequence of a lumican gene. The coding sequence of any lumican gene (including any isoform thereof) from any suitable species known in the art may be encoded by a polynucleotide of the present disclosure, including, for example, a human lumican gene (see e.g., NCBI Gene ID: 4060), a mouse lumican gene (see, e.g., NCBI Gene ID: 17022), a chimpanzee lumican gene (see e.g., NCBI Gene ID: 452119), a rat lumican gene (see e.g., NCBI Gene ID: 81682), a rabbit lumican gene (see e.g., NCBI Gene ID: 100008665), etc. Methods of identifying lumican gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the lumican genes (and/or coding sequences thereof) described herein or known in the art. In some embodiments, a polynucleotide of the present disclosure comprises a codon-optimized variant of any of the lumican genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human lumican gene. In some embodiments, a polynucleotide of the present disclosure comprises the coding sequence of the human LUM gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 39 or SEQ ID NO: 40. In some embodiments, a polynucleotide of the present disclosure comprises the sequence of SEQ ID NO: 39 or SEQ ID NO: 40.

In some embodiments, a polynucleotide of the present disclosure comprises a 5' truncation, a 3' truncation, or a fragment of the sequence of SEQ ID NO: 39 or SEQ ID NO: 40. In some embodiments, the 5' truncation, 3' truncation, or fragment of the sequence of SEQ ID NO: 39 or SEQ ID NO: 40 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, but fewer than 1017, consecutive nucleotides of SEQ ID NO: 39 or SEQ ID NO: 40. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-1014 of SEQ ID NO: 39 or SEQ ID NO: 40. In some embodiments, a polynucleotide of the present disclosure comprises the sequence of nucleic acids 1-1014 of SEQ ID NO: 39 or SEQ ID NO: 40.

Polynucleotides Encoding Vitronectin and Vitronectin Receptor Proteins

In some embodiments, the present disclosure relates to a recombinant nucleic acid comprising one or more polynucleotides comprising the coding sequence of a vitronectin or vitronectin receptor gene. The coding sequence of any vitronectin or vitronectin receptor gene (including any isoform thereof) from any suitable species known in the art may be encoded by a polynucleotide of the present disclosure, including, for example, a human vitronectin or vitronectin receptor gene (see e.g., NCBI Gene IDs: 7448 and 3685), a mouse vitronectin or vitronectin receptor gene (see, e.g., NCBI Gene IDs: 22370 and 16410), a chimpanzee vitronectin or vitronectin receptor gene (see e.g., NCBI Gene IDs: 738261 and 459807), a rat vitronectin or vitronectin receptor gene (see e.g., NCBI Gene IDs: 29169 and 257645), a rabbit vitronectin or vitronectin receptor gene (see e.g., NCBI Gene IDs: 100009128 and 100008956), etc. Methods of identifying vitronectin or vitronectin receptor gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the vitronectin or vitronectin receptor genes (and/or coding sequences thereof) described herein or known in the art. In some embodiments, a polynucleotide of the present disclosure comprises a codon-optimized variant of any of the vitronectin or vitronectin receptor genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human vitronectin or vitronectin receptor gene. In some embodiments, a polynucleotide of the present disclosure comprises the coding sequence of the human VTN gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 41 or SEQ ID NO: 42. In some embodiments, a polynucleotide of the present disclosure comprises the sequence of SEQ ID NO: 41 or SEQ ID NO: 42.

In some embodiments, a polynucleotide of the present disclosure comprises a 5' truncation, a 3' truncation, or a fragment of the sequence of SEQ ID NO: 41 or SEQ ID NO: 42. In some embodiments, the 5' truncation, 3' truncation, or fragment of the sequence of SEQ ID NO: 41 or SEQ ID NO: 42 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least about 1250, but fewer than 1437, consecutive nucleotides of SEQ ID NO: 41 or SEQ ID NO: 42. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-1034 of SEQ ID NO: 41 or SEQ ID NO: 42. In some embodiments, a polynucleotide of the present disclosure comprises the sequence of nucleic acids 1-1034 of SEQ ID NO: 41 or SEQ ID NO: 42.

Polynucleotides Encoding Laminin Proteins

In some embodiments, the present disclosure relates to a recombinant nucleic acid comprising one or more polynucleotides comprising the coding sequence of a laminin gene. The coding sequence of any laminin gene (including any isoform thereof) from any suitable species known in the art may be encoded by a polynucleotide of the present disclosure, including, for example, human laminin genes (see e.g., NCBI Gene IDs: 284217, 3908, 3909, 3910, 3911, 3912, 3913, 3914, 3915, 3918, and 10319), mouse laminin genes (see e.g., NCBI Gene IDs: 16774, 16780, and 16782), chimpanzee laminin genes (see e.g., NCBI Gene IDs: 455339, 469668, and 457571), rat laminin genes (see e.g., NCBI Gene IDs: 307582, 305078, and 192362), rabbit laminin genes (see e.g., NCBI Gene IDs: 100346886 and 100342905), etc. Methods of identifying laminin gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the laminin genes (and/or coding sequences thereof) described herein or known in the art. In some embodiments, a polynucleotide of the present disclosure comprises a codon-optimized variant of any of the laminin genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human laminin gene, such as a human LAMA1 gene (see e.g., NCBI Gene ID: 284217), a human LAMA2 gene (see e.g., NCBI Gene ID: 3908), a human LAMA3 gene (see e.g., NCBI Gene ID: 3909), a human LAMA4 gene (see e.g., NCBI Gene ID: 3910), a human LAMA5 gene (see e.g., NCBI Gene ID: 3911), a human LAMB1 gene (see e.g., NCBI Gene ID: 3912), a human LAMB2 gene (see e.g., NCBI Gene ID: 3913), a human LAMB3 gene (see e.g., NCBI Gene ID: 3914), a human LAMC1 gene (see e.g., NCBI Gene ID: 3915), a human LAMC2 gene (see e.g., NCBI Gene ID: 3918), or a human LAMC3 gene (see e.g., NCBI Gene ID: 10319).

In some embodiments, a polynucleotide of the present disclosure comprises the coding sequence of the human LAMA3 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 43 or SEQ ID NO: 44. In some embodiments, a polynucleotide of the present disclosure comprises the sequence of SEQ ID NO: 43 or SEQ ID NO: 44.

In some embodiments, a polynucleotide of the present disclosure comprises a 5' truncation, a 3' truncation, or a fragment of the sequence of SEQ ID NO: 43 or SEQ ID NO: 44. In some embodiments, the 5' truncation, 3' truncation, or fragment of the sequence of SEQ ID NO: 43 or SEQ ID NO: 44 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, at least about 4500, at least about 5000, but fewer than 5175, consecutive nucleotides of SEQ ID NO: 43 or SEQ ID NO: 44. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-5172 of SEQ ID NO: 43 or SEQ ID NO: 44. In some embodiments, a polynucleotide of the present disclosure comprises the sequence of nucleic acids 1-5172 of SEQ ID NO: 43 or SEQ ID NO: 44.

In some embodiments, a polynucleotide of the present disclosure comprises the coding sequence of the human LAMB3 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 45 or SEQ ID NO: 46. In some embodiments, a polynucleotide of the present disclosure comprises the sequence of SEQ ID NO: 45 or SEQ ID NO: 46.

In some embodiments, a polynucleotide of the present disclosure comprises a 5' truncation, a 3' truncation, or a fragment of the sequence of SEQ ID NO: 45 or SEQ ID NO: 46. In some embodiments, the 5' truncation, 3' truncation, or fragment of the sequence of SEQ ID NO: 45 or SEQ ID NO: 46 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, but fewer than 3519, consecutive nucleotides of SEQ ID NO: 45 or SEQ ID NO: 46. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3516 of SEQ ID NO: 45 or SEQ ID NO: 46. In some embodiments, a polynucleotide of the present disclosure comprises the sequence of nucleic acids 1-3516 of SEQ ID NO: 45 or SEQ ID NO: 46.

In some embodiments, a polynucleotide of the present disclosure comprises the coding sequence of the human LAMC2 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 47 or SEQ ID NO: 48. In some embodiments, a polynucleotide of the present disclosure comprises the sequence of SEQ ID NO: 47 or SEQ ID NO: 48.

In some embodiments, a polynucleotide of the present disclosure comprises a 5' truncation, a 3' truncation, or a fragment of the sequence of SEQ ID NO: 47 or SEQ ID NO: 48. In some embodiments, the 5' truncation, 3' truncation, or fragment of the sequence of SEQ ID NO: 47 or SEQ ID NO: 48 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, but fewer than 3582, consecutive nucleotides of SEQ ID NO: 47 or SEQ ID NO: 48. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3579 of SEQ ID NO: 47 or SEQ ID NO: 48. In some embodiments, a polynucleotide of the present disclosure comprises the sequence of nucleic acids 1-3579 of SEQ ID NO: 47 or SEQ ID NO: 48.

Polynucleotides Encoding Neuromodulator Proteins

In some embodiments, the present disclosure relates to a recombinant nucleic acid comprising one or more polynucleotides comprising the coding sequence of a neuromodulator gene. The coding sequence of any neuromodulator gene (including any isoform thereof) from any suitable species known in the art may be encoded by a polynucleotide of the present disclosure, including, for example, a *Clostridium botulinum* neuromodulator gene (see e.g., NCBI Gene IDs: 5185061 and 39483740), etc. Methods of identifying neuromodulator gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the neuromodulator genes (and/or coding sequences thereof) described herein or known in the art. In some embodiments, a polynucleotide of the present disclosure comprises a codon-optimized variant of any of the neuromodulator genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a *Clostridium botulinum* neuromodulator gene.

In some embodiments, a polynucleotide of the present disclosure comprises the coding sequence of the *Clostridium botulinum* botA gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 49 or SEQ ID NO: 50. In some embodiments, a polynucleotide of the present disclosure comprises the sequence of SEQ ID NO: 49 or SEQ ID NO: 50.

In some embodiments, a polynucleotide of the present disclosure comprises a 5' truncation, a 3' truncation, or a fragment of the sequence of SEQ ID NO: 49 or SEQ ID NO: 50. In some embodiments, the 5' truncation, 3' truncation, or fragment of the sequence of SEQ ID NO: 49 or SEQ ID NO: 50 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least about 1250, at least 1500, at least 1750, at least 2000, at least 2500, at least 3000, at least 3500, but fewer than 3891, consecutive nucleotides of SEQ ID NO: 49 or SEQ ID NO: 50. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3888 of SEQ ID NO: 49 or SEQ ID NO: 50. In some embodiments, a polynucleotide of the present disclosure comprises the sequence of nucleic acids 1-3888 of SEQ ID NO: 49 or SEQ ID NO: 50.

In some embodiments, a polynucleotide of the present disclosure comprises the coding sequence of the *Clostridium botulinum* botB gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 51 or SEQ ID NO: 52. In some embodiments, a polynucleotide of the present disclosure comprises the sequence of SEQ ID NO: 51 or SEQ ID NO: 52.

In some embodiments, a polynucleotide of the present disclosure comprises a 5' truncation, a 3' truncation, or a fragment of the sequence of SEQ ID NO: 51 or SEQ ID NO: 52. In some embodiments, the 5' truncation, 3' truncation, or fragment of the sequence of SEQ ID NO: 51 or SEQ ID NO: 52 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least about 1250, at least 1500, at least 1750, at least 2000, at least 2500, at least 3000, at least 3500, but fewer than 3876, consecutive nucleotides of SEQ ID NO: 51 or SEQ ID NO: 52. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3873 of SEQ ID NO: 51 or SEQ ID NO: 52. In some embodiments, a polynucleotide of the present disclosure comprises the sequence of nucleic acids 1-3873 of SEQ ID NO: 51 or SEQ ID NO: 52.

Polynucleotides Encoding Fibrillin Proteins

In some embodiments, the present disclosure relates to a recombinant nucleic acid comprising one or more polynucleotides comprising the coding sequence of a fibrillin gene. The coding sequence of any fibrillin gene (including any isoform thereof) from any suitable species known in the art may be encoded by a polynucleotide of the present disclosure, including, for example, human fibrillin genes (see e.g., NCBI Gene IDs: 2200, 2201, and 84467), mouse fibrillin genes (see e.g., NCBI Gene IDs: 14118 and 14119), chimpanzee fibrillin genes (see e.g., NCBI Gene IDs: 453411, 471621, and 455669), rat fibrillin genes (see e.g., NCBI Gene IDs: 83727 and 689008), rabbit fibrillin genes (see e.g., NCBI Gene IDs: 100350931, 100357126, and 100359336), etc. Methods of identifying fibrillin gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the fibrillin genes (and/or coding sequences thereof) described herein or known in the art. In some embodiments, a polynucleotide of the present disclosure comprises a codon-optimized variant of any of the fibrillin genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human fibrillin gene, such as a human FBN1 gene (see e.g., NCBI Gene ID: 2200), a human FBN2 gene (see e.g., NCBI Gene ID: 2201), or a human FBN3 gene (see e.g., NCBI Gene ID: 84467).

Exemplary Polynucleotides

In some embodiments, a polynucleotide of the present disclosure encoding one or more cosmetic proteins (e.g., a first cosmetic protein, a further cosmetic protein, an additional cosmetic protein, and/or a second cosmetic protein) has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14 or 35-52. In some embodiments, a polynucleotide of the present disclosure encoding one or more cosmetic proteins (e.g., a first cosmetic protein, a further cosmetic protein, an additional cosmetic protein, and/or a second cosmetic protein) comprises a sequence selected from SEQ ID NOS: 1-14 or 35-52.

In some embodiments, a polynucleotide of the present disclosure encoding one or more cosmetic proteins (e.g., a first cosmetic protein, a further cosmetic protein, an additional cosmetic protein, and/or a second cosmetic protein) has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14, 35-38, or 43-48. In some embodiments, a polynucleotide of the present disclosure encoding one or more cosmetic proteins (e.g., a first cosmetic protein, a further cosmetic protein, an additional cosmetic protein, and/or a second cosmetic protein) comprises a sequence selected from SEQ ID NOS: 1-14, 35-38, or 43-48.

A polynucleotide of the present disclosure encoding a cosmetic protein (e.g., a human collagen protein) may further encode additional coding and non-coding sequences. Examples of additional coding and non-coding sequences may include, but are not limited to, sequences encoding additional polypeptide tags (e.g., encoded in-frame with the cosmetic protein in order to produce a fusion protein), introns (e.g., native, modified, or heterologous introns), 5' and/or 3' UTRs (e.g., native, modified, or heterologous 5' and/or 3' UTRs), and the like. Examples of suitable polypeptide tags may include, but are not limited, to any combination of purification tags, such as his-tags, flag-tags, maltose binding protein and glutathione-S-transferase tags, detection tags, such as tags that may be detected photometrically (e.g., green fluorescent protein, red fluorescent protein, etc.) and tags that have a detectable enzymatic activity (e.g., alkaline phosphatase, etc.), tags containing secretory sequences, signal sequences, leader sequences, and/or stabilizing sequences, protease cleavage sites (e.g., furin cleavage sites, TEV cleavage sites, Thrombin cleavage sites, etc.), and the like. In some embodiments, the 5' and/or 3'UTRs increase the stability, localization, and/or translational efficiency of the polynucleotides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance cosmetic protein expression in specific cell types (such as human keratinocytes and/or fibroblasts).

In some embodiments, a polynucleotide of the present disclosure encoding a cosmetic protein (e.g., a human collagen protein) is operably linked to one or more (e.g., one or more, two or more, three or more, four or more, five or more, ten or more, etc.) regulatory sequences. The term "regulatory sequence" may include enhancers, insulators, promoters, and other expression control elements (e.g., polyadenylation signals). Any suitable enhancer(s) known in the art may be used, including, for example, enhancer sequences from mammalian genes (such as globin, elastase, albumin, α-fetoprotein, insulin and the like), enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like), and any combinations thereof. Any suitable insulator(s) known in the art may be used, including, for example, HSV chromatin boundary (CTRL/CTCF-binding/insulator) elements CTRL1 and/or CTRL2, chicken hypersensitive site 4 insulator (cHS4), human HNRPA2B1—CBX3 ubiquitous chromatin opening element (UCOE), the scaffold/matrix attachment region (S/MAR) from the human interferon beta gene (IFNB1), and any combinations thereof. Any suitable promoter (e.g., suitable for transcription in mammalian host cells) known in the art may be used, including, for example, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), promoters from heterologous mammalian genes (such as the actin promoter (e.g., the (3-actin promoter), a ubiquitin promoter (e.g., a ubiquitin C (UbC) promoter), a phosphoglycerate kinase (PGK) promoter, an immunoglobulin promoter, from heat-shock promoters, and the like), promoters from homologous mammalian genes (e.g., native human collagen, fibronectin, elastin, lumican, vitronectin, laminin, and/or fibrillin promoters), synthetic promoters (such as the CAGG promoter), and any combinations thereof, provided such promoters are compatible with the host cells. Regulatory sequences may include those which direct constitutive expression of a nucleic acid, as well as tissue-specific regulatory and/or inducible or repressible sequences.

In some embodiments, a polynucleotide of the present disclosure encoding cosmetic protein (e.g., a human collagen protein) is operably linked to one or more heterologous promoters. In some embodiments, the one or more heterologous promoters are one or more of constitutive promoters, tissue-specific promoters, temporal promoters, spatial promoters, inducible promoters and repressible promoters. In some embodiments, the one or more heterologous promoters are one or more of the human cytomegalovirus (HCMV) immediate early promoter, the human elongation factor-1 (EF1) promoter, the human β-actin promoter, the human UbC promoter, the human PGF promoter, the synthetic CAGG promoter, and any combinations thereof. In some embodiments, a polynucleotide of the present disclosure encoding a cosmetic protein (e.g., a human collagen protein) is operably linked to an HCMV promoter.

In some embodiments, a polynucleotide of the present disclosure does not comprise the coding sequence of (e.g., a transgene encoding) a Collagen alpha-1 (VII) chain polypeptide (COL7). In some embodiments, a polynucleotide of the present disclosure does not comprise the coding sequence of (e.g., a transgene encoding) a Lysyl hydroxylase 3 polypeptide (LH3). In some embodiments, a polynucleotide of the present disclosure does not comprise the coding sequence of (e.g., a transgene encoding) a Keratin type I cytoskeletal 17 polypeptide (KRT17). In some embodiments, a polynucleotide of the present disclosure does not comprise the coding sequence of (e.g., a transgene encoding) a transglutaminase (TGM) polypeptide (e.g., a human transglutaminase polypeptide such as a human TGM1 polypeptide). In some embodiments, a polynucleotide of the present disclosure does not comprise the coding sequence of (e.g., a transgene encoding) a laminin subunit beta-3 polypeptide (LAMB3). In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, and/or any chimeric polypeptides thereof. In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, a transglutaminase (TGM) polypeptide (e.g., a human transglutaminase polypeptide such as a human TGM1 polypeptide), a laminin subunit beta-3 (LAMB3) polypeptide (e.g., a human LamB3 polypeptide) and/or any chimeric polypeptides thereof.

Cosmetic Proteins

Collagen Proteins

In some embodiments, the present disclosure relates to one or more polynucleotides encoding a full-length collagen protein or any isoforms or portions thereof. Any collagen protein from any suitable species known in the art may be encoded by a polynucleotide of the present disclosure, including, for example, human collagen proteins (see e.g., UniProt accession numbers P02452, P08123, P02461, P02462, P08572, P12109, Q02388, Q9UMD9. etc.), mouse collagen proteins (see, e.g., UniProt accession numbers P11087, Q01149, P08121, P02463, P08122, Q04857, Q63870, Q07563, etc.), chimpanzee collagen proteins (see e.g., UniProt accession numbers A0A2I3 SM98, A0A2J8L483, H2QJ46, K7C8P4, K7C8WO, A0A2J8M8U9, H2QMJ5, H2Q2J4, etc.), rat collagen proteins (see e.g., UniProt accession numbers P02454, P02466, P13941, P02466, F1M6Q3, D3ZUL3, D3ZE04, D3ZE04, etc.), rabbit collagen proteins (see e.g., UniProt accession numbers G1T4A5, Q28668, G1T8J0, G1U9R7, G1T548, G1T380, G1T548, etc.) etc. Methods of identifying collagen protein homologs/orthologs from additional species are known to one of ordinary skill in the art, including, for example, using an amino acid sequence alignment program such as the BLAST® blastp suite or OrthoDB. In some embodiments, a collagen polypeptide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the collagen polypeptides described herein or known in the art.

In some embodiments, the present disclosure relates to one or more polynucleotides encoding a human collagen protein. Any suitable human collagen protein known in the art may be encoded by a polynucleotide of the present disclosure, including, for example, a Collagen alpha-1(I) chain polypeptide (COL1-1) (see e.g., UniProt accession number P02452; SEQ ID NO: 15), a Collagen alpha-2(I) chain polypeptide (COL1-2) (see e.g., UniProt accession number P08123; SEQ ID NO: 16), a Collagen alpha-1(II) chain polypeptide (COL2) (see e.g., UniProt accession number P02458), a Collagen alpha-1(III) chain polypeptide (COL3) (see e.g., UniProt accession number P2461; SEQ ID NO: 17), a Collagen alpha-1(IV) chain polypeptide (COL4-1) (see e.g., UniProt accession number P02462; SEQ ID NO: 18), a Collagen alpha-2(IV) chain polypeptide (COL4-2) (see e.g., UniProt accession number P08572), a Collagen alpha-3(IV) chain polypeptide (COL4-3) (see e.g., UniProt accession number Q01955), a Collagen alpha-4(IV) chain polypeptide (COL4-4) (see e.g., UniProt accession number P53420), a Collagen alpha-5(IV) chain polypeptide (COL4-5) (see e.g., UniProt accession number 29400), a Collagen alpha-6(IV) chain polypeptide (COL4-6) (see e.g., UniProt accession number Q14031), a Collagen alpha-1(V) chain polypeptide (COL5-1) (see e.g., UniProt accession number P20908), a Collagen alpha-2(V) chain polypeptide (COL5-2) (see e.g., UniProt accession number P05997), a Collagen alpha-3(V) chain polypeptide (COL5-3) (see e.g., UniProt accession number P25940), a Collagen alpha-1(VI) chain polypeptide (COL6-1) (see e.g., UniProt accession number P12109; SEQ ID NO: 19), a Collagen alpha-2(VI) chain polypeptide (COL6-2) (see e.g., UniProt accession number P12110), a Collagen alpha-3(VI) chain polypeptide (COL6-3) (see e.g., UniProt accession number P12111), a Collagen alpha-4(VI) chain polypeptide (COL6-4), a Collagen alpha-5(VI) chain polypeptide (COL6-5) (see e.g., UniProt accession number A8TX70), a Collagen alpha-6(VI) chain polypeptide (COL6-6) (see e.g., UniProt accession number A6NMZ7), a Collagen alpha-1(VII) chain polypeptide (COL7) (see e.g., UniProt accession number Q02388; SEQ ID NO: 20), a Collagen alpha-1(VIII) chain polypeptide (COL8) (see e.g., UniProt accession number P27658), a Collagen alpha-1(IX) chain polypeptide (COL9-1) (see e.g., UniProt accession number P20849), a Collagen alpha-2(IX) chain polypeptide (COL9-2) (see e.g., UniProt accession number Q14055), a Collagen alpha-3(IX) chain polypeptide (COL9-3) (see e.g., UniProt accession number Q14050), a Collagen alpha-1(X) chain polypeptide (COL10) (see e.g., UniProt accession number Q03692), a Collagen alpha-1(XI) chain polypeptide (COL11-1) (see e.g., UniProt accession number P12107), a Collagen alpha-2(XI) chain polypeptide (COL11-2) (see e.g., UniProt accession number P13942), a Collagen alpha-1(XII) chain polypeptide (COL12) (see e.g., UniProt accession number Q99715), a Collagen alpha-1 (XIII) chain polypeptide (COL13) (see e.g., UniProt accession number Q5TAT6), a Collagen alpha-1(XIV) chain polypeptide (COL14) (see e.g., UniProt accession number Q05707), a Collagen alpha-1(XV) chain polypeptide (COL15) (see e.g., UniProt accession number P39059), a Collagen alpha-1(XVI) chain polypeptide (COL16) (see e.g., UniProt accession number Q07092), a Collagen alpha-1(XVII) chain polypeptide (COL17) (see e.g., UniProt accession number Q9UMD9; SEQ ID NO: 21), a Collagen alpha-1(XVIII) chain polypeptide (COL18) (see e.g., UniProt accession number P39060), a Collagen alpha-1(XIX) chain polypeptide (COL19) (see e.g., UniProt accession number Q14993), a Collagen alpha-1(XX) chain polypeptide (COL20) (see e.g., UniProt accession number Q9P218), a Collagen alpha-1(XXI) chain polypeptide (COL21) (see e.g., UniProt accession number Q96P44), a Collagen alpha-1(XXII) chain polypeptide (COL22) (see e.g., UniProt accession number Q8NFW1), a Collagen alpha-1(XXIII) chain polypeptide (COL23) (see e.g., UniProt accession number Q86Y22), a Collagen alpha-1(XXIV) chain polypeptide (COL24) (see e.g., UniProt accession number Q17RW2), a Collagen alpha-1(XXV) chain polypeptide (COL25) (see e.g., UniProt accession number Q9BXS0), a Collagen alpha-1(XXVI) chain polypeptide (COL26) (see e.g., UniProt accession number Q96A83), a Collagen alpha-1(XXVII) chain polypeptide (COL27) (see e.g., UniProt accession number Q8IZC6), a Collagen alpha-1(XXVIII) chain polypeptide (COL28) (see e.g., UniProt accession number Q2UY09), etc. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence encoding any of the human collagen polypeptides described herein or known in the art. Methods of identifying additional human collagen or collagen-like polypeptide homologs/orthologs are known to one of ordinary skill in the art, including, for example, using an amino acid sequence alignment program such as the BLAST® blastp suite or OrthoDB.

In some embodiments, a polynucleotide of the present disclosure encodes a human COL1-1 protein. In some embodiments, a polynucleotide encoding a COL1-1 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 15. In some embodiments, a polynucleotide encoding a human COL1-1 protein is a polynucleotide that encodes a polypeptide comprising the amino acid sequence of SEQ ID NO: 15.

In some embodiments, a polynucleotide encoding a COL1-1 protein is a polynucleotide that encodes an N-terminal truncation, a C-terminal truncation, or a fragment of the amino acid sequence of SEQ ID NO: 15. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, but fewer than 1464, consecutive amino acids of SEQ ID NO: 15.

In some embodiments, a polynucleotide of the present disclosure encodes a human COL1-2 protein. In some embodiments, a polynucleotide encoding a COL1-2 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 16. In some embodiments, a polynucleotide encoding a human COL1-2 protein is a polynucleotide that encodes a polypeptide comprising the amino acid sequence of SEQ ID NO: 16.

In some embodiments, a polynucleotide encoding a COL1-2 protein is a polynucleotide that encodes an N-terminal truncation, a C-terminal truncation, or a fragment of the amino acid sequence of SEQ ID NO: 16. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, but fewer than 1366, consecutive amino acids of SEQ ID NO: 16.

In some embodiments, a polynucleotide of the present disclosure encodes a human COL3 protein. In some embodiments, a polynucleotide encoding a COL3 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 17. In some embodiments, a polynucleotide encoding a human COL3 protein is a polynucleotide that encodes a polypeptide comprising the amino acid sequence of SEQ ID NO: 17.

In some embodiments, a polynucleotide encoding a COL3 protein is a polynucleotide that encodes an N-terminal truncation, a C-terminal truncation, or a fragment of the amino acid sequence of SEQ ID NO: 17. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, but fewer than 1466, consecutive amino acids of SEQ ID NO: 17.

In some embodiments, a polynucleotide of the present disclosure encodes a human COL4-1 protein. In some embodiments, a polynucleotide encoding a COL4-1 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 18. In some embodiments, a polynucleotide encoding a human COL4-1 protein is a polynucleotide that encodes a polypeptide comprising the amino acid sequence of SEQ ID NO: 18.

In some embodiments, a polynucleotide encoding a COL4-1 protein is a polynucleotide that encodes an N-terminal truncation, a C-terminal truncation, or a fragment of the amino acid sequence of SEQ ID NO: 18. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, at least 1500, at least 1600, but fewer than 1669, consecutive amino acids of SEQ ID NO: 18.

In some embodiments, a polynucleotide of the present disclosure encodes a human COL6-1 protein. In some embodiments, a polynucleotide encoding a COL6-1 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 19. In some embodiments, a polynucleotide encoding a human COL6-1 protein is a polynucleotide that encodes a polypeptide comprising the amino acid sequence of SEQ ID NO: 19.

In some embodiments, a polynucleotide encoding a COL6-1 protein is a polynucleotide that encodes an N-terminal truncation, a C-terminal truncation, or a fragment of the amino acid sequence of SEQ ID NO: 19. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, but fewer than 1028, consecutive amino acids of SEQ ID NO: 19.

In some embodiments, a polynucleotide of the present disclosure encodes a human COL7 protein. In some embodiments, a polynucleotide encoding a COL7 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 20. In some embodiments, a polynucleotide encoding a human COL7 protein is a polynucleotide that encodes a polypeptide comprising the amino acid sequence of SEQ ID NO: 20.

In some embodiments, a polynucleotide encoding a COL7 protein is a polynucleotide that encodes an N-terminal truncation, a C-terminal truncation, or a fragment of the amino acid sequence of SEQ ID NO: 20. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, at least 2000, at least 2100, at least 2200, at least 2300, at least 2400, at least 2500, at least 2600, at least 2700, at least 2800, at least 2900, but fewer than 2944, consecutive amino acids of SEQ ID NO: 20.

In some embodiments, a polynucleotide of the present disclosure encodes a human COL17 protein. In some embodiments, a polynucleotide encoding a COL17 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 21. In some embodiments, a polynucleotide encoding a human COL17 protein is a polynucleotide that encodes a polypeptide comprising the amino acid sequence of SEQ ID NO: 21.

In some embodiments, a polynucleotide encoding a COL17 protein is a polynucleotide that encodes an N-terminal truncation, a C-terminal truncation, or a fragment of the amino acid sequence of SEQ ID NO: 21. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, but fewer than 1497, consecutive amino acids of SEQ ID NO: 21.

In some embodiments, one or more human collagen proteins of the present disclosure (e.g., a first human collagen protein, a further human collagen protein, an additional human collagen protein, and/or a second human collagen protein) comprise an amino acid sequence comprising at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, one or more human collagen proteins of the present disclosure (e.g., a first human collagen protein, a further human collagen protein, an additional human collagen protein, and/or a second human collagen protein) comprise a sequence selected from SEQ ID NOS: 15-21.

In some embodiments, one or more human collagen proteins of the present disclosure (e.g., a first human collagen protein, a further human collagen protein, an additional human collagen protein, and/or a second human collagen protein) comprise an amino acid sequence comprising at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-17. In some embodiments, one or more human collagen proteins of the present disclosure (e.g., a first human collagen protein, a further human collagen protein, an additional human collagen protein, and/or a second human collagen protein) comprise a sequence selected from SEQ ID NOS: 15-17.

Fibronectin Proteins

In some embodiments, the present disclosure relates to one or more polynucleotides encoding a full-length fibronectin protein or any isoforms or portions thereof. Any fibronectin protein from any suitable species known in the art may be encoded by a polynucleotide of the present disclosure, including, for example, a human fibronectin protein (see e.g., UniProt accession number P02751), a mouse fibronectin protein (see, e.g., UniProt accession number P11276), a chimpanzee fibronectin protein (see e.g., UniProt accession number P11276), a rat fibronectin protein (see e.g., UniProt accession number P04937), a rabbit fibronectin protein (see e.g., UniProt accession number P04937), etc. Methods of identifying fibronectin protein homologs/orthologs from additional species are known to one of ordinary skill in the art. In some embodiments, a fibronectin protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the fibronectin proteins described herein or known in the art.

In some embodiments, a polynucleotide of the present disclosure encodes a human fibronectin protein. In some embodiments, a polynucleotide encoding a human fibronectin protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 53. In some embodiments, a polynucleotide encoding a human fibronectin protein is a polynucleotide that encodes a polypeptide comprising the amino acid sequence of SEQ ID NO: 53.

In some embodiments, a polynucleotide encoding a human fibronectin protein is a polynucleotide that encodes an N-terminal truncation, a C-terminal truncation, or a fragment of the amino acid sequence of SEQ ID NO: 53. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, at least 2000, at least 2100, at least 2200, at least 2300, at least 2400, but fewer than 2477, consecutive amino acids of SEQ ID NO: 53.

Elastin and Associated Proteins

Elastic fibers in the extracellular matrix give elastic properties to the tissue. The elastic fibers generally contain two morphologically distinct components—the mature elastin fibers, and the micro-fibrills which mainly contain fibrillin and are associated with further proteins such as the micro-fibrills associated glycoproteins (MAGPs), fibulines, and the elastin-micro-fibrills-interface localized proteins (EMILIN). Elastin and its soluble precursor tropoelastin belong to the major structural proteins of the body.

In some embodiments, the present disclosure relates to one or more polynucleotides encoding an elastin or elastin-associated protein, including a tropoelastin, a fibrillin, a micro-fibrills associated glycoprotein, a fibuline, or an elastin-micro-fibrills-interface localized protein. In some embodiments, the present disclosure relates to one or more polynucleotides encoding a full-length elastin protein or any isoforms or portions thereof. Any elastin protein from any suitable species known in the art may be encoded by a polynucleotide of the present disclosure, including, for example, a human elastin protein (see e.g., UniProt accession number P15502), a mouse elastin protein (see, e.g., UniProt accession number P15502), a chimpanzee elastin protein (see e.g., UniProt accession number H2QUQ6), a rat elastin protein (see e.g., UniProt accession number Q99372), etc. Methods of identifying elastin protein homologs/orthologs from additional species are known to one of ordinary skill in the art. In some embodiments, an elastin protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the elastin proteins described herein or known in the art.

In some embodiments, a polynucleotide of the present disclosure encodes a human elastin protein. In some embodiments, a polynucleotide encoding a human elastin protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 54. In some embodiments, a polynucleotide encoding a human elastin protein is a polynucleotide that encodes a polypeptide comprising the amino acid sequence of SEQ ID NO: 54.

In some embodiments, a polynucleotide encoding a human elastin protein is a polynucleotide that encodes an N-terminal truncation, a C-terminal truncation, or a fragment of the amino acid sequence of SEQ ID NO: 54. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, but fewer than 786, consecutive amino acids of SEQ ID NO: 54.

Lumican Proteins

In some embodiments, the present disclosure relates to one or more polynucleotides encoding a full-length lumican protein or any isoforms or portions thereof. Any lumican protein from any suitable species known in the art may be encoded by a polynucleotide of the present disclosure, including, for example, a human lumican protein (see e.g., UniProt accession number P51884), a mouse lumican protein (see, e.g., UniProt accession number P51885), a chimpanzee lumican protein (see e.g., UniProt accession number H2Q6L3), a rat lumican protein (see e.g., UniProt accession number H2Q6L3), a rabbit lumican protein (see e.g., UniProt accession number 046379), etc. Methods of identifying lumican protein homologs/orthologs from additional species are known to one of ordinary skill in the art. In some embodiments, a lumican protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the lumican proteins described herein or known in the art.

In some embodiments, a polynucleotide of the present disclosure encodes a human lumican protein. In some embodiments, a polynucleotide encoding a human lumican protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 55. In some embodiments, a polynucleotide encoding a human lumican protein is a polynucleotide that encodes a polypeptide comprising the amino acid sequence of SEQ ID NO: 55.

In some embodiments, a polynucleotide encoding a human lumican protein is a polynucleotide that encodes an N-terminal truncation, a C-terminal truncation, or a fragment of the amino acid sequence of SEQ ID NO: 55. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, but fewer than 338, consecutive amino acids of SEQ ID NO: 55.

Vitronectin and Vitronectin Receptor Proteins

In some embodiments, the present disclosure relates to one or more polynucleotides encoding a full-length vitronectin or vitronectin receptor protein or any isoforms or portions thereof. Any vitronectin or vitronectin receptor protein from any suitable species known in the art may be encoded by a polynucleotide of the present disclosure, including, for example, a human vitronectin or vitronectin receptor protein (see e.g., UniProt accession numbers P04004 and P06756), a mouse vitronectin or vitronectin receptor protein (see, e.g., UniProt accession numbers P29788 and P43406), a chimpanzee vitronectin or vitronectin receptor protein (see e.g., UniProt accession numbers H2QCH3 and H2R6C3), a rat vitronectin or vitronectin receptor protein (see e.g., UniProt accession number Q7TQ11), a rabbit vitronectin or vitronectin receptor protein (see e.g., UniProt accession number P22458), etc. Methods of identifying vitronectin or vitronectin receptor protein homologs/orthologs from additional species are known to one of ordinary skill in the art. In some embodiments, a vitronectin or vitronectin receptor protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the vitronectin or vitronectin receptor proteins described herein or known in the art.

In some embodiments, a polynucleotide of the present disclosure encodes a human vitronectin protein. In some embodiments, a polynucleotide encoding a human vitronectin protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 56. In some embodiments, a polynucleotide encoding a human vitronectin protein is a polynucleotide that encodes a polypeptide comprising the amino acid sequence of SEQ ID NO: 56.

In some embodiments, a polynucleotide encoding a human vitronectin protein is a polynucleotide that encodes an N-terminal truncation, a C-terminal truncation, or a fragment of the amino acid sequence of SEQ ID NO: 56. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, but fewer than 478, consecutive amino acids of SEQ ID NO: 56.

Laminin Proteins

In some embodiments, the present disclosure relates to one or more polynucleotides encoding a full-length laminin protein or any isoforms or portions thereof. Any laminin protein from any suitable species known in the art may be encoded by a polynucleotide of the present disclosure, including, for example, a human laminin protein (see e.g., UniProt accession numbers P25391, P24043, Q16787, Q16363, 015230, P07942, P55268, Q13751, P11047, Q13753, and Q9Y6N6), a mouse laminin protein (see e.g., UniProt accession numbers Q61789, Q61087, and Q61092), a chimpanzee laminin protein (see e.g., UniProt accession numbers H2QEC7, H2R041, and H2Q0R2), a rat laminin protein (see e.g., UniProt accession numbers D3ZN05, F1LPI5, and F1LRH4), a rabbit laminin protein (see e.g., UniProt accession numbers G1SY40 and A0A0B5JSHO), etc. Methods of identifying laminin protein homologs/orthologs from additional species are known to one of ordinary skill in the art. In some embodiments, a laminin protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the laminin proteins described herein or known in the art.

In some embodiments, a polynucleotide of the present disclosure encodes a human laminin protein, such as a human Laminin subunit alpha-1 (LamA1) polypeptide (see e.g., UniProt accession number P25391), a human Laminin subunit alpha-2 (LamA2) polypeptide (see e.g., UniProt accession number P24043), a human Laminin subunit alpha-3 (LamA3) polypeptide (see e.g., UniProt accession number Q16787), a human Laminin subunit alpha-4 (LamA4) polypeptide (see e.g., UniProt accession number Q16363), a human Laminin subunit alpha-5 (LamA5) polypeptide (see e.g., UniProt accession number 015230), a human Laminin subunit beta-1 (LamB1) polypeptide (see e.g., UniProt accession number P07942), a human Laminin subunit beta-2 (LamB2) polypeptide (see e.g., UniProt accession number P55268), a human Laminin subunit beta-3 (LamB3) polypeptide (see e.g., UniProt accession number Q13751), a human Laminin subunit gamma-1 (LamC1) polypeptide (see e.g., UniProt accession number P11047), a human Laminin subunit gamma-2 (LamC2) polypeptide (see e.g., UniProt accession number Q13753), a human Laminin subunit gamma-3 (LamC3) polypeptide (see e.g., UniProt accession number Q9Y6N6), etc.

In some embodiments, a polynucleotide of the present disclosure encodes a human LamA3 polypeptide. In some embodiments, a polynucleotide encoding a human LamA3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 57. In some embodiments, a polynucleotide encoding a human LamA3 polypeptide is a polynucleotide that encodes a polypeptide comprising the amino acid sequence of SEQ ID NO: 57.

In some embodiments, a polynucleotide encoding a human LamA3 polypeptide is a polynucleotide that encodes an N-terminal truncation, a C-terminal truncation, or a fragment of the amino acid sequence of SEQ ID NO: 57. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, at least 1750, at least 2000, at least 2250, at least 2500, at least 2750, at least 3000, at least 3250, but fewer than 3333, consecutive amino acids of SEQ ID NO: 57.

In some embodiments, a polynucleotide of the present disclosure encodes a human LamB3 polypeptide. In some embodiments, a polynucleotide encoding a human LamB3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 58. In some embodiments, a polynucleotide encoding a human LamB3 polypeptide is a polynucleotide that encodes a polypeptide comprising the amino acid sequence of SEQ ID NO: 58.

In some embodiments, a polynucleotide encoding a LamB3 polypeptide is a polynucleotide that encodes an N-terminal truncation, a C-terminal truncation, or a fragment of the amino acid sequence of SEQ ID NO: 58. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, but fewer than 1172, consecutive amino acids of SEQ ID NO: 58.

In some embodiments, a polynucleotide of the present disclosure encodes a human LamC2 polypeptide. In some embodiments, a polynucleotide encoding a human LamC2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 59. In some embodiments, a polynucleotide encoding a human LamC2 polypeptide is a polynucleotide that encodes a polypeptide comprising the amino acid sequence of SEQ ID NO: 59.

In some embodiments, a polynucleotide encoding a LamC2 polypeptide is a polynucleotide that encodes an N-terminal truncation, a C-terminal truncation, or a fragment of the amino acid sequence of SEQ ID NO: 59. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, but fewer than 1193, consecutive amino acids of SEQ ID NO: 59.

Neuromodulator Proteins

In some embodiments, the present disclosure relates to one or more polynucleotides encoding a full-length neuromodulator protein or any isoforms or portions thereof. Any neuromodulator protein from any suitable species known in the art may be encoded by a polynucleotide of the present disclosure, including, for example, a *Clostridium botulinum* protein (see e.g., UniProt accession numbers P0DPI0, Q45894, P0DPI1, P10844, and B1INP5), etc. Methods of identifying neuromodulator protein homologs/orthologs from additional species are known to one of ordinary skill in the art. In some embodiments, a neuromodulator protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the neuromodulator proteins described herein or known in the art.

In some embodiments, a polynucleotide of the present disclosure encodes a *Clostridium botulinum* neuromodulator protein.

In some embodiments, a polynucleotide of the present disclosure encodes a *Clostridium botulinum* neurotoxin type A protein In some embodiments, a polynucleotide encoding a *Clostridium botulinum* neurotoxin type A protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 60. In some embodiments, a polynucleotide encoding a *Clostridium botulinum* neurotoxin type A protein is a polynucleotide that encodes a polypeptide comprising the amino acid sequence of SEQ ID NO: 60. In some embodiments, a *Clostridium botulinum* neurotoxin type A protein of the present disclosure comprises an alanine to valine mutation at a position corresponding to position 27 of SEQ ID NO: 60.

In some embodiments, a polynucleotide encoding a *Clostridium botulinum* neurotoxin type A protein is a polynucleotide that encodes an N-terminal truncation, a C-terminal truncation, or a fragment of the amino acid sequence of SEQ ID NO: 60. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, but fewer than 1296, consecutive amino acids of SEQ ID NO: 60.

In some embodiments, a polynucleotide of the present disclosure encodes a *Clostridium botulinum* neurotoxin type B protein In some embodiments, a polynucleotide encoding a *Clostridium botulinum* neurotoxin type B protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 61. In some embodiments, a polynucleotide encoding a *Clostridium botulinum* neurotoxin type B protein is a polynucleotide that encodes a polypeptide comprising the amino acid sequence of SEQ ID NO: 61.

In some embodiments, a polynucleotide encoding a *Clostridium botulinum* neurotoxin type B protein is a polynucleotide that encodes an N-terminal truncation, a C-terminal truncation, or a fragment of the amino acid sequence of SEQ ID NO: 61. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, but fewer than 1291, consecutive amino acids of SEQ ID NO: 61.

Fibrillin Proteins

In some embodiments, the present disclosure relates to one or more polynucleotides encoding a full-length fibrillin protein or any isoforms or portions thereof. Any fibrillin protein from any suitable species known in the art may be encoded by a polynucleotide of the present disclosure, including, for example, a human fibrillin protein (see e.g., UniProt accession numbers P35555, P35556, and Q75N90), a mouse fibrillin protein (see, e.g., UniProt accession numbers Q61554 and Q61555), a chimpanzee fibrillin protein (see e.g., UniProt accession numbers A0A2I3RTE4 and K7CZX0), a rat fibrillin protein (see e.g., UniProt accession number G3V9M6 and F1M5Q4), a rabbit fibrillin protein (see e.g., UniProt accession number G1SKM2, G1SUS5, and G1T1H4), etc. Methods of identifying fibrillin protein homologs/orthologs from additional species are known to one of ordinary skill in the art. In some embodiments, a fibrillin protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the fibrillin proteins described herein or known in the art.

In some embodiments, a polynucleotide of the present disclosure encodes a human fibrillin protein.

In some embodiments, a polynucleotide of the present disclosure encodes a human fibrillin-1 protein. In some embodiments, a polynucleotide encoding a human fibrillin-1 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 62. In some embodiments, a polynucleotide encoding a human fibrillin-1 protein is a polynucleotide that encodes a polypeptide comprising the amino acid sequence of SEQ ID NO: 62.

In some embodiments, a polynucleotide encoding a human fibrillin-1 protein is a polynucleotide that encodes an N-terminal truncation, a C-terminal truncation, or a fragment of the amino acid sequence of SEQ ID NO: 62. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, at least 1750, at least 2000, at least 2250, at least 2500, at least 2750, but fewer than 2871, consecutive amino acids of SEQ ID NO: 62.

In some embodiments, a polynucleotide of the present disclosure encodes a human fibrillin-2 protein. In some embodiments, a polynucleotide encoding a human fibrillin-2 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 63. In some embodiments, a polynucleotide encoding a human fibrillin-2 protein is a polynucleotide that encodes a polypeptide comprising the amino acid sequence of SEQ ID NO: 63.

In some embodiments, a polynucleotide encoding a human fibrillin-2 protein is a polynucleotide that encodes an N-terminal truncation, a C-terminal truncation, or a fragment of the amino acid sequence of SEQ ID NO: 63. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, at least 1750, at least 2000, at least 2250, at least 2500, at least 2750, but fewer than 2912, consecutive amino acids of SEQ ID NO: 63.

In some embodiments, a polynucleotide of the present disclosure encodes a human fibrillin-3 protein. In some embodiments, a polynucleotide encoding a human fibrillin-3 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 64. In some embodiments, a polynucleotide encoding a human fibrillin-3 protein is a polynucleotide that encodes a polypeptide comprising the amino acid sequence of SEQ ID NO: 64.

In some embodiments, a polynucleotide encoding a human fibrillin-3 protein is a polynucleotide that encodes an N-terminal truncation, a C-terminal truncation, or a fragment of the amino acid sequence of SEQ ID NO: 64. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, at least 1750, at least 2000, at least 2250, at least 2500, at least 2750, but fewer than 2809, consecutive amino acids of SEQ ID NO: 64.

Exemplary Cosmetic Polypeptides

In some embodiments, one or more cosmetic proteins of the present disclosure (e.g., a first cosmetic protein, a further cosmetic protein, an additional cosmetic protein, and/or a second cosmetic protein) comprise an amino acid sequence comprising at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21 or 53-64. In some embodiments, one or more cosmetic proteins of the present disclosure (e.g., a first cosmetic protein, a further cosmetic protein, an additional cosmetic protein, and/or a second cosmetic protein) comprises a sequence selected from SEQ ID NOS: 15-21 or 53-64.

In some embodiments, one or more cosmetic proteins of the present disclosure (e.g., a first cosmetic protein, a further cosmetic protein, an additional cosmetic protein, and/or a second cosmetic protein) comprise an amino acid sequence comprising at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21, 53-54, or 57-59. In some embodiments, one or more cosmetic proteins of the present disclosure (e.g., a first cosmetic protein, a further cosmetic protein, an additional cosmetic protein, and/or a second cosmetic protein) comprise a sequence selected from SEQ ID NOS: 15-21, 53-54, or 57-59.

First Polynucleotides

In some embodiments, the present disclosure relates to a recombinant nucleic acid comprising a first polynucleotide encoding a first polypeptide comprising a first cosmetic protein. The first cosmetic protein may be any of the cosmetic proteins described herein or known in the art, including, for example a collagen protein, a fibronectin, an elastin, a lumican, a vitronectin/vitronectin receptor, a laminin, a neuromodulator, a fibrillin, etc. In some embodiments, the first cosmetic protein is a structural extracellular matrix protein (e.g., a collagen, elastin, fibronectin, laminin, fibrillin, etc.). In some embodiments, the first cosmetic protein is a collagen, elastin, fibronectin, or laminin protein (e.g., a human collagen, elastin, fibronectin, or laminin protein).

In some embodiments, a recombinant nucleic acid of the present disclosure comprises one copy of the first polynucleotide. In some embodiments, a recombinant nucleic acid of the present disclosure comprises two or more (e.g., two or more, three or more, four or more, five or more, ten or more, etc.) copies of the first polynucleotide. In some embodiments, a recombinant nucleic acid of the present disclosure comprises two copies of the first polynucleotide.

In some embodiments, the first cosmetic protein is a first human collagen protein. The first human collagen protein may be any of the human collagen proteins described herein or known in the art. In some embodiments, the first human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, or COL28. In some embodiments, the first human collagen protein is selected from COL1-1, COL1-2, COL3, COL4-1, COL4-2, COL6-1, COL7, or COL17. In some embodiments, the first human collagen protein is COL1-1. In some embodiments, the first human collagen protein is COL1-2. In some embodiments, the first human collagen protein is COL3. In some embodiments, the first human collagen protein is COL4-1. In some embodiments, the first human collagen protein is COL4-2. In some embodiments, the first human collagen protein is COL6-1. In some embodiments, the first human collagen protein is COL7. In some embodiments, the first human collagen protein is not COL7. In some embodiments, the first human collagen protein is COL17.

In some embodiments, the first polypeptide consists essentially of the first cosmetic protein. In some embodiments, the first polypeptide consists of the first cosmetic protein. In some embodiments, the first polypeptide is the first cosmetic protein.

Chimeric Polypeptides

In some embodiments, the first polypeptide is a chimeric polypeptide comprising the first cosmetic protein. In some embodiments, the first polypeptide is a chimeric polypeptide comprising the first cosmetic protein and a further cosmetic protein. In some embodiments, the chimeric polypeptide comprises a linker polypeptide linking the first cosmetic protein and the further cosmetic protein. In some embodiments, the chimeric polypeptide comprises, from n-terminus to c-terminus, the first cosmetic protein—the linker polypeptide—the further cosmetic protein. The first and/or further cosmetic proteins may be any of the cosmetic proteins described herein or known in the art, including, for example a collagen protein, a fibronectin, an elastin, a lumican, a vitronectin/vitronectin receptor, a laminin, a neuromodulator, a fibrillin, etc. In some embodiments, the first and/or further cosmetic protein is a structural extracellular matrix protein (e.g., a collagen, elastin, fibronectin, laminin, fibrillin, etc.). In some embodiments, the first and/or further cosmetic protein is a collagen, elastin, fibronectin, or laminin protein (e.g., a human collagen, elastin, fibronectin, or laminin protein). In some embodiments, the first and further cosmetic proteins are the same. In some embodiments, the first and further cosmetic proteins are different.

In some embodiments, the linker polypeptide is a cleavable linker polypeptide. Any cleavable linker polypeptide known in the art may be used in the chimeric polypeptides of the present disclosure, including, for example, a T2A linker, a P2A linker, a E2A linker, and F2A linker, etc. In some embodiments, the linker polypeptide is a T2A linker polypeptide. An exemplary nucleic acid sequence encoding a T2A linker polypeptide is provided as SEQ ID NO: 24. An exemplary amino acid sequence of a T2A linker polypeptide is provided as SEQ ID NO: 28. In some embodiments, the linker polypeptide is a P2A linker polypeptide. An exemplary nucleic acid sequence encoding a P2A linker polypeptide is provided as SEQ ID NO: 25. An exemplary amino acid sequence of a P2A linker polypeptide is provided as SEQ ID NO: 29. In some embodiments, the linker polypeptide is an E2A linker polypeptide. An exemplary nucleic acid sequence encoding an E2A linker polypeptide is provided as SEQ ID NO: 26. An exemplary amino acid sequence of an E2A linker polypeptide is provided as SEQ ID NO: 30. In some embodiments, the linker polypeptide is an F2A linker polypeptide. An exemplary nucleic acid sequence encoding an F2A linker polypeptide is provided as SEQ ID NO: 27. An exemplary amino acid sequence of an F2A linker polypeptide is provided as SEQ ID NO: 31.

In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 28-31. In some embodiments, the linker polypeptide comprises a sequence selected from SEQ ID NOS: 28-31.

In some embodiments, the first cosmetic protein is a first collagen protein (e.g., a first human collagen protein), and the further cosmetic protein is a further collagen protein (e.g., a further human collagen protein). An exemplary nucleic acid sequence encoding a chimeric polypeptide comprising a first human collagen protein, a linker polypeptide, and a further human collagen protein is provided as SEQ ID NO: 32.

In some embodiments, the first cosmetic protein is a first human collagen protein, and the further cosmetic protein is a further human collagen protein. The further human collagen protein may be any of the human collagen proteins described herein or known in the art. In some embodiments, the further human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, or COL28. In some embodiments, the further human collagen protein is selected from COL1-1, COL1-2, COL3, COL4-1, COL4-2, COL6-1, COL7, or COL17. In some embodiments, the further human collagen protein is COL1-1. In some embodiments, the further human collagen protein is COL1-2. In some embodiments, the further human collagen protein is COL3. In some embodiments, the further human collagen protein is COL4-1. In some embodiments, the further human collagen protein is COL4-2. In some embodiments, the further human collagen protein is COL6-1. In some embodiments, the further human collagen protein is COL7. In some embodiments, the further human collagen protein is not COL7. In some embodiments, the further human collagen protein is COL17. In some embodiments, the first human collagen protein and the further human collagen protein are the same. In some embodiments, the first human collagen protein and the further human collagen protein are different.

In some embodiments, the first human collagen protein is COL1-1, and the further human collagen protein is selected from COL1-2, COL3, COL4-1, COL4-2, COL6-1, COL7, or COL17. In some embodiments, the first human collagen protein is COL1-1, and the further human collagen protein is COL1-2. In some embodiments, the first human collagen protein is COL1-1, and the further human collagen protein is COL3.

In some embodiments, the first human collagen protein is COL1-2, and the further human collagen protein is COL1-1, COL3, COL4-1, COL4-2, COL6-1, COL7, or COL17. In some embodiments, the first human collagen protein is COL1-2, and the further human collagen protein is COL1-1.

In some embodiments, the first human collagen protein is COL3, and the further human collagen protein is selected from COL1-1, COL1-2, COL4-1, COL4-2, COL6-1, COL7, or COL17.

In some embodiments, the first human collagen protein is COL4-1, and the further human collagen protein is COL1-1, COL1-2, COL3, COL4-2, COL6-1, COL7, or COL17. In some embodiments, the first human collagen protein is COL4-1, and the further human collagen protein is COL4-2.

In some embodiments, the first human collagen protein is COL6-1, and the further human collagen protein is selected from COL1-1, COL1-2, COL3, COL4-1, COL4-2, COL7, or COL17.

In some embodiments, the first human collagen protein is COL7, and the further human collagen protein is COL1-1, COL1-2, COL3, COL4-1, COL4-2, COL6-1, or COL17.

In some embodiments, the first human collagen protein is COL17, and the further human collagen protein is COL1-1, COL1-2, COL3, COL4-1, COL4-2, COL6-1, or COL7.

In some embodiments, the first cosmetic protein is a first laminin protein (e.g., a first human laminin protein), and the further cosmetic protein is a further laminin protein (e.g., a further human laminin protein). In some embodiments, the first cosmetic protein is a first human laminin protein, and the further cosmetic protein is a further human laminin protein. The further human laminin protein may be any of the human laminin proteins described herein or known in the art. In some embodiments, the first human laminin protein is a human *LamA*3 polypeptide and the further human laminin protein is a human LamB3 polypeptide. In some embodiments, the first human laminin protein is a human *LamA*3 polypeptide and the further human laminin protein is a human LamC2 polypeptide. In some embodiments, the first human laminin protein is a human LamB3 polypeptide and the further human laminin protein is a human LamC2 polypeptide.

In some embodiments, the first polynucleotide encodes a monocistronic mRNA. In some embodiments, the monocistronic mRNA comprises an open reading frame (ORF) encoding the first polypeptide.

In some embodiments, the first polynucleotide encodes a polycistronic mRNA. In some embodiments, the polycistronic mRNA comprises an open reading frame (ORF) encoding the first polypeptide.

Polycistronic mRNA

In some embodiments, the first polynucleotide encodes a polycistronic mRNA. In some embodiments, the polycistronic mRNA comprises an open reading frame (ORF) encoding the first polypeptide. In some embodiments, the first polynucleotide encodes a polycistronic mRNA comprising: 1) a first open reading frame (ORF) encoding the first polypeptide, and 2) a second open reading frame (ORF) encoding an additional cosmetic protein. In some embodiments, the polycistronic mRNA further comprises an internal ribosomal entry site (IRES) separating the first ORF and the second ORF. In some embodiments, the polycistronic mRNA comprises, from 5' to 3', the first ORF encoding the first polypeptide—the IRES—the second ORF encoding the additional cosmetic protein. The first polypeptide may be any of the first polypeptides described herein. The additional cosmetic protein may be any of the cosmetic proteins described herein or known in the art, including, for example a collagen protein, a fibronectin, an elastin, a lumican, a vitronectin/vitronectin receptor, a laminin, a neuromodulator, a fibrillin, etc. In some embodiments, the additional cosmetic protein is a structural extracellular matrix protein (e.g., a collagen, elastin, fibronectin, laminin, fibrillin, etc.). In some embodiments, the additional cosmetic protein is a collagen, elastin, fibronectin, or laminin protein (e.g., a human collagen, elastin, fibronectin, or laminin protein).

Any suitable IRES known in the art may be used in the polycistronic mRNAs of the present disclosure, including, for example, a virally-derived IRES (e.g. an IRES derived from a poliovirus, rhinovirus, encephalomyocarditis virus (EMCV), foot-and-mouth disease virus, hepatitis C virus, classic swine fever virus, rous sarcoma virus, human immunodeficiency virus, cricket paralysis virus, Kaposi's sarcoma-associated herpesvirus, etc.), a cellular mRNA-derived IRES (e.g. an IRES derived from growth factor mRNAs, such as fibroblast growth factor 2, platelet-derived growth factor B, and vascular endothelial growth factor; an IRES derived from transcription factor mRNAs, such as antennapedia, ultrabithorax, and NF-κB repressing factor; an IRES derived from oncogene mRNAs, such as c-myc, pim-1, and protein kinase $p58^{PITSLRE}$, etc.), a synthetic IRES (e.g., a CP148 IRES), and others (see e.g., Mokrejs et al. (2007) A Bioinformatical Approach to the Analysis of Viral and Cellular Internal Ribosome Entry Sites. Columbus F editors. New Messenger RNA Research Communications. Hauppauge, N.Y.: Nova Science Publishers; pp. 133-166). In some embodiments, the IRES is a CP148 IRES. An exemplary nucleic acid sequence encoding a CP148 IRES is provided as SEQ ID NO: 22. In some embodiments, the IRES is an EMCV IRES. An exemplary nucleic acid sequence encoding an EMCV IRES is provided as SEQ ID NO: 23.

In some embodiments, the nucleic acid sequence encoding the IRES comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23. In some embodiments, the nucleic acid sequence encoding the IRES comprises the sequence of SEQ ID NO: 22 or SEQ ID NO: 23.

In some embodiments, the first polypeptide is a first collagen protein (e.g., a first human collagen protein), and the additional cosmetic protein is an additional collagen protein (e.g., an additional human collagen protein). An exemplary nucleic acid encoding a polycistronic mRNA comprising a first ORF, an IRES, and second ORF is provided as SEQ ID NO: 33 or SEQ ID NO: 34. The additional human collagen protein may be any of the human collagen proteins described herein. In some embodiments, the additional human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, or COL28. In some embodiments, the additional human collagen protein is selected from COL1-1, COL1-2, COL3, COL4-1, COL4-2, COL6-1, COL7, or COL17. In some embodiments, the additional human collagen protein is COL1-1. In some embodiments, the additional human collagen protein is COL1-2. In some embodiments, the additional human collagen protein is COL3. In some embodiments, the additional human collagen protein is COL4-1. In some embodiments, the additional human collagen protein is COL4-2. In some embodiments, the additional human collagen protein is COL6-1. In some embodiments, the additional human collagen protein is COL7. In some embodiments, the additional human collagen protein is not COL7. In some embodiments, the additional human collagen protein is COL17. In some embodiments, the first human collagen protein and the additional human collagen protein are the same. In some embodiments, the first human collagen protein and the additional human collagen protein are different.

In some embodiments, the first human collagen protein is COL1-1, and the additional human collagen protein is selected from COL1-2, COL3, COL4-1, COL4-2, COL6-1, COL7, or COL17. In some embodiments, the first human collagen protein is COL1-1, and the additional human collagen protein is COL1-2. In some embodiments, the first human collagen protein is COL1-1, and the additional human collagen protein is COL3.

In some embodiments, the first human collagen protein is COL1-2, and the additional human collagen protein is selected from COL1-1, COL3, COL4-1, COL4-2, COL6-1, COL7, or COL17. In some embodiments, the first human collagen protein is COL1-2, and the additional human collagen protein is COL1-1.

In some embodiments, the first human collagen protein is COL3, and the additional human collagen protein is selected from COL1-1, COL1-2, COL4-1, COL4-2, COL6-1, COL7, or COL17.

In some embodiments, the first human collagen protein is COL4-1, and the additional human collagen protein is selected from COL1-1, COL1-2, COL3, COL4-2, COL6-1, COL7, or COL17. In some embodiments, the first human collagen protein is COL4-1, and the additional human collagen protein is COL4-2.

In some embodiments, the first human collagen protein is COL6-1, and the additional human collagen protein is selected from COL1-1, COL1-2, COL3, COL4-1, COL4-2, COL7, or COL17.

In some embodiments, the first human collagen protein is COL7, and the additional human collagen protein is selected from COL1-1, COL1-2, COL3, COL4-1, COL4-2, COL6-1, or COL17.

In some embodiments, the first human collagen protein is COL17, and the additional human collagen protein is selected from COL1-1, COL1-2, COL3, COL4-1, COL4-2, COL6-1, or COL7.

In some embodiments, the first polypeptide is a first collagen protein (e.g., a first human collagen protein), and the additional cosmetic protein is an additional collagen protein (e.g., an additional human collagen protein).

In some embodiments, the first polypeptide is a first laminin protein (e.g., a first human laminin protein), and the additional cosmetic protein is an additional laminin protein (e.g., an additional human laminin protein). In some embodiments, the first polypeptide is a first human laminin protein, and the additional cosmetic protein is an additional human laminin protein. The additional human laminin protein may be any of the human laminin proteins described herein or known in the art. In some embodiments, the first human laminin protein is a human LamA3 polypeptide and the additional human laminin protein is a human LamB3 polypeptide. In some embodiments, the first human laminin protein is a human LamA3 polypeptide and the additional human laminin protein is a human LamC2 polypeptide. In some embodiments, the first human laminin protein is a human LamB3 polypeptide and the additional human laminin protein is a human LamC2 polypeptide.

Second Polynucleotides

In some embodiments, the present disclosure relates to a recombinant nucleic acid further comprising a second polynucleotide encoding a second cosmetic protein. The second cosmetic protein may be any of the cosmetic proteins described herein or known in the art, including, for example a collagen protein, a fibronectin, an elastin, a lumican, a vitronectin/vitronectin receptor, a laminin, a neuromodulator, a fibrillin, etc. In some embodiments, the second cosmetic protein is a structural extracellular matrix protein (e.g., a collagen, elastin, fibronectin, laminin, fibrillin, etc.). In some embodiments, the second cosmetic protein is a collagen, elastin, fibronectin, or laminin protein (e.g., a human collagen, elastin, fibronectin, or laminin protein). In some embodiments, the first and second cosmetic proteins are the same. In some embodiments, the first and second cosmetic proteins are different. In some embodiments, the recombinant nucleic acid comprises one copy of the second polynucleotide. In some embodiments, the recombinant nucleic acid comprises two or more (e.g., two or more, three or more, four or more, five or more, ten or more, etc.) copies of the second polynucleotide. In some embodiments, the recombinant nucleic acid comprises two copies of the second polynucleotide.

In some embodiments, the second cosmetic protein is a collagen protein. In some embodiments, the second cosmetic protein is a second human collagen protein. The second human collagen protein may be any of the human collagen proteins described herein. In some embodiments, the second human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, or COL28. In some embodiments, the second human collagen protein is selected from COL1-1, COL1-2, COL3, COL4-1, COL6-1, COL7, or COL17. In some embodiments, the second human collagen protein is COL1-1. In some embodiments, the second human collagen protein is COL1-2. In some embodiments, the second human collagen protein is COL3. In some embodiments, the second human collagen protein is COL4-1. In some embodiments, the second human collagen protein is COL4-2. In some embodiments, the second human collagen protein is COL6-1. In some embodiments, the second human collagen protein is COL7. In some embodiments, the second human collagen protein is not COL7. In some embodiments, the second human collagen protein is COL17.

In some embodiments, the first polynucleotide encodes a first collagen protein and the second polynucleotide encodes a second collagen protein. In some embodiments, the first polynucleotide encodes a first human collagen protein and the second polynucleotide encodes a second human collagen protein. In some embodiments, the first human collagen protein (encoded by the first polynucleotide) and the second human collagen protein (encoded by the second polynucleotide) are the same. In some embodiments, the first human collagen protein (encoded by the first polynucleotide) and the second human collagen protein (encoded by the second polynucleotide) are different.

In some embodiments, the first human collagen protein is COL1-1, and the second human collagen protein is selected from COL1-2, COL3, COL4-1, COL4-2, COL6-1, COL7, or COL17. In some embodiments, the first human collagen protein is COL1-1, and the second human collagen protein is COL1-2. In some embodiments, the first human collagen protein is COL1-1, and the second human collagen protein is COL3.

In some embodiments, the first human collagen protein is COL1-2, and the second human collagen protein is selected from COL1-1, COL3, COL4-1, COL4-2, COL6-1, COL7, or COL17. In some embodiments, the first human collagen protein is COL1-2, and the second human collagen protein is COL1-1.

In some embodiments, the first human collagen protein is COL3, and the second human collagen protein is selected from COL1-1, COL1-2, COL4-1, COL4-2, COL6-1, COL7, or COL17.

In some embodiments, the first human collagen protein is COL4-1, and the second human collagen protein is selected from COL1-2, COL1-2, COL3, COL4-2, COL6-1, COL7, or COL17. In some embodiments, the first human collagen protein is COL4-1, and the second human collagen protein is COL4-2.

In some embodiments, the first human collagen protein is COL6-1, and the second human collagen protein is selected from COL1-1, COL1-2, COL3, COL4-1, COL4-2, COL7, or COL17.

In some embodiments, the first human collagen protein is COL7, and the second human collagen protein is selected from COL1-1, COL1-2, COL3, COL4-1, COL4-2, COL6-1, or COL17.

In some embodiments, the first human collagen protein is COL17, and the second human collagen protein is selected from COL1-1, COL1-2, COL3, COL4-1, COL4-2, COL6-1, or COL7.

In some embodiments, the first polynucleotide encodes a first laminin protein (e.g., a first human laminin protein), and the second polynucleotide encodes a second laminin protein (e.g., a second human laminin protein). In some embodiments, the first polynucleotide encodes a first human laminin polypeptide and the second polynucleotide encodes a second human laminin protein. The second human laminin protein may be any of the human laminin proteins described herein or known in the art. In some embodiments, the first human laminin protein is a human LamA3 polypeptide and the second human laminin protein is a human LamB3 polypeptide. In some embodiments, the first human laminin protein is a human LamA3 polypeptide and the second human laminin protein is a human LamC2 polypeptide. In some embodiments, the first human laminin protein is a human LamB3 polypeptide and the second human laminin protein is a human LamC2 polypeptide Recombinant Nucleic Acids In some embodiments, the present disclosure relates to recombinant nucleic acids comprising any one or more of the polynucleotides described herein. In some embodiments, the recombinant nucleic acid comprises one copy of the first polynucleotide. In some embodiments, the recombinant nucleic acid comprises two copies of the first polynucleotide. In some embodiments, the recombinant nucleic acid comprises one copy of the first polynucleotide and one copy of the second polynucleotide. In some embodiments, the recombinant nucleic acid comprises one copy of the first polynucleotide and two copies of the second polynucleotide. In some embodiments, the recombinant nucleic acid comprises two copies of the first polynucleotide and one copy of the second polynucleotide. In some embodiments, the recombinant nucleic acid comprises two copies of the first polynucleotide and two copies of the second polynucleotide.

In some embodiments, the recombinant nucleic acid is a vector (e.g., an expression vector, a display vector, etc.). In some embodiments, the vector is a DNA vector or an RNA vector. Generally, vectors suitable to maintain, propagate, and/or express polynucleotides to produce one or more polypeptides in a subject may be used. Examples of suitable vectors may include, for example, plasmids, cosmids, episomes, transposons, and viral vectors (e.g., adenoviral vectors, adeno-associated viral vectors, vaccinia viral vectors, Sindbis-viral vectors, measles vectors, herpes viral vectors, lentiviral vectors, retroviral vectors, etc.). In some embodiments, the vector is a herpes viral vector. In some embodiments, the vector is capable of autonomous replication in a host cell. In some embodiments, the vector is incapable of autonomous replication in a host cell. In some embodiments, the vector can integrate into a host DNA. In some embodiments, the vector cannot integrate into a host DNA (e.g., is episomal). Methods of making vectors containing one or more polynucleotides of interest are well known to one of ordinary skill in the art, including, for example, by chemical synthesis, or by artificial manipulation of isolated segments of nucleic acids (e.g., by genetic engineering techniques).

In some embodiments, a recombinant nucleic acid of the present disclosure is a herpes simplex virus (HSV) amplicon. Herpes virus amplicons, including the structural features and methods of making the same, are generally known to one of ordinary skill in the art (see e.g., de Silva S. and Bowers W. "Herpes Virus Amplicon Vectors". *Viruses* 2009, 1, 594-629). In some embodiments, the herpes simplex virus amplicon is an HSV-1 amplicon. In some embodiments, the herpes simplex virus amplicon is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and/or HSV/Sleeping Beauty hybrid amplicons. In some embodiments, the amplicon is an HSV/AAV hybrid amplicon. In some embodiments, the amplicon is an HSV/Sleeping Beauty hybrid amplicon.

In some embodiments, a recombinant nucleic acid of the present disclosure is a recombinant herpes virus genome. The recombinant herpes virus genome may be a recombinant genome from any member of the Herpesviridae family of DNA viruses known in the art, including, for example, a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any combinations or any derivatives thereof. In some embodiments, the recombinant herpes virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes virus genes. In some embodiments, the recombinant herpes virus genome is attenuated (e.g., as compared to a corresponding, wild-type herpes virus genome). In some embodiments, the recombinant herpes virus genome is replication-competent. In some embodiments, the recombinant herpes virus genome is replication-defective In some embodiments, the recombinant nucleic acid is a recombinant herpes simplex virus (HSV) genome. In some embodiments, the recombinant herpes simplex virus genome is a recombinant type 1 herpes simplex virus (HSV-1) genome, a recombinant type 2 herpes simplex virus (HSV-2) genome, or any derivatives thereof. In some embodiments, the recombinant herpes simplex virus genome is a recombinant HSV-1 genome. In some embodiments, the recombinant herpes simplex virus genome is replication-competent. In some embodiments, the recombinant herpes simplex virus genome is replication-defective. In some embodiments, the recombinant herpes simplex virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes simplex virus genes. As used herein, an "inactivating mutation" may refer to any mutation that results in a gene or regulon product (RNA or protein) having reduced, undetectable, or eliminated quantity and/or function (e.g., as compared to a corresponding sequence lacking the inactivating mutation). Examples of inactivating mutations may include, but are not limited to, deletions, insertions, point mutations, and rearrangements in transcriptional control sequences (promoters, enhancers, insulators, etc.) and/or coding sequences of a given gene or regulon. Any suitable method of measuring the quantity of a gene or regulon product known in the art may be used, including, for example, qPCR, Northern blots, RNAseq, western blots, ELISAs, etc.

In some embodiments, the recombinant herpes simplex virus genome comprises an inactivating mutation in at least one, at least two, at least three, at least four, at least five, at least six, at least seven, or all eight of the Infected Cell Protein (or Infected Cell Polypeptide) (ICP) 0, ICP4, ICP22, ICP27, ICP47, thymidine kinase (tk), Long Unique Region (UL) 41 and/or UL55 herpes simplex virus genes. In some embodiments, the recombinant herpes simplex virus genome does not comprise an inactivating mutation in the ICP34.5 and/or ICP47 herpes simplex virus genes (e.g., to avoid production of an immune-stimulating virus). In some embodiments, the recombinant herpes simplex virus genome does not comprise an inactivating mutation in the ICP34.5 herpes simplex virus gene (one or both copies). In some embodiments, the recombinant herpes simplex virus genome does not comprise an inactivating mutation in the ICP47 herpes simplex virus gene. In some embodiments, the recombinant herpes simplex virus genome does not comprise an inactivating mutation in the ICP34.5 (one or both copies) and ICP47 herpes simplex virus genes. In some embodiments, the recombinant herpes simplex virus genome is not oncolytic.

In some embodiments, the recombinant herpes simplex virus genome comprises an inactivating mutation in the ICP0 gene (one or both copies). In some embodiments, the recombinant herpes simplex virus genome comprises an inactivating mutation in the ICP0 gene (one or both copies), and further comprises an initiating mutation in the ICP4 (one or both copies) ICP22, ICP27, ICP47, UL41, and/or UL55 genes. In some embodiments, the recombinant herpes simplex virus genome comprises an inactivating mutation in the ICP0 gene (one or both copies), and an inactivating mutation in the ICP4 gene (one or both copies). In some embodiments, the recombinant herpes simplex virus genome comprises an inactivating mutation in the ICP0 gene (one or both copies), and an inactivating mutation in the ICP22 gene. In some embodiments, the recombinant herpes simplex virus genome comprises an inactivating mutation in the ICP0 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), and an inactivating mutation in the ICP22 gene. In some embodiments, the recombinant herpes simplex virus genome comprises an inactivating mutation in the ICP0 gene (one or both copies), an inactivating mutation in the ICP4 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP22 gene, and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP0 (one or both copies), ICP4 (one or both copies), ICP22, and/or UL41 genes. In some embodiments, the recombinant herpes simplex virus genome further comprises an inactivating mutation in the ICP27, ICP47, and/or UL55 genes.

In some embodiments, the recombinant herpes simplex virus genome comprises an inactivating mutation in the ICP4 gene (one or both copies). In some embodiments, the recombinant herpes complex virus genome comprises an inactivating mutation in the ICP4 (one or both copies, and further comprises an inactivating mutation in the ICP0 (one or both copies), ICP22, ICP27, ICP47, UL41, and/or UL55 genes. In some embodiments, the recombinant herpes simplex virus genome comprises an inactivating mutation in the ICP4 gene (one or both copies), and an inactivating mutation in the ICP22 gene. In some embodiments, the recombinant herpes simplex virus genome comprises an inactivating mutation in the ICP4 gene (one or both copies), and an inactivating mutation in the UL41 gene. In some embodiments, the recombinant herpes simplex virus genome comprises an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP4 (one or both copies), ICP22, and/or UL41 genes. In some embodiments, the recombinant herpes simplex virus genome further comprises an inactivating mutation in the ICP0, ICP27, ICP47, and/or UL55 genes.

In some embodiments, the recombinant herpes simplex virus genome comprises an inactivating mutation in the ICP22 gene. In some embodiments, the recombinant herpes simplex virus genome comprises an inactivating mutation in the ICP22 gene, and further comprises an inactivating mutation in the ICP0 (one or both copies), ICP4 (one or both copies), ICP27, ICP47, UL41, and/or UL55 genes. In some embodiments, the recombinant herpes simplex virus genome comprises an inactivating mutation in the ICP22 gene, and an inactivating mutation UL41 gene. In some embodiments, the inactivating mutation is a deletion of the coding sequence of the ICP22 and/or UL41 genes. In some embodiments, the recombinant herpes simplex virus genome further comprises an inactivating mutation in the ICP0 (one or both copies), ICP4 (one or both copies), ICP27, ICP47, and/or UL55 genes.

In some embodiments, the recombinant herpes simplex virus genome comprises an inactivating mutation in the ICP27 gene. In some embodiments, the recombinant herpes simplex virus genome comprises an inactivating mutation in the ICP27 gene, and further comprises an inactivating mutation in the ICP0 (one or both copies), ICP4 (one or both copies), ICP22, ICP47, UL41, and/or UL55 genes. In some embodiments, the inactivating mutation is a deletion of the coding sequence of the ICP27 gene.

In some embodiments, the recombinant herpes simplex virus genome comprises an inactivating mutation in the ICP47 gene. In some embodiments, the recombinant herpes simplex virus genome comprises an inactivating mutation in the ICP47 gene, and further comprises an inactivating mutation in the ICP0 (one or both copies), ICP4 (one or both copies), ICP22, ICP27, UL41, and/or UL55 genes. In some embodiments, the inactivating mutation is a deletion of the coding sequence of the ICP47 gene.

In some embodiments, the recombinant herpes simplex virus genome comprises an inactivating mutation in the UL41 gene. In some embodiments, the recombinant herpes simplex virus genome comprises an inactivating mutation in the UL41 gene, and further comprises an inactivating mutation in the ICP0 (one or both copies), ICP4 (one or both copies), ICP22, ICP27, ICP47, and/or UL55 genes. In some embodiments, the inactivating mutation is a deletion of the coding sequence of the UL41 gene.

In some embodiments, the recombinant herpes simplex virus genome comprises an inactivating mutation in the UL55 gene. In some embodiments, the recombinant herpes simplex virus genome comprises an inactivating mutation in the UL55 gene, and further comprises an inactivating mutation in the ICP0 (one or both copies), ICP4 (one or both copies), ICP22, ICP27, ICP47, and/or UL41 genes. In some embodiments, the inactivating mutation is a deletion of the coding sequence of the UL55 gene.

In some embodiments, the recombinant herpes simplex virus genome comprises an inactivating mutation in (e.g., a deletion of) the internal repeat (Joint) region comprising the internal repeat long (IRL) and internal repeat short (IRS) regions. In some embodiments, inactivation (e.g., deletion) of the Joint region eliminates one copy each of the ICP4 and ICP0 genes. In some embodiments, inactivation (e.g., deletion) of the Joint region further inactivates (e.g., deletes) the promoter for the ICP22 and ICP47 genes. If desired, expression of one or both of these genes can be restored by insertion of an immediate early promoter into the recombinant herpes simplex virus genome (see e.g., Hill et al. (1995). Nature 375(6530): 411-415; Goldsmith et al. (1998). J Exp Med 187(3): 341-348). Without wishing to be bound by theory, it is believed that inactivating (e.g., deleting) the Joint region may contribute to the stability of the recombinant herpes simplex virus genome and/or allow for the recombinant herpes simplex virus genome to accommodate more and/or larger transgenes.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes, and a deletion in the promoter region of the ICP22 and ICP47 genes. In some embodiments, the recombinant herpes simplex virus genome further comprises an inactivating mutation in the ICP0 and/or UL41 genes.

In some embodiments, the recombinant herpes simplex virus genome comprises an inactivating mutation in the ICP0 (one or both copies) gene. In some embodiments, the recombinant herpes simplex virus genome comprises an inactivating mutation in the ICP0 (one or both copies) and ICP4 (one or both copies) genes. In some embodiments, the recombinant herpes simplex virus genome comprises an inactivating mutation in the ICP0 (one or both copies), ICP4 (one or both copies), and ICP22 genes. In some embodiments, the recombinant herpes simplex virus genome comprises an inactivating mutation in the ICP0 (one or both copies), ICP4 (one or both copies), ICP22, and ICP27 genes. In some embodiments, the recombinant herpes simplex virus genome comprises an inactivating mutation in the ICP0 (one or both copies), ICP4 (one or both copies), ICP22, ICP27 and UL55 genes. In some embodiments, the inactivating mutation in the ICP0 (one or both copies), ICP4 (one or both copies), ICP22, ICP27 and/or UL55 genes comprises a deletion of the coding sequence of the ICP0, ICP4 (one or both copies), ICP22, ICP27 and/or UL55 genes. In some embodiments, the recombinant herpes simplex virus genome further comprises an inactivating mutation in the ICP47 and/or the UL41 genes.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0 (one or both copies), ICP4 (one or both copies), ICP22, ICP27, ICP47, tk, UL41 and UL55 herpes simplex viral gene loci. In some embodiments, a recombinant herpes simplex virus genome comprises one or more polynucleotides of the present disclosure within one or both of the viral ICP4 gene loci (e.g., a recombinant virus carrying a first polynucleotide encoding a first human collagen protein in one or both of the ICP4 loci; a recombinant virus carrying a second polynucleotide encoding a second human collagen protein in one or both of the ICP4 loci; etc.). In some embodiments, a recombinant herpes simplex virus genome comprises one or more polynucleotide of the present disclosure within the viral ICP22 gene locus (e.g., a recombinant virus carrying a first polynucleotide encoding a first human collagen protein in the ICP22 locus; a recombinant virus carrying a second polynucleotide encoding a second human collagen protein in the ICP22 locus; etc.). In some embodiments, a recombinant herpes simplex virus genome comprises one or more polynucleotide of the present disclosure within the viral UL41 gene locus (e.g., a recombinant virus carrying a first polynucleotide encoding a first human collagen protein in the UL41 locus; a recombinant virus carrying a second polynucleotide encoding a second human collagen protein in the UL41 locus; etc.). In some embodiments, a recombinant herpes simplex virus genome comprises one or more polynucleotides of the present disclosure within one or both of the viral ICP4 gene loci, and one or more polynucleotides of the present disclosure within the viral ICP22 locus (e.g., a recombinant virus carrying a first polynucleotide encoding a first human collagen protein in one or both of the ICP4 loci and a second polynucleotide encoding a second human collagen protein in the ICP22 locus; a recombinant virus carrying a second polynucleotide encoding a second human collagen protein in one or both of the ICP4 loci and a first polynucleotide encoding a first human collagen protein in the ICP22 locus; etc.). In some embodiments, a recombinant herpes simplex virus genome comprises one or more polynucleotides of the present disclosure within one or both of the viral ICP4 gene loci, and one or more polynucleotides of the present disclosure within the viral UL41 locus (e.g., a recombinant virus carrying a first polynucleotide encoding a first human collagen protein in one or both of the ICP4 loci and a second polynucleotide encoding a second human collagen protein in the UL41 locus; a recombinant virus carrying a second polynucleotide encoding a second human collagen protein in one or both of the ICP4 loci and a first polynucleotide encoding a first human collagen protein in the UL41 locus; etc.). In some embodiments, a recombinant herpes simplex virus genome comprises one or more polynucleotides of the present disclosure within one or both of the viral ICP4 gene loci, one or more polynucleotides of the present disclosure within the viral ICP22 locus, and one or more polynucleotides of the present disclosure within the viral UL41 locus (e.g., a recombinant virus carrying a first polynucleotide encoding a first human collagen protein in one or both of the ICP4 loci and a second polynucleotide encoding a second human collagen protein in the ICP22 and UL41 loci; a recombinant virus carrying a second polynucleotide encoding a second human collagen protein in one or both of the ICP4 loci and a first polynucleotide encoding a first human collagen protein in the ICP22 and UL41 loci; etc.).

In some embodiments, the recombinant herpes virus genome (e.g., a recombinant herpes simplex virus genome) has been engineered to decrease or eliminate expression of one or more toxic herpes simplex genes (such as one or both copies of the HSV ICP0 gene, one or both copied of the HSV ICP4 gene, the ICP22 gene, and/or the UL41 gene). In some embodiments, the recombinant herpes virus genome (e.g., a recombinant herpes simplex virus genome) has been engineered to reduce cytotoxicity of the recombinant genome (e.g., when introduced into a target cell) as compared to a corresponding wild-type herpes virus genome (e.g., a wild-type herpes simplex virus genome). In some embodiments, cytotoxicity (e.g., in human keratinocytes and/or fibroblast cells) of the recombinant virus genome (e.g., a recombinant herpes simplex virus genome) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% as compared to a corresponding wild-type herpes virus genome (e.g., measuring the relative cytotoxicity of a recombinant ΔICP4 (one or both copies) herpes simplex virus genome vs. a wild-type herpes simplex virus genome in human keratinocytes or fibroblasts (primary cells or cell lines); measuring the relative cytotoxicity of a recombinant ΔICP4 (one or both copies)/ΔICP22 herpes simplex virus genome vs. a wild-type herpes simplex virus genome in human keratinocytes or fibroblasts (primary cells or cell lines); etc.). In some embodiments, cytotoxicity (e.g., in human keratinocytes and/or fibroblast cells) of the recombinant herpes virus genome (e.g., a recombinant herpes simplex virus genome) is reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more as compared to a corresponding wild-type herpes virus genome (e.g., measuring the relative cytotoxicity of a recombinant ΔICP4 (one or both copies) herpes simplex virus genome vs. a wild-type herpes simplex virus genome in human keratinocytes or fibroblasts (primary cells or cell lines); measuring the relative cytotoxicity of a recombinant ΔICP4 (one or both copies)/ΔICP22 herpes simplex virus genome vs. a wild-type herpes simplex virus genome in human keratinocytes or fibroblasts (primary cells or cell lines); etc.). Methods of measuring cytotoxicity are known to one of ordinary skill in the art, including, for example, through the use of vital dyes (formazan dyes), protease biomarkers, an MTT assay (or an assay using related tetrazolium salts such as XTT, MTS, water-soluble tetrazolium salts, etc.), measuring ATP content, etc.

In some embodiments, the recombinant herpes virus genome (e.g., a recombinant herpes simplex virus genome) has been engineered to reduce its impact on host cell proliferation after exposure of the target cell to the recombinant genome, as compared to a corresponding wild-type herpes virus genome (e.g., a wild-type herpes simplex virus genome). In some embodiments, the target cell is a human cell. In some embodiments, the target cell is a cell of the epidermis and/or dermis. In some embodiments, the target cell is a keratinocyte and/or fibroblast. In some embodiments, host cell proliferation (e.g., human keratinocytes and/or fibroblast cells) after exposure to the recombinant genome is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% faster as compared to host cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in human keratinocytes or fibroblasts (primary cells or cell lines); measuring the relative cellular proliferation after exposure to a recombinant ΔICP4 (one or both copies)/ΔICP22 herpes simplex virus genome vs. cellular proliferation after exposure to a wild-type herpes simplex virus genome in human keratinocytes or fibroblasts (primary cells or cell lines); etc.). In some embodiments, host cell proliferation (e.g., human keratinocytes and/or fibroblast cells) after exposure to the recombinant genome is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, or at least about 1000-fold faster as compared to host cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in human keratinocytes or fibroblasts (primary cells or cell lines); measuring the relative cellular proliferation after exposure to a recombinant ΔICP4 (one or both copies)/ΔICP22 herpes simplex virus genome vs. cellular proliferation after exposure to a wild-type herpes simplex virus genome in human keratinocytes or fibroblasts (primary cells or cell lines); etc.). Methods of measuring cellular proliferation are known to one of ordinary skill in the art, including, for example, through the use of a Ki67 cell proliferation assay, a BrdU cell proliferation assay, etc.

A vector (e.g., herpes viral vector) may include one or more polynucleotides of the present disclosure in a form suitable for expression of the polynucleotide in a host cell. Vectors may include one or more regulatory sequences operatively linked to the polynucleotide to be expressed (e.g., as described above).

In some embodiments, a recombinant nucleic acid of the present disclosure (e.g., a recombinant herpes simplex virus genome) comprises one or more of the polynucleotides described herein inserted in any orientation in the recombinant nucleic acid. If the recombinant nucleic acid comprises two or more polynucleotides described herein (e.g., two or more, three or more, etc.), the polynucleotides may be inserted in the same orientation or opposite orientations to one another. Without wishing to be bound be theory, incorporating two polynucleotides (e.g., two transgenes) into a recombinant nucleic acid (e.g., a vector) in an antisense orientation may help to avoid read-through and ensure proper expression of each polynucleotide.

IV. Viruses

Certain aspects of the present disclosure relate to viruses comprising any of the polynucleotides and/or recombinant nucleic acids described herein. In some embodiments, the virus is capable of infecting one or more target cells of a subject (e.g., a human). In some embodiments, the virus is suitable for delivering the polynucleotides and/or recombinant nucleic acids into one or more target cells of a subject (e.g., a human subject). In some embodiments, the one or more target cell are one or more human cells. In some embodiments, the one or more target cells are one or more cells of the skin (e.g., one or more cells of the epidermis, dermis, and/or subcutis). In some embodiments, the one or more cells are selected from keratinocytes, melanocytes, Langerhans cells, Merkel cells, mast cells, fibroblasts, and/or adipocytes. In some embodiments, the one or more cells are keratinocytes. In some embodiments, the one or more cells reside in the stratum corneum, stratum granulosum, stratum spinulosum, stratum basale, and/or basement membrane. In some embodiments, the one or more target cells are one or more epidermal cells.

Any suitable virus known in the art may be used, including, for example, adenovirus, adeno-associated virus, retrovirus, lentivirus, sendai virus, herpes virus (e.g., a herpes simplex virus), vaccinia virus, and/or any hybrid virus thereof. In some embodiments, the virus is attenuated. In some embodiments, the virus is replication-defective. In some embodiments, the virus is replication-competent. In some embodiments, the virus has been modified to alter its tissue tropism relative to the tissue tropism of an unmodified, wild-type virus. In some embodiments, the virus has reduced cytotoxicity as compared to a corresponding wild-type virus. Methods for producing a virus comprising recombinant nucleic acids are well known to one of ordinary skill in the art.

In some embodiments, the virus is a member of the Herpesviridae family of DNA viruses, including, for example, a herpes simplex virus, a varicella zoster virus, a human cytomegalovirus, a herpesvirus 6A, a herpesvirus 6B, a herpesvirus 7, and a Kaposi's sarcoma-associated herpesvirus, etc. In some embodiments, the herpes virus is attenuated. In some embodiments, the herpes virus is replication-defective. In some embodiments, the herpes virus is replication-competent. In some embodiments, the herpes virus has reduced cytotoxicity as compared to a corresponding wild-type herpes virus. In some embodiments, the herpes virus is not oncolytic.

In some embodiments, the virus is a herpes simplex virus. Herpes simplex viruses comprising recombinant nucleic acids may be produced by a process disclosed, for example, in WO2015/009952 and/or WO2017/176336. In some embodiments, the herpes simplex virus is attenuated. In some embodiments, the herpes simplex virus is replication-competent. In some embodiments, the herpes simplex virus is replication-defective. In some embodiments, the herpes simplex virus is a herpes simplex type 1 virus (HSV-1), a herpes simplex type 2 virus (HSV-2), or any derivatives thereof. In some embodiments, the herpes simplex virus is a herpes simplex type 1 virus (HSV-1). In some embodiments, the HSV-1 is attenuated. In some embodiments, the HSV-1 has reduced cytotoxicity as compared to a corresponding wild-type HSV-1. In some embodiments, the HSV-1 is not oncolytic.

In some embodiments, the herpes simplex virus has been modified to alter its tissue tropism relative to the tissue tropism of an unmodified, wild-type herpes simplex virus. In some embodiments, the herpes simplex virus comprises a modified envelope. In some embodiments, the modified envelope comprises one or more (e.g., one or more, two or more, three or more, four or more, etc.) mutant herpes simplex virus glycoproteins. Examples of herpes simplex virus glycoproteins may include, but are not limited to, the glycoproteins gB, gC, gD, gH, and gL. In some embodiments, the modified envelope alters the herpes simplex virus tissue tropism relative to a wild-type herpes simplex virus.

In some embodiments, the transduction efficiency (in vitro and/or in vivo) of a virus of the present disclosure (e.g., a herpes virus) for one or more target cells (e.g., one or more human keratinocytes and/or fibroblasts) is at least about 25%. For example, the transduction efficiency of the virus for one or more target cells may be at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 99.5%, or more. In some embodiments, the virus is a herpes simplex virus and the transduction efficiency of the virus for one or more target cells (e.g., one or more human keratinocytes and/or fibroblasts) is about 85% to about 100%. In some embodiments, the virus is a herpes simplex virus and the transduction efficiency of the virus for one or more target cells (e.g., one or more human keratinocytes and/or fibroblasts) is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%. Methods of measuring viral transduction efficiency in vitro or in vivo are well known to one of ordinary skill in the art, including, for example, qPCR analysis, deep sequencing, western blotting, fluorometric analysis (such as fluorescent in situ hybridization (FISH), fluorescent reporter gene expression, immunofluorescence, FACS), etc.

V. Compositions and Formulations

Certain aspects of the present disclosure relate to compositions and formulations (e.g., pharmaceutical compositions and formulations) comprising any of the recombinant nucleic acids (e.g., a recombinant herpes virus genome) and/or viruses (e.g., a herpes virus comprising a recombinant genome described herein (such as a herpes simplex virus comprising a recombinant herpes simplex virus genome), and an excipient or carrier (e.g., a pharmaceutically acceptable excipient or carrier). In some embodiments, the composition or formulation is a cosmetic composition or formulation (e.g., a skin care product).

In some embodiments, the composition or formulation comprises any one or more of the viruses (e.g., herpes viruses) described herein. In some embodiments, the composition or formulation comprises from about $10^4$ to about $10^{12}$ plaque forming units (PFU)/mL of the virus. For example, the composition or formulation may comprise from about $10^4$ to about $10^{12}$, about $10^5$ to about $10^{12}$, about $10^6$ to about $10^{12}$, about $10^7$ to about $10^{12}$, about $10^8$ to about $10^{12}$, about $10^9$ to about $10^{12}$, about $10^{10}$ to about $10^{12}$, about $10^{11}$ to about $10^{12}$, about $10^4$ to about $10^{11}$, about $10^5$ to about $10^{11}$, about $10^6$ to about $10^{11}$, about $10^7$ to about $10^{11}$, about $10^8$ to about $10^{11}$, about $10^9$ to about $10^{11}$, about $10^{10}$ to about $10^{11}$, about $10^4$ to about $10^{10}$, about $10^5$ to about $10^{10}$, about $10^6$ to about $10^{10}$, about $10^7$ to about $10^{10}$, about $10^8$ to about $10^{10}$, about $10^9$ to about $10^{10}$, about $10^4$ to about $10^9$, about $10^5$ to about $10^9$, about $10^6$ to about $10^9$, about $10^7$ to about $10^9$, about $10^8$ to about $10^9$, about $10^4$ to about $10^8$, about $10^5$ to about $10^8$, about $10^6$ to about $10^8$, about $10^7$ to about $10^8$, about $10^4$ to about $10^7$, about $10^5$ to about $10^7$, about $10^6$ to about $10^7$, about $10^4$ to about $10^6$, about $10^5$ to about $10^6$, or about $10^4$ to about $10^5$ PFU/mL of the virus. In some embodiments, the composition or formulation comprises about $10^4$, about $10^5$, about $10^6$, about $10^7$, about $10^8$, about $10^9$, about $10^{10}$, about $10^{11}$, or about $10^{12}$ PFU/mL of the virus.

Compositions and formulations (e.g., pharmaceutical compositions and formulations) as described herein can be prepared by mixing the active ingredient(s) (such as a recombinant nucleic acid or a virus) having the desired degree of purity with one or more acceptable carriers or excipients. Acceptable carriers or excipients (e.g., pharmaceutically acceptable carriers or excipients) are generally nontoxic to recipients at the dosages and concentrations employed, and may include, but are not limited to: buffers (such as phosphate, citrate, acetate, and other organic acids); antioxidants (such as ascorbic acid and methionine); preservatives (such as octadecyldimethylbenzyl ammonium chloride, benzalkonium chloride, benzethonium chloride, phenol, butyl or benzyl alcohol, alkyl parabens, catechol, resorcinol, cyclohexanol, 3-pentanol, and m-cresol); amino acids (such as glycine, glutamine, asparagine, histidine, arginine, or lysine); low molecular weight (less than about 10 residues) polypeptides; proteins (such as serum albumin, gelatin, or immunoglobulins); polyols (such as glycerol, e.g., formulations including 10% glycerol); hydrophilic polymers (such as polyvinylpyrrolidone); monosaccharides, disaccharides, and other carbohydrates (including glucose, mannose, or dextrins); chelating agents (such as EDTA); sugars (such as sucrose, mannitol, trehalose, or sorbitol); salt-forming counter-ions (such as sodium); metal complexes (such as Zn-protein complexes); liposomes (e.g., cationic lipids); nanoparticle carriers; and/or non-ionic surfactants (such as polyethylene glycol (PEG)). A thorough discussion of carriers is available in REMINGTON'S PHARMACEUTICAL SCIENCES (Mack Pub. Co., N.J. 1991).

In some embodiments, the composition or formulation comprises one or more lipid (e.g., cationic lipid) carriers. In some embodiments, the composition or formulation comprises one or more nanoparticle carriers. Nanoparticles are submicron (less than about 1000 nm) sized drug delivery vehicles that can carry encapsulated drugs (such as synthetic small molecules, proteins, peptides, cells, viruses, and nucleic acid-based biotherapeutics for rapid or controlled release. A variety of molecules (e.g., proteins, peptides, recombinant nucleic acids, etc.) can be efficiently encapsulated in nanoparticles using processes well known in the art. In some embodiments, a molecule "encapsulated" in a nanoparticle may refer to a molecule (such as a virus) that is contained within the nanoparticle or attached to and/or associated with the surface of the nanoparticle, or any combination thereof. Nanoparticles for use in the compositions or formulations described herein may be any type of biocompatible nanoparticle known in the art, including, for example, nanoparticles comprising poly(lactic acid), poly (glycolic acid), PLGA, PLA, PGA, and any combinations thereof (see e.g., Vauthier et al. Adv Drug Del Rev. (2003) 55: 519-48; US2007/0148074; US2007/0092575; US2006/0246139; U.S. Pat. Nos. 5,753,234; 7,081,483; and WO2006/052285).

In some embodiments, the carrier or excipient (e.g., a pharmaceutically acceptable carrier or excipient) may be adapted for or suitable for any administration route known in the art, including, for example, intravenous, intramuscular, subcutaneous, cutaneous, intranasal, intratracheal, sublingual, buccal, topical, oral, transdermal, intradermal, intraperitoneal, intraorbital, intravitreal, subretinal, transmucosal, intraarticular, by superficial injection, by implantation, by inhalation, intrathecal, intraventricular, and/or intranasal administration. In some embodiments, the carrier or excipient (e.g., pharmaceutically acceptable carrier or excipient) is adapted for or suitable for topical, transdermal, subcutaneous, and/or intradermal administration. In some embodiments, the carrier or excipient is adapted for or suitable for topical, transdermal, and/or intradermal administration. In some embodiments, the carrier or excipient is adapted for or suitable for superficial injection.

Examples of carriers or excipients adapted for or suitable for use in a topical, transdermal, subcutaneous, superficial, and/or intradermal application/administration may include, but are not limited to, ointments, oils, pastes, creams, aerosols, suspensions, emulsions, fatty ointments, gels, powders, liquids, lotions, solutions, sprays, patches (e.g., transdermal patches or microneedle patches), adhesive strips, a microneedle or microneedle arrays, and inhalants. In some embodiments, the carrier or excipient (e.g., the pharmaceutically acceptable carrier or excipient) comprises one or more (e.g., one or more, two or more, three or more, four or more, five or more, etc.) of an ointment, oil, paste, cream, aerosol, suspension, emulsion, fatty ointment, gel, powder, liquid lotion, solution, spray, adhesive strip, and an inhalant. In some embodiments, the carrier comprises a patch (e.g. a patch that adheres to the skin), such as a transdermal patch or a microneedle patch. In some embodiments, the carrier comprises a microneedle or microneedle array. Methods for making and using microneedle arrays suitable for composition delivery are generally known in the art (Kim Y. et al. "Microneedles for drug and vaccine delivery". *Advanced Drug Delivery Reviews* 2012, 64 (14): 1547-68).

In some embodiments, the composition or formulation (e.g., the pharmaceutical composition or formulation) is adapted for or suitable for any administration route known in the art, including, for example, intravenous, intramuscular, subcutaneous, cutaneous, oral, intranasal, intratracheal, sublingual, buccal, topical, transdermal, intradermal, intraperitoneal, intraorbital, intravitreal, subretinal, transmucosal, intraarticular, by superficial injection, by implantation, by inhalation, intrathecal, intraventricular, and/or intranasal administration. In some embodiments, the composition or formulation is adapted for or suitable for cutaneous, topical, transdermal, subcutaneous, and/or intradermal administration. In some embodiments, the pharmaceutical composition or formulation is adapted for or suitable for topical, transdermal, and/or intradermal administration. In some embodiments, the composition or formulation is adapted for or suitable for intradermal administration. In some embodiments, the composition of formulation is adapted for or suitable for superficial injection.

In some embodiments, the composition or formulation (e.g., pharmaceutical composition or formulation) further comprises one or more additional components. Examples of additional components may include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; sweetenings; flavorings; perfuming agents; colorants; moisturizers; sunscreens; antibacterial agents; agents able to stabilize polynucleotides or prevent their degradation, and the like. In some embodiments, the composition or formulation comprises a hydroxypropyl methylcellulose gel. In some embodiments, the composition or formulation comprises a phosphate buffer. In some embodiments, the composition or formulation comprises glycerol (e.g., at about 1%, about 2%, about 3%, about 4%, about 5%, about 6%, about 7%, about 8%, about 9%, about 10%, about 15%, etc.).

Compositions and formulations (e.g., pharmaceutical compositions and formulations) to be used for in vivo administration are generally sterile. Sterility may be readily accomplished, e.g., by filtration through sterile filtration membranes.

In some embodiments, any of the recombinant nucleic acids, viruses, and/or compositions or formulations described herein may be used to deliver one or more polynucleotides encoding a collagen protein (e.g., a human collagen protein such as Collagen 3) into one or more cells of a subject (e.g., one or more collagen-deficient cells). In some embodiments, any of the recombinant nucleic acids, viruses, and/or compositions or formulations described herein may be used in a therapy. In some embodiments, any of the recombinant nucleic acids, viruses, and/or compositions or formulations described herein may be used in the treatment of a cosmetic or aesthetic condition that would benefit from the expression of a collagen polypeptide (e.g., a cosmetic or aesthetic condition associated with a collagen deficiency (such as aged and/or UV-damaged skin)). In some embodiments, any of the recombinant nucleic acids, viruses, and/or compositions or formulations described herein may be used in the treatment of dermatological aging (e.g., as described below).

In some embodiments, any of the recombinant nucleic acids, viruses, and/or compositions or formulations described herein may be used in the preparation or manufacture of a medicament. In some embodiments, any of the recombinant nucleic acids, viruses, and/or compositions or formulations described herein may be used in the preparation or manufacture of a medicament useful for delivering one or more polynucleotides encoding a collagen protein (e.g., a human collagen protein such as Collagen 3) into one or more cells of a subject (e.g., one or more collagen-deficient cells). In some embodiments, any of the recombinant nucleic acids, viruses, and/or compositions or formulations described herein may be used in the preparation or manufacture of a medicament useful for the treatment of a cosmetic or aesthetic condition that would benefit from the expression of a collagen polypeptide (e.g., a cosmetic or aesthetic condition associated with a collagen deficiency (such as aged and/or UV-damaged skin)). In some embodiments, any of the recombinant nucleic acids, viruses, and/or compositions or formulations described herein may be used in the preparation or manufacture of a medicament useful for the treatment of dermatological aging (e.g., as described below).

VI. Methods

Certain aspects of the present disclosure relate to a method of enhancing, increasing, augmenting, and/or supplementing the levels of one or more dermal extracellular matrix proteins in a subject (e.g., in one or more cells of a subject) comprising administering to the subject any of the recombinant nucleic acids, viruses, medicaments, and/or compositions described herein. In some embodiments, the subject is a human.

Other aspects of the present disclosure relate to method of stabilizing or improving the structure and/or organization of the dermal extracellular matrix in a subject comprising administering to the subject any of the recombinant nucleic acids, viruses, medicaments, and/or compositions described herein. In some embodiments, the subject is a human.

Other aspects of the present disclosure relate to a method of enhancing, increasing, augmenting, and/or supplementing the levels of one or more human collagen proteins in a subject (e.g., in one or more cells of a subject) comprising administering to the subject any of the recombinant nucleic acids, viruses, medicaments, and/or compositions described herein. In some embodiments, the subject is a human.

In some embodiments, administration of the recombinant nucleic acid, virus, medicament, and/or composition to the subject increases collagen (e.g., COL1-1; COL1-2; COL3; COL1-1 and COL1-2; COL1-1 and COL3; etc.) levels (transcript or protein levels) in one or more cells of the subject by at least about 10%, as compared to the endogenous levels of the collagen(s) in one or more corresponding untreated cells (e.g., one or more cells prior to treatment, one or more uninfected cells during treatment, etc.) of the subject. For example, administration of the recombinant nucleic acid, virus, medicament, and/or composition may increase collagen levels (transcript or protein levels) in one or more cells of the subject by at least about 10%, at least about 15%, at least about 20%, at least about 25%, at least about 30%, at least about 40%, at least about 50%, at least about 60%, at least about 70%, at least about 80%, at least about 90%, at least about 95%, at least about 99%, or more, as compared to the endogenous levels of the collagen(s) in one or more corresponding untreated cells of the subject. In some embodiments, administration of the recombinant nucleic acid, virus, medicament, and/or composition to the subject increases collagen levels (transcript or protein levels) in one or more cells of the subject by at least about 2-fold, as compared to the endogenous levels of the collagen(s) in one or more corresponding untreated cells (e.g., one or more cells prior to treatment, one or more uninfected cells during treatment, etc.) of the subject. For example, administration of the recombinant nucleic acid, virus, medicament, and/or composition may increase collagen levels (transcript or protein levels) in one or more cells of the subject by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more, as compared to the endogenous levels of the collagen(s) in one or more corresponding untreated cells of the subject. Methods of measuring transcript or protein levels from a sample are well known to one of ordinary skill in the art, including, for example, by qPCR, RNAseq, ELISA, western blot, mass spectrometry, etc.

Other aspects of the present disclosure relate to a method of enhancing, increasing, augmenting, and/or supplementing the soft tissue of a subject comprising administering to the subject any of the recombinant nucleic acids, viruses, medicaments, and/or compositions described herein. In some embodiments, the subject is a human. In some embodiments, the recombinant nucleic acids, viruses, medicaments, and/or compositions are injected into a soft tissue of the subject. In some embodiments, the skin of the subject is aging skin. In some embodiments, the skin of the subject has been damaged due to exposure to ultraviolet light (e.g., from the sun, from a tanning bed, etc.). In some embodiments, the skin of the subject is wrinkled.

In some embodiments, the recombinant nucleic acids, viruses, medicaments, and/or compositions may be used in a method to repair and/or augment the soft tissue of a subject. In some embodiments, "tissue repair" refers to the restoration of tissue architecture and/or function and encompasses tissue regeneration and replacement. In some embodiments, repair or augmentation of the soft tissue refers to procedures that are used to restore the youthful appearance of skin (e.g., as compared to "aged" skin whose appearance is due to defects resulting from chronological aging or other physical, chemical, or UV damage). In some embodiments, the recombinant nucleic acids, viruses, medicaments, and/or compositions are useful in cosmetic soft tissue applications, such as to fill wrinkles, lines, folds, scars, and to enhance dermal tissue (e.g., plump thin lips, fill in sunken eyes and/or shallow cheeks, etc.).

Other aspects of the present disclosure relate to a method of improving skin quality, condition, and/or appearance in a subject in need thereof comprising administering to the subject any of the recombinant nucleic acids, viruses, medicaments, and/or compositions described herein. In some embodiments, the subject is a human. In some embodiments, the skin condition is one or more of sun damage, aging, UV exposure, rough texture, skin sagging, and/or wrinkles. Improvement of skin quality, condition, and/or appearance (e.g., as compared to before treatment) may be assessed using any appropriate method or scale known in the art, including, for example, FACE Q, GAIS, etc. In some embodiments, the skin of the subject is aging skin. In some embodiments, the skin of the subject has been damaged due to exposure to ultraviolet light (e.g., from the sun, from a tanning bed, etc.). In some embodiments, the skin of the subject is wrinkled.

Other aspects of the present disclosure relate to a method of reducing the appearance of one or more superficial depressions in the skin of a subject in need thereof comprising administering to the subject any of the recombinant nucleic acids, viruses, medicaments, and/or compositions described herein. In some embodiments, the subject is a human. In some embodiments, administration of the recombinant nucleic acid, virus, medicaments, and/or composition reduces the appearance of one or more superficial depressions in the skin of the subject for at least about three months, at least about six months, at least about nine months, or at least about 12 months. In some embodiments, the appearance of one or more superficial depressions in the skin of the subject is reduced after administration of the composition, as compared to the appearance of the one or more superficial depression in the skin of the subject prior to administration of the composition. In some embodiments, the one or more superficial depressions in the skin are one or more of fine lines and wrinkles (e.g., forehead wrinkles, "crow's feet", wrinkles at the edges of the eye or mouth, etc.). In some embodiments, the treatment of one or more superficial skin depressions is measured by an improvement in skin texture or skin quality, such as smoothness, hydration, and elasticity, as compared to non-treated skin. In some embodiments, the treatment of one or more superficial skin depressions is measured by a reduction in the severity (e.g., depth) of the superficial depressions and/or a reduction in the number of fine lines or wrinkles in a given area of skin. In some embodiments, the skin of the subject is aging skin. In some embodiments, the skin of the subject has been damaged due to exposure to ultraviolet light (e.g., from the sun, from a tanning bed, etc.). In some embodiments, the skin of the subject is wrinkled.

Other aspects of the present disclosure relate to a method of increasing and/or improving at least one of texture, smoothness, elasticity, and/or tension of the skin of a subject comprising administering to the subject any of the recombinant nucleic acids, viruses, medicaments, and/or compositions described herein. In some embodiments, the subject is a human. In some embodiments, the skin of the subject maintains at least one of an increased and/or improved texture, smoothness, elasticity, or tension for at least about three months, at least about six months, at least about nine months, or at least about 12 months after administration of the composition. In some embodiments, at least one of texture, smoothness, elasticity, or tension of the skin of the subject is increased and/or improved after administration of the composition, as compared to the texture, smoothness, elasticity, or tension of the skin of the subject prior to administration of the composition. Methods of measuring texture, smoothness, elasticity, and/or tensions of the skin are known to one of skill in the art. In some embodiments, the skin of the subject is aging skin. In some embodiments, the skin of the subject has been damaged due to exposure to ultraviolet light (e.g., from the sun, from a tanning bed, etc.). In some embodiments, the skin of the subject is wrinkled.

Other aspects of the present disclosure relate to a method of diminishing one or more dermatological signs of aging in a subject in need thereof comprising administering to the subject an effective amount of any of the recombinant nucleic acids, viruses, medicaments, and/or compositions described herein. In some embodiments, the subject is a human. In some embodiments, diminishing one or more dermatological signs of aging include any one of more of the following: treatment, reduction, and/or prevention of fine lines and/or wrinkles; reduction of skin pore size; improvement in skin thickness, plumpness, and/or tautness; improvement in skin smoothness, suppleness, and/or softness; improvement in skin tone, radiance, and/or clarity; improvement in procollagen and/or collagen production; improvement in skin texture and or promotion of retexturization; improvement in appearance of skin contours; restoration of skin luster and/or brightness; improvement of skin appearance decreased by aging and/or menopause; improvement in skin moisturization; increase in skin elasticity and/or resiliency; treatment, reduction, and/or prevention or skin sagging; improvement in skin firmness; reduction of pigment spots, mottled skin, and/or scars (such as acne scars); and/or improvement of optical properties of skin by light diffraction or reflection. In some embodiments, the one or more dermatological signs of aging in the subject is diminished after administration of the composition, as compared to the one or more dermatological signs of aging in the subject prior to administration of the composition. Any suitable method for measuring one or more signs of dermatological aging known in the art may be used.

In some embodiments, one or more portions of the skin of the subject is abraded or made more permeable prior to treatment with an effective amount of any of the recombinant nucleic acids, viruses, medicaments, and/or compositions described herein. Any suitable method of abrading the skin or increasing skin permeability known in the art may be used, including, for example, use of a dermal roller, repeated use of adhesive strips to remove layers of skin cells (tape stripping), scraping with a scalpel or blade, use of sandpaper, use of chemical permeation enhancers or electrical energy, use of sonic or ultrasonic energy, use of light (e.g., laser) energy, use of micron-sized needles or blades with a length suitable to pierce but not completely pass through the epidermis, etc.

In some embodiments, the methods of the present disclosure are for cosmetic applications, such as to reduce or eliminate one or more superficial depressions in the skin, to reduce or eliminate one or more wrinkles, and/or to prevent the occurrence or reoccurrence of one or more wrinkles. In some embodiments, the one or more superficial depressions in the skin or wrinkles are selected from nasolabial folds, crows' feet, frown lines, worry lines, scars, glabellar lines, brow ptosis, tear troughs, nasojugal lines, bunny lines, cheek/mid-face ptosis, marionette lines, poppy dimpling, smile lines, laugh lines, chin creases, neck lines, platysma bands, and any combinations thereof.

In some embodiments, an "effective amount" is at least the minimum amount required to affect a measurable improvement in or prevention of one or more signs or symptoms of a particular condition (e.g., a cosmetic condition such as skin aging). An "effective amount" may vary according to factors such as the age, sex, and weight of the patient. An effective amount is also one in which any toxic or detrimental effects of the treatment are outweighed by the beneficial effects. An effective amount can be administered in one or more administrations. For purposes of the present disclosure, an effective amount of a recombinant nucleic acid, virus, medicament, and/or composition is an amount sufficient to accomplish a measurable improvement either directly or indirectly. As is understood in the clinical context, an effective amount of a recombinant nucleic acid, virus, medicament, and/or composition may or may not be achieved in conjunction with another drug, compound, or composition. Thus, an "effective amount" may be considered in the context of administering one or more agents, and a single agent may be considered to be given in an effective amount if, in conjunction with one or more other agents, a desirable result may be or is achieved.

In some embodiments, the recombinant nucleic acid, virus, medicament, and/or composition is administered once to the subject. In some embodiments, the recombinant nucleic acid, virus, medicament, and/or composition is administered at least twice (e.g., at least 2 times, at least 3 times, at least 4 times, at least 5 times, at least 10 times, etc.) to the subject. In some embodiments, at least about 15 days (e.g., at least about 15 days, at least about 20 days, at least about 30 days, at least about 40 days, at least about 50 days, at least about 60 days, at least about 70 days, at least about 80 days, at least about 90 days, at least about 100 days, at least about 120 days, etc.) pass between administrations (e.g., between the first and second administrations, between the second and third administrations, etc.).

The recombinant nucleic acids, viruses, medicaments, and/or compositions or formulations described herein may be administered by any suitable method or route known in the art, including, without limitation, by oral administration, sublingual administration, buccal administration, topical administration, rectal administration, via inhalation, transdermal administration, subcutaneous injection, intradermal injection, superficial injection, intravenous (IV) injection, intra-arterial injection, intramuscular injection, intracardiac injection, intraosseous injection, intraperitoneal injection, transmucosal administration, vaginal administration, intraurethral administration, intravitreal administration, intraorbital administration, subretinal administration, intra-articular administration, peri-articular administration, local administration, epicutaneous administration, or any combinations thereof. The present disclosure thus encompasses methods of delivering any of the recombinant nucleic acids, viruses, medicaments, and/or compositions or formulations described herein to an individual.

In some embodiments, the recombinant nucleic acids, viruses, medicaments, and/or compositions or formulations are administered cutaneously, topically, transdermally, subcutaneously, or intradermally to the subject. In some embodiments, the recombinant nucleic acids, viruses, medicaments, and/or compositions or formulations are administered intradermally and/or subcutaneously. In some embodiments, the recombinant nucleic acids, viruses, medicaments, and/or compositions or formulations are administered via superficial injection. In some embodiments, the recombinant nucleic acids, viruses, medicaments, and/or compositions or formulations are administered topically and/or transdermally. In some embodiments, the recombinant nucleic acids, viruses, medicaments, and/or compositions or formulations are administered one, two, three, four, five or more times per day. In some embodiments, the recombinant nucleic acids, viruses, medicaments, and/or compositions or formulations are administered to one or more affected (e.g., wrinkled) areas of an individual. In some embodiments, the composition is administered to one or more unaffected areas of the individual.

In some embodiments, the recombinant nucleic acids, viruses, medicaments, and/or compositions are administered at a superficial depth in the skin. In some embodiments, the recombinant nucleic acids, viruses, medicaments, and/or compositions are introduced into the skin at a depth of about 2000 microns or less. For example, the recombinant nucleic acids, viruses, medicaments, and/or compositions may be administered into the skin at a depth of about 2000 microns or less, at about 1750 microns or less, at about 1500 microns or less, at about 1250 microns or less, at about 1000 microns or less, at about 900 microns or less, at about 800 microns or less, at about 700 microns or less, at about 600 microns or less, or at about 500 microns or less. In some embodiments, the recombinant nucleic acids, viruses, medicaments, and/or compositions are introduced at an injection depth between about 0.5 mm and 5.0 mm. For example, the recombinant nucleic acids, viruses, medicaments, and/or compositions may be introduced at an injection depth of between about 0.5 mm and 5.0 mm, about 0.5 mm and 4.5 mm, about 0.5 mm and 4.0 mm, about 0.5 mm and 3.5 mm, about 0.5 mm and 3.0 mm, about 0.5 mm and 2.5 mm, about 0.5 mm and 2.0 mm, about 0.5 mm and 1.5 mm, about 0.5 mm and 1.0 mm, 1.0 mm and 5.0 mm, about 1.0 mm and 4.5 mm, about 1.0 mm and 4.0 mm, about 1.0 mm and 3.5 mm, about 1.0 mm and 3.0 mm, about 1.0 mm and 2.5 mm, about 1.0 mm and 2.0 mm, about 1.0 mm and 1.5 mm, 1.5 mm and 5.0 mm, about 1.5 mm and 4.5 mm, about 1.5 mm and 4.0 mm, about 1.5 mm and 3.5 mm, about 1.5 mm and 3.0 mm, about 1.5 mm and 2.5 mm, about 1.5 mm and 2.0 mm, etc.

In some embodiments, the recombinant nucleic acids, viruses, medicaments, and/or compositions are administered by injections spaced apart by a distance of between about 1 mm to about 30 mm. For example, the recombinant nucleic acids, viruses, medicaments, and/or compositions may be administered by injections spaced apart by a distance of between about 1 mm and 30 mm, 2 mm and 30 mm, 5 mm and 30 mm, 10 mm and 30 mm, 15 mm and 30 mm, 1 mm and 20 mm, 2 mm and 20 mm, 5 mm and 20 mm, 10 mm and 20 mm, 15 mm and 20 mm, 1 mm and 15 mm, 2 mm and 15 mm, 5 mm and 15 mm, 10 mm and 15 mm, 1 mm and 10 mm, 2 mm and 10 mm, 5 mm and 10 mm, 1 mm and 5 mm, 2 mm and 5 mm, etc. In some embodiments, the injections are spaced apart by a distance of at least about 1 mm, at least about 2 mm, at least about 5 mm, at least about 10 mm, at least about 15 mm, at least about 20 mm, at least about 30 mm or more.

Numerous areas of the body may be treated with the recombinant nucleic acids, viruses, medicaments, and/or compositions described herein, including, for example, the face, forehead, lips, scalp, neck, arms, hands, legs, knees, feet, chest, back, groin, buttocks, thighs, etc. In some embodiments, the recombinant nucleic acids, viruses, medicaments, and/or compositions are administered to the face. In some embodiments, the recombinant nucleic acids, viruses, medicaments, and/or compositions are administered to one or more nasolabial folds. In some embodiments, the recombinant nucleic acids, viruses, medicaments, and/or compositions are administered around one or both eyes. In some embodiments, the recombinant nucleic acids, viruses, medicaments, and/or compositions are administered to one or more crows' feet. In some embodiments, the recombinant nucleic acids, viruses, medicaments, and/or compositions are administered to one or more frown lines. In some embodiments, the recombinant nucleic acids, viruses, medicaments, and/or compositions are administered to one or more scars (e.g., acne scars). In some embodiments, the recombinant nucleic acids, viruses, medicaments, and/or compositions are administered to one or more glabellar lines. In some embodiments, the recombinant nucleic acids, viruses, medicaments, and/or compositions are administered to one or more brow ptosis. In some embodiments, the recombinant nucleic acids, viruses, medicaments, and/or compositions are administered to one or more deep tear troughs. In some embodiments, the recombinant nucleic acids, viruses, medicaments, and/or compositions are administered to one or more nasojugal lines. In some embodiments, the recombinant nucleic acids, viruses, medicaments, and/or compositions are administered to one or more bunny lines. In some embodiments, the recombinant nucleic acids, viruses, medicaments, and/or compositions are administered to one or more cheek/mid-face ptosis. In some embodiments, the recombinant nucleic acids, viruses, medicaments, and/or compositions are administered to one or more marionette lines. In some embodiments, the recombinant nucleic acids, viruses, medicaments, and/or compositions are administered to one or sites of poppy dimpling. In some embodiments, the recombinant nucleic acids, viruses, medicaments, and/or compositions are administered to one or more chin creases. In some embodiments, the recombinant nucleic acids, viruses, medicaments, and/or compositions are administered to one or more neck lines. In some embodiments, the recombinant nucleic acids, viruses, medicaments, and/or compositions are administered to one or more platysma bands.

In some embodiments, the recombinant nucleic acid expresses the cosmetic protein(s) (e.g., human collagens) when the recombinant nucleic acid is delivered into one or more target cells of a subject. In some embodiments, expression of the cosmetic protein(s) (e.g., human collagens) enhances, increases, augments, and/or supplements the levels of human collagen in one or more target cells. In some embodiments, expression of the cosmetic protein(s) (e.g., human collagens) enhances, increases, augments, and/or supplements the levels of human collagen secreted by one or more target cells. In some embodiments, expression of the cosmetic protein(s) (e.g., human collagens) enhances, increases, augments, and/or supplements the levels of human collagen in the extracellular matrix. In some embodiments, expression of the cosmetic protein(s) (e.g., human collagens) enhances, increases, augments, and/or supplements the stability of the extracellular matrix in the subject. In some embodiments, expression of the cosmetic protein(s) (e.g., human collagens) enhances, augments, and/supplements the soft tissue of the subject. In some embodiments, expression of the cosmetic protein(s) (e.g., human collagens) improves the skin quality, condition, and/or appearance of the individual. In some embodiments, expression of the cosmetic protein(s) (e.g., human collagens) reduces one or more superficial depressions (e.g., wrinkles) in the skin of the subject. In some embodiments, expression of the cosmetic protein(s) (e.g., human collagens) improves the texture, smoothness, elasticity, and/or tension of the skin of the subject. In some embodiments, expression of the cosmetic protein(s) (e.g., human collagens) reduces one or more dermatological signs of aging in the subject.

VII. Host Cells

Certain aspects of the present disclosure relate to one or more host cells comprising any of the recombinant nucleic acids described herein. Any suitable host cell (prokaryotic or eukaryotic) known in the art may be used, including, for example: prokaryotic cells including eubacteria, such as Gram-negative or Gram-positive organisms, for example Enterobacteriaceae such as *Escherichia* (e.g., *E. coli*), *Enterobacter, Erminia, Klebsiella, Proteus, Salmonella* (e.g., *S. typhimurium*), *Serratia* (e.g., *S. marcescans*), and *Shigella*, as well as Bacilli such as *B. subtilis* and *B. licheniformis*; fungal cells (e.g., *S. cerevisiae*); insect cells (e.g., S2 cells, etc.); and mammalian cells, including monkey kidney CV1 line transformed by SV40 (COS-7, ATCC CRL 1651), human embryonic kidney line (293 or 293 cells subcloned for growth in suspension culture), baby hamster kidney cells (BHK, ATCC CCL 10), mouse Sertoli cells (TM4), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TRI cells, MRC 5 cells, FS4 cells, human hepatoma line (Hep G2), Chinese hamster ovary (CHO) cells, including DHFR" CHO cells, and myeloma cell lines such as NS0 and Sp2/0. In some embodiments, the host cell is a human or non-human primate cell. In some embodiments, the host cell is a Vero cell. In some embodiments, the host cell is a complementing host cell. In some embodiments, the host cell (e.g., the Vero cell) expresses one or more herpes simplex virus genes (e.g., an ICP4 gene). In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-K1, MDCK, HUVEC, Vero, N20, COS-7, PSN1, VCaP, CHO cells, and the like.

In some embodiments, the recombinant nucleic acid is a herpes simplex viral vector. In some embodiments, the recombinant nucleic acid is a herpes simplex virus amplicon. In some embodiments, the recombinant nucleic acid is an HSV-1 amplicon or HSV-1 hybrid amplicon. In some embodiments, a host cell comprising a helper virus is contacted with an HSV-1 amplicon or HSV-1 hybrid amplicon described herein, resulting in the production of a virus comprising one or more recombinant nucleic acids described herein. In some embodiments, the virus is collected from the supernatant of the contacted host cell. Methods of generating virus by contacting host cells comprising a helper virus with an HSV-1 amplicon or HSV-1/hybrid amplicon are known in the art.

In some embodiments, the host cell is a complementing host cell. In some embodiments, the complementing host cell expresses one or more genes that are inactivated in any of the viral vectors described herein. In some embodiments, the complementing host cell is contacted with a recombinant herpes virus genome (e.g., a recombinant herpes simplex virus genome) described herein. In some embodiments, contacting a complementing host cell with a recombinant herpes virus genome results in the production of a herpes virus comprising one or more recombinant nucleic acids described herein. In some embodiments, the virus is collected from the supernatant of the contacted host cell. Methods of generating virus by contacting complementing host cells with a recombinant herpes simplex virus are generally described in WO2015/009952 and/or WO2017/176336.

VIII. Articles of Manufacture or Kits

Certain aspects of the present disclosure relate to an article of manufacture or a kit comprising any of the recombinant nucleic acids, viruses, medicaments and/or compositions or formulations (e.g., pharmaceutical compositions or formulations) described herein. In some embodiments, the article of manufacture or kit comprises a package insert comprising instructions for administering the recombinant nucleic acid, virus, medicament, and/or composition or formulation (e.g., to treat a dermal extracellular matrix protein (e.g., collagen) deficiency and/or to correct one or more dermatological signs of aging).

Suitable containers for the recombinant nucleic acids, viruses, medicaments and/or compositions or formulations may include, for example, bottles, vials, bags, tubes, and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, needles, syringes, package inserts, and the like.

IX. Enumerated Embodiments

Embodiment 1: a composition comprising: (a) a herpes simplex virus (HSV) comprising a recombinant nucleic acid, wherein the recombinant nucleic acid comprises a first polynucleotide encoding a first polypeptide comprising a first human collagen protein, and (b) an excipient.

Embodiment 2: the composition of embodiments 1, wherein the recombinant nucleic acid comprises two or more copies of the first polynucleotide.

Embodiment 3: the composition of embodiment 1 or 2, wherein the HSV is replication-defective.

Embodiment 4: the composition of embodiment 1 or 2, wherein the HSV is replication-competent.

Embodiment 5: the composition of any one of embodiments 1-4, wherein the HSV is a herpes simplex type 1 virus, a herpes simplex type 2 virus, or any derivatives thereof.

Embodiment 6: the composition of any one of embodiments 1-5, wherein the recombinant nucleic acid is a herpes simplex virus amplicon.

Embodiment 7: the composition of embodiment 6, wherein the herpes simplex virus amplicon is an HSV-1 amplicon or an HSV-1 hybrid amplicon.

Embodiment 8: the composition of embodiment 7, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 9: the composition of any one of embodiments 1-5, wherein the recombinant nucleic acid is a recombinant herpes simplex virus genome.

Embodiment 10: the composition of embodiment 9, wherein the recombinant herpes simplex virus genome is a recombinant HSV-1 genome, a recombinant HSV-2 genome, or any derivatives thereof.

Embodiment 11: the composition of embodiment 9 or 10, wherein the recombinant herpes simplex virus genome comprises an inactivating mutation in a herpes simplex virus gene.

Embodiment 12: the composition of embodiment 11, wherein the herpes simplex virus gene is selected from the group consisting of Infected Cell Protein (ICP) 0, ICP4, ICP22, ICP27, ICP47, thymidine kinase (tk), Long Unique Region (UL) 41, and UL55.

Embodiment 13: the composition of embodiment 12, wherein the recombinant herpes simplex virus genome comprises an inactivation mutation in one or both copies of the ICP4 gene.

Embodiment 14: the composition of embodiment 12 or 13, wherein the recombinant herpes simplex virus genome comprises an inactivating mutation in the ICP22 gene.

Embodiment 15: the composition of any one of embodiments 12-14, wherein the recombinant herpes simplex virus genome comprises an inactivation mutation in the UL41 gene.

Embodiment 16: the composition of any one of embodiments 12-15, wherein the recombinant herpes simplex virus genome comprises an inactivation mutation in the ICP0 gene.

Embodiment 17: the composition of any one of embodiments 12-16, wherein the recombinant herpes simplex virus genome comprises an inactivation mutation in the ICP27 gene.

Embodiment 18: the composition of any one of embodiments 11-17, wherein the inactivating mutation is a deletion of the coding sequence of the gene(s).

Embodiment 19: the composition of any one of embodiments 9-18, wherein the recombinant herpes simplex virus genome comprises the first polynucleotide within a viral gene locus.

Embodiment 20: The composition of any one of embodiments 9-19, wherein the recombinant herpes simplex virus genome comprises the first polynucleotide within one or both copies of the ICP4 viral gene loci.

Embodiment 21: the composition of any one of embodiments 9-20, wherein the recombinant herpes simplex virus genome comprises the first polynucleotide within the ICP22 viral gene locus.

Embodiment 22: the composition of any one of embodiment 9-21, wherein the recombinant herpes simplex virus genome comprises the first polynucleotide within the UL41 viral gene locus.

Embodiment 23: the composition of any one of embodiments 1-22, wherein the HSV has reduced cytotoxicity as compared to a wild-type herpes simplex virus.

Embodiment 24: the composition of any one of embodiments 1-23, wherein the first human collagen protein is selected from the group consisting of Collagen alpha-1(I) chain polypeptide (COL1-1), Collagen alpha-2(I) chain polypeptide (COL1-2), a Collagen alpha-1(II) chain polypeptide (COL2), a Collagen alpha-1(III) chain polypeptide (COL3), a Collagen alpha-1(IV) chain polypeptide (COL4-1), a Collagen alpha-2(IV) chain polypeptide (COL4-2), a Collagen alpha-3(IV) chain polypeptide (COL4-3), a Collagen alpha-4(IV) chain polypeptide (COL4-4), a Collagen alpha-5(IV) chain polypeptide (COL4-5), a Collagen alpha-6(IV) chain polypeptide (COL4-6), a Collagen alpha-1(V) chain polypeptide (COL5-1), a Collagen alpha-2(V) chain polypeptide (COL5-2), a Collagen alpha-3(V) chain polypeptide (COL5-3), a Collagen alpha-1(VI) chain polypeptide (COL6-1), a Collagen alpha-2(VI) chain polypeptide (COL6-2), a Collagen alpha-3(VI) chain polypeptide (COL6-3), a Collagen alpha-4(VI) chain polypeptide (COL6-4), a Collagen alpha-5(VI) chain polypeptide (COL6-5), a Collagen alpha-6(VI) chain polypeptide (COL6-6), a Collagen alpha-1(VII) chain polypeptide (COL7), a Collagen alpha-1(VIII) chain polypeptide (COL8), a Collagen alpha-1(IX) chain polypeptide (COL9-1), a Collagen alpha-2(IX) chain polypeptide (COL9-2), a Collagen alpha-3(IX) chain polypeptide (COL9-3), a Collagen alpha-1(X) chain polypeptide (COL10), a Collagen alpha-1(XI) chain polypeptide (COL11-1), a Collagen alpha-2(XI) chain polypeptide (COL11-2), a Collagen alpha-1(XII) chain polypeptide (COL12), a Collagen alpha-1(XIII) chain polypeptide (COL13), a Collagen alpha-1 (XIV) chain polypeptide (COL14), a Collagen alpha-1(XV) chain polypeptide (COL15), a Collagen alpha-1(XVI) chain polypeptide (COL16), a Collagen alpha-1(XVII) chain polypeptide (COL17), a Collagen alpha-1(XVIII) chain polypeptide (COL18), a Collagen alpha-1(XIX) chain polypeptide (COL19), a Collagen alpha-1(XX) chain polypeptide (COL20), a Collagen alpha-1(XXI) chain polypeptide (COL21), a Collagen alpha-1(XXII) chain polypeptide (COL22), a Collagen alpha-1(XXIII) chain polypeptide (COL23), a Collagen alpha-1(XXIV) chain polypeptide (COL24), a Collagen alpha-1(XXV) chain polypeptide (COL25), a Collagen alpha-1(XXVI) chain polypeptide (COL26), a Collagen alpha-1(XXVII) chain polypeptide (COL27), and a Collagen alpha-1(XXVIII) chain polypeptide (COL28).

Embodiment 25: the composition of any one of embodiments 1-24, wherein the first human collagen protein is selected from the group consisting of COL1-1, COL1-2, COL3, COL4-1, COL6-1, COL7, and COL17.

Embodiment 26: the composition of any one of embodiments 1-25, wherein the nucleic acid sequence encoding the first human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 27: the composition of any one of embodiments 1-26, wherein the first human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 28: the composition of any one of embodiments 1-27, wherein the first human collagen protein is not COL7.

Embodiment 29: the composition of any one of embodiments 1-28, wherein the first polypeptide comprises: (a) the first human collagen protein; (b) a further human collagen protein; and (c) a linker polypeptide linking (a) to (b).

Embodiment 30: the composition of embodiment 29, wherein the linker polypeptide is a cleavable linker polypeptide.

Embodiment 31: the composition of embodiment 29 or 30, wherein the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 28-31

Embodiment 32: the composition of any one of embodiments 29-31, wherein the further human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 33: the composition of any one of embodiments 29-32, wherein the further human collagen protein is selected from the group consisting of COL1-1, COL1-2, COL3, COL4-1, COL6-1, COL7, and COL17.

Embodiment 34: the composition of any one of embodiments 29-33, wherein the nucleic acid sequence encoding the further human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 35: the composition of any one of embodiments 29-34, wherein the further human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 36: the composition of any one of embodiments 29-35, wherein the first human collagen protein and the further human collagen protein are different.

Embodiment 37: the composition of any one of embodiments 1-36, wherein the first polynucleotide encodes a polycistronic mRNA comprising: (a) a first open reading frame (ORF) encoding the first polypeptide; (b) a second ORF encoding an additional human collagen protein; and (c) an internal ribosomal entry site (IRES) separating (a) and (b).

Embodiment 38: the composition of embodiment 37, wherein the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23.

Embodiment 39: the composition of embodiment 37 or 38, wherein the additional human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 40: the composition of any one of embodiments 37-39, wherein the additional human collagen protein is selected from the group consisting of COL1-1, COL1-2, COL3, COL4-1, COL6-1, COL7, and COL17.

Embodiment 41: the composition of any one of embodiments 37-40, wherein the nucleic acid sequence encoding the additional human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 42: the composition of any one of embodiments 37-41, wherein the additional human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 43: the composition of any one of embodiments 37-42, wherein the first human collagen protein and the additional human collagen protein are different.

Embodiment 44: the composition of any one of embodiments 1-43, wherein the recombinant nucleic acid further comprises a second polynucleotide encoding a second human collagen protein.

Embodiment 45: the composition of embodiment 44, wherein the recombinant nucleic acid comprises two or more copies of the second polynucleotide.

Embodiment 46, the composition of embodiment 44 or 45, wherein the second human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 47: the composition of any one of embodiments 44-46, wherein the second human collagen protein is selected from the group consisting of COL1-1, COL1-2, COL3, COL4-1, COL6-1, COL7, and COL17.

Embodiment 48: the composition of any one of embodiments 44-48, wherein the nucleic acid sequence encoding the second human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 49: the composition of any one of embodiments 44-48, wherein the second human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 50: the composition of any one of embodiments 44-49, wherein the first and second human collagen proteins are different.

Embodiment 51: the composition of any one of embodiments 44-50, wherein the recombinant nucleic acid is a recombinant herpes simplex virus genome, and wherein the recombinant herpes simplex virus genome comprises the second polynucleotide within a viral gene locus.

Embodiment 52: the composition of embodiment 51, wherein the recombinant herpes simplex virus genome comprises the second polynucleotide within one or both copies of the ICP4 viral gene loci.

Embodiment 53: the composition of embodiment 51 or 52, wherein the recombinant herpes simplex virus genome comprises the second polynucleotide within the ICP22 viral gene locus.

Embodiment 54: the composition of any one of embodiments 51-53, wherein the recombinant herpes simplex virus genome comprises the second polynucleotide within the UL41 viral gene locus.

Embodiment 55: the composition of any one of embodiments 51-54, wherein the recombinant herpes simplex virus genome comprises the first polynucleotide within one or both copies of the ICP4 viral gene loci and the second polynucleotide within the ICP22 viral gene locus.

Embodiment 56: the composition of any one of embodiments 51-54, wherein the recombinant herpes simplex virus genome comprises the first polynucleotide within one or both copies of the ICP4 viral gene loci and the second polynucleotide within the UL41 viral gene locus.

Embodiment 57: the composition of any one of embodiments 1-56, wherein the excipient is adapted for cutaneous (systemic or topical), transdermal, subcutaneous, and/or intradermal administration.

Embodiment 58: the composition of any one of embodiments 1-57, wherein the excipient comprises a hydroxypropyl methylcellulose gel.

Embodiment 59: the composition of any one of embodiments 1-58, wherein the excipient is adapted for intradermal administration.

Embodiment 60: the composition of any one of embodiments 1-59, wherein the excipient comprises a phosphate buffer.

Embodiment 61: the composition of any one of embodiments 1-60, wherein the excipient comprises glycerol.

Embodiment 62: the composition of any one of embodiments 1-61, wherein the excipient comprises a lipid carrier.

Embodiment 63: the composition of any one of embodiments 1-62, wherein the excipient comprises a nanoparticle carrier.

Embodiment 64: the composition of any one of embodiments 1-63, wherein the composition is a cosmetic composition.

Embodiment 65: the composition of embodiment 64, wherein the cosmetic composition is a skin care product.

Embodiment 66: a kit comprising: (a) the composition of any one of embodiment 1-65; and (b) instructions for administering the composition.

Embodiment 67: a method of enhancing, increasing, augmenting, and/or supplementing the levels of one or more human collagen proteins in a subject, the method comprising administering to the subject an effective amount of the composition of any one of embodiments 1-65.

Embodiment 68: a method of enhancing, increasing, augmenting, and/or supplementing soft tissue of a subject, the method comprising administering to the subject an effective amount of the composition of any one of embodiments 1-65.

Embodiment 69: the method of embodiment 68, wherein the composition is injected into a soft tissue of the subject.

Embodiment 70: a method of improving skin quality, condition and/or appearance in a subject in need thereof, the method comprising administering to the subject an effective amount of the composition of any one of embodiments 1-65.

Embodiment 71: the method of embodiment 70, wherein the condition is selected from the group consisting of sun damage, aging, UV exposure, rough texture, skin sagging, wrinkles, and any combinations thereof.

Embodiment 72: a method of reducing the appearance of one or more superficial depressions in the skin of a subject in need thereof, the method comprising administering to the subject an effective amount of the composition of any one of embodiments 1-65.

Embodiment 73: the method of embodiment 72, wherein administration of the composition reduces the appearance of the one or more superficial depressions in the skin of the subject for at least about three months, at least about six months, at least about nine months, or at least about 12 months.

Embodiment 74: the method of embodiment 72 or 73, wherein the appearance of the one or more superficial depressions in the skin of the subject is reduced after administration of the composition, as compared to the appearance of the one or more superficial depression in the skin of the subject prior to administration of the composition.

Embodiment 75: a method of increasing and/or improving at least one of texture, smoothness, elasticity, or tension of the skin of a subject in need thereof, the method comprising administering to the subject an effective amount of the composition of any one of embodiments 1-65.

Embodiment 76: the method of embodiment 75, wherein the skin of the subject maintains at least one of an increased and/or improved texture, smoothness, elasticity, or tension for at least about three months, at least about six months, at least about nine months, or at least about 12 months after administration of the composition.

Embodiment 77: the method of embodiment 75 or 76, wherein at least one of texture, smoothness, elasticity, or tension of the skin of the subject is increased and/or improved after administration of the composition, as compared to the texture, smoothness, elasticity, or tension of the skin of the subject prior to administration of the composition.

Embodiment 78: the method of any one of embodiments 70-77, wherein the skin of the subject is aging skin.

Embodiment 79: the method of any one of embodiments 70-78, wherein the skin of the subject has been damaged due to exposure to ultraviolet light.

Embodiment 80: the method of any one of embodiments 70-79, wherein the skin of the subject is wrinkled.

Embodiment 81: a method of diminishing one or more dermatological signs of aging in a subject in need thereof, the method comprising administering to the subject an effective amount of the composition of any one of embodiments 1-65.

Embodiment 82: the method of embodiment 81, wherein the diminishing of one or more dermatological signs of aging is selected from the group consisting of: (a) treatment, reduction, and/or prevention of fine lines and/or wrinkles; (b) reduction of skin pore size; (c) improvement in skin thickness, plumpness, and/or tautness; (d) improvement in skin smoothness, suppleness, and/or softness; (e) improvement in skin tone, radiance and/or clarity; (f) improvement in procollagen and/or collagen production; (g) improvement in skin texture and or promotion of retexturization; (h) improvement in appearance of skin contours; (i) restoration of skin luster and/or brightness; (j) improvement of skin appearance decreased by aging and/or menopause; (k) improvement in skin moisturization; (1) increase in skin elasticity and/or resiliency; (m) treatment, reduction, and/or prevention or skin sagging; (n) improvement in skin firmness; (o) reduction of pigment spots, mottled skin, and/or acne scars; (p) improvement of optical properties of skin by light diffraction or reflection; and (q) any combinations thereof.

Embodiment 83: the method of embodiment 81 or 82, wherein the one or more dermatological signs of aging in the subject is diminished after administration of the composition, as compared to the one or more dermatological signs of aging in the subject prior to administration of the composition.

Embodiment 84: the method of any one of embodiments 67-83, wherein the subject is a human.

Embodiment 85: the method of any one of embodiments 67-84, wherein the composition is administered cutaneously (systemically or topically), transdermally, subcutaneously, or intradermally to the subject.

Embodiment 86: the method of any one of embodiments 67-85, wherein the composition is administered by superficial injection.

Embodiment 87: the method of any one of embodiments 67-85, wherein the composition is administered intradermally to the subject.

Embodiment 88: the method of any one of embodiments 67-87, wherein the composition is administered once to the subject.

Embodiment 89: the method of any one of embodiments 67-87, wherein the composition is administered at least twice to the subject.

Embodiment 90: the method of embodiment 89, wherein at least about 15, at least about 30, at least about 60, at least about 90, or at least about 120 days passes between administrations.

Embodiment 91: the method of any one of embodiments 67-90, wherein the composition is administered to one or more affected and/or unaffected areas of the subject.

Embodiment 92: the method of any one of embodiments 67-91, wherein the skin of the subject is abraded prior to administration.

Embodiment 93: a recombinant nucleic acid comprising a first polynucleotide encoding a first polypeptide comprising a first human collagen protein, wherein the recombinant nucleic acid is a recombinant herpes simplex virus genome.

Embodiment 94: the recombinant nucleic acid of embodiment 93, wherein the recombinant nucleic acid comprises two or more copies of the first polynucleotide.

Embodiment 95: the recombinant nucleic acid of embodiment 93 or 94, wherein the recombinant herpes simplex virus genome is a recombinant HSV-1 genome, a recombinant HSV-2 genome, or any derivatives thereof.

Embodiment 96: the recombinant nucleic acid of any one of embodiments 93-95, wherein the recombinant herpes simplex virus genome comprises an inactivating mutation in a herpes simplex virus gene.

Embodiment 97: the recombinant nucleic acid of embodiment 96, wherein the herpes simplex virus gene is selected from the group consisting of ICP0, ICP4, ICP22, ICP27, ICP47, tk, UL41, and UL55.

Embodiment 98: the recombinant nucleic acid of embodiment 97, wherein the recombinant herpes simplex virus genome comprises an inactivation mutation in one or both copies of the ICP4 gene.

Embodiment 99: the recombinant nucleic acid of embodiment 97 or 98, wherein the recombinant herpes simplex virus genome comprises an inactivating mutation in the ICP22 gene.

Embodiment 100: the recombinant nucleic acid of any one of embodiments 97-99, wherein the recombinant herpes simplex virus genome comprises an inactivation mutation in the UL41 gene.

Embodiment 101: the recombinant nucleic acid of any one of embodiments 97-100, wherein the recombinant herpes simplex virus genome comprises an inactivation mutation in the ICP0 gene.

Embodiment 102: the recombinant nucleic acid of any one of embodiments 97-101, wherein the recombinant herpes simplex virus genome comprises an inactivation mutation in the ICP27 gene.

Embodiment 103: the recombinant nucleic acid of any one of embodiments 96-102, wherein the inactivating mutation is a deletion of the coding sequence of the gene(s).

Embodiment 104: the recombinant nucleic acid of any one of embodiments 93-103, wherein the recombinant herpes simplex virus genome comprises the first polynucleotide within a viral gene locus.

Embodiment 105: the recombinant nucleic acid of any one of embodiments 93-104, wherein the recombinant herpes simplex virus genome comprises the first polynucleotide within one or both copies of the ICP4 viral gene loci.

Embodiment 106: the recombinant nucleic acid of any one of embodiments 93-105, wherein the recombinant herpes simplex virus genome comprises the first polynucleotide within the ICP22 viral gene locus.

Embodiment 107: the recombinant nucleic acid of any one of 93-106, wherein the recombinant herpes simplex virus genome comprises the first polynucleotide within the UL41 viral gene locus.

Embodiment 108: the recombinant nucleic acid of any one of embodiments 93-107, wherein the first human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 109: the recombinant nucleic acid of any one of embodiments 93-108, wherein the first human collagen protein is selected from the group consisting of COL1-1, COL1-2, COL3, COL4-1, COL6-1, COL7, and COL17.

Embodiment 110: the recombinant nucleic acid of any one of embodiments 93-109, wherein the nucleic acid sequence encoding the first human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 111: the recombinant nucleic acid of any one of embodiments 93-110, wherein the first human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 112: the recombinant nucleic acid of any one of embodiments 93-111, wherein the first human collagen protein is not COL7.

Embodiment 113: the recombinant nucleic acid of any one of embodiments 93-112, wherein the first polypeptide comprises: (a) the first human collagen protein; (b) a further human collagen protein; and (c) a linker polypeptide linking (a) to (b).

Embodiment 114: The recombinant nucleic acid of embodiment 113, wherein the linker polypeptide is a cleavable linker polypeptide.

Embodiment 115: the recombinant nucleic acid of embodiment 113 or 114, wherein the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 28-31.

Embodiment 116: the recombinant nucleic acid of any one of embodiments 113-115, wherein the further human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 117: the recombinant nucleic acid of any one of embodiments 113-116, wherein the further human collagen protein is selected from the group consisting of COL1-1, COL1-2, COL3, COL4-1, COL6-1, COL7, and COL17.

Embodiment 118: the recombinant nucleic acid of any one of embodiments 113-117, wherein the nucleic acid sequence encoding the further human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 119: the recombinant nucleic acid of any one of embodiments 113-118, wherein the further human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 120: the recombinant nucleic acid of any one of embodiments 113-119, wherein the first human collagen protein and the further human collagen protein are different.

Embodiment 121: the recombinant nucleic acid of any one of embodiments 93-120, wherein the first polynucleotide encodes a polycistronic mRNA comprising: (a) a first open reading frame (ORF) encoding the first polypeptide; (b) a second ORF encoding an additional human collagen protein; and (c) an internal ribosomal entry site (IRES) separating (a) and (b).

Embodiment 122: the recombinant nucleic acid of embodiment 121, wherein the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23.

Embodiment 123: the recombinant nucleic acid of embodiment 121 or 122, wherein the additional human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 124: the recombinant nucleic acid of any one of embodiments 121-123, wherein the additional human collagen protein is selected from the group consisting of COL1-1, COL1-2, COL3, COL4-1, COL6-1, COL7, and COL17.

Embodiment 125: the recombinant nucleic acid of any one of embodiments 121-124, wherein the nucleic acid sequence encoding the additional human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 126: the recombinant nucleic acid of any one of embodiments 121-125, wherein the additional human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 127: the recombinant nucleic acid of any one of embodiments 121-126, wherein the first human collagen protein and the additional human collagen protein are different.

Embodiment 128: the recombinant nucleic acid of any one of embodiments 93-127, wherein the recombinant nucleic acid further comprises a second polynucleotide encoding a second human collagen protein.

Embodiment 129: the recombinant nucleic acid of embodiment 128, wherein the recombinant nucleic acid comprises two or more copies of the second polynucleotide.

Embodiment 130: the recombinant nucleic acid of embodiment 128 or 129, wherein the second human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 131: the recombinant nucleic acid of any one of embodiments 128-130, wherein the second human collagen protein is selected from the group consisting of COL1-1, COL1-2, COL3, COL4-1, COL6-1, COL7, and COL17.

Embodiment 132: the recombinant nucleic acid of any one of embodiments 128-131, wherein the nucleic acid sequence encoding the second human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 133: the recombinant nucleic acid of any one of embodiments 128-132, wherein the second human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 134: the recombinant nucleic acid of any one of embodiments 128-133, wherein the first and second human collagen proteins are different.

Embodiment 135: the recombinant nucleic acid of any one of embodiments 128-134, wherein the recombinant herpes simplex virus genome comprises the second polynucleotide within a viral gene locus.

Embodiment 136: the recombinant nucleic acid of embodiment 135, wherein the recombinant herpes simplex virus genome comprises the second polynucleotide within one or both copies of the ICP4 viral gene loci.

Embodiment 137: the recombinant nucleic acid of embodiment 135 or 136, wherein the recombinant herpes simplex virus genome comprises the second polynucleotide within the ICP22 viral gene locus.

Embodiment 138: the recombinant nucleic acid of any one of embodiments 135-137, wherein the recombinant herpes simplex virus genome comprises the second polynucleotide within the UL41 viral gene locus.

Embodiment 139: the recombinant nucleic acid of any one of embodiments 135-138, wherein the recombinant herpes simplex virus genome comprises the first polynucleotide within one or both copies of the ICP4 viral gene loci and the second polynucleotide within the ICP22 viral gene locus.

Embodiment 140: the recombinant nucleic acid of any one of embodiments 135-138, wherein the recombinant herpes simplex virus genome comprises the first polynucleotide within one or both copies of the ICP4 viral gene loci and the second polynucleotide within the UL41 viral gene locus.

Embodiment 141: a host cell comprising the recombinant nucleic acid of any one embodiments 93-140.

Embodiment 142: the host cell of embodiment 141, wherein the host cell is a eukaryotic cell.

Embodiment 143: the hose cell of embodiment 141 or 142, wherein the host cell is a mammalian cell.

Embodiment 144: the host cell of any one of embodiments 141-143, wherein the host cell is a human cell or a non-human primate cell.

Embodiment 145: the host cell of any one of embodiments 141-144, wherein the host cell is a Vero cell.

Embodiment 146: the host cell of any one of embodiments 141-145, wherein the cost cell is a complementing host cell.

Embodiment 147: a method of collecting a herpes simplex virus, the method comprising: (a) contacting a complementing host cell with the recombinant nucleic acid of any one of embodiments 93-140; and (b) collecting the herpes simplex virus generated by the complementing host cell.

Embodiment 148: a method of collecting a herpes simplex virus, the method comprising: (a) culturing the host cell of any one of embodiments 141-146; and (b) collecting the herpes simplex virus generated by the host cell.

The specification is considered to be sufficient to enable one skilled in the art to practice the present disclosure. Various modifications of the present disclosure in addition to those shown and described herein will become apparent to those skilled in the art from the foregoing description and fall within the scope of the appended claims.

EXAMPLES

The present disclosure will be more fully understood by reference to the following examples. It should not, however, be construed as limiting the scope of the present disclosure. It is understood that the examples and embodiments described herein are for illustrative purposes only and that various modifications or changes in light thereof will be suggested to persons skilled in the art, and are to be included within the spirit and purview of this application and scope of the appended claims.

Example 1: Modified Herpes Simplex Virus Vectors Encoding Human Collagen Protein(s)

Figure 1B:
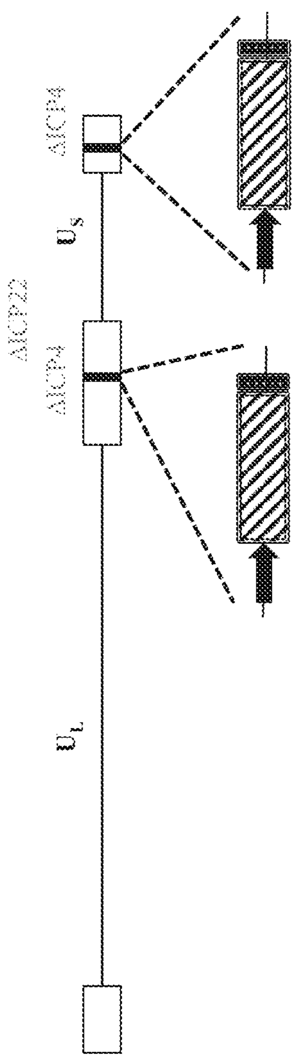
FIG. 1B shows a modified herpes simplex virus genome comprising deletions of the coding sequences of ICP4 (both copies) and ICP22, with a polynucleotide containing the coding sequence of a first human collagen polypeptide operably linked to a heterologous promoter integrated at each of the ICP4 loci.
Figure 1C:
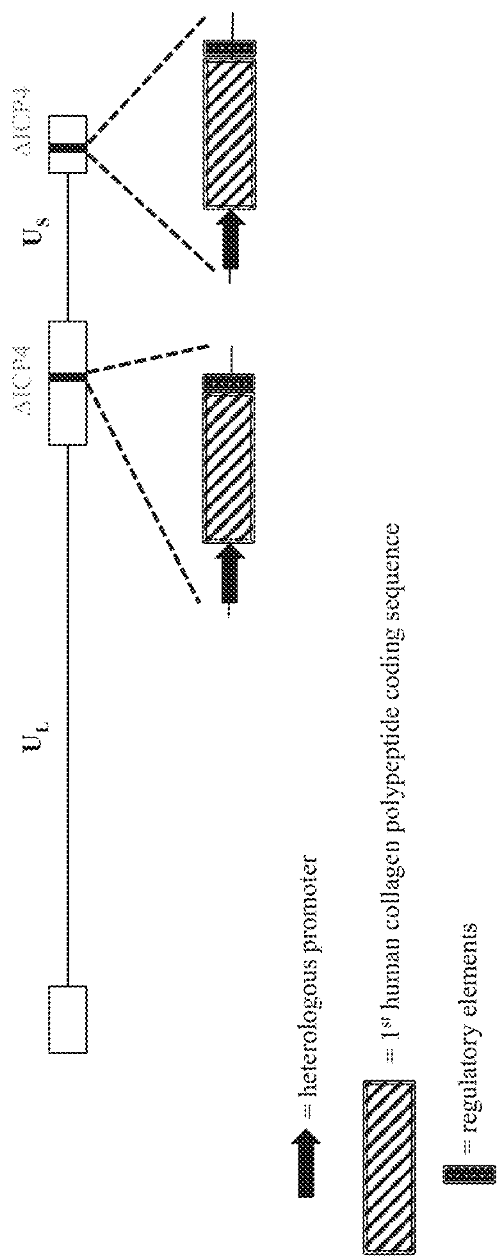
FIG. 1C shows a modified herpes simplex virus genome comprising deletions of the coding sequence of ICP4 (both copies), with a polynucleotide containing the coding sequence of a first human collagen polypeptide operably linked to a heterologous promoter integrated at each of the ICP4 loci.
Figure 1D:
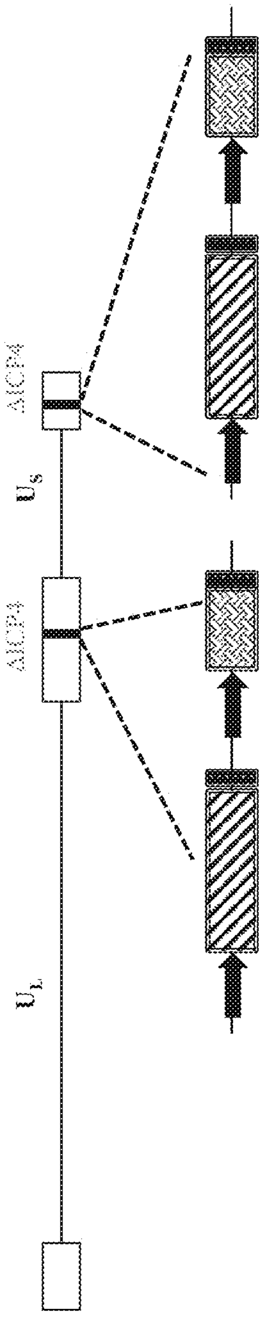
FIG. 1D shows a modified herpes simplex virus genome comprising deletions of the coding sequences of ICP4 (both copies) and ICP22, with a polynucleotide containing 1) the coding sequence of a first human collagen polypeptide operably linked to a first heterologous promoter, and 2) the coding sequence of a second human collagen polypeptide operably linked to a second heterologous promoter, integrated at each of the ICP4 loci. Both the first and second human collagen polypeptides are encoded on the same strand of DNA.
Figure 1E:
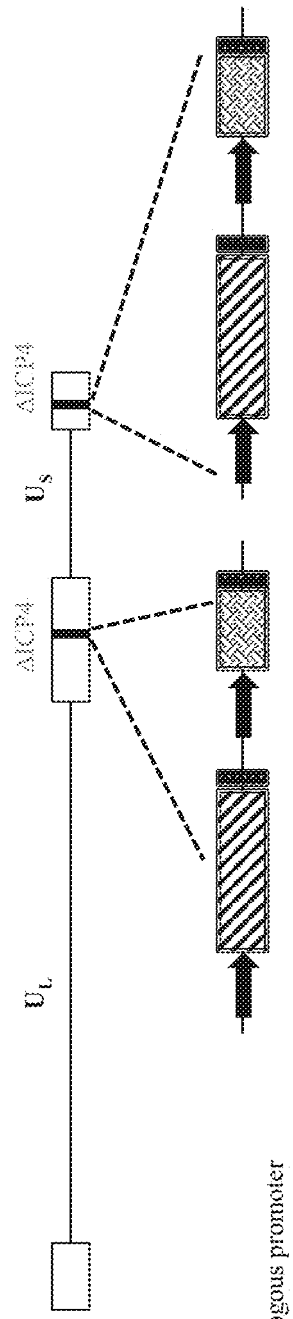
FIG. 1E shows a modified herpes simplex virus genome comprising deletions of the coding sequence of ICP4 (both copies), with a polynucleotide containing 1) the coding sequence of a first human collagen polypeptide operably linked to a first heterologous promoter, and 2) the coding sequence of a second human collagen polypeptide operably linked to a second heterologous promoter, integrated at each of the ICP4 loci. Both the first and second human collagen polypeptides are encoded on the same strand of DNA. FIG.
Figure 1E:
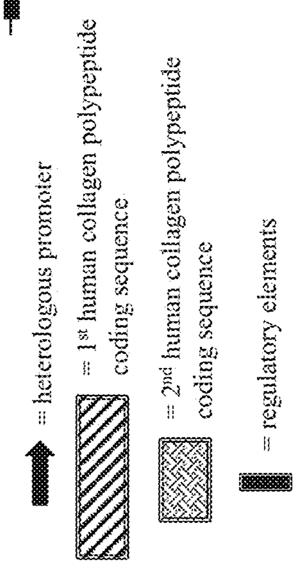
Figures 1F, 1G:
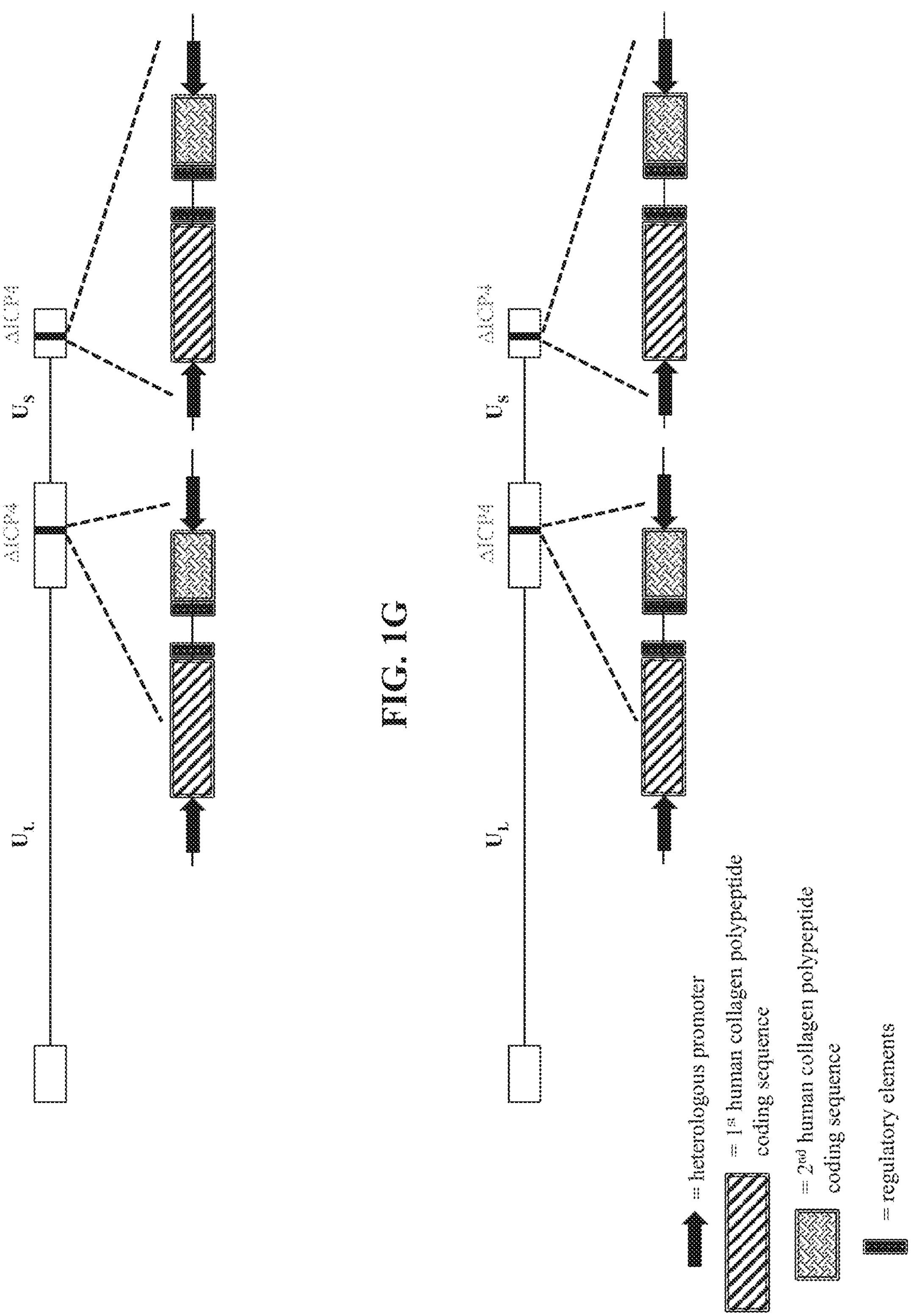
FIG. 1G shows a modified herpes simplex virus genome comprising deletions of the coding sequence of ICP4 (both copies), with a polynucleotide containing 1) the coding sequence of a first human collagen polypeptide operably linked to a first heterologous promoter, and 2) the coding sequence of a second human collagen polypeptide operably linked to a second heterologous promoter, integrated at each of the ICP4 loci. The first and second human collagen polypeptides are encoded on opposite strands of DNA.
Figure 1H:
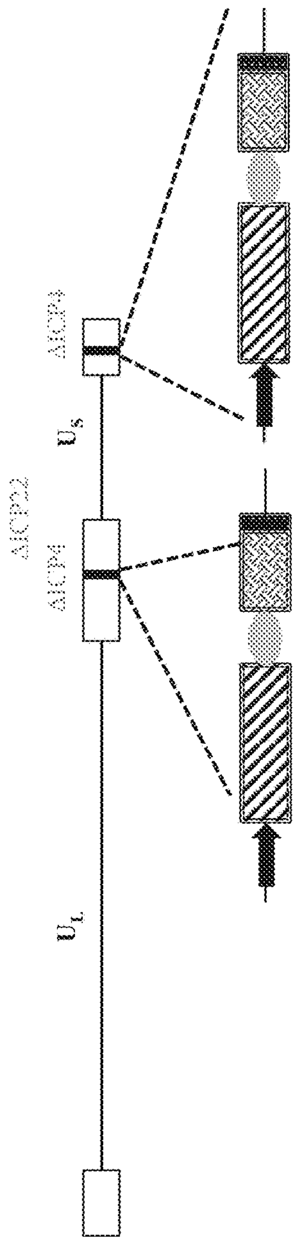
FIG. 1H shows a modified herpes simplex virus genome comprising deletions of the coding sequences of ICP4 (both copies) and ICP22, with a polynucleotide encoding a polycistronic mRNA operably linked to a heterologous promoter integrated at each of the ICP4 loci. The polycistronic mRNA contains the coding sequence of a first human collagen polypeptide and a second human collagen polypeptide separated by an internal ribosomal entry site (IRES).
Figure 1I:
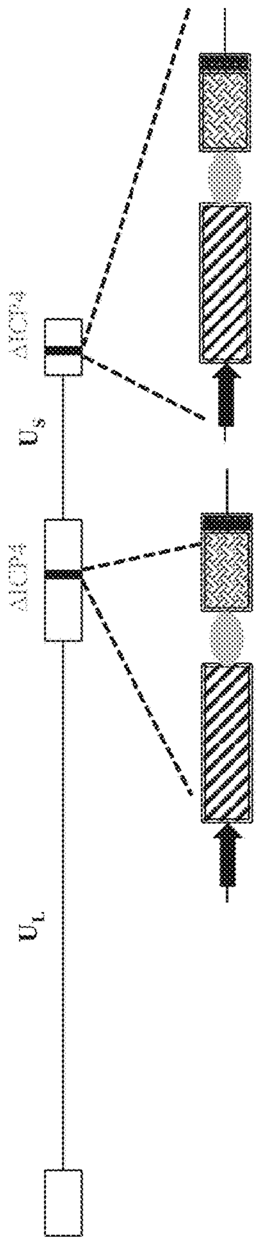
FIG. 1I shows a modified herpes simplex virus genome comprising deletions of the coding sequence of ICP4 (both copies), with a polynucleotide encoding a polycistronic mRNA operably linked to a heterologous promoter integrated at each of the ICP4 loci. The polycistronic mRNA contains the coding sequence of a first human collagen polypeptide and a second human collagen polypeptide separated by an internal ribosomal entry site (IRES).
Figure 1I:
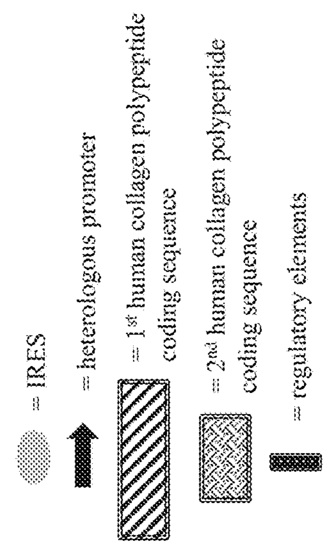
Figures 1J, 1K:
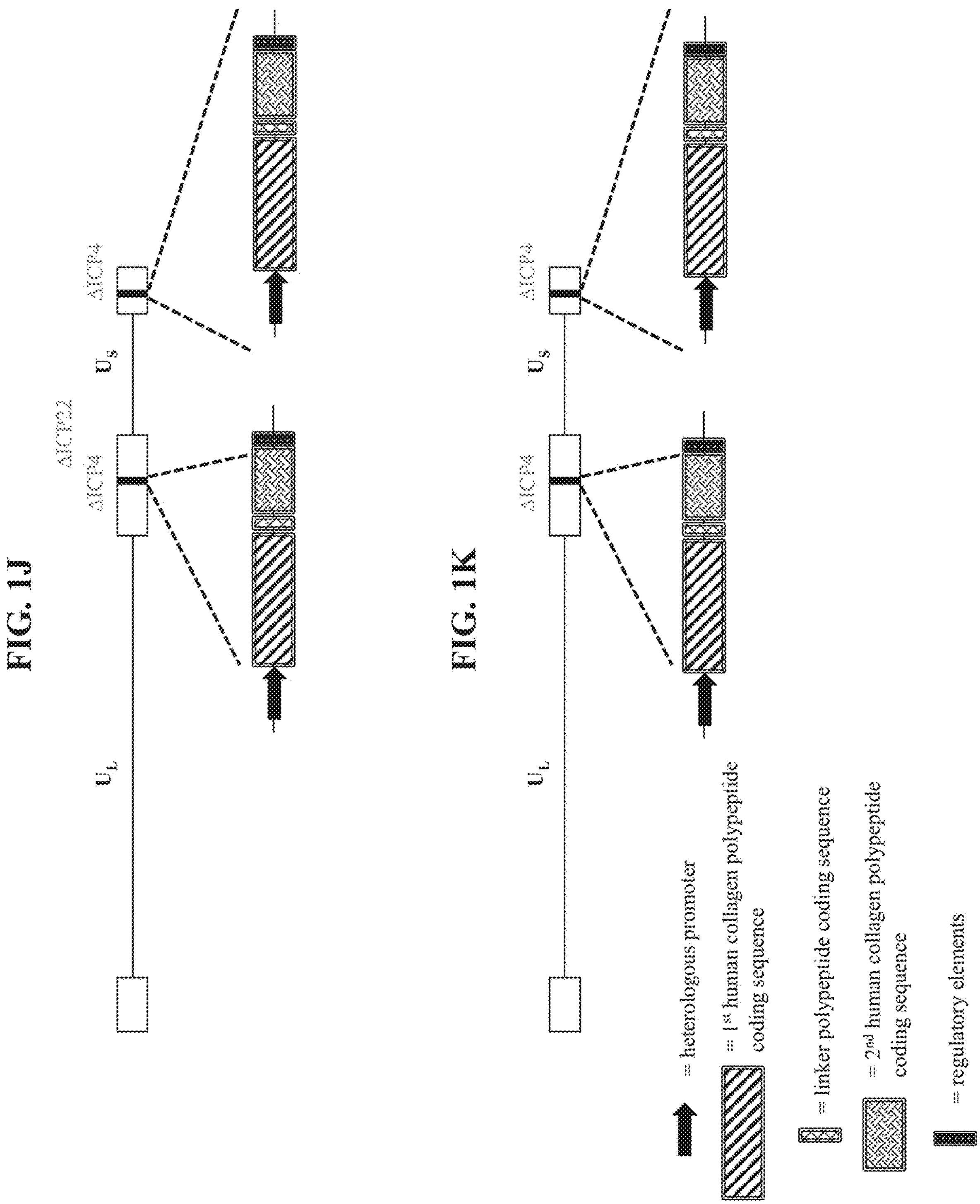
FIG. 1J shows a modified herpes simplex virus genome comprising deletions of the coding sequences of ICP4 (both copies) and ICP22, with a polynucleotide containing the coding sequence of a chimeric polypeptide operably linked to a heterologous promoter integrated at each of the ICP4 loci. The chimeric polypeptide comprises the amino acid sequence of a first human collagen polypeptide and second human collagen polypeptide separated by a cleavable linker.
FIG. 1K shows a modified herpes simplex virus genome comprising deletions of the coding sequence of ICP4 (both copies), with a polynucleotide containing the coding sequence of a chimeric polypeptide operably linked to a heterologous promoter integrated at each of the ICP4 loci. The chimeric polypeptide comprises the amino acid sequence of a first human collagen polypeptide and second human collagen polypeptide separated by a cleavable linker.
Figure 1L:
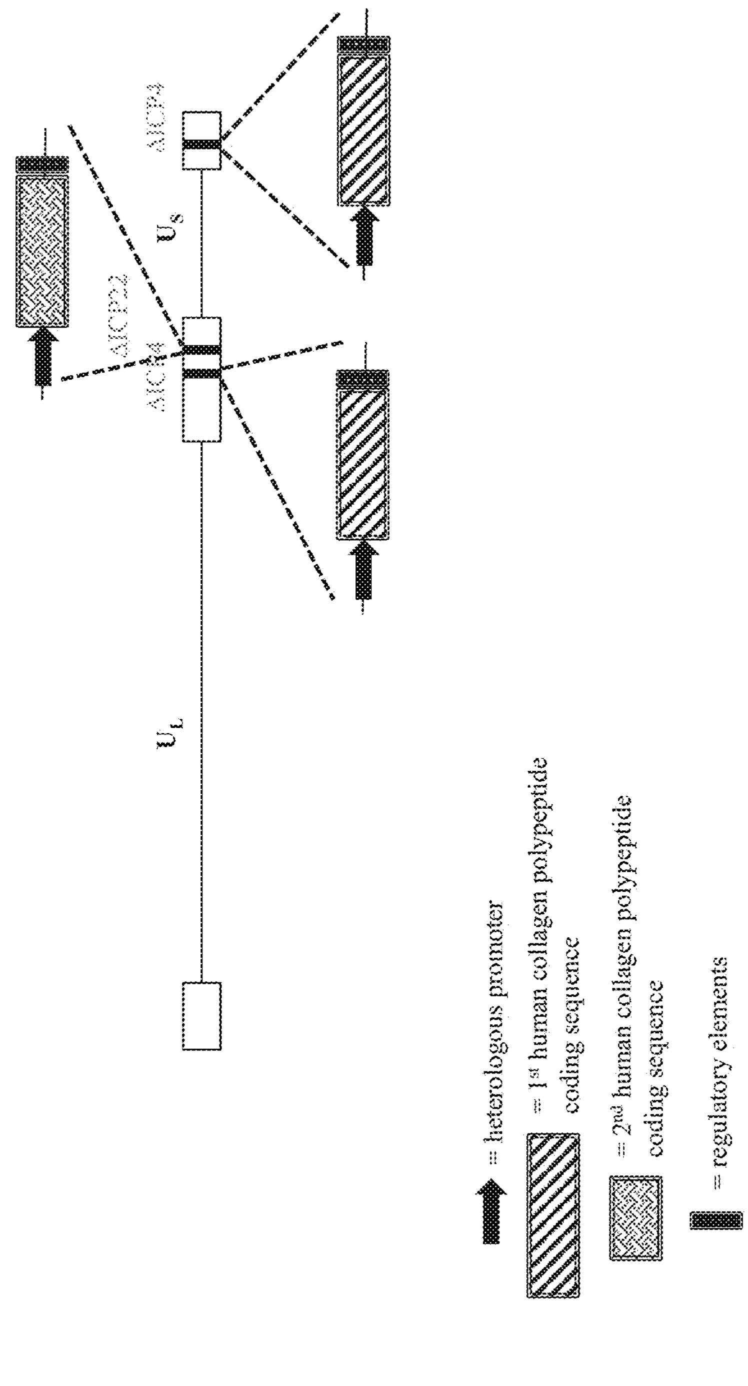
FIG. 1L shows a modified herpes simplex virus genome comprising deletions of the coding sequences of ICP4 (both copies) and ICP22, with a first polynucleotide containing the coding sequence of a first human collagen polypeptide operably linked to a heterologous promoter integrated at each of the ICP4 loci, and a second polynucleotide containing the coding sequence of a second human collagen polypeptide operably linked to a heterologous promoter integrated at the ICP22 locus.
Figure 1M:
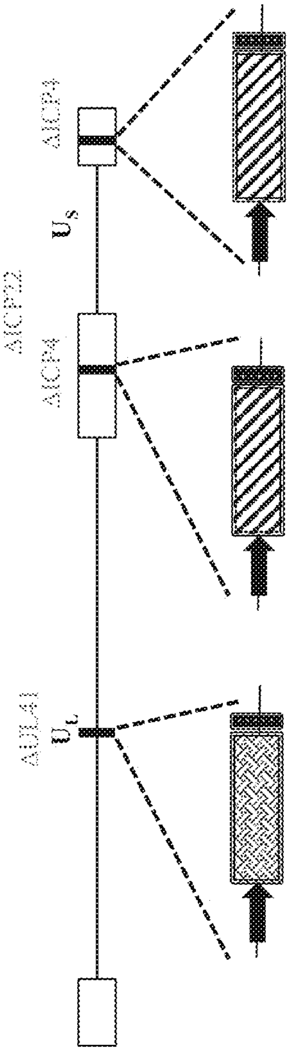
FIG. 1M shows a modified herpes simplex virus genome comprising deletions of the coding sequences of ICP4 (both copies), ICP22, and UL41, with a first polynucleotide containing the coding sequence of a first human collagen polypeptide operably linked to a heterologous promoter integrated at each of the ICP4 loci, and a second polynucleotide containing the coding sequence of a second human collagen polypeptide operably linked to a heterologous promoter integrated at the UL41 locus.
Figure 1N:
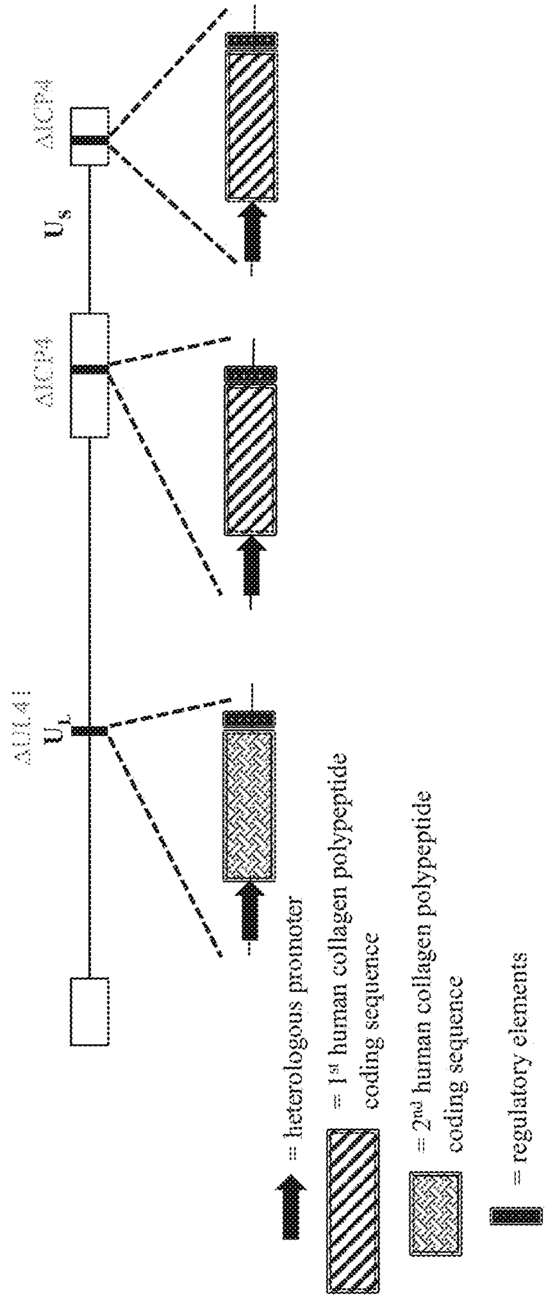

To make modified herpes simplex virus genome vectors capable of expressing human collagen protein(s) in a target mammalian cell (such as a human keratinocyte or fibroblast), a herpes simplex virus genome (FIG. 1A) is first modified to inactivate one or more herpes simplex virus genes. Such modifications may decrease the toxicity of the genome in mammalian cells. Next, variants of these modified/attenuated recombinant viral constructs are generated such that they carry one or more polynucleotides encoding human collagen protein(s). These variants include: 1) a recombinant ΔICP4/ΔICP22-modified HSV-1 genome comprising expression cassettes containing the coding sequence of a first human collagen protein under the control of a heterologous promoter integrated at each ICP4 locus (FIG. 1B); 2) a recombinant ΔICP4-modified HSV-1 genome comprising expression cassettes containing the coding sequence of a first human collagen protein under the control of a heterologous promoter integrated at each ICP4 locus (FIG. 1C); 3) a recombinant ΔICP4/ΔICP22-modified HSV-1 genome comprising expression cassettes containing the coding sequence of a first human collagen protein under the control of a first heterologous promoter and the coding sequence of a second human collagen protein under the control of a second heterologous promoter on the same strand of DNA integrated at each ICP4 locus (FIG. 1D); 4) a recombinant ΔICP4-modified HSV-1 genome comprising expression cassettes containing the coding sequence of a first human collagen protein under the control of a first heterologous promoter and the coding sequence of a second human collagen protein under the control of a second heterologous promoter on the same strand of DNA integrated at each ICP4 locus (FIG. 1E); 5) a recombinant ΔICP4/ΔICP22-modified HSV-1 genome comprising expression cassettes containing the coding sequence of a first human collagen protein under the control of a first heterologous promoter and the coding sequence of a second human collagen protein under the control of a second heterologous promoter on opposite strands of DNA integrated at each ICP4 locus (FIG. 1F); 6) a recombinant ΔICP4-modified HSV-1 genome comprising expression cassettes containing the coding sequence of a first human collagen protein under the control of a first heterologous promoter and the coding sequence of a second human collagen protein under the control of a second heterologous promoter on opposite strands of DNA integrated at each ICP4 locus (FIG. 1G); 7) a recombinant ΔICP4/ΔICP22-modified HSV-1 genome comprising expression cassettes encoding a polycistronic mRNA under the control of a heterologous promoter integrated at each of the ICP4 loci, where the polycistronic mRNA contains the coding sequence of a first human collagen protein and the coding sequence of a second human collagen protein separated by an internal ribosomal entry site (IRES) (FIG. 1H); 8) a recombinant ΔICP4-modified HSV-1 genome comprising expression cassettes encoding a polycistronic mRNA under the control of a heterologous promoter integrated at each of the ICP4 loci, where the polycistronic mRNA contains the coding sequence of a first human collagen protein and the coding sequence of a second human collagen protein separated by an internal ribosomal entry site (IRES) (FIG. 1I); 9) a recombinant ΔICP4/ΔICP22-modified HSV-1 genome comprising expression cassettes containing the coding sequence of a chimeric protein under the control of a heterologous promoter integrated at each of the ICP4 loci, where the chimeric protein contains the amino acid sequence of a first human collagen protein and the amino acid sequence of a second human collagen protein separated by the amino acid sequence of a linker polypeptide (FIG. 1J); 10) a recombinant ΔICP4-modified HSV-1 genome comprising expression cassettes containing the coding sequence of a chimeric protein under the control of a heterologous promoter integrated at each of the ICP4 loci, where the chimeric protein contains the amino acid sequence of a first human collagen protein and the amino acid sequence of a second human collagen protein separated by the amino acid sequence of a linker polypeptide (FIG. 1K); 11) a recombinant ΔICP4/ΔICP22-modified HSV-1 genome comprising expression cassettes containing the coding sequence of a first human collagen protein under the control of a heterologous promoter integrated at each of the ICP4 loci, and an expression cassette containing the coding sequence of a second human collagen protein under the control of a heterologous promoter integrated at the ICP22 locus (FIG. 1L); 12) a recombinant ΔICP4/ΔICP22/ΔUL41-modified HSV-1 genome comprising expression cassettes containing the coding sequence of a first human collagen protein under the control of a heterologous promoter integrated at each of the ICP4 loci, and an expression cassette containing the coding sequence of a second human collagen protein under the control of a heterologous promoter integrated at the UL41 locus (FIG. 1M); and 13) a recombinant ΔICP4/ΔUL41-modified HSV-1 genome comprising expression cassettes containing the coding sequence of a first human collagen protein under the control of a heterologous promoter integrated at each of the ICP4 loci, and an expression cassette containing the coding sequence of a second human collagen protein under the control of a heterologous promoter integrated at the UL41 locus (FIG. 1N).

These modified herpes simplex virus genome vectors are transfected into engineered Vero cells that are modified to express one or more herpes virus genes. These engineered Vero cells secrete replication-defective herpes simplex virus with the modified genomes packaged therein into the supernatant. The supernatant is then collected, concentrated, and sterile filtered through a 5 μm filter.

Example 2: Construction and In Vitro Analysis of HSV Candidates Encoding Human COL7

Collagen alpha-1(VII) chain protein (COL7) functions to strengthen and stabilize the skin. Briefly, COL7A1 transcripts are translated, the resulting COL7 peptides are post-translationally modified by hydroxylation and glycosylation, and glycosylated COL7 tri-peptides form a triple helix known as pro-collagen, which is secreted from the cell. The pro-collagen associates into higher-order structures upon secretion, forming anchoring fibrils, which are then available to help organize, stabilize, and aid in the adherence of the epithelial basement membrane. The epithelial basement membrane is responsible for anchoring the epithelium to the underlying loose connective tissue and is essential for dermal-epidermal stability (dermo-epidermal junction integrity). Dystrophic epidermolysis bullosa is an inherited genetic condition caused by mutations in the COL7A1 gene; mutations in this gene impair the ability of COL7 to properly connect the epidermis to the dermis in dystrophic epidermolysis bullosa patients, leading to fragile skin. Recessive dystrophic epidermolysis bullosa (RDEB), the most severe form of epidermolysis bullosa, is most often characterized by extensive blistering and scarring of the skin and mucosal membranes.

The following example describes the construction of a recombinant herpes simplex type-1 viruses modified to express human Collagen alpha-1(VII) chain polypeptide (COL7), and further provides experiments showing that the recombinant HSV was capable of expressing functional human collagen in vitro in primary human keratinocytes and fibroblasts from healthy and RDEB patients.

Materials and Methods

Virus Construction

Figures 2A, 2B:
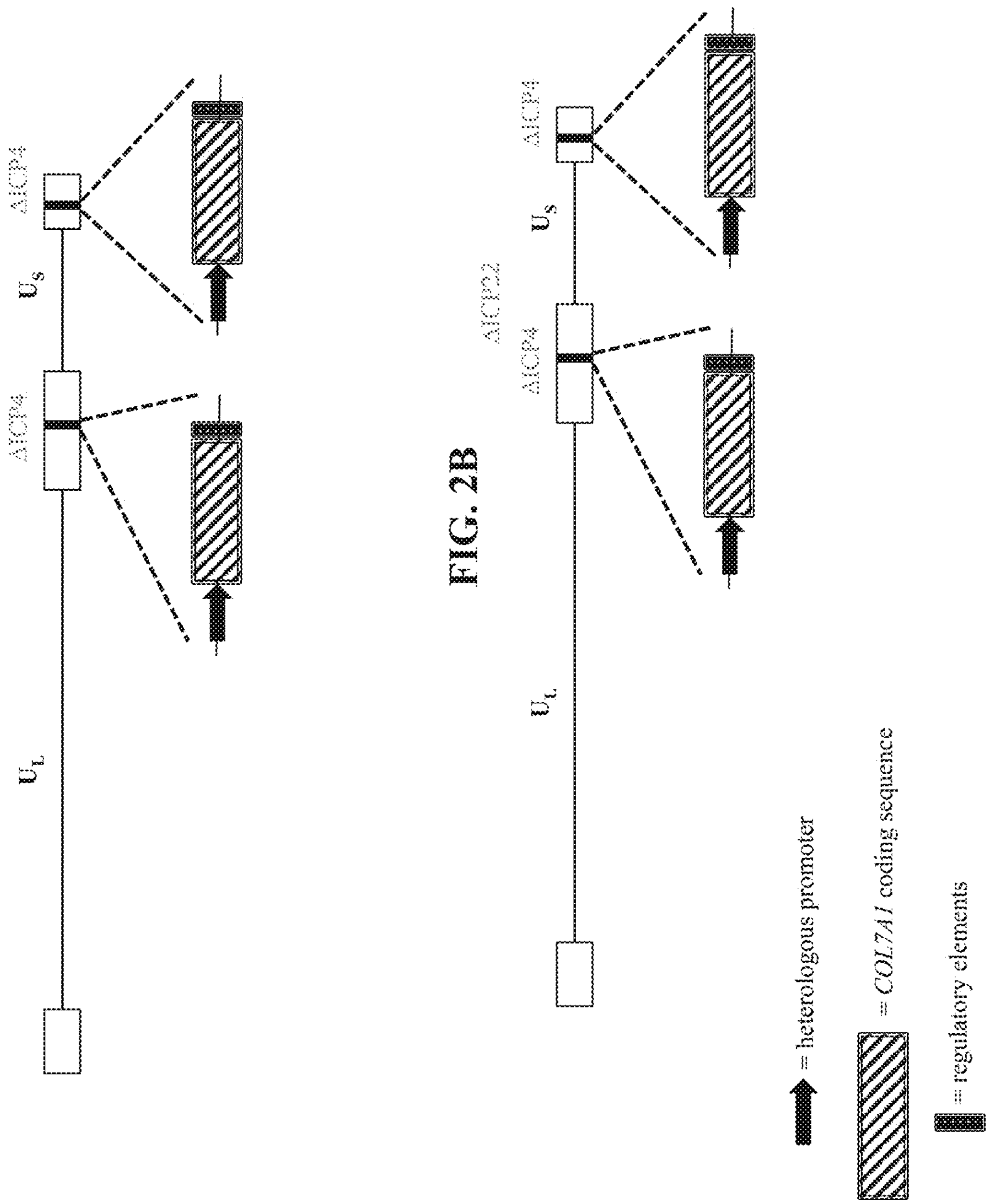
FIGS. 2A-B show schematics of replication-defective herpes simplex type-1 viruses carrying human collagen 7 (COL7) expression cassettes.

The "KCA211" viral vector (FIG. 2A) was generated as follows: a wild-type herpes simplex virus genome was first modified by deleting the coding sequence of both copies of the viral ICP4 gene (ΔICP4). The ΔICP4-modified viral genome was also engineered to contain an mCherry expression cassette in each of the ICP4 loci. The viral genome was then further modified to encode wild-type human COL7. Briefly, a plasmid containing the coding sequence for wild-type COL7 (under control of the hCMV promoter) flanked by the upstream (US) and downstream (DS) regions of ICP4 was transfected into Vero cells modified to express the herpes virus ICP4 gene. These transfected cells were then infected with the modified ΔICP4 mCherry-expressing virus described above. The US and DS ICP4 regions flanking COL7 allowed for a double crossover and replacement of each of the mCherry loci. Visual screening for the absence of mCherry fluorescence was then used to identify cells containing recombined virus.

The "SAR-COL7" viral vector (FIG. 2B) was generated as follows: a wild-type herpes simplex virus genome was first modified by deleting the coding sequence of both copies of the viral ICP4 gene as well as the single copy ICP22 gene (ΔICP4/ΔICP22). The ΔICP4/ΔICP22-modified viral genome was also engineered to contain an mCherry expression cassette in each of the ICP4 loci. The viral genome was then further modified to encode wild-type human COL7. Briefly, a plasmid containing the coding sequence for wild-type COL7 (under control of the hCMV promoter) flanked by the upstream (US) and downstream (DS) regions of ICP4 was transfected into Vero cells modified to express the herpes virus ICP4 gene. These transfected cells were then infected with the modified ΔICP4/ΔICP22 mCherry-expressing virus described above. The US and DS ICP4 regions flanking COL7 allowed for a double crossover and replacement of each of the mCherry loci. Visual screening for the absence of mCherry fluorescence was then used to identify cells containing recombined virus.

Cell Culture

Cells were previously isolated from skin biopsies taken as part of routine surgical or diagnostic procedures. Informed written consent was obtained from each patient, or in the case of children, from the parent or legal guardian. This study was performed in accordance with the Helsinki declaration. All cells were cultured at 37° C. in 5% $CO_2$. Human fibroblasts were grown in Dulbecco's modified essential medium supplemented with 10% fetal bovine serum (PEAK® serum, cat. no. PS-FB1). RDEB and normal keratinocytes were cultured in DMEM/Ham's F12 medium (3:1)

supplemented with 10% FBS, 10 ng/mL epidermal growth factor, 10-10 cholera toxin, 0.4 μg/mL hydrocortisone, 5 μg/mL transferrin, 5 μg/mL insulin, and 5 μg/mL liothyronine. All media contained ascorbic acid (150 μM). Keratinocytes were grown in the presence of a mitotically activated feeder layer of 3T3 cells and in the presence of 10 μM of the Rho-kinase inhibitor Y-27632.

Virus Infections

Viral aliquots were stored at −80° C., and were left to defrost under the tissue culture laminar flow hood before use. Target cell number was determined prior to infection after detaching cells from the tissue culture plastic and counting on a hemocytometer. Multiplicity of infection (MOI) was calculated from the virus titer and target cell number, and the appropriate volume of virus stock was diluted in 10% serum containing DMEM and incubated with the target cells for 2 hours at 37° C. Virus was then removed, and fresh media was supplied to target cells after washing twice with pre-warmed media.

Western Blots

Keratinocytes were plated in a 100 mm dish at $8\times10^5$ to achieve 70-80% confluency the following day. 48 hours after infection, cells were lysed with radioimmunoprecipitation assay buffer. Lysate was placed in a centrifuge for 5 minutes at 4° C., and the supernatant was mixed with a 6× Laemmli loading buffer. Before loading onto SDS-PAGE, the samples were boiled for 5 minutes at 95° C. For COL7 detection, 5-30 μg of protein was loaded on a 6% acrylamide gel. The primary antibody used for COL7 detection was a rabbit antibody (Sigma, cat. no. HPA042420). Resolved proteins were transferred onto a nitrocellulose membrane, blocked in PBS-0.1% Tween with 5% milk or 5% BSA according to requirements of the primary antibody, and incubated overnight with the primary antibody. After incubation with IgG-HRP conjugated secondary antibody (Santa Cruz Biotechnology), the membrane was incubated with western blotting substrate (ThermoFisher Scientific, cat. no. 32106) and exposed to film (ThermoFisher Scientific, cat. no. 34090).

qRT-PCR

RNA was isolated using RNeasy® Mini Kit (Qiagen) according to the manufacturer's protocol. RNA extractions were quantified using a NanoDrop™ spectrophotometer (Fisher Scientific), and 1.5 μg RNA was used for cDNA synthesis using a SuperScript III First-Strand Synthesis system (Invitrogen). For qPCR, SYBR Select Master mix (Life Technologies) was used, and cDNA samples were diluted 1:25 to serve as template. Experiments were performed in triplicate.

Adhesion Assay 96-well plates were left uncoated, or were coated with 10, 20, or 50 μg/mL rat tail collagen 1 (BD Biosciences) or human fibronectin (Millipore) in 100 μL, reaction volume at 4° C. overnight, then washed with PBS, and blocked with PBS+0.1% BSA for 1 hour at 37° C. Mock (control) or SAR-COL7 infected RDEB keratinocytes ($2.4\times10^4$ cells in 1004 μL, of DMEM/HamF12+0.1% BSA) were added to the plates and incubated at 37° C. for 90 minutes. Wells were washed three times with PBS to remove any unbound cells, and adherent cells were fixed with PFE for 20 minutes. The fixed cells were then treated with 70% ethanol, stained with crystal violet, resolved in 100% ethanol, and quantified by measuring absorbance at 630 nM with a Flex Station 3 plate reader (Molecular Devices).

Organotypic Skin Equivalents

Bovine fibrinogen (90% clottable, MP Biomedicals) was dissolved in 1.1% NaCl at 37° C. for 4 hours and then filtered with a 0.45 μm nylon membrane filter. Fibroblasts were collected with the use of trypsin and centrifugation and were resuspended in media to a final concentration of $2\times10^6$ cells/mL. 150 μL, of the cell suspension was mixed with 1 mL of thrombin (3 IU—Sigma Aldrich), and the cell/thrombin mix was added to fibrinogen at a ratio of 1:1. The mixture was quickly but gently distributed at 1 mL/well into a 12-well plate and incubated at 37° C. After 20 minutes, medium supplemented with ascorbic acid and aprotinin (Sigma) at a final concentration of 10 μg/mL was added. The matrices were left to mature for 5-7 days while medium was changed every other day. Keratinocytes were plated on top at $2\times10^6$ cells/well, and on the next day the culture was raised to the air-liquid interface on a metal grid, and treatment with amlexanox was started. Medium was changed every other day with fresh drug, ascorbic acid and aprotinin. Cultures were collected at one or two weeks of treatment and frozen with OCT in liquid nitrogen-cooled isopentane. 8 μm sections were cut using a cryostat (Avantik QS11) and immunostained with polyclonal anti-COL7 antibody at a dilution of 1:800. Nuclei were counterstained with DAPI (Invitrogen).

Results

Figure 3A:
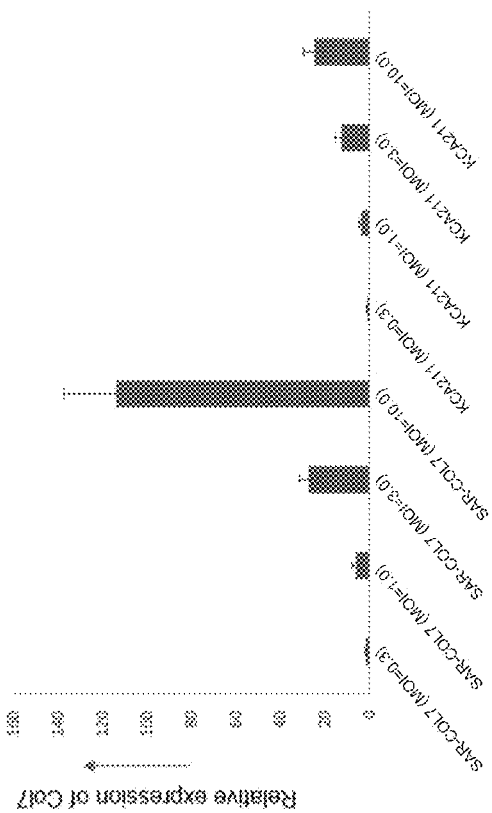
FIGS. 3A-B show human COL7 expression in HaCaT cells infected with KCA211 or SAR-COL7 at the indicated MOIs.
Figure 3B:
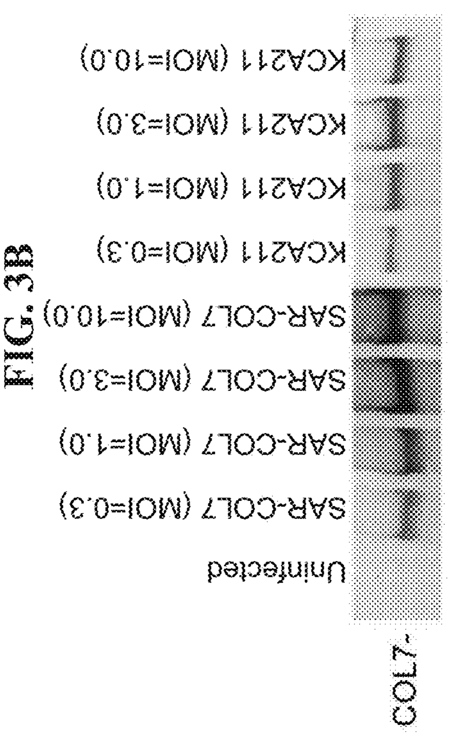

First, COL7 expression from modified HSV was assessed by qPCR and western blot analyses in the HaCaT human keratinocyte cell line to determine whether the modified HSVs were capable of expressing their cargo. HaCaT cells were transduced with either SAR-COL7 or KCA211 at MOIs ranging from 0.3-10. 48 hours after infection, cells were collected and processed for either qPCR (FIG. 3A) or western blot (FIG. 3B) analyses. The results demonstrated that full length COL7 was expressed in a dose-dependent manner from human keratinocytes infected with either modified HSV.

Figure 4A:
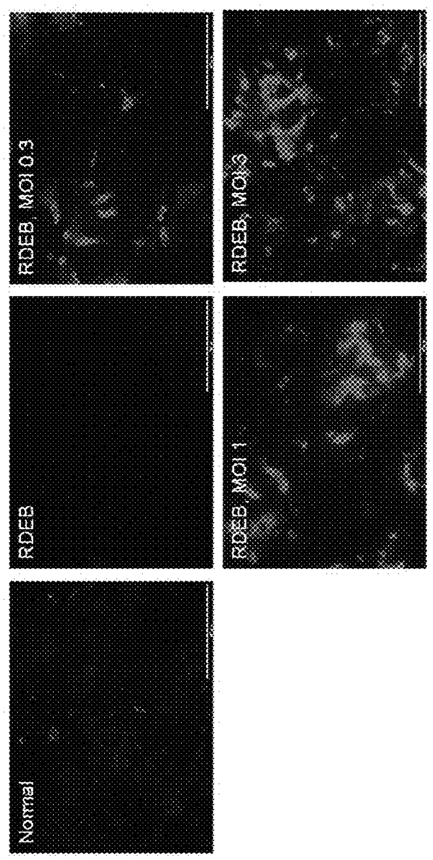
FIGS. 4A-B show immunofluorescence images of human COL7 expression in mock infected primary human cells isolated from a healthy patient (Normal), and mock or SAR-COL7 infected primary human cells isolated from a patient suffering from recessive dystrophic epidermolysis bullosa (RDEB).
Figure 4B:
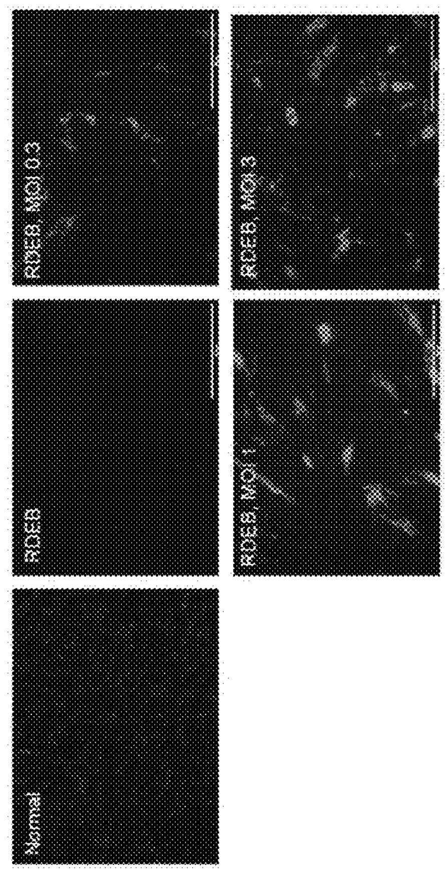

Next, immunofluorescence experiments were conducted to visualize COL7 expression in primary RDEB keratinocytes or RDEB fibroblasts infected for 24-48 hours with SAR-COL7 at various MOIs (ranging from 0.1 to 10). A strong COL7 signal was observed at all doses of SAR-COL7 tested for both keratinocytes (FIG. 4A) and fibroblasts (FIG. 4B), as compared to uninfected normal and RDEB keratinocytes and fibroblasts. The infection efficiencies of SAR-COL7 at MOIs of 0.1-1 in fibroblasts ranged from 16-36%. The infection efficiencies of SAR-COL7 at MOIs of 3.0 and above in fibroblasts were >90%.

Figure 5A:
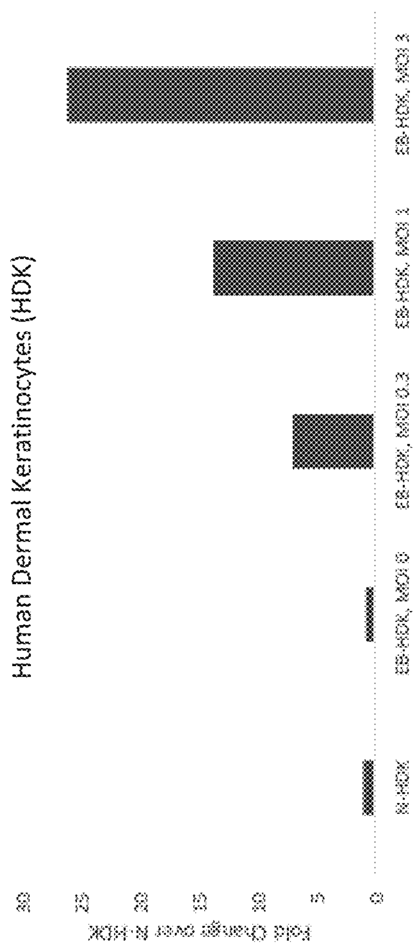
FIGS. 5A-B show quantitative PCR analysis of human COL7 expression in mock infected primary human cells isolated from a healthy patient, and mock or SAR-COL7 infected primary human cells isolated from a patient suffering from recessive dystrophic epidermolysis bullosa (EB).
Figure 5B:
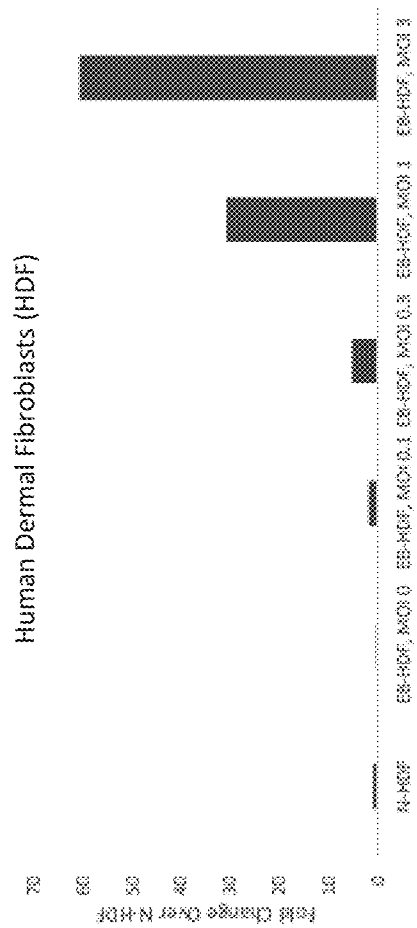

RDEB patient-derived human dermal keratinocytes (HDKs) and fibroblasts (HDFs) were infected with SAR-COL7 at varying MOIs in order to evaluate COL7A1 RNA expression. Normal HDKs and HDFs, as well as mock infected RDEB HDKs and HDFs, were used as negative controls. Dose-dependent increases in COL7A1 transcripts were observed in both HDKs (FIG. 5A) and HDFs (FIG. 5B) infected with SAR-COL7. The relative fold change in COL7A1 transcript expression after infection vs. uninfected healthy HDKs (Table 1A) or uninfected healthy HDFs (Table 1B) was also calculated. The use of COL7A1-encoding HSV was capable of increasing COL7A1 transcript expression by approximately 26-fold in RDEB HDKs and 60-fold in RDEB HDFs relative to wild-type COL7A1 transcript levels in healthy HDKs and HDFs at an MOI of 3.

TABLE 1A

| COL7A1 expression in HDKs | | |
|---|---|---|
| Cell type: | MOI: | Fold change over N-HDK: |
| Normal HDKs (N-HDK) | 0 | 1.00 |
| RDEB HDKs (EB-HDK) | 0 | 0.79 |
| RDEB HDKs (EB-HDK) | 0.3 | 7.00 |
| RDEB HDKs (EB-HDK) | 1.0 | 13.73 |
| RDEB HDKs (EB-HDK) | 3.0 | 26.25 |

TABLE 1B

| COL7A1 expression in HDFs | | |
|---|---|---|
| Cell type: | MOI: | Fold change over N-HDF: |
| Normal HDFs (N-HDF) | 0 | 1.000 |
| RDEB HDFs (EB-HDF) | 0 | 0.340 |
| RDEB HDFs (EB-HDF) | 0.1 | 1.805 |
| RDEB HDFs (EB-HDF) | 0.3 | 5.134 |
| RDEB HDFs (EB-HDF) | 1.0 | 30.788 |
| RDEB HDFs (EB-HDF) | 3.0 | 60.571 |

Figure 6A:
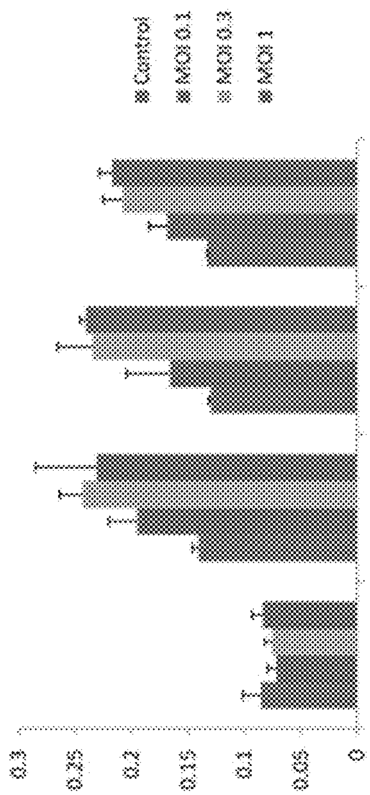
FIGS. 6A-B show cellular adhesion of uninfected (control) or SAR-COL7 infected RDEB primary human keratinocytes to untreated (plastic) or treated wells of a microwell plate.
Figure 6B:
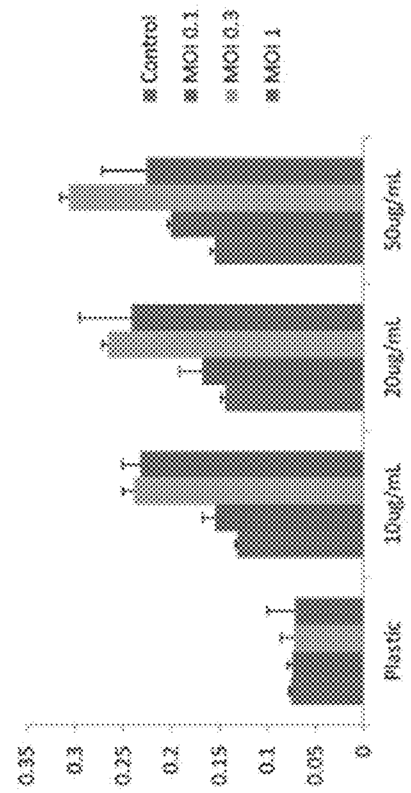

Next, the functionality of human COL7 expressed from SAR-COL7 was tested by a cell adhesion assay. The ability of uninfected RDEB keratinocytes, and RDEB keratinocytes infected with SAR-COL7 at varying MOIs, to adhere to wells treated with Collagen 1 or fibronectin was studied. Interestingly, RDEB keratinocytes infected with SAR-COL7 showed increased adhesion to Collagen 1 (FIG. 6A) and fibronectin (FIG. 6B) in dose-dependent manner using a plate-based adhesion assay.

Figure 7:
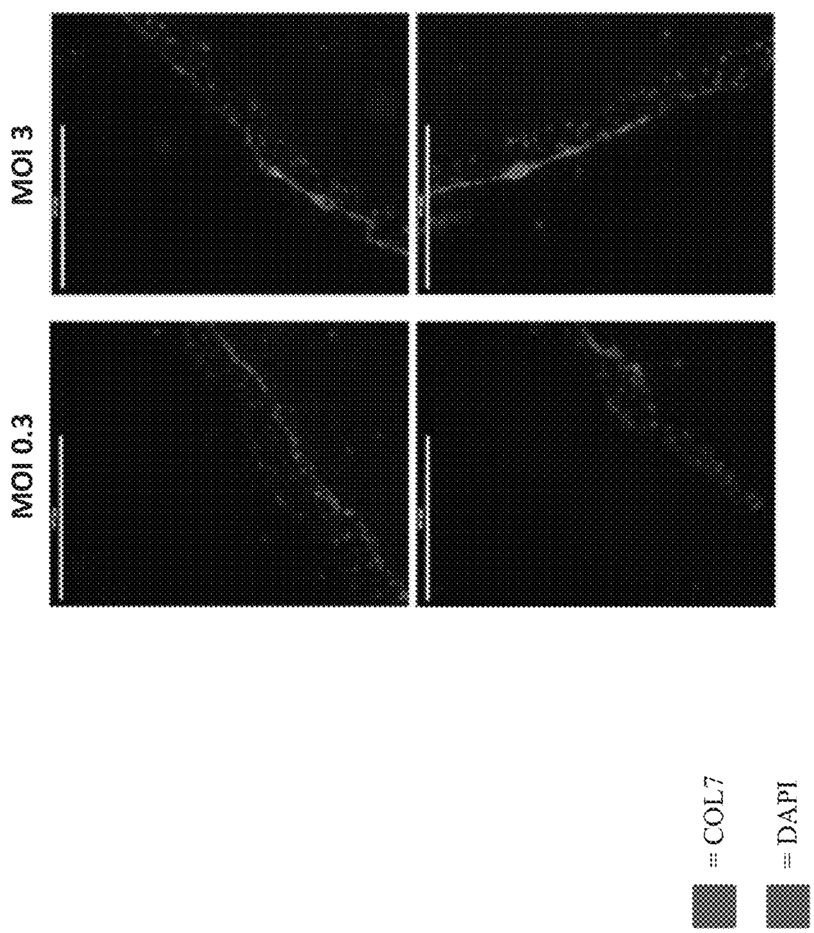
FIG. 7 show representative immunofluorescence images of human COL7 expression and deposition at the basement membrane zone (BMZ) at day 5 in organotypic cultures constructed with SAR-COL7 infected RDEB primary human keratinocytes and fibroblasts. Both keratinocytes and fibroblasts were infected in situ at the indicated MOI after culture construction.

Finally, a skin equivalent (SE) organotypic culture composed of RDEB fibroblasts and keratinocytes was used to evaluate the expression of COL7 from SAR-COL7 at the Basement Membrane Zone (BMZ). Organ cultures were constructed with RDEB or normal fibroblasts and keratinocytes. RDEB cells were either infected with SAR-COL7 prior to organ culture construction (data not shown), or SAR-COL7 was added drop-wise onto the cultures prior to raising at the air-liquid interface (FIG. 7). The resulting skin equivalents (SEs) were isolated, sectioned, and stained for immunofluorescence to detect COL7 protein expression. COL7 was detected in these organotypic cultures from cells infected with SAR-COL7, and the initiation of COL7 protein deposition at the BMZ was observed. This data suggested that not only could SAR-COL7 deliver COL7A1 and express COL7 protein efficiently, but the COL7 protein began to organize in organotypic cultures similar to the pattern of organization expected for COL7 protein in vivo.

Taken together, the data provided herein indicated that replication-defective HSV may be employed as a vehicle for effectively delivering and expressing high levels of functional human collagen in wild-type primary human cells, as well as primary human cells isolated from patients suffering from a collagen deficiency, without any obvious toxicity in either 2D or 3D culture systems.

Example 3: In Vivo Analysis of an HSV Candidate Encoding Human COL7 in Wild-Type Animals The following example describes experiments showing that recombinant viruses constructed and validated in vitro in human cells (see Example 2 above) were capable of expressing the encoded human collagen in vivo in wild-type animals. The purpose of the study was, in part, to evaluate the skin biodistribution of HSV-mediated collagen expression in healthy immunocompetent animals.

Materials and Methods

Test Article

The active ingredient in the formulations administered to mice was the modified herpes simplex virus SAR-COL7 or KCA211 (see Example 2 above) at a titer of $4.8\times10^8$ plaque forming units (PFU)/mL formulated in PBS+10% glycerol. The vehicle used for intradermal administration was Dulbecco's phosphate-buffered saline (DPBS)+10% glycerol. The vehicle used for topical administration was 3% hydroxypropyl methylcellulose (HPMC) gel formulated in sterile double distilled water.

Animals

Healthy male BALB/c mice between 6 and 10 weeks of age were used. All procedures used in the protocol were in compliance with applicable animal welfare acts and were approved by the local Institutional Animal Care and Use Committee (IACUC).

Intradermal Injections

Prior to and during test article administration, mice were anesthetized using a cocktail of Dexdomitor (30 μL or 0.05 mg/mL) and Telzol (50 μL of 10 mg/mL). The sedative was reversed with Antisedan (50 μL of 0.5 mg/mL). The back and flank areas were shaved using an electrical pet clipper, and the area was wiped with an alcohol wipe. Intradermal injections were performed using the Mantoux technique with a syringe and 27 G needle (VWR, cat. no. BD305620), ensuring creation of a superficial "bleb" at each site. The virus was kept on dry ice, was thawed at room temperature, and was administered within 30 minutes of thawing. Two intradermal injections were administered to the back of each mouse, and the edges of the "bleb" were marked with a permanent marker.

Topical Application

Topical administration was conducted either on open wounds or abraded or scarified skin. The back and flank regions were shaved using electrical clippers. Scarification was performed by gently abrading the skin with a mechanical Dremel followed by superficial perforation with a 22 G needle. For creation of a wound, a 5-6 mm diameter biopsy of the skin was removed using sharp scissors. In order to contain the topical formulation to the abraded or wounded site, a well was created from cut and autoclaved tops of 1.5 mL micro-centrifuge tubes. The lids were retained, and the cut side was covered with transparent adhesive dressing. The "wells" were adhered to the abraded/wounded region using surgical glue with the lid side down. 100 μL, of SAR-COL7 was mixed with 20 μL, of topical vehicle and was applied to the wound site by injection through the transparent adhesive in order to contain the topical gel on the wound and prevent leakage.

Tissue Collection

At the indicated time points following SAR-COL7 administration, the mice were euthanized, and the injection site was removed using an 8 mm biopsy punch. One half of the biopsy was quick-frozen using liquid nitrogen, while the other half was embedded in OCT and cryopreserved for immunofluorescence staining.

Real Time Quantitative PCR

Quick-frozen biopsy halves were stored at −80° C. until analysis. For processing and analysis, samples were resuspended in 350 μL, RLT buffer prepared with fresh DTT following the manufacturer's protocol (Qiagen). The sample were sonicated 3 times at 25% amplitude with intermittent incubation for 1 minute on ice, and DNA and RNA extractions were performed according to the manufacturer's protocol (Qiagen AllPrep DNA and RNA extraction kit). Both RNA and DNA samples were resuspended in distilled, deionized RNAse free water and quantified spectrophotometrically on a Take3 microplate reader (BioRad).

Absolute quantification of COL7A1 DNA copies and RNA transcripts was performed by Taqman Real Time PCR analysis using a custom primer/probe assay that spanned the 3' end of the human COL7A1 open reading frame and the 3' UTR, specifically detecting the COL7A1 transgene. 100 ng of DNA and RNA was used for the qPCR and qRT-PCR assays respectively, and a plasmid standard containing the region to be amplified was prepared in 100 ng mouse genomic or RNA matrix. GAPDH was used as the control for both analyses.

Immunofluorescent Staining

OCT frozen tissue was sectioned at 5-8 μm and left to air dry for up to 1 hour. The slides were dipped in 100% methanol for 10 minutes at −20° C. and left to air dry. The methanol-fixed sections were rehydrated through 3 washes in PBS (5 minutes each) at room temperature. The sections were incubated with a blocking solution composed of 10% serum (mixed species) for 1 hour at room temperature in a humid chamber. The excess blocking solution was removed and a drop of primary antibody (anti-human collagen 7, Sigma, cat. no. HPA042420; anti-integrin alpha 6 (clone goH3), BD Biosciences, cat. no. 555734) solution, prepared in 5% blocking solution, was applied on each section (30-50 μL/section). The sections were incubated with the primary antibody for 16 hours at 4° C., washed 3 time in PBS for 5 minutes each at room temperature, and secondary antibody (anti-rabbit AF 647, Invitrogen, cat. no. A21244; anti-rat AF-594, Invitrogen, cat. no. A11007) was applied at a 1:400 dilution in PBS for 1 hour at room temperature in a humid chamber. The 3 times PBS wash was repeated, then slides were immersed in Hoechst solution (1:1000) for 5 minutes at room temperature. The 3 times PBS wash was repeated, and the stained sections were mounted with mounting media (Fluorometer G, Southern Biotech, cat. no. 0100-01) and covered with a coverslip. The sections were imaged after dehydration (approximately 24 hours) using a Widefield Fluorescence Microscope.

Results

A total of 30 male BALB/c mice divided into 6 groups were used for this study. SAR-COL7 was administered either by intradermal injection or topical application on day 1, and a subset of mice were harvested on day 3, and the remaining mice on day 6. Animals in group 2 received a low dose of SAR-COL7 ($4.8\times10^6$pfu/site) in the same volume by intradermal injection, and group 1 served as a control for the intradermal cohorts. In groups 4, 5, and 6, the topical vehicle (group 4) or SAR-COL7 in topical gel (groups 5 and 6) was applied either to a wounded (groups 4 and 6) or abraded (group 5) area in a total volume of 120 μL. Tissues were harvested and processed for qPCR and immunofluorescence analysis as described above.

Figure 8A:
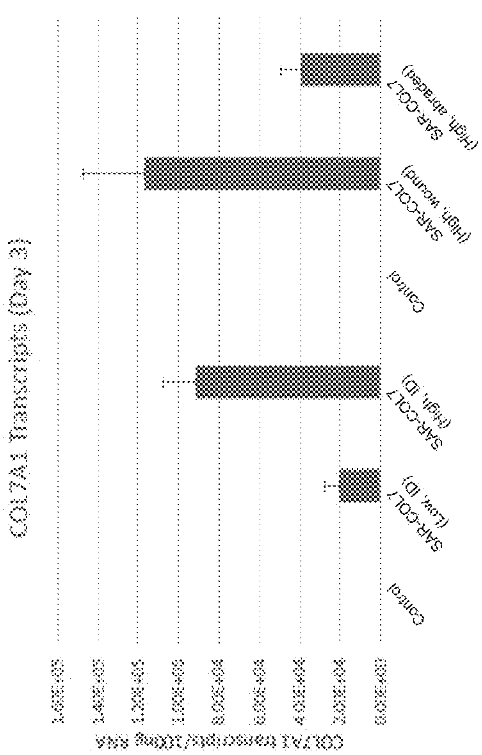
FIGS. 8A-D show human COL7A1 transcript and genome levels observed in uninfected mouse skin (control), or in mouse skin after topical or intradermal delivery of SAR-COL7, as assessed by qPCR. Error bars represent SEM.
Figure 8B:
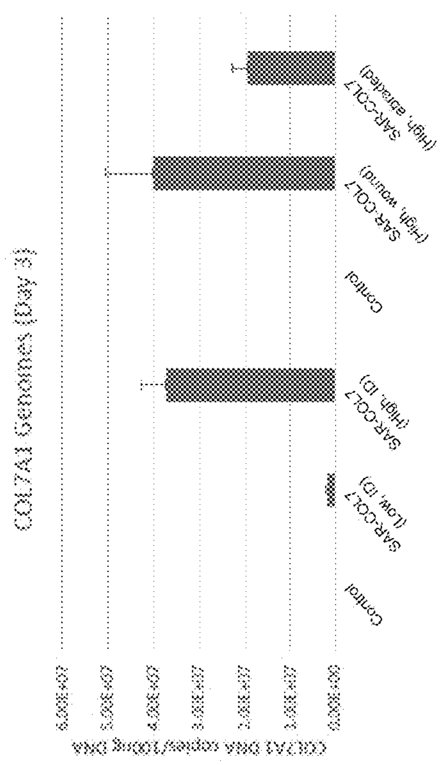
Figure 8C:
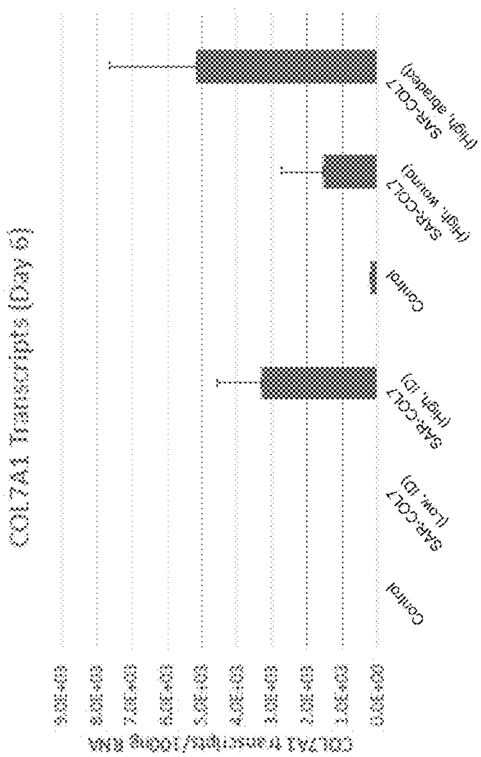
Figure 8D:
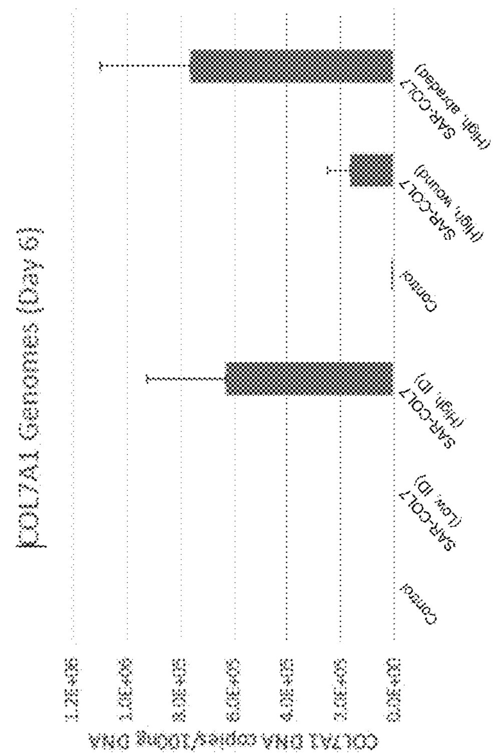

Post-sacrifice qPCR analysis was undertaken. COL7A1 transcripts and DNA levels were detected in all cohorts that received SAR-COL7 either by intradermal or topical application (FIGS. 8A-D), and a clear dose response was observed. Transcript and DNA levels were comparable between intradermal and topical cohorts (SAR-COL7 high ID, high wound, and high abraded), suggesting that topical application was as efficient at delivering COL7A1 as intradermal injection. Overall, the DNA and RNA levels were lower in the day 6 samples (FIGS. 8C-D) than the day 3 samples (FIGS. 8A-B), which was not unexpected since SAR-COL7 is a non-integrating vector that remains episomal (which would be expected to clear over time).

Figure 9A:
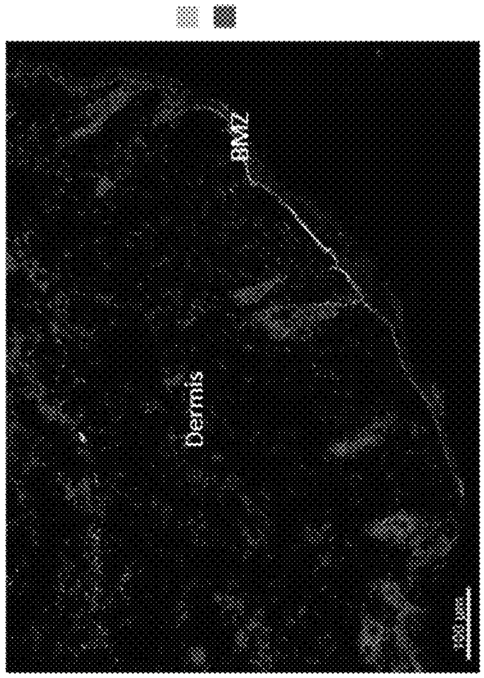
FIGS. 9A-B show representative immunofluorescence images of human COL7 expression in mouse skin after delivery of SAR-COL7.
Figure 9B:
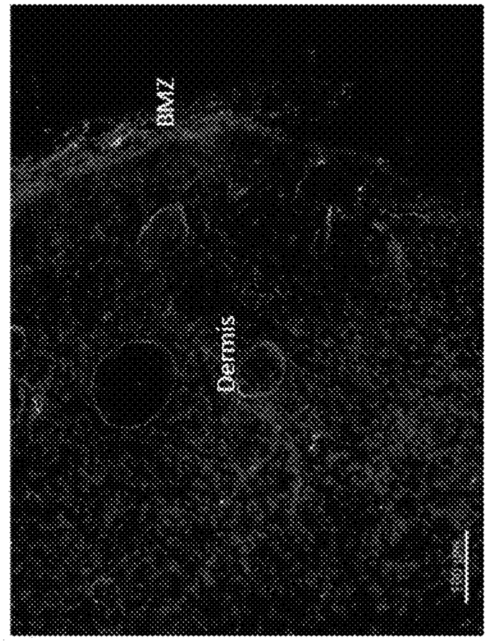

Next, immunofluorescence experiments were conducted to visualize COL7 expression after SAR-COL7 infection in vivo. As observed in the representative images provided in FIGS. 9A-B, COL7 was detected in most of the animal cohorts at both time points examined. Many samples showed correct localization of COL7 at the BMZ and around the hair follicles. In some instances, specifically with intradermal application, strong COL7 expression was observed in deeper layers of the skin, closer to the underlying fascia, possibly due to the injection being subcutaneous rather than intradermal. Similarly, in many of the abraded skin samples where the BMZ was likely removed during abrasion (as suggested by the lack of representative goH3 staining), the strong COL7 staining was limited to the skin surface. Overall, the presence of COL7 in the immunofluorescence samples strongly supported the robust efficacy of the modified HSV SAR-COL7.

Figure 10A:
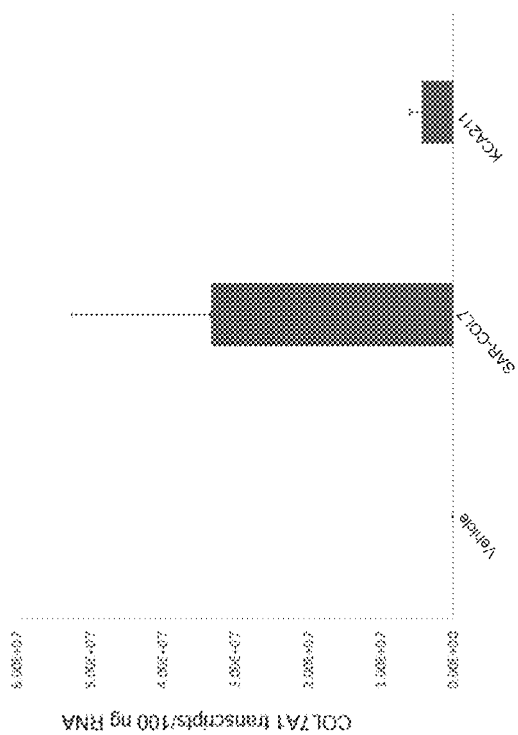
FIGS. 10A-B show human COL7A1 transcript and genome levels observed in BALB/c mouse skin after intradermal delivery of vehicle, SAR-COL7, or KCA211, as assessed by qPCR.
Figure 10B:
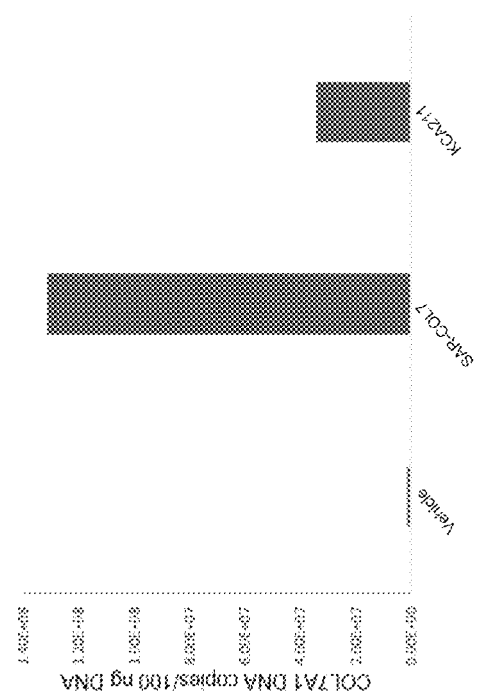

In addition, the ability of KCA211 to express human COL7 was tested in vivo and compared to SAR-COL7 administration. KCA211 was found to also express the COL7 transgene in vivo in immunocompetent mice (FIGS. 10A-B).

Taken together, the data indicated that modified HSV was capable of delivering and expressing a human collagen protein in vivo in healthy, immunocompetent animals after topical or intradermal administration, and further, that collagen expression from topically administered virus into compromised skin or open wounds was comparable to intradermal administration into intact skin.

Example 4: In Vivo Analysis of Low and High Doses of an HSV Candidate Encoding Human COL7 in Hypomorphic Animals The following example describes experiments showing that recombinant viruses constructed and validated in vitro in human cells (see Example 2 above) and in vivo in wild-type mice (see Example 3 above) were capable of expressing functional human collagen in vivo in COL7 hypomorphic mice. The purpose of the study was, in part, to evaluate the skin biodistribution of HSV-mediated collagen expression in COL7-deficient, immunocompetent animals.

Materials and Methods

Unless indicated to the contrary, experiments were conducted as described in Example 3 above.

Hypomorphic Mice

The COL7 hypomorphic mouse model (Fritsch et al. J Clin Invest. 2008 May; 118(5):1669-79) was used in this study. This hypomorphic mouse model is an immunocompetent animal model for dystrophic epidermolysis bullosa (DEB) in which the mice express about 10% of normal levels of COL7. Their phenotype closely resembles characteristics of severe human DEB, including mucocutaneous blistering, nail dystrophy, and mitten deformities of the extremities.

The mice were generated by flp/frt-mediated removal of exon 2 of mouse COL7A1. Animals lacking both functional copies of COL7A1 (Col7a1flNew/flNeo), referred to as COL7 "hypomorphic mice", expressed about 10% of normal levels of COL7. From a total of 15 breeding pairs, 58 pups were obtained, with the litters ranging from 2-7 mice/litter. Out of these 58 pups, 6 were genotyped to be hypomorphs.

Mice were genotyped with DNA extracted from an ear punch tissue sample. PCR analysis detected the presence of a loxP site upstream of exon 2 of COL7A1. Wild-type (WT) mice showed a band at 269 base pairs (bp), hypomorph mice showed a band at 435 bp, and heterozygous mice showed both bands. All procedures were in compliance with applicable animal welfare acts and were approved by the local Institutional Animal Care and Use Committee (IACUC).

Intradermal Injections

Prior to and during test article administration, mice were maintained under inhalation anesthesia using 2% isoflurane. Eye ointment (Puralube® Vet) was applied on the eyes to prevent dryness. Intradermal injections were performed using the Mantoux technique with a 31 G needle. Up to four intradermal injections were administered to the back of each mouse at the specified doses.

Tissue Collection

Prior to tissue collection, animals were euthanized by $CO_2$ inhalation followed by cervical dislocation. The injection sites were biopsied using sharp scissors.

Hematoxylin and Eosin (H&E) Staining

Cryopreserved tissues were sectioned at a thickness of 5-8 μm and left to air dry for up to one hour. The slides were dipped in 100% methanol for ten minutes at −20° C. and left to air dry. Methanol fixed sections were rehydrated in PBS for 5 minutes at room temperature. The sections were incubated in hematoxylin (Weigert's modified hematoxylin) for 5-10 minutes at room temperature, followed by a wash in PBS for 15 minutes at room temperature. The sections were then rinsed in Eosin (Eosin Y solution, cat. no. HT110116) 3 times followed by one rinse in water.

The sections were gradually dehydrated with ethanol by dipping in 70% ethyl alcohol 10 times, 95% ethyl alcohol ten time, and 100% ethyl alcohol ten times. The sections were set to dry, mounted with mounting media (Fischer Scientific, cat. no. SPF15-100) and covered with a coverslip. The sections were imaged after dehydration (approximately 24 hours) using a bright field microscope.

Electron Microscopy

Skin was prepared for electron microscopy by immersion in 1.5% glutaraldehyde/1.5% paraformaldehyde in Dulbecco's serum free media (SFM) containing 0.05% tannic acid for a minimum of one hour, followed by an extensive rinse in SFM, and a post-fixation step in 1% $OsO_4$ for 60 minutes. The samples were washed in SFM then dehydrated in a graded series of ethanol to 100%, rinsed in propylene oxide, and infiltrated in Spurr's epoxy over a total time of two hours, accelerated via microwave energy. Samples were polymerized at 70° C. over 18 hours. Additional samples were prepared by extensively rinsing in SFM then immersing in mouse IgM LH24 antibody or mouse IgG NP185 antibody diluted 1:5 in SFM overnight at 4° C. The samples were then rinsed extensively in SFM, exposed to gold enhancement solution (Nanoprobes) for 15 minutes on ice, then rapidly warmed to 25° C. and incubated an additional 5 minutes. The samples were rinsed with ice cold SFM, fixed, and embedded.

Results

Three hypomorphic mice were used for the high-dose SAR-COL7 study. All mice received a dose of $4.6\times10^7$ PFU/50 μL/injection site by intradermal injection on day 1 (Table 2). Each animal was shaved and injected at 4 sites on the back, including 1 control injection and 3 SAR-COL7 injections. One animal (mouse 3) received a second injection at the same 4 sites on day 3. One mouse (mouse 1) was sacrificed on day 3, while mouse 2 and mouse 3 were sacrificed on day 7.

TABLE 2 study design for intradermal injection of high-dose SAR-COL7

| Sample: | Mouse: | Treatment (Day 1): | Treatment (Day 3): | Day of Sacrifice: |
|---|---|---|---|---|
| 1 | 1 | HSV-GFP | PBS | Day 3 |
| 2 | | SAR-COL7 | — | |
| 3 | | SAR-COL7 | — | |
| 4 | | SAR-COL7 | — | |
| 5 | 2 | PBS | PBS | Day 7 |
| 6 | | SAR-COL7 | — | |
| 7 | | SAR-COL7 | — | |
| 8 | | SAR-COL7 | — | |
| 9 | 3 | PBS | PBS | Day 7 |
| 10 | | SAR-COL7 | SAR-COL7 | |
| 11 | | SAR-COL7 | SAR-COL7 | |
| 12 | | SAR-COL7 | SAR-COL7 | |

Figure 11A:
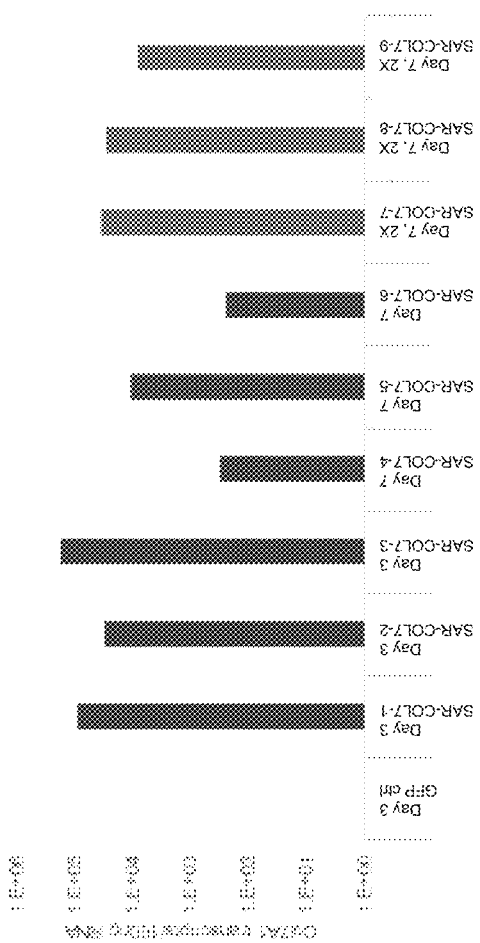
FIGS. 11A-B show human COL7A1 transcript and genome levels observed at each injection site in hypomorph mouse skin after high-dose intradermal delivery of HSV-GFP (GFP ctrl) or SAR-COL7, as assessed by qPCR. Each bar represents a single sample at the indicated time point.
Figure 11B:
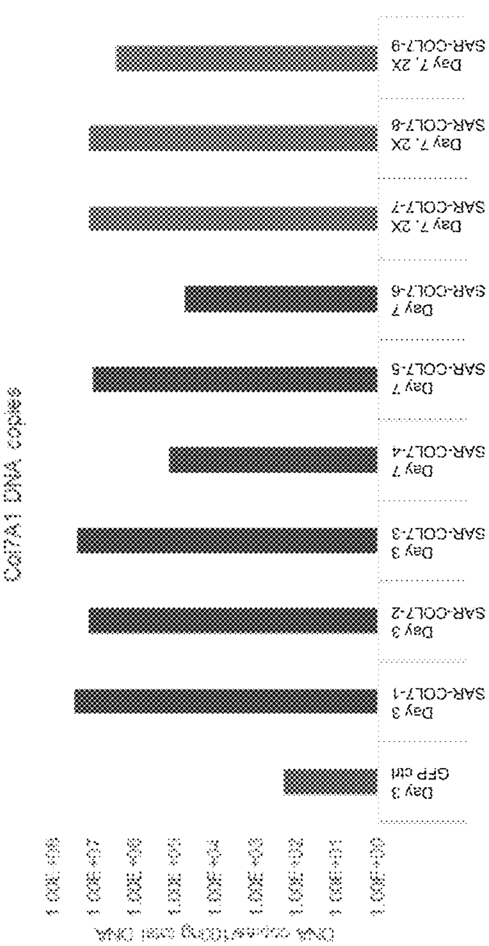

Post-sacrifice qPCR analysis was undertaken. COL7A1 transcripts (FIG. 11A) and DNA levels (FIG. 11B) were detected at each viral injection site in all three mice. Transcript levels in all of the control samples (PBS or HSV-GFP) were at or below the level of detection in the assay, so only 1 control (day 3, sample 1, HSV-GFP) was included for comparison in the graphs. Some decrease in DNA and transcript levels by day 7 after single administration of SAR-COL7 (mouse 2) was observed; however, DNA and transcript levels increased upon re-administration of SAR-COL7 (mouse 3).

Figure 12A:
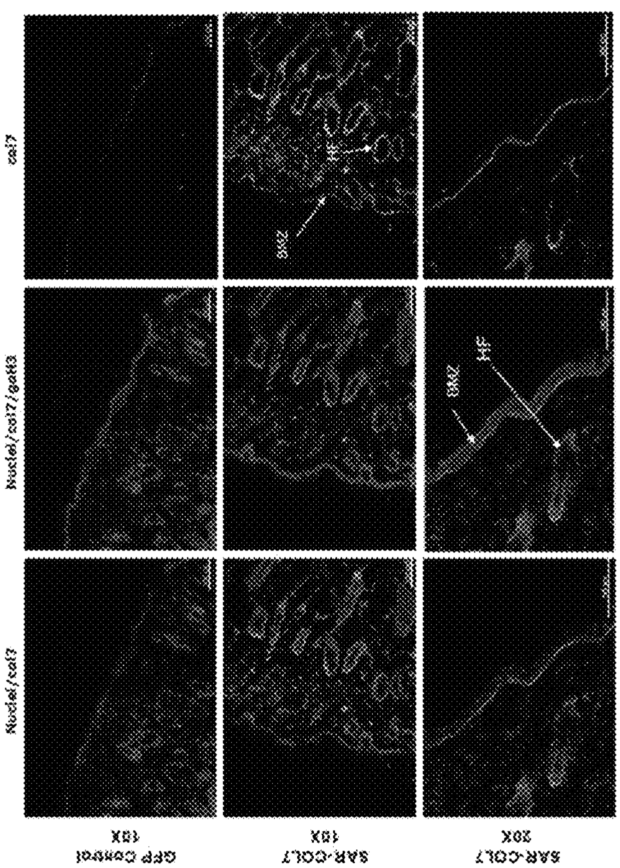
FIGS. 12A-B show representative immunofluorescence images of human COL7 expression in hypomorph mouse skin after high-dose intradermal delivery of HSV-GFP (GFP Control) or SAR-COL7.
Figure 12B:
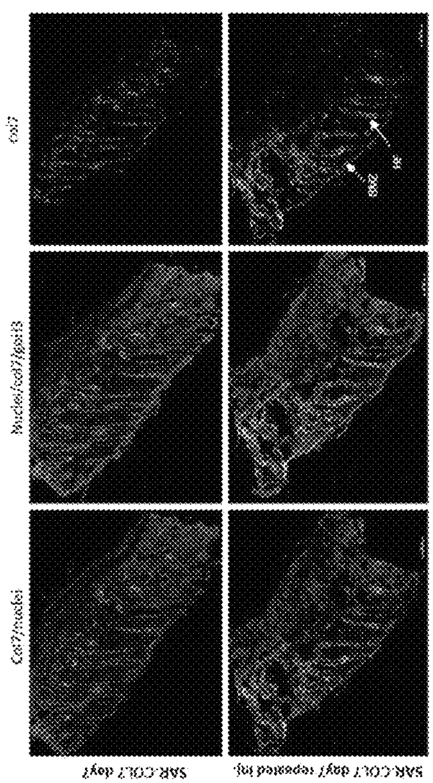
Figure 13:
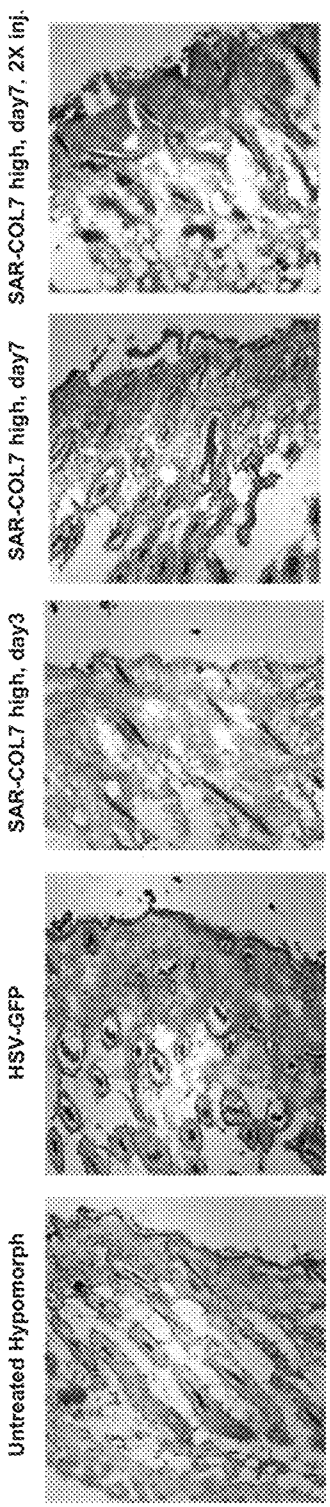
FIG. 13 shows H&E stained samples from hypomorph mouse 1, 2, and 3 (harvested at days 3 and 3). The samples were taken from untreated hypomorph mouse skin, and hypomorph mouse skin after intradermal delivery of HSV-GFP or SAR-COL7.

Next, immunofluorescence (IF) experiments were conducted to visualize COL7 expression in hypomorphic mice after SAR-COL7 infection in vivo (FIGS. 12A-B). The IF experiments demonstrated that robust and widespread COL7 protein expression was observed in the BMZ, as well as around the hair follicles (HF), at both the day 3 and day 7 timepoints. No negative impact on skin morphology (even after repeat administration) was observed, as the SAR-COL7 treated samples showed a normal skin morphology with no obvious signs of fibrosis or acute inflammation (FIG. 13). Overall, the presence of COL7 in the immunofluorescence samples strongly supported the robust efficacy of SAR-COL7 in delivering human collagen capable of being secreted and appropriately organized in the underlying skin substructures.

Figure 14A:
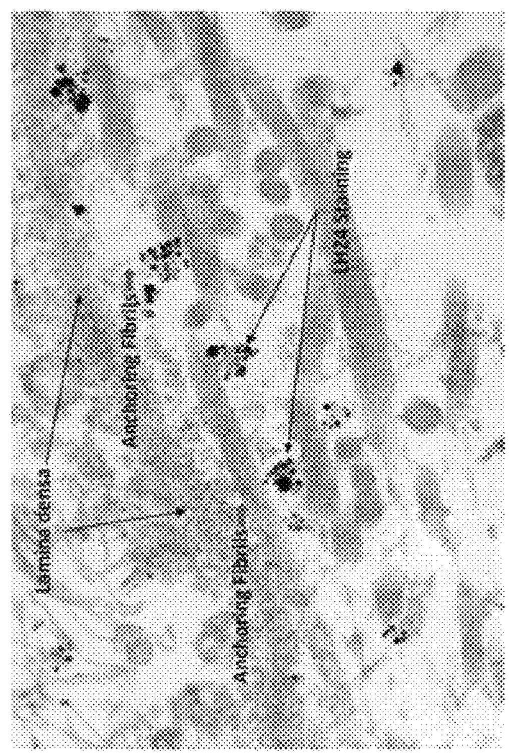
FIGS. 14A-B show representative electron micrograph images of human COL7 expression in hypomorph mouse skin after intradermal delivery of SAR-COL7. The lamina densa is the dark band indicated through the middle of the images; the black dots are the stained NC domains of human COL71 the blue arrows indicate the formation of anchoring fibrils.
Figure 14B:
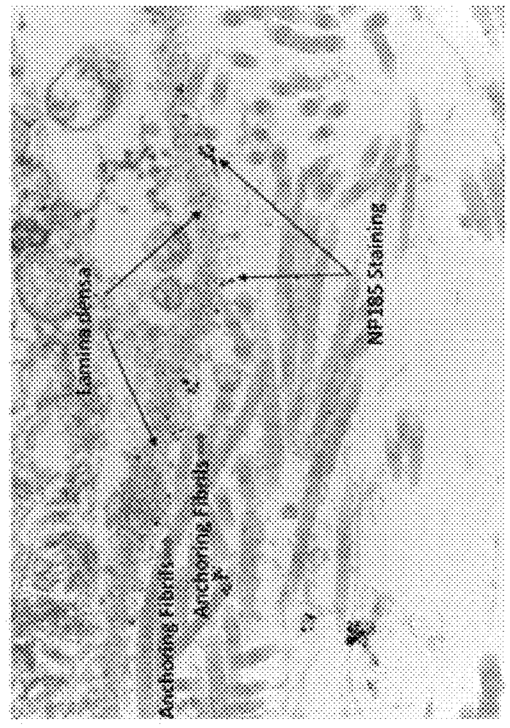

Day 3 biopsies were also evaluated for anchoring fibril formation by electron microscopy. In appropriately structured anchoring fibrils, the NC1 domain of COL7 (which is stained with the NP158 antibody) aligns towards the lamina densa, while the NC2 domain of COL7 (which is stained with the LH24 antibody) aligns away from the lamina densa. Biopsies from SAR-COL7-injected mice showed COL7 staining with both the LH24 (FIG. 14A) and NP185 (FIG. 14B) antibodies, and importantly, the electron microscopy (EM) images revealed the formation of anchoring fibrils. The lamina densa was observed as a dark band through the middle of the EM images. The NC2 domains of the exogenous human COL7 were positioned away from the lamina densa, while the NC1 domains of the exogenous human COL7 were positioned along the lamina densa, as would be expected in properly formed anchoring fibrils. This data indicated that SAR-COL7 could not only express an encoded human COL7 that was capable of being secreted and appropriately organized at the BMZ, but that the secreted COL7 was functional and properly positioned in the resulting anchoring fibrils, supporting the skin tissue of the hypomorphic mice.

Three additional hypomorphic mice were used for the low-dose SAR-COL7 study. All mice received a dose of $6.4\times10^6$ PFU/50 µL/injection site of SAR-COL7 in 3 (mouse 1) or 2 (mouse 2 and 3) sites by intradermal injection on day 1 (Table 3).

TABLE 3 study design for intradermal injection of low-dose SAR-COL7

| Mouse: | Treatment Day: | No. of Injection Sites: | Termination Day: |
|---|---|---|---|
| 1 | 1 | 3 | 3 |
| 2 | 1 | 2 | 3 |
| 3 | 1 | 2 | 7 |

Figure 15A:
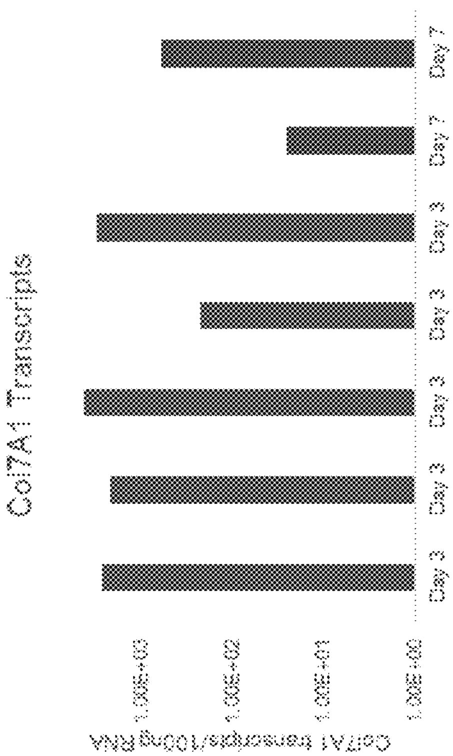
FIGS. 15A-B show human COL7A1 transcript and genome levels observed at each injection site in hypomorph mouse skin after low-dose intradermal delivery of SAR-COL7, as assessed by qPCR. Each bar represents a single sample at the indicated time point.
Figure 15B:
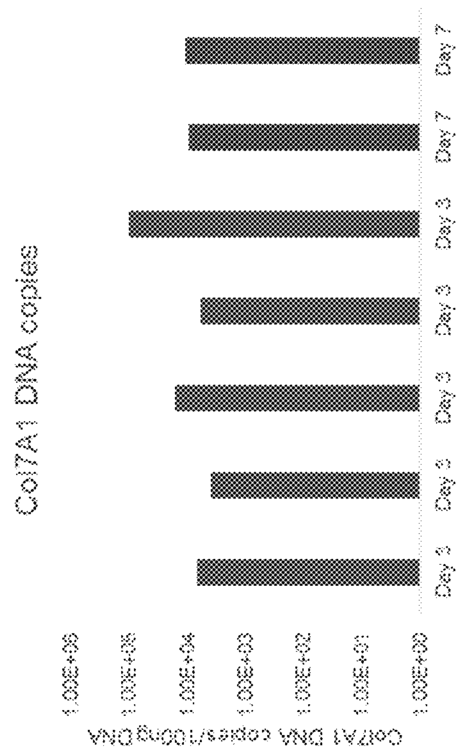
Figure 16:
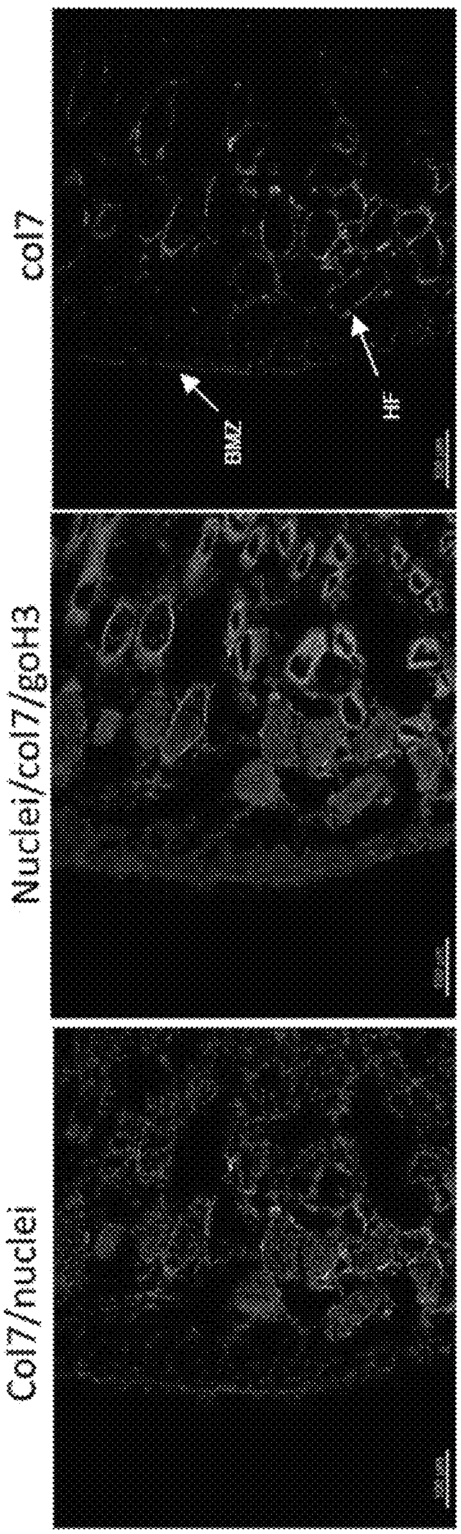
FIG. 16 shows representative immunofluorescence images of human COL7 expression in hypomorph mouse skin (from mouse 1) after low-dose intradermal delivery of SAR-COL7.

Post-sacrifice qPCR analysis was undertaken. COL7A1 transcripts (FIG. 15A) and DNA levels (FIG. 15B) were detected at each viral injection site in all three mice. A dose response was observed. While both DNA and transcript levels of COL7A1 were lower in these low-dose samples relative to those observed in high-dose study, COL7A1 expression was still detectable. Despite an approximate 2 log reduction in DNA or RNA levels, COL7 protein was still detectable in the skin of low-dose SAR-COL7 injected animals (FIG. 16). The COL7 protein was observed in both the BMZ and around the hair follicles. The data indicated that even at lower dosages, the modified HSV was still effective at delivering and expressing the encoded human collagen protein, which was then secreted and localized to the appropriate region of the skin.

Taken together, the data provided in the examples indicated that the modified HSVs described herein were able to: 1) transduce skin cells to produce functional human collagen in vitro and in organotypic culture (see Example 2); 2) transduce skin and deliver human collagen in vivo in healthy, immunocompetent animals after both topical and intradermal applications (see Example 3); and 3) transduce skin, deliver human collagen, and initiate the formation of anchoring fibrils in vivo in collagen-deficient animals (see Example 4). Without wishing to be bound by theory, it is believed that the recombinant vectors described herein provide a desirable strategy for delivering functional human collagen to the skin, allowing for novel approaches to support the dermis and/or epidermis in cosmetic settings.

Example 5: Construction and Validation of Multiple Engineered HSVs Encoding Human Collagen 1

The following example describes two different approaches for engineering a recombinant HSV-1 to successfully express human Collagen 1. Because human Collagen 1 is a heterotrimeric macromolecule comprising two copies of a COL1A1 polypeptide and one copy of a COL1A2 polypeptide, two distinct strategies were undertaken to generate a single HSV genome encoding both human COL1A1 and COL1A2; these two approaches are generally depicted in FIGS. 1H-1I and 1L, and described in detail below.

As a first approach, a recombinant HSV-1 was initially engineered to incorporate a human COL1A1 expression cassette, containing a heterologous promoter and polyA sequence, into each of the ICP4 loci as described in Example 2 above. Multiple plaques of viruses putatively containing the human COL1A1 cassette were picked and screened by infection in Vero cells to test for COL1A1 expression (data not shown). At least three isolates (clones 1A1, 2A1, and 3A1) were positive for human COL1A1 transgene expression. Next, the human COL1A1-positive clones 1A1 and 2A1 were then engineered to incorporate a human COL1A2 expression cassette, containing a different heterologous promoter than the COL1A1 cassette and its own polyA sequence, inserted into the ICP22 locus. Seven isolates (clones 1A2-1A1, 1B2-1A1, 1C1-1A1, 1B3-2A1, 3B1-1A1, and 3B1-2A1) were then screened to identify attenuated HSV-1 viruses capable of expressing both human COL1A1 and COL1A2, and thus, full-length human Collagen 1.

Figure 17C:
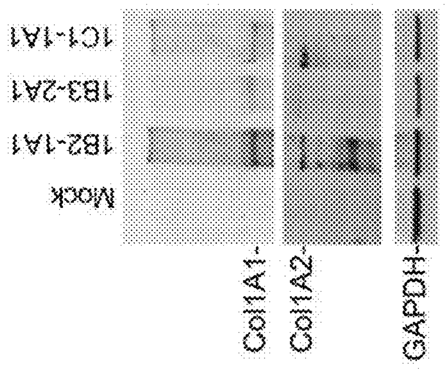
FIGS. 17A-C show human COL1A1 and COL1A2 nucleic acid and protein analyses in Vero cells infected with the indicated clones of HSV encoding COL1A1 alone (inserted into the ICP4 loci) or COL1A1 and COL1A2 (inserted into the ICP4 and ICP22 loci, respectively).
Figure 17A:
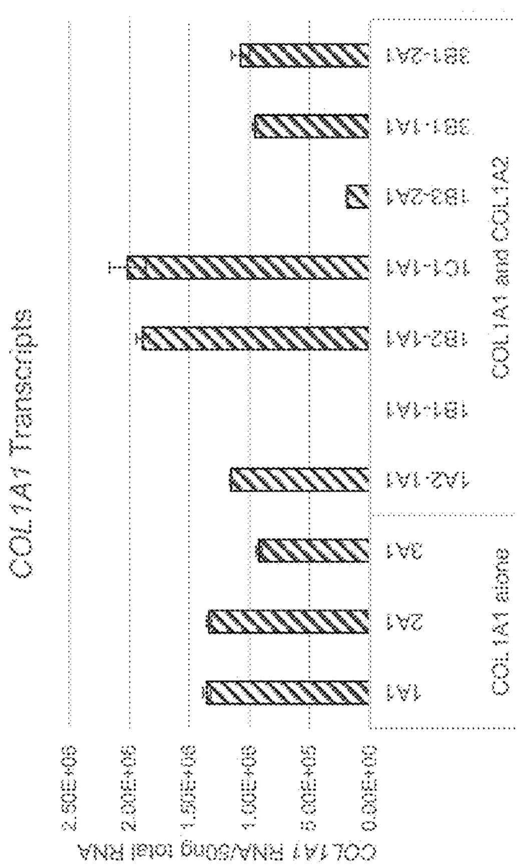
Figure 17B:
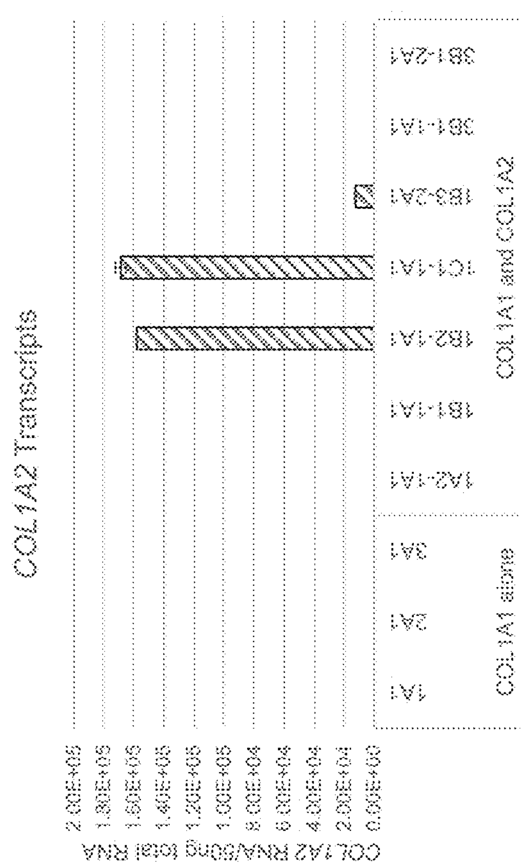

Vero cells were infected with one of the seven putative COL1A1-COL1A2-positive isolates or one of three of the COL1A1-alone isolates (as a negative control for COL1A2 expression) in order to identify recombinant HSV-1 clones capable of expressing both transgenes. Infections of the Vero cells were allowed to proceed for five days, cells were harvested by gentle scraping, and cell pellets were collected by centrifugation at 6000×g for five minutes. Half of each pellet was harvested for qRT-PCR analysis, while the other half was processed for western botting. Absolute quantification of COL1A1 or COL1A2 RNA copies was performed by Taqman Real-Time PCR analysis using custom primer/probe assays that span the 3' end of the human COL1A1 or COL1A2 open reading frame (ORF) and the 3' untranslated region (UTR), and are specific to the transgene. RNA extracted from cells infected with all three COL1A1-alone viruses, and cells infected with 6/7 of the COL1A1-COL1A2 viruses, were positive for human COL1A1 transgene expression (FIG. 17A). Interestingly, only 3/7 of the COL1A1-COL1A2 viruses (clones 1B2-1A1, 1C1-1A1, and 1B3-2A1) also expressed detectable levels of human COL1A2 (FIG. 17B). Western blotting of COL1A1 and COL1A2 protein expression in cell lysates infected with these three isolates was performed to ensure that the transgenes were expressed at both the nucleic acid and protein levels. Briefly, cell pellets were resuspended in RIPA buffer containing Halt protease inhibitor cocktail, incubated at 4° C. for ten minutes, and were then treated with benzonase for 10 minutes at room temperature. Samples were then diluted with 4×LDS sample buffer containing 5% 2-mercaptoethanol, and resolved on Tris-Glycine gels. Mock-infected Vero cell lysate was loaded on the gel as a negative control. Proteins were transferred to PVDF, blocked, and then stained overnight with primary antibody (anti-human COL1A1, ThermoFisher cat. no. PA5-29569; anti-human COL1A2, Abcam cat. no. ab96723; or anti-GAPDH, Abcam cat. no. ab9485). Stained membranes were then washed, incubated with secondary antibody, then developed. In agreement with the qRT-PCR analysis, all three clones were capable of expressing both human COL1A1 and COL1A2 proteins at detectable levels (FIG. 17C).

Figure 18:
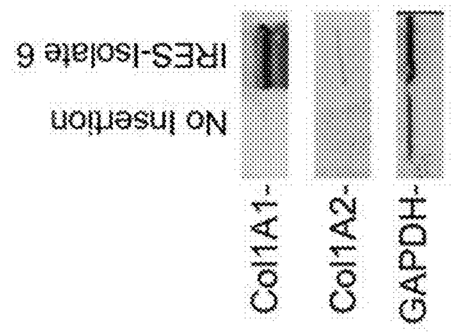
FIG. 18 shows western blot analysis of human COL1A1 and COL1A2 protein expression in Vero cells 5 days after infection with an HSV isolate encoding a COL1A1-IRES-COL1A2 sequence (IRES-Isolate 6) inserted into the ICP4 loci. Infection with an isolate that does not contain the IRES construct (no insertion) was used as a negative control; GAPDH was used as a loading control.

A second approach was pursued in parallel to generate COL1A1-COL1A2-positive recombinant, attenuated HSV vectors. Here, a polynucleotide construct was generated which encoded, from 5' to 3', a human COL1A1 ORF, a synthetic IRES, and a human COL1A2 ORF. This IRES-based construct (encoded in an expression cassette also containing a heterologous promoter and a polyA sequence) was then inserted into each of the ICP4 loci, as described in Example 2 above. Multiple plaques were picked and screened to identify vectors with correctly inserted IRES constructs. Briefly, Vero cells were infected with putative IRES viral isolates, infections were allowed to proceed for five days, and cells were harvested and processed for qPCR and qRT-PCR analysis. Absolute quantification of insert DNA and RNA copies was performed by Taqman Real-Time PCR analysis using custom primer/probe assays that recognize the synthetic IRES. 13 viral isolates were screened by qPCR and qRT-PCR analysis; only one of these isolates (isolate 6) tested positive for the IRES DNA and RNA transcripts comprising the IRES sequence (data not shown). To confirm that this isolate was capable of expressing both human COL1A1 and COL1A2 at the protein level, infected Vero cells were processed for western blotting as described above. A viral isolate (isolate 1) that showed no expression cassette incorporation by qPCR and transgene expression by qRT-PCR was used as a negative control. Paralleling the qPCR/qRT-PCR data, viral isolate 6 was capable of expressing both human COL1A1 and COL1A2 protein after infection (FIG. 18).

Taken together, the data presented in this sample indicate that: (1) multiple recombinant HSV-1 vectors were successfully constructed that were proficient in expressing both human COL1A1 and COL1A2 after infecting targeted cells; (2) vectors can be engineered to express heterotrimeric human collagen proteins; and (3) multiple different approaches can be taken to express multiple proteins from a single recombinant genome. Without wishing to be bound by theory, it is believed that successful expression of human Collagen 1 from a recombinant HSV-1 genome provides support for the use of engineered HSV to express any heterotrimeric collagen protein (e.g., human Collagen 4).

Example 6: Construction, Validation, and In Vitro Characterization of an Engineered HSV Encoding Human Collagen 3

The following example describes the engineering of a recombinant HSV-1 that successfully expressed human Collagen 3 (termed C3vec01). In addition, the following example describes in vitro experiments establishing multiple relevant 2D cell culture model systems suitable for characterizing the efficacy of C3vec01, including the use of immortalized human keratinocytes and fibroblasts in dose-ranging studies, the use of primary human dermal fibroblasts biopsied from multiple aged human patients as a model of C3vec01-mediated Collagen 3 rescue in older patients, and the use of in vitro UV-irradiated immortalized human fibroblasts as a model for sun exposure/skin aging.

Human skin is largely composed of collagen-rich connective tissue which is produced, organized, and maintained by dermal fibroblasts. Dermal collagen represents >90% (dry weight) of human skin and is composed primarily of COL1 and COL3 fibrils at a typical ratio of about 85:15. These fibrils provide strength to the skin and are critical for the maintenance of skin tissue architecture.

Skin aging characteristics are largely due to aberrant collagen homeostasis, resulting in a net collagen deficiency; biosynthesis of collagen is reduced, collagen fibril fragmentation is increased, and there is a progressive loss of dermal collagen, all of which contribute to the aged phenotype. Skin aging is influenced by a combination of both internal and external factors: intrinsic factors—the passage of time, genetics, cellular metabolism, hormones, etc.; and extrinsic—chronic light exposure, pollution, ionizing radiation, etc. These factors together lead to cumulative structural and physiological alterations to the skin, ultimately leading to the appearance of, and worsening in, skin wrinkles.

Skin rejuvenation, the process of reversing or repairing irregularities in the skin (such as wrinkles), is achieved, in part, by the synthesis of new collagen (neocollagenesis). In the skin, neocollagenesis is affected by the deposition of, and complex interactions between, collagens 1 and 3. COL3 appears early during collagen fibrillogenesis, and the subsequent replacement of this COL3 by COL1 is a critical step for collagen fibril maturation and extracellular matrix reorganization (Wang, et al., 2018, Journal of the Chinese Medical Association, 81(2), pp. 94-101). In addition, COL3 both regulates the dimensions of COL1 fibers (Liu, et al., 1997, Proc Natl Acad Sci USA, 94(5), pp. 1853-6) and enhances COL1 elasticity (Asgari, et al., 2017, Sci Rep, 7(1), p. 1392). As such, the appearance of early COL3 expression, and ensuing replacement with COL1, has been used as a marker of efficacy for injectable facial fillers in humans (Yutskovskaya, et al., 2014, J Drugs Dermatol, 13(9), pp. 1047-52).

All experiments were conducted as described above unless noted otherwise.

To begin, a recombinant HSV-1 was engineered to incorporate a human COL3A1 expression cassette, containing a heterologous promoter and polyA sequence, into each of the ICP4 loci. Multiple plaques of viruses putatively containing the human COL3A1 cassette were picked and screened by infection in Vero cells to test for COL3A1 expression (data not shown). One of the high expressing clones, termed C3vec01, was subsequently selected for additional in vitro (described below) and in vivo (Example 7) analyses.

Figure 19A:
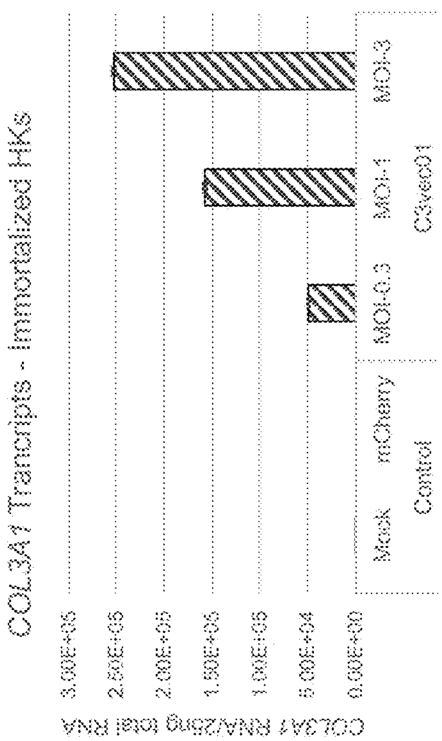
FIGS. 19A-B show human COL3 nucleic acid and protein analyses in immortalized human keratinocytes (HaCaTs) infected with C3vec01.
Figure 20A:
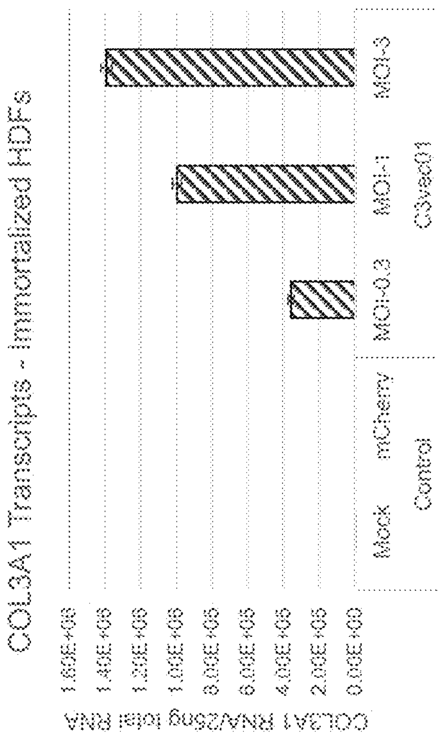
FIGS. 20A-B show human COL3 nucleic acid and protein analyses in immortalized human dermal fibroblasts (HDFs) infected with C3vec01.
Figure 19B:
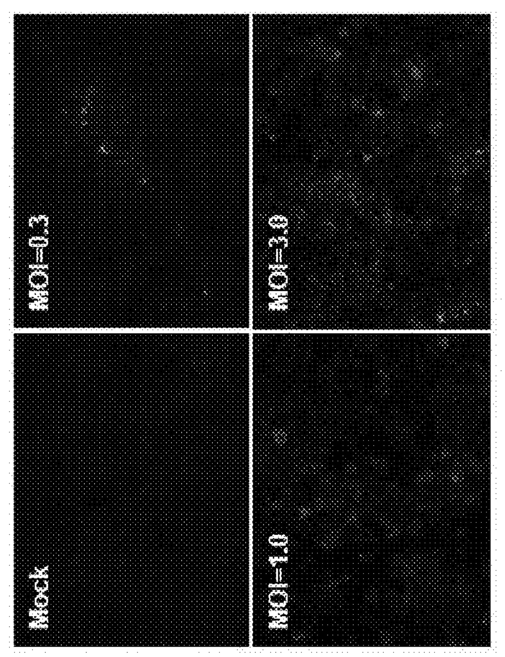
Figure 20B:
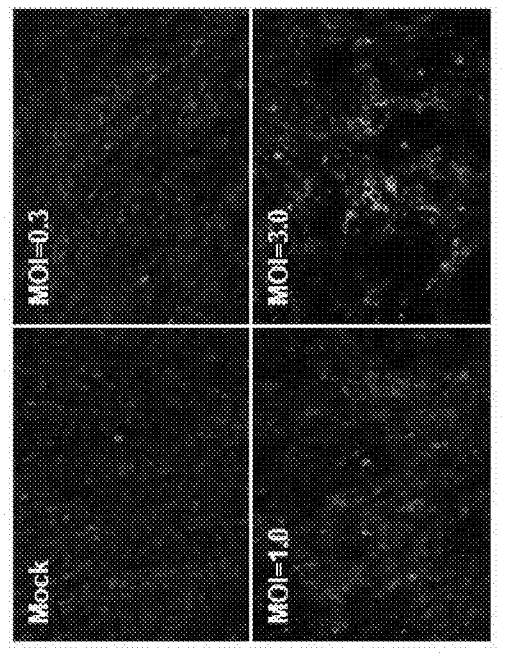

First, a dose-ranging study was conducted to determine the efficacy of C3vec01-mediated delivery of its encoded human cargo in both immortalized human keratinocytes (FIG. 19) and immortalized human dermal fibroblasts (FIG. 20). The immortalized cells were infected for 48 hours at various multiplicities of infection (MOI) ranging from 0.3 to 3, and human Collagen 3 expression was quantitatively and qualitatively measured via multiple assays. Dose-dependent increases were observed in both effector DNA by qPCR analysis (data not shown) and effector transcript levels by qRT-PCR analysis in the immortalized HKs and HDFs (FIGS. 19A and 20A, respectively). Mock infected cells, and cells infected with a virus containing the same HSV-1 backbone as C3vec01 but instead encoding an mCherry effector, were used as negative controls. Paralleling these results, a dose-dependent increase in COL3 protein expression after C3vec01 infection was observed by immunofluorescence in immortalized HKs (FIG. 19B) and HDFs (FIG. 20B). While the immortalized HDFs expressed endogenous human COL3 prior to infection (as expected), a significant increase in COL3 expression was observed after infection with C3vec01, even at a low dose (primary anti-COL3 antibody, Abcam cat. no. ab7778). Little-to-no detectable endogenous COL3 was observed in the uninfected immortalized keratinocytes. Importantly, no significant effect on cell morphology or viability was observed in immortalized keratinocytes or fibroblasts infected with C3vec01, even at high doses.

As the skin ages, resident dermal fibroblasts produce less Collagen 3, and the ratio of COL1:COL3 in the skin skews towards Collagen 1. In order to provide skin rejuvenation through the synthesis of new Collagen 3, it was important to understand whether C3vec01 would be capable of effectively infecting aged dermal fibroblasts and robustly express its encoded human Collagen 3. As such, the ability of C3vec01 to infect aged primary dermal fibroblasts and express exogenous Collagen 3 at multiple MOIs was tested in cells sourced from two different vendors. Table 4 below provides donor information for the four primary HDF samples used in this study.

TABLE 4

| primary human dermal fibroblast donors | | | | | | |
|---|---|---|---|---|---|---|
| Age | Sex | Race | Tissue | Cat. No. | Lot No. | Company |
| 73 | M | Caucasian | Skin/ eyelid | C-12302 | 435Z009.2 | PromoCell |
| 65 | F | Caucasian | Skin/ eyelid | C-12302 | 417Z010.2 | PromoCell |
| 73 | M | Caucasian | Left lower back | CC-2511 | 0000633428 | Lonza |
| 75 | F | Caucasian | Back | CC-2511 | 18TL057585 | Lonza |

Figure 21A:
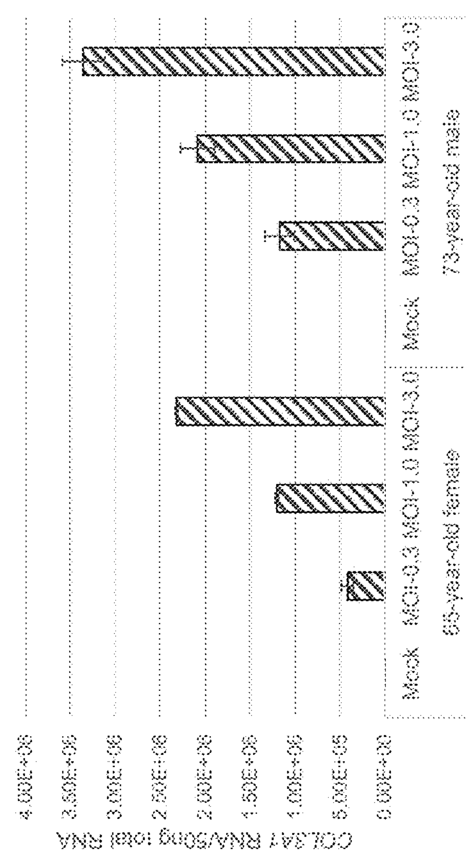
FIGS. 21A-D show human COL3 nucleic acid and protein analyses in aged primary human fibroblasts (HDFs), sourced from two different vendors, infected with C3vec01 at the indicated MOIs.
Figure 21B:
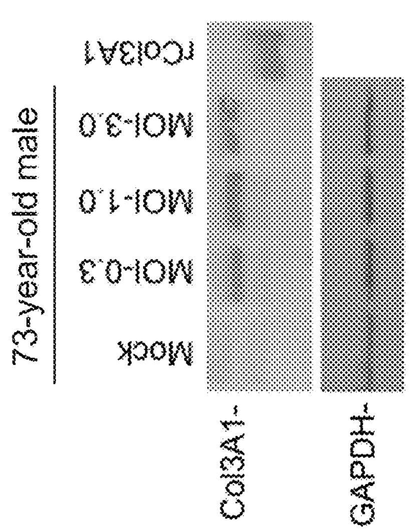
Figure 21C:
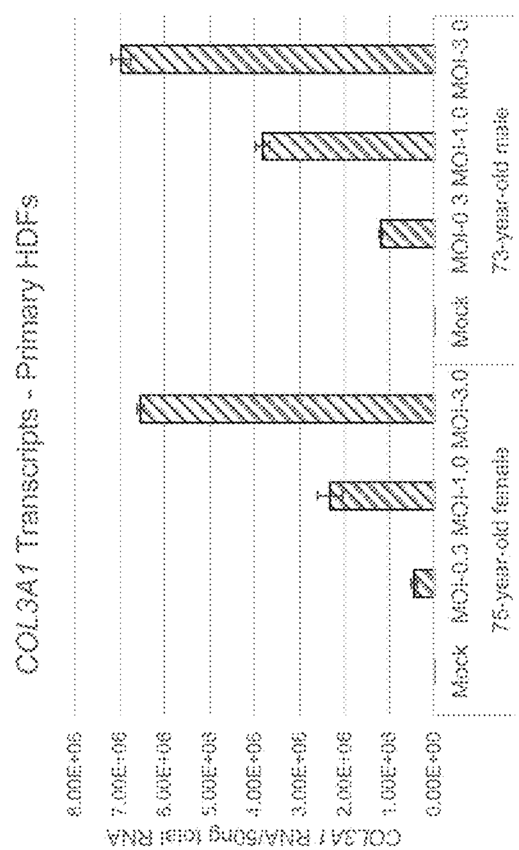
Figure 21D:
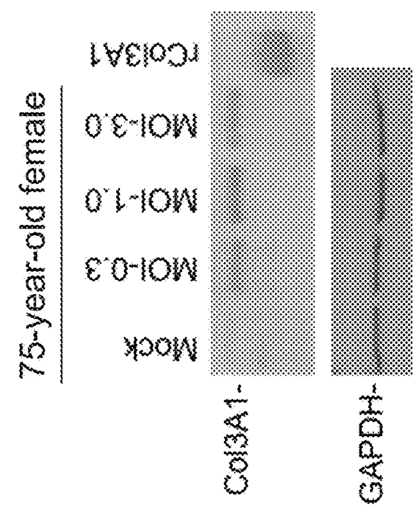

As compared to the immortalized HDFs, a similar dose-dependent increase with comparable or higher COL3 transcript levels was observed after C3vec01 infection of the primary HDFs from vendor 1 (FIG. 21A) and vendor 2 (FIG. 21C). A sample of representative primary cells from each vendor was also tested for COL3 expression by western blot analysis (primary anti-COL3 antibody, Abcam cat. no. ab7778). C3vec01 was capable of rescuing high levels of human Collagen 3 expression in primary HDFs biopsied from a 73-year-old male patient (FIR. 21B) and a 75-year-ol female patient (FIG. 21D), even at the lowest MOI tested.

Figure 22A:
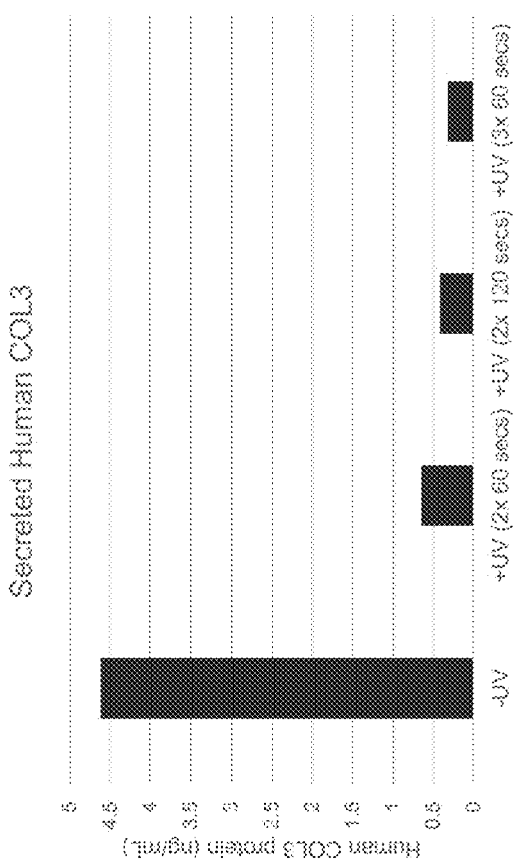
FIGS. 22A-B show human COL3 nucleic acid and protein analyses in immortalized human dermal fibroblasts (HDFs) upon UV exposure.
Figure 22B:
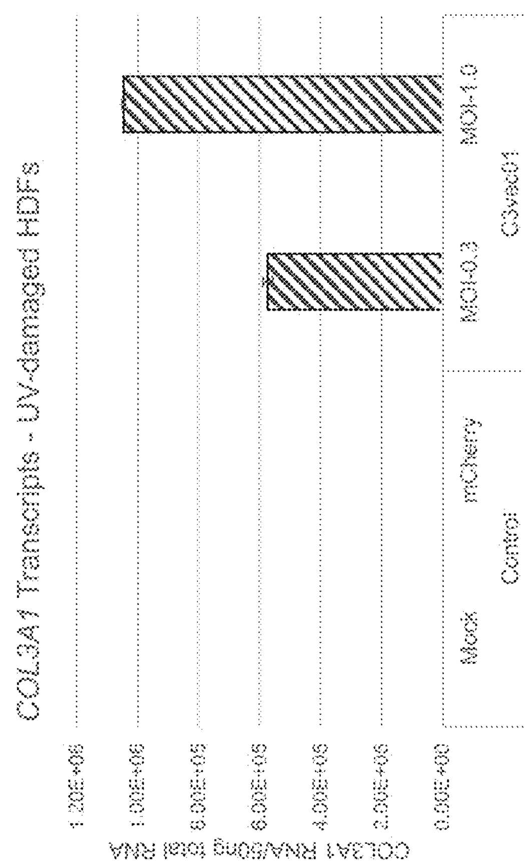

Finally, the ability of C3vec01 to induce robust Collagen 3 expression in UV-exposed immortalized human fibroblasts was tested. Sun exposure, and the corresponding UV damage, is known to be the single largest extrinsic contributor to the aged skin phenotype, and multiple groups have employed an in vitro skin fibroblast UV-exposure system to model certain aspects of photoaging (see e.g., Qin et al. 2018, Cell Physiol Biochem 46(5):1849-1860). To confirm that UV exposure caused human dermal fibroblasts to secrete less Collagen 3 (as would be expected given the phenotype of photo-aged skin), COL3 secretion into the supernatants of cultured immortalized human dermal fibroblasts was measured by ELISA before and after three different levels of UV exposure (FIG. 22A). Indeed, UV irradiation of cultured fibroblasts significantly reduced endogenous COL3 expression. COL1 expression were monitored in parallel in this experiment, and were not significantly affected by UV irradiation, indicating that UV exposure induced specific repression of COL3, as opposed to global suppression of protein synthesis. Next, the ability of C3vec01 to infect UV-irradiated immortalized HDFs and express exogenous COL3 was tested. Here, immortalized HDFs were exposed to UV-irradiation, and then allowed to recover for 24 hours prior to infection with C3vec01 at an MOI of 0.3 or 1. 48 hours after infection, exogenous human COL3 was assessed by qRT-PCR analysis. Strong COL3 expression was detected in C3vec01-infected, UV-irradiated HDFs at both tested MOIs (FIG. 22B), indicating that C3vec01 efficiently transduced photo-damaged cells and delivered its encoded cargo. Mock infected cells, and cells infected with a virus containing the same HSV-1 backbone as C3vec01 but instead encoding an mCherry effector, were used as negative controls to ensure specificity of transgene detection.

Taken together, the data presented in this example indicates that the recombinant HSV-1 vector C3vec01 efficiently transduces multiple human skin cell types, is capable of rescuing Collagen 3 expression in aged primary fibroblasts harvested from old patients, and is capable of salvaging Collagen 3 expression from UV-damaged HDFs. Without wishing to be bound by theory, it is believed that the data supports the use of a recombinant HSV encoding human Collagen 3 to correct the collagen defects of aged skin.

Example 7: In Vivo Characterization of Intradermally Administered C3vec01

The following example described in vivo experiments establishing methods of intradermally administering C3vec01 in young and old healthy immunocompetent animals.

All experiments were conducted as described above unless noted otherwise.

All procedures conducted in this example were in compliance with applicable animal welfare acts and were approved by the local Institutional Animal Care and Use Committee (IACUC).

The backs of mice were shaved before further manipulations. C3vec01 (or vehicle control) was then injected intradermally to four sites in the backs of the mice. After infection and the subsequent recovery period, the animals were euthanized, and the treatment sites were removed using an 8 mm punch biopsy. One half of each biopsy was quick-frozen in liquid nitrogen for qPCR/qRT-PCR analysis, while the other half was processed for immunofluorescence analysis.

Tissue samples were processed for nucleic acid and protein analysis as described above. For COL3 immunofluorescence staining, a rabbit anti-human Collagen 3 primary antibody (Abcam, cat. no. ab7778), and an Alexa Fluor® 488-conjugated secondary antibody were used. Tissue samples were mounted in mounting media containing DAPI to visualize nuclei.

An in vivo pharmacology study was conducted in young (6-8-week-old) and old (approximately 13-month-old) C57BL/6 mice to evaluate C3vec01-mediated expression of human COL3 in immunocompetent animals upon intradermal administration of the vector. A total of 10 animals were used for this study. The back of each mouse was first shaved and then intradermally injected with $2\times10^8$ PFU/site of C3vec01 (or vehicle control) at 4 sites/animal. Injected sited were biopsied at either 48-hours or 1-week post-dosing, and were evaluated for human COL3 expression by qPCR and immunofluorescence. Table 5 below provides a synopsis of the experimental design.

TABLE 5

| study design and test article administration | | | | | | | |
|---|---|---|---|---|---|---|---|
| Group No. | N | Test Article | Mouse | Route of Adminis-tration | Vol-ume of Test Article | Loca-tion, No. of Sites | Ter-mina-tion (day) |
| 1 | 1 | Vehicle | Young | Intra-dermal | 100 μL | Back, 4 | 2 |
| 2 | 2 | C3vec01 | Young | Intra-dermal | 100 μL | Back, 4 | 2 |
| 3 | 2 | C3vec01 | Young | Intra-dermal | 100 μL | Back, 4 | 7 |
| 4 | 1 | Vehicle | Old | Intra-dermal | 100 μL | Back, 4 | 2 |
| 5 | 2 | C3vec01 | Old | Intra-dermal | 100 μL | Back, 4 | 2 |
| 6 | 2 | C3vec01 | Old | Intra-dermal | 100 μL | Back, 4 | 7 |

Figure 23A:
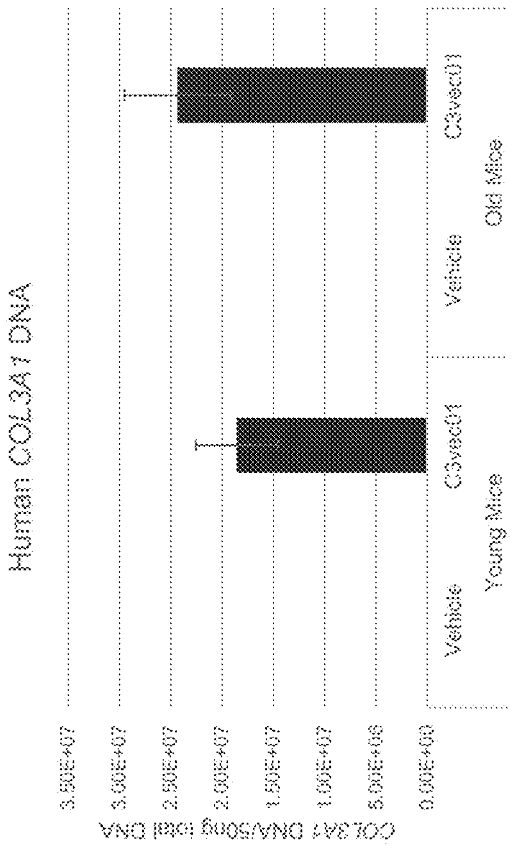
FIGS. 23A-C show COL3 nucleic acid and protein analyses of skin biopsies taken from control- or C3vec01-treated young (6-8-week-old) and old (~13-months-old) C57BL/6 mice 48 hours after intradermal application.
Figure 23B:
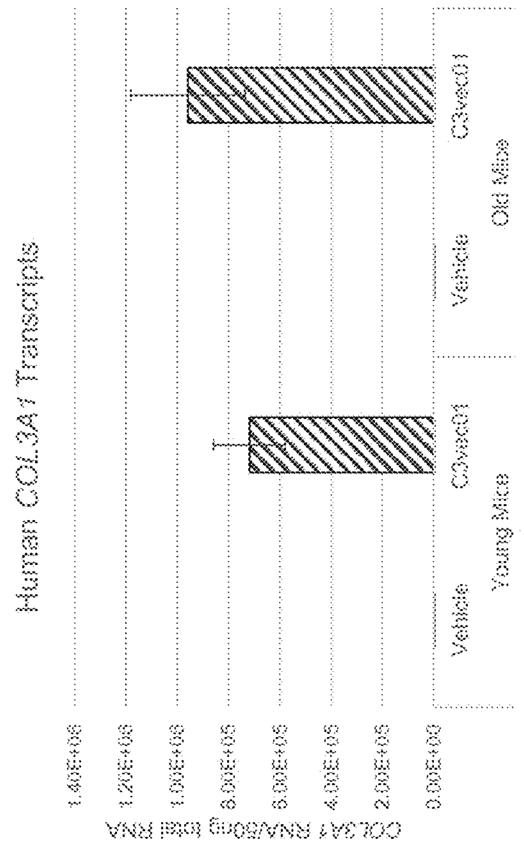
Figure 23C:
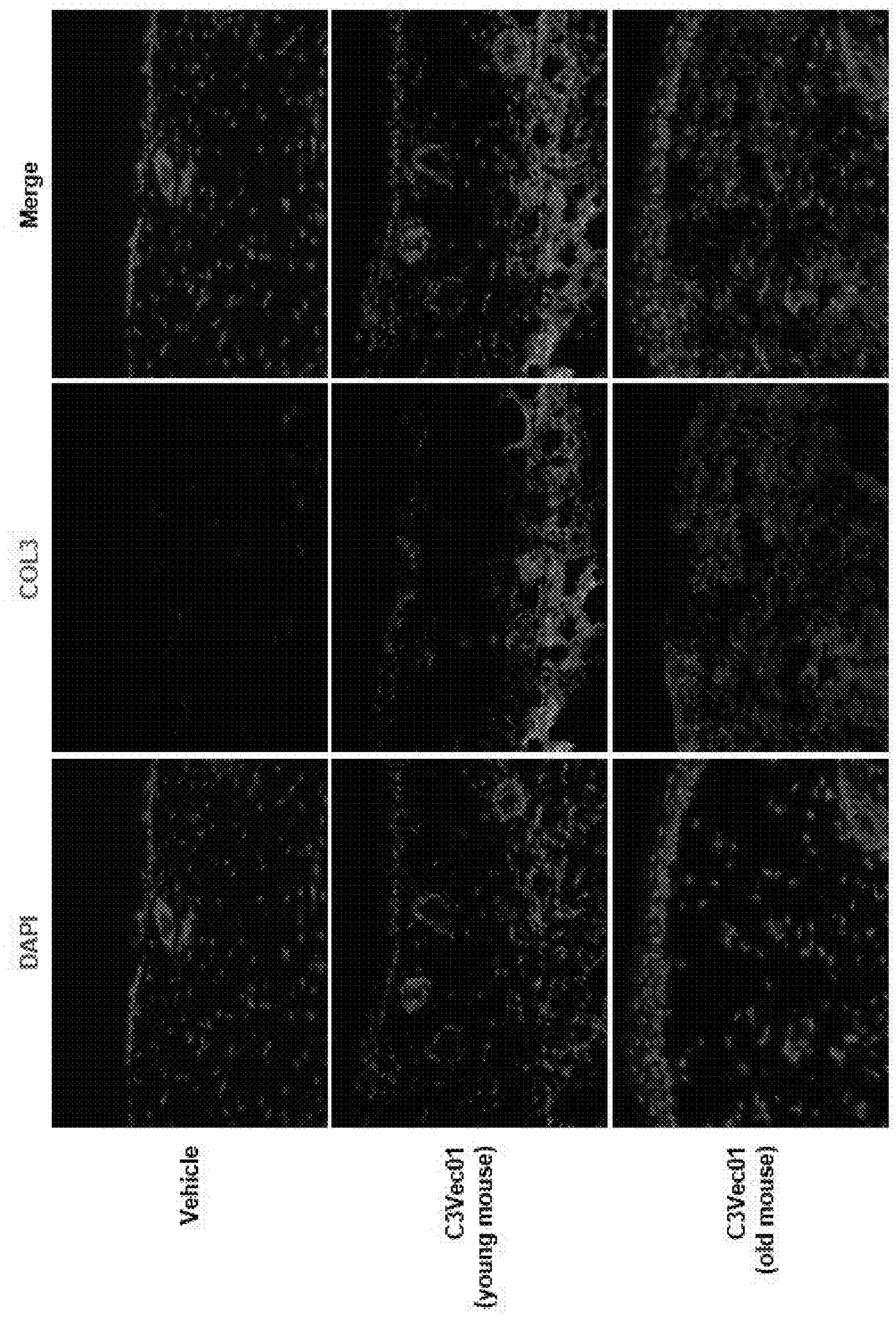

Intradermal delivery of C3vec01 led to high levels of transduced vector genomes detected in skin biopsies harvested 48-hours post-injection (FIG. 23A), as well as yielded high levels of human Collagen 3 transcripts in both young and old mice (FIG. 23B). Immunofluorescence-based detection also showed visibly increased levels of human COL3 throughout the dermis in C3vec01-treated skin relative to vehicle-treated skin (FIG. 23C), correlating with transcript levels.

Taken together, the data provided in this example indicates that can efficiently transduce skin and express human Collagen 3 in vivo after intradermal injection. Without wishing to be bound by theory, it is believed that the in vivo study presented here lends further support for the use of HSV-1 as a novel gene therapy to delivery human Collagen 3 in the aesthetic setting.

Figure 24A:
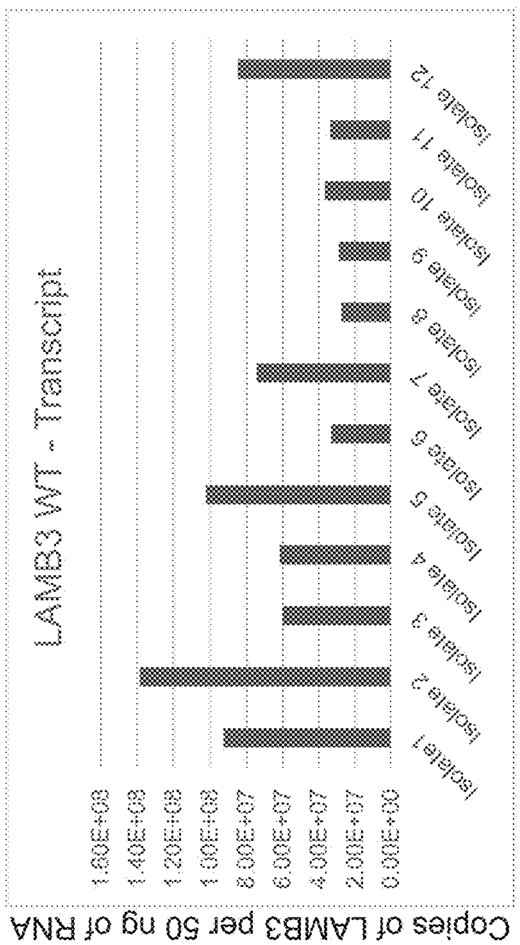
FIGS. 24A-B show expression of wild-type (WT) human LamB3 in Vero cells infected with the indicated viral isolates.
Figure 24B:
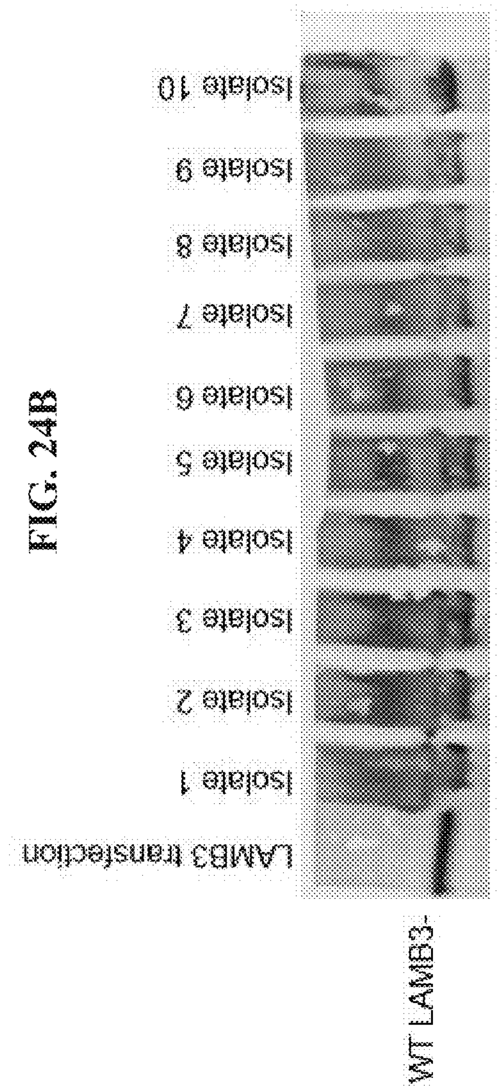

Example 8: Generation and Validation of Modified Herpes Simplex Virus Vectors Encoding Human Laminins To begin, recombinant herpes virus vectors were engineered to incorporate either wild-type or codon-optimized variants of two human laminin proteins, LAMB3 or LAMC2, as described in Example 3 above. A number of isolates were picked for each type of virus. To test whether certain isolates were capable of expressing the encoded wild-type human LAMB3 protein, ICP4-complementing Vero cells were plated in 6-well plates and were infected with 12 untitered viral isolates of wild-type LamB3-encoding viruses until completion of infection. After infection, RNA was harvested, cDNA was generated, and expression of wild-type LamB3 from each isolate was determined by qPCR (FIG. 24A). All 12 isolates were capable of expressing wild-type human LamB3 in the transduced Vero cells at varying levels. The ability of 10 of these isolates to express human LamB3 was also tested by western blot. ICP4-complementing Vero cells were plated in 6-well plates and were infected with 10 untitered viral isolates of wild-type LamB3 expressing viruses until completion of infection. A well of Vero cells was transfected with a LamB3 expression plasmid as a positive control. After infection, the cells were collected by gentle scraping, centrifuged to collect cell pellets, culture medium was aspirated, and the cell pellets were washed once with PBS. Following washing, each cell pellet was resuspended in 200 μL RIPA buffer containing protease inhibitors, and the resuspensions were incubated at 4° C. for 20 minutes with gentile agitation every 5 minutes. After incubation, the samples were centrifuged at 17,000×g for 5 minutes, the supernatant was removed, and 4×LDS reducing sample buffer containing 5% 2-mercaptomethanol was added to each clarified supernatant. The samples were then boiled for 10 minutes before loading on a 4-20% Tris-Glycine polyacrylamide gel. After electrophoresis, the protein was transferred to a PVDF membrane, and the membrane was blocked for 30 minutes in 5% milk/TBS. Primary rabbit anti-LamB3 antibody (Abcam, cat. No. ab128864) was then added to the PVDF membrane at 1:1000 dilution in 5% milk/TBS and incubated overnight at RT° C. (~16 hours). The blots were then washed 3× for 5 minutes each with TBS, and then stained with an AP-conjugated goat anti-rabbit IgG antibody (Sigma, cat. No. A3687) in 5% milk/TBS for 1 hour at RT° C. The membranes were then washed 3× for 5 minutes each with TBS, BCIP/NBT was added, and the blots were developed for ~10 minutes at RT° C. In agreement with the qPCR data, all 10 viral isolates were capable of expressing the encoded wild-type human LamB3 at varying levels (FIG. 24B).

Figure 25:
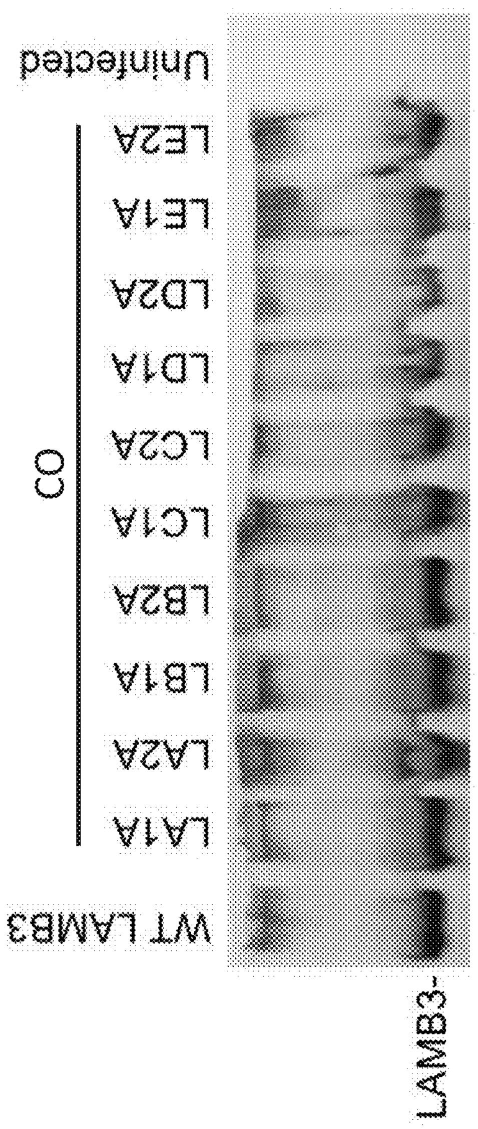
FIG. 25 shows expression of wild-type (WT) or codon-optimized (CO) human LamB3 protein in Vero cells infected with the indicated viral isolates, as assessed by western blot. Uninfected Vero cells were used as a negative control.

Viruses encoding codon-optimized variants of human LamB3 were also tested for their ability to express their cargo in Vero cells by western blot analysis. Briefly, 10 untitered viral isolates of codon-optimized (CO) LamB3-encoding viruses were used to infect Vero cells, cell pellets were collected, each pellet was resuspended in RIPA buffer containing protease inhibitors, and western blots were conducted using these cell lysates, as described above. All 10 viral isolates were capable of expressing the encoded codon-optimized human LamB3 in Vero cells (FIG. 25).

Figure 26:
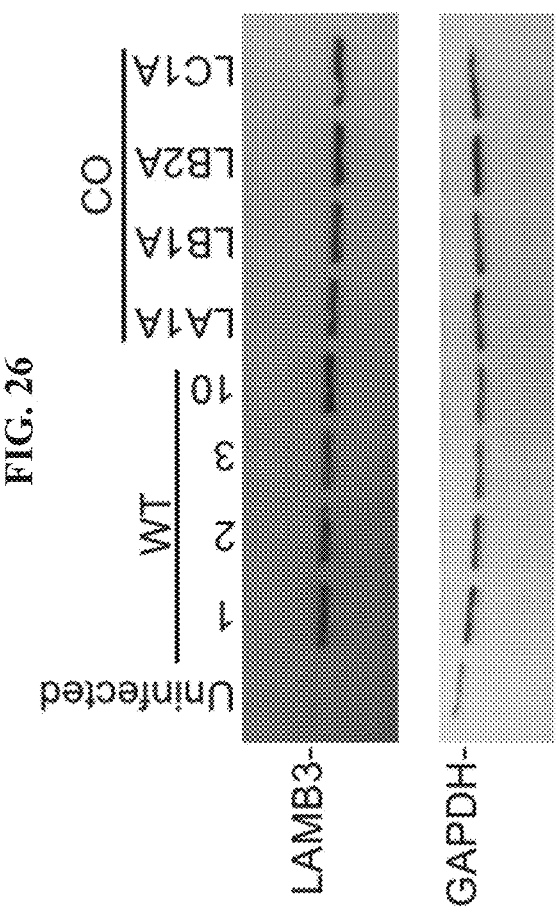
FIG. 26 shows expression of wild-type (WT) or codon-optimized (CO) human LamB3 protein in primary human keratinocytes infected with the indicated viral isolates, as assessed by western blot. Uninfected primary keratinocytes were used as a negative control.

Next, four viral isolates encoding either wild-type or codon-optimized LAMB3 were tested for their capacity to transduce primary human cells and express their cargo. Immortalized primary normal keratinocytes were infected at a multiplicity of infection (MOI) of 1.0 for 48 hours. Uninfected cells were used as a negative control. Expression of LamB3 in the infected human keratinocytes was then examined by western blot. Western blots were carried out as described above using a primary rabbit anti-LamB3 antibody (Abcam, cat. No. ab 128864). In line with the data generated using Vero cells, the viral isolates expressing either wild-type and codon-optimized LamB3 were confirmed to effectively transduce primary human keratinocytes and express their encoded construct at suitable levels (FIG. 26).

Figure 27A:
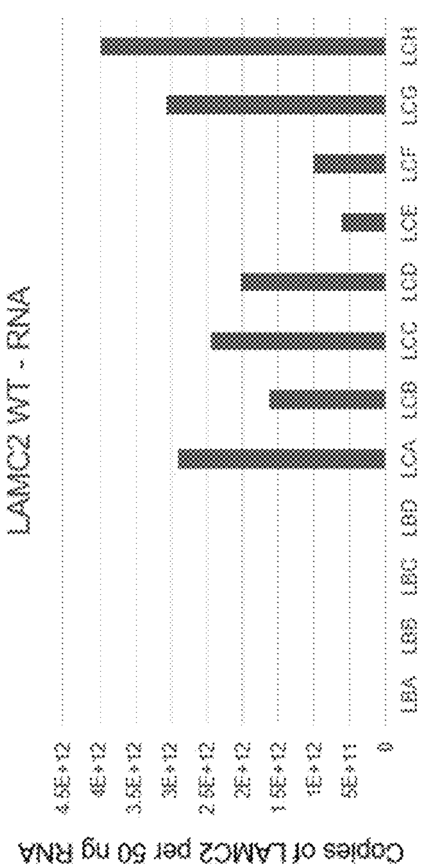
FIGS. 27A-C show expression of wild-type (WT) and codon-optimized (CO) human LamC2 in Vero cells infected with the indicated viral isolates.
Figure 27B:
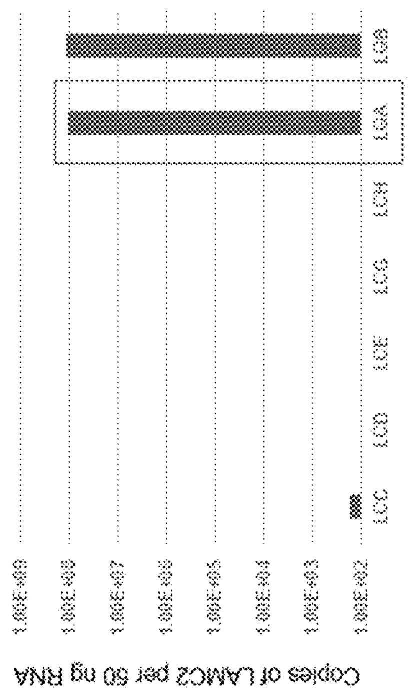
Figure 27C:
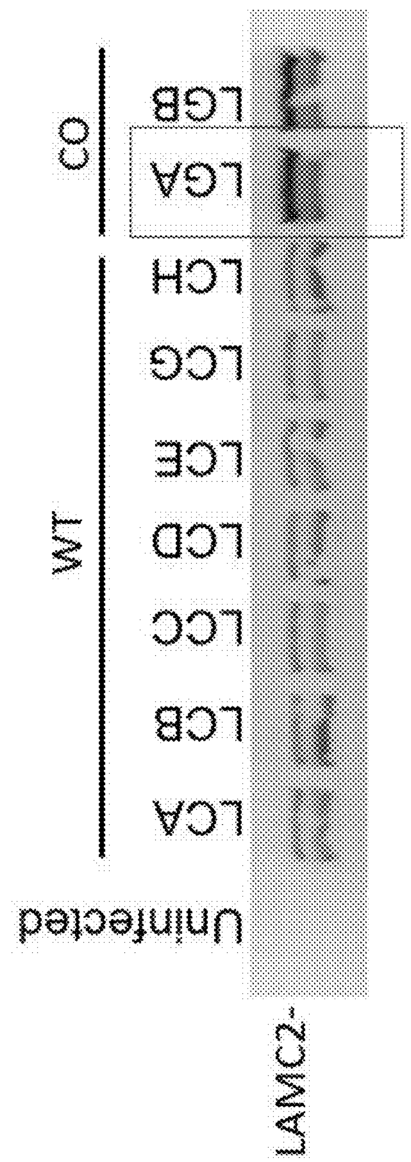

To test whether LamC2-containing isolates were capable of expressing the encoded wild-type or codon-optimized human LAMC2, ICP4-complementing Vero cells were plated in 6-well plates and were infected with a number of untitered wild-type or codon-optimized LamC2-expressing viral isolates until completion of infection. After infection, RNA was harvested, cDNA was generated, and expression of wild-type LamC2 (FIG. 27A) or codon-optimized LamC2 (FIG. 27B) from each isolate was determined by qPCR. 8/12 isolates were capable of expressing wild-type human LamC2 in the transduced Vero cells at varying levels, while 3/7 isolates were capable of expressing codon-optimized human LamC2. The ability of certain wild-type and codon-optimized isolates to express human LamC2 was next tested by western blot. ICP4-complementing Vero cells were plated in 6-well plates and were infected with untitered viral isolates until completion of infection. A well of Vero cells was left uninfected as a negative control. After infection, the cells were collected by gentle scraping, centrifuged to collect cell pellets, culture medium was aspirated, and the cell pellets were washed once with PBS. Following washing, each cell pellet was resuspended in 200 μL RIPA buffer containing protease inhibitors, and the resuspensions were incubated at 4° C. for 20 minutes with gentile agitation every 5 minutes. After incubation, the samples were centrifuged at 17,000×g for 5 minutes, the supernatant was removed, and 4×LDS reducing sample buffer containing 5% 2-mercaptomethanol was added to each clarified supernatant. The samples were then boiled for 10 minutes before loading on a 4-20% Tris-Glycine polyacrylamide gel. After electrophoresis, the protein was transferred to a PVDF membrane, and the membrane was blocked for 30 minutes in 5% milk/TBS. Primary rabbit anti-LamC2 antibody (Abcam, cat. No. ab96327) was then added to the PVDF membrane at 1:1000 dilution in 5% milk/TBS and incubated overnight at RT° C. (~16 hours). The blots were then washed 3× for 5 minutes each with TBS, and then stained with an AP-conjugated goat anti-rabbit IgG antibody (Sigma, cat. No. A3687) in 5% milk/TB S for 1 hour at RT° C. The membranes were then washed 3× for 5 minutes each with TBS, BCIP/NBT was added, and the blots were developed for ~10 minutes at RT° C. In agreement with the qPCR data, all 9 of the tested viral isolates were also able to express the encoded human LamC2 (FIG. 27C).

Figure 28A:
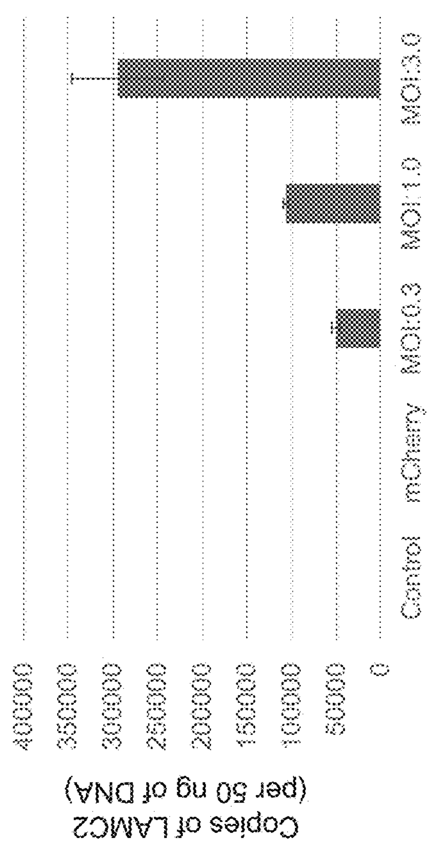
FIGS. 28A-C show human LAMC2 expressed from viral isolate "LGA" in immortalized primary human keratinocytes infected at the indicated multiplicities of infection (MOIs).
Figure 28B:
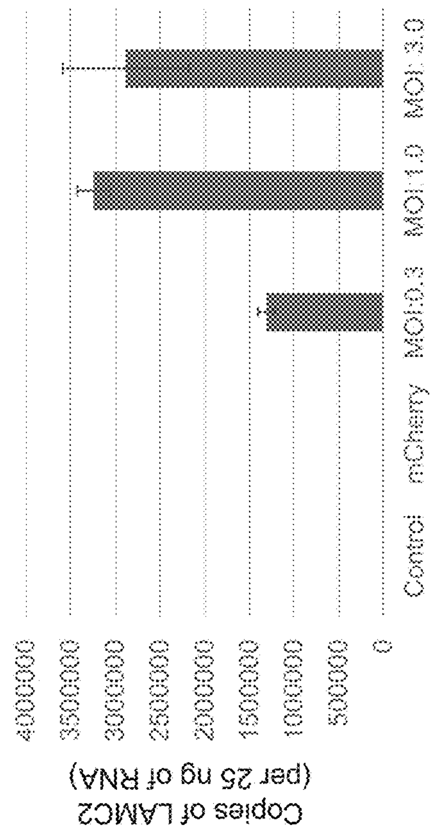
Figure 28C:
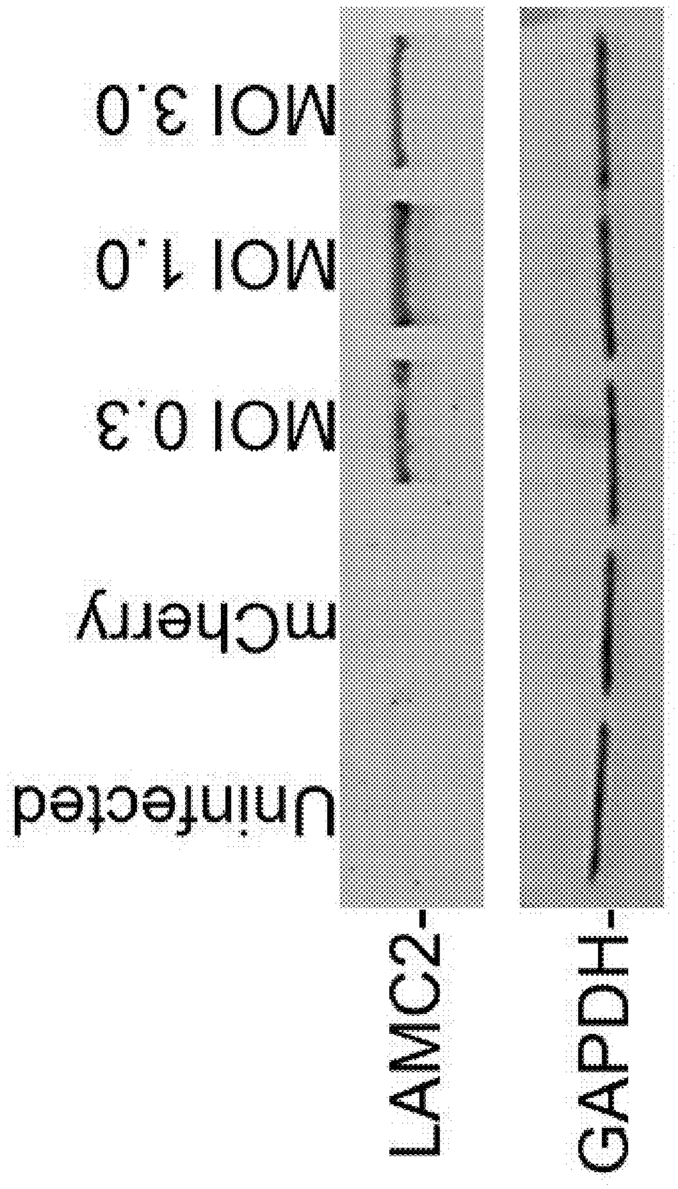

The codon-optimized LamC2-expressing viral isolate "LGA" was selected for further testing in human cells. Immortalized primary normal keratinocytes were infected with the LGA isolate at a multiplicity of infection (MOI) of 0.3, 1.0, or 3.0 for 48 hours. Uninfected (control) and mCherry-expressing virus infected cells were used as a negative control. DNA and RNA were extracted from the immortalized keratinocytes after 48 hours of infection, and qPCR/qRT-PCR was performed (FIGS. 28A-B). A good dose-response was observed for the LGA isolate in the immortalized keratinocytes, as assessed by viral genome copies detected per 50 ng of DNA (FIG. 28A). Interestingly, while a dose response was observed at the transcript level when increasing the MOI from 0.3 to 1.0, no additional increase in transcript levels were observed when increasing from an MOI of 1.0 to 3.0 (FIG. 28B). Expression of LamC2 in the infected human keratinocytes were also examined by western blot. Western blots were carried out as described above (primary rabbit anti-LamC2 antibody (Abcam, cat. No. ab96327) was used). In line with the transcript analysis, a dose response was observed at the protein level when increasing MOI from 0.3 to 1.0, but not from 1.0 to 3.0 (FIG. 28C).

Figure 29A:
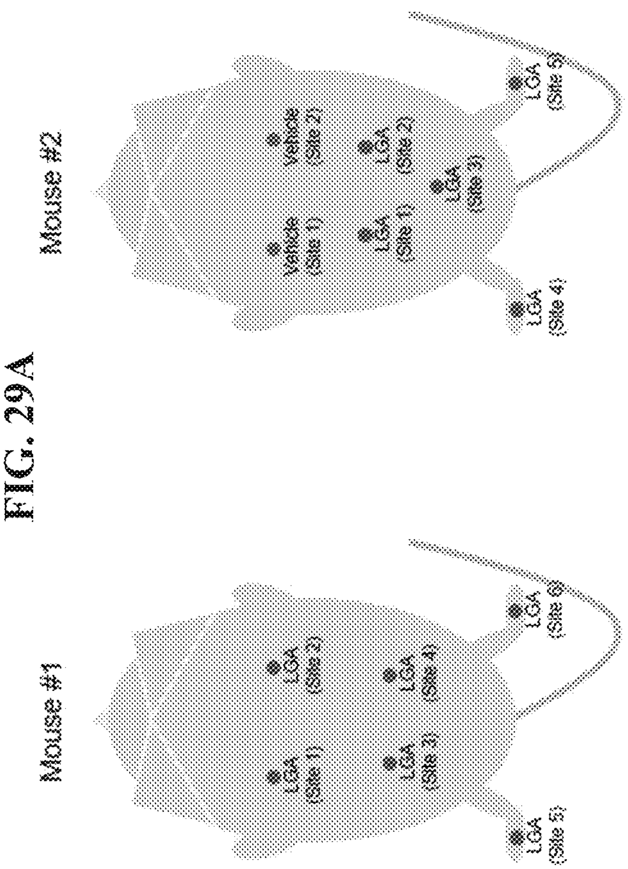
FIGS. 29A-D show LAMC2 nucleic acid and protein analysis of skin biopsies taken from control (vehicle)—or HSV isolate "LGA"-treated mice 72 hours after intradermal application.

Finally, to test whether isolate "LGA" was capable of expressing its human laminin when delivered in vivo, human LAMC2 expression was assessed by qPCR, qRT-PCR, and immunofluorescence after intradermal injection in animals. $1\times10^8$ PFUs of LGA formulated in PBS+10% glycerol (vehicle) was intradermally injected into the dorsal skin and footpads of two mice. An equivalent volume of vehicle alone was intradermally administered to the dorsal skin of one mouse to act as a negative control. A schematic of the injection sites for the two animals treated in this study is provided in FIG. 29A.

Figure 29B:
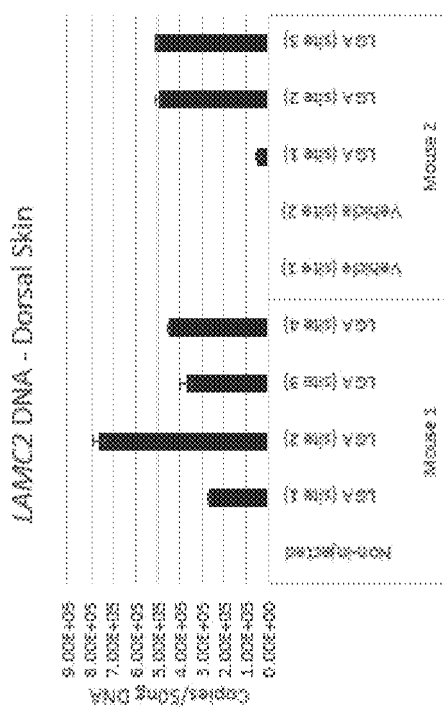
Figure 29C:
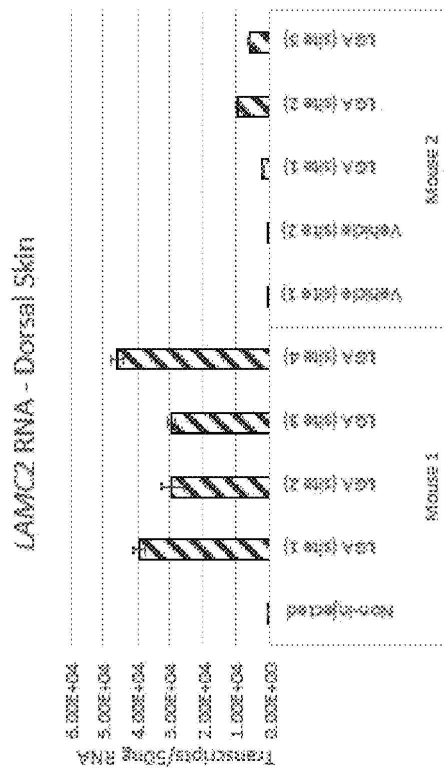
Figure 29D:
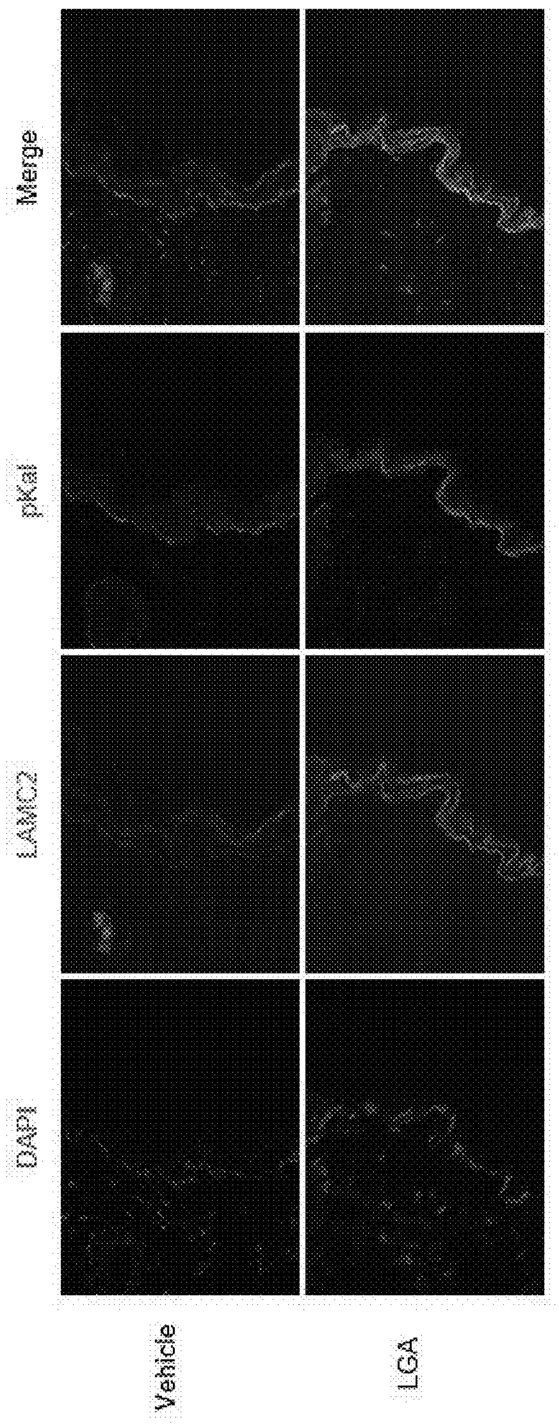

72 hours post-administration, a full thickness 8 mm biopsy was taken from each treatment site and split in half. One half of each section was flash frozen in liquid nitrogen and subsequently processed for qPCR and qRT-PCR analysis in order to quantify LAMC2 DNA copy numbers (FIG. 29B) and transcript levels (FIG. 29C) in the dorsal skin. The remaining half of each biopsy was embedded in OCT for immunofluorescence (IF). LAMC2 expression in cryosections was determined by immunofluorescent analysis using an anti-human LAMC2 antibody (Abcam, cat. no. ab96327). To confirm that the human LAMC2 expressed from LGA was correctly localized to the region of the skin where native laminin-332 is found, the dorsal skin samples were also counterstained for mouse laminin-332 (pKal). Intradermal administration of LGA led to successful transduction of mouse skin, with robust expression of the encoded human transgene in the correct layer of the epidermis. Histological evaluation showed no inflammatory infiltration at the treated site, demonstrating the safety of this therapy.

Taken together, the data presented in this example demonstrates that (1) HSV vectors could be successfully engineered to robustly express human laminin proteins (specifically, the or γ subunit of human laminin-332), (2) an HSV-based vector (LGA) could successfully deliver a human laminin-332 subunit in vivo, and (3) the recombinant human laminin-332 subunit was expressed in, and localized to, the appropriate region of the epidermis of treated animals.

What is claimed is:

1. A composition for topical, transdermal, superficial, or intradermal administration comprising:

(a) a replication defective herpes simplex virus type 1 (HSV-1) comprising a recombinant HSV-1 genome, wherein the recombinant HSV-1 genome comprises a first polynucleotide encoding a first protein; and (b) an excipient;

wherein the first protein is selected from the group consisting of a first collagen protein, a first fibronectin protein, a first elastin protein, a first lumican protein, a first vitronectin protein, a first vitronectin receptor protein, a first laminin protein, a first neuromodulator protein, and a first fibrillin protein, wherein the recombinant HSV-1 genome comprises an inactivating mutation in one or both copies of the Infected Cell Protein (ICP) 4 herpes simplex virus gene, and wherein the recombinant HSV-1 genome does not comprise a polynucleotide encoding a Collagen alpha-1 (VII) chain (COL7) polypeptide.

2. The composition of claim 1, wherein the recombinant HSV-1 genome further comprises an inactivating mutation in a herpes simplex virus gene selected from the group consisting of ICP0, ICP22, ICP27, ICP47, thymidine kinase (tk), Long Unique Region (UL) 41, and UL55.

3. The composition of claim 1, wherein the first collagen protein is selected from the group consisting of a human Collagen alpha-1 (I) chain polypeptide (COL1-1), a human Collagen alpha-2 (I) chain polypeptide (COL1-2), a human Collagen alpha-1 (II) chain polypeptide (COL2), a human Collagen alpha-1 (III) chain polypeptide (COL3), a human Collagen alpha-1 (IV) chain polypeptide (COL4-1), a human Collagen alpha-2 (IV) chain polypeptide (COL4-2), a human Collagen alpha-3 (IV) chain polypeptide (COL4-3), a human Collagen alpha-4 (IV) chain polypeptide (COL4-4), a human Collagen alpha-5 (IV) chain polypeptide (COL4-5), a human Collagen alpha-6 (IV) chain polypeptide (COL4-6), a human Collagen alpha-1 (V) chain polypeptide (COL5-1), a human Collagen alpha-2 (V) chain polypeptide (COL5-2), a human Collagen alpha-3 (V) chain polypeptide (COL5-3), a human Collagen alpha-1 (VI) chain polypeptide (COL6-1), a human Collagen alpha-2 (VI) chain polypeptide (COL6-2), a human Collagen alpha-3 (VI) chain polypeptide (COL6-3), a human Collagen alpha-4 (VI) chain polypeptide (COL6-4), a human Collagen alpha-5 (VI) chain polypeptide (COL6-5), a human Collagen alpha-6 (VI) chain polypeptide (COL6-6), a human Collagen alpha-1 (VIII) chain polypeptide (COL8), a human Collagen alpha-1 (IX) chain polypeptide (COL9-1), a human Collagen alpha-2 (IX) chain polypeptide (COL9-2), a human Collagen alpha-3 (IX) chain polypeptide (COL9-3), a human Collagen alpha-1 (X) chain polypeptide (COL10), a human Collagen alpha-1 (XI) chain polypeptide (COL11-1), a human Collagen alpha-2 (XI) chain polypeptide (COL11-2), a human Collagen alpha-1

(XII) chain polypeptide (COL12), a human Collagen alpha-1 (XIII) chain polypeptide (COL13), a human Collagen alpha-1 (XIV) chain polypeptide (COL14), a human Collagen alpha-1 (XV) chain polypeptide (COL15), a human Collagen alpha-1 (XVI) chain polypeptide (COL16), a human Collagen alpha-1 (XVII) chain polypeptide (COL17), a human Collagen alpha-1 (XVIII) chain polypeptide (COL18), a human Collagen alpha-1 (XIX) chain polypeptide (COL19), a human Collagen alpha-1 (XX) chain polypeptide (COL20), a human Collagen alpha-1 (XXI) chain polypeptide (COL21), a human Collagen alpha-1 (XXII) chain polypeptide (COL22), a human Collagen alpha-1 (XXIII) chain polypeptide (COL23), a human Collagen alpha-1 (XXIV) chain polypeptide (COL24), a human Collagen alpha-1 (XXV) chain polypeptide (COL25), a human Collagen alpha-1 (XXVI) chain polypeptide (COL26), a human Collagen alpha-1 (XXVII) chain polypeptide (COL27), and a human Collagen alpha-1 (XXVIII) chain polypeptide (COL28).

4. The composition of claim 1, wherein the recombinant HSV-1 genome further comprises a second polynucleotide encoding a second protein.

5. The composition of claim 1, wherein the composition is suitable for intradermal administration or superficial injection.

6. A method of improving skin condition, quality, and/or appearance in a subject, the method comprising administering to the subject an effective amount of a composition comprising:

(a) a replication defective HSV-1 comprising a recombinant HSV-1 genome, wherein the recombinant HSV-1 genome comprises a first polynucleotide encoding a first protein; and (b) an excipient;

wherein the first protein is selected from the group consisting of a first collagen protein, a first fibronectin protein, a first elastin protein, a first lumican protein, a first vitronectin protein, a first vitronectin receptor protein, a first laminin protein, a first neuromodulator protein, and a first fibrillin protein, wherein the recombinant HSV-1 genome comprises an inactivating mutation in one or both copies of the ICP4 herpes simplex virus gene, wherein the composition is administered topically, transdermally, intradermally, or via superficial injection to the subject, and wherein the recombinant HSV-1 genome does not comprise a polynucleotide encoding a COL7 polypeptide.

7. The method of claim 6, wherein the subject's skin comprises one or more of sun or UV damage, rough texture, sagging, wrinkles, or any combinations thereof.

8. The method of claim 6, wherein the subject is a human.

9. The method of claim 6, wherein the composition is administered intradermally or via superficial injection to the subject.

10. The method of claim 6, wherein the recombinant HSV-1 genome further comprises an inactivating mutation in a herpes simplex virus gene selected from the group consisting of ICP0, ICP22, ICP27, ICP47, tk, UL41, and UL55.

11. The method of claim 6, wherein the first collagen protein is selected from the group consisting of a human COL1-1 polypeptide, a human COL1-2, a human COL2 polypeptide, a human COL3 polypeptide, a human COL4-1 polypeptide, a human COL4-2 polypeptide, a human COL4-3 polypeptide, a human COL4-4 polypeptide, a human COL4-5 polypeptide, a human COL4-6 polypeptide, a human COL5-1 polypeptide, a human COL5-2 polypeptide, a human COL5-3 polypeptide, a human COL6-1 polypeptide, a human COL6-2 polypeptide, a human COL6-3 polypeptide, a human COL6-4 polypeptide, a human COL6-5 polypeptide, a human COL6-6 polypeptide, a human COL8 polypeptide, a human COL9-1 polypeptide, a human COL9-2 polypeptide, a human COL9-3 polypeptide, a human COL10 polypeptide, a human COL11-1 polypeptide, a human COL11-2 polypeptide, a human COL12 polypeptide, a human COL13 polypeptide, a human COL14 polypeptide, a human COL15 polypeptide, a human COL16 polypeptide, a human COL17 polypeptide, a human COL18 polypeptide, a human COL19 polypeptide, a human COL20 polypeptide, a human COL21 polypeptide, a human COL22 polypeptide, a human COL23 polypeptide, a human COL24 polypeptide, a human COL25 polypeptide, a human COL26 polypeptide, a human COL27 polypeptide, and a human COL28 polypeptide.

12. The method of claim 6, wherein the recombinant HSV-1 further comprises a second polynucleotide encoding a second protein.

13. The composition of claim 4, wherein the first protein is a first collagen protein, and the second protein is selected from the group consisting of a fibronectin protein, an elastin protein, a lumican protein, a vitronectin protein, a vitronectin receptor protein, a laminin protein, a neuromodulator protein, and a fibrillin protein.

14. The method of claim 12, wherein the first protein is a first collagen protein, and the second protein is selected from the group consisting of a fibronectin protein, an elastin protein, a lumican protein, a vitronectin protein, a vitronectin receptor protein, a laminin protein, a neuromodulator protein, and a fibrillin protein.

* * * * *

SEQUENCE LISTING

<160> NUMBER OF SEQ ID NOS: 64

<210> SEQ ID NO 1
<211> LENGTH: 4395
<212> TYPE: DNA
<213> ORGANISM: Homo sapiens

<400> SEQUENCE: 1
atgttcagct ttgtggacct ccggctcctg ctcctcttag cggccaccgc cctcctgacg 60
cacggccaag aggaaggcca agtcgagggc caagacgaag acatcccacc aatcacctgc 120
gtacagaacg gcctcaggta ccatgaccga gacgtgtgga aacccgagcc ctgccggatc 180
tgcgtctgcg acaacggcaa ggtgttgtgc gatgacgtga tctgtgacga gaccaagaac 240
tgccccggcg ccgaagtccc cgagggcgag tgctgtcccg tctgccccga cggctcagag 300
tcacccaccg accaagaaac caccggcgtc gagggaccca agggagacac tggcccccga 360
ggcccaaggg gacccgcagg cccccctggc cgagatggca tccctggaca gcctggactt 420
cccggacccc ccggaccccc cggacctccc ggacccccctg gcctcggagg aaactttgct 480
ccccagctgt cttatggcta tgatgagaaa tcaaccggag gaatttccgt gcctggcccc 540
atgggtccct ctggtcctcg tggtctccct ggccccccctg gtgcacctgg tccccaaggc 600
ttccaaggtc cccctggtga gcctggcgag cctggagctt caggtcccat gggtccccga 660
ggtcccccag gtcccccctgg aaagaatgga gatgatgggg aagctggaaa acctggtcgt 720
cctggtgagc gtgggcctcc tgggcctcag ggtgctcgag gattgcccgg aacagctggc 780
ctccctggaa tgaagggaca cagaggtttc agtggtttgg atggtgccaa gggagatgct 840
ggtcctgctg gtcctaaggg tgagcctggc agccctggtg aaaatggagc tcctggtcag 900

```
atgggccccc gtggcctgcc tggtgagaga ggtcgccctg gagcccctgg ccctgctggt    960
gctcgtggaa atgatggtgc tactggtgct gccgggcccc ctggtcccac cggccccgct   1020
ggtcctcctg gcttccctgg tgctgttggt gctaagggtg aagctggtcc ccaagggccc   1080
cgaggctctg aaggtcccca gggtgtgcgt ggtgagcctg gcccccctgg ccctgctggt   1140
gctgctggcc ctgctggaaa ccctggtgct gatggacagc ctggtgctaa aggtgccaat   1200
ggtgctcctg gtattgctgg tgctcctggc ttccctggtg cccgaggccc ctctggaccc   1260
cagggccccg gcggccctcc tggtcccaag ggtaacagcg gtgaacctgg tgctcctggc   1320
agcaaaggag acactggtgc taagggagag cctggccctg ttggtgttca aggacccccct  1380
ggccctgctg gagaggaagg aaagcgagga gctcgaggtg aacccggacc cactggcctg   1440
cccggacccc ctggcgagcg tggtggacct ggtagccgtg gtttccctgg cgcagatggt   1500
gttgctggtc ccaagggtcc cgctggtgaa cgtggttctc ctggccctgc tggccccaaa   1560
ggatctcctg gtgaagctgg tcgtcccggt gaagctggtc tgcctggtgc caagggtctg   1620
actggaagcc ctggcagccc tggtcctgat ggcaaaactg gcccccctgg tcccgccggt   1680
caagatggtc gccccggacc cccaggccca cctggtgccc gtggtcaggc tggtgtgatg   1740
ggattccctg gacctaaagg tgctgctgga gagcccggca aggctggaga gcgaggtgtt   1800
cccggacccc ctggcgctgt cggtcctgct ggcaaagatg gagaggctgg agctcaggga   1860
cccccctggcc ctgctggtcc cgctggcgag agaggtgaac aaggccctgc tggctccccc  1920
ggattccagg gtctccctgg tcctgctggt cctccaggtg aagcaggcaa acctggtgaa   1980
cagggtgttc ctggagacct tggcgcccct ggcccctctg gagcaagagg cgagagaggt   2040
ttccctggcg agcgtggtgt gcaaggtccc cctggtcctg ctggtccccg aggggccaac   2100
ggtgctcccg gcaacgatgg tgctaagggt gatgctggtg cccctggagc tcccggtagc   2160
cagggcgccc ctggccttca gggaatgcct ggtgaacgtg gtgcagctgg tcttccaggg   2220
cctaagggtg acagaggtga tgctggtccc aaaggtgctg atggctctcc tggcaaagat   2280
ggcgtccgtg gtctgactgg ccccattggt cctcctggcc ctgctggtgc ccctggtgac   2340
aagggtgaaa gtggtcccag cggccctgct ggtcccactg gagctcgtgg tgcccccgga   2400
gaccgtggtg agcctggtcc ccccggccct gctggctttg ctggcccccc tggtgctgac   2460
ggccaacctg gtgctaaagg cgaacctggt gatgctggtg ctaaaggcga tgctggtccc   2520
cctggccctg ccggacccgc tggacccccct ggccccattg gtaatgttgg tgctcctgga  2580
gccaaaggtg ctcgcggcag cgctggtccc cctggtgcta ctggtttccc tggtgctgct   2640
ggccgagtcg gtcctcctgg cccctctgga aatgctggac cccctggccc tcctggtcct   2700
gctggcaaag aaggcggcaa aggtccccgt ggtgagactg gccctgctgg acgtcctggt   2760
gaagttggtc cccctggtcc ccctggccct gctggcgaga aaggatcccc tggtgctgat   2820
ggtcctgctg gtgctcctgg tactcccggg cctcaaggta ttgctggaca gcgtggtgtg   2880
gtcggcctgc ctggtcagag aggagagaga ggcttccctg gtcttcctgg cccctctggt   2940
gaacctggca aacaaggtcc ctctggagca agtggtgaac gtggtccccc tggtcccatg   3000
ggcccccctg gattggctgg accccctggt gaatctggac gtgagggggc tcctggtgcc   3060
gaaggttccc ctggacgaga cggttctcct ggcgccaagg gtgaccgtgg tgagaccggc   3120
cccgctggac cccctggtgc tcctggtgct cctggtgccc ctggccccgt tggccctgct   3180
ggcaagagtg gtgatcgtgg tgagactggt cctgctggtc ccgccggtcc tgtcggccct   3240
```

-continued

```
gttggcgccc gtggccccgc cggaccccaa ggcccccgtg gtgacaaggg tgagacaggc   3300

gaacagggcg acagaggcat aaagggtcac cgtggcttct ctggcctcca gggtccccct   3360

ggccctcctg gctctcctgg tgaacaaggt ccctctggag cctctggtcc tgctggtccc   3420

cgaggtcccc ctggctctgc tggtgctcct ggcaaagatg gactcaacgg tctccctggc   3480

cccattgggc cccctggtcc tcgcggtcgc actggtgatg ctggtcctgt tggtcccccc   3540

ggccctcctg gacctcctgg tccccctggt cctcccagcg ctggtttcga cttcagcttc   3600

ctgccccagc cacctcaaga gaaggctcac gatggtggcc gctactaccg ggctgatgat   3660

gccaatgtgg ttcgtgaccg tgacctcgag gtggacacca ccctcaagag cctgagccag   3720

cagatcgaga acatccggag cccagagggc agccgcaaga accccgcccg cacctgccgt   3780

gacctcaaga tgtgccactc tgactggaag agtggagagt actggattga ccccaaccaa   3840

ggctgcaacc tggatgccat caaagtcttc tgcaacatgg agactggtga gacctgcgtg   3900

taccccactc agcccagtgt ggcccagaag aactggtaca tcagcaagaa ccccaaggac   3960

aagaggcatg tctggttcgg cgagagcatg accgatggat tccagttcga gtatggcggc   4020

cagggctccg accctgccga tgtggccatc cagctgacct tcctgcgcct gatgtccacc   4080

gaggcctccc agaacatcac ctaccactgc aagaacagcg tggcctacat ggaccagcag   4140

actggcaacc tcaagaaggc cctgctcctc cagggctcca acgagatcga gatccgcgcc   4200

gagggcaaca gccgcttcac ctacagcgtc actgtcgatg gctgcacgag tcacaccgga   4260

gcctggggca agacagtgat tgaatacaaa accaccaaga cctcccgcct gcccatcatc   4320

gatgtggccc ccttggacgt tggtgcccca gaccaggaat tcggcttcga cgttggccct   4380

gtctgcttcc tgtaa                                                    4395
```

<210> SEQ ID NO 2
<211> LENGTH: 4395
<212> TYPE: DNA
<213> ORGANISM: Artificial Sequence
<220> FEATURE:
<223> OTHER INFORMATION: Synthetic Construct

<400> SEQUENCE: 2

```
atgttcagct tcgtggacct gagactgctg ctgctcctgg ctgctacagc cctgctgaca     60

cacggacaag aggaaggcca ggtcgaagga caggacgagg acatccctcc tatcacctgt    120

gtgcagaacg gcctgagata ccacgaccgg gatgtgtgga agcccgagcc ttgcagaatc    180

tgcgtgtgcg acaatggcaa ggtgctgtgc gacgacgtga tctgcgacga gacaaagaat    240

tgccctggcg ccgaagtgcc tgagggcgaa tgttgtcctg tgtgccctga tggcagcgag    300

agccccacag atcaagagac aacaggcgtg gaaggcccca agggcgatac aggacctaga    360

ggtcctagag gacctgccgg acctcctggc agagatggaa ttcctggaca gcctggactg    420

cccggaccac ctggacctcc agggcctcca ggtccaccag gactcggagg aaattttgcc    480

ccacagctga gctacggcta cgacgagaaa agcacaggcg gcatctctgt gcctggacct    540

atgggacctt ctggcccaag aggacttcct ggtcctcctg gtgctccagg acctcaggga    600

tttcaaggac caccaggcga acctggcgaa ccaggcgcta gtggtccaat gggaccaaga    660

ggccctcctg ggccaccagg caaaaatggc gacgatggcg aagccggaaa gcctggaagg    720

cctggcgaaa gaggcccgcc aggaccgcaa ggcgctagag ggttgcctgg aactgcagga    780

ctgcctggca tgaagggcca cagaggcttt tctggactgg atggcgctaa gggcgacgct    840

ggaccagcag gacctaaagg cgagcctgga tctcctggcg agaatggtgc acctggacag    900
```

-continued

```
atgggtccca gaggattgcc aggcgagaga ggtagacctg gcgctccggg accagccggt    960
gctagaggaa atgatggcgc aacaggtgct gctgggcctc ctggaccaac cggaccagct   1020
ggcccacctg gatttccagg cgctgttgga gcaaagggcg aagcaggccc acaaggacct   1080
aggggatctg aaggtcctca gggcgttaga ggcgagccag ggccacctgg gcctgccggt   1140
gcagctggac ctgctggaaa ccctggtgct gatggacagc caggtgccaa aggtgctaat   1200
ggcgcccctg gaattgccgg cgctccaggt tttcccggcg caagagggcc atctggacct   1260
caaggcccag gcggacctcc gggtcctaag ggaaatagcg gagagccagg cgctcctggg   1320
agtaaaggcg atactggcgc aaaaggcgaa cccggacctg tgggagttca aggacctcct   1380
ggaccagctg gcgaggaagg caaaagaggc gctaggggag aaccaggacc aacagggctc   1440
cctggtccac ctggcgagcg cggaggacct ggatctagag gattccctgg cgcagatggc   1500
gtggccggac caaaaggacc tgcaggcgaa aggggatcac caggtcctgc aggccctaag   1560
ggttctccag gcgaggctgg cagacccggc gaagctggac tcccaggtgc taagggactg   1620
acaggctcac caggatctcc cggaccagac ggaaaaacag gacctccagg accggcagga   1680
caggatggta gacccggtcc tcctggaccg cctggtgcaa gaggacaagc tggcgtgatg   1740
ggctttcctg gaccaaaagg tgcagccggc gaacctggaa aagcaggcga gaggggagtt   1800
cccggacctc caggtgctgt tggacctgcc ggaaaagatg gcgaagctgg tgcacaaggt   1860
cctccagggc cagccggacc agccggcgag agaggcgaac aaggaccagc cggatctcca   1920
ggatttcagg gactgccagg gcctgctggc ccgcctggcg aggcagggaa gccaggcgaa   1980
cagggtgttc ctggcgatct tggagcccct ggtcctagcg gagctagagg cgaaagagga   2040
tttcctggcg aaaggggcgt tcagggtcca ccgggaccag ctggaccaag ggtgcaaat   2100
ggtgccccag gcaatgacgg tgctaaaggc gacgcaggcg ccccaggtgc tcctggatct   2160
caaggcgcac ctggacttca gggaatgcct ggcgaacggg gagctgctgg acttcccggt   2220
ccaaaaggcg ataggggaga tgctggtcct aagggcgctg atggctctcc tggaaaggat   2280
ggcgtcagag gcctgacagg cccaattggc cctccgggac ctgctggcgc tccaggcgat   2340
aagggcgaat ctggacctag tggacccgct ggtcctacag gtgctagggg agccccaggc   2400
gaccggggag agcctggtcc accaggacct gctggatttg ctggacctcc tggcgctgat   2460
ggtcaacctg gtgctaaggg cgagccaggc gacgctggtg caaaaggcga cgctggtcca   2520
cctggaccgg ccggacctgc tggcccgcca ggacctattg gaaatgttgg tgcccctggc   2580
gccaaaggcg caagaggatc tgctggccca ccaggcgcta caggattccc aggtgccgct   2640
ggaagagttg gaccaccggg gccaagtgga aatgctggac caccgggacc gccaggacca   2700
gccggcaaag aaggtggaaa aggccctagg ggcgaaactg gccctgcagg caggccaggc   2760
gaagtgggcc ctccaggacc tccggggcct gccggcgaaa aaggatctcc aggcgcagat   2820
ggacccgcag gcgctcccgg aacaccaggt ccacagggaa ttgctggaca aaggggagtt   2880
gtcggcctgc caggacagag gggagagaga ggttttccag gactccctgg gccaagcgga   2940
gaacctggca aacagggacc atctggtgcc agcggagaga gagggccacc aggaccaatg   3000
ggtcctccag gattggcagg gcctcctggc gaatctggta gagaaggtgc tccaggcgcc   3060
gagggatctc ctggacgtga tggttctcct ggcgccaagg gcgatagagg cgaaacaggc   3120
ccagctggac ctccaggcgc acccggcgct ccaggcgcac caggacctgt tggccctgct   3180
ggaaaatctg gcgacagagg cgaaactgga cccgcaggac cagccggacc tgttggacct   3240
```

-continued

```
gtgggtgcta gaggacccgc tggaccacaa ggtcctagag gcgacaaggg cgaaacaggc   3300

gagcaaggcg acagaggcat caagggacac agaggattca gcggactgca gggaccacca   3360

gggccgcctg gaagtcccgg cgagcaggga ccaagcggag ctagtggtcc cgccggacct   3420

agaggaccac ctggttctgc tggtgcaccc ggaaaggacg gactgaatgg gctccccgga   3480

cctattgggc cacctggacc tagaggaaga acaggcgacg caggaccagt tggaccacct   3540

gggccacctg gaccgcctgg tcctcctgga cctccttctg ccggattcga cttcagcttc   3600

ctgcctcagc ctcctcaaga gaaggcccat gacggcggca gatattacag agccgacgac   3660

gccaacgtcg tgcgggacag agatctggaa gtggacacca cactgaagtc cctgtctcag   3720

cagatcgaga acatcagaag ccccgagggc agcagaaaga accctgccag aacctgtcgg   3780

gacctgaaga tgtgccacag cgattggaag tctggcgagt actggatcga ccccaaccag   3840

ggctgcaacc tggatgccat caaggtgttc tgcaacatgg aaaccggcga gacatgcgtg   3900

taccccacac agccatctgt ggctcagaag aactggtaca tcagcaagaa ccccaaggac   3960

aagcggcacg tttggttcgg cgagagcatg accgatggct tccagtttga gtatggcggc   4020

cagggctctg accctgccga tgttgctatc cagctgacct tcctgcggct gatgtctaca   4080

gaggccagcc agaacatcac ctaccactgc aagaacagcg tggcctacat ggatcagcag   4140

accggcaacc tgaagaaggc actgctgctt cagggcagca acgagatcga gatcagagcc   4200

gagggcaaca gccggttcac ctacagcgtg acagtggatg gctgcaccag ccatacaggc   4260

gcttggggca agaccgtgat cgagtacaag accaccaaga ccagcagact gcccatcatc   4320

gatgtggccc ctctggatgt tggggcaccc gatcaagagt tcggcttcga tgtgggccca   4380

gtgtgcttcc tgtaa                                                    4395
```

<210> SEQ ID NO 3
<211> LENGTH: 4101
<212> TYPE: DNA
<213> ORGANISM: Homo sapiens

<400> SEQUENCE: 3

```
atgctcagct ttgtggatac gcggactttg ttgctgcttg cagtaacctt atgcctagca     60

acatgccaat ctttacaaga ggaaactgta agaaagggcc cagccggaga tagaggacca    120

cgtggagaaa ggggtccacc aggcccccca ggcagagatg gtgaagatgg tcccacaggc    180

cctcctggtc cacctggtcc tcctggcccc cctggtctcg gtgggaactt tgctgctcag    240

tatgatggaa aaggagttgg acttggccct ggaccaatgg gcttaatggg acctagaggc    300

ccacctggtg cagctggagc cccaggccct caaggtttcc aaggacctgc tggtgagcct    360

ggtgaacctg gtcaaactgg tcctgcaggt gctcgtggtc cagctggccc tcctggcaag    420

gctggtgaag atggtcaccc tggaaaaccc ggacgacctg gtgagagagg agttgttgga    480

ccacagggtg ctcgtggttt ccctggaact cctggacttc ctggcttcaa aggcattagg    540

ggacacaatg gtctggatgg attgaaggga cagcccggtg ctcctggtgt gaagggtgaa    600

cctggtgccc ctggtgaaaa tggaactcca ggtcaaacag gagcccgtgg gcttcctggt    660

gagagaggac gtgttggtgc ccctggccca gctggtgccc gtggcagtga tggaagtgtg    720

ggtcccgtgg gtcctgctgg tcccattggg tctgctggcc ctccaggctt cccaggtgcc    780

cctggcccca agggtgaaat tggagctgtt ggtaacgctg gtcctgctgg tcccgccggt    840

ccccgtggtg aagtgggtct tccaggcctc tccggccccg ttggacctcc tggtaatcct    900

ggagcaaacg gccttactgg tgccaagggt gctgctggcc ttcccggcgt tgctggggct    960
```

-continued

```
cccggcctcc ctggaccccg cggtattcct ggccctgttg gtgctgccgg tgctactggt   1020
gccagaggac ttgttggtga gcctggtcca gctggctcca aaggagagag cggtaacaag   1080
ggtgagcccg gctctgctgg gccccaaggt cctcctggtc ccagtggtga agaaggaaag   1140
agaggcccta atggggaagc tggatctgcc ggccctccag gacctcctgg gctgagaggt   1200
agtcctggtt ctcgtggtct tcctggagct gatggcagag ctggcgtcat gggccctcct   1260
ggtagtcgtg gtgcaagtgg ccctgctgga gtccgaggac ctaatggaga tgctggtcgc   1320
cctggggagc ctggtctcat gggacccaga ggtcttcctg gttcccctgg aaatatcggc   1380
cccgctggaa aagaaggtcc tgtcggcctc cctggcatcg acggcaggcc tggcccaatt   1440
ggcccagctg gagcaagagg agagcctggc aacattggat tccctggacc caaaggcccc   1500
actggtgatc ctggcaaaaa cggtgataaa ggtcatgctg gtcttgctgg tgctcggggt   1560
gctccaggtc ctgatggaaa caatggtgct cagggacctc ctggaccaca gggtgttcaa   1620
ggtggaaaag gtgaacaggg tccccctggt cctccaggct tccagggtct gcctggcccc   1680
tcaggtcccg ctggtgaagt tggcaaacca ggagaaaggg gtctccatgg tgagtttggt   1740
ctccctggtc ctgctggtcc aagaggggaa cgcggtcccc caggtgagag tggtgctgcc   1800
ggtcctactg gtcctattgg aagccgaggt ccttctggac ccccagggcc tgatggaaac   1860
aagggtgaac ctggtgtggt tggtgctgtg ggcactgctg gtccatctgg tcctagtgga   1920
ctcccaggag agaggggtgc tgctggcata cctggaggca agggagaaaa gggtgaacct   1980
ggtctcagag gtgaaattgg taaccctggc agagatggtg ctcgtggtgc tcctggtgct   2040
gtaggtgccc ctggtcctgc tggagccaca ggtgaccggg gcgaagctgg ggctgctggt   2100
cctgctggtc ctgctggtcc tcggggaagc cctggtgaac gtggtgaggt cggtcctgct   2160
ggccccaatg gatttgctgg tcctgctggt gctgctggtc aacctggtgc taaaggagaa   2220
agaggagcca aagggcctaa gggtgaaaac ggtgttgttg gtcccacagg ccccgttgga   2280
gctgctggcc cagctggtcc aaatggtccc cccggtcctg ctggaagtcg tggtgatgga   2340
ggccccccctg gtatgactgg tttccctggt gctgctggac ggactggtcc cccaggaccc   2400
tctggtattt ctggccctcc tggtcccccct ggtcctgctg ggaaagaagg gcttcgtggt   2460
cctcgtggtg accaaggtcc agttggccga actggagaag taggtgcagt tggtcccccct   2520
ggcttcgctg gtgagaaggg tccctctgga gaggctggta ctgctggacc tcctggcact   2580
ccaggtcctc agggtcttct tggtgctcct ggtattctgg gtctccctgg ctcgagaggt   2640
gaacgtggtc taccaggtgt tgctggtgct gtgggtgaac ctggtcctct tggcattgcc   2700
ggccctcctg gggcccgtgg tcctcctggt gctgtgggta gtcctggagt caacggtgct   2760
cctggtgaag ctggtcgtga tggcaaccct gggaacgatg gtcccccagg tcgcgatggt   2820
caacccggac acaagggaga gcgcggttac cctggcaata ttggtcccgt tggtgctgca   2880
ggtgcacctg gtcctcatgg ccccgtgggt cctgctggca aacatggaaa ccgtggtgaa   2940
actggtcctt ctggtcctgt tggtcctgct ggtgctgttg gcccaagagg tcctagtggc   3000
ccacaaggca ttcgtggcga taagggagag cccggtgaaa aggggcccag aggtcttcct   3060
ggcttaaagg gacacaatgg attgcaaggt ctgcctggta tcgctggtca ccatggtgat   3120
caaggtgctc ctggctccgt gggtcctgct ggtcctaggg gccctgctgg tccttctggc   3180
cctgctggaa aagatggtcg cactggacat cctggtacag ttggacctgc tggcattcga   3240
ggccctcagg gtcaccaagg ccctgctggc ccccctggtc cccctggccc tcctggacct   3300
```

```
ccaggtgtaa gcggtggtgg ttatgacttt ggttacgatg gagacttcta cagggctgac   3360
cagcctcgct cagcaccttc tctcagaccc aaggactatg aagttgatgc tactctgaag   3420
tctctcaaca accagattga gacccttctt actcctgaag gctctagaaa gaacccagct   3480
cgcacatgcc gtgacttgag actcagccac ccagagtgga gcagtggtta ctactggatt   3540
gaccctaacc aaggatgcac tatggatgct atcaaagtat actgtgattt ctctactggc   3600
gaaacctgta tccgggccca acctgaaaac atcccagcca agaactggta taggagctcc   3660
aaggacaaga aacacgtctg gctaggagaa actatcaatg ctggcagcca gtttgaatat   3720
aatgtagaag gagtgacttc caaggaaatg gctacccaac ttgccttcat gcgcctgctg   3780
gccaactatg cctctcagaa catcacctac cactgcaaga acagcattgc atacatggat   3840
gaggagactg gcaacctgaa aaaggctgtc attctacagg gctctaatga tgttgaactt   3900
gttgctgagg gcaacagcag gttcacttac actgttcttg tagatggctg ctctaaaaag   3960
acaaatgaat ggggaaagac aatcattgaa tacaaaacaa ataagccatc acgcctgccc   4020
ttccttgata ttgcaccttt ggacatcggt ggtgctgacc aggaattctt tgtggacatt   4080
ggcccagtct gtttcaaata a                                               4101
```

<210> SEQ ID NO 4
<211> LENGTH: 4101
<212> TYPE: DNA
<213> ORGANISM: Artificial Sequence
<220> FEATURE:
<223> OTHER INFORMATION: Synthetic Construct

<400> SEQUENCE: 4

```
atgctgagct tcgtggacac cagaacactg ctgctgctgg ccgtgacact gtgtctggcc     60
acttgtcaga gcctgcaaga ggaaacagtg cggaaaggac ctgccggcga tagaggacct    120
agaggcgaaa gaggtcctcc tggacctcct ggtagagatg gcgaggatgg acctacagga    180
ccacctggtc caccaggacc tccagggcct cctggccttg gaggaaattt tgccgctcag    240
tacgatggca aaggcgtcgg acttggccct ggacctatgg gacttatggg cccaagagga    300
ccaccaggtg ctgcaggcgc tccaggacca caaggatttc aaggaccagc tggcgagcct    360
ggcgaacctg gacaaacagg tcctgctggt gctagaggac cagccgggcc acctggaaaa    420
gctggcgaag atgggcaccc tggaaagcct ggtagacccg gcgaaagggg tgttgttgga    480
cctcaaggcg ccagaggctt tcctggaaca cctggactgc ctggcttcaa gggcatcaga    540
ggccacaatg gcctggacgg actgaaagga caacctggtg ctcctggcgt gaaaggcgaa    600
ccaggcgcac ctggcgaaaa tggcacacca ggacaaaccg gcgcaagagg acttcctggc    660
gagagaggaa gagttggagc ccaggtcca gcaggcgcac gaggatctga tggatctgtg    720
ggacctgttg gccctgccgg acctattgga agtgctggcc ctcctggatt tcctggcgca    780
cccggaccaa agggcgaaat tggagctgtg ggaaacgccg gacctgcagg cccagctgga    840
ccaaggggag aagttggatt gcctggactg agcggaccag ttgggccacc agggaatcct    900
ggtgccaatg gactgacagg cgctaaaggt gcagctggcc ttccaggcgt tgccggtgca    960
ccaggactgc caggaccaag aggtatccct ggtcctgttg gagctgctgg cgctacgggt   1020
gccagaggac ttgttggaga acctgggcca gccggatcta agggcgagtc tggaaacaag   1080
ggcgagccag gatctgctgg tccacaaggc ccgcctggac catcaggcga agaaggcaaa   1140
cgaggcccta atggcgaagc cggtagtgcc gggcctcctg gaccaccagg ccttagagga   1200
tctcctggct ctagaggatt gccaggcgct gatggtagag caggcgttat gggtccacct   1260
```

-continued

```
ggatcaagag gcgcttctgg ccctgctggc gttagaggtc caaatggcga cgctggcaga   1320
ccaggcgagc ccggtcttat ggggcctaga gggttgcctg gaagccctgg caatatcggc   1380
ccagccggaa aagaaggccc tgttggactc cctggcatcg acggtagacc tggaccaatc   1440
ggacccgcag gcgctagggg agagcctgga aatattggct tccctgggcc taaaggcccc   1500
acaggcgatc ctggaaagaa cggcgataag ggccatgctg gactcgctgg tgcaagggga   1560
gcacctggac ctgacggaaa caatggtgct caagggccgc ctgggccaca aggtgttcaa   1620
ggtggaaaag gcgagcaggg cccacctggg cctccaggct tccaaggact tcccggacca   1680
tctgggccag caggcgaagt tggaaagcct ggcgaaagag gactgcacgg cgagtttggc   1740
ttgccgggtc ctgccggtcc acggggagag agaggccctc caggcgaatc tggcgccgca   1800
ggacctactg gccctatcgg aagcagagga cctagtggac ctccaggacc tgatggcaac   1860
aaaggcgaac ctggtgttgt gggcgctgtg ggaacagctg gaccttctgg tccttctgga   1920
ttgcccggcg agcgcggagc agctggtatt cctggtggca aaggcgaaaa gggcgagcct   1980
ggactcagag gcgagatcgg caatcccgga cgagatggcg ctagaggcgc cccaggtgca   2040
gttggtgccc cgggacctgc tggcgcaaca ggcgacagag gcgaggctgg tgccgctggt   2100
cctgccgggc cagccggtcc tagaggaagt ccaggcgaga ggggcgaagt gggacccgct   2160
ggacccaatg gatttgctgg gcccgctggc gctgctggtc aacctggcgc caaaggcgag   2220
cggggagcta aaggtcctaa aggcgagaat ggcgtcgtgg gccctactgg accagtggga   2280
gcagcaggcc ccgcaggtcc taacggacca cctggaccag ctgggtctag aggcgacggc   2340
ggaccgcctg gaatgacagg ttttccaggc gccgctggaa gaacaggtcc tccaggacca   2400
tctggcatct ctggtccacc agggccacct ggtcctgctg gaaaagaagg actgagaggc   2460
cctaggggcg atcagggtcc agttggaaga accggcgaag tcggagctgt cggcccacca   2520
ggttttgccg gcgaaaaagg ccctagcgga gaagctggaa ctgcaggacc gccgggaact   2580
cccggtcctc aaggattgct tggcgcccct ggaattctgg gactgcccgg tagtcgcgga   2640
gaacgtggac tcccaggtgt tgctggcgcc gtcggagaac cgggaccact tggaattgct   2700
ggaccacctg gtgcaagagg tccacctggt gcagttggaa gtcctggcgt taacggtgct   2760
ccaggcgaag ccggcagaga tggaaatccc ggcaatgatg gcccgcctgg gagagatgga   2820
cagcctggac ataagggcga gcgaggctac ccaggcaata ttggacctgt cggcgcagcc   2880
ggtgctcccg gacctcatgg tccagtcggt ccagccggga agcacggaaa taggggagaa   2940
acaggaccct ccggtcctgt tggcccagct ggcgcagttg gaccaagagg cccatccgga   3000
cctcagggaa tccgcggaga taagggcgaa cctggcgaga agggacctag aggactgcct   3060
gggctgaaag gccataacgg actgcaaggc ctgccaggca ttgctggcca tcatggcgat   3120
caaggtgcac ccggtagtgt gggtcccgcc ggaccgaggg gtcccgctgg tccatctgga   3180
cccgccggaa aagatggcag aacaggacat cctggcacag tggggcctgc cggaattaga   3240
ggcccacagg gacatcaagg ccccgctggg ccgccaggac ctccgggacc gccagggcca   3300
ccaggcgtta gtggcggagg atacgatttc ggctacgacg gcgacttcta cagagccgac   3360
cagcctagat ctgcccctag cctgaggcct aaggactacg aagtggacgc cacactgaag   3420
tccctgaaca accagatcga gacactgctg acccctgagg gcagcagaaa gaaccctgcc   3480
agaacctgca gggacctgag actgtctcac cccgaatggt cctccggcta ctactggatc   3540
gaccccaatc agggctgcac catggacgcc atcaaggtgt actgcgactt cagcaccggc   3600
```

-continued

```
gagacatgca tcagagccca gcctgagaac atccccgcca agaactggta cagaagcagc   3660
aaggacaaga aacacgtgtg gctgggcgag acaatcaacg ccggcagcca gttcgagtac   3720
aacgtggaag gcgtgaccag caaagagatg gccacacagc tggctttcat gagactgctg   3780
gccaattacg ccagccagaa catcacctac cactgcaaga acagcattgc ctacatggac   3840
gaggaaaccg gcaacctgaa gaaagccgtg atcctgcagg gctctaacga cgtggaactg   3900
gtggccgagg gcaacagcag attcacctac accgtgctgg tggacggctg cagcaaaaag   3960
accaacgagt ggggcaagac catcatcgag tataagacca acaagcccag cagactgccc   4020
ttcctggata tcgccccact ggatattgga ggcgccgacc aagagttctt tgtggacatc   4080
ggccccgtgt gcttcaagtg a                                             4101
```

<210> SEQ ID NO 5
<211> LENGTH: 4401
<212> TYPE: DNA
<213> ORGANISM: Homo sapiens

<400> SEQUENCE: 5

```
atgatgagct ttgtgcaaaa ggggagctgg ctacttctcg ctctgcttca tcccactatt     60
attttggcac aacaggaagc tgttgaagga ggatgttccc atcttggtca gtcctatgcg    120
gatagagatg tctggaagcc agaaccatgc caaatatgtg tctgtgactc aggatccgtt    180
ctctgcgatg acataatatg tgacgatcaa gaattagact gccccaaccc agaaattcca    240
tttggagaat gttgtgcagt ttgcccacag cctccaactg ctcctactcg ccctcctaat    300
ggtcaaggac ctcaaggccc caagggagat ccaggccctc ctggtattcc tgggagaaat    360
ggtgaccctg gtattccagg acaaccaggg tcccctggtt ctcctggccc ccctggaatc    420
tgtgaatcat gccctactgg tcctcagaac tattctcccc agtatgattc atatgatgtc    480
aagtctggag tagcagtagg aggactcgca ggctatcctg gaccagctgg cccccccaggc   540
cctcccggtc cccctggtac atctggtcat cctggttccc ctggatctcc aggataccaa    600
ggaccccctg gtgaacctgg gcaagctggt ccttcaggcc ctccaggacc tcctggtgct    660
ataggtccat ctggtcctgc tggaaaagat ggagaatcag gtagacccgg acgacctgga    720
gagcgaggat tgcctggacc tccaggtatc aaaggtccag ctgggatacc tggattccct    780
ggtatgaaag gacacagagg cttcgatgga cgaaatggag aaaagggtga aacaggtgct    840
cctggattaa agggtgaaaa tggtcttcca ggcgaaaatg gagctcctgg acccatgggt    900
ccaagagggg ctcctggtga gcgaggacgg ccaggacttc ctggggctgc aggtgctcgg    960
ggtaatgacg gtgctcgagg cagtgatggt caaccaggcc ctcctggtcc tcctggaact   1020
gccggattcc ctggatcccc tggtgctaag ggtgaagttg gacctgcagg gtctcctggt   1080
tcaaatggtg cccctggaca aagaggagaa cctggacctc agggacacgc tggtgctcaa   1140
ggtcctcctg gccctcctgg gattaatggt agtcctggtg gtaaaggcga aatgggtccc   1200
gctggcattc ctggagctcc tggactgatg ggagcccggg gtcctccagg accagccggt   1260
gctaatggtg ctcctggact gcgaggtggt gcaggtgagc ctggtaagaa tggtgccaaa   1320
ggagagcccg gaccacgtgg tgaacgcggt gaggctggta ttccaggtgt tccaggagct   1380
aaaggcgaag atggcaagga tggatcacct ggagaacctg gtgcaaatgg gcttccagga   1440
gctgcaggag aaaggggtgc ccctgggttc cgaggacctg ctggaccaaa tggcatccca   1500
ggagaaaagg gtcctgctgg agagcgtggt gctccaggcc ctgcagggcc cagaggagct   1560
gctggagaac ctggcagaga tggcgtccct ggaggtccag gaatgagggg catgcccgga   1620
```

-continued

```
agtccaggag gaccaggaag tgatgggaaa ccagggcctc ccggaagtca aggagaaagt   1680
ggtcgaccag gtcctcctgg gccatctggt ccccgaggtc agcctggtgt catgggcttc   1740
cccggtccta aaggaaatga tggtgctcct ggtaagaatg gagaacgagg tggccctgga   1800
ggacctggcc ctcagggtcc tcctggaaag aatggtgaaa ctggacctca gggaccccca   1860
gggcctactg ggcctggtgg tgacaaagga gacacaggac cccctggtcc acaaggatta   1920
caaggcttgc ctggtacagg tggtcctcca ggagaaaatg gaaaacctgg ggaaccaggt   1980
ccaaagggtg atgccggtgc acctggagct ccaggaggca agggtgatgc tggtgcccct   2040
ggtgaacgtg gacctcctgg attggcaggg gccccaggac ttagaggtgg agctggtccc   2100
cctggtcccg aaggaggaaa gggtgctgct ggtcctcctg ggccacctgg tgctgctggt   2160
actcctggtc tgcaaggaat gcctggagaa agaggaggtc ttggaagtcc tggtccaaag   2220
ggtgacaagg gtgaaccagg cggtccaggt gctgatggtg tcccagggaa agatggccca   2280
aggggtccta ctggtcctat tggtcctcct ggcccagctg gccagcctgg agataagggt   2340
gaaggtggtg cccccggact tccaggtata gctggacctc gtggtagccc tggtgagaga   2400
ggtgaaactg gccctccagg acctgctggt ttccctggtg ctcctggaca gaatggtgaa   2460
cctggtggta aaggagaaag aggggctccg ggtgagaaag gtgaaggagg ccctcctgga   2520
gttgcaggac cccctggagg ttctggacct gctggtcctc ctggtcccca aggtgtcaaa   2580
ggtgaacgtg gcagtcctgg tggacctggt gctgctggct tccctggtgc tcgtggtctt   2640
cctggtcctc ctggtagtaa tggtaaccca ggacccccag gtcccagcgg ttctccaggc   2700
aaggatgggc ccccaggtcc tgcgggtaac actggtgctc ctggcagccc tggagtgtct   2760
ggaccaaaag gtgatgctgg ccaaccagga gagaagggat cgcctggtgc ccagggccca   2820
ccaggagctc caggcccact tgggattgct gggatcactg gagcacgggg tcttgcagga   2880
ccaccaggca tgccaggtcc taggggaagc cctggccctc agggtgtcaa gggtgaaagt   2940
gggaaaccag gagctaacgg tctcagtgga gaacgtggtc cccctggacc ccagggtctt   3000
cctggtctgg ctggtacagc tggtgaacct ggaagagatg gaaaccctgg atcagatggt   3060
cttccaggcc gagatggatc tcctggtggc aagggtgatc gtggtgaaaa tggctctcct   3120
ggtgcccctg gcgctcctgg tcatccaggc ccacctggtc ctgtcggtcc agctggaaag   3180
agtggtgaca gaggagaaag tggccctgct ggccctgctg gtgctcccgg tcctgctggt   3240
tcccgaggtg ctcctggtcc tcaaggccca cgtggtgaca aaggtgaaac aggtgaacgt   3300
ggagctgctg gcatcaaagg acatcgagga ttccctggta atccaggtgc cccaggttct   3360
ccaggccctg ctggtcagca gggtgcaatc ggcagtccag gacctgcagg ccccagagga   3420
cctgttggac ccagtggacc tcctggcaaa gatggaacca gtggacatcc aggtcccatt   3480
ggaccaccag ggcctcgagg taacagaggt gaaagaggat ctgagggctc ccccaggccac   3540
ccagggcaac caggccctcc tggacctcct ggtgcccctg gtccttgctg tggtggtgtt   3600
ggagccgctg ccattgctgg gattggaggt gaaaaagctg gcggttttgc cccgtattat   3660
ggagatgaac caatggattt caaaatcaac accgatgaga ttatgacttc actcaagtct   3720
gttaatggac aaatagaaag cctcattagt cctgatggtt ctcgtaaaaa ccccgctaga   3780
aactgcagag acctgaaatt ctgccatcct gaactcaaga gtggagaata ctgggttgac   3840
cctaaccaag gatgcaaatt ggatgctatc aaggtattct gtaatatgga aactggggaa   3900
acatgcataa gtgccaatcc tttgaatgtt ccacggaaac actggtggac agattctagt   3960
```

```
gctgagaaga aacacgtttg gtttggagag tccatggatg gtggttttca gtttagctac   4020

ggcaatcctg aacttcctga agatgtcctt gatgtgcagc tggcattcct tcgacttctc   4080

tccagccgag cttcccagaa catcacatat cactgcaaaa atagcattgc atacatggat   4140

caggccagtg gaaatgtaaa gaaggccctg aagctgatgg ggtcaaatga aggtgaattc   4200

aaggctgaag gaaatagcaa attcacctac acagttctgg aggatggttg cacgaaacac   4260

actggggaat ggagcaaaac agtctttgaa tatcgaacac gcaaggctgt gagactacct   4320

attgtagata ttgcacccta tgacattggt ggtcctgatc aagaatttgg tgtggacgtt   4380

ggccctgttt gctttttata a                                             4401
```

```
<210> SEQ ID NO 6
<211> LENGTH: 4401
<212> TYPE: DNA
<213> ORGANISM: Artificial Sequence
<220> FEATURE:
<223> OTHER INFORMATION: Synthetic Construct

<400> SEQUENCE: 6
```

```
atgatgagct tcgtgcagaa aggcagctgg ctgctgctgg cactgctgca ccctacaatc     60

attctggccc agcaagaggc cgtggaaggc ggatgttctc acctgggaca gagctacgcc    120

gacagggatg tgtggaagcc tgagccttgc cagatctgcg tgtgtgatag cggcagcgtg    180

ctgtgcgacg acatcatctg cgacgaccaa gagctggact gccccaatcc tgagatccct    240

ttcggcgagt gctgtgccgt ttgtccccaa cctcctaccg ctcctaccag acctcctaat    300

ggacagggac ctcagggccc taaaggcgat cctggacctc ctggaatccc cggcagaaat    360

ggcgatccag gcattcctgg acagcctggc tctcctggaa gtccaggtcc acctggcatc    420

tgcgagagct gtcctacagg ccctcagaac tacagcccac agtacgacag ctacgacgtg    480

aagtctggcg tggccgttgg aggactggct ggttatccag gacctgctgg accaccaggg    540

cctccaggac cgcctggaac aagtggacat ccaggatctc ccggcagtcc cggttatcag    600

ggaccacctg gcgaacctgg acaggcagga cctagtggtc ctcctggtcc accaggtgcc    660

attggaccat ctggacctgc cggaaaggat ggcgaatctg gcagaccagg cagacctggc    720

gagagaggat tgcctggtcc tccgggtatt aagggcccag ccggcattcc aggattcccc    780

ggaatgaagg gccacagagg cttcgatgga cggaatggcg agaagggcga aacaggtgcc    840

cctggactga aaggcgaaaa tggactgcca ggcgagaatg gcgcacccgg acctatggga    900

cctagaggtg ctccaggcga aagaggaagg ccaggacttc ctggtgctgc aggcgctaga    960

ggcaatgatg gcgccagagg atctgatggc caacctgggc cgccaggacc tccaggcaca   1020

gctggctttc ccggatctcc tggtgcaaag ggcgaagtgg gaccagctgg aagccctgga   1080

tctaatggtg ccccaggaca gaggggagaa ccaggaccac aaggacatgc tggtgctcaa   1140

ggccctccgg gtcctccagg gatcaatgga tctccaggcg gcaaaggcga gatgggccct   1200

gctggaattc ctggcgctcc aggtcttatg ggagccagag ggccacctgg accagcaggc   1260

gcaaatggcg ctcctggact tagaggcgga gcaggcgagc ctggaaaaaa tggcgcaaaa   1320

ggcgagcccg gaccaagggg agaaagaggc gaagctggta ttccaggtgt ccctggtgcc   1380

aaaggcgagg acggcaaaga tggtagtcct ggcgagccag gcgccaatgg actccctggc   1440

gcagctggcg aaaggggagc acctggtttt agaggacccg ccggacctaa tggcattccc   1500

ggcgaaaaag gtccagccgg cgagcgtggt gctcccggac ctgcaggccc aagaggtgct   1560

gctggcgaac caggcagaga tggtgtccca ggcggaccag ggatgagagg catgccaggc   1620
```

tcacccggcg gacctggttc tgatggaaaa cccgggcctc ctggtagcca gggcgaatcc 1680
ggtagacccg gacctccggg accatcagga ccaagaggac aacctggcgt gatgggcttc 1740
cctggaccta agggaaatga cggcgctccc ggaaagaacg gcgaacgcgg tggccctggc 1800
ggtcccggtc ctcaagggcc accaggcaaa aacggcgaaa ccggtccaca aggaccacct 1860
ggacctacag gacctggcgg agataagggc gatacaggtc caccaggacc tcagggactg 1920
caaggactgc ctggaactgg cggacctcct ggcgagaatg gaaaaccagg cgaaccagga 1980
cctaagggcg acgctggtgc acctggcgca ccaggcggaa agggcgacgc aggcgctcca 2040
ggcgagaggg gacctccagg attggctggt gctccaggct tgagaggcgg agctggtcct 2100
ccaggacctg aaggtggaaa aggtgctgca ggacctcctg ggccacctgg cgctgctgga 2160
actccaggac ttcaagggat gcctggcgaa cgaggtggac ttggaagccc aggaccaaaa 2220
ggcgataagg gcgaacctgg cggaccgggt gcagatggtg ttcccggaaa agatggacca 2280
cggggcccaa caggacctat aggccctcca gggccagcag gacagccggg cgacaaaggc 2340
gaaggtggcg cccctggctt gcctggaatt gctggtccta gaggttcacc tggcgagcgg 2400
ggagaaacag gccctcctgg accggccgga tttcccggtg ctcctggcca aaatggcgag 2460
cctggcggaa aaggcgaaag aggtgcaccg ggcgaaaaag gcgaaggcgg acctcctggt 2520
gttgctggac ctcctggcgg atctggacca gctgggcctc ctggtcctca aggtgttaag 2580
ggcgaaagag gctctccagg cggacccggt gctgctggat ttcccggcgc aagaggattg 2640
cccggaccac caggctctaa tggcaatcca ggtcctcctg gacctagcgg ctctcctggc 2700
aaagatggcc caccaggacc agccggaaat actggtgctc ctggatcacc tggcgtgtcc 2760
ggaccgaaag gcgacgccgg acaaccaggc gaaaaaggat ctcctggcgc tcaagggcct 2820
cctggcgcac ctggtccatt gggaattgcc ggaattacag gtgccagagg cctggctggc 2880
ccacctggaa tgcctgggcc aagaggtagc ccgggacctc aaggcgtgaa aggcgaatct 2940
ggaaagcctg gcgccaacgg actgagcgga gaaagaggac ctccaggtcc acaaggcctg 3000
cctggattgg ctggaacagc tggcgaacct ggaagagatg gcaatcctgg ctctgatggc 3060
ttgccgggga gagatggctc cccaggtggc aagggcgatc gcggagaaaa tggtagccca 3120
ggcgctcccg gcgctccagg acacccagga ccacctggtc cagtcggacc tgctggaaag 3180
tctggcgata gaggcgagtc tggacccgca ggtcccgctg gcgccccagg gcctgccgga 3240
tctaggggag cccctggacc gcaaggacct aggggagaca aaggcgagac tggcgaacgc 3300
ggagccgctg gaatcaaagg ccatagagga ttcccaggca accctggtgc acccggatca 3360
ccaggaccgg caggacaaca aggcgctatt ggcagtccgg ggcctgctgg gccgagagga 3420
ccagttggac ctagtggacc accgggcaaa gatggaacaa gcggacaccc tggacctatc 3480
ggaccaccag gacctagagg caatagaggc gagagaggca gcgagggatc tcccggacat 3540
cctggacaac ccggtccacc ggggccacca ggcgcaccag ggccatgttg tggcggagtt 3600
ggagctgctg ccattgctgg aatcggcgga gagaaagccg gcggatttgc cccttattac 3660
ggcgacgagc ccatggattt caagatcaac accgacgaga tcatgaccag cctgaagtcc 3720
gtgaacggcc agatcgagag cctgatcagc cctgacggca gcagaaagaa ccccgccaga 3780
aactgccgcg acctgaagtt ctgtcacccc gagctgaaaa gcggcgagta ctgggttgac 3840
cccaaccagg gctgtaaact ggacgccatt aaggtgttct gcaacatgga aaccggcgag 3900
acatgcatca gcgccaatcc tctgaacgtg cccagaaagc actggtggac agatagcagc 3960

```
gccgagaaga agcacgtttg gttcggcgag agcatggacg gcggcttcca gttctcttac   4020

ggcaatcccg agctgcccga ggacgtgctg gatgtgcaac tggcctttct gagactgctg   4080

agcagccgcg ccagccagaa tatcacctac cactgcaaga acagcattgc ctacatggat   4140

caggccagcg gcaacgtgaa gaaagccctg aagctgatgg gcagcaacga gggcgagttt   4200

aaggccgagg gcaacagcaa gttcacctac accgtgctgg aagatggctg caccaagcac   4260

acaggcgagt ggtccaagac cgtgttcgag taccggacaa gaaaggccgt gcggctgcct   4320

atcgtggata tcgcccctta cgatatcgga ggccccgatc aagagttcgg cgttgacgtg   4380

ggccctgtgt gtttcctgta a                                             4401
```

<210> SEQ ID NO 7
<211> LENGTH: 5010
<212> TYPE: DNA
<213> ORGANISM: Homo sapiens

<400> SEQUENCE: 7

```
atggggcccc ggctcagcgt ctggctgctg ctgctgcccg ccgcccttct gctccacgag     60

gagcacagcc gggccgctgc gaagggtggc tgtgctggct ctggctgtgg caaatgtgac    120

tgccatggag tgaagggaca aaagggtgaa agaggcctcc cggggttaca aggtgtcatt    180

gggtttcctg gaatgcaagg acctgagggg ccacagggac caccaggaca aaagggtgat    240

actggagaac caggactacc tggaacaaaa gggacaagag gacctccggg agcatctggc    300

taccctggaa acccaggact tcccggaatt cctggccaag acggcccgcc aggcccccca    360

ggtattccag gatgcaatgg cacaaagggg gagagagggc cgctcgggcc tcctggcttg    420

cctggtttcg ctggaaatcc cggaccacca ggcttaccag ggatgaaggg tgatccaggt    480

gagatacttg gccatgtgcc cgggatgctg ttgaaaggtg aaagaggatt tcccggaatc    540

ccagggactc caggcccacc aggactgcca gggcttcaag gtcctgttgg gcctccagga    600

tttaccggac caccaggtcc cccaggccct cccggccctc caggtgaaaa gggacaaatg    660

ggcttaagtt ttcaaggacc aaaaggtgac aagggtgacc aaggggtcag tgggcctcca    720

ggagtaccag gacaagctca agttcaagaa aaaggagact tcgccaccaa gggagaaaag    780

ggccaaaaag gtgaacctgg atttcagggg atgccagggg tcggagagaa aggtgaaccc    840

ggaaaaccag gacccagagg caaacccgga aaagatggtg acaaagggga aaaagggagt    900

cccggttttc ctggtgaacc cgggtaccca ggactcatag gccgccaggg cccgcaggga    960

gaaaagggtg aagcaggtcc tcctggccca cctggaattg ttataggcac aggacctttg   1020

ggagaaaaag gagagagggg ctaccctgga actccggggc caagaggaga gccaggccca   1080

aaaggtttcc caggactacc aggccaaccc ggacctccag gcctccctgt acctgggcag   1140

gctggtgccc ctggcttccc tggtgaaaga ggagaaaaag gtgaccgagg atttcctggt   1200

acatctctgc caggaccaag tggaagagat gggctcccgg gtcctcctgg ttcccctggg   1260

ccccctgggc agcctggcta cacaaatgga attgtggaat gtcagcccgg acctccaggt   1320

gaccagggtc ctcctggaat tccagggcag ccaggattta taggcgaaat tggagagaaa   1380

ggtcaaaaag gagagagttg cctcatctgt gatatagacg gatatcgggg gcctcccggg   1440

ccacagggac ccccgggaga aataggtttc ccagggcagc caggggccaa gggcgacaga   1500

ggtttgcctg gcagagatgg tgttgcagga gtgccaggcc ctcaaggtac accagggctg   1560

ataggccagc caggagccaa gggggagcct ggtgagtttt atttcgactt gcggctcaaa   1620

ggtgacaaag gagacccagg ctttccagga cagcccggca tgccagggag agcgggttct   1680
```

-continued

```
cctggaagag atggccatcc gggtcttcct ggccccaagg gctcgccggg ttctgtagga   1740
ttgaaaggag agcgtggccc ccctggagga gttggattcc caggcagtcg tggtgacacc   1800
ggcccccctg ggcctccagg atatggtcct gctggtccca ttggtgacaa aggacaagca   1860
ggctttcctg gaggccctgg atccccaggc ctgccaggtc caaagggtga accaggaaaa   1920
attgttcctt taccaggccc ccctggagca gaaggactgc cggggtcccc aggcttccca   1980
ggtccccaag gagaccgagg ctttcccgga accccaggaa ggccaggcct gccaggagag   2040
aagggcgctg tgggccagcc aggcattgga tttccagggc cccccggccc caaaggtgtt   2100
gacggcttac ctggagacat ggggccaccg gggactccag gtcgcccggg atttaatggc   2160
ttacctggga acccaggtgt gcagggccag aagggagagc ctggagttgg tctaccggga   2220
ctcaaaggtt tgccaggtct tcccggcatt cctggcacac ccggggagaa ggggagcatt   2280
ggggtaccag gcgttcctgg agaacatgga gcgatcggac cccctgggct tcaggggatc   2340
agaggtgaac cgggacctcc tggattgcca ggctccgtgg ggtctccagg agttccagga   2400
ataggccccc ctggagctag gggtcccccct ggaggacagg gaccaccggg gttgtcaggc   2460
cctcctggaa taaaaggaga gaagggtttc cccggattcc ctggactgga catgccgggc   2520
cctaaaggag ataaaggggc tcaaggactc cctggcataa cgggacagtc ggggctccct   2580
ggccttcctg gacagcaggg ggctcctggg attcctgggt ttccaggttc caagggagaa   2640
atgggcgtca tggggacccc cgggcagccg ggctcaccag gaccagtggg tgctcctgga   2700
ttaccgggtg aaaaagggga ccatggcttt ccgggctcct caggacccag gggagaccct   2760
ggcttgaaag gtgataaggg ggatgtcggt ctccctggca agcctggctc catggataag   2820
gtggacatgg gcagcatgaa gggccagaaa ggagaccaag gagagaaagg acaaattgga   2880
ccaattggtg agaagggatc ccgaggagac cctgggaccc caggagtgcc tggaaaggac   2940
gggcaggcag gacagcctgg gcagccagga cctaaaggtg atccaggtat aagtggaacc   3000
ccaggtgctc caggacttcc gggaccaaaa ggatctgttg gtggaatggg cttgccagga   3060
acacctggag agaaaggtgt gcctggcatc cctggcccac aaggttcacc tggcttacct   3120
ggagacaaag gtgcaaaagg agagaaaggg caggcaggcc cacctggcat aggcatccca   3180
gggctgcgag gtgaaaaggg agatcaaggg atagcgggtt tcccaggaag ccctggagag   3240
aagggagaaa aaggaagcat tgggatccca ggaatgccag ggtccccagg ccttaaaggg   3300
tctcccggga gtgttggcta tccaggaagt cctgggctac ctggagaaaa aggtgacaaa   3360
ggcctcccag gattggatgg catccctggt gtcaaaggag aagcaggtct tcctgggact   3420
cctggcccca caggcccagc tggccagaaa ggggagccag gcagtgatgg aatcccgggg   3480
tcagcaggag agaagggtga accaggtcta ccaggaagag gattcccagg gtttccaggg   3540
gccaaaggag acaaaggttc aaagggtgag gtgggtttcc caggattagc cgggagccca   3600
ggaattcctg gatccaaagg agagcaagga ttcatgggtc ctccggggcc ccagggacag   3660
ccggggttac cgggatcccc aggccatgcc acggaggggc ccaaaggaga ccgcggacct   3720
cagggccagc ctggcctgcc aggacttccg ggacccatgg ggcctccagg gcttcctggg   3780
attgatggag ttaaaggtga caaaggaaat ccaggctggc caggagcacc cggtgtccca   3840
gggcccaagg gagaccctgg attccagggc atgcctggta ttggtggctc tccaggaatc   3900
acaggctcta agggtgatat ggggcctcca ggagttccag gatttcaagg tccaaaaggt   3960
cttcctggcc tccagggaat taaaggtgat caaggcgatc aaggcgtccc gggagctaaa   4020
```

-continued

```
ggtctcccgg gtcctcctgg ccccccaggt ccttacgaca tcatcaaagg ggagcccggg   4080

ctccctggtc ctgagggccc cccagggctg aaagggcttc agggactgcc aggcccgaaa   4140

ggccagcaag gtgttacagg attggtgggt atacctggac ctccaggtat tcctgggttt   4200

gacggtgccc ctggccagaa aggagagatg ggacctgccg ggcctactgg tccaagagga   4260

tttccaggtc caccaggccc cgatgggttg ccaggatcca tggggccccc aggcacccca   4320

tctgttgatc acggcttcct tgtgaccagg catagtcaaa caatagatga cccacagtgt   4380

ccttctggga ccaaaattct ttaccacggg tactctttgc tctacgtgca aggcaatgaa   4440

cgggcccatg gccaggactt gggcacggcc ggcagctgcc tgcgcaagtt cagcacaatg   4500

cccttcctgt tctgcaatat taacaacgtg tgcaactttg catcacgaaa tgactactcg   4560

tactggctgt ccacccctga gcccatgccc atgtcaatgg cacccatcac gggggaaaac   4620

ataagaccat ttattagtag gtgtgctgtg tgtgaggcgc ctgccatggt gatggccgtg   4680

cacagccaga ccattcagat cccaccgtgc cccagcgggt ggtcctcgct gtggatcggc   4740

tactcttttg tgatgcacac cagcgctggt gcagaaggct ctggccaagc cctggcgtcc   4800

cccggctcct gcctggagga gtttagaagt gcgccattca tcgagtgtca cggccgtggg   4860

acctgcaatt actacgcaaa cgcttacagc ttttggctcg ccaccataga gaggagcgag   4920

atgttcaaga agcctacgcc gtccaccttg aaggcagggg agctgcgcac gcacgtcagc   4980

cgctgccaag tctgtatgag aagaacataa                                   5010
```

<210> SEQ ID NO 8
<211> LENGTH: 5010
<212> TYPE: DNA
<213> ORGANISM: Artificial Sequence
<220> FEATURE:
<223> OTHER INFORMATION: Synthetic Construct

<400> SEQUENCE: 8

```
atgggcccta gactgtctgt gtggctgctg cttcttcctg ccgctctgct gctgcacgag     60

gaacattcta gagccgccgc taaaggcgga tgtgccggat ctggatgcgg caagtgtgat    120

tgtcacggcg tgaagggcca gaagggcgaa agaggacttc ctggactgca gggcgtgatc    180

ggatttcctg gaatgcaagg acctgaggga ccacagggac ctccaggaca aaaaggcgat    240

acaggcgaac ctggcctgcc tggcacaaag ggaacaagag gaccacctgg cgcctctggc    300

tatcctggaa atccaggact gcctggaatc ccaggacagg atggacctcc tggtcctcct    360

ggcattcctg gctgtaatgg caccaaaggc gagagaggtc cactcggacc accaggactc    420

ccaggatttg ctggaaaccc tgggccacct ggattgcctg gcatgaaggg cgatcctggc    480

gaaattctgg gacacgttcc cggcatgctg ctgaaaggcg aaaggggctt tcccggaatt    540

cctggcacac ctggtccacc aggcttgcca ggacttcaag gaccagttgg cccacctggc    600

tttacaggtc ctccaggtcc accggggcct ccagggccgc caggcgaaaa aggacaaatg    660

ggactgagct ttcagggccc caagggcgac aaaggcgatc aaggtgttag tggccctcca    720

ggtgttcctg gacaggccca ggttcaagag aaaggcgatt tcgccaccaa gggcgagaag    780

ggacagaaag gcgaaccagg ctttcaggga atgcctggcg tgggagaaaa gggcgaaccc    840

ggaaaacctg gacctagagg caaacccggc aaggatggcg ataagggcga gaaaggatct    900

cctggattcc ctggcgaacc tggatatcct ggactgatcg gtagacaggg ccctcaaggc    960

gagaagggcg aagctggacc gcctggacca ccgggaatag tgattggaac aggccctctc   1020

ggagaaaaag gcgagcgagg ataccctgga actcccggac ctaggggaga accaggacct   1080
```

-continued aaaggttttc ccggactgcc aggacaacca gggcctcctg ggcttcctgt gcctggacaa 1140
gctggtgctc caggatttcc cggcgaacgt ggcgaaaagg gcgatagagg ttttcctggc 1200
acaagcctgc ctgggccttc tggaagagat ggacttcccg ggccaccagg ttctcccgga 1260
ccacctggac agcctggcta taccaatggc atcgtcgagt gtcaacccgg tccacctggc 1320
gatcaaggac ctcctggaat accaggccag cctggcttta tcggcgagat tggagagaaa 1380
gggcaaaaag gggagagctg cctgatctgc gacatcgatg gatacagagg ccctcctgga 1440
cctcaaggcc caccaggcga gataggtttt ccagggcaac ctggcgcaaa aggcgaccgt 1500
ggactccctg gtagagatgg tgttgctggc gttccaggac cacaaggcac ccctggactt 1560
attggacagc caggtgcaaa gggcgagcca ggcgagttct acttcgacct gagacttaaa 1620
ggcgacaagg gcgaccctgg ctttcctgga caacctggaa tgcccggtag agctggatca 1680
ccaggccgtg atggacatcc agggttgccc ggaccaaaag gctctccagg atctgtgggc 1740
ctcaaaggcg aaagaggccc tccaggcgga gttggatttc ctggctctag aggcgatact 1800
ggcccaccag gtccacctgg atatggacct gctggcccta ttggagataa gggccaagca 1860
ggattcccag gcggacccgg ttctccaggc cttccgggtc ctaaaggcga gcctggaaaa 1920
atcgttccac tgcctggacc tccaggcgct gaaggattgc ctggatctcc cggttttcct 1980
ggaccgcaag gcgatagagg attccccgga acacccggta gaccaggcct tcctggcgag 2040
aaaggtgctg tgggtcaacc tggaatcggc tttcctgggc ctcctggtcc aaaaggtgtt 2100
gatggactgc ccggcgatat gggcccaccg ggaacaccag gcagacccgg ctttaatgga 2160
ttgcccggaa atcccggcgt ccaaggccag aaaggcgagc ccggtgttgg ccttcctgga 2220
cttaaaggac ttccaggcct gccaggcata cctgggacac ctggcgaaaa gggatctatc 2280
ggagttcctg gcgtgccagg cgaacatggt gcaattggtc cacctgggct gcaaggcatt 2340
agaggcgaac ccgggcctcc aggactccct ggctctgttg gaagtccagg cgtccccgga 2400
attggaccac caggtgctag gggacctcct ggcggacaag gtccaccagg attgtctgga 2460
ccacctggga tcaaaggcga gaaaggcttc cccggctttc ccggccttga tatgcctgga 2520
cctaaaggcg ataagggtgc ccagggcctg cctggaatta ctggacaaag cggcttgccc 2580
gggcttcccg gacaacaggg tgctccgggt attcctgggt ttcccggatc taagggcgaa 2640
atgggcgtga tgggtacacc tgggcaacca ggatcaccgg gacctgttgg agcaccgggg 2700
ttgcccggcg aaaaaggcga ccacggattc ccaggatcaa gcggaccaag aggcgatccg 2760
ggattgaaag gcgataaggg cgacgtggga cttcctggca aaccaggctc tatggacaag 2820
gtggacatgg gctccatgaa gggacaaaag ggcgatcagg gcgaaaaggg ccagatcgga 2880
cctatcggcg aaaagggtag tagaggcgat cctggaacac ccggcgttcc cggaaaagat 2940
ggacaagcag gccaaccggg gcagccaggg ccaaaaggcg atcctggtat ttctggaaca 3000
ccaggtgcac caggactgcc cggacctaaa ggatctgttg gaggaatggg attgccaggg 3060
acacccggcg agaaaggtgt tcctggaata cctggacctc agggctctcc tggactgcca 3120
ggcgacaaag gtgctaaagg cgaaaaggga caagccggac ctcctggcat tggcatacct 3180
ggacttaggg gagagaaggg cgaccaggga attgctggtt ttcctgggag cccaggcgag 3240
aaaggcgaaa aaggctctat cggcatcccc ggcatgcccg gatctccagg tcttaaaggt 3300
tcacctggca gcgtgggcta tccgggatca cctggccttc caggcgaaaa gggcgacaaa 3360
ggactgcctg gccttgatgg catacctggc gtgaaaggcg aagcaggact tcccggtaca 3420

-continued

```
cctggaccta caggaccagc tggccaaaaa ggcgaaccgg gatctgatgg aattcccggc   3480
tctgctggcg aaaaaggcga gccaggcctt cctggaagag gcttcccagg atttcctggc   3540
gcaaagggcg ataagggctc taagggcgaa gtcggctttc caggacttgc cggttctcct   3600
ggcatcccag gttccaaggg cgaacaagga ttcatgggtc ctccgggtcc tcagggtcaa   3660
ccagggttgc ctggaagccc tggacatgcc acagaaggac caaaaggcga cagaggacct   3720
cagggacaac ctgggcttcc cggccttcca ggaccaatgg gtcctcctgg actccccggt   3780
attgatggcg tcaagggcga caagggaaat ccaggatggc caggtgctcc aggcgttccc   3840
ggtccaaagg gcgatcccgg gtttcaaggg atgcctggta tcggaggaag ccccggcatt   3900
actggaagca aaggcgacat gggaccacca ggcgtgcccg gttttcaggg acctaaaggg   3960
ttgccaggcc tgcagggaat caaaggcgac cagggcgatc aaggcgttcc aggtgccaag   4020
ggattgcctg ggccaccagg accgccagga ccttacgata tcattaaggg cgagcccgga   4080
ctgcctggtc ctgagggtcc tccaggattg aaaggacttc aggggctccc tggaccaaaa   4140
ggacagcagg gtgttacagg cctcgtcggt attcctggac ctccggggat acctggattt   4200
gatggtgctc ctgggcagaa aggcgaaatg ggtccagcag gaccaacagg cccaagaggt   4260
ttccccggac ctccagggcc tgatggcctg ccaggatcta tgggtccacc agggacacca   4320
tccgtggatc acggctttct ggtcaccaga cacagccaga ccatcgacga tcctcagtgt   4380
cctagcggca ccaagatcct gtatcacggc tacagcctgc tgtacgtgca gggcaatgag   4440
agagcacacg gacaggatct gggcacagcc ggcagctgtc tgcggaagtt tagcaccatg   4500
ccttttctgt tctgcaacat caacaacgtg tgcaacttcg ccagccggaa cgactacagc   4560
tactggctgt ctacccctga gcctatgcct atgagcatgg cccctatcac cggggagaac   4620
atcagaccct tcatcagcag atgtgccgtg tgcgaagccc ctgccatggt tatggctgtg   4680
cactcccaga ccattcagat ccctccatgt ccaagcggct ggtctagcct gtggatcggc   4740
tactcctttg tgatgcacac atctgccggc gcagaaggat caggacaagc ccttgctagc   4800
cccggctcct gtctggaaga attcagaagc gccccttca tcgagtgcca cggcagaggc   4860
acctgtaact actacgccaa cgcctacagc ttttggctgg ccaccatcga gcggagcgag   4920
atgttcaaga agcccacacc ttctacactg aaggccggcg agctgagaac acacgtgtcc   4980
agatgtcaag tgtgcatgcg gcggacctga                                   5010
```

<210> SEQ ID NO 9
<211> LENGTH: 3087
<212> TYPE: DNA
<213> ORGANISM: Homo sapiens

<400> SEQUENCE: 9

```
atgagggcgg cccgtgctct gctgcccctg ctgctgcagg cctgctggac agccgcgcag     60
gatgagccgg agaccccgag ggccgtggcc ttccaggact gccccgtgga cctgttcttt    120
gtgctggaca cctctgagag cgtggccctg aggctgaagc cctacggggc cctcgtggac    180
aaagtcaagt ccttcaccaa gcgcttcatc gacaacctga gggacaggta ctaccgctgt    240
gaccgaaacc tggtgtggaa cgcaggcgcg ctgcactaca gtgacgaggt ggagatcatc    300
caaggcctca cgcgcatgcc tggcggccgc gacgcactca aaagcagcgt ggacgcggtc    360
aagtactttg ggaagggcac ctacaccgac tgcgctatca agaaggggct ggagcagctc    420
ctcgtggggg gctcccacct gaaggagaat aagtacctga ttgtggtgac cgacgggcac    480
cccctggagg gctacaagga accctgtggg gggctggagg atgctgtgaa cgaggccaag    540
```

```
cacctgggcg tcaaagtctt ctcggtggcc atcacacccg accacctgga gccgcgtctg    600
agcatcatcg ccacggacca cacgtaccgg cgcaacttca cggcggctga ctggggccag    660
agccgcgacg cagaggaggc catcagccag accatcgaca ccatcgtgga catgatcaaa    720
aataacgtgg agcaagtgtg ctgctccttc gaatgccagc ctgcaagagg acctccgggg    780
ctccggggcg accccggctt tgagggagaa cgaggcaagc cggggctccc aggagagaag    840
ggagaagccg gagatcctgg aagacccggg gacctcggac ctgttgggta ccagggaatg    900
aagggagaaa aagggagccg tggggagaag ggctccaggg gacccaaggg ctacaaggga    960
gagaagggca agcgtggcat cgacggggtg gacggcgtga agggggagat ggggtaccca   1020
ggcctgccag gctgcaaggg ctcgcccggg tttgacggca ttcaaggacc ccctggcccc   1080
aagggagacc ccggtgcctt tggactgaaa ggagaaaagg gcgagcctgg agctgacggg   1140
gaggcgggga gaccagggag ctcgggacca tctggagacg agggccagcc gggagagcct   1200
gggcccccg gagagaaagg agaggcgggc gacgagggga acccaggacc tgacggtgcc    1260
cccggggagc ggggtggccc tggagagaga ggaccacggg ggaccccagg cacgcgggga   1320
ccaagaggag accctggtga agctggcccg cagggtgatc agggaagaga aggccccgtt   1380
ggtgtccctg gagacccggg cgaggctggc cctatcggac ctaaaggcta ccgaggcgat   1440
gagggtcccc cagggtccga gggtgccaga ggagccccag gacctgccgg acccccctgga  1500
gacccggggc tgatgggtga aaggggagaa gacggccccg ctggaaatgg caccgagggc   1560
ttccccggct tccccgggta tccgggcaac aggggcgctc ccgggataaa cggcacgaag   1620
ggctaccccg gcctcaaggg ggacgaggga gaagccgggg accccggaga cgataacaac   1680
gacattgcac cccgaggagt caaaggagca aaggggtacc ggggtcccga gggcccccag   1740
ggacccccag gacaccaagg accgcctggg ccggacgaat gcgagatttt ggacatcatc   1800
atgaaaatgt gctcttgctg tgaatgcaag tgcggcccca tcgacctcct gttcgtgctg   1860
gacagctcag agagcattgg cctgcagaac ttcgagattg ccaaggactt cgtcgtcaag   1920
gtcatcgacc ggctgagccg ggacgagctg gtcaagttcg agccagggca gtcgtacgcg   1980
ggtgtggtgc agtacagcca cagccagatg caggagcacg tgagcctgcg cagccccagc   2040
atccggaacg tgcaggagct caaggaagcc atcaagagcc tgcagtggat ggcgggcggc   2100
accttcacgg gggaggccct gcagtacacg cgggaccagc tgctgccgcc cagcccgaac   2160
aaccgcatcg ccctggtcat cactgacggg cgctcagaca ctcagaggga caccacaccg   2220
ctcaacgtgc tctgcagccc cggcatccag gtggtctccg tgggcatcaa agacgtgttt   2280
gacttcatcc caggctcaga ccagctcaat gtcatttctt gccaaggcct ggcaccatcc   2340
cagggccggc ccggcctctc gctggtcaag gagaactatg cagagctgct ggaggatgcc   2400
ttcctgaaga atgtcaccgc ccagatctgc atagacaaga agtgtccaga ttacacctgc   2460
cccatcacgt tctcctcccc ggctgacatc accatcctgc tggacggctc cgccagcgtg   2520
ggcagccaca actttgacac caccaagcgc ttcgccaagc gcctggccga gcgcttcctc   2580
acagcgggca ggacggaccc cgcccacgac gtgcgggtgg cggtggtgca gtacagcggc   2640
acgggccagc agcgcccaga gcgggcgtcg ctgcagttcc tgcagaacta cacggccctg   2700
gccagtgccg tcgatgccat ggactttatc aacgacgcca ccgacgtcaa cgatgccctg   2760
ggctatgtga cccgcttcta ccgcgaggcc tcgtccggcg ctgccaagaa gaggctgctg   2820
ctcttctcag atggcaactc gcagggcgcc acgcccgctg ccatcgagaa ggccgtgcag   2880
```

-continued gaagcccagc gggcaggcat cgagatcttc gtggtggtcg tgggccgcca ggtgaatgag 2940
ccccacatcc gcgtcctggt caccggcaag acggccgagt acgacgtggc ctacggcgag 3000
agccacctgt tccgtgtccc cagctaccag gccctgctcc gcggtgtctt ccaccagaca 3060
gtctccagga aggtggcgct gggctag 3087

<210> SEQ ID NO 10
<211> LENGTH: 3087
<212> TYPE: DNA
<213> ORGANISM: Artificial Sequence
<220> FEATURE:
<223> OTHER INFORMATION: Synthetic Construct

<400> SEQUENCE: 10
atgagagccg ctagagccct tctgcctctg ctgctgcaag cctgttggac agccgctcag 60
gatgagcccg aaacacctag agccgtggca ttccaggact gccccgtgga tctgttcttc 120
gtgctggata ccagcgagag cgtggccctg agactgaaac cttatggcgc cctggtggac 180
aaagtgaagt ccttcaccaa gcggttcatc gacaacctgc gcgaccggta ctacagatgc 240
gacagaaacc tcgtgtggaa cgcaggcgcc ctgcactact ctgacgaggt ggaaatcatc 300
cagggcctga ccagaatgcc tggcggaaga gatgccctga agtctagcgt ggacgccgtg 360
aagtactttg gcaagggcac ctacaccgac tgcgccatca agaaaggcct ggaacagctg 420
ctcgtcggcg gcagccatct gaaagagaac aagtacctga tcgtggttac cgacggacac 480
cctctggaag gctacaaaga accttgtggc ggactggaag atgccgtgaa cgaggccaaa 540
cacctgggcg tgaaggtgtt cagcgtggcc atcacacccg accacctgga acctcggctg 600
agcatcattg ccaccgacca cacctaccgg cggaatttca cagccgctga ttggggccag 660
agcagggatg ccgaagaggc catcagccag accatcgaca ccatcgtgga catgatcaag 720
aacaacgtgg aacaagtgtg ctgcagcttc gagtgccagc ctgctagagg acctcctgga 780
cttagaggcg accctggctt tgagggcgag agaggaaaac ctggactgcc cggcgaaaaa 840
ggcgaagctg gcgatcctgg tagacctggc gatctgggac ctgtgggcta tcagggaatg 900
aagggcgaga aaggctcccg gggagagaag ggatctagag gccctaaggg ctacaagggc 960
gaaaaaggca agaggggcat cgatggcgtg gacggcgtca aaggcgagat gggatatcct 1020
ggactccctg gctgtaaagg cagccctggc ttcgatggaa tccagggacc tccaggacct 1080
aagggcgatc caggcgcctt tggactgaaa ggcgaaaagg gcgaaccagg tgccgatggc 1140
gaagcaggca gacctggatc ttctggccct agcggagatg aaggacagcc tggcgaacct 1200
ggaccacctg gcgagaaggg cgaagccggc gacgagggaa atccaggacc agatggtgct 1260
cctggcgaaa gaggtggacc aggcgaaagg ggacctagag gaacaccagg cacaagaggc 1320
ccaagaggcg atcccggcga ggctggacct caaggcgatc agggaagaga aggaccagtg 1380
ggagttcctg gcgacccagg cgaagcagga cctatcggcc ctaagggata tagaggcgac 1440
gaaggccctc ctggatctga aggtgctaga ggcgcaccag gtccagcagg ccctccaggc 1500
gaccccggac ttatgggaga acgcggagaa gatggccctg ccggcaatgg cacagagggc 1560
tttccaggct ttcctggcta ccccggaaat agaggcgctc ctggaatcaa cggcaccaag 1620
ggatatccag ggctcaaagg cgacgaaggc gaggcaggcg atccagggga tgacaacaac 1680
gatatcgccc ctagaggcgt gaaaggcgcc aaaggctata gaggaccaga gggaccacaa 1740
ggcccacctg gtcatcaagg gccaccagga cctgacgagt gcgagatcct ggacatcatt 1800
atgaagatgt gcagctgctg cgagtgcaag tgcggcccta tcgatctgct gtttgtgctg 1860
gacagctccg agagcatcgg cctgcagaat ttcgagatcg ccaaggactt cgtggtcaaa 1920
gtgatcgaca gactgagccg ggacgagctg gtcaagtttg agcctggcca gtcttatgcc 1980
ggcgtggtgc agtacagcca cagccagatg caagagcacg tgtccctgag aagccccagc 2040
atcagaaacg tgcaagagct gaaagaagcc atcaagtccc tgcagtggat ggctggcgga 2100
acctttactg gcgaggccct gcagtacacc agagatcaac tgctgcctcc ttctcctaac 2160
aaccggattg ccctcgtgat caccgacggc agaagcgaca cccagagaga caccacacct 2220
ctgaacgtgc tgtgcagccc cggcattcag gtggtgtctg tgggcatcaa ggacgtgttc 2280
gacttcatcc ccggcagcga ccagctgaac gtgatctctt gtcaaggact ggcccctagc 2340
caaggcagac caggactgtc tctggtcaaa gagaactacg ccgagctgct cgaggacgcc 2400
ttcctgaaga atgtgacagc ccagatctgc atcgacaaga agtgccccga ctacacatgc 2460
cccatcacct ttagcagccc tgccgacatc accatcctgc tggatggctc tgctagcgtg 2520
ggcagccaca acttcgacac caccaagaga ttcgccaagc ggctggccga gagatttctg 2580
acagccggca gaaccgatcc tgctcacgat gtgcgagtgg ccgtggtcca gtattctggc 2640
acaggccagc aaagacccga gagagcctct ctgcagttcc tgcagaacta cactgccctg 2700
gcctctgccg tggatgccat ggactttatc aacgacgcca ccgacgtgaa cgacgccctg 2760
ggctatgtga cccggtttta cagagaagcc tctagcggag ccgccaagaa gagactgctg 2820
ctgttcagcg acggcaactc ccaaggtgct acaccagccg ccattgagaa ggccgtgcaa 2880
gaagctcaga gagccggcat cgagatcttc gtggtggtcg tgggcagaca agtgaacgag 2940
cctcacatca gagtgctggt caccggcaag accgccgagt acgatgtggc ttatggcgag 3000
agccacctgt tcagagtgcc cagctatcag gctctgctga gaggcgtgtt ccaccagacc 3060
gtgtctagaa aggtggccct gggatga 3087

<210> SEQ ID NO 11
<211> LENGTH: 8835
<212> TYPE: DNA
<213> ORGANISM: Homo sapiens

<400> SEQUENCE: 11
atgacgctgc ggcttctggt ggccgcgctc tgcgccggga tcctggcaga ggcgccccga 60
gtgcgagccc agcacaggga gagagtgacc tgcacgcgcc tttacgccgc tgacattgtg 120
ttcttactgg atggctcctc atccattggc cgcagcaatt tccgcgaggt ccgcagcttt 180
ctcgaagggc tggtgctgcc tttctctgga gcagccagtg cacagggtgt gcgctttgcc 240
acagtgcagt acagcgatga cccacggaca gagttcggcc tggatgcact tggctctggg 300
ggtgatgtga tccgcgccat ccgtgagctt agctacaagg ggggcaacac tcgcacaggg 360
gctgcaattc tccatgtggc tgaccatgtc ttcctgcccc agctggcccg acctggtgtc 420
cccaaggtct gcatcctgat cacagacggg aagtcccagg acctggtgga cacagctgcc 480
caaaggctga aggggcaggg ggtcaagcta tttgctgtgg ggatcaagaa tgctgaccct 540
gaggagctga agcgagttgc ctcacagccc accagtgact tcttcttctt cgtcaatgac 600
ttcagcatct tgaggacact actgcccctc gtttcccgga gagtgtgcac gactgctggt 660
ggcgtgcctg tgacccgacc tccggatgac tcgacctctg ctccacgaga cctggtgctg 720
tctgagccaa gcagccaatc cttgagagta cagtggacag cggccagtgg ccctgtgact 780
ggctacaagg tccagtacac tcctctgacg gggctgggac agccactgcc gagtgagcgg 840

-continued

```
caggaggtga acgtcccagc tggtgagacc agtgtgcggc tgcggggtct ccggccactg    900
accgagtacc aagtgactgt gattgccctc tacgccaaca gcatcgggga ggctgtgagc    960
gggacagctc ggaccactgc cctagaaggg ccggaactga ccatccagaa taccacagcc   1020
cacagcctcc tggtggcctg gcggagtgtg ccaggtgcca ctggctaccg tgtgacatgg   1080
cgggtcctca gtggtgggcc cacacagcag caggagctgg gccctgggca gggttcagtg   1140
ttgctgcgtg acttggagcc tggcacggac tatgaggtga ccgtgagcac cctatttggc   1200
cgcagtgtgg ggcccgccac ttccctgatg gctcgcactg acgcttctgt tgagcagacc   1260
ctgcgcccgg tcatcctggg ccccacatcc atcctccttt cctggaactt ggtgcctgag   1320
gcccgtggct accggttgga atggcggcgt gagactggct tggagccacc gcagaaggtg   1380
gtactgccct ctgatgtgac ccgctaccag ttggatgggc tgcagccggg cactgagtac   1440
cgcctcacac tctacactct gctggagggc cacgaggtgg ccacccctgc aaccgtggtt   1500
cccactggac cagagctgcc tgtgagccct gtaacagacc tgcaagccac cgagctgccc   1560
gggcagcggg tgcgagtgtc ctggagccca gtccctggtg ccacccagta ccgcatcatt   1620
gtgcgcagca cccagggggt tgagcggacc ctggtgcttc ctgggagtca gacagcattc   1680
gacttggatg acgttcaggc tgggcttagc tacactgtgc gggtgtctgc tcgagtgggt   1740
ccccgtgagg gcagtgccag tgtcctcact gtccgccggg agccggaaac tccacttgct   1800
gttccagggc tgcgggttgt ggtgtcagat gcaacgcgag tgagggtggc ctggggaccc   1860
gtccctggag ccagtggatt tcggattagc tggagcacag gcagtggtcc ggagtccagc   1920
cagacactgc ccccagactc tactgccaca gacatcacag ggctgcagcc tggaaccacc   1980
taccaggtgg ctgtgtcggt actgcgaggc agagaggagg gccctgctgc agtcatcgtg   2040
gctcgaacgg acccactggg cccagtgagg acggtccatg tgactcaggc cagcagctca   2100
tctgtcacca ttacctggac cagggttcct ggcgccacag gatacagggt ttcctggcac   2160
tcagcccacg gcccagagaa atcccagttg gtttctgggg aggccacggt ggctgagctg   2220
gatggactgg agccagatac tgagtatacg gtgcatgtga gggcccatgt ggctggcgtg   2280
gatgggcccc ctgcctctgt ggttgtgagg actgcccctg agcctgtggg tcgtgtgtcg   2340
aggctgcaga tcctcaatgc ttccagcgac gttctacgga tcacctgggt aggggtcact   2400
ggagccacag cttacagact ggcctggggc cggagtgaag gcggccccat gaggcaccag   2460
atactcccag gaaacacaga ctctgcagag atccggggtc tcgaaggtgg agtcagctac   2520
tcagtgcgag tgactgcact tgtcggggac cgcgagggca cacctgtctc cattgttgtc   2580
actacgccgc ctgaggctcc gccagccctg gggacgcttc acgtggtgca gcgcggggag   2640
cactcgctga ggctgcgctg ggagccggtg cccagagcgc agggcttcct tctgcactgg   2700
caacctgagg gtggccagga acagtcccgg gtcctggggc ccgagctcag cagctatcac   2760
ctggacgggc tggagccagc gacacagtac cgcgtgaggc tgagtgtcct agggccagct   2820
ggagaagggc cctctgcaga ggtgactgcg cgcactgagt cacctcgtgt tccaagcatt   2880
gaactacgtg tggtggacac ctcgatcgac tcggtgactt tggcctggac tccagtgtcc   2940
agggcatcca gctacatcct atcctggcgg ccactcagag gccctggcca ggaagtgcct   3000
gggtccccgc agacacttcc agggatctca agctcccagc gggtgacagg gctagagcct   3060
ggcgtctctt acatcttctc cctgacgcct gtcctggatg gtgtgcgggg tcctgaggca   3120
tctgtcacac agacgccagt gtgcccccgt ggcctggcgg atgtggtgtt cctaccacat   3180
gccactcaag acaatgctca ccgtgcggag gctacgagga gggtcctgga gcgtctggtg   3240
```

-continued

```
ttggcacttg ggcctcttgg gccacaggca gttcaggttg gcctgctgtc ttacagtcat   3300
cggccctccc cactgttccc actgaatggc tcccatgacc ttggcattat cttgcaaagg   3360
atccgtgaca tgccctacat ggacccaagt gggaacaacc tgggcacagc cgtggtcaca   3420
gctcacagat acatgttggc accagatgct cctgggcgcc gccagcacgt accaggggtg   3480
atggttctgc tagtggatga acccttgaga ggtgacatat tcagccccat ccgtgaggcc   3540
caggcttctg ggcttaatgt ggtgatgttg ggaatggctg gagcggaccc agagcagctg   3600
cgtcgcttgg cgccgggtat ggactctgtc cagaccttct tcgccgtgga tgatgggcca   3660
agcctggacc aggcagtcag tggtctggcc acagccctgt gtcaggcatc cttcactact   3720
cagccccggc cagagccctg cccagtgtat tgtccaaagg gccagaaggg ggaacctgga   3780
gagatgggcc tgagaggaca agttgggcct cctggcgacc ctggcctccc gggcaggacc   3840
ggtgctcccg gcccccaggg gccccctgga agtgccactg ccaagggcga gaggggcttc   3900
cctggagcag atgggcgtcc aggcagccct ggccgcgccg ggaatcctgg gacccctgga   3960
gcccctggcc taaagggctc tccagggttg cctggccctc gtggggaccc gggagagcga   4020
ggacctcgag gcccaaaggg ggagccgggg gctcccggac aagtcatcgg aggtgaagga   4080
cctgggcttc ctgggcggaa aggggaccct ggaccatcgg gcccccctgg acctcgtgga   4140
ccactggggg acccaggacc ccgtggcccc ccagggcttc ctggaacagc catgaagggt   4200
gacaaaggcg atcgtgggga gcggggtccc cctggaccag gtgaaggtgg cattgctcct   4260
ggggagcctg ggctgccggg tcttcccgga agccctggac cccaaggccc cgttggcccc   4320
cctggaaaga aaggagaaaa aggtgactct gaggatggag ctccaggcct cccaggacaa   4380
cctgggtctc cgggtgagca gggcccacgg ggacctcctg gagctattgg ccccaaaggt   4440
gaccggggct ttccagggcc cctgggtgag gctggagaga agggcgaacg tggaccccca   4500
ggcccagcgg gatcccgggg gctgccaggg gttgctggac gtcctggagc caagggtcct   4560
gaagggccac caggacccac tggccgccaa ggagagaagg gggagcctgg tcgccctggg   4620
gaccctgcag tggtgggacc tgctgttgct ggacccaaag gagaaaaggg agatgtgggg   4680
cccgctgggc ccagaggagc taccggagtc caaggggaac ggggcccacc cggcttggtt   4740
cttcctggag accctggccc caagggagac cctggagacc ggggtcccat tggccttact   4800
ggcagagcag gacccccagg tgactcaggg cctcctggag agaagggaga ccctgggcgg   4860
cctggccccc caggacctgt tggcccccga ggacgagatg gtgaagttgg agagaaaggt   4920
gacgagggtc ctccgggtga cccgggtttg cctggaaaag caggcgagcg tggccttcgg   4980
ggggcacctg gagttcgggg gcctgtgggt gaaaagggag accagggaga tcctggagag   5040
gatggacgaa atggcagccc tggatcatct ggacccaagg gtgaccgtgg ggagccgggt   5100
cccccaggac ccccgggacg gctggtagac acaggacctg gagccagaga gaagggagag   5160
cctggggacc gcggacaaga gggtcctcga gggcccaagg gtgatcctgg cctccctgga   5220
gcccctgggg aaaggggcat tgaagggttt cggggacccc caggcccaca gggggaccca   5280
ggtgtccgag gcccagcagg agaaaagggt gaccggggtc cccctgggct ggatggccgg   5340
agcggactgg atgggaaacc aggagccgct gggccctctg ggccgaatgg tgctgcaggc   5400
aaagctgggg acccagggag agacgggctt ccaggcctcc gtggagaaca gggcctccct   5460
ggcccctctg gtccccctgg attaccggga aagccaggcg aggatggcaa acctggcctg   5520
aatggaaaaa acggagaacc tggggaccct ggagaagacg ggaggaaggg agagaaagga   5580
```

-continued

```
gattcaggcg cctctgggag agaaggtcgt gatggcccca agggtgagcg tggagctcct   5640
ggtatccttg gaccccaggg gcctccaggc ctcccagggc cagtgggccc tcctggccag   5700
ggttttcctg gtgtcccagg aggcacgggc cccaagggtg accgtgggga gactggatcc   5760
aaaggggagc agggcctccc tggagagcgt ggcctgcgag gagagcctgg aagtgtgccg   5820
aatgtggatc ggttgctgga aactgctggc atcaaggcat ctgccctgcg ggagatcgtg   5880
gagacctggg atgagagctc tggtagcttc ctgcctgtgc ccgaacggcg tcgaggcccc   5940
aaggggact caggcgaaca gggcccccca ggcaaggagg gccccatcgg ctttcctgga    6000
gaacgcgggc tgaagggcga ccgtggagac cctggccctc aggggccacc tggtctggcc   6060
cttggggaga ggggcccccc cgggccttcc ggccttgccg gggagcctgg aaagcctggt   6120
attcccgggc tcccaggcag ggctgggggt gtgggagagg caggaaggcc aggagagagg   6180
ggagaacggg gagagaaagg agaacgtgga gaacagggca gagatggccc tcctggactc   6240
cctggaaccc ctgggccccc cggacccccct ggccccaagg tgtctgtgga tgagccaggt  6300
cctggactct ctggagaaca gggacccccct ggactcaagg gtgctaaggg ggagccgggc  6360
agcaatggtg accaaggtcc caaaggagac aggggtgtgc caggcatcaa aggagaccgg   6420
ggagagcctg gaccgagggg tcaggacggc aacccgggtc taccaggaga gcgtggtatg   6480
gctgggcctg aagggaagcc gggtctgcag ggtccaagag gcccccctgg cccagtgggt   6540
ggtcatggag accctggacc acctggtgcc ccgggtcttg ctggccctgc aggaccccaa   6600
ggaccttctg gcctgaaggg ggagcctgga gagacaggac ctccaggacg gggcctgact   6660
ggacctactg gagctgtggg acttcctgga cccccccggcc cttcaggcct tgtgggtcca  6720
caggggtctc caggtttgcc tggacaagtg ggggagacag ggaagccggg agccccaggt   6780
cgagatggtg ccagtggaaa agatggagac agagggagcc ctggtgtgcc agggtcacca   6840
ggtctgcctg gccctgtcgg acctaaagga gaacctggcc ccacgggggc ccctggacag   6900
gctgtggtcg ggctccctgg agcaaaggga gagaagggag cccctggagg ccttgctgga   6960
gacctggtgg gtgagccggg agccaaaggt gaccgaggac tgccagggcc gcgaggcgag   7020
aagggtgaag ctggccgtgc aggggagccc ggagaccctg ggaagatgg tcagaaaggg    7080
gctccaggac ccaaaggttt caagggtgac ccaggagtcg ggtcccgggg ctcccctggg   7140
cctcctggcc ctccaggtgt gaagggagat ctgggcctcc ctggcctgcc cggtgctcct   7200
ggtgttgttg ggttcccggg tcagacaggc cctcgaggag agatgggtca gccaggccct   7260
agtggagagc ggggtctggc aggccccccca gggagagaag gaatcccagg accccctgggg 7320
ccacctggac caccggggtc agtgggacca cctggggcct ctggactcaa aggagacaag   7380
ggagaccctg gagtagggct gcctgggccc cgaggcgagc gtggggagcc aggcatccgg   7440
ggtgaagatg gccgccccgg ccaggaggga ccccgaggac tcacggggcc ccctggcagc   7500
aggggagagc gtggggagaa gggtgatgtt gggagtgcag gactaaaggg tgacaaggga   7560
gactcagctg tgatcctggg gcctccaggc ccacggggtg ccaaggggga catgggtgaa   7620
cgagggcctc ggggcttgga tggtgacaaa ggacctcggg gagacaatgg ggaccctggt   7680
gacaagggca gcaagggaga gcctggtgac aagggctcag ccgggttgcc aggactgcgt   7740
ggactcctgg gaccccaggg tcaacctggt gcagcaggga tccctggtga cccgggatcc   7800
ccaggaaagg atggagtgcc tggtatccga ggagaaaaag gagatgttgg cttcatgggt   7860
ccccggggcc tcaagggtga acggggagtg aagggagcct gtggccttga tggagagaag   7920
ggagacaagg gagaagctgg tcccccaggc cgccccgggc tggcaggaca caaaggagag   7980
```

atgggggagc ctggtgtgcc gggccagtcg ggggcccctg gcaaggaggg cctgatcggt 8040
cccaagggtg accgaggctt tgacgggcag ccaggcccca agggtgacca gggcgagaaa 8100
ggggagcggg gaaccccagg aattgggggc ttcccaggcc ccagtggaaa tgatggctct 8160
gctggtcccc cagggccacc tggcagtgtt ggtcccagag gccccgaagg acttcagggc 8220
cagaagggtg agcgaggtcc ccccggagag agagtggtgg gggctcctgg ggtccctgga 8280
gctcctggcg agagagggga gcaggggcgg ccagggcctg ccggtcctcg aggcgagaag 8340
ggagaagctg cactgacgga ggatgacatc cggggctttg tgcgccaaga gatgagtcag 8400
cactgtgcct gccagggcca gttcatcgca tctggatcac gacccctccc tagttatgct 8460
gcagacactg ccggctccca gctccatgct gtgcctgtgc tccgcgtctc tcatgcagag 8520
gaggaagagc gggtaccccc tgaggatgat gagtactctg aatactccga gtattctgtg 8580
gaggagtacc aggaccctga agctccttgg gatagtgatg acccctgttc cctgccactg 8640
gatgagggct cctgcactgc ctacaccctg cgctggtacc atcgggctgt gacaggcagc 8700
acagaggcct gtcacccttt tgtctatggt ggctgtggag ggaatgccaa ccgttttggg 8760
acccgtgagg cctgcgagcg ccgctgccca ccccgggtgg tccagagcca ggggacaggt 8820
actgcccagg actga 8835

<210> SEQ ID NO 12
<211> LENGTH: 8835
<212> TYPE: DNA
<213> ORGANISM: Artificial Sequence
<220> FEATURE:
<223> OTHER INFORMATION: Synthetic Construct

<400> SEQUENCE: 12
atgaccctga gactgctggt ggctgccctg tgtgctggaa ttctggctga ggctcctaga 60
gtgcgggccc agcatagaga aagagtgacc tgtacacggc tgtacgccgc cgatatcgtg 120
tttctgctgg atggcagcag cagcatcggc cggtccaatt tcagagaagt gcggagcttt 180
ctggaaggcc tggtgctgcc tttttctggc gctgcttctg cccagggcgt cagatttgcc 240
accgtgcagt acagcgacga ccctagaaca gagtttggcc tggatgctct cggcagcggc 300
ggagatgtga tcagagccat cagagagctg agctacaaag gcggcaatac cagaacaggc 360
gccgctattc tgcacgtggc cgaccatgtt tttctgcccc aactggctag acccggcgtg 420
ccaaaagtgt gcatcctgat cacagacggc aagagccagg acctggtgga tacagccgct 480
cagagactga aggacagggg cgtgaaactg ttcgccgtgg gcatcaagaa cgccgatcct 540
gaggaactga agagagtggc cagccagcct accagcgatt tcttcttctt cgtgaacgac 600
ttcagcatcc tgcggaccct gctgcctctg gtgtctagaa gagtgtgtac aacagccggc 660
ggagtgcctg tgaccagacc tcctgatgat agcacaagcg cccctagaga tctggtgctg 720
tctgagccaa gcagccagag tctgagagtg cagtggacag ctgctagcgg ccctgtgaca 780
ggctacaagg tgcagtatac acctctgaca ggcctgggcc agcctctgcc ttctgagaga 840
caagaagtga acgtcccagc cggcgaaaca tctgtcagac tgagaggact gaggcccctg 900
accgagtacc aagtgacagt gatcgccctg tacgccaatt ctatcggcga ggccgtgtct 960
ggcacagcca gaacaacagc tctggaagga ccagagctga ccatccagaa cacaacagcc 1020
cattctctgc tggttgcttg gagatctgtg cctggcgcca ccggctatag agtgacttgg 1080
agagttctga gcggaggccc cacacagcag caagaacttg gacctggaca gggctccgtg 1140

-continued ctgctgagag atctcgagcc tggcaccgat tacgaagtga ccgtgtctac cctgttcggc 1200
agatctgtgg gacctgccac aagcctgatg gccagaacag atgccagcgt ggaacagacc 1260
ctgaggcctg tgattctggg ccctacatct atcctgctga gctggaatct ggtgcccgag 1320
gccagaggct atagactgga atggcggaga gaaaccggcc tggaacctcc tcagaaagtg 1380
gtcctgccta gcgacgtgac aagataccag ctggatggac tgcagcccgg caccgagtac 1440
agactgacac tgtatacact gctcgagggc cacgaagtgg ccacaccagc tacagttgtg 1500
ccaacaggac ctgagctgcc tgtgtctcct gtgactgatc tgcaggccac agaactgcct 1560
ggccagagag tcagagttag ctggtcacct gttccaggcg ccacacagta cagaatcatc 1620
gtgcggtcta cacagggcgt cgagagaaca ctggttctgc ctggaagcca gaccgccttc 1680
gatctggatg atgtgcaggc cggactgtcc tacacagtca gagtgtctgc cagagtgggc 1740
cctagagaag gatctgcctc tgtgctgacc gtgcggagag agcctgaaac accactggca 1800
gtgcctggac tgagagtggt ggtgtcagat gccaccagag ttagagtggc ttggggacca 1860
gttcctggcg cctctggctt tagaatcagc tggtctacag gctctggccc cgaaagctct 1920
cagacactgc ctccagatag caccgccacc gatattacag gcctgcagcc tggaactacc 1980
taccaggtgg ccgttagcgt gctgagagga agagaagaag gccctgccgc cgtcatcgtg 2040
gctagaactg atcctctggg acctgtgcgg acagtgcacg tgacacaagc ctctagcagc 2100
agcgtgacca tcacctggac aagagtgcca ggcgctacag gatacagagt gtcctggcat 2160
tctgctcacg gccctgagaa gtctcagctg gtgtctggcg aagccacagt ggctgaactc 2220
gacggactgg aacctgacac agagtatact gtgcacgtgc gggctcatgt ggctggtgtt 2280
gatggacctc ctgcttctgt ggtcgtcaga acagcccctg aacctgtggg aagagtgtcc 2340
agactgcaga tcctgaatgc cagcagcgac gtgctgagga tcacatgggt tggagtgacc 2400
ggcgccacag cttatagact cgcctggggt agaagcgaag gcggccctat gagacatcag 2460
atcctgcctg gcaataccga ctccgccgag attagaggcc ttgaaggcgg agtgtcttac 2520
agcgttagag tgacagccct cgtgggcgat agagaaggca cacctgtgtc catcgtggtc 2580
accacacctc cagaagctcc tccagctctg ggaacactgc atgtggtgca gagaggcgag 2640
cactctctga gactgagatg ggaacctgtg ccacgcgctc agggatttct gctgcattgg 2700
caaccagaag gcggacaaga gcagagcaga gtgctgggac cagaactgag cagctaccac 2760
ctcgatggac ttgagcctgc cactcagtat agagtcagac tgtcagtgct ggggcctgcc 2820
ggcgaaggac cttctgctga agtgacagct agaaccgagt ctcccagagt gcccagcatc 2880
gagctgagag tcgtggatac ctccatcgat agcgtgacac tggcctggac acccgtgtct 2940
agagccagct cttacatcct gtcttggcgg cctctcagag gaccaggcca agaagttcct 3000
ggatctccac agacactccc aggcatcagt agctcccaga gagtgactgg acttgaacca 3060
ggcgtgtcct acatcttcag cctgacacct gtgctggacg gcgttagagg acctgaagcc 3120
tctgtgaccc agactccagt gtgtcctaga ggactggccg atgtggtgtt cctgcctcac 3180
gctacacagg acaatgccca tagagccgag gccacaagac gcgtgctgga aagactggtt 3240
cttgcccttg gaccactggg acctcaggct gttcaagtgg gcctgctgtc ctactctcac 3300
agaccctctc cactgttccc tctgaacggc tctcacgacc tgggcatcat cctgcagaga 3360
atccgggaca tgccctacat ggacccctct ggcaacaatc tgggcacagc cgttgtgact 3420
gcccacagat atatgctggc cccagatgct cctggcagac gacaacatgt ccctggcgtt 3480
atggtgctgc tggtcgatga acccctgcgg ggcgatatct ttagccctat tagagaagcc 3540

-continued

```
caggccagcg gcctgaatgt ggttatgctt ggaatggctg gcgccgatcc agagcagctt   3600
agaaggcttg cccctggcat ggatagcgtg cagaccttct ttgccgtgga cgatggacct   3660
tctctggatc aggctgtgtc tggactggct acagcactgt gccaggcaag cttcaccaca   3720
cagcctagac ctgagccttg tccagtgtac tgccctaagg gacagaaggg cgaacctggc   3780
gaaatgggac ttagaggcca agtgggacca cctggcgatc ctggacttcc tggaagaact   3840
ggtgctcctg gacctcaagg tcctcctgga agtgccacag ccaagggcga aagaggattc   3900
cctggcgctg atggcagacc aggatctcct ggtagagccg gcaatcctgg aacacctggc   3960
gcaccaggac tcaaaggatc tccaggactg cctggaccta gaggcgatcc aggcgagaga   4020
ggaccaagag gtccaaaagg cgaacccggt gctccaggac aagtgattgg cggagaagga   4080
cccggattgc ccggaagaaa aggcgaccct ggaccaagtg gacctccagg acctagggga   4140
cctttgggag atcccggtcc aagaggccct cctggattgc ctggtacagc catgaagggc   4200
gacaaaggcg ataggggaga aagaggacca ccaggaccag gcgaaggtgg aattgctcct   4260
ggcgaaccag ggttgcctgg actccctggc tcacctggac cacaaggacc tgttggccca   4320
cctggaaaga aaggcgaaaa gggcgattct gaggatggcg ccccagggct tcctggacaa   4380
ccaggctctc caggcgaaca aggacccaga gggcctccag gtgctattgg ccctaaaggc   4440
gacagagggt ttcccggacc acttggagaa gctggcgaaa aaggcgaacg aggacctcct   4500
ggacctgccg gatctagagg acttccaggt gttgctggca gacctggcgc taaaggtcct   4560
gaaggcccac cagggcctac aggcagacaa ggcgagaaag gcgagccagg cagacccggc   4620
gatcctgctg ttgttggacc agctgttgca ggcccaaagg gcgagaaggg cgacgttgga   4680
cctgctggac caaggggagc tacaggcgtt caaggcgaaa ggggtccacc tggacttgtt   4740
ttgccgggcg atcccggacc taagggcgac cccggcgaca ggggaccaat tggattgaca   4800
ggcagagctg ggccaccagg cgatagtggg cctccaggcg aaaaaggcga tcctggtaga   4860
cctggacctc ctgggccagt tggaccaaga ggaagagatg gcgaagtcgg agagaaaggc   4920
gacgaaggtc ctccaggcga cccaggactc cctggaaaag caggcgaaag aggtcttaga   4980
ggcgctcctg gtgttagagg ccctgttgga gaaaagggcg accaaggcga ccctggcgag   5040
gatggaagaa atggctcccc tggatctagc ggcccaaaag gcgatcgcgg cgagcccggt   5100
ccaccgggtc caccaggcag gcttgttgat actggacccg gcgctcgtga aaaaggcgag   5160
cccggcgatc gtggacaaga aggcccaaga ggacccaagg gcgatccggg actgccaggt   5220
gcaccaggcg agcgaggtat tgaaggattc agaggccctc caggaccaca aggcgatccc   5280
ggtgtcagag gacctgctgg cgagaagggc gatagaggtc ctccaggact ggatggcaga   5340
tccggacttg atggaaaacc cggcgcagct ggcccttctg gacctaatgg tgcagccgga   5400
aaagctggcg acccaggcag agatggattg ccaggattga ggggagaaca gggactcccc   5460
ggaccttctg ggccgcctgg gttgcccgga aagcctggcg aagatggcaa acctggcctg   5520
aacggcaaaa acggcgaacc gggcgatcca ggcgaagatg gcagaaaggg cgaaaaaggc   5580
gacagcggag cctctggccg agagggtaga gatggaccta aaggcgagag gggcgctcct   5640
ggaattttgg gaccccaagg accgcctggg ctgccaggtc cagttgggcc tcctggtcaa   5700
ggttttcctg gtgtcccagg cggaactgga ccaaaaggcg atagaggcga aacaggctct   5760
aagggcgagc aaggacttcc tggcgaacgt ggactgagag gcgaacctgg aagcgtgccc   5820
aatgtggaca gactcctgga aaccgccgga atcaaagcca gcgctctgcg ggaaatcgtg   5880
```

-continued gaaacctggg atgagagcag cggctctttt ctgcctgtgc ctgaaagaag aaggggaccg 5940
aaaggcgatt ctggcgaaca aggtccacct ggcaaagagg gccctatcgg atttcccggc 6000
gagcggggtc ttaaaggcga ccggggagat ccgggacctc aagggccacc aggacttgct 6060
cttggagaaa gaggtcctcc ggggccatct ggacttgctg gcgagcctgg aaaacctgga 6120
ataccaggac ttcccggcag agcaggcgga gttggagagg ccggacgacc tggcgaacgc 6180
ggagaaaggg gagagaaggg cgagcgaggc gaacagggac gagatggacc accggggctc 6240
cctggaactc ctggaccgcc aggaccacct ggtcctaaag tgtcagtgga tgagcctgga 6300
ccaggtctta gcggagaaca aggacctcca ggcctgaaag gcgctaaggg cgaaccaggt 6360
tcaaatggcg atcagggacc caaaggcgat cggggcgttc caggcattaa gggcgaccgt 6420
ggcgaaccag gacctagagg acaagatggc aatcccggac tgcctggcga aagaggaatg 6480
gccggacctg agggaaagcc agggctgcaa gggcctcgcg ggccacctgg gcctgtcgga 6540
ggacatggcg accccggacc accaggtgct cccggacttg ctggaccagc aggacctcaa 6600
ggaccatctg gacttaaagg cgaaccaggc gaaacagggc caccaggcag aggacttaca 6660
ggacctacag gtgctgttgg gttgcctggt ccaccagggc caagtggact tgttggtcct 6720
caaggttcac ctggactgcc cggacaagtg ggagaaactg gcaaaccagg cgcacctggg 6780
cgagatggcg catctggaaa agacggcgat cgaggtagcc ctggtgttcc cggttctcct 6840
gggctcccag gacctgtggg ccccaagggc gaacccggac caactggcgc acctggtcaa 6900
gcagttgttg gattgcctgg cgcaaagggc gagaaaggtg ctccaggcgg attggctggc 6960
gatcttgttg gagaaccagg tgccaaaggc gacaggggct tgccaggtcc taggggagag 7020
aaaggcgaag ctggtagagc aggcgagcct ggcgatcccg gcgaggacgg acaaaaaggt 7080
gcccctgggc ctaaaggctt taagggcgat cctggtgtcg gcgtcccagg ttctcctgga 7140
ccacctgggc cgccaggcgt taagggcgat ttgggacttc ctgggctgcc tggcgctcct 7200
ggcgttgtgg gatttccagg acaaactggc cctcggggag aaatgggtca acctgggcct 7260
agcggagaaa gaggccttgc cggacctcct ggaagagagg gaatacctgg accacttgga 7320
ccgcctggac ctccaggttc tgttggacct cctggcgctt caggattgaa gggcgataag 7380
ggcgaccctg gtgttggact tcccggtcct cgtggcgaaa ggggagaacc aggcattaga 7440
ggcgaagatg gacggcctgg acaagaggga cctagaggtc ttacaggccc accaggctct 7500
agaggcgaaa ggggcgagaa aggcgacgtg ggttctgcag gacttaaggg cgacaagggc 7560
gattccgctg tgattttggg accaccggga ccaagaggcg ctaaaggcga tatgggcgag 7620
agaggcccta gaggcctgga tggcgataag gggccaagag gcgacaacgg cgacccaggc 7680
gataagggat ctaaaggcga acccggcgat aagggctctg ctggactgcc aggacttcga 7740
ggacttctgg gtccacaagg ccaacctggc gccgcaggca ttcccggcga tccgggttct 7800
cctggcaaag atggtgttcc tggcatcagg ggcgaaaagg gcgacgtcgg ttttatgggc 7860
cctcgcggat tgaaaggcga gagaggtgtt aagggcgcct gtggacttga cggcgaaaaa 7920
ggcgataagg gcgaagctgg acctcctggc agacctggat tggctggaca caagggcgag 7980
atgggagagc ccggtgttcc tggacaaagt ggcgcccctg gaaaagaagg actgatcggt 8040
ccaaagggcg accgcggatt tgatggccaa ccgggtccta aaggcgatca gggcgagaaa 8100
ggcgaaagag gcactcctgg catcggaggc tttccaggac caagcggcaa tgatggatct 8160
gctggcccgc cagggcctcc tggatctgtt ggtccaagag gaccagaagg cctgcaggga 8220
caaaaaggcg agcgcggacc accaggcgaa agagttgttg gagcacccgg cgttcccggt 8280
gctcccggcg aaagaggcga acaaggcaga cctggaccag ctggccctag aggcgaaaaa 8340
ggggaagccg ctctgaccga ggacgatatc agaggctttg tgcggcaaga gatgagccag 8400
cattgtgcct gtcaggggca gtttatcgcc agcggttcta gacctctgcc tagctatgcc 8460
gctgataccg ccggatctca gctgcatgct gtgcctgtgc ttagagtgtc tcacgccgag 8520
gaagaggaaa gagtccctcc agaggacgac gagtactccg agtatagcga gtactctgtg 8580
gaagagtatc aggaccccga ggctccttgg gatagcgacg atccatgttc tctgccactg 8640
gatgagggca gctgtaccgc ctacacactg aggtggtatc acagagccgt gaccggaagc 8700
accgaggcct gccatccttt tgtttatggc ggctgcggcg gcaacgccaa tagatttgga 8760
acaagagagg cctgcgagcg gagatgccct ccaagagtgg ttcagtctca aggcaccggc 8820
actgcccagg actaa 8835

<210> SEQ ID NO 13
<211> LENGTH: 4494
<212> TYPE: DNA
<213> ORGANISM: Homo sapiens

<400> SEQUENCE: 13
atggatgtaa ccaagaaaaa caaacgagat ggaactgaag tcactgagag aattgtcact 60
gaaacagtaa ccacaagact tacatcctta ccaccaaaag gcgggaccag caatggctat 120
gctaaaacag cctctcttgg tggagggagc cggctggaga aacaaagcct gactcatggc 180
agcagcggct acataaactc aactggaagc acacgaggcc atgcctccac ctctagttac 240
aggagggctc actcacctgc ctccactctg cccaactccc caggctcaac ctttgaaagg 300
aaaactcacg ttacccgcca tgcgtatgaa gggagctcca gtggcaactc ttctccggag 360
taccctcgga aggaatttgc atcttcttca accagaggac ggagtcaaac acgagagagt 420
gaaattcgag ttcgactgca gagtgcgtcc ccatccaccc gatggacaga attggatgat 480
gttaagcgtt tgctcaaggg gagtcgatcg gcaagtgtga gccccacccg gaattcctcc 540
aacacactcc ccatccccaa gaaaggcact gtggagacca aaattgtgac agcgagctcc 600
cagtcggtgt caggcaccta cgatgcaacg atcctggatg ccaaccttcc ctcccatgtg 660
tggtcctcca ccctgcccgc ggggtcctcc atggggacct atcacaacaa catgacaacc 720
cagagctcat ccctcctcaa caccaatgcc tactctgcgg gatcagtctt cggagttcca 780
aacaacatgg cgtcctgctc acccactttg caccctggac tcagcacatc ctcctcagtg 840
tttggcatgc agaacaatct ggcccccagc ttgaccaccc tgtcccatgg caccaccacc 900
acttccacag catatggggt gaagaaaaac atgccccaga gtcctgcggc tgtgaacact 960
ggcgtttcca cctccgccgc ctgcaccaca agtgtgcaga gcgatgacct tttgcacaag 1020
gactgcaagt tcctgatcct agagaaagac aacacacctg ccaagaagga gatggagctg 1080
ctcatcatga ccaaggacag cgggaaggtc tttacagcct cccctgccag catcgctgca 1140
acttcttttt cagaagacac cctaaaaaaa gaaaagcaag ctgcctacaa tgctgactca 1200
ggcctaaaag ccgaagctaa tggagacctg aagactgtgt ccacaaaggg caagaccacc 1260
actgcagata tccacagcta cggcagcagt ggtggtggtg gcagtggagg aggtggcggt 1320
gttggtggcg ctggcggcgg cccttgggga ccagcgccag cctggtgccc ctgcggctcc 1380
tgctgcagct ggtggaagtg gctgctgggc ctgctgctca cctggctgct actcctgggg 1440
ctgctcttcg gcctcattgc tctggcggag gaggtgagga agctgaaggc gcgtgtggat 1500

-continued gagctggaga ggatcaggag gagcatactg ccctatgggg acagcatgga tagaatagaa 1560
aaggaccgcc tccagggcat ggcacccgcg gcgggagcag acctggacaa aattgggctg 1620
cacagtgaca gccaggagga gctctggatg ttcgtgagga agaagctaat gatggaacag 1680
gaaaatggaa atctccgagg aagccctggc cctaaaggtg acatgggaag tccaggccct 1740
aaaggagatc gagggttccc tgggactcca ggtatccctg ggcccttggg ccacccaggt 1800
ccacaaggac caaagggtca aaaaggcagc gtgggagatc ctggcatgga aggccccatg 1860
ggccagagag ggcgagaagg ccccatggga cctcgtggtg aggcagggcc tcctggatct 1920
ggagagaaag ggaaagaggg ggctgctggt gaaccaggtc ctcatggccc acctggtgtc 1980
ccaggttctg tgggtcccaa aggttccagc ggctctcctg gcccacaggg ccctccaggt 2040
cctgtaggtc tccaagggct ccgaggtgaa gtaggacttc ctggtgtcaa aggtgacaaa 2100
ggaccaatgg gaccaccagg acccaaaggt gaccagggtg agaaaggacc tcgaggcctc 2160
acaggcgagc ctggcatgag aggtttgcct ggtgctgttg gtgagcccgg ggctaaagga 2220
gcaatgggtc ctgctggccc agacggacac caaggcccaa gaggtgaaca aggtcttact 2280
gggatgcctg gaatccgtgg cccaccagga ccttctggag acccaggaaa gccaggtctc 2340
acaggacccc agggacctca gggacttccc ggtacccctg gccgaccagg aataaaaggt 2400
gaaccaggag ctccaggcaa gatcgtgact tcggaggggt catcgatgct cactgtccca 2460
ggcccccag gacctcctgg agccatggga cccccaggac ctccaggtgc cccaggccct 2520
gccggcccag ctggtctccc aggacatcaa gaagttctta atttacaagg tcccccaggc 2580
ccacccggcc cacgcgggcc accagggcct tccattccag gcccaccagg accccgaggc 2640
ccaccagggg agggtttgcc aggcccacca ggcccaccag gatcgttcct gtccaactca 2700
gaaaccttcc tctccggccc cccaggccca cctggccccc caggtcccaa gggagaccaa 2760
ggtcccccag gccccagagg acaccaaggc gagcaaggcc tcccaggttt ctcaacctca 2820
gggtccagtt ctttcggact caaccttcag ggaccaccag gcccacctgg cccccaggga 2880
cccaaaggtg acaaaggtga tccaggtgtt ccaggggctc ttggcattcc tagtggtcct 2940
tctgaagggg gatcatcaag taccatgtac gtgtcaggcc cgccagggcc ccctgggccc 3000
cctgggcctc cgggctctat cagcagctct ggccaggaga ttcagcagta catctctgag 3060
tacatgcaga gtgacagtat tagatcttac ctatccggag ttcagggtcc cccaggccca 3120
cctggtcccc caggacctgt caccaccatc acaggcgaga ctttcgacta ctcagagctg 3180
gcaagccacg ttgtgagcta cttacggact tcggggtacg gtgtcagctt gttctcgtcc 3240
tccatctctt ctgaagacat tctggctgtg ctgcagcggg atgacgtgcg tcagtaccta 3300
cgtcagtact tgatgggccc tcggggtccg ccagggccac caggagccag tggagatggg 3360
tccctcctgt ctttggacta tgcagagctg agtagtcgca ttctcagcta catgtcgagt 3420
tctgggatca gcattgggct tcctggtccc ccggggcccc ctggcttgcc gggaacctcc 3480
tatgaggagc tcctctcctt gctgcgaggg tctgaattca gaggcatcgt tggaccccca 3540
ggtcccccgg gtccaccagg gatcccaggc aatgtgtggt ccagcatcag cgtggaggac 3600
ctctcgtctt acttacatac tgccggcttg tcattcatcc caggccctcc aggacctcct 3660
ggtcccccag ggcctcgagg gcccccgggt gtctcaggag ccctggcaac ctatgcagct 3720
gaaaacagcg acagcttccg gagcgagctg atcagctacc tcacaagtcc tgatgtgcgc 3780
agcttcattg ttggcccccc aggccctcct gggccgcagg gaccccctgg ggacagccgc 3840
ctcctgtcca cggatgcctc ccacagtcgg ggtagcagct cctcctcaca cagctcatct 3900
gtcaggcggg gcagctccta cagctcttcc atgagcacag gaggaggtgg tgcaggctcc 3960
ctgggtgcag gcggtgcctt tggtgaagct gcaggagaca ggggtcccta tggcactgac 4020
atcggcccag gcggaggcta tggggcagca gcagaaggcg gcatgtatgc tggcaatggc 4080
ggactattgg gagctgactt tgctggagat ctggattaca atgagctggc tgtgagggtg 4140
tcagagagca tgcagcgtca gggcctactg caagggatgg cctacactgt ccagggccca 4200
ccaggccagc ctgggccaca ggggccaccc ggcatcagca aggtcttctc tgcctacagc 4260
aacgtgactg cggacctcat ggacttcttc caaacttatg gagccattca aggacccccct 4320
gggcaaaaag gagagatggg cactccagga cccaaaggtg acaggggccc tgctgggcca 4380
ccaggtcatc ctgggccacc tggccctcga ggacacaagg gagaaaaagg agacaaaggt 4440
gaccaagtct atgctgggcg gagaaggaga agaagtattg ctgtcaagcc gtga 4494

<210> SEQ ID NO 14
<211> LENGTH: 4494
<212> TYPE: DNA
<213> ORGANISM: Artificial Sequence
<220> FEATURE:
<223> OTHER INFORMATION: Synthetic Construct

<400> SEQUENCE: 14
atggacgtga ccaagaagaa caagcgcgac ggcaccgaag tgaccgagag aatcgtgacc 60
gaaaccgtga ccaccagact gaccagcctg cctcctaaag gcggcacctc taatggctac 120
gccaagacag cttctctcgg cggaggcagc agactggaaa agcagtctct gacacacggc 180
agcagcggct acatcaatag caccggctct acaagaggcc acgccagcac aagcagctac 240
agaagggctc acagccctgc cagcacactg cctaatagcc caggcagcac cttcgagaga 300
aagacccacg tgaccagaca cgcctacgag ggctctagca gcggcaatag cagccctgag 360
taccccagaa aagagttcgc cagcagcagc accagaggca gaagccagac acgggaaagc 420
gagatcagag tgcggctgca gtctgctagc cctagcacca gatggaccga gctggacgac 480
gtgaagaggc tgctgaaggg aagcagatcc gccagcgtgt cccctaccag aaacagcagc 540
aacaccctgc ctattcctaa gaaaggcacc gtcgagacta agatcgtgac agccagcagc 600
cagagcgtgt ccggcacata cgatgccaca atcctggacg ccaacctgcc tagccatgtg 660
tggtcctcta cactgcctgc cggaagcagc atgggcacct accacaacaa catgaccaca 720
cagagcagca gcctgctgaa caccaatgcc tactctgccg gctccgtgtt cggcgtgcca 780
aacaatatgg ccagctgcag ccctacactg caccctggcc tgagcacaag ctcctccgtg 840
tttggaatgc agaacaatct ggcccctagc ctgacaaccc tgagccacgg aacaaccacc 900
accagcacag cctacggcgt gaagaaaaac atgcctcagt ctccagccgc cgtgaacaca 960
ggcgttagca catctgccgc ctgtaccaca agcgtgcaga gcgacgatct gctgcacaag 1020
gactgcaagt ttctgatcct ggaaaaggac aacacgcccg ccaagaaaga gatggaactg 1080
ctgatcatga ccaaggacag cggcaaggtg ttcaccgcct ctccagcctc tatcgccgcc 1140
acaagcttta gcgaggacac cctgaagaaa gaaaagcagg ccgcctacaa cgccgactct 1200
ggactgaaag ccgaggccaa cggcgacctg aaaaccgtgt ctaccaaggg caagaccacc 1260
accgccgaca tccacagcta tggatctagc ggaggcggag gatctggtgg tggcggcgga 1320
gttggaggtg ctggcggagg accttgggga cctgctcctg cttggtgtcc ttgtggctcc 1380
tgttgcagct ggtggaagtg gctgcttggc ctgctgctga cttggctgct tcttctgggc 1440

```
ctgctgtttg gcctgattgc cctggctgag gaagtgcgga agctgaaggc cagagtggat   1500
gagctggaac ggatcaggcg gagcatcctg ccttacggcg acagcatgga ccggatcgag   1560
aaggacagac tgcaaggcat ggctccagca gctggcgccg atctggataa gatcggactg   1620
cacagcgaca gccaagagga actctggatg ttcgtgcgga agaaactgat gatggaacaa   1680
gagaacggca acctgagagg cagccctgga cctaagggcg atatgggaag cccaggacca   1740
aaaggcgaca gaggctttcc tggcacacct ggcattccag gacctctggg acatcctggt   1800
cctcagggcc ctaaaggcca gaaaggctct gtgggagatc ccggcatgga aggccctatg   1860
ggacagagag gtagagaagg accaatgggc cctagaggcg aagctggacc tcctggatct   1920
ggcgagaaag gcgaaagggg agctgcaggc gaaccaggac cacatggacc tccaggtgtt   1980
cccggatctg tgggccctaa gggatcttct ggttcccctg gaccacaagg cccacctgga   2040
cctgttggac tccaaggact gaggggcgaa gttggactgc caggcgtcaa gggcgacaag   2100
ggtccaatgg gaccacctgg tccaaagggc gatcagggcg aaaagggacc tagaggactg   2160
acaggcgagc ccggaatgag aggacttcct ggtgctgttg gagagcctgg cgctaaaggt   2220
gctatgggac ctgcaggccc cgacggacat caaggaccta ggggagaaca gggcctgacc   2280
ggcatgcctg gaattagagg tcctcctgga ccttccggcg atcctggcaa accaggattg   2340
actggacctc agggaccaca gggactgcct ggaacaccag gcagacctgg aatcaaaggc   2400
gaacctggcg ctcccggcaa gattgtgaca tctgagggca gctccatgct gaccgtgcct   2460
ggtccacctg ggcctccagg cgccatgggt cctccgggtc caccaggtgc tccaggacca   2520
gccggaccag caggacttcc aggccatcaa gaagtgctga acctgcaggg gcctcctggg   2580
ccgcctggac caagagggcc accagggcca tctattccag gaccaccagg tcctagaggc   2640
cctccaggcg aaggattgcc aggtcctcca gggccacctg gcagctttct gagcaacagc   2700
gagacattcc tgagcggccc tccaggacct cctggaccac caggacctaa aggcgatcaa   2760
ggacctccag gaccgagagg acatcagggc gaacaaggac tgcctggctt tagcacaagc   2820
ggcagctcta gcttcggcct caatctgcag ggtccaccag ggccaccagg acctcaaggt   2880
cctaaaggcg ataagggcga tccaggcgtt ccaggcgctc tgggtattcc ttctggacca   2940
tctgaaggcg gctcctccag cactatgtac gtgtcaggtc caccgggtcc acctggaccg   3000
ccaggaccac ctggatctat ctctagctcc ggccaagaga tccagcagta catcagcgag   3060
tacatgcagt ctgacagcat ccggtcctac ctgtctggcg ttcaaggtcc accgggacct   3120
ccggggcctc ctggacctgt tacaacaatc accggcgaga ctttcgacta cagcgagctg   3180
gcctctcacg tggtgtccta tctgagaacc agcggctatg gcgtgtccct gttcagctcc   3240
agcatcagct ccgaggacat tctggcagtg ctgcagaggg atgacgtgcg gcagtacctg   3300
agacagtatc tgatggggcc cagagggcca cctggtccac caggcgctag cggagatgga   3360
tctctgctga gcctggatta cgccgagctg agcagcagaa tcctgagcta catgagcagc   3420
tccggcatct ccattgggtt gcctggacct ccaggtccac caggattgcc tggcacaagc   3480
tacgaggaac tgctgtccct gctgaggggc agcgagttta gaggaatcgt tggaccacct   3540
gggccaccag gtccacctgg tatccctgga aatgtgtggt ctagcatcag cgtggaagat   3600
ctgagcagct acctgcacac agccggcctg agctttattc caggacctcc agggccgcca   3660
gggcctcctg gtcctcgggg accgcctggc gttagcggag cacttgcaac atatgccgcc   3720
gagaacagcg actccttcag aagcgagctg atctcctacc tgactagccc cgatgtgcgg   3780
agctttatcg ttggcccgcc tggtcctcca ggacctcaag gacctcctgg cgattctaga   3840
```

-continued

```
ctgctgagca cagatgccag ccacagcaga ggcagctcct ctagctctca ctccagttct   3900

gtgcggagag gctccagcta cagcagctct atgtcaacag gtggcggagg cgctggaagt   3960

cttggagctg gtggcgcttt tggagaagcc gctggcgatc gtggcccata cggaacagat   4020

attggacccg gcggtggata tggcgctgcc gctgaaggcg ggatgtatgc cggaaatggt   4080

ggactgctgg gcgccgattt tgctggcgac ctggactata atgagctggc cgtcagagtg   4140

tccgagagca tgcaaagaca ggggctgctt caaggcatgg cctacacagt tcaaggccca   4200

ccaggacagc ctggtccaca gggaccaccg ggaatcagca aagtgttctc tgcctacagc   4260

aacgtgaccg ccgacctgat ggacttcttc cagacctacg gcgccattca gggacctcca   4320

ggccaaaagg gcgaaatggg tacacctggg ccgaaaggcg accgaggacc tgctgggcca   4380

cctggacatc ccgggcctcc agggcctaga ggacacaaag gcgaaaaagg cgacaaaggg   4440

gaccaagtct acgccggcag acggcggaga agatccattg ccgtgaagcc ctaa         4494
```

```
<210> SEQ ID NO 15
<211> LENGTH: 1464
<212> TYPE: PRT
<213> ORGANISM: Homo sapiens

<400> SEQUENCE: 15

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
            20                  25                  30

Glu Asp Ile Pro Pro Ile Thr Cys Val Gln Asn Gly Leu Arg Tyr His
        35                  40                  45

Asp Arg Asp Val Trp Lys Pro Glu Pro Cys Arg Ile Cys Val Cys Asp
    50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255
```

-continued

```
Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
        355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
    450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
    610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
            660                 665                 670

Ser Gly Ala Arg Gly Glu Arg Gly Phe Pro Gly Glu Arg Gly Val Gln
```

-continued

```
        675                 680                 685

Gly Pro Pro Gly Pro Ala Gly Pro Arg Gly Ala Asn Gly Ala Pro Gly
    690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
        755                 760                 765

Ile Gly Pro Pro Gly Pro Ala Gly Ala Pro Gly Asp Lys Gly Glu Ser
    770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
        835                 840                 845

Pro Pro Gly Pro Ile Gly Asn Val Gly Ala Pro Gly Ala Lys Gly Ala
    850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Gly Lys Gly Pro Arg Gly Glu
            900                 905                 910

Thr Gly Pro Ala Gly Arg Pro Gly Glu Val Gly Pro Pro Gly Pro Pro
        915                 920                 925

Gly Pro Ala Gly Glu Lys Gly Ser Pro Gly Ala Asp Gly Pro Ala Gly
    930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
        995                 1000                1005

Pro Gly Glu Ser Gly Arg Glu Gly Ala Pro Gly Ala Glu Gly Ser Pro
    1010                1015                1020

Gly Arg Asp Gly Ser Pro Gly Ala Lys Gly Asp Arg Gly Glu Thr Gly
1025                1030                1035                1040

Pro Ala Gly Pro Pro Gly Ala Pro Gly Ala Pro Gly Ala Pro Gly Pro
                1045                1050                1055

Val Gly Pro Ala Gly Lys Ser Gly Asp Arg Gly Glu Thr Gly Pro Ala
            1060                1065                1070

Gly Pro Ala Gly Pro Val Gly Pro Val Gly Ala Arg Gly Pro Ala Gly
        1075                1080                1085

Pro Gln Gly Pro Arg Gly Asp Lys Gly Glu Thr Gly Glu Gln Gly Asp
    1090                1095                1100
```

Arg Gly Ile Lys Gly His Arg Gly Phe Ser Gly Leu Gln Gly Pro Pro
1105 1110 1115 1120

Gly Pro Pro Gly Ser Pro Gly Glu Gln Gly Pro Ser Gly Ala Ser Gly
1125 1130 1135

Pro Ala Gly Pro Arg Gly Pro Pro Gly Ser Ala Gly Ala Pro Gly Lys
1140 1145 1150

Asp Gly Leu Asn Gly Leu Pro Gly Pro Ile Gly Pro Pro Gly Pro Arg
1155 1160 1165

Gly Arg Thr Gly Asp Ala Gly Pro Val Gly Pro Pro Gly Pro Pro Gly
1170 1175 1180

Pro Pro Gly Pro Pro Gly Pro Pro Ser Ala Gly Phe Asp Phe Ser Phe
1185 1190 1195 1200

Leu Pro Gln Pro Pro Gln Glu Lys Ala His Asp Gly Gly Arg Tyr Tyr
1205 1210 1215

Arg Ala Asp Asp Ala Asn Val Val Arg Asp Arg Asp Leu Glu Val Asp
1220 1225 1230

Thr Thr Leu Lys Ser Leu Ser Gln Gln Ile Glu Asn Ile Arg Ser Pro
1235 1240 1245

Glu Gly Ser Arg Lys Asn Pro Ala Arg Thr Cys Arg Asp Leu Lys Met
1250 1255 1260

Cys His Ser Asp Trp Lys Ser Gly Glu Tyr Trp Ile Asp Pro Asn Gln
1265 1270 1275 1280

Gly Cys Asn Leu Asp Ala Ile Lys Val Phe Cys Asn Met Glu Thr Gly
1285 1290 1295

Glu Thr Cys Val Tyr Pro Thr Gln Pro Ser Val Ala Gln Lys Asn Trp
1300 1305 1310

Tyr Ile Ser Lys Asn Pro Lys Asp Lys Arg His Val Trp Phe Gly Glu
1315 1320 1325

Ser Met Thr Asp Gly Phe Gln Phe Glu Tyr Gly Gly Gln Gly Ser Asp
1330 1335 1340

Pro Ala Asp Val Ala Ile Gln Leu Thr Phe Leu Arg Leu Met Ser Thr
1345 1350 1355 1360

Glu Ala Ser Gln Asn Ile Thr Tyr His Cys Lys Asn Ser Val Ala Tyr
1365 1370 1375

Met Asp Gln Gln Thr Gly Asn Leu Lys Lys Ala Leu Leu Leu Gln Gly
1380 1385 1390

Ser Asn Glu Ile Glu Ile Arg Ala Glu Gly Asn Ser Arg Phe Thr Tyr
1395 1400 1405

Ser Val Thr Val Asp Gly Cys Thr Ser His Thr Gly Ala Trp Gly Lys
1410 1415 1420

Thr Val Ile Glu Tyr Lys Thr Thr Lys Thr Ser Arg Leu Pro Ile Ile
1425 1430 1435 1440

Asp Val Ala Pro Leu Asp Val Gly Ala Pro Asp Gln Glu Phe Gly Phe
1445 1450 1455

Asp Val Gly Pro Val Cys Phe Leu
1460

<210> SEQ ID NO 16
<211> LENGTH: 1366
<212> TYPE: PRT
<213> ORGANISM: Homo sapiens

<400> SEQUENCE: 16

Met Leu Ser Phe Val Asp Thr Arg Thr Leu Leu Leu Leu Ala Val Thr

-continued

```
1               5                   10                  15

Leu Cys Leu Ala Thr Cys Gln Ser Leu Gln Glu Glu Thr Val Arg Lys
            20                  25                  30

Gly Pro Ala Gly Asp Arg Gly Pro Arg Gly Glu Arg Gly Pro Pro Gly
        35                  40                  45

Pro Pro Gly Arg Asp Gly Glu Asp Gly Pro Thr Gly Pro Pro Gly Pro
    50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
        195                 200                 205

Thr Pro Gly Gln Thr Gly Ala Arg Gly Leu Pro Gly Glu Arg Gly Arg
    210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
            260                 265                 270

Ala Gly Pro Ala Gly Pro Ala Gly Pro Arg Gly Glu Val Gly Leu Pro
        275                 280                 285

Gly Leu Ser Gly Pro Val Gly Pro Pro Gly Asn Pro Gly Ala Asn Gly
    290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Val Gly Ala Ala
                325                 330                 335

Gly Ala Thr Gly Ala Arg Gly Leu Val Gly Glu Pro Gly Pro Ala Gly
            340                 345                 350

Ser Lys Gly Glu Ser Gly Asn Lys Gly Glu Pro Gly Ser Ala Gly Pro
        355                 360                 365

Gln Gly Pro Pro Gly Pro Ser Gly Glu Glu Gly Lys Arg Gly Pro Asn
    370                 375                 380

Gly Glu Ala Gly Ser Ala Gly Pro Pro Gly Pro Pro Gly Leu Arg Gly
385                 390                 395                 400

Ser Pro Gly Ser Arg Gly Leu Pro Gly Ala Asp Gly Arg Ala Gly Val
                405                 410                 415

Met Gly Pro Pro Gly Ser Arg Gly Ala Ser Gly Pro Ala Gly Val Arg
            420                 425                 430
```

-continued

```
Gly Pro Asn Gly Asp Ala Gly Arg Pro Gly Glu Pro Gly Leu Met Gly
        435                 440                 445

Pro Arg Gly Leu Pro Gly Ser Pro Gly Asn Ile Gly Pro Ala Gly Lys
    450                 455                 460

Glu Gly Pro Val Gly Leu Pro Gly Ile Asp Gly Arg Pro Gly Pro Ile
465                 470                 475                 480

Gly Pro Ala Gly Ala Arg Gly Glu Pro Gly Asn Ile Gly Phe Pro Gly
                485                 490                 495

Pro Lys Gly Pro Thr Gly Asp Pro Gly Lys Asn Gly Asp Lys Gly His
            500                 505                 510

Ala Gly Leu Ala Gly Ala Arg Gly Ala Pro Gly Pro Asp Gly Asn Asn
        515                 520                 525

Gly Ala Gln Gly Pro Pro Gly Pro Gln Gly Val Gln Gly Gly Lys Gly
    530                 535                 540

Glu Gln Gly Pro Pro Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
                565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
        595                 600                 605

Arg Gly Pro Ser Gly Pro Pro Gly Pro Asp Gly Asn Lys Gly Glu Pro
    610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
                645                 650                 655

Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
        675                 680                 685

Ala Thr Gly Asp Arg Gly Glu Ala Gly Ala Ala Gly Pro Ala Gly Pro
    690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
                725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
        755                 760                 765

Gly Pro Pro Gly Pro Ala Gly Ser Arg Gly Asp Gly Gly Pro Pro Gly
    770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
                805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
        835                 840                 845
```

-continued

```
Ser Gly Glu Ala Gly Thr Ala Gly Pro Pro Gly Thr Pro Gly Pro Gln
    850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
                885                 890                 895

Leu Gly Ile Ala Gly Pro Pro Gly Ala Arg Gly Pro Pro Gly Ala Val
            900                 905                 910

Gly Ser Pro Gly Val Asn Gly Ala Pro Gly Glu Ala Gly Arg Asp Gly
        915                 920                 925

Asn Pro Gly Asn Asp Gly Pro Pro Gly Arg Asp Gly Gln Pro Gly His
    930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly Pro Gln Gly Ile Arg Gly Asp Lys
        995                 1000                1005

Gly Glu Pro Gly Glu Lys Gly Pro Arg Gly Leu Pro Gly Leu Lys Gly
    1010                1015                1020

His Asn Gly Leu Gln Gly Leu Pro Gly Ile Ala Gly His His Gly Asp
1025                1030                1035                1040

Gln Gly Ala Pro Gly Ser Val Gly Pro Ala Gly Pro Arg Gly Pro Ala
                1045                1050                1055

Gly Pro Ser Gly Pro Ala Gly Lys Asp Gly Arg Thr Gly His Pro Gly
            1060                1065                1070

Thr Val Gly Pro Ala Gly Ile Arg Gly Pro Gln Gly His Gln Gly Pro
        1075                1080                1085

Ala Gly Pro Pro Gly Pro Pro Gly Pro Pro Gly Pro Pro Gly Val Ser
    1090                1095                1100

Gly Gly Gly Tyr Asp Phe Gly Tyr Asp Gly Asp Phe Tyr Arg Ala Asp
1105                1110                1115                1120

Gln Pro Arg Ser Ala Pro Ser Leu Arg Pro Lys Asp Tyr Glu Val Asp
                1125                1130                1135

Ala Thr Leu Lys Ser Leu Asn Asn Gln Ile Glu Thr Leu Leu Thr Pro
            1140                1145                1150

Glu Gly Ser Arg Lys Asn Pro Ala Arg Thr Cys Arg Asp Leu Arg Leu
        1155                1160                1165

Ser His Pro Glu Trp Ser Ser Gly Tyr Tyr Trp Ile Asp Pro Asn Gln
    1170                1175                1180

Gly Cys Thr Met Asp Ala Ile Lys Val Tyr Cys Asp Phe Ser Thr Gly
1185                1190                1195                1200

Glu Thr Cys Ile Arg Ala Gln Pro Glu Asn Ile Pro Ala Lys Asn Trp
                1205                1210                1215

Tyr Arg Ser Ser Lys Asp Lys Lys His Val Trp Leu Gly Glu Thr Ile
            1220                1225                1230

Asn Ala Gly Ser Gln Phe Glu Tyr Asn Val Glu Gly Val Thr Ser Lys
        1235                1240                1245

Glu Met Ala Thr Gln Leu Ala Phe Met Arg Leu Leu Ala Asn Tyr Ala
    1250                1255                1260

Ser Gln Asn Ile Thr Tyr His Cys Lys Asn Ser Ile Ala Tyr Met Asp
```

-continued

```
1265                1270                1275                1280

Glu Glu Thr Gly Asn Leu Lys Lys Ala Val Ile Leu Gln Gly Ser Asn
                1285                1290                1295

Asp Val Glu Leu Val Ala Glu Gly Asn Ser Arg Phe Thr Tyr Thr Val
            1300                1305                1310

Leu Val Asp Gly Cys Ser Lys Lys Thr Asn Glu Trp Gly Lys Thr Ile
        1315                1320                1325

Ile Glu Tyr Lys Thr Asn Lys Pro Ser Arg Leu Pro Phe Leu Asp Ile
    1330                1335                1340

Ala Pro Leu Asp Ile Gly Gly Ala Asp Gln Glu Phe Phe Val Asp Ile
1345                1350                1355                1360

Gly Pro Val Cys Phe Lys
                1365


<210> SEQ ID NO 17
<211> LENGTH: 1466
<212> TYPE: PRT
<213> ORGANISM: Homo sapiens

<400> SEQUENCE: 17

Met Met Ser Phe Val Gln Lys Gly Ser Trp Leu Leu Leu Ala Leu Leu
1               5                   10                  15

His Pro Thr Ile Ile Leu Ala Gln Gln Glu Ala Val Glu Gly Gly Cys
            20                  25                  30

Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn
            260                 265                 270
```

-continued

```
Gly Glu Lys Gly Glu Thr Gly Ala Pro Gly Leu Lys Gly Glu Asn Gly
        275                 280                 285

Leu Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu
            340                 345                 350

Val Gly Pro Ala Gly Ser Pro Gly Ser Asn Gly Ala Pro Gly Gln Arg
        355                 360                 365

Gly Glu Pro Gly Pro Gln Gly His Ala Gly Ala Gln Gly Pro Pro Gly
    370                 375                 380

Pro Pro Gly Ile Asn Gly Ser Pro Gly Gly Lys Gly Glu Met Gly Pro
385                 390                 395                 400

Ala Gly Ile Pro Gly Ala Pro Gly Leu Met Gly Ala Arg Gly Pro Pro
                405                 410                 415

Gly Pro Ala Gly Ala Asn Gly Ala Pro Gly Leu Arg Gly Gly Ala Gly
            420                 425                 430

Glu Pro Gly Lys Asn Gly Ala Lys Gly Glu Pro Gly Pro Arg Gly Glu
        435                 440                 445

Arg Gly Glu Ala Gly Ile Pro Gly Val Pro Gly Ala Lys Gly Glu Asp
    450                 455                 460

Gly Lys Asp Gly Ser Pro Gly Glu Pro Gly Ala Asn Gly Leu Pro Gly
465                 470                 475                 480

Ala Ala Gly Glu Arg Gly Ala Pro Gly Phe Arg Gly Pro Ala Gly Pro
                485                 490                 495

Asn Gly Ile Pro Gly Glu Lys Gly Pro Ala Gly Glu Arg Gly Ala Pro
            500                 505                 510

Gly Pro Ala Gly Pro Arg Gly Ala Ala Gly Glu Pro Gly Arg Asp Gly
        515                 520                 525

Val Pro Gly Gly Pro Gly Met Arg Gly Met Pro Gly Ser Pro Gly Gly
    530                 535                 540

Pro Gly Ser Asp Gly Lys Pro Gly Pro Pro Gly Ser Gln Gly Glu Ser
545                 550                 555                 560

Gly Arg Pro Gly Pro Pro Gly Pro Ser Gly Pro Arg Gly Gln Pro Gly
                565                 570                 575

Val Met Gly Phe Pro Gly Pro Lys Gly Asn Asp Gly Ala Pro Gly Lys
            580                 585                 590

Asn Gly Glu Arg Gly Gly Pro Gly Gly Pro Gly Pro Gln Gly Pro Pro
        595                 600                 605

Gly Lys Asn Gly Glu Thr Gly Pro Gln Gly Pro Pro Gly Pro Thr Gly
    610                 615                 620

Pro Gly Gly Asp Lys Gly Asp Thr Gly Pro Pro Gly Pro Gln Gly Leu
625                 630                 635                 640

Gln Gly Leu Pro Gly Thr Gly Gly Pro Pro Gly Glu Asn Gly Lys Pro
                645                 650                 655

Gly Glu Pro Gly Pro Lys Gly Asp Ala Gly Ala Pro Gly Ala Pro Gly
            660                 665                 670

Gly Lys Gly Asp Ala Gly Ala Pro Gly Glu Arg Gly Pro Pro Gly Leu
        675                 680                 685

Ala Gly Ala Pro Gly Leu Arg Gly Gly Ala Gly Pro Pro Gly Pro Glu
```

-continued

```
    690                 695                 700

Gly Gly Lys Gly Ala Ala Gly Pro Pro Gly Pro Pro Gly Ala Ala Gly
705                 710                 715                 720

Thr Pro Gly Leu Gln Gly Met Pro Gly Glu Arg Gly Gly Leu Gly Ser
                725                 730                 735

Pro Gly Pro Lys Gly Asp Lys Gly Glu Pro Gly Gly Pro Gly Ala Asp
            740                 745                 750

Gly Val Pro Gly Lys Asp Gly Pro Arg Gly Pro Thr Gly Pro Ile Gly
        755                 760                 765

Pro Pro Gly Pro Ala Gly Gln Pro Gly Asp Lys Gly Glu Gly Gly Ala
    770                 775                 780

Pro Gly Leu Pro Gly Ile Ala Gly Pro Arg Gly Ser Pro Gly Glu Arg
785                 790                 795                 800

Gly Glu Thr Gly Pro Pro Gly Pro Ala Gly Phe Pro Gly Ala Pro Gly
                805                 810                 815

Gln Asn Gly Glu Pro Gly Gly Lys Gly Glu Arg Gly Ala Pro Gly Glu
            820                 825                 830

Lys Gly Glu Gly Gly Pro Pro Gly Val Ala Gly Pro Pro Gly Gly Ser
        835                 840                 845

Gly Pro Ala Gly Pro Pro Gly Pro Gln Gly Val Lys Gly Glu Arg Gly
    850                 855                 860

Ser Pro Gly Gly Pro Gly Ala Ala Gly Phe Pro Gly Ala Arg Gly Leu
865                 870                 875                 880

Pro Gly Pro Pro Gly Ser Asn Gly Asn Pro Gly Pro Pro Gly Pro Ser
                885                 890                 895

Gly Ser Pro Gly Lys Asp Gly Pro Pro Gly Pro Ala Gly Asn Thr Gly
            900                 905                 910

Ala Pro Gly Ser Pro Gly Val Ser Gly Pro Lys Gly Asp Ala Gly Gln
        915                 920                 925

Pro Gly Glu Lys Gly Ser Pro Gly Ala Gln Gly Pro Pro Gly Ala Pro
    930                 935                 940

Gly Pro Leu Gly Ile Ala Gly Ile Thr Gly Ala Arg Gly Leu Ala Gly
945                 950                 955                 960

Pro Pro Gly Met Pro Gly Pro Arg Gly Ser Pro Gly Pro Gln Gly Val
                965                 970                 975

Lys Gly Glu Ser Gly Lys Pro Gly Ala Asn Gly Leu Ser Gly Glu Arg
            980                 985                 990

Gly Pro Pro Gly Pro Gln Gly Leu Pro Gly Leu Ala Gly Thr Ala Gly
        995                 1000                1005

Glu Pro Gly Arg Asp Gly Asn Pro Gly Ser Asp Gly Leu Pro Gly Arg
    1010                1015                1020

Asp Gly Ser Pro Gly Gly Lys Gly Asp Arg Gly Glu Asn Gly Ser Pro
1025                1030                1035                1040

Gly Ala Pro Gly Ala Pro Gly His Pro Gly Pro Pro Gly Pro Val Gly
                1045                1050                1055

Pro Ala Gly Lys Ser Gly Asp Arg Gly Glu Ser Gly Pro Ala Gly Pro
            1060                1065                1070

Ala Gly Ala Pro Gly Pro Ala Gly Ser Arg Gly Ala Pro Gly Pro Gln
        1075                1080                1085

Gly Pro Arg Gly Asp Lys Gly Glu Thr Gly Glu Arg Gly Ala Ala Gly
    1090                1095                1100

Ile Lys Gly His Arg Gly Phe Pro Gly Asn Pro Gly Ala Pro Gly Ser
1105                1110                1115                1120
```

```
Pro Gly Pro Ala Gly Gln Gln Gly Ala Ile Gly Ser Pro Gly Pro Ala
                1125                1130                1135

Gly Pro Arg Gly Pro Val Gly Pro Ser Gly Pro Pro Gly Lys Asp Gly
            1140                1145                1150

Thr Ser Gly His Pro Gly Pro Ile Gly Pro Pro Gly Pro Arg Gly Asn
        1155                1160                1165

Arg Gly Glu Arg Gly Ser Glu Gly Ser Pro Gly His Pro Gly Gln Pro
    1170                1175                1180

Gly Pro Pro Gly Pro Pro Gly Ala Pro Gly Pro Cys Cys Gly Gly Val
1185                1190                1195                1200

Gly Ala Ala Ala Ile Ala Gly Ile Gly Gly Glu Lys Ala Gly Gly Phe
                1205                1210                1215

Ala Pro Tyr Tyr Gly Asp Glu Pro Met Asp Phe Lys Ile Asn Thr Asp
            1220                1225                1230

Glu Ile Met Thr Ser Leu Lys Ser Val Asn Gly Gln Ile Glu Ser Leu
        1235                1240                1245

Ile Ser Pro Asp Gly Ser Arg Lys Asn Pro Ala Arg Asn Cys Arg Asp
    1250                1255                1260

Leu Lys Phe Cys His Pro Glu Leu Lys Ser Gly Glu Tyr Trp Val Asp
1265                1270                1275                1280

Pro Asn Gln Gly Cys Lys Leu Asp Ala Ile Lys Val Phe Cys Asn Met
                1285                1290                1295

Glu Thr Gly Glu Thr Cys Ile Ser Ala Asn Pro Leu Asn Val Pro Arg
            1300                1305                1310

Lys His Trp Trp Thr Asp Ser Ser Ala Glu Lys Lys His Val Trp Phe
        1315                1320                1325

Gly Glu Ser Met Asp Gly Gly Phe Gln Phe Ser Tyr Gly Asn Pro Glu
    1330                1335                1340

Leu Pro Glu Asp Val Leu Asp Val Gln Leu Ala Phe Leu Arg Leu Leu
1345                1350                1355                1360

Ser Ser Arg Ala Ser Gln Asn Ile Thr Tyr His Cys Lys Asn Ser Ile
                1365                1370                1375

Ala Tyr Met Asp Gln Ala Ser Gly Asn Val Lys Lys Ala Leu Lys Leu
            1380                1385                1390

Met Gly Ser Asn Glu Gly Glu Phe Lys Ala Glu Gly Asn Ser Lys Phe
        1395                1400                1405

Thr Tyr Thr Val Leu Glu Asp Gly Cys Thr Lys His Thr Gly Glu Trp
    1410                1415                1420

Ser Lys Thr Val Phe Glu Tyr Arg Thr Arg Lys Ala Val Arg Leu Pro
1425                1430                1435                1440

Ile Val Asp Ile Ala Pro Tyr Asp Ile Gly Gly Pro Asp Gln Glu Phe
                1445                1450                1455

Gly Val Asp Val Gly Pro Val Cys Phe Leu
            1460                1465


<210> SEQ ID NO 18
<211> LENGTH: 1669
<212> TYPE: PRT
<213> ORGANISM: Homo sapiens

<400> SEQUENCE: 18

Met Gly Pro Arg Leu Ser Val Trp Leu Leu Leu Leu Pro Ala Ala Leu
1               5                   10                  15

Leu Leu His Glu Glu His Ser Arg Ala Ala Ala Lys Gly Gly Cys Ala
```

-continued

```
            20                  25                  30

Gly Ser Gly Cys Gly Lys Cys Asp Cys His Gly Val Lys Gly Gln Lys
        35                  40                  45

Gly Glu Arg Gly Leu Pro Gly Leu Gln Gly Val Ile Gly Phe Pro Gly
    50                  55                  60

Met Gln Gly Pro Glu Gly Pro Gln Gly Pro Pro Gly Gln Lys Gly Asp
65                  70                  75                  80

Thr Gly Glu Pro Gly Leu Pro Gly Thr Lys Gly Thr Arg Gly Pro Pro
                85                  90                  95

Gly Ala Ser Gly Tyr Pro Gly Asn Pro Gly Leu Pro Gly Ile Pro Gly
            100                 105                 110

Gln Asp Gly Pro Pro Gly Pro Pro Gly Ile Pro Gly Cys Asn Gly Thr
        115                 120                 125

Lys Gly Glu Arg Gly Pro Leu Gly Pro Pro Gly Leu Pro Gly Phe Ala
    130                 135                 140

Gly Asn Pro Gly Pro Pro Gly Leu Pro Gly Met Lys Gly Asp Pro Gly
145                 150                 155                 160

Glu Ile Leu Gly His Val Pro Gly Met Leu Leu Lys Gly Glu Arg Gly
                165                 170                 175

Phe Pro Gly Ile Pro Gly Thr Pro Gly Pro Pro Gly Leu Pro Gly Leu
            180                 185                 190

Gln Gly Pro Val Gly Pro Pro Gly Phe Thr Gly Pro Pro Gly Pro Pro
        195                 200                 205

Gly Pro Pro Gly Pro Pro Gly Glu Lys Gly Gln Met Gly Leu Ser Phe
    210                 215                 220

Gln Gly Pro Lys Gly Asp Lys Gly Asp Gln Gly Val Ser Gly Pro Pro
225                 230                 235                 240

Gly Val Pro Gly Gln Ala Gln Val Gln Glu Lys Gly Asp Phe Ala Thr
                245                 250                 255

Lys Gly Glu Lys Gly Gln Lys Gly Glu Pro Gly Phe Gln Gly Met Pro
            260                 265                 270

Gly Val Gly Glu Lys Gly Glu Pro Gly Lys Pro Gly Pro Arg Gly Lys
        275                 280                 285

Pro Gly Lys Asp Gly Asp Lys Gly Glu Lys Gly Ser Pro Gly Phe Pro
    290                 295                 300

Gly Glu Pro Gly Tyr Pro Gly Leu Ile Gly Arg Gln Gly Pro Gln Gly
305                 310                 315                 320

Glu Lys Gly Glu Ala Gly Pro Pro Gly Pro Pro Gly Ile Val Ile Gly
                325                 330                 335

Thr Gly Pro Leu Gly Glu Lys Gly Glu Arg Gly Tyr Pro Gly Thr Pro
            340                 345                 350

Gly Pro Arg Gly Glu Pro Gly Pro Lys Gly Phe Pro Gly Leu Pro Gly
        355                 360                 365

Gln Pro Gly Pro Pro Gly Leu Pro Val Pro Gly Gln Ala Gly Ala Pro
    370                 375                 380

Gly Phe Pro Gly Glu Arg Gly Glu Lys Gly Asp Arg Gly Phe Pro Gly
385                 390                 395                 400

Thr Ser Leu Pro Gly Pro Ser Gly Arg Asp Gly Leu Pro Gly Pro Pro
                405                 410                 415

Gly Ser Pro Gly Pro Pro Gly Gln Pro Gly Tyr Thr Asn Gly Ile Val
            420                 425                 430

Glu Cys Gln Pro Gly Pro Pro Gly Asp Gln Gly Pro Pro Gly Ile Pro
        435                 440                 445
```

-continued

```
Gly Gln Pro Gly Phe Ile Gly Glu Ile Gly Glu Lys Gly Gln Lys Gly
    450                 455                 460

Glu Ser Cys Leu Ile Cys Asp Ile Asp Gly Tyr Arg Gly Pro Pro Gly
465                 470                 475                 480

Pro Gln Gly Pro Pro Gly Glu Ile Gly Phe Pro Gly Gln Pro Gly Ala
                485                 490                 495

Lys Gly Asp Arg Gly Leu Pro Gly Arg Asp Gly Val Ala Gly Val Pro
            500                 505                 510

Gly Pro Gln Gly Thr Pro Gly Leu Ile Gly Gln Pro Gly Ala Lys Gly
        515                 520                 525

Glu Pro Gly Glu Phe Tyr Phe Asp Leu Arg Leu Lys Gly Asp Lys Gly
    530                 535                 540

Asp Pro Gly Phe Pro Gly Gln Pro Gly Met Pro Gly Arg Ala Gly Ser
545                 550                 555                 560

Pro Gly Arg Asp Gly His Pro Gly Leu Pro Gly Pro Lys Gly Ser Pro
                565                 570                 575

Gly Ser Val Gly Leu Lys Gly Glu Arg Gly Pro Pro Gly Gly Val Gly
            580                 585                 590

Phe Pro Gly Ser Arg Gly Asp Thr Gly Pro Pro Gly Pro Pro Gly Tyr
        595                 600                 605

Gly Pro Ala Gly Pro Ile Gly Asp Lys Gly Gln Ala Gly Phe Pro Gly
    610                 615                 620

Gly Pro Gly Ser Pro Gly Leu Pro Gly Pro Lys Gly Glu Pro Gly Lys
625                 630                 635                 640

Ile Val Pro Leu Pro Gly Pro Pro Gly Ala Glu Gly Leu Pro Gly Ser
                645                 650                 655

Pro Gly Phe Pro Gly Pro Gln Gly Asp Arg Gly Phe Pro Gly Thr Pro
            660                 665                 670

Gly Arg Pro Gly Leu Pro Gly Glu Lys Gly Ala Val Gly Gln Pro Gly
        675                 680                 685

Ile Gly Phe Pro Gly Pro Pro Gly Pro Lys Gly Val Asp Gly Leu Pro
    690                 695                 700

Gly Asp Met Gly Pro Pro Gly Thr Pro Gly Arg Pro Gly Phe Asn Gly
705                 710                 715                 720

Leu Pro Gly Asn Pro Gly Val Gln Gly Gln Lys Gly Glu Pro Gly Val
                725                 730                 735

Gly Leu Pro Gly Leu Lys Gly Leu Pro Gly Leu Pro Gly Ile Pro Gly
            740                 745                 750

Thr Pro Gly Glu Lys Gly Ser Ile Gly Val Pro Gly Val Pro Gly Glu
        755                 760                 765

His Gly Ala Ile Gly Pro Pro Gly Leu Gln Gly Ile Arg Gly Glu Pro
    770                 775                 780

Gly Pro Pro Gly Leu Pro Gly Ser Val Gly Ser Pro Gly Val Pro Gly
785                 790                 795                 800

Ile Gly Pro Pro Gly Ala Arg Gly Pro Pro Gly Gly Gln Gly Pro Pro
                805                 810                 815

Gly Leu Ser Gly Pro Pro Gly Ile Lys Gly Glu Lys Gly Phe Pro Gly
            820                 825                 830

Phe Pro Gly Leu Asp Met Pro Gly Pro Lys Gly Asp Lys Gly Ala Gln
        835                 840                 845

Gly Leu Pro Gly Ile Thr Gly Gln Ser Gly Leu Pro Gly Leu Pro Gly
    850                 855                 860
```

-continued

```
Gln Gln Gly Ala Pro Gly Ile Pro Gly Phe Pro Gly Ser Lys Gly Glu
865                 870                 875                 880

Met Gly Val Met Gly Thr Pro Gly Gln Pro Gly Ser Pro Gly Pro Val
                885                 890                 895

Gly Ala Pro Gly Leu Pro Gly Glu Lys Gly Asp His Gly Phe Pro Gly
            900                 905                 910

Ser Ser Gly Pro Arg Gly Asp Pro Gly Leu Lys Gly Asp Lys Gly Asp
        915                 920                 925

Val Gly Leu Pro Gly Lys Pro Gly Ser Met Asp Lys Val Asp Met Gly
    930                 935                 940

Ser Met Lys Gly Gln Lys Gly Asp Gln Gly Glu Lys Gly Gln Ile Gly
945                 950                 955                 960

Pro Ile Gly Glu Lys Gly Ser Arg Gly Asp Pro Gly Thr Pro Gly Val
                965                 970                 975

Pro Gly Lys Asp Gly Gln Ala Gly Gln Pro Gly Gln Pro Gly Pro Lys
            980                 985                 990

Gly Asp Pro Gly Ile Ser Gly Thr Pro Gly Ala Pro Gly Leu Pro Gly
        995                 1000                1005

Pro Lys Gly Ser Val Gly Gly Met Gly Leu Pro Gly Thr Pro Gly Glu
    1010                1015                1020

Lys Gly Val Pro Gly Ile Pro Gly Pro Gln Gly Ser Pro Gly Leu Pro
1025                1030                1035                1040

Gly Asp Lys Gly Ala Lys Gly Glu Lys Gly Gln Ala Gly Pro Pro Gly
                1045                1050                1055

Ile Gly Ile Pro Gly Leu Arg Gly Glu Lys Gly Asp Gln Gly Ile Ala
            1060                1065                1070

Gly Phe Pro Gly Ser Pro Gly Glu Lys Gly Glu Lys Gly Ser Ile Gly
        1075                1080                1085

Ile Pro Gly Met Pro Gly Ser Pro Gly Leu Lys Gly Ser Pro Gly Ser
    1090                1095                1100

Val Gly Tyr Pro Gly Ser Pro Gly Leu Pro Gly Glu Lys Gly Asp Lys
1105                1110                1115                1120

Gly Leu Pro Gly Leu Asp Gly Ile Pro Gly Val Lys Gly Glu Ala Gly
                1125                1130                1135

Leu Pro Gly Thr Pro Gly Pro Thr Gly Pro Ala Gly Gln Lys Gly Glu
            1140                1145                1150

Pro Gly Ser Asp Gly Ile Pro Gly Ser Ala Gly Glu Lys Gly Glu Pro
        1155                1160                1165

Gly Leu Pro Gly Arg Gly Phe Pro Gly Phe Pro Gly Ala Lys Gly Asp
    1170                1175                1180

Lys Gly Ser Lys Gly Glu Val Gly Phe Pro Gly Leu Ala Gly Ser Pro
1185                1190                1195                1200

Gly Ile Pro Gly Ser Lys Gly Glu Gln Gly Phe Met Gly Pro Pro Gly
                1205                1210                1215

Pro Gln Gly Gln Pro Gly Leu Pro Gly Ser Pro Gly His Ala Thr Glu
            1220                1225                1230

Gly Pro Lys Gly Asp Arg Gly Pro Gln Gly Gln Pro Gly Leu Pro Gly
        1235                1240                1245

Leu Pro Gly Pro Met Gly Pro Pro Gly Leu Pro Gly Ile Asp Gly Val
    1250                1255                1260

Lys Gly Asp Lys Gly Asn Pro Gly Trp Pro Gly Ala Pro Gly Val Pro
1265                1270                1275                1280

Gly Pro Lys Gly Asp Pro Gly Phe Gln Gly Met Pro Gly Ile Gly Gly
```

-continued

```
                1285                1290                1295

Ser Pro Gly Ile Thr Gly Ser Lys Gly Asp Met Gly Pro Pro Gly Val
            1300                1305                1310

Pro Gly Phe Gln Gly Pro Lys Gly Leu Pro Gly Leu Gln Gly Ile Lys
        1315                1320                1325

Gly Asp Gln Gly Asp Gln Gly Val Pro Gly Ala Lys Gly Leu Pro Gly
    1330                1335                1340

Pro Pro Gly Pro Pro Gly Pro Tyr Asp Ile Ile Lys Gly Glu Pro Gly
1345                1350                1355                1360

Leu Pro Gly Pro Glu Gly Pro Pro Gly Leu Lys Gly Leu Gln Gly Leu
                1365                1370                1375

Pro Gly Pro Lys Gly Gln Gln Gly Val Thr Gly Leu Val Gly Ile Pro
            1380                1385                1390

Gly Pro Pro Gly Ile Pro Gly Phe Asp Gly Ala Pro Gly Gln Lys Gly
        1395                1400                1405

Glu Met Gly Pro Ala Gly Pro Thr Gly Pro Arg Gly Phe Pro Gly Pro
    1410                1415                1420

Pro Gly Pro Asp Gly Leu Pro Gly Ser Met Gly Pro Pro Gly Thr Pro
1425                1430                1435                1440

Ser Val Asp His Gly Phe Leu Val Thr Arg His Ser Gln Thr Ile Asp
                1445                1450                1455

Asp Pro Gln Cys Pro Ser Gly Thr Lys Ile Leu Tyr His Gly Tyr Ser
            1460                1465                1470

Leu Leu Tyr Val Gln Gly Asn Glu Arg Ala His Gly Gln Asp Leu Gly
        1475                1480                1485

Thr Ala Gly Ser Cys Leu Arg Lys Phe Ser Thr Met Pro Phe Leu Phe
    1490                1495                1500

Cys Asn Ile Asn Asn Val Cys Asn Phe Ala Ser Arg Asn Asp Tyr Ser
1505                1510                1515                1520

Tyr Trp Leu Ser Thr Pro Glu Pro Met Pro Met Ser Met Ala Pro Ile
                1525                1530                1535

Thr Gly Glu Asn Ile Arg Pro Phe Ile Ser Arg Cys Ala Val Cys Glu
            1540                1545                1550

Ala Pro Ala Met Val Met Ala Val His Ser Gln Thr Ile Gln Ile Pro
        1555                1560                1565

Pro Cys Pro Ser Gly Trp Ser Ser Leu Trp Ile Gly Tyr Ser Phe Val
    1570                1575                1580

Met His Thr Ser Ala Gly Ala Glu Gly Ser Gly Gln Ala Leu Ala Ser
1585                1590                1595                1600

Pro Gly Ser Cys Leu Glu Glu Phe Arg Ser Ala Pro Phe Ile Glu Cys
                1605                1610                1615

His Gly Arg Gly Thr Cys Asn Tyr Tyr Ala Asn Ala Tyr Ser Phe Trp
            1620                1625                1630

Leu Ala Thr Ile Glu Arg Ser Glu Met Phe Lys Lys Pro Thr Pro Ser
        1635                1640                1645

Thr Leu Lys Ala Gly Glu Leu Arg Thr His Val Ser Arg Cys Gln Val
    1650                1655                1660

Cys Met Arg Arg Thr
1665


<210> SEQ ID NO 19
<211> LENGTH: 1028
<212> TYPE: PRT
<213> ORGANISM: Homo sapiens
```

<400> SEQUENCE: 19

```
Met Arg Ala Ala Arg Ala Leu Leu Pro Leu Leu Leu Gln Ala Cys Trp
1               5                   10                  15

Thr Ala Ala Gln Asp Glu Pro Glu Thr Pro Arg Ala Val Ala Phe Gln
            20                  25                  30

Asp Cys Pro Val Asp Leu Phe Phe Val Leu Asp Thr Ser Glu Ser Val
        35                  40                  45

Ala Leu Arg Leu Lys Pro Tyr Gly Ala Leu Val Asp Lys Val Lys Ser
    50                  55                  60

Phe Thr Lys Arg Phe Ile Asp Asn Leu Arg Asp Arg Tyr Tyr Arg Cys
65                  70                  75                  80

Asp Arg Asn Leu Val Trp Asn Ala Gly Ala Leu His Tyr Ser Asp Glu
                85                  90                  95

Val Glu Ile Ile Gln Gly Leu Thr Arg Met Pro Gly Gly Arg Asp Ala
            100                 105                 110

Leu Lys Ser Ser Val Asp Ala Val Lys Tyr Phe Gly Lys Gly Thr Tyr
        115                 120                 125

Thr Asp Cys Ala Ile Lys Lys Gly Leu Glu Gln Leu Leu Val Gly Gly
    130                 135                 140

Ser His Leu Lys Glu Asn Lys Tyr Leu Ile Val Val Thr Asp Gly His
145                 150                 155                 160

Pro Leu Glu Gly Tyr Lys Glu Pro Cys Gly Gly Leu Glu Asp Ala Val
                165                 170                 175

Asn Glu Ala Lys His Leu Gly Val Lys Val Phe Ser Val Ala Ile Thr
            180                 185                 190

Pro Asp His Leu Glu Pro Arg Leu Ser Ile Ile Ala Thr Asp His Thr
        195                 200                 205

Tyr Arg Arg Asn Phe Thr Ala Ala Asp Trp Gly Gln Ser Arg Asp Ala
    210                 215                 220

Glu Glu Ala Ile Ser Gln Thr Ile Asp Thr Ile Val Asp Met Ile Lys
225                 230                 235                 240

Asn Asn Val Glu Gln Val Cys Cys Ser Phe Glu Cys Gln Pro Ala Arg
                245                 250                 255

Gly Pro Pro Gly Leu Arg Gly Asp Pro Gly Phe Glu Gly Glu Arg Gly
            260                 265                 270

Lys Pro Gly Leu Pro Gly Glu Lys Gly Glu Ala Gly Asp Pro Gly Arg
        275                 280                 285

Pro Gly Asp Leu Gly Pro Val Gly Tyr Gln Gly Met Lys Gly Glu Lys
    290                 295                 300

Gly Ser Arg Gly Glu Lys Gly Ser Arg Gly Pro Lys Gly Tyr Lys Gly
305                 310                 315                 320

Glu Lys Gly Lys Arg Gly Ile Asp Gly Val Asp Gly Val Lys Gly Glu
                325                 330                 335

Met Gly Tyr Pro Gly Leu Pro Gly Cys Lys Gly Ser Pro Gly Phe Asp
            340                 345                 350

Gly Ile Gln Gly Pro Pro Gly Pro Lys Gly Asp Pro Gly Ala Phe Gly
        355                 360                 365

Leu Lys Gly Glu Lys Gly Glu Pro Gly Ala Asp Gly Glu Ala Gly Arg
    370                 375                 380

Pro Gly Ser Ser Gly Pro Ser Gly Asp Glu Gly Gln Pro Gly Glu Pro
385                 390                 395                 400

Gly Pro Pro Gly Glu Lys Gly Glu Ala Gly Asp Glu Gly Asn Pro Gly
```

-continued

```
                405                 410                 415

Pro Asp Gly Ala Pro Gly Glu Arg Gly Gly Pro Gly Glu Arg Gly Pro
            420                 425                 430

Arg Gly Thr Pro Gly Thr Arg Gly Pro Arg Gly Asp Pro Gly Glu Ala
        435                 440                 445

Gly Pro Gln Gly Asp Gln Gly Arg Glu Gly Pro Val Gly Val Pro Gly
    450                 455                 460

Asp Pro Gly Glu Ala Gly Pro Ile Gly Pro Lys Gly Tyr Arg Gly Asp
465                 470                 475                 480

Glu Gly Pro Pro Gly Ser Glu Gly Ala Arg Gly Ala Pro Gly Pro Ala
                485                 490                 495

Gly Pro Pro Gly Asp Pro Gly Leu Met Gly Glu Arg Gly Glu Asp Gly
            500                 505                 510

Pro Ala Gly Asn Gly Thr Glu Gly Phe Pro Gly Phe Pro Gly Tyr Pro
        515                 520                 525

Gly Asn Arg Gly Ala Pro Gly Ile Asn Gly Thr Lys Gly Tyr Pro Gly
    530                 535                 540

Leu Lys Gly Asp Glu Gly Glu Ala Gly Asp Pro Gly Asp Asp Asn Asn
545                 550                 555                 560

Asp Ile Ala Pro Arg Gly Val Lys Gly Ala Lys Gly Tyr Arg Gly Pro
                565                 570                 575

Glu Gly Pro Gln Gly Pro Pro Gly His Gln Gly Pro Pro Gly Pro Asp
            580                 585                 590

Glu Cys Glu Ile Leu Asp Ile Ile Met Lys Met Cys Ser Cys Cys Glu
        595                 600                 605

Cys Lys Cys Gly Pro Ile Asp Leu Leu Phe Val Leu Asp Ser Ser Glu
    610                 615                 620

Ser Ile Gly Leu Gln Asn Phe Glu Ile Ala Lys Asp Phe Val Val Lys
625                 630                 635                 640

Val Ile Asp Arg Leu Ser Arg Asp Glu Leu Val Lys Phe Glu Pro Gly
                645                 650                 655

Gln Ser Tyr Ala Gly Val Val Gln Tyr Ser His Ser Gln Met Gln Glu
            660                 665                 670

His Val Ser Leu Arg Ser Pro Ser Ile Arg Asn Val Gln Glu Leu Lys
        675                 680                 685

Glu Ala Ile Lys Ser Leu Gln Trp Met Ala Gly Gly Thr Phe Thr Gly
    690                 695                 700

Glu Ala Leu Gln Tyr Thr Arg Asp Gln Leu Leu Pro Pro Ser Pro Asn
705                 710                 715                 720

Asn Arg Ile Ala Leu Val Ile Thr Asp Gly Arg Ser Asp Thr Gln Arg
                725                 730                 735

Asp Thr Thr Pro Leu Asn Val Leu Cys Ser Pro Gly Ile Gln Val Val
            740                 745                 750

Ser Val Gly Ile Lys Asp Val Phe Asp Phe Ile Pro Gly Ser Asp Gln
        755                 760                 765

Leu Asn Val Ile Ser Cys Gln Gly Leu Ala Pro Ser Gln Gly Arg Pro
    770                 775                 780

Gly Leu Ser Leu Val Lys Glu Asn Tyr Ala Glu Leu Leu Glu Asp Ala
785                 790                 795                 800

Phe Leu Lys Asn Val Thr Ala Gln Ile Cys Ile Asp Lys Lys Cys Pro
                805                 810                 815

Asp Tyr Thr Cys Pro Ile Thr Phe Ser Ser Pro Ala Asp Ile Thr Ile
            820                 825                 830
```

Leu Leu Asp Gly Ser Ala Ser Val Gly Ser His Asn Phe Asp Thr Thr
835 840 845

Lys Arg Phe Ala Lys Arg Leu Ala Glu Arg Phe Leu Thr Ala Gly Arg
850 855 860

Thr Asp Pro Ala His Asp Val Arg Val Ala Val Val Gln Tyr Ser Gly
865 870 875 880

Thr Gly Gln Gln Arg Pro Glu Arg Ala Ser Leu Gln Phe Leu Gln Asn
885 890 895

Tyr Thr Ala Leu Ala Ser Ala Val Asp Ala Met Asp Phe Ile Asn Asp
900 905 910

Ala Thr Asp Val Asn Asp Ala Leu Gly Tyr Val Thr Arg Phe Tyr Arg
915 920 925

Glu Ala Ser Ser Gly Ala Ala Lys Lys Arg Leu Leu Leu Phe Ser Asp
930 935 940

Gly Asn Ser Gln Gly Ala Thr Pro Ala Ala Ile Glu Lys Ala Val Gln
945 950 955 960

Glu Ala Gln Arg Ala Gly Ile Glu Ile Phe Val Val Val Val Gly Arg
965 970 975

Gln Val Asn Glu Pro His Ile Arg Val Leu Val Thr Gly Lys Thr Ala
980 985 990

Glu Tyr Asp Val Ala Tyr Gly Glu Ser His Leu Phe Arg Val Pro Ser
995 1000 1005

Tyr Gln Ala Leu Leu Arg Gly Val Phe His Gln Thr Val Ser Arg Lys
1010 1015 1020

Val Ala Leu Gly
1025

<210> SEQ ID NO 20
<211> LENGTH: 2944
<212> TYPE: PRT
<213> ORGANISM: Homo sapiens

<400> SEQUENCE: 20

Met Thr Leu Arg Leu Leu Val Ala Ala Leu Cys Ala Gly Ile Leu Ala
1 5 10 15

Glu Ala Pro Arg Val Arg Ala Gln His Arg Glu Arg Val Thr Cys Thr
20 25 30

Arg Leu Tyr Ala Ala Asp Ile Val Phe Leu Leu Asp Gly Ser Ser Ser
35 40 45

Ile Gly Arg Ser Asn Phe Arg Glu Val Arg Ser Phe Leu Glu Gly Leu
50 55 60

Val Leu Pro Phe Ser Gly Ala Ala Ser Ala Gln Gly Val Arg Phe Ala
65 70 75 80

Thr Val Gln Tyr Ser Asp Asp Pro Arg Thr Glu Phe Gly Leu Asp Ala
85 90 95

Leu Gly Ser Gly Gly Asp Val Ile Arg Ala Ile Arg Glu Leu Ser Tyr
100 105 110

Lys Gly Gly Asn Thr Arg Thr Gly Ala Ala Ile Leu His Val Ala Asp
115 120 125

His Val Phe Leu Pro Gln Leu Ala Arg Pro Gly Val Pro Lys Val Cys
130 135 140

Ile Leu Ile Thr Asp Gly Lys Ser Gln Asp Leu Val Asp Thr Ala Ala
145 150 155 160

Gln Arg Leu Lys Gly Gln Gly Val Lys Leu Phe Ala Val Gly Ile Lys

-continued

```
                165                 170                 175

Asn Ala Asp Pro Glu Glu Leu Lys Arg Val Ala Ser Gln Pro Thr Ser
            180                 185                 190

Asp Phe Phe Phe Phe Val Asn Asp Phe Ser Ile Leu Arg Thr Leu Leu
        195                 200                 205

Pro Leu Val Ser Arg Arg Val Cys Thr Thr Ala Gly Gly Val Pro Val
    210                 215                 220

Thr Arg Pro Pro Asp Asp Ser Thr Ser Ala Pro Arg Asp Leu Val Leu
225                 230                 235                 240

Ser Glu Pro Ser Ser Gln Ser Leu Arg Val Gln Trp Thr Ala Ala Ser
                245                 250                 255

Gly Pro Val Thr Gly Tyr Lys Val Gln Tyr Thr Pro Leu Thr Gly Leu
            260                 265                 270

Gly Gln Pro Leu Pro Ser Glu Arg Gln Glu Val Asn Val Pro Ala Gly
        275                 280                 285

Glu Thr Ser Val Arg Leu Arg Gly Leu Arg Pro Leu Thr Glu Tyr Gln
    290                 295                 300

Val Thr Val Ile Ala Leu Tyr Ala Asn Ser Ile Gly Glu Ala Val Ser
305                 310                 315                 320

Gly Thr Ala Arg Thr Thr Ala Leu Glu Gly Pro Glu Leu Thr Ile Gln
                325                 330                 335

Asn Thr Thr Ala His Ser Leu Leu Val Ala Trp Arg Ser Val Pro Gly
            340                 345                 350

Ala Thr Gly Tyr Arg Val Thr Trp Arg Val Leu Ser Gly Gly Pro Thr
        355                 360                 365

Gln Gln Gln Glu Leu Gly Pro Gly Gln Gly Ser Val Leu Leu Arg Asp
    370                 375                 380

Leu Glu Pro Gly Thr Asp Tyr Glu Val Thr Val Ser Thr Leu Phe Gly
385                 390                 395                 400

Arg Ser Val Gly Pro Ala Thr Ser Leu Met Ala Arg Thr Asp Ala Ser
                405                 410                 415

Val Glu Gln Thr Leu Arg Pro Val Ile Leu Gly Pro Thr Ser Ile Leu
            420                 425                 430

Leu Ser Trp Asn Leu Val Pro Glu Ala Arg Gly Tyr Arg Leu Glu Trp
        435                 440                 445

Arg Arg Glu Thr Gly Leu Glu Pro Pro Gln Lys Val Val Leu Pro Ser
    450                 455                 460

Asp Val Thr Arg Tyr Gln Leu Asp Gly Leu Gln Pro Gly Thr Glu Tyr
465                 470                 475                 480

Arg Leu Thr Leu Tyr Thr Leu Leu Glu Gly His Glu Val Ala Thr Pro
                485                 490                 495

Ala Thr Val Val Pro Thr Gly Pro Glu Leu Pro Val Ser Pro Val Thr
            500                 505                 510

Asp Leu Gln Ala Thr Glu Leu Pro Gly Gln Arg Val Arg Val Ser Trp
        515                 520                 525

Ser Pro Val Pro Gly Ala Thr Gln Tyr Arg Ile Ile Val Arg Ser Thr
    530                 535                 540

Gln Gly Val Glu Arg Thr Leu Val Leu Pro Gly Ser Gln Thr Ala Phe
545                 550                 555                 560

Asp Leu Asp Asp Val Gln Ala Gly Leu Ser Tyr Thr Val Arg Val Ser
                565                 570                 575

Ala Arg Val Gly Pro Arg Glu Gly Ser Ala Ser Val Leu Thr Val Arg
            580                 585                 590
```

-continued

```
Arg Glu Pro Glu Thr Pro Leu Ala Val Pro Gly Leu Arg Val Val Val
        595                 600                 605

Ser Asp Ala Thr Arg Val Arg Val Ala Trp Gly Pro Val Pro Gly Ala
    610                 615                 620

Ser Gly Phe Arg Ile Ser Trp Ser Thr Gly Ser Gly Pro Glu Ser Ser
625                 630                 635                 640

Gln Thr Leu Pro Pro Asp Ser Thr Ala Thr Asp Ile Thr Gly Leu Gln
                645                 650                 655

Pro Gly Thr Thr Tyr Gln Val Ala Val Ser Val Leu Arg Gly Arg Glu
            660                 665                 670

Glu Gly Pro Ala Ala Val Ile Val Ala Arg Thr Asp Pro Leu Gly Pro
        675                 680                 685

Val Arg Thr Val His Val Thr Gln Ala Ser Ser Ser Ser Val Thr Ile
    690                 695                 700

Thr Trp Thr Arg Val Pro Gly Ala Thr Gly Tyr Arg Val Ser Trp His
705                 710                 715                 720

Ser Ala His Gly Pro Glu Lys Ser Gln Leu Val Ser Gly Glu Ala Thr
                725                 730                 735

Val Ala Glu Leu Asp Gly Leu Glu Pro Asp Thr Glu Tyr Thr Val His
            740                 745                 750

Val Arg Ala His Val Ala Gly Val Asp Gly Pro Pro Ala Ser Val Val
        755                 760                 765

Val Arg Thr Ala Pro Glu Pro Val Gly Arg Val Ser Arg Leu Gln Ile
    770                 775                 780

Leu Asn Ala Ser Ser Asp Val Leu Arg Ile Thr Trp Val Gly Val Thr
785                 790                 795                 800

Gly Ala Thr Ala Tyr Arg Leu Ala Trp Gly Arg Ser Glu Gly Gly Pro
                805                 810                 815

Met Arg His Gln Ile Leu Pro Gly Asn Thr Asp Ser Ala Glu Ile Arg
            820                 825                 830

Gly Leu Glu Gly Gly Val Ser Tyr Ser Val Arg Val Thr Ala Leu Val
        835                 840                 845

Gly Asp Arg Glu Gly Thr Pro Val Ser Ile Val Val Thr Thr Pro Pro
    850                 855                 860

Glu Ala Pro Pro Ala Leu Gly Thr Leu His Val Val Gln Arg Gly Glu
865                 870                 875                 880

His Ser Leu Arg Leu Arg Trp Glu Pro Val Pro Arg Ala Gln Gly Phe
                885                 890                 895

Leu Leu His Trp Gln Pro Glu Gly Gly Gln Glu Gln Ser Arg Val Leu
            900                 905                 910

Gly Pro Glu Leu Ser Ser Tyr His Leu Asp Gly Leu Glu Pro Ala Thr
        915                 920                 925

Gln Tyr Arg Val Arg Leu Ser Val Leu Gly Pro Ala Gly Glu Gly Pro
    930                 935                 940

Ser Ala Glu Val Thr Ala Arg Thr Glu Ser Pro Arg Val Pro Ser Ile
945                 950                 955                 960

Glu Leu Arg Val Val Asp Thr Ser Ile Asp Ser Val Thr Leu Ala Trp
                965                 970                 975

Thr Pro Val Ser Arg Ala Ser Ser Tyr Ile Leu Ser Trp Arg Pro Leu
            980                 985                 990

Arg Gly Pro Gly Gln Glu Val Pro Gly Ser Pro Gln Thr Leu Pro Gly
        995                 1000                1005
```

```
Ile Ser Ser Ser Gln Arg Val Thr Gly Leu Glu Pro Gly Val Ser Tyr
    1010                1015                1020

Ile Phe Ser Leu Thr Pro Val Leu Asp Gly Val Arg Gly Pro Glu Ala
1025                1030                1035                1040

Ser Val Thr Gln Thr Pro Val Cys Pro Arg Gly Leu Ala Asp Val Val
                1045                1050                1055

Phe Leu Pro His Ala Thr Gln Asp Asn Ala His Arg Ala Glu Ala Thr
            1060                1065                1070

Arg Arg Val Leu Glu Arg Leu Val Leu Ala Leu Gly Pro Leu Gly Pro
        1075                1080                1085

Gln Ala Val Gln Val Gly Leu Leu Ser Tyr Ser His Arg Pro Ser Pro
    1090                1095                1100

Leu Phe Pro Leu Asn Gly Ser His Asp Leu Gly Ile Ile Leu Gln Arg
1105                1110                1115                1120

Ile Arg Asp Met Pro Tyr Met Asp Pro Ser Gly Asn Asn Leu Gly Thr
                1125                1130                1135

Ala Val Val Thr Ala His Arg Tyr Met Leu Ala Pro Asp Ala Pro Gly
            1140                1145                1150

Arg Arg Gln His Val Pro Gly Val Met Val Leu Leu Val Asp Glu Pro
        1155                1160                1165

Leu Arg Gly Asp Ile Phe Ser Pro Ile Arg Glu Ala Gln Ala Ser Gly
    1170                1175                1180

Leu Asn Val Val Met Leu Gly Met Ala Gly Ala Asp Pro Glu Gln Leu
1185                1190                1195                1200

Arg Arg Leu Ala Pro Gly Met Asp Ser Val Gln Thr Phe Phe Ala Val
                1205                1210                1215

Asp Asp Gly Pro Ser Leu Asp Gln Ala Val Ser Gly Leu Ala Thr Ala
            1220                1225                1230

Leu Cys Gln Ala Ser Phe Thr Thr Gln Pro Arg Pro Glu Pro Cys Pro
        1235                1240                1245

Val Tyr Cys Pro Lys Gly Gln Lys Gly Glu Pro Gly Glu Met Gly Leu
    1250                1255                1260

Arg Gly Gln Val Gly Pro Pro Gly Asp Pro Gly Leu Pro Gly Arg Thr
1265                1270                1275                1280

Gly Ala Pro Gly Pro Gln Gly Pro Pro Gly Ser Ala Thr Ala Lys Gly
                1285                1290                1295

Glu Arg Gly Phe Pro Gly Ala Asp Gly Arg Pro Gly Ser Pro Gly Arg
            1300                1305                1310

Ala Gly Asn Pro Gly Thr Pro Gly Ala Pro Gly Leu Lys Gly Ser Pro
        1315                1320                1325

Gly Leu Pro Gly Pro Arg Gly Asp Pro Gly Glu Arg Gly Pro Arg Gly
    1330                1335                1340

Pro Lys Gly Glu Pro Gly Ala Pro Gly Gln Val Ile Gly Gly Glu Gly
1345                1350                1355                1360

Pro Gly Leu Pro Gly Arg Lys Gly Asp Pro Gly Pro Ser Gly Pro Pro
                1365                1370                1375

Gly Pro Arg Gly Pro Leu Gly Asp Pro Gly Pro Arg Gly Pro Pro Gly
            1380                1385                1390

Leu Pro Gly Thr Ala Met Lys Gly Asp Lys Gly Asp Arg Gly Glu Arg
        1395                1400                1405

Gly Pro Pro Gly Pro Gly Glu Gly Gly Ile Ala Pro Gly Glu Pro Gly
    1410                1415                1420

Leu Pro Gly Leu Pro Gly Ser Pro Gly Pro Gln Gly Pro Val Gly Pro
```

-continued

```
1425                1430                1435                1440

Pro Gly Lys Lys Gly Glu Lys Gly Asp Ser Glu Asp Gly Ala Pro Gly
                1445                1450                1455

Leu Pro Gly Gln Pro Gly Ser Pro Gly Glu Gln Gly Pro Arg Gly Pro
            1460                1465                1470

Pro Gly Ala Ile Gly Pro Lys Gly Asp Arg Gly Phe Pro Gly Pro Leu
        1475                1480                1485

Gly Glu Ala Gly Glu Lys Gly Glu Arg Gly Pro Pro Gly Pro Ala Gly
    1490                1495                1500

Ser Arg Gly Leu Pro Gly Val Ala Gly Arg Pro Gly Ala Lys Gly Pro
1505                1510                1515                1520

Glu Gly Pro Pro Gly Pro Thr Gly Arg Gln Gly Glu Lys Gly Glu Pro
                1525                1530                1535

Gly Arg Pro Gly Asp Pro Ala Val Val Gly Pro Ala Val Ala Gly Pro
            1540                1545                1550

Lys Gly Glu Lys Gly Asp Val Gly Pro Ala Gly Pro Arg Gly Ala Thr
        1555                1560                1565

Gly Val Gln Gly Glu Arg Gly Pro Pro Gly Leu Val Leu Pro Gly Asp
    1570                1575                1580

Pro Gly Pro Lys Gly Asp Pro Gly Asp Arg Gly Pro Ile Gly Leu Thr
1585                1590                1595                1600

Gly Arg Ala Gly Pro Pro Gly Asp Ser Gly Pro Pro Gly Glu Lys Gly
                1605                1610                1615

Asp Pro Gly Arg Pro Gly Pro Pro Gly Pro Val Gly Pro Arg Gly Arg
            1620                1625                1630

Asp Gly Glu Val Gly Glu Lys Gly Asp Glu Gly Pro Pro Gly Asp Pro
        1635                1640                1645

Gly Leu Pro Gly Lys Ala Gly Glu Arg Gly Leu Arg Gly Ala Pro Gly
    1650                1655                1660

Val Arg Gly Pro Val Gly Glu Lys Gly Asp Gln Gly Asp Pro Gly Glu
1665                1670                1675                1680

Asp Gly Arg Asn Gly Ser Pro Gly Ser Ser Gly Pro Lys Gly Asp Arg
                1685                1690                1695

Gly Glu Pro Gly Pro Pro Gly Pro Pro Gly Arg Leu Val Asp Thr Gly
            1700                1705                1710

Pro Gly Ala Arg Glu Lys Gly Glu Pro Gly Asp Arg Gly Gln Glu Gly
        1715                1720                1725

Pro Arg Gly Pro Lys Gly Asp Pro Gly Leu Pro Gly Ala Pro Gly Glu
    1730                1735                1740

Arg Gly Ile Glu Gly Phe Arg Gly Pro Pro Gly Pro Gln Gly Asp Pro
1745                1750                1755                1760

Gly Val Arg Gly Pro Ala Gly Glu Lys Gly Asp Arg Gly Pro Pro Gly
                1765                1770                1775

Leu Asp Gly Arg Ser Gly Leu Asp Gly Lys Pro Gly Ala Ala Gly Pro
            1780                1785                1790

Ser Gly Pro Asn Gly Ala Ala Gly Lys Ala Gly Asp Pro Gly Arg Asp
        1795                1800                1805

Gly Leu Pro Gly Leu Arg Gly Glu Gln Gly Leu Pro Gly Pro Ser Gly
    1810                1815                1820

Pro Pro Gly Leu Pro Gly Lys Pro Gly Glu Asp Gly Lys Pro Gly Leu
1825                1830                1835                1840

Asn Gly Lys Asn Gly Glu Pro Gly Asp Pro Gly Glu Asp Gly Arg Lys
                1845                1850                1855
```

```
Gly Glu Lys Gly Asp Ser Gly Ala Ser Gly Arg Glu Gly Arg Asp Gly
            1860                1865                1870

Pro Lys Gly Glu Arg Gly Ala Pro Gly Ile Leu Gly Pro Gln Gly Pro
        1875                1880                1885

Pro Gly Leu Pro Gly Pro Val Gly Pro Pro Gly Gln Gly Phe Pro Gly
    1890                1895                1900

Val Pro Gly Gly Thr Gly Pro Lys Gly Asp Arg Gly Glu Thr Gly Ser
1905                1910                1915                1920

Lys Gly Glu Gln Gly Leu Pro Gly Glu Arg Gly Leu Arg Gly Glu Pro
                1925                1930                1935

Gly Ser Val Pro Asn Val Asp Arg Leu Leu Glu Thr Ala Gly Ile Lys
            1940                1945                1950

Ala Ser Ala Leu Arg Glu Ile Val Glu Thr Trp Asp Glu Ser Ser Gly
        1955                1960                1965

Ser Phe Leu Pro Val Pro Glu Arg Arg Arg Gly Pro Lys Gly Asp Ser
    1970                1975                1980

Gly Glu Gln Gly Pro Pro Gly Lys Glu Gly Pro Ile Gly Phe Pro Gly
1985                1990                1995                2000

Glu Arg Gly Leu Lys Gly Asp Arg Gly Asp Pro Gly Pro Gln Gly Pro
                2005                2010                2015

Pro Gly Leu Ala Leu Gly Glu Arg Gly Pro Pro Gly Pro Ser Gly Leu
            2020                2025                2030

Ala Gly Glu Pro Gly Lys Pro Gly Ile Pro Gly Leu Pro Gly Arg Ala
        2035                2040                2045

Gly Gly Val Gly Glu Ala Gly Arg Pro Gly Glu Arg Gly Glu Arg Gly
    2050                2055                2060

Glu Lys Gly Glu Arg Gly Glu Gln Gly Arg Asp Gly Pro Pro Gly Leu
2065                2070                2075                2080

Pro Gly Thr Pro Gly Pro Pro Gly Pro Pro Gly Pro Lys Val Ser Val
                2085                2090                2095

Asp Glu Pro Gly Pro Gly Leu Ser Gly Glu Gln Gly Pro Pro Gly Leu
            2100                2105                2110

Lys Gly Ala Lys Gly Glu Pro Gly Ser Asn Gly Asp Gln Gly Pro Lys
        2115                2120                2125

Gly Asp Arg Gly Val Pro Gly Ile Lys Gly Asp Arg Gly Glu Pro Gly
    2130                2135                2140

Pro Arg Gly Gln Asp Gly Asn Pro Gly Leu Pro Gly Glu Arg Gly Met
2145                2150                2155                2160

Ala Gly Pro Glu Gly Lys Pro Gly Leu Gln Gly Pro Arg Gly Pro Pro
                2165                2170                2175

Gly Pro Val Gly Gly His Gly Asp Pro Gly Pro Pro Gly Ala Pro Gly
            2180                2185                2190

Leu Ala Gly Pro Ala Gly Pro Gln Gly Pro Ser Gly Leu Lys Gly Glu
        2195                2200                2205

Pro Gly Glu Thr Gly Pro Pro Gly Arg Gly Leu Thr Gly Pro Thr Gly
    2210                2215                2220

Ala Val Gly Leu Pro Gly Pro Pro Gly Pro Ser Gly Leu Val Gly Pro
2225                2230                2235                2240

Gln Gly Ser Pro Gly Leu Pro Gly Gln Val Gly Glu Thr Gly Lys Pro
                2245                2250                2255

Gly Ala Pro Gly Arg Asp Gly Ala Ser Gly Lys Asp Gly Asp Arg Gly
            2260                2265                2270
```

-continued

Ser Pro Gly Val Pro Gly Ser Pro Gly Leu Pro Gly Pro Val Gly Pro
2275 2280 2285

Lys Gly Glu Pro Gly Pro Thr Gly Ala Pro Gly Gln Ala Val Val Gly
2290 2295 2300

Leu Pro Gly Ala Lys Gly Glu Lys Gly Ala Pro Gly Gly Leu Ala Gly
2305 2310 2315 2320

Asp Leu Val Gly Glu Pro Gly Ala Lys Gly Asp Arg Gly Leu Pro Gly
2325 2330 2335

Pro Arg Gly Glu Lys Gly Glu Ala Gly Arg Ala Gly Glu Pro Gly Asp
2340 2345 2350

Pro Gly Glu Asp Gly Gln Lys Gly Ala Pro Gly Pro Lys Gly Phe Lys
2355 2360 2365

Gly Asp Pro Gly Val Gly Val Pro Gly Ser Pro Gly Pro Pro Gly Pro
2370 2375 2380

Pro Gly Val Lys Gly Asp Leu Gly Leu Pro Gly Leu Pro Gly Ala Pro
2385 2390 2395 2400

Gly Val Val Gly Phe Pro Gly Gln Thr Gly Pro Arg Gly Glu Met Gly
2405 2410 2415

Gln Pro Gly Pro Ser Gly Glu Arg Gly Leu Ala Gly Pro Pro Gly Arg
2420 2425 2430

Glu Gly Ile Pro Gly Pro Leu Gly Pro Pro Gly Pro Pro Gly Ser Val
2435 2440 2445

Gly Pro Pro Gly Ala Ser Gly Leu Lys Gly Asp Lys Gly Asp Pro Gly
2450 2455 2460

Val Gly Leu Pro Gly Pro Arg Gly Glu Arg Gly Glu Pro Gly Ile Arg
2465 2470 2475 2480

Gly Glu Asp Gly Arg Pro Gly Gln Glu Gly Pro Arg Gly Leu Thr Gly
2485 2490 2495

Pro Pro Gly Ser Arg Gly Glu Arg Gly Glu Lys Gly Asp Val Gly Ser
2500 2505 2510

Ala Gly Leu Lys Gly Asp Lys Gly Asp Ser Ala Val Ile Leu Gly Pro
2515 2520 2525

Pro Gly Pro Arg Gly Ala Lys Gly Asp Met Gly Glu Arg Gly Pro Arg
2530 2535 2540

Gly Leu Asp Gly Asp Lys Gly Pro Arg Gly Asp Asn Gly Asp Pro Gly
2545 2550 2555 2560

Asp Lys Gly Ser Lys Gly Glu Pro Gly Asp Lys Gly Ser Ala Gly Leu
2565 2570 2575

Pro Gly Leu Arg Gly Leu Leu Gly Pro Gln Gly Gln Pro Gly Ala Ala
2580 2585 2590

Gly Ile Pro Gly Asp Pro Gly Ser Pro Gly Lys Asp Gly Val Pro Gly
2595 2600 2605

Ile Arg Gly Glu Lys Gly Asp Val Gly Phe Met Gly Pro Arg Gly Leu
2610 2615 2620

Lys Gly Glu Arg Gly Val Lys Gly Ala Cys Gly Leu Asp Gly Glu Lys
2625 2630 2635 2640

Gly Asp Lys Gly Glu Ala Gly Pro Pro Gly Arg Pro Gly Leu Ala Gly
2645 2650 2655

His Lys Gly Glu Met Gly Glu Pro Gly Val Pro Gly Gln Ser Gly Ala
2660 2665 2670

Pro Gly Lys Glu Gly Leu Ile Gly Pro Lys Gly Asp Arg Gly Phe Asp
2675 2680 2685

Gly Gln Pro Gly Pro Lys Gly Asp Gln Gly Glu Lys Gly Glu Arg Gly 2690 2695 2700

Thr Pro Gly Ile Gly Gly Phe Pro Gly Pro Ser Gly Asn Asp Gly Ser
2705 2710 2715 2720

Ala Gly Pro Pro Gly Pro Pro Gly Ser Val Gly Pro Arg Gly Pro Glu
2725 2730 2735

Gly Leu Gln Gly Gln Lys Gly Glu Arg Gly Pro Pro Gly Glu Arg Val
2740 2745 2750

Val Gly Ala Pro Gly Val Pro Gly Ala Pro Gly Glu Arg Gly Glu Gln
2755 2760 2765

Gly Arg Pro Gly Pro Ala Gly Pro Arg Gly Glu Lys Gly Glu Ala Ala
2770 2775 2780

Leu Thr Glu Asp Asp Ile Arg Gly Phe Val Arg Gln Glu Met Ser Gln
2785 2790 2795 2800

His Cys Ala Cys Gln Gly Gln Phe Ile Ala Ser Gly Ser Arg Pro Leu
2805 2810 2815

Pro Ser Tyr Ala Ala Asp Thr Ala Gly Ser Gln Leu His Ala Val Pro
2820 2825 2830

Val Leu Arg Val Ser His Ala Glu Glu Glu Glu Arg Val Pro Pro Glu
2835 2840 2845

Asp Asp Glu Tyr Ser Glu Tyr Ser Glu Tyr Ser Val Glu Glu Tyr Gln
2850 2855 2860

Asp Pro Glu Ala Pro Trp Asp Ser Asp Asp Pro Cys Ser Leu Pro Leu
2865 2870 2875 2880

Asp Glu Gly Ser Cys Thr Ala Tyr Thr Leu Arg Trp Tyr His Arg Ala
2885 2890 2895

Val Thr Gly Ser Thr Glu Ala Cys His Pro Phe Val Tyr Gly Gly Cys
2900 2905 2910

Gly Gly Asn Ala Asn Arg Phe Gly Thr Arg Glu Ala Cys Glu Arg Arg
2915 2920 2925

Cys Pro Pro Arg Val Val Gln Ser Gln Gly Thr Gly Thr Ala Gln Asp
2930 2935 2940

<210> SEQ ID NO 21
<211> LENGTH: 1497
<212> TYPE: PRT
<213> ORGANISM: Homo sapiens

<400> SEQUENCE: 21

Met Asp Val Thr Lys Lys Asn Lys Arg Asp Gly Thr Glu Val Thr Glu
1 5 10 15

Arg Ile Val Thr Glu Thr Val Thr Thr Arg Leu Thr Ser Leu Pro Pro
20 25 30

Lys Gly Gly Thr Ser Asn Gly Tyr Ala Lys Thr Ala Ser Leu Gly Gly
35 40 45

Gly Ser Arg Leu Glu Lys Gln Ser Leu Thr His Gly Ser Ser Gly Tyr
50 55 60

Ile Asn Ser Thr Gly Ser Thr Arg Gly His Ala Ser Thr Ser Ser Tyr
65 70 75 80

Arg Arg Ala His Ser Pro Ala Ser Thr Leu Pro Asn Ser Pro Gly Ser
85 90 95

Thr Phe Glu Arg Lys Thr His Val Thr Arg His Ala Tyr Glu Gly Ser
100 105 110

Ser Ser Gly Asn Ser Ser Pro Glu Tyr Pro Arg Lys Glu Phe Ala Ser
115 120 125

```
Ser Ser Thr Arg Gly Arg Ser Gln Thr Arg Glu Ser Glu Ile Arg Val
    130                 135                 140

Arg Leu Gln Ser Ala Ser Pro Ser Thr Arg Trp Thr Glu Leu Asp Asp
145                 150                 155                 160

Val Lys Arg Leu Leu Lys Gly Ser Arg Ser Ala Ser Val Ser Pro Thr
                165                 170                 175

Arg Asn Ser Ser Asn Thr Leu Pro Ile Pro Lys Lys Gly Thr Val Glu
            180                 185                 190

Thr Lys Ile Val Thr Ala Ser Ser Gln Ser Val Ser Gly Thr Tyr Asp
        195                 200                 205

Ala Thr Ile Leu Asp Ala Asn Leu Pro Ser His Val Trp Ser Ser Thr
    210                 215                 220

Leu Pro Ala Gly Ser Ser Met Gly Thr Tyr His Asn Asn Met Thr Thr
225                 230                 235                 240

Gln Ser Ser Ser Leu Leu Asn Thr Asn Ala Tyr Ser Ala Gly Ser Val
                245                 250                 255

Phe Gly Val Pro Asn Asn Met Ala Ser Cys Ser Pro Thr Leu His Pro
            260                 265                 270

Gly Leu Ser Thr Ser Ser Ser Val Phe Gly Met Gln Asn Asn Leu Ala
        275                 280                 285

Pro Ser Leu Thr Thr Leu Ser His Gly Thr Thr Thr Thr Ser Thr Ala
    290                 295                 300

Tyr Gly Val Lys Lys Asn Met Pro Gln Ser Pro Ala Ala Val Asn Thr
305                 310                 315                 320

Gly Val Ser Thr Ser Ala Ala Cys Thr Thr Ser Val Gln Ser Asp Asp
                325                 330                 335

Leu Leu His Lys Asp Cys Lys Phe Leu Ile Leu Glu Lys Asp Asn Thr
            340                 345                 350

Pro Ala Lys Lys Glu Met Glu Leu Leu Ile Met Thr Lys Asp Ser Gly
        355                 360                 365

Lys Val Phe Thr Ala Ser Pro Ala Ser Ile Ala Ala Thr Ser Phe Ser
    370                 375                 380

Glu Asp Thr Leu Lys Lys Glu Lys Gln Ala Ala Tyr Asn Ala Asp Ser
385                 390                 395                 400

Gly Leu Lys Ala Glu Ala Asn Gly Asp Leu Lys Thr Val Ser Thr Lys
                405                 410                 415

Gly Lys Thr Thr Thr Ala Asp Ile His Ser Tyr Gly Ser Ser Gly Gly
            420                 425                 430

Gly Gly Ser Gly Gly Gly Gly Gly Val Gly Gly Ala Gly Gly Gly Pro
        435                 440                 445

Trp Gly Pro Ala Pro Ala Trp Cys Pro Cys Gly Ser Cys Cys Ser Trp
    450                 455                 460

Trp Lys Trp Leu Leu Gly Leu Leu Leu Thr Trp Leu Leu Leu Leu Gly
465                 470                 475                 480

Leu Leu Phe Gly Leu Ile Ala Leu Ala Glu Glu Val Arg Lys Leu Lys
                485                 490                 495

Ala Arg Val Asp Glu Leu Glu Arg Ile Arg Arg Ser Ile Leu Pro Tyr
            500                 505                 510

Gly Asp Ser Met Asp Arg Ile Glu Lys Asp Arg Leu Gln Gly Met Ala
        515                 520                 525

Pro Ala Ala Gly Ala Asp Leu Asp Lys Ile Gly Leu His Ser Asp Ser
    530                 535                 540

Gln Glu Glu Leu Trp Met Phe Val Arg Lys Lys Leu Met Met Glu Gln
```

-continued

```
545                 550                 555                 560

Glu Asn Gly Asn Leu Arg Gly Ser Pro Gly Pro Lys Gly Asp Met Gly
                565                 570                 575

Ser Pro Gly Pro Lys Gly Asp Arg Gly Phe Pro Gly Thr Pro Gly Ile
            580                 585                 590

Pro Gly Pro Leu Gly His Pro Gly Pro Gln Gly Pro Lys Gly Gln Lys
        595                 600                 605

Gly Ser Val Gly Asp Pro Gly Met Glu Gly Pro Met Gly Gln Arg Gly
    610                 615                 620

Arg Glu Gly Pro Met Gly Pro Arg Gly Glu Ala Gly Pro Pro Gly Ser
625                 630                 635                 640

Gly Glu Lys Gly Glu Arg Gly Ala Ala Gly Glu Pro Gly Pro His Gly
                645                 650                 655

Pro Pro Gly Val Pro Gly Ser Val Gly Pro Lys Gly Ser Ser Gly Ser
            660                 665                 670

Pro Gly Pro Gln Gly Pro Pro Gly Pro Val Gly Leu Gln Gly Leu Arg
        675                 680                 685

Gly Glu Val Gly Leu Pro Gly Val Lys Gly Asp Lys Gly Pro Met Gly
    690                 695                 700

Pro Pro Gly Pro Lys Gly Asp Gln Gly Glu Lys Gly Pro Arg Gly Leu
705                 710                 715                 720

Thr Gly Glu Pro Gly Met Arg Gly Leu Pro Gly Ala Val Gly Glu Pro
                725                 730                 735

Gly Ala Lys Gly Ala Met Gly Pro Ala Gly Pro Asp Gly His Gln Gly
            740                 745                 750

Pro Arg Gly Glu Gln Gly Leu Thr Gly Met Pro Gly Ile Arg Gly Pro
        755                 760                 765

Pro Gly Pro Ser Gly Asp Pro Gly Lys Pro Gly Leu Thr Gly Pro Gln
    770                 775                 780

Gly Pro Gln Gly Leu Pro Gly Thr Pro Gly Arg Pro Gly Ile Lys Gly
785                 790                 795                 800

Glu Pro Gly Ala Pro Gly Lys Ile Val Thr Ser Glu Gly Ser Ser Met
                805                 810                 815

Leu Thr Val Pro Gly Pro Pro Gly Pro Pro Gly Ala Met Gly Pro Pro
            820                 825                 830

Gly Pro Pro Gly Ala Pro Gly Pro Ala Gly Pro Ala Gly Leu Pro Gly
        835                 840                 845

His Gln Glu Val Leu Asn Leu Gln Gly Pro Pro Gly Pro Pro Gly Pro
    850                 855                 860

Arg Gly Pro Pro Gly Pro Ser Ile Pro Gly Pro Pro Gly Pro Arg Gly
865                 870                 875                 880

Pro Pro Gly Glu Gly Leu Pro Gly Pro Pro Gly Pro Pro Gly Ser Phe
                885                 890                 895

Leu Ser Asn Ser Glu Thr Phe Leu Ser Gly Pro Pro Gly Pro Pro Gly
            900                 905                 910

Pro Pro Gly Pro Lys Gly Asp Gln Gly Pro Pro Gly Pro Arg Gly His
        915                 920                 925

Gln Gly Glu Gln Gly Leu Pro Gly Phe Ser Thr Ser Gly Ser Ser Ser
    930                 935                 940

Phe Gly Leu Asn Leu Gln Gly Pro Pro Gly Pro Pro Gly Pro Gln Gly
945                 950                 955                 960

Pro Lys Gly Asp Lys Gly Asp Pro Gly Val Pro Gly Ala Leu Gly Ile
                965                 970                 975
```

-continued

```
Pro Ser Gly Pro Ser Glu Gly Gly Ser Ser Ser Thr Met Tyr Val Ser
            980                 985                 990

Gly Pro Pro Gly Pro Pro Gly Pro Pro Gly Pro Pro Gly Ser Ile Ser
        995                 1000                1005

Ser Ser Gly Gln Glu Ile Gln Gln Tyr Ile Ser Glu Tyr Met Gln Ser
    1010                1015                1020

Asp Ser Ile Arg Ser Tyr Leu Ser Gly Val Gln Gly Pro Pro Gly Pro
1025                1030                1035                1040

Pro Gly Pro Pro Gly Pro Val Thr Thr Ile Thr Gly Glu Thr Phe Asp
                1045                1050                1055

Tyr Ser Glu Leu Ala Ser His Val Val Ser Tyr Leu Arg Thr Ser Gly
            1060                1065                1070

Tyr Gly Val Ser Leu Phe Ser Ser Ser Ile Ser Ser Glu Asp Ile Leu
        1075                1080                1085

Ala Val Leu Gln Arg Asp Asp Val Arg Gln Tyr Leu Arg Gln Tyr Leu
    1090                1095                1100

Met Gly Pro Arg Gly Pro Pro Gly Pro Pro Gly Ala Ser Gly Asp Gly
1105                1110                1115                1120

Ser Leu Leu Ser Leu Asp Tyr Ala Glu Leu Ser Ser Arg Ile Leu Ser
                1125                1130                1135

Tyr Met Ser Ser Ser Gly Ile Ser Ile Gly Leu Pro Gly Pro Pro Gly
            1140                1145                1150

Pro Pro Gly Leu Pro Gly Thr Ser Tyr Glu Glu Leu Leu Ser Leu Leu
        1155                1160                1165

Arg Gly Ser Glu Phe Arg Gly Ile Val Gly Pro Pro Gly Pro Pro Gly
    1170                1175                1180

Pro Pro Gly Ile Pro Gly Asn Val Trp Ser Ser Ile Ser Val Glu Asp
1185                1190                1195                1200

Leu Ser Ser Tyr Leu His Thr Ala Gly Leu Ser Phe Ile Pro Gly Pro
                1205                1210                1215

Pro Gly Pro Pro Gly Pro Pro Gly Pro Arg Gly Pro Pro Gly Val Ser
            1220                1225                1230

Gly Ala Leu Ala Thr Tyr Ala Ala Glu Asn Ser Asp Ser Phe Arg Ser
        1235                1240                1245

Glu Leu Ile Ser Tyr Leu Thr Ser Pro Asp Val Arg Ser Phe Ile Val
    1250                1255                1260

Gly Pro Pro Gly Pro Pro Gly Pro Gln Gly Pro Pro Gly Asp Ser Arg
1265                1270                1275                1280

Leu Leu Ser Thr Asp Ala Ser His Ser Arg Gly Ser Ser Ser Ser Ser
                1285                1290                1295

His Ser Ser Ser Val Arg Arg Gly Ser Ser Tyr Ser Ser Ser Met Ser
            1300                1305                1310

Thr Gly Gly Gly Gly Ala Gly Ser Leu Gly Ala Gly Gly Ala Phe Gly
        1315                1320                1325

Glu Ala Ala Gly Asp Arg Gly Pro Tyr Gly Thr Asp Ile Gly Pro Gly
    1330                1335                1340

Gly Gly Tyr Gly Ala Ala Ala Glu Gly Gly Met Tyr Ala Gly Asn Gly
1345                1350                1355                1360

Gly Leu Leu Gly Ala Asp Phe Ala Gly Asp Leu Asp Tyr Asn Glu Leu
                1365                1370                1375

Ala Val Arg Val Ser Glu Ser Met Gln Arg Gln Gly Leu Leu Gln Gly
            1380                1385                1390
```

```
Met Ala Tyr Thr Val Gln Gly Pro Pro Gly Gln Pro Gly Pro Gln Gly
        1395                1400                1405

Pro Pro Gly Ile Ser Lys Val Phe Ser Ala Tyr Ser Asn Val Thr Ala
    1410                1415                1420

Asp Leu Met Asp Phe Phe Gln Thr Tyr Gly Ala Ile Gln Gly Pro Pro
1425                1430                1435                1440

Gly Gln Lys Gly Glu Met Gly Thr Pro Gly Pro Lys Gly Asp Arg Gly
                1445                1450                1455

Pro Ala Gly Pro Pro Gly His Pro Gly Pro Pro Gly Pro Arg Gly His
            1460                1465                1470

Lys Gly Glu Lys Gly Asp Lys Gly Asp Gln Val Tyr Ala Gly Arg Arg
        1475                1480                1485

Arg Arg Arg Ser Ile Ala Val Lys Pro
    1490                1495
```

<210> SEQ ID NO 22
<211> LENGTH: 148
<212> TYPE: DNA
<213> ORGANISM: Artificial Sequence
<220> FEATURE:
<223> OTHER INFORMATION: Synthetic Construct

<400> SEQUENCE: 22

```
gaattcgtcg attcggttgc agcatttaaa gcggttgaca actttaaaag aaggaaaaag     60

aaggttgaag aaaagggtgt agtaagtaag tataagtaca gaccggagaa gtacgccggt    120

cctgattcgt ttaatttgaa agaagaaa                                       148
```

<210> SEQ ID NO 23
<211> LENGTH: 491
<212> TYPE: DNA
<213> ORGANISM: Artificial Sequence
<220> FEATURE:
<223> OTHER INFORMATION: Synthetic Construct

<400> SEQUENCE: 23

```
gttattttcc accatattgc cgtcttttgg caatgtgagg gcccggaaac ctggccctgt     60

cttcttgacg agcattccta ggggtctttc ccctctcgcc aaaggaatgc aaggtctgtt    120

gaatgtcgtg aaggaagcag ttcctctgga agcttcttga agacaaacaa cgtctgtagc    180

gaccctttgc aggcagcgga acccccacc tggcgacagg tgcctctgcg gccaaaagcc    240

acgtgtataa gatacacctg caaaggcggc acaaccccag tgccacgttg tgagttggat    300

agttgtggaa agagtcaaat ggctcacctc aagcgtattc aacaaggggc tgaaggatgc    360

ccagaaggta ccccattgta tgggatctga tctggggcct cggtgcacat gctttacatg    420

tgtttagtcg aggttaaaaa gcgtctaggc cccccgaacc acggggacgt ggttttcctt    480

tgaaaaacac g                                                         491
```

<210> SEQ ID NO 24
<211> LENGTH: 75
<212> TYPE: DNA
<213> ORGANISM: Artificial Sequence
<220> FEATURE:
<223> OTHER INFORMATION: Synthetic Construct

<400> SEQUENCE: 24

```
agggccaaga ggggcagcgg cgagggcagg ggcagcctgc tgacctgcgg cgacgtggag     60

gagaaccccg gcccc                                                      75
```

<210> SEQ ID NO 25
<211> LENGTH: 66
<212> TYPE: DNA
<213> ORGANISM: Artificial Sequence
<220> FEATURE:
<223> OTHER INFORMATION: Synthetic Construct

<400> SEQUENCE: 25
ggaagcggag ctactaactt cagcctgctg aagcaggctg gagacgtgga ggagaaccct 60
ggacct 66

<210> SEQ ID NO 26
<211> LENGTH: 69
<212> TYPE: DNA
<213> ORGANISM: Artificial Sequence
<220> FEATURE:
<223> OTHER INFORMATION: Synthetic Construct

<400> SEQUENCE: 26
ggaagcggac agtgtactaa ttatgctctc ttgaaattgg ctggagatgt tgagagcaac 60
cctggacct 69

<210> SEQ ID NO 27
<211> LENGTH: 75
<212> TYPE: DNA
<213> ORGANISM: Artificial Sequence
<220> FEATURE:
<223> OTHER INFORMATION: Synthetic Construct

<400> SEQUENCE: 27
ggaagcggag tgaaacagac tttgaatttt gaccttctca agttggcggg agacgtggag 60
tccaaccctg gacct 75

<210> SEQ ID NO 28
<211> LENGTH: 25
<212> TYPE: PRT
<213> ORGANISM: Artificial Sequence
<220> FEATURE:
<223> OTHER INFORMATION: Synthetic Construct

<400> SEQUENCE: 28

Arg Ala Lys Arg Gly Ser Gly Glu Gly Arg Gly Ser Leu Leu Thr Cys
1 5 10 15

Gly Asp Val Glu Glu Asn Pro Gly Pro
20 25

<210> SEQ ID NO 29
<211> LENGTH: 22
<212> TYPE: PRT
<213> ORGANISM: Artificial Sequence
<220> FEATURE:
<223> OTHER INFORMATION: Synthetic Construct

<400> SEQUENCE: 29

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 30
<211> LENGTH: 23
<212> TYPE: PRT
<213> ORGANISM: Artificial Sequence
<220> FEATURE:
<223> OTHER INFORMATION: Synthetic Construct

<400> SEQUENCE: 30

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 31
<211> LENGTH: 25
<212> TYPE: PRT
<213> ORGANISM: Artificial Sequence
<220> FEATURE:
<223> OTHER INFORMATION: Synthetic Construct

<400> SEQUENCE: 31

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 32
<211> LENGTH: 8565
<212> TYPE: DNA
<213> ORGANISM: Artificial Sequence
<220> FEATURE:
<223> OTHER INFORMATION: Synthetic Construct

<400> SEQUENCE: 32
atgttcagct tcgtggacct gagactgctg ctgctcctgg ctgctacagc cctgctgaca 60
cacggacaag aggaaggcca ggtcgaagga caggacgagg acatccctcc tatcacctgt 120
gtgcagaacg gcctgagata ccacgaccgg gatgtgtgga agcccgagcc ttgcagaatc 180
tgcgtgtgcg acaatggcaa ggtgctgtgc gacgacgtga tctgcgacga gacaaagaat 240
tgccctggcg ccgaagtgcc tgagggcgaa tgttgtcctg tgtgccctga tggcagcgag 300
agccccacag atcaagagac aacaggcgtg gaaggcccca agggcgatac aggacctaga 360
ggtcctagag gacctgccgg acctcctggc agagatggaa ttcctggaca gcctggactg 420
cccggaccac ctggacctcc agggcctcca ggtccaccag gactcggagg aaattttgcc 480
ccacagctga gctacggcta cgacgagaaa agcacaggcg gcatctctgt gcctggacct 540
atgggacctt ctggcccaag aggacttcct ggtcctcctg gtgctccagg acctcaggga 600
tttcaaggac caccaggcga acctggcgaa ccaggcgcta gtggtccaat gggaccaaga 660
ggccctcctg gccaccagg caaaaatggc gacgatggcg aagccggaaa gcctggaagg 720
cctggcgaaa gaggcccgcc aggaccgcaa ggcgctagag ggttgcctgg aactgcagga 780
ctgcctggca tgaagggcca cagaggcttt tctggactgg atggcgctaa gggcgacgct 840
ggaccagcag gacctaaagg cgagcctgga tctcctggcg agaatggtgc acctggacag 900
atgggtccca gaggattgcc aggcgagaga ggtagacctg gcgctccggg accagccggt 960
gctagaggaa atgatggcgc aacaggtgct gctgggcctc ctggaccaac cggaccagct 1020
ggcccacctg gatttccagg cgctgttgga gcaaagggcg aagcaggccc acaaggacct 1080
aggggatctg aaggtcctca gggcgttaga ggcgagccag ggccacctgg gcctgccggt 1140
gcagctggac ctgctggaaa ccctggtgct gatggacagc caggtgccaa aggtgctaat 1200
ggcgcccctg gaattgccgg cgctccaggt tttcccggcg caagagggcc atctggacct 1260

-continued

```
caaggcccag gcggacctcc gggtcctaag ggaaatagcg gagagccagg cgctcctggg   1320
agtaaaggcg atactggcgc aaaaggcgaa cccggacctg tgggagttca aggacctcct   1380
ggaccagctg gcgaggaagg caaaagaggc gctaggggag aaccaggacc aacagggctc   1440
cctggtccac ctggcgagcg cggaggacct ggatctagag gattccctgg cgcagatggc   1500
gtggccggac caaaaggacc tgcaggcgaa aggggatcac caggtcctgc aggccctaag   1560
ggttctccag gcgaggctgg cagacccggc gaagctggac tcccaggtgc taagggactg   1620
acaggctcac caggatctcc cggaccagac ggaaaaacag gacctccagg accggcagga   1680
caggatggta gacccggtcc tcctggaccg cctggtgcaa gaggacaagc tggcgtgatg   1740
ggctttcctg gaccaaaagg tgcagccggc gaacctggaa aagcaggcga gaggggagtt   1800
cccggacctc caggtgctgt tggacctgcc ggaaaagatg gcgaagctgg tgcacaaggt   1860
cctccagggc cagccggacc agccggcgag agaggcgaac aaggaccagc cggatctcca   1920
ggatttcagg gactgccagg gcctgctggc ccgcctggcg aggcagggaa gccaggcgaa   1980
cagggtgttc ctggcgatct tggagcccct ggtcctagcg gagctagagg cgaaagagga   2040
tttcctggcg aaaggggcgt tcagggtcca ccgggaccag ctggaccaag ggtgcaaat    2100
ggtgccccag gcaatgacgg tgctaaaggc gacgcaggcg ccccaggtgc tcctggatct   2160
caaggcgcac ctggacttca gggaatgcct ggcgaacggg gagctgctgg acttcccggt   2220
ccaaaaggcg ataggggaga tgctggtcct aagggcgctg atggctctcc tggaaaggat   2280
ggcgtcagag gcctgacagg cccaattggc cctccgggac ctgctggcgc tccaggcgat   2340
aagggcgaat ctggacctag tggacccgct ggtcctacag gtgctagggg agccccaggc   2400
gaccggggag agcctggtcc accaggacct gctggatttg ctggacctcc tggcgctgat   2460
ggtcaacctg gtgctaaggg cgagccaggc gacgctggtg caaaaggcga cgctggtcca   2520
cctggaccgg ccggacctgc tgggccgcca ggacctattg gaaatgttgg tgcccctggc   2580
gccaaaggcg caagaggatc tgctggccca ccaggcgcta caggattccc aggtgccgct   2640
ggaagagttg gaccaccggg gccaagtgga aatgctggac caccgggacc gccaggacca   2700
gccggcaaag aaggtggaaa aggccctagg ggcgaaactg gccctgcagg caggccaggc   2760
gaagtgggcc ctccaggacc tccggggcct gccggcgaaa aaggatctcc aggcgcagat   2820
ggacccgcag gcgctcccgg aacaccaggt ccacagggaa ttgctggaca aaggggagtt   2880
gtcggcctgc caggacagag gggagagaga ggttttccag gactccctgg gccaagcgga   2940
gaacctggca aacagggacc atctggtgcc agcggagaga gagggccacc aggaccaatg   3000
ggtcctccag gattggcagg gcctcctggc gaatctggta gagaaggtgc tccaggcgcc   3060
gagggatctc ctggacgtga tggttctcct ggcgccaagg gcgatagagg cgaaacaggc   3120
ccagctggac ctccaggcgc acccggcgct ccaggcgcac caggacctgt tggccctgct   3180
ggaaaatctg gcgacagagg cgaaactgga cccgcaggac cagccggacc tgttggacct   3240
gtgggtgcta gaggacccgc tggaccacaa ggtcctagag gcgacaaggg cgaaacaggc   3300
gagcaaggcg acagaggcat caagggacac agaggattca gcggactgca gggaccacca   3360
gggccgcctg gaagtcccgg cgagcaggga ccaagcggag ctagtggtcc cgccggacct   3420
agaggaccac ctggttctgc tggtgcaccc ggaaaggacg gactgaatgg gctccccgga   3480
cctattgggc cacctggacc tagaggaaga acaggcgacg caggaccagt tggaccacct   3540
gggccacctg gaccgcctgg tcctcctgga cctccttctg ccggattcga cttcagcttc   3600
ctgcctcagc ctcctcaaga gaaggcccat gacggcggca gatattacag agccgacgac   3660
```

-continued

```
gccaacgtcg tgcgggacag agatctggaa gtggacacca cactgaagtc cctgtctcag   3720
cagatcgaga acatcagaag ccccgagggc agcagaaaga accctgccag aacctgtcgg   3780
gacctgaaga tgtgccacag cgattggaag tctggcgagt actggatcga ccccaaccag   3840
ggctgcaacc tggatgccat caaggtgttc tgcaacatgg aaaccggcga gacatgcgtg   3900
taccccacac agccatctgt ggctcagaag aactggtaca tcagcaagaa ccccaaggac   3960
aagcggcacg tttggttcgg cgagagcatg accgatggct tccagtttga gtatggcggc   4020
cagggctctg accctgccga tgttgctatc cagctgacct tcctgcggct gatgtctaca   4080
gaggccagcc agaacatcac ctaccactgc aagaacagcg tggcctacat ggatcagcag   4140
accggcaacc tgaagaaggc actgctgctt cagggcagca acgagatcga gatcagagcc   4200
gagggcaaca gccggttcac ctacagcgtg acagtggatg gctgcaccag ccatacaggc   4260
gcttggggca agaccgtgat cgagtacaag accaccaaga ccagcagact gcccatcatc   4320
gatgtggccc ctctggatgt tggggcaccc gatcaagagt tcggcttcga tgtgggccca   4380
gtgtgcttcc tgagggccaa gaggggcagc ggcgagggca ggggcagcct gctgacctgc   4440
ggcgacgtgg aggagaaccc cggcccccctg agcttcgtgg acaccagaac actgctgctg   4500
ctggccgtga cactgtgtct ggccacttgt cagagcctgc aagaggaaac agtgcggaaa   4560
ggacctgccg gcgatagagg acctagaggc gaaagaggtc ctcctggacc tcctggtaga   4620
gatggcgagg atggacctac aggaccacct ggtccaccag gacctccagg gcctcctggc   4680
cttggaggaa attttgccgc tcagtacgat ggcaaaggcg tcggacttgg ccctggacct   4740
atgggactta tgggcccaag aggaccacca ggtgctgcag gcgctccagg accacaagga   4800
tttcaaggac cagctggcga gcctggcgaa cctggacaaa caggtcctgc tggtgctaga   4860
ggaccagccg ggccacctgg aaaagctggc gaagatgggc accctggaaa gcctggtaga   4920
cccggcgaaa ggggtgttgt tggacctcaa ggcgccagag gctttcctgg aacacctgga   4980
ctgcctggct tcaagggcat cagaggccac aatggcctgg acggactgaa aggacaacct   5040
ggtgctcctg gcgtgaaagg cgaaccaggc gcacctggcg aaaatggcac accaggacaa   5100
accggcgcaa gaggacttcc tggcgagaga ggaagagttg gagccccagg tccagcaggc   5160
gcacgaggat ctgatggatc tgtgggacct gttggccctg ccggacctat tggaagtgct   5220
ggccctcctg gatttcctgg cgcacccgga ccaaagggcg aaattggagc tgtgggaaac   5280
gccggacctg caggcccagc tggaccaagg ggagaagttg gattgcctgg actgagcgga   5340
ccagttgggc caccagggaa tcctggtgcc aatggactga caggcgctaa aggtgcagct   5400
ggccttccag gcgttgccgg tgcaccagga ctgccaggac caagaggtat ccctggtcct   5460
gttggagctg ctggcgctac gggtgccaga ggacttgttg gagaacctgg gccagccgga   5520
tctaagggcg agtctggaaa caagggcgag ccaggatctg ctggtccaca aggcccgcct   5580
ggaccatcag gcgaagaagg caaacgaggc cctaatggcg aagccggtag tgccgggcct   5640
cctggaccac caggccttag aggatctcct ggctctagag gattgccagg cgctgatggt   5700
agagcaggcg ttatgggtcc acctggatca agaggcgctt ctggccctgc tggcgttaga   5760
ggtccaaatg gcgacgctgg cagaccaggc gagcccggtc ttatggggcc tagagggttg   5820
cctggaagcc ctggcaatat cggcccagcc ggaaaagaag gccctgttgg actccctggc   5880
atcgacggta gacctggacc aatcggaccc gcaggcgcta ggggagagcc tggaaatatt   5940
ggcttccctg ggcctaaagg ccccacaggc gatcctggaa agaacggcga taagggccat   6000
```

-continued

```
gctggactcg ctggtgcaag gggagcacct ggacctgacg gaaacaatgg tgctcaaggg   6060
ccgcctgggc cacaaggtgt tcaaggtgga aaaggcgagc agggcccacc tgggcctcca   6120
ggcttccaag gacttcccgg accatctggg ccagcaggcg aagttggaaa gcctggcgaa   6180
agaggactgc acggcgagtt tggcttgccg ggtcctgccg gtccacgggg agagagaggc   6240
cctccaggcg aatctggcgc cgcaggacct actggcccta tcggaagcag aggacctagt   6300
ggacctccag gacctgatgg caacaaaggc gaacctggtg ttgtgggcgc tgtgggaaca   6360
gctggacctt ctggtccttc tggattgccc ggcgagcgcg gagcagctgg tattcctggt   6420
ggcaaaggcg aaaagggcga gcctggactc agaggcgaga tcggcaatcc cggacgagat   6480
ggcgctagag gcgccccagg tgcagttggt gccccgggac ctgctggcgc aacaggcgac   6540
agaggcgagg ctggtgccgc tggtcctgcc gggccagccg gtcctagagg aagtccaggc   6600
gagaggggcg aagtgggacc cgctggaccc aatggatttg ctgggcccgc tggcgctgct   6660
ggtcaacctg gcgccaaagg cgagcgggga gctaaaggtc ctaaaggcga gaatggcgtc   6720
gtgggcccta ctggaccagt gggagcagca ggccccgcag gtcctaacgg accacctgga   6780
ccagctgggt ctagaggcga cggcggaccg cctggaatga caggttttcc aggcgccgct   6840
ggaagaacag gtcctccagg accatctggc atctctggtc caccagggcc acctggtcct   6900
gctggaaaag aaggactgag aggccctagg ggcgatcagg gtccagttgg aagaaccggc   6960
gaagtcggag ctgtcggccc accaggtttt gccggcgaaa aaggccctag cggagaagct   7020
ggaactgcag gaccgccggg aactcccggt cctcaaggat tgcttggcgc ccctggaatt   7080
ctgggactgc ccggtagtcg cggagaacgt ggactcccag gtgttgctgg cgccgtcgga   7140
gaaccgggac cacttggaat tgctggacca cctggtgcaa gaggtccacc tggtgcagtt   7200
ggaagtcctg gcgttaacgg tgctccaggc gaagccggca gagatggaaa tcccggcaat   7260
gatggcccgc ctgggagaga tggacagcct ggacataagg gcgagcgagg ctacccaggc   7320
aatattggac ctgtcggcgc agccggtgct cccggacctc atggtccagt cggtccagcc   7380
gggaagcacg gaaatagggg agaaacagga ccctccggtc ctgttggccc agctggcgca   7440
gttggaccaa gaggcccatc cggacctcag ggaatccgcg gagataaggg cgaacctggc   7500
gagaagggac ctagaggact gcctgggctg aaaggccata acggactgca aggcctgcca   7560
ggcattgctg gccatcatgg cgatcaaggt gcacccggta gtgtgggtcc cgccggaccg   7620
aggggtcccg ctggtccatc tggacccgcc ggaaaagatg gcagaacagg acatcctggc   7680
acagtggggc ctgccggaat tagaggccca cagggacatc aaggccccgc tgggccgcca   7740
ggacctccgg gaccgccagg gccaccaggc gttagtggcg gaggatacga tttcggctac   7800
gacggcgact tctacagagc cgaccagcct agatctgccc ctagcctgag gcctaaggac   7860
tacgaagtgg acgccacact gaagtccctg aacaaccaga tcgagacact gctgacccct   7920
gagggcagca gaaagaaccc tgccagaacc tgcagggacc tgagactgtc tcaccccgaa   7980
tggtcctccg gctactactg gatcgacccc aatcagggct gcaccatgga cgccatcaag   8040
gtgtactgcg acttcagcac cggcgagaca tgcatcagag cccagcctga gaacatcccc   8100
gccaagaact ggtacagaag cagcaaggac aagaaacacg tgtggctggg cgagacaatc   8160
aacgccggca gccagttcga gtacaacgtg gaaggcgtga ccagcaaaga gatggccaca   8220
cagctggctt tcatgagact gctggccaat tacgccagcc agaacatcac ctaccactgc   8280
aagaacagca ttgcctacat ggacgaggaa accggcaacc tgaagaaagc cgtgatcctg   8340
cagggctcta acgacgtgga actggtggcc gagggcaaca gcagattcac ctacaccgtg   8400
```

ctggtggacg gctgcagcaa aaagaccaac gagtggggca agaccatcat cgagtataag 8460
accaacaagc ccagcagact gcccttcctg gatatcgccc cactggatat tggaggcgcc 8520
gaccaagagt tctttgtgga catcggcccc gtgtgcttca agtga 8565

<210> SEQ ID NO 33
<211> LENGTH: 8644
<212> TYPE: DNA
<213> ORGANISM: Artificial Sequence
<220> FEATURE:
<223> OTHER INFORMATION: Synthetic Construct

<400> SEQUENCE: 33
atgttcagct tcgtggacct gagactgctg ctgctcctgg ctgctacagc cctgctgaca 60
cacggacaag aggaaggcca ggtcgaagga caggacgagg acatccctcc tatcacctgt 120
gtgcagaacg gcctgagata ccacgaccgg gatgtgtgga agcccgagcc ttgcagaatc 180
tgcgtgtgcg acaatggcaa ggtgctgtgc gacgacgtga tctgcgacga gacaaagaat 240
tgccctggcg ccgaagtgcc tgagggcgaa tgttgtcctg tgtgccctga tggcagcgag 300
agccccacag atcaagagac aacaggcgtg gaaggcccca agggcgatac aggacctaga 360
ggtcctagag gacctgccgg acctcctggc agagatggaa ttcctggaca gcctggactg 420
cccggaccac ctggacctcc agggcctcca ggtccaccag gactcggagg aaattttgcc 480
ccacagctga gctacggcta cgacgagaaa agcacaggcg gcatctctgt gcctggacct 540
atgggacctt ctggcccaag aggacttcct ggtcctcctg gtgctccagg acctcaggga 600
tttcaaggac caccaggcga acctggcgaa ccaggcgcta gtggtccaat gggaccaaga 660
ggccctcctg ggccaccagg caaaaatggc gacgatggcg aagccggaaa gcctggaagg 720
cctggcgaaa gaggcccgcc aggaccgcaa ggcgctagag ggttgcctgg aactgcagga 780
ctgcctggca tgaagggcca cagaggcttt tctggactgg atggcgctaa gggcgacgct 840
ggaccagcag gacctaaagg cgagcctgga tctcctggcg agaatggtgc acctggacag 900
atgggtccca gaggattgcc aggcgagaga ggtagacctg gcgctccggg accagccggt 960
gctagaggaa atgatggcgc aacaggtgct gctgggcctc ctggaccaac cggaccagct 1020
ggcccacctg gatttccagg cgctgttgga gcaaagggcg aagcaggccc acaaggacct 1080
aggggatctg aaggtcctca gggcgttaga ggcgagccag ggccacctgg gcctgccggt 1140
gcagctggac ctgctggaaa ccctggtgct gatggacagc caggtgccaa aggtgctaat 1200
ggcgcccctg gaattgccgg cgctccaggt tttcccggcg caagagggcc atctggacct 1260
caaggcccag gcggacctcc gggtcctaag ggaaatagcg gagagccagg cgctcctggg 1320
agtaaaggcg atactggcgc aaaaggcgaa cccggacctg tgggagttca aggacctcct 1380
ggaccagctg gcgaggaagg caaaagaggc gctaggggag aaccaggacc aacagggctc 1440
cctggtccac ctggcgagcg cggaggacct ggatctagag gattccctgg cgcagatggc 1500
gtggccggac caaaaggacc tgcaggcgaa aggggatcac caggtcctgc aggccctaag 1560
ggttctccag gcgaggctgg cagacccggc gaagctggac tcccaggtgc taagggactg 1620
acaggctcac caggatctcc cggaccagac ggaaaaacag gacctccagg accggcagga 1680
caggatggta gacccggtcc tcctggaccg cctggtgcaa gaggacaagc tggcgtgatg 1740
ggctttcctg gaccaaaagg tgcagccggc gaacctggaa aagcaggcga gaggggagtt 1800
cccggacctc caggtgctgt tggacctgcc ggaaaagatg gcgaagctgg tgcacaaggt 1860

```
cctccagggc cagccggacc agccggcgag agaggcgaac aaggaccagc cggatctcca   1920
ggatttcagg gactgccagg gcctgctggc ccgcctggcg aggcagggaa gccaggcgaa   1980
cagggtgttc ctggcgatct tggagcccct ggtcctagcg gagctagagg cgaaagagga   2040
tttcctggcg aaaggggcgt tcagggtcca ccgggaccag ctggaccaag ggtgcaaat    2100
ggtgccccag gcaatgacgg tgctaaaggc gacgcaggcg ccccaggtgc tcctggatct   2160
caaggcgcac ctggacttca gggaatgcct ggcgaacggg gagctgctgg acttcccggt   2220
ccaaaaggcg ataggggaga tgctggtcct aagggcgctg atggctctcc tggaaaggat   2280
ggcgtcagag gcctgacagg cccaattggc cctccgggac ctgctggcgc tccaggcgat   2340
aagggcgaat ctggacctag tggacccgct ggtcctacag gtgctagggg agccccaggc   2400
gaccggggag agcctggtcc accaggacct gctggatttg ctggacctcc tggcgctgat   2460
ggtcaacctg gtgctaaggg cgagccaggc gacgctggtg caaaaggcga cgctggtcca   2520
cctggaccgg ccggacctgc tgggccgcca ggacctattg gaaatgttgg tgcccctggc   2580
gccaaaggcg caagaggatc tgctggccca ccaggcgcta caggattccc aggtgccgct   2640
ggaagagttg gaccaccggg gccaagtgga aatgctggac caccgggacc gccaggacca   2700
gccggcaaag aaggtggaaa aggccctagg ggcgaaactg gccctgcagg caggccaggc   2760
gaagtgggcc ctccaggacc tccggggcct gccggcgaaa aaggatctcc aggcgcagat   2820
ggacccgcag gcgctcccgg aacaccaggt ccacagggaa ttgctggaca aaggggagtt   2880
gtcggcctgc caggacagag gggagagaga ggttttccag gactccctgg gccaagcgga   2940
gaacctggca aacagggacc atctggtgcc agcggagaga gagggccacc aggaccaatg   3000
ggtcctccag gattggcagg gcctcctggc gaatctggta gagaaggtgc tccaggcgcc   3060
gagggatctc ctggacgtga tggttctcct ggcgccaagg gcgatagagg cgaaacaggc   3120
ccagctggac ctccaggcgc acccggcgct ccaggcgcac caggacctgt tggccctgct   3180
ggaaaatctg gcgacagagg cgaaactgga cccgcaggac cagccggacc tgttggacct   3240
gtgggtgcta gaggacccgc tggaccacaa ggtcctagag gcgacaaggg cgaaacaggc   3300
gagcaaggcg acagaggcat caagggacac agaggattca gcggactgca gggaccacca   3360
gggccgcctg gaagtcccgg cgagcaggga ccaagcggag ctagtggtcc cgccggacct   3420
agaggaccac ctggttctgc tggtgcaccc ggaaaggacg gactgaatgg gctcccgga    3480
cctattgggc cacctggacc tagaggaaga acaggcgacg caggaccagt tggaccacct   3540
gggccacctg gaccgcctgg tcctcctgga cctccttctg ccggattcga cttcagcttc   3600
ctgcctcagc ctcctcaaga gaaggcccat gacggcggca gatattacag agccgacgac   3660
gccaacgtcg tgcgggacag agatctggaa gtggacacca cactgaagtc cctgtctcag   3720
cagatcgaga acatcagaag ccccgagggc agcagaaaga accctgccag aacctgtcgg   3780
gacctgaaga tgtgccacag cgattggaag tctggcgagt actggatcga ccccaaccag   3840
ggctgcaacc tggatgccat caaggtgttc tgcaacatgg aaaccggcga gacatgcgtg   3900
taccccacac agccatctgt ggctcagaag aactggtaca tcagcaagaa ccccaaggac   3960
aagcggcacg tttggttcgg cgagagcatg accgatggct tccagtttga gtatggcggc   4020
cagggctctg accctgccga tgttgctatc cagctgacct tcctgcggct gatgtctaca   4080
gaggccagcc agaacatcac ctaccactgc aagaacagcg tggcctacat ggatcagcag   4140
accggcaacc tgaagaaggc actgctgctt cagggcagca acgagatcga gatcagagcc   4200
gagggcaaca gccggttcac ctacagcgtg acagtggatg gctgcaccag ccatacaggc   4260
```

```
gcttggggca agaccgtgat cgagtacaag accaccaaga ccagcagact gcccatcatc   4320
gatgtggccc ctctggatgt tggggcaccc gatcaagagt tcggcttcga tgtgggccca   4380
gtgtgcttcc tgtaagaatt cgtcgattcg gttgcagcat ttaaagcggt tgacaacttt   4440
aaaagaagga aaaagaaggt tgaagaaaag ggtgtagtaa gtaagtataa gtacagaccg   4500
gagaagtacg ccggtcctga ttcgtttaat ttgaaagaag aaaatgctga gcttcgtgga   4560
caccagaaca ctgctgctgc tggccgtgac actgtgtctg gccacttgtc agagcctgca   4620
agaggaaaca gtgcggaaag gacctgccgg cgatagagga cctagaggcg aaagaggtcc   4680
tcctggacct cctggtagag atggcgagga tggacctaca ggaccacctg gtccaccagg   4740
acctccaggg cctcctggcc ttggaggaaa ttttgccgct cagtacgatg gcaaaggcgt   4800
cggacttggc cctggaccta tgggacttat gggcccaaga ggaccaccag gtgctgcagg   4860
cgctccagga ccacaaggat ttcaaggacc agctggcgag cctggcgaac ctggacaaac   4920
aggtcctgct ggtgctagag gaccagccgg gccacctgga aagctggcg aagatgggca   4980
ccctggaaag cctggtagac ccggcgaaag ggtgttgtt ggacctcaag gcgccagagg   5040
ctttcctgga acacctggac tgcctggctt caagggcatc agaggccaca atggcctgga   5100
cggactgaaa ggacaacctg gtgctcctgg cgtgaaaggc gaaccaggcg cacctggcga   5160
aaatggcaca ccaggacaaa ccggcgcaag aggacttcct ggcgagagag gaagagttgg   5220
agccccaggt ccagcaggcg cacgaggatc tgatggatct gtgggacctg ttggccctgc   5280
cggacctatt ggaagtgctg gccctcctgg atttcctggc gcacccggac caaagggcga   5340
aattggagct gtgggaaacg ccggacctgc aggcccagct ggaccaaggg gagaagttgg   5400
attgcctgga ctgagcggac cagttgggcc accagggaat cctggtgcca atggactgac   5460
aggcgctaaa ggtgcagctg gccttccagg cgttgccggt gcaccaggac tgccaggacc   5520
aagaggtatc cctggtcctg ttggagctgc tggcgctacg ggtgccagag gacttgttgg   5580
agaacctggg ccagccggat ctaagggcga gtctggaaac aagggcgagc caggatctgc   5640
tggtccacaa ggcccgcctg gaccatcagg cgaagaaggc aaacgaggcc ctaatggcga   5700
agccggtagt gccgggcctc ctggaccacc aggccttaga ggatctcctg gctctagagg   5760
attgccaggc gctgatggta gagcaggcgt tatgggtcca cctggatcaa gaggcgcttc   5820
tggccctgct ggcgttagag gtccaaatgg cgacgctggc agaccaggcg agcccggtct   5880
tatggggcct agagggttgc ctggaagccc tggcaatatc ggcccagccg gaaaagaagg   5940
ccctgttgga ctccctggca tcgacggtag acctggacca atcggacccg caggcgctag   6000
gggagagcct ggaaatattg gcttccctgg gcctaaaggc cccacaggcg atcctggaaa   6060
gaacggcgat aagggccatg ctggactcgc tggtgcaagg ggagcacctg gacctgacgg   6120
aaacaatggt gctcaagggc cgcctgggcc acaaggtgtt caaggtggaa aaggcgagca   6180
gggcccacct gggcctccag gcttccaagg acttcccgga ccatctgggc cagcaggcga   6240
agttggaaag cctggcgaaa gaggactgca cggcgagttt ggcttgccgg gtcctgccgg   6300
tccacgggga gagagaggcc ctccaggcga atctggcgcc gcaggaccta ctggccctat   6360
cggaagcaga ggacctagtg gacctccagg acctgatggc aacaaaggcg aacctggtgt   6420
tgtgggcgct gtgggaacag ctggaccttc tggtccttct ggattgcccg gcgagcgcgg   6480
agcagctggt attcctggtg gcaaaggcga aaagggcgag cctggactca gaggcgagat   6540
cggcaatccc ggacgagatg gcgctagagg cgccccaggt gcagttggtg ccccgggacc   6600
```

```
tgctggcgca acaggcgaca gaggcgaggc tggtgccgct ggtcctgccg ggccagccgg   6660

tcctagagga agtccaggcg agaggggcga agtgggaccc gctggaccca atggatttgc   6720

tgggcccgct ggcgctgctg gtcaacctgg cgccaaaggc gagcggggag ctaaaggtcc   6780

taaaggcgag aatggcgtcg tgggccctac tggaccagtg ggagcagcag gccccgcagg   6840

tcctaacgga ccacctggac cagctgggtc tagaggcgac ggcggaccgc ctggaatgac   6900

aggttttcca ggcgccgctg gaagaacagg tcctccagga ccatctggca tctctggtcc   6960

accagggcca cctggtcctg ctggaaaaga aggactgaga ggccctaggg gcgatcaggg   7020

tccagttgga agaaccggcg aagtcggagc tgtcggccca ccaggttttg ccggcgaaaa   7080

aggccctagc ggagaagctg gaactgcagg accgccggga actcccggtc ctcaaggatt   7140

gcttggcgcc cctggaattc tgggactgcc cggtagtcgc ggagaacgtg gactcccagg   7200

tgttgctggc gccgtcggag aaccgggacc acttggaatt gctggaccac ctggtgcaag   7260

aggtccacct ggtgcagttg gaagtcctgg cgttaacggt gctccaggcg aagccggcag   7320

agatggaaat cccggcaatg atggcccgcc tgggagagat ggacagcctg gacataaggg   7380

cgagcgaggc tacccaggca atattggacc tgtcggcgca gccggtgctc ccggacctca   7440

tggtccagtc ggtccagccg ggaagcacgg aaatagggga gaaacaggac cctccggtcc   7500

tgttggccca gctggcgcag ttggaccaag aggcccatcc ggacctcagg gaatccgcgg   7560

agataagggc gaacctggcg agaagggacc tagaggactg cctgggctga aaggccataa   7620

cggactgcaa ggcctgccag gcattgctgg ccatcatggc gatcaaggtg cacccggtag   7680

tgtgggtccc gccggaccga ggggtcccgc tggtccatct ggacccgccg gaaaagatgg   7740

cagaacagga catcctggca cagtggggcc tgccggaatt agaggcccac agggacatca   7800

aggccccgct gggccgccag gacctccggg accgccaggg ccaccaggcg ttagtggcgg   7860

aggatacgat ttcggctacg acggcgactt ctacagagcc gaccagccta gatctgcccc   7920

tagcctgagg cctaaggact acgaagtgga cgccacactg aagtccctga acaaccagat   7980

cgagacactg ctgacccctg agggcagcag aaagaaccct gccagaacct gcagggacct   8040

gagactgtct caccccgaat ggtcctccgg ctactactgg atcgacccca atcagggctg   8100

caccatggac gccatcaagg tgtactgcga cttcagcacc ggcgagacat gcatcagagc   8160

ccagcctgag aacatccccg ccaagaactg gtacagaagc agcaaggaca agaaacacgt   8220

gtggctgggc gagacaatca acgccggcag ccagttcgag tacaacgtgg aaggcgtgac   8280

cagcaaagag atggccacac agctggcttt catgagactg ctggccaatt acgccagcca   8340

gaacatcacc taccactgca agaacagcat tgcctacatg gacgaggaaa ccggcaacct   8400

gaagaaagcc gtgatcctgc agggctctaa cgacgtggaa ctggtggccg agggcaacag   8460

cagattcacc tacaccgtgc tggtggacgg ctgcagcaaa aagaccaacg agtggggcaa   8520

gaccatcatc gagtataaga ccaacaagcc cagcagactg cccttcctgg atatcgcccc   8580

actggatatt ggaggcgccg accaagagtt ctttgtggac atcggccccg tgtgcttcaa   8640

gtga                                                                8644
```

<210> SEQ ID NO 34
<211> LENGTH: 8987
<212> TYPE: DNA
<213> ORGANISM: Artificial Sequence
<220> FEATURE:
<223> OTHER INFORMATION: Synthetic Construct

<400> SEQUENCE: 34

-continued

```
atgttcagct tcgtggacct gagactgctg ctgctcctgg ctgctacagc cctgctgaca     60
cacggacaag aggaaggcca ggtcgaagga caggacgagg acatccctcc tatcacctgt    120
gtgcagaacg gcctgagata ccacgaccgg gatgtgtgga agcccgagcc ttgcagaatc    180
tgcgtgtgcg acaatggcaa ggtgctgtgc gacgacgtga tctgcgacga gacaaagaat    240
tgccctggcg ccgaagtgcc tgagggcgaa tgttgtcctg tgtgccctga tggcagcgag    300
agccccacag atcaagagac aacaggcgtg gaaggcccca agggcgatac aggacctaga    360
ggtcctagag gacctgccgg acctcctggc agagatggaa ttcctggaca gcctggactg    420
cccggaccac ctggacctcc agggcctcca ggtccaccag gactcggagg aaattttgcc    480
ccacagctga gctacggcta cgacgagaaa agcacaggcg gcatctctgt gcctggacct    540
atgggacctt ctggcccaag aggacttcct ggtcctcctg gtgctccagg acctcaggga    600
tttcaaggac caccaggcga acctggcgaa ccaggcgcta gtggtccaat gggaccaaga    660
ggccctcctg gccaccaggg caaaaatggc gacgatggcg aagccggaaa gcctggaagg    720
cctggcgaaa gaggcccgcc aggaccgcaa ggcgctagag ggttgcctgg aactgcagga    780
ctgcctggca tgaagggcca cagaggcttt tctggactgg atggcgctaa gggcgacgct    840
ggaccagcag gacctaaagg cgagcctgga tctcctggcg agaatggtgc acctggacag    900
atgggtccca gaggattgcc aggcgagaga ggtagacctg gcgctccggg accagccggt    960
gctagaggaa atgatggcgc aacaggtgct gctgggcctc ctggaccaac cggaccagct   1020
ggcccacctg gatttccagg cgctgttgga gcaaagggcg aagcaggccc acaaggacct   1080
aggggatctg aaggtcctca gggcgttaga ggcgagccag ggccacctgg gcctgccggt   1140
gcagctggac ctgctggaaa ccctggtgct gatggacagc caggtgccaa aggtgctaat   1200
ggcgcccctg gaattgccgg cgctccaggt tttcccggcg caagagggcc atctggacct   1260
caaggcccag gcggacctcc gggtcctaag ggaaatagcg gagagccagg cgctcctggg   1320
agtaaaggcg atactggcgc aaaaggcgaa cccggacctg tgggagttca aggacctcct   1380
ggaccagctg gcgaggaagg caaaagaggc gctaggggag aaccaggacc aacagggctc   1440
cctggtccac ctggcgagcg cggaggacct ggatctagag gattccctgg cgcagatggc   1500
gtggccggac caaaaggacc tgcaggcgaa aggggatcac caggtcctgc aggccctaag   1560
ggttctccag gcgaggctgg cagacccggc gaagctggac tcccaggtgc taagggactg   1620
acaggctcac caggatctcc cggaccagac ggaaaaacag gacctccagg accggcagga   1680
caggatggta gacccggtcc tcctggaccg cctggtgcaa gaggacaagc tggcgtgatg   1740
ggctttcctg gaccaaaagg tgcagccggc gaacctggaa aagcaggcga gaggggagtt   1800
cccggacctc caggtgctgt tggacctgcc ggaaaagatg gcgaagctgg tgcacaaggt   1860
cctccagggc cagccggacc agccggcgag agaggcgaac aaggaccagc cggatctcca   1920
ggatttcagg gactgccagg gcctgctggc ccgcctggcg aggcagggaa gccaggcgaa   1980
cagggtgttc ctggcgatct tggagcccct ggtcctagcg gagctagagg cgaaagagga   2040
tttcctggcg aaaggggcgt tcagggtcca ccgggaccag ctggaccaag ggtgcaaat   2100
ggtgccccag gcaatgacgg tgctaaaggc gacgcaggcg ccccaggtgc tcctggatct   2160
caaggcgcac ctggacttca gggaatgcct ggcgaacggg gagctgctgg acttcccggt   2220
ccaaaaggcg ataggggaga tgctggtcct aagggcgctg atggctctcc tggaaaggat   2280
ggcgtcagag gcctgacagg cccaattggc cctccgggac ctgctggcgc tccaggcgat   2340
```

aagggcgaat ctggacctag tggacccgct ggtcctacag gtgctagggg agccccaggc 2400
gaccggggag agcctggtcc accaggacct gctggatttg ctggacctcc tggcgctgat 2460
ggtcaacctg gtgctaaggg cgagccaggc gacgctggtg caaaaggcga cgctggtcca 2520
cctggaccgg ccggacctgc tgggccgcca ggacctattg gaaatgttgg tgcccctggc 2580
gccaaaggcg caagaggatc tgctggccca ccaggcgcta caggattccc aggtgccgct 2640
ggaagagttg gaccaccggg gccaagtgga aatgctggac caccgggacc gccaggacca 2700
gccggcaaag aaggtggaaa aggccctagg ggcgaaactg gccctgcagg caggccaggc 2760
gaagtgggcc ctccaggacc tccggggcct gccggcgaaa aaggatctcc aggcgcagat 2820
ggacccgcag gcgctcccgg aacaccaggt ccacagggaa ttgctggaca aaggggagtt 2880
gtcggcctgc caggacagag gggagagaga ggttttccag gactccctgg gccaagcgga 2940
gaacctggca aacagggacc atctggtgcc agcggagaga gagggccacc aggaccaatg 3000
ggtcctccag gattggcagg gcctcctggc gaatctggta gagaaggtgc tccaggcgcc 3060
gagggatctc ctggacgtga tggttctcct ggcgccaagg gcgatagagg cgaaacaggc 3120
ccagctggac ctccaggcgc acccggcgct ccaggcgcac caggacctgt tggccctgct 3180
ggaaaatctg gcgacagagg cgaaactgga cccgcaggac cagccggacc tgttggacct 3240
gtgggtgcta gaggacccgc tggaccacaa ggtcctagag gcgacaaggg cgaaacaggc 3300
gagcaaggcg acagaggcat caagggacac agaggattca gcggactgca gggaccacca 3360
gggccgcctg gaagtcccgg cgagcaggga ccaagcggag ctagtggtcc cgccggacct 3420
agaggaccac ctggttctgc tggtgcaccc ggaaaggacg gactgaatgg gctccccgga 3480
cctattgggc cacctggacc tagaggaaga acaggcgacg caggaccagt tggaccacct 3540
gggccacctg gaccgcctgg tcctcctgga cctccttctg ccggattcga cttcagcttc 3600
ctgcctcagc ctcctcaaga gaaggcccat gacggcggca gatattacag agccgacgac 3660
gccaacgtcg tgcgggacag agatctggaa gtggacacca cactgaagtc cctgtctcag 3720
cagatcgaga acatcagaag ccccgagggc agcagaaaga accctgccag aacctgtcgg 3780
gacctgaaga tgtgccacag cgattggaag tctggcgagt actggatcga ccccaaccag 3840
ggctgcaacc tggatgccat caaggtgttc tgcaacatgg aaaccggcga gacatgcgtg 3900
taccccacac agccatctgt ggctcagaag aactggtaca tcagcaagaa ccccaaggac 3960
aagcggcacg tttggttcgg cgagagcatg accgatggct tccagtttga gtatggcggc 4020
cagggctctg accctgccga tgttgctatc cagctgacct tcctgcggct gatgtctaca 4080
gaggccagcc agaacatcac ctaccactgc aagaacagcg tggcctacat ggatcagcag 4140
accggcaacc tgaagaaggc actgctgctt cagggcagca acgagatcga gatcagagcc 4200
gagggcaaca gccggttcac ctacagcgtg acagtggatg gctgcaccag ccatacaggc 4260
gcttggggca agaccgtgat cgagtacaag accaccaaga ccagcagact gcccatcatc 4320
gatgtggccc ctctggatgt tggggcaccc gatcaagagt tcggcttcga tgtgggccca 4380
gtgtgcttcc tgtaagttat tttccaccat attgccgtct tttggcaatg tgagggcccg 4440
gaaacctggc cctgtcttct tgacgagcat tcctaggggt ctttcccctc tcgccaaagg 4500
aatgcaaggt ctgttgaatg tcgtgaagga agcagttcct ctggaagctt cttgaagaca 4560
aacaacgtct gtagcgaccc tttgcaggca gcggaacccc ccacctggcg acaggtgcct 4620
ctgcggccaa aagccacgtg tataagatac acctgcaaag gcggcacaac cccagtgcca 4680
cgttgtgagt tggatagttg tggaaagagt caaatggctc acctcaagcg tattcaacaa 4740

```
ggggctgaag gatgcccaga aggtacccca ttgtatggga tctgatctgg ggcctcggtg   4800
cacatgcttt acatgtgttt agtcgaggtt aaaaagcgtc taggcccccc gaaccacggg   4860
gacgtggttt tcctttgaaa aacacgatgc tgagcttcgt ggacaccaga acactgctgc   4920
tgctggccgt gacactgtgt ctggccactt gtcagagcct gcaagaggaa acagtgcgga   4980
aaggacctgc cggcgataga ggacctagag gcgaaagagg tcctcctgga cctcctggta   5040
gagatggcga ggatggacct acaggaccac ctggtccacc aggacctcca gggcctcctg   5100
gccttggagg aaattttgcc gctcagtacg atggcaaagg cgtcggactt ggccctggac   5160
ctatgggact tatgggccca agaggaccac caggtgctgc aggcgctcca ggaccacaag   5220
gatttcaagg accagctggc gagcctggcg aacctggaca aacaggtcct gctggtgcta   5280
gaggaccagc cgggccacct ggaaaagctg gcgaagatgg gcaccctgga aagcctggta   5340
gacccggcga aaggggtgtt gttggacctc aaggcgccag aggctttcct ggaacacctg   5400
gactgcctgg cttcaagggc atcagaggcc acaatggcct ggacggactg aaaggacaac   5460
ctggtgctcc tggcgtgaaa ggcgaaccag gcgcacctgg cgaaaatggc acaccaggac   5520
aaaccggcgc aagaggactt cctggcgaga gaggaagagt tggagcccca ggtccagcag   5580
gcgcacgagg atctgatgga tctgtgggac ctgttggccc tgccggacct attggaagtg   5640
ctggccctcc tggatttcct ggcgcacccg gaccaaaggg cgaaattgga gctgtgggaa   5700
acgccggacc tgcaggccca gctggaccaa ggggagaagt tggattgcct ggactgagcg   5760
gaccagttgg gccaccaggg aatcctggtg ccaatggact gacaggcgct aaaggtgcag   5820
ctggccttcc aggcgttgcc ggtgcaccag gactgccagg accaagaggt atccctggtc   5880
ctgttggagc tgctggcgct acgggtgcca gaggacttgt tggagaacct gggccagccg   5940
gatctaaggg cgagtctgga aacaagggcg agccaggatc tgctggtcca caaggcccgc   6000
ctggaccatc aggcgaagaa ggcaaacgag gccctaatgg cgaagccggt agtgccgggc   6060
ctcctggacc accaggcctt agaggatctc ctggctctag aggattgcca ggcgctgatg   6120
gtagagcagg cgttatgggt ccacctggat caagaggcgc ttctggccct gctggcgtta   6180
gaggtccaaa tggcgacgct ggcagaccag gcgagcccgg tcttatgggg cctagagggt   6240
tgcctggaag ccctggcaat atcggcccag ccggaaaaga aggccctgtt ggactccctg   6300
gcatcgacgg tagacctgga ccaatcggac ccgcaggcgc taggggagag cctggaaata   6360
ttggcttccc tgggcctaaa ggccccacag gcgatcctgg aaagaacggc gataagggcc   6420
atgctggact cgctggtgca aggggagcac ctggacctga cggaaacaat ggtgctcaag   6480
ggccgcctgg gccacaaggt gttcaaggtg gaaaaggcga gcagggccca cctgggcctc   6540
caggcttcca aggacttccc ggaccatctg ggccagcagg cgaagttgga aagcctggcg   6600
aaagaggact gcacggcgag tttggcttgc cgggtcctgc cggtccacgg ggagagagag   6660
gccctccagg cgaatctggc gccgcaggac ctactggccc tatcggaagc agaggaccta   6720
gtggacctcc aggacctgat ggcaacaaag gcgaacctgg tgttgtgggc gctgtgggaa   6780
cagctggacc ttctggtcct tctggattgc ccggcgagcg cggagcagct ggtattcctg   6840
gtggcaaagg cgaaaagggc gagcctggac tcagaggcga gatcggcaat cccggacgag   6900
atggcgctag aggcgcccca ggtgcagttg gtgccccggg acctgctggc gcaacaggcg   6960
acagaggcga ggctggtgcc gctggtcctg ccgggccagc cggtcctaga ggaagtccag   7020
gcgagagggg cgaagtggga cccgctggac ccaatggatt tgctgggccc gctggcgctg   7080
```

ctggtcaacc tggcgccaaa ggcgagcggg gagctaaagg tcctaaaggc gagaatggcg 7140
tcgtgggccc tactggacca gtgggagcag caggccccgc aggtcctaac ggaccacctg 7200
gaccagctgg gtctagaggc gacggcggac cgcctggaat gacaggtttt ccaggcgccg 7260
ctggaagaac aggtcctcca ggaccatctg gcatctctgg tccaccaggg ccacctggtc 7320
ctgctggaaa agaaggactg agaggcccta ggggcgatca gggtccagtt ggaagaaccg 7380
gcgaagtcgg agctgtcggc ccaccaggtt ttgccggcga aaaaggccct agcggagaag 7440
ctggaactgc aggaccgccg ggaactcccg gtcctcaagg attgcttggc gcccctggaa 7500
ttctgggact gcccggtagt cgcggagaac gtggactccc aggtgttgct ggcgccgtcg 7560
gagaaccggg accacttgga attgctggac cacctggtgc aagaggtcca cctggtgcag 7620
ttggaagtcc tggcgttaac ggtgctccag gcgaagccgg cagagatgga aatcccggca 7680
atgatggccc gcctgggaga gatggacagc ctggacataa gggcgagcga ggctacccag 7740
gcaatattgg acctgtcggc gcagccggtg ctcccggacc tcatggtcca gtcggtccag 7800
ccgggaagca cggaaatagg ggagaaacag gaccctccgg tcctgttggc ccagctggcg 7860
cagttggacc aagaggccca tccggacctc agggaatccg cggagataag ggcgaacctg 7920
gcgagaaggg acctagagga ctgcctgggc tgaaaggcca taacggactg caaggcctgc 7980
caggcattgc tggccatcat ggcgatcaag gtgcacccgg tagtgtgggt cccgccggac 8040
cgaggggtcc cgctggtcca tctggacccg ccggaaaaga tggcagaaca ggacatcctg 8100
gcacagtggg gcctgccgga attagaggcc cacagggaca tcaaggcccc gctgggccgc 8160
caggacctcc gggaccgcca gggccaccag gcgttagtgg cggaggatac gatttcggct 8220
acgacggcga cttctacaga gccgaccagc ctagatctgc ccctagcctg aggcctaagg 8280
actacgaagt ggacgccaca ctgaagtccc tgaacaacca gatcgagaca ctgctgaccc 8340
ctgagggcag cagaaagaac cctgccagaa cctgcaggga cctgagactg tctcaccccg 8400
aatggtcctc cggctactac tggatcgacc ccaatcaggg ctgcaccatg gacgccatca 8460
aggtgtactg cgacttcagc accggcgaga catgcatcag agcccagcct gagaacatcc 8520
ccgccaagaa ctggtacaga agcagcaagg acaagaaaca cgtgtggctg ggcgagacaa 8580
tcaacgccgg cagccagttc gagtacaacg tggaaggcgt gaccagcaaa gagatggcca 8640
cacagctggc tttcatgaga ctgctggcca attacgccag ccagaacatc acctaccact 8700
gcaagaacag cattgcctac atggacgagg aaaccggcaa cctgaagaaa gccgtgatcc 8760
tgcagggctc taacgacgtg gaactggtgg ccgagggcaa cagcagattc acctacaccg 8820
tgctggtgga cggctgcagc aaaaagacca acgagtgggg caagaccatc atcgagtata 8880
agaccaacaa gcccagcaga ctgcccttcc tggatatcgc ccccactggat attggaggcg 8940 ccgaccaaga gttctttgtg gacatcggcc ccgtgtgctt caagtga 8987

<210> SEQ ID NO 35
<211> LENGTH: 7434
<212> TYPE: DNA
<213> ORGANISM: Homo sapiens

<400> SEQUENCE: 35
atgcttaggg gtccggggcc cgggctgctg ctgctggccg tccagtgcct ggggacagcg 60
gtgccctcca cgggagcctc gaagagcaag aggcaggctc agcaaatggt tcagccccag 120
tccccggtgg ctgtcagtca aagcaagccc ggttgttatg acaatggaaa acactatcag 180
ataaatcaac agtgggagcg gacctaccta ggcaatgcgt tggtttgtac ttgttatgga 240

-continued

```
ggaagccgag gttttaactg cgagagtaaa cctgaagctg aagagacttg ctttgacaag    300
tacactggga acacttaccg agtgggtgac acttatgagc gtcctaaaga ctccatgatc    360
tgggactgta cctgcatcgg ggctgggcga gggagaataa gctgtaccat cgcaaaccgc    420
tgccatgaag gggtcagtc ctacaagatt ggtgacacct ggaggagacc acatgagact    480
ggtggttaca tgttagagtg tgtgtgtctt ggtaatggaa aaggagaatg gacctgcaag    540
cccatagctg agaagtgttt tgatcatgct gctgggactt cctatgtggt cggagaaacg    600
tgggagaagc cctaccaagg ctggatgatg gtagattgta cttgcctggg agaaggcagc    660
ggacgcatca cttgcacttc tagaaataga tgcaacgatc aggacacaag gacatcctat    720
agaattggag acacctggag caagaaggat aatcgaggaa acctgctcca gtgcatctgc    780
acaggcaacg gccgaggaga gtggaagtgt gagaggcaca cctctgtgca gaccacatcg    840
agcggatctg gccccttcac cgatgttcgt gcagctgttt accaaccgca gcctcacccc    900
cagcctcctc cctatggcca ctgtgtcaca gacagtggtg tggtctactc tgtggggatg    960
cagtggctga agacacaagg aaataagcaa atgctttgca cgtgcctggg caacggagtc   1020
agctgccaag agacagctgt aacccagact tacggtggca actcaaatgg agagccatgt   1080
gtcttaccat tcacctacaa tggcaggacg ttctactcct gcaccacaga agggcgacag   1140
gacggacatc tttggtgcag cacaacttcg aattatgagc aggaccagaa atactctttc   1200
tgcacagacc acactgtttt ggttcagact cgaggaggaa attccaatgg tgccttgtgc   1260
cacttcccct tcctatacaa caaccacaat tacactgatt gcacttctga gggcagaaga   1320
gacaacatga agtggtgtgg gaccacacag aactatgatg ccgaccagaa gtttgggttc   1380
tgccccatgg ctgcccacga ggaaatctgc acaaccaatg aaggggtcat gtaccgcatt   1440
ggagatcagt gggataagca gcatgacatg ggtcacatga tgaggtgcac gtgtgttggg   1500
aatggtcgtg gggaatggac atgcattgcc tactcgcagc ttcgagatca gtgcattgtt   1560
gatgacatca cttacaatgt gaacgacaca ttccacaagc gtcatgaaga ggggcacatg   1620
ctgaactgta catgcttcgg tcagggtcgg ggcaggtgga agtgtgatcc cgtcgaccaa   1680
tgccaggatt cagagactgg gacgttttat caaattggag attcatggga gaagtatgtg   1740
catggtgtca gataccagtg ctactgctat ggccgtggca ttggggagtg gcattgccaa   1800
cctttacaga cctatccaag ctcaagtggt cctgtcgaag tatttatcac tgagactccg   1860
agtcagccca actcccaccc catccagtgg aatgcaccac agccatctca catttccaag   1920
tacattctca ggtggagacc taaaaattct gtaggccgtt ggaaggaagc taccatacca   1980
ggccacttaa actcctacac catcaaaggc ctgaagcctg gtgtggtata cgagggccag   2040
ctcatcagca tccagcagta cggccaccaa gaagtgactc gctttgactt caccaccacc   2100
agcaccagca cacctgtgac cagcaacacc gtgacaggag agacgactcc cttttctcct   2160
cttgtggcca cttctgaatc tgtgaccgaa atcacagcca gtagctttgt ggtctcctgg   2220
gtctcagctt ccgacaccgt gtcgggattc cgggtggaat atgagctgag tgaggaggga   2280
gatgagccac agtacctgga tcttccaagc acagccactt ctgtgaacat ccctgacctg   2340
cttcctggcc gaaaatacat tgtaaatgtc tatcagatat ctgaggatgg ggagcagagt   2400
ttgatcctgt ctacttcaca aacaacagcg cctgatgccc ctcctgaccc gactgtggac   2460
caagttgatg acacctcaat tgttgttcgc tggagcagac cccaggctcc catcacaggg   2520
tacagaatag tctattcgcc atcagtagaa ggtagcagca cagaactcaa ccttcctgaa   2580
```

-continued

```
actgcaaact ccgtcaccct cagtgacttg caacctggtg ttcagtataa catcactatc   2640
tatgctgtgg aagaaaatca agaaagtaca cctgttgtca ttcaacaaga aaccactggc   2700
accccacgct cagatacagt gccctctccc agggacctgc agtttgtgga agtgacagac   2760
gtgaaggtca ccatcatgtg gacaccgcct gagagtgcag tgaccggcta ccgtgtggat   2820
gtgatccccg tcaacctgcc tggcgagcac gggcagaggc tgcccatcag caggaacacc   2880
tttgcagaag tcaccgggct gtcccctggg gtcacctatt acttcaaagt ctttgcagtg   2940
agccatggga gggagagcaa gcctctgact gctcaacaga caaccaaact ggatgctccc   3000
actaacctcc agtttgtcaa tgaaactgat tctactgtcc tggtgagatg gactccacct   3060
cgggcccaga taacaggata ccgactgacc gtgggcctta cccgaagagg acagcccagg   3120
cagtacaatg tgggtccctc tgtctccaag tacccactga ggaatctgca gcctgcatct   3180
gagtacaccg tatccctcgt ggccataaag ggcaaccaag agagccccaa agccactgga   3240
gtctttacca cactgcagcc tgggagctct attccacctt acaacaccga ggtgactgag   3300
accaccattg tgatcacatg gacgcctgct ccaagaattg gttttaagct gggtgtacga   3360
ccaagccagg gaggagaggc accacgagaa gtgacttcag actcaggaag catcgttgtg   3420
tccggcttga ctccaggagt agaatacgtc tacaccatcc aagtcctgag agatggacag   3480
gaaagagatg cgccaattgt aaacaaagtg gtgacaccat tgtctccacc aacaaacttg   3540
catctggagg caaaccctga cactggagtg ctcacagtct cctgggagag gagcaccacc   3600
ccagacatta ctggttatag aattaccaca acccctacaa acggccagca gggaaattct   3660
ttggaagaag tggtccatgc tgatcagagc tcctgcactt ttgataacct gagtcccggc   3720
ctggagtaca atgtcagtgt ttacactgtc aaggatgaca aggaaagtgt ccctatctct   3780
gataccatca tcccagaggt gccccaactc actgacctaa gctttgttga tataaccgat   3840
tcaagcatcg gcctgaggtg gaccccgcta aactcttcca ccattattgg gtaccgcatc   3900
acagtagttg cggcaggaga aggtatccct atttttgaag attttgtgga ctcctcagta   3960
ggatactaca cagtcacagg gctggagccg ggcattgact atgatatcag cgttatcact   4020
ctcattaatg gcggcgagag tgcccctact acactgacac aacaaacggc tgttcctcct   4080
cccactgacc tgcgattcac caacattggt ccagacacca tgcgtgtcac ctgggctcca   4140
cccccatcca ttgatttaac caacttcctg gtgcgttact cacctgtgaa aaatgaggaa   4200
gatgttgcag agttgtcaat ttctccttca gacaatgcag tggtcttaac aaatctcctg   4260
cctggtacag aatatgtagt gagtgtctcc agtgtctacg aacaacatga gagcacacct   4320
cttagaggaa gacagaaaac aggtcttgat tccccaactg gcattgactt ttctgatatt   4380
actgccaact cttttactgt gcactggatt gctcctcgag ccaccatcac tggctacagg   4440
atccgccatc atcccgagca cttcagtggg agacctcgag aagatcgggt gccccactct   4500
cggaattcca tcaccctcac caacctcact ccaggcacag agtatgtggt cagcatcgtt   4560
gctcttaatg gcagagagga aagtccctta ttgattggcc aacaatcaac agtttctgat   4620
gttccgaggg acctggaagt tgttgctgcg acccccacca gcctactgat cagctgggat   4680
gctcctgctg tcacagtgag atattacagg atcacttacg gagagacagg aggaaatagc   4740
cctgtccagg agttcactgt gcctgggagc aagtctacag ctaccatcag cggccttaaa   4800
cctggagttg attataccat cactgtgtat gctgtcactg gccgtggaga cagccccgca   4860
agcagcaagc caatttccat taattaccga acagaaattg acaaaccatc ccagatgcaa   4920
gtgaccgatg ttcaggacaa cagcattagt gtcaagtggc tgccttcaag ttccccctgtt   4980
```

-continued

```
actggttaca gagtaaccac cactcccaaa aatggaccag gaccaacaaa aactaaaact   5040
gcaggtccag atcaaacaga aatgactatt gaaggcttgc agcccacagt ggagtatgtg   5100
gttagtgtct atgctcagaa tccaagcgga gagagtcagc ctctggttca gactgcagta   5160
accaacattg atcgccctaa aggactggca ttcactgatg tggatgtcga ttccatcaaa   5220
attgcttggg aaagcccaca ggggcaagtt tccaggtaca gggtgaccta ctcgagccct   5280
gaggatggaa tccatgagct attccctgca cctgatggtg aagaagacac tgcagagctg   5340
caaggcctca gaccgggttc tgagtacaca gtcagtgtgg ttgccttgca cgatgatatg   5400
gagagccagc ccctgattgg aacccagtcc acagctattc ctgcaccaac tgacctgaag   5460
ttcactcagg tcacacccac aagcctgagc gcccagtgga caccacccaa tgttcagctc   5520
actggatatc gagtgcgggt gacccccaag gagaagaccg gaccaatgaa agaaatcaac   5580
cttgctcctg acagctcatc cgtggttgta tcaggactta tggtggccac caaatatgaa   5640
gtgagtgtct atgctcttaa ggacactttg acaagcagac cagctcaggg agttgtcacc   5700
actctggaga atgtcagccc accaagaagg gctcgtgtga cagatgctac tgagaccacc   5760
atcaccatta gctggagaac caagactgag acgatcactg gcttccaagt tgatgccgtt   5820
ccagccaatg gccagactcc aatccagaga accatcaagc cagatgtcag aagctacacc   5880
atcacaggtt tacaaccagg cactgactac aagatctacc tgtacacctt gaatgacaat   5940
gctcggagct cccctgtggt catcgacgcc tccactgcca ttgatgcacc atccaacctg   6000
cgtttcctgg ccaccacacc caattccttg ctggtatcat ggcagccgcc acgtgccagg   6060
attaccggct acatcatcaa gtatgagaag cctgggtctc ctcccagaga agtggtccct   6120
cggccccgcc ctggtgtcac agaggctact attactggcc tggaaccggg aaccgaatat   6180
acaatttatg tcattgccct gaagaataat cagaagagcg agcccctgat tggaaggaaa   6240
aagacagacg agcttcccca actggtaacc cttccacacc ccaatcttca tggaccagag   6300
atcttggatg ttccttccac agttcaaaag acccctttcg tcacccaccc tgggtatgac   6360
actggaaatg gtattcagct tcctggcact tctggtcagc aacccagtgt tgggcaacaa   6420
atgatctttg aggaacatgg ttttaggcgg accacaccgc ccacaacggc cacccccata   6480
aggcataggc caagaccata cccgccgaat gtaggtgagg aaatccaaat tggtcacatc   6540
cccagggaag atgtagacta tcacctgtac ccacacggtc cgggactcaa tccaaatgcc   6600
tctacaggac aagaagctct ctctcagaca accatctcat gggccccatt ccaggacact   6660
tctgagtaca tcatttcatg tcatcctgtt ggcactgatg aagaaccctt acagttcagg   6720
gttcctggaa cttctaccag tgccactctg acaggcctca ccagaggtgc cacctacaac   6780
atcatagtgg aggcactgaa agaccagcag aggcataagg ttcgggaaga ggttgttacc   6840
gtgggcaact ctgtcaacga aggcttgaac caacctacgg atgactcgtg ctttgacccc   6900
tacacagttt cccattatgc cgttggagat gagtgggaac gaatgtctga atcaggcttt   6960
aaactgttgt gccagtgctt aggctttgga agtggtcatt tcagatgtga ttcatctaga   7020
tggtgccatg acaatggtgt gaactacaag attggagaga agtgggaccg tcagggagaa   7080
aatggccaga tgatgagctg cacatgtctt gggaacggaa aaggagaatt caagtgtgac   7140
cctcatgagg caacgtgtta tgatgatggg aagacatacc acgtaggaga acagtggcag   7200
aaggaatatc tcggtgccat ttgctcctgc acatgctttg gaggccagcg gggctggcgc   7260
tgtgacaact gccgcagacc tgggggtgaa cccagtcccg aaggcactac tggccagtcc   7320
```

tacaaccagt attctcagag ataccatcag agaacaaaca ctaatgttaa ttgcccaatt 7380
gagtgcttca tgcctttaga tgtacaggct gacagagaag attcccgaga gtaa 7434

<210> SEQ ID NO 36
<211> LENGTH: 7434
<212> TYPE: DNA
<213> ORGANISM: Artificial Sequence
<220> FEATURE:
<223> OTHER INFORMATION: Synthetic Construct

<400> SEQUENCE: 36
atgctgagag gacctggacc aggactgctg ctgctggctg ttcagtgtct gggaacagcc 60
gtgcctagca caggcgccag caagtctaaa agacaggccc agcagatggt gcagcctcag 120
tctcctgtgg ccgtgtctca gtctaagccc ggctgctacg acaacggcaa gcactaccag 180
atcaaccagc agtgggagag aacctacctg ggcaacgccc tcgtgtgtac atgttacggc 240
ggcagcagag gcttcaactg cgagtctaaa cccgaggccg aggaaacctg cttcgacaag 300
tacaccggca acacctacag agtgggcgac acctacgaga ggcccaagga cagcatgatc 360
tgggactgca catgtatcgg agccggcaga ggcagaatca gctgcacaat cgccaaccgg 420
tgtcacgaag gcggccagag ctataagatc ggcgacactt ggagaaggcc ccacgagaca 480
ggcggctaca tgctggaatg cgtgtgtctc ggcaacggca aaggcgagtg gacctgcaag 540
cctatcgccg agaagtgctt cgatcatgcc gccggaacaa gctacgtcgt gggcgagaca 600
tgggagaagc cttaccaagg ctggatgatg gtggactgta cctgcctcgg cgaaggcagc 660
ggaagaatca cctgtaccag ccggaaccgg tgcaacgacc aggataccag aaccagctac 720
cggatcggcg atacctggtc caagaaggac aaccggggca acctgctgca gtgcatctgt 780
accggaaatg gaagaggcga atggaagtgc gagcggcaca caagcgtgca gacaacatct 840
tctggcagcg gccccttttac cgatgtgcgg gctgctgttt atcagcccca gcctcatcct 900
cagcctccac cttatggcca ctgcgtgaca gatagcggcg tggtgtatag cgtgggcatg 960
cagtggctga aaacccaggg caacaagcag atgctgtgca catgcctcgg caatggcgtg 1020
tcctgccaag agacagccgt gacacagacc tatggcggca atagcaatgg cgagccttgc 1080
gtgctgccct tcacctacaa tggccggacc ttctacagct gcaccaccga gggtagacag 1140
gacggacacc tgtggtgtag caccaccagc aactacgagc aggaccagaa gtacagcttc 1200
tgcaccgacc acaccgtgct ggtgcaaacc agaggcggca attctaacgg cgccctgtgt 1260
cacttcccct ttctgtacaa caaccacaac tacaccgact gcacctccga aggcagacgg 1320
gacaacatga agtggtgcgg cacaacccag aactacgacg ccgatcagaa gttcggcttc 1380
tgtcccatgg ccgctcacga ggaaatctgt accaccaacg aaggcgtgat gtacagaatc 1440
ggcgaccagt gggacaagca gcacgacatg ggccacatga tgcggtgtac ctgcgttggc 1500
aatggtcgcg gagagtggac atgcattgcc tacagccagc tgcgggacca gtgcatcgtg 1560
gacgacatca catacaacgt gaacgacacc ttccacaagc ggcacgaaga gggacacatg 1620
ctgaactgca cctgtttcgg ccaaggcaga ggccggtgga agtgtgatcc tgtggatcag 1680
tgccaggaca gcgaaaccgg caccttttac cagatcggag actcctggga gaaatacgtg 1740
cacggcgtgc gctaccagtg ctactgttac ggcagaggaa ttggcgagtg gcactgtcag 1800
cccctgcaga catacccctag ctctagcgga cctgtcgagg tgttcatcac cgagacaccc 1860
agccagccta actctcaccc catccagtgg aatgcccctc agcctagcca catcagcaag 1920
tacatcctga gatggcggcc caagaactcc gtcggcagat ggaaagaggc caccattcct 1980

-continued ggccacctga acagctacac catcaaggga ctgaagcccg gcgtggtcta tgagggccag 2040
ctgatctcta tccagcagta cggccaccaa gaagtgacca gattcgactt caccaccacc 2100
tccaccagca cacccgtgac cagcaatacc gtgaccggcg agacaacccc tttctctcca 2160
ctggtggcca caagcgagag cgtgaccgag attaccgcca gcagctttgt ggtgtcttgg 2220
gtgtccgcca gcgatacagt gtccggcttc agagtggaat acgagctgag cgaggaaggc 2280
gacgagcccc agtatctgga tctgccaagc accgccacca gcgtgaacat ccctgatctg 2340
ctgcccggca gaaagtacat cgtgaacgtg taccagatct ccgaggacgg cgagcagagc 2400
ctgatcctga gcacaagcca gacaacagcc cctgacgctc ctcctgatcc taccgttgat 2460
caggtggacg ataccagcat cgtcgtgcgg tggtcaagac cccaggctcc tatcaccggc 2520
tacaggatcg tgtacagccc tagcgtggaa ggcagcagca ccgagctgaa tctgcccgag 2580
acagccaata gcgtgaccct gtctgatctg cagcctggcg tgcagtacaa tatcaccatc 2640
tacgccgtgg aagagaatca agagtctacc cctgtggtca tccagcaaga gacaaccggc 2700
actcccagat ccgacaccgt tccatctcca cgggatctgc agttcgtgga agtgaccgac 2760
gtgaaagtga caatcatgtg gaccccacct gagagcgccg tgacaggcta tagagtggac 2820
gtgatccccg tgaacctgcc aggcgaacat ggacagagac tgcccatcag cagaaacacc 2880
tttgccgaag tgacaggact gtcccctggc gtgacctact acttcaaggt gttcgctgtg 2940
tcccacggca gagagagcaa acctctgaca gctcagcaga ccaccaagct ggacgcccct 3000
accaacctgc agtttgtgaa cgagacagac agcacagtgc ttgtgcggtg gacccctcca 3060
agagcacaga tcacaggata ccggctgacc gtgggcctga ccagaagagg acagcccaga 3120
cagtacaacg tgggccccag cgtgtccaag tatcccctga gaaatctcca gcctgccagc 3180
gagtacaccg tgtctctggt ggctatcaag ggcaatcaag agagccctaa ggccaccggc 3240
gtgttcacta cactgcagcc cggaagcagc atccctccat acaacacaga agtgactgaa 3300
accaccatcg tgatcacctg gacacccgct cctcggatcg gctttaagct gggcgtcaga 3360
ccttctcaag gcggcgaagc tcccagagaa gtgacaagcg atagcggcag catcgtggtg 3420
tctggactga caccaggcgt ggaatatgtg tacaccatcc aggtgctgcg cgacggccaa 3480
gaaagggatg cccctatcgt gaacaaggtg gtcacccctc tgagcccacc aacaaacctg 3540
cacctggaag ccaatcctga taccggcgtg ctgactgtgt cctgggaaag aagcaccaca 3600
cctgacatta ccggctatcg gatcaccaca acacccacca atggccagca gggcaactcc 3660
ctggaagagg tggtgcatgc cgatcagtcc agctgtacct tcgacaatct gagccctggc 3720
ctcgagtaca atgtgtccgt gtacacagtg aaggacgaca aagaaagcgt gcccatctcc 3780
gacacaatca tccctgaggt gccccagctg accgacctga gcttcgtgga tatcaccgac 3840
agcagcatcg gcctgaggtg gacacctctg aactcctcta ccatcatcgg atacagaatc 3900
accgtggtgg ccgctggcga gggcatccca atcttcgagg actttgtgga cagcagcgtg 3960
ggctactaca ccgtgactgg actggaaccc ggcatcgact acgacatcag cgtcatcacc 4020
ctgatcaatg gcggcgagag cgcccctaca acactgacac aacagactgc cgtgcctcct 4080
cctaccgatc tgcggttcac aaatatcggc cccgacacca tgagagtgac ttgggctcct 4140
ccaccaagta tcgacctgac caacttcctc gtgcggtaca gccccgtgaa gaacgaggaa 4200
gatgtggccg agctgtccat ctctcccagc gataatgccg tggtgctgac caatctgctc 4260
cccggaacag agtacgtggt gtccgttagc agcgtgtacg aacagcacga gagcacaccc 4320

-continued

```
ctgcggggca gacaaaaaac aggcctggat agccccaccg gaatcgactt cagcgatatc   4380
acagccaaca gcttcaccgt gcattggatc gcccctagag ccaccatcac cgggtataga   4440
atccggcatc accccgagca cttcagcggc agacctagag aagatagagt gccccactcc   4500
agaaacagca tcaccctcac caatctgaca cccggcaccg aatatgtggt gtccatcgtg   4560
gccctgaacg gcagggaaga gtctcctctg ctgatcggcc agcagagcac agtgtctgac   4620
gtgcccagag atctggaagt ggtggctgcc acacctacca gcctgctgat tagctgggat   4680
gctcctgctg tgacagtgcg gtattaccgg atcacctacg gcgagactgg cggcaactct   4740
cccgtgcaag agtttacagt gcctggcagc aagagcaccg ctaccatctc tggactcaag   4800
ccaggcgtcg actacaccat taccgtgtac gctgtgaccg gcaggggcga ttctcctgcc   4860
tcttctaagc ctatcagcat caactaccgg accgagatcg acaagccaag ccagatgcaa   4920
gtgacagatg tgcaggacaa cagcatctcc gtgaagtggc tgcctagcag ctctccagtg   4980
accgggtaca gagtgaccac cacaccaaag aacggccctg gacctaccaa gaccaagacc   5040
gctggacctg atcagaccga gatgaccatt gagggcctgc agcctaccgt cgagtatgtc   5100
gtgtctgtgt acgcccagaa tcctagcggc gagtctcagc ctcttgtgca gaccgccgtg   5160
accaacatcg acagacctaa aggcctggcc ttcaccgacg tggacgtgga ctctatcaag   5220
atcgcctggg agtcccctca gggccaagtg tccagatata gagtgaccta cagctcccct   5280
gaggacggca tccacgagct gtttccagca ccagacggcg aagaggatac cgccgaactg   5340
caaggactga ggcctggctc cgagtataca gtctcagtgg tggccctgca cgacgacatg   5400
gaaagccagc ctctgatcgg aacccagtcc accgctattc ccgctcctac agacctgaag   5460
ttcacccaag tgaccccaac cagcctgagc gcacaatgga ctcctccaaa cgtccagctg   5520
actggttata gagtgcgcgt gacacccaaa gaaaagactg gccccatgaa ggaaatcaat   5580
ctggcccctg actccagctc cgtggttgtg tctggtctta tggtggctac caaatacgag   5640
gtttccgtgt atgccctgaa ggacaccctg acctccagac ctgcacaggg cgttgtgacc   5700
acactggaaa acgtgtcccc acctcggaga gccagagtga cagacgccac cgaaaccaca   5760
atcaccattt cttggcggac caagacagag acaatcaccg gattccaggt cgacgccgtg   5820
cctgccaatg gacagacacc tatccagcgg accatcaagc ctgacgtgcg gagctacaca   5880
atcacaggcc tgcaacctgg caccgactac aagatctacc tgtacaccct gaacgacaac   5940
gcccgctcta gccccgtggt tatcgatgcc tctaccgcca tcgacgcccc aagcaatctg   6000
agatttctgg ccacaactcc caacagtctg ctcgtgtctt ggcagcctcc tcgggccaga   6060
atcactggct acatcattaa gtacgagaag ccaggcagcc ctcctagaga ggtggtccct   6120
agacctagac ctggcgtcac agaggccaca attaccggac tcgagcccgg cactgagtac   6180
acaatctacg tgatcgccct gaagaacaac cagaagtccg agccactgat tggccggaag   6240
aaaaccgacg agctgcctca gctggtcacc ctgcctcatc caaatctgca cggccccgag   6300
atcctggatg tgccatctac cgtgcagaaa accccatttg tgacacaccc cggctacgac   6360
accggaaacg gaattcagct gcctggaacc tctgggcagc agccttctgt gggacagcag   6420
atgatctttg aggaacacgg cttccggcgg accacacctc ctacaacagc cacaccaatc   6480
aggcacagac cccggcctta tcctcctaac gtgggcgaag agattcagat cggacacatc   6540
cccagagagg atgtcgacta ccacctgtat cctcacggcc caggactgaa ccctaatgcc   6600
agcacaggac aagaggccct gagccagacc actatcagct gggctccatt ccaggacacc   6660
tccgagtaca tcatctcttg tcaccccgtg ggcaccgacg aggaaccact gcaattcaga   6720
```

```
gtgcccggca cctctaccag cgccacactt acaggactga ctagaggcgc cacctataac   6780

atcatcgtgg aagccctgaa agaccagcag cggcacaaag tgcgcgaaga ggttgtgact   6840

gtgggcaatt ccgtgaacga gggcctgaat cagcccaccg acgacagctg ctttgacccc   6900

tacacagtgt cccactatgc cgtgggagat gagtgggaac gcatgtccga gagcggcttc   6960

aagctgctct gtcagtgcct cggctttggc tccggccact tcagatgcga tagctccagg   7020

tggtgccacg ataacggcgt gaactacaaa atcggagaga agtgggacag acagggcgag   7080

aacggccaga tgatgagctg cacttgtctc ggaaatggaa agggcgagtt caagtgcgac   7140

cctcacgagg ccacctgtta cgacgatggc aagacctacc acgtgggaga gcagtggcag   7200

aaagagtacc tgggcgccat ctgtagctgc acatgctttg gcgggcagcg cggctggcgc   7260

tgtgataatt gccgtagacc aggcggcgag ccatctcctg agggaacaac aggccagtcc   7320

tacaaccagt acagccagag ataccaccag cgcaccaaca ccaatgtgaa ctgccccatc   7380

gagtgcttca tgcccctgga cgtgcaggcc gacagggaag attctagaga gtga         7434
```

```
<210> SEQ ID NO 37
<211> LENGTH: 2361
<212> TYPE: DNA
<213> ORGANISM: Homo sapiens

<400> SEQUENCE: 37

atggcgggtc tgacggcggc ggccccgcgg cccggagtcc tcctgctcct gctgtccatc     60

ctccacccct ctcggcctgg aggggtccct ggggccattc ctggtggagt tcctggagga    120

gtcttttatc caggggctgg tctcggagcc cttggaggag gagcgctggg gcctggaggc    180

aaacctctta agccagttcc cggagggctt gcgggtgctg gccttggggc agggctcggc    240

gccttccccg cagttacctt tccgggggct ctggtgcctg gtggagtggc tgacgctgct    300

gcagcctata aagctgctaa ggctggcgct gggcttggtg gtgtcccagg agttggtggc    360

ttaggagtgt ctgcaggtgc ggtggttcct cagcctggag ccggagtgaa gcctgggaaa    420

gtgccgggtg tggggctgcc aggtgtatac ccaggtggcg tgctcccagg agctcggttc    480

cccggtgtgg gggtgctccc tggagttccc actggagcag gagttaagcc caaggctcca    540

ggtgtaggtg gagcttttgc tggaatccca ggagttggac cctttggggg accgcaacct    600

ggagtcccac tggggtatcc catcaaggcc cccaagctgc ctggtggcta tggactgccc    660

tacaccacag ggaaactgcc ctatggctat gggcccggag gagtggctgg tgcagcgggc    720

aaggctggtt acccaacagg gacaggggtt ggcccccagg cagcagcagc agcggcagct    780

aaagcagcag caaagttcgg tgctggagca gccggagtcc tccctggtgt tggaggggct    840

ggtgttcctg gcgtgcctgg ggcaattcct ggaattggag gcatcgcagg cgttgggact    900

ccagctgcag ctgcagctgc agcagcagcc gctaaggcag ccaagtatgg agctgctgca    960

ggcttagtgc ctggtgggcc aggctttggc ccgggagtag ttggtgtccc aggagctggc   1020

gttccaggtg ttggtgtccc aggagctggg attccagttg tcccaggtgc tgggatccca   1080

ggtgctgcgg ttccaggggt tgtgtcacca gaagcagctg ctaaggcagc tgcaaaggca   1140

gccaaatacg gggccaggcc cggagtcgga gttggaggca ttcctactta cggggttgga   1200

gctgggggct ttcccggctt tggtgtcgga gtcggaggta tccctggagt cgcaggtgtc   1260

cctggtgtcg gaggtgttcc cggagtcgga ggtgtcccgg gagttggcat ttcccccgaa   1320

gctcaggcag cagctgccgc caaggctgcc aagtacggtg ctgcaggagc aggagtgctg   1380
```

-continued

```
ggtgggctag tgccaggtgc cccaggcgca gtcccaggtg tgccgggcac gggaggagtg   1440
ccaggagtgg ggaccccagc agctgcagct gctaaagcag ccgccaaagc cgcccagttt   1500
gggttagttc ctggtgtcgg cgtggctcct ggagttggcg tggctcctgg tgtcggtgtg   1560
gctcctggag ttggcttggc tcctggagtt ggcgtggctc ctggagttgg tgtggctcct   1620
ggcgttggcg tggctcccgg cattggccct ggtggagttg cagctgcagc aaaatccgct   1680
gccaaggtgg ctgccaaagc ccagctccga gctgcagctg ggcttggtgc tggcatccct   1740
ggacttggag ttggtgtcgg cgtccctgga cttggagttg gtgctggtgt tcctggactt   1800
ggagttggtg ctggtgttcc tggcttcggg gcaggtgcag atgagggagt taggcggagc   1860
ctgtcccctg agctcaggga aggagatccc tcctcctctc agcacctccc cagcaccccc   1920
tcatcaccca gggtacctgg agccctggct gccgctaaag cagccaaata tggagcagca   1980
gtgcctgggg tccttggagg gctcggggct ctcggtggag taggcatccc aggcggtgtg   2040
gtgggagccg gacccgccgc cgccgctgcc gcagccaaag ctgctgccaa agccgcccag   2100
tttggcctag tgggagccgc tgggctcgga ggactcggag tcggagggct tggagttcca   2160
ggtgttgggg gccttggagg tatacctcca gctgcagccg ctaaagcagc taaatacggt   2220
gctgctggcc ttggaggtgt cctagggggt gccgggcagt tcccacttgg aggagtggca   2280
gcaagacctg gcttcggatt gtctcccatt ttcccaggtg gggcctgcct ggggaaagct   2340
tgtggccgga agagaaaatg a                                               2361
```

```
<210> SEQ ID NO 38
<211> LENGTH: 2361
<212> TYPE: DNA
<213> ORGANISM: Artificial Sequence
<220> FEATURE:
<223> OTHER INFORMATION: Synthetic Construct

<400> SEQUENCE: 38
```

```
atggctggac tgacagccgc tgctcctaga cctggtgttc tgctgctgct cctgagcatt     60
ctgcaccctt ctagaccagg cggagtgcct ggtgctattc ctggcggagt tcccggcgga    120
gtgttttatc ctggtgctgg actgggagcc cttggcggag gtgctcttgg acctggtgga    180
aagcctctga aacctgtgcc tggcggactt gctggtgcag gtcttggagc cggacttgga    240
gcttttcccg ccgtgacatt tcctggcgct cttgtgccag gtggcgtggc agatgctgcc    300
gctgcttata aggctgccaa agccggcgct ggactcggag gtgttcctgg tgttggaggc    360
ctgggagttt ctgctggtgc tgtggttcct caacctggcg ctggtgttaa gcctggcaaa    420
gttccaggcg ttggactgcc tggtgtttac cctggtggtg ttctccctgg cgctagattc    480
cctggcgttg gagttcttcc tggcgtgcca acaggtgccg gcgtgaaacc taaagctcct    540
ggtgtcggcg gagccttcgc tggaatacct ggcgtgggac cttttggcgg acctcaacca    600
ggtgtccctc tgggctatcc tatcaaggcc cctaaactgc caggcggcta cggcctgcct    660
tacacaactg gcaagctgcc ctatggctat ggacctggcg gtgttgctgg cgccgctgga    720
aaagctggat accctactgg aacaggcgtg ggccctcaag cagcagctgc cgcagcagct    780
aaagccgccg ctaaatttgg agctggcgct gcaggcgttt tgcccggcgt tggcggagca    840
ggcgtcccag gtgttccagg ggcaatacct ggaatcggag gaattgccgg cgtcggaact    900
ccagctgcag cagccgcagc cgccgctgcc gcaaaagctg ctaaatatgg cgcagctgca    960
ggcttggtcc caggcggacc tggatttgga ccaggtgttg ttggagtgcc aggcgctggc   1020
gtccccggcg tgggagttcc tggtgccgga attcctgttg ttcctggcgc tggtattcct   1080
```

ggcgctgctg ttccaggtgt tgtgtctcct gaagccgctg ccaaggccgc tgctaaggca 1140
gctaaatacg gtgcccgacc aggcgtcgga gttggcggaa ttccaacata tggtgtcgga 1200
gccggcggat tcccaggatt tggagttgga gtcggaggca tcccgggtgt tgcaggcgtt 1260
ccaggcgtcg gcggagttcc tggcgttggt ggtgttccag gcgtgggaat ttctcctgaa 1320
gctcaggccg ctgccgctgc caaagcagcc aaatatggcg ctgccggtgc tggcgttctc 1380
ggaggattgg ttccgggtgc tccaggtgct gttccgggcg ttcccggaac tggcggtgtc 1440
cctggtgtcg gaacaccagc cgctgcagca gcaaaggctg ctgctaaagc cgctcagttt 1500
ggactggttc ctggcgtcgg agtggcacca ggtgttggag ttgcacctgg cgttggcgtg 1560
gcccctggcg tgggtcttgc tcctggtgtt ggtgttgccc caggtgtcgg agtcgctccc 1620
ggtgtcggtg tcgcacctgg tattggtcct ggtggcgttg ccgcagctgc caaatctgct 1680
gcaaaggtgg ccgccaaagc acagctgaga gctgctgccg gtcttggcgc tggaatccca 1740
ggactcggtg ttggagtggg agtgccaggt cttggtgttg gagcaggcgt gcccggactc 1800
ggagtcggag ctggtgtccc aggttttgga gctggtgcag atgaaggcgt gcggagatct 1860
ctgagccctg agctgagaga gggcgatcct agctctagcc agcatctccc tagcacacct 1920
agcagcccta gagtccctgg ggctcttgct gcagccaaag ccgctaagta tggggctgct 1980
gtccctggtg ttcttggagg acttggagca ctcggcggag tgggaattcc aggcggtgtc 2040
gttggtgcag gacctgctgc tgccgccgca gctgcaaaag cagcagctaa ggcagcccag 2100
tttggccttg ttggagccgc tggacttggt ggcctcggag ttggtggtct tggtgtcccc 2160
ggtgttggcg gacttggagg aattccacca gccgcagcag ccaaggctgc taaatacggc 2220
gctgcaggac ttggcggtgt tcttggcgga gctggacagt ttccacttgg aggcgttgca 2280
gccagacctg gctttggcct gtctcctatt tttcctggcg gcgcttgtct gggcaaagcc 2340
tgcggcagaa agcggaagta a 2361

<210> SEQ ID NO 39
<211> LENGTH: 1017
<212> TYPE: DNA
<213> ORGANISM: Homo sapiens

<400> SEQUENCE: 39
atgagtctaa gtgcatttac tctcttcctg gcattgattg gtggtaccag tggccagtac 60
tatgattatg attttcccct atcaatttat gggcaatcat caccaaactg tgcaccagaa 120
tgtaactgcc ctgaaagcta cccaagtgcc atgtactgtg atgagctgaa attgaaaagt 180
gtaccaatgg tgcctcctgg aatcaagtat ctttacctta ggaataacca gattgaccat 240
attgatgaaa aggcctttga gaatgtaact gatctgcagt ggctcattct agatcacaac 300
cttctagaaa actccaagat aaaagggaga gttttctcta aattgaaaca actgaagaag 360
ctgcatataa accacaacaa cctgacagag tctgtgggcc cacttcccaa atctctggag 420
gatctgcagc ttactcataa caagatcaca aagctgggct cttttgaagg attggtaaac 480
ctgaccttca tccatctcca gcacaatcgg ctgaaagagg atgctgtttc agctgctttt 540
aaaggtctta aatcactcga ataccttgac ttgagcttca atcagatagc cagactgcct 600
tctggtctcc ctgtctctct tctaactctc tacttagaca acaataagat cagcaacatc 660
cctgatgagt atttcaagcg ttttaatgca ttgcagtatc tgcgtttatc tcacaacgaa 720
ctggctgata gtggaatacc tggaaattct ttcaatgtgt catccctggt tgagctggat 780

```
ctgtcctata acaagcttaa aaacatacca actgtcaatg aaaaccttga aaactattac     840

ctggaggtca atcaacttga gaagtttgac ataaagagct tctgcaagat cctggggcca     900

ttatcctact ccaagatcaa gcatttgcgt ttggatggca atcgcatctc agaaaccagt     960

cttccaccgg atatgtatga atgtctacgt gttgctaacg aagtcactct taattaa       1017
```

<210> SEQ ID NO 40
<211> LENGTH: 1017
<212> TYPE: DNA
<213> ORGANISM: Artificial Sequence
<220> FEATURE:
<223> OTHER INFORMATION: Synthetic Construct

<400> SEQUENCE: 40

```
atgagcctga gcgccttcac actgtttctg gccctgatcg gcggcacaag cggccagtac      60

tacgactacg atttcccact gagcatctac ggccagagca gccctaattg cgcccctgag     120

tgcaattgcc ccgagagcta tcctagcgcc atgtactgcg acgagctgaa gctgaagtcc     180

gtgcctatgg tgcctcctgg catcaagtac ctgtacctgc ggaacaacca gatcgaccac     240

atcgacgaga aggcctttga gaacgtgacc gacctgcagt ggctgatcct ggaccacaac     300

ctgctggaaa acagcaagat caagggccgc gtgttcagca agctgaagca gctgaagaaa     360

ctgcacatca accacaacaa cctgaccgag agcgtgggcc ctctgcctaa gtctctggaa     420

gatctgcagc tgacccacaa caagatcacc aagctgggca gcttcgaggg cctcgtgaac     480

ctgaccttca tccatctgca gcacaaccgg ctgaaagagg atgccgttag cgccgccttc     540

aagggcctga agagtctgga atacctggac ctgagcttca atcagatcgc cagactgcct     600

agcggcctgc ctgtttctct gctgacactg tacctggaca acaacaaaat cagcaacatc     660

cccgacgagt acttcaagcg gttcaacgcc ctgcagtacc tgagactgag ccacaacgag     720

ctggccgatt ctggcatccc cggcaacagc ttcaatgtgt ccagcctggt ggaactggac     780

ctgtcctaca acaagctgaa aaacatcccc accgtgaacg agaacctcga gaactactac     840

ctggaagtga accagctcga gaagttcgat atcaagagct tctgcaagat cctggggcct     900

ctgagctact ccaagattaa gcacctgagg ctggacggca accggatcag cgaaacaagc     960

ctgcctcctg atatgtacga gtgcctgaga gtggccaacg aagtgaccct gaactga       1017
```

<210> SEQ ID NO 41
<211> LENGTH: 1437
<212> TYPE: DNA
<213> ORGANISM: Homo sapiens

<400> SEQUENCE: 41

```
atggcacccc tgagacccct tctcatactg gccctgctgg catgggttgc tctggctgac      60

caagagtcat gcaagggccg ctgcactgag ggcttcaacg tggacaagaa gtgccagtgt     120

gacgagctct gctcttacta ccagagctgc tgcacagact atacggctga gtgcaagccc     180

caagtgactc gcggggatgt gttcactatg ccggaggatg agtacacggt ctatgacgat     240

ggcgaggaga aaaacaatgc cactgtccat gaacaggtgg ggggcccctc cctgacctct     300

gacctccagg cccagtccaa agggaatcct gagcagacac ctgttctgaa acctgaggaa     360

gaggcccctg cgcctgaggt gggcgcctct aagcctgagg ggatagactc aaggcctgag     420

acccttcatc cagggagacc tcagcccca gcagaggagg agctgtgcag tgggaagccc     480

ttcgacgcct tcaccgacct caagaacggt tccctctttg ccttccgagg gcagtactgc     540

tatgaactgg acgaaaaggc agtgaggcct gggtacccca agctcatccg agatgtctgg     600
```

```
ggcatcgagg gccccatcga tgccgccttc acccgcatca actgtcaggg gaagacctac     660

ctcttcaagg gtagtcagta ctggcgcttt gaggatggtg tcctggaccc tgattacccc     720

cgaaatatct ctgacggctt cgatggcatc ccggacaacg tggatgcagc cttggccctc     780

cctgcccata gctacagtgg ccgggagcgg gtctacttct tcaaggggaa acagtactgg     840

gagtaccagt tccagcacca gcccagtcag gaggagtgtg aaggcagctc cctgtcggct     900

gtgtttgaac actttgccat gatgcagcgg gacagctggg aggacatctt cgagcttctc     960

ttctggggca gaacctctgc tggtaccaga cagccccagt tcattagccg ggactggcac    1020

ggtgtgccag ggcaagtgga cgcagccatg gctggccgca tctacatctc aggcatggca    1080

ccccgcccct ccttggccaa gaaacaaagg tttaggcatc gcaaccgcaa aggctaccgt    1140

tcacaacgag gccacagccg tggccgcaac cagaactccc gccggccatc ccgcgccacg    1200

tggctgtcct tgttctccag tgaggagagc aacttgggag ccaacaacta tgatgactac    1260

aggatggact ggcttgtgcc tgccacctgt gaacccatcc agagtgtctt cttcttctct    1320

ggagacaagt actaccgagt caatcttcgc acacggcgag tggacactgt ggaccctccc    1380

tacccacgct ccatcgctca gtactggctg ggctgcccag ctcctggcca tctgtag       1437
```

<210> SEQ ID NO 42
<211> LENGTH: 1437
<212> TYPE: DNA
<213> ORGANISM: Artificial Sequence
<220> FEATURE:
<223> OTHER INFORMATION: Synthetic Construct

<400> SEQUENCE: 42

```
atggcccctc ttagacccct gctgattctg gctctgctgg cttgggttgc cctggccgat      60

caagagtctt gcaagggcag atgcaccgag ggcttcaacg tggacaagaa atgccagtgc     120

gacgagctgt gcagctacta ccagagctgc tgcaccgatt acaccgccga gtgcaagccc     180

caagtgacaa gaggcgacgt gttcaccatg cctgaggacg agtacaccgt gtacgacgac     240

ggcgaggaaa agaacaacgc caccgtgcac gagcaagttg gcggaccttc tctgaccagc     300

gatctgcagg ctcagagcaa gggcaatcct gagcagaccc ctgtgctgaa gcctgaggaa     360

gaagcccctg ctcctgaagt gggagcctct aagcctgaag gcatcgacag cagacccgag     420

acactgcatc caggcagacc tcagcctcct gccgaagagg aactgtgtag cggcaagcct     480

ttcgacgcct tcaccgacct gaagaacggc agcctgttcg cctttagagg ccagtactgc     540

tacgagctgg acgagaaggc cgtgcggcct ggatatccta agctgatcag agatgtgtgg     600

ggcatcgagg gccccatcga cgccgctttc accagaatca actgtcaggg caagacctac     660

ctgttcaagg gcagccagta ttggagattc gaggacggcg tgctggaccc tgactacccc     720

agaaatatca gcgacggctt cgacggcatc cccgacaatg ttgatgctgc tctggccctg     780

cctgctcaca gctactctgg cagagaacgg gtgtacttct ttaagggcaa acagtactgg     840

gagtaccagt tccagcacca gcctagccaa gaggaatgcg agggcagctc tctgagcgcc     900

gtgtttgagc acttcgccat gatgcagaga gacagctggg aagatatttt cgagctgctg     960

ttctggggca gaaccagcgc cggaacaaga cagcctcagt tcatcagcag agactggcat    1020

ggcgtgccag gacaagtgga tgctgccatg gccggcagaa tctacatcag cggaatggcc    1080

cctagaccta gcctggccaa gaagcagcgg ttccggcaca gaaaccggaa gggctacaga    1140

agccagagag gccactccag aggccggaac cagaatagca gaaggccctc tagagccacc    1200
```

-continued tggctgagcc tgtttagcag cgaggaaagc aacctgggcg ccaacaacta cgacgactac 1260
cggatggatt ggctggtgcc tgccacatgc gagcctatcc agagcgtgtt cttcttcagc 1320
ggcgacaaat attaccgcgt gaacctgcgg actcggagag tggatacagt ggaccctcct 1380
tatcctcggt ctatcgctca gtattggctg ggctgtccag ctcctggaca cctgtaa 1437

<210> SEQ ID NO 43
<211> LENGTH: 5175
<212> TYPE: DNA
<213> ORGANISM: Homo sapiens

<400> SEQUENCE: 43
atgcctccag cagtgaggcg gtcagcctgc agcatgggat ggctgtggat ctttggggca 60
gccctggggc agtgtctggg ctacagttca cagcagcaaa gggtgccatt tcttcagcct 120
cccggtcaaa gtcaactgca agcgagttat gtggagttta gacccagcca gggttgtagc 180
cctggatact atcgggatca taaaggcttg tataccggac ggtgtgttcc ctgcaattgc 240
aacggacatt caaatcaatg ccaggatggc tcaggcatat gtgttaactg tcagcacaac 300
accgcgggag agcactgtga acgctgccag gagggctact atggcaacgc cgtccacgga 360
tcctgcaggg cctgcccatg tcctcacact aacagctttg ccactggctg tgtggtgaat 420
gggggagacg tgcggtgctc ctgcaaagct gggtacacag gaacacagtg tgaaaggtgt 480
gcaccgggat atttcgggaa tccccagaaa ttcggaggta gctgccaacc atgcagttgt 540
aacagcaatg gccagctggg cagctgtcat cccctgactg gagactgcat aaaccaagaa 600
cccaaagata gcagccctgc agaagaatgt gatgattgcg acagctgtgt gatgaccctc 660
ctgaacgacc tggccaccat gggcgagcag ctccgcctgg tcaagtctca gctgcagggc 720
ctgagtgcca gcgcagggct tctggagcag atgaggcaca tggagaccca ggccaaggac 780
ctgaggaatc agttgctcaa ctaccgttct gccatttcaa atcatggatc aaaaatagaa 840
ggcctggaaa gagaactgac tgatttgaat caagaatttg agactttgca agaaaaggct 900
caagtaaatt ccagaaaagc acaaacatta aacaacaatg ttaatcgggc aacacaaagc 960
gcaaaagaac tggatgtgaa gattaaaaat gtcatccgga atgtgcacat tcttttaaag 1020
cagatctctg ggacagatgg agagggaaac aacgtgcctt caggtgactt ttccagagag 1080
tgggctgaag cccagcgcat gatgagggaa ctgcggaaca ggaactttgg aaagcacctc 1140
agagaagcag aagctgataa aagggagtcg cagctcttgc tgaaccggat aaggacctgg 1200
cagaaaaccc accaggggga gaacaatggg cttgctaaca gtatccggga ttctttaaat 1260
gaatacgaag ccaaactcag tgaccttcgt gctcggctgc aggaggcagc tgcccaagcc 1320
aagcaggcaa atggcttgaa ccaagaaaac gagagagctt tgggagccat tcagagacaa 1380
gtgaaagaaa taaattccct gcagagtgat ttcaccaagt atctaaccac tgcagactca 1440
tctttgttgc aaaccaacat tgcgctgcag ctgatggaga aaagccagaa ggaatatgaa 1500
aaattagctg ccagtttaaa tgaagcaaga caagaactaa gtgacaaagt aagagaactt 1560
tccagatctg ctggcaaaac atcccttgtg gaggaggcag aaaagcacgc gcggtcctta 1620
caagagctgg caaagcagct ggaagagatc aagagaaacg ccagcgggga tgagctggtg 1680
cgctgtgctg tggatgccgc caccgcctac gagaacatcc tcaatgccat caaagcggcc 1740
gaggacgcag ccaacagggc tgccagtgca tctgaatctg ccctccagac agtgataaag 1800
gaagatctgc caagaaaagc taaaaccctg agttccaaca gtgataaact gttaaatgaa 1860
gccaagatga cacaaaagaa gctaaagcaa gaagtcagtc cagctctcaa caacctacag 1920

-continued

```
caaaccctga atattgtgac agttcagaaa gaagtgatag acaccaatct cacaactctc   1980
cgagatggtc ttcatgggat acagagaggt gatattgatg ctatgatcag tagtgcaaag   2040
agcatggtca gaaaggccaa cgacatcaca gatgaggttc tggatgggct caaccccatc   2100
cagacagatg tggaaagaat taaggacacc tatgggagga cacagaacga agacttcaaa   2160
aaggctctga ctgatgcaga taactcggtg aataagttaa ccaacaaact acctgatctt   2220
tggcgcaaga ttgaaagtat caaccaacag ctgttgccct tgggaaacat ctctgacaac   2280
atggacagaa tacgagaact aattcagcag gccagagatg ctgccagtaa ggttgctgtc   2340
cccatgaggt tcaatggtaa atctggagtc gaagtccgac tgccaaatga cctggaagat   2400
ttgaaaggat atacatctct gtccttgttt ctccaaaggc ccaactcaag agaaaatggg   2460
ggtactgaga atatgtttgt gatgtacctt ggaaataaag atgcctcccg ggactacatc   2520
ggcatggcag ttgtggatgg ccagctcacc tgtgtctaca acctggggga ccgtgaggct   2580
gaactccaag tggaccagat cttgaccaag agtgagacta aggaggcagt tatggatcgg   2640
gtgaaatttc agagaattta tcagtttgca aggcttaatt acaccaaagg agccacatcc   2700
agtaaaccag aaacacccgg agtctatgac atggatggta gaaatagcaa tacactcctt   2760
aatttggatc ctgaaaatgt tgtattttat gttggaggtt acccacctga ttttaaactt   2820
cccagtcgac taagtttccc tccatacaaa ggttgtattg aattagatga cctcaatgaa   2880
aatgttctga gcttgtacaa cttcaaaaaa acattcaatc tcaacacaac tgaagtggag   2940
ccttgtagaa ggaggaagga agagtcagac aaaaattatt ttgaaggtac gggctatgct   3000
cgagttccaa ctcaaccaca tgctcccatc ccaacctttg gacagacaat tcagaccacc   3060
gtggatagag gcttgctgtt ctttgcagaa aacggggatc gcttcatatc tctaaatata   3120
gaagatggca agctcatggt gagatacaaa ctgaattcag agctaccaaa agagagagga   3180
gttggagacg ccataaacaa cggcagagac cattcgattc agatcaaaat tggaaaactc   3240
caaaagcgta tgtggataaa tgtggacgtt caaaacacta taattgatgg tgaagtattt   3300
gatttcagca catattatct gggaggaatt ccaattgcaa tcagggaaag atttaacatt   3360
tctacgcctg ctttccgagg ctgcatgaaa aatttgaaga aaaccagtgg tgtcgttaga   3420
ttgaatgata ctgtgggagt aaccaaaaag tgctcggaag actggaagct tgtgcgatct   3480
gcctcattct ccagaggagg acaattgagt ttcactgatt tgggcttacc acctactgac   3540
cacctccagg cctcatttgg atttcagacc tttcaaccca gtggcatatt attagatcat   3600
cagacatgga caaggaacct gcaggtcact ctggaagatg gttacattga attgagcacc   3660
agcgatagcg gcggcccaat ttttaaatct ccacagacgt atatggatgg tttactgcat   3720
tatgtatctg taataagcga caactctgga ctacggcttc tcatcgatga ccagcttctg   3780
agaaatagca aaaggctaaa acacatttca agttcccggc agtctctgcg tctgggcggg   3840
agcaattttg agggttgtat tagcaatgtt tttgtccaga ggttatcact gagtcctgaa   3900
gtcctagatt tgaccagtaa ctctctcaag agagatgtgt ccctgggagg ctgcagttta   3960
aacaaaccac cttttctaat gttgcttaaa ggttctacca ggtttaacaa gaccaagact   4020
tttcgtatca accagctgtt gcaggacaca ccagtggcct ccccaaggag cgtgaaggtg   4080
tggcaagatg cttgctcacc acttcccaag acccaggcca atcatggagc cctccagttt   4140
ggggacattc ccaccagcca cttgctattc aagcttcctc aggagctgct gaaacccagg   4200
tcacagtttg ctgtggacat gcagacaaca tcctccagag gactggtgtt tcacacgggc   4260
```

-continued

```
actaagaact cctttatggc tctttatctt tcaaaaggac gtctggtctt tgcactgggg   4320

acagatggga aaaaattgag gatcaaaagc aaggagaaat gcaatgatgg gaaatggcac   4380

acggtggtgt ttggccatga tggggaaaag ggcgcttgg ttgtggatgg actgagggcc   4440

cgggagggaa gtttgcctgg aaactccacc atcagcatca gagcgccagt ttacctggga   4500

tcacctccat cagggaaacc aaagagcctc cccacaaaca gctttgtggg atgcctgaag   4560

aactttcagc tggattcaaa acccttgtat accccttctt caagcttcgg ggtgtcttcc   4620

tgcttgggtg gtcctttgga gaaaggcatt tatttctctg aagaaggagg tcatgtcgtc   4680

ttggctcact ctgtattgtt ggggccagaa tttaagcttg ttttcagcat ccgcccaaga   4740

agtctcactg ggatcctaat acacatcgga agtcagcccg ggaagcactt atgtgtttac   4800

ctggaggcag gaaaggtcac ggcctctatg gacagtgggg caggtgggac ctcaacgtcg   4860

gtcacaccaa agcagtctct gtgtgatgga cagtggcact cggtggcagt caccataaaa   4920

caacacatcc tgcacctgga actggacaca gacagtagct acacagctgg acagatcccc   4980

ttcccacctg ccagcactca agagccacta caccttggag gtgctccagc caatttgacg   5040

acactgagga tccctgtgtg gaaatcattc tttggctgtc tgaggaatat tcatgtcaat   5100

cacatccctg tccctgtcac tgaagccttg gaagtccagg ggcctgtcag tctgaatggt   5160

tgtcctgacc agtaa                                                     5175
```

```
<210> SEQ ID NO 44
<211> LENGTH: 5175
<212> TYPE: DNA
<213> ORGANISM: Artificial Sequence
<220> FEATURE:
<223> OTHER INFORMATION: Synthetic Construct

<400> SEQUENCE: 44

atgcctcctg ctgtgcggag aagcgcctgt tctatgggat ggctgtggat ctttggcgcc     60

gctctgggac agtgtctggg ctactcttct cagcagcagc gggtgccatt tctgcagcca    120

cctggacagt ctcagctgca ggccagctac gtggaattca gacctagcca gggctgtagc    180

cccggctact acagagatca caagggcctg tacaccggca gatgcgtgcc ctgcaactgt    240

aacggccaca gcaaccagtg tcaggacggc tctggcatct gcgtgaactg ccagcataat    300

actgccggcg agcactgcga gagatgccaa gagggctact acggcaatgc cgtgcatggc    360

agctgtcggg cttgtccttg tcctcacacc aacagctttg ccaccggctg cgttgtgaac    420

ggcggagatg ttcggtgttc ttgcaaggcc ggctacacag gcacacagtg cgaaagatgt    480

gcccctggct actttggcaa ccctcagaag tttggcggct cctgccagcc ttgctcctgc    540

aattctaatg gccagctggg ctcttgtcac cctctgaccg gcgactgcat caatcaagag    600

cctaaggaca gcagccctgc cgaggaatgc gacgattgcg atagctgcgt gatgaccctg    660

ctgaacgacc tggccacaat gggagaacag ctgcggctgg ttaagagcca gctccaggga    720

ctgtctgcct ctgctggact gctggaacag atgcggcaca tggaaaccca ggccaaggac    780

ctgagaaacc agctgctgaa ctacagaagc gccatctcca accacggcag caagatcgaa    840

ggcctggaaa gagagctgac cgacctgaat caagagttcg agacactgca agagaaggcc    900

caagtgaaca gccggaaggc ccagactctg aacaacaacg tgaaccgggc cacacagtcc    960

gccaaagaac tggacgtgaa gatcaagaac gtgatccgga acgtgcacat cctgctgaag   1020

cagatcagcg gcacagatgg cgagggcaac aatgtgccta gcggcgactt tagcagagag   1080

tgggccgaag ctcagcggat gatgagagag ctgcggaacc ggaacttcgg caagcacctg   1140
```

-continued

```
agagaagccg aggccgacaa gagagagagc caactgctgc tcaaccggat cagaacctgg   1200
cagaaaaccc accagggcga gaacaacggc ctggccaaca gcatcagaga cagcctgaat   1260
gagtacgagg ccaagctgag cgatctgcgg gccagacttc aagaagctgc cgctcaggcc   1320
aagcaggcca acggccttaa tcaagagaac gagagagccc tgggcgccat ccagagacaa   1380
gtgaaagaga tcaacagcct gcagagcgac ttcaccaagt acctgaccac cgccgatagc   1440
agcctgctgc agacaaatat cgccctgcag ctcatggaaa agagccagaa agagtacgaa   1500
aagctggccg ccagcctgaa cgaggccagg caagaactgt ctgacaaagt gcgcgagctg   1560
agcagatccg ccggcaagac atctctggtg gaagaggccg agaagcacgc cagatctctg   1620
caagagctgg ccaaacagct ggaagagatt aagcggaacg ccagcggcga cgaactcgtc   1680
agatgtgcag tggatgccgc caccgcctac gagaacatcc tgaatgccat caaggccgcc   1740
gaggacgccg ctaatagagc cgcttctgct tctgagtctg ccctgcagac cgtgatcaaa   1800
gaggacctgc ctagaaaggc caagacactg agcagcaaca gcgacaaact gctgaatgag   1860
gccaagatga cccagaagaa actgaagcaa gaggtgtccc ctgcactgaa caacctgcag   1920
cagaccctga acatcgtgac cgtgcagaaa gaagtgatcg acaccaacct gacaaccctg   1980
agagatggcc tgcacggaat ccagagaggc gacatcgacg ccatgatcag cagcgccaag   2040
agcatggttc gaaaagccaa cgacatcacc gacgaggtgc tggacggcct gaatcctatc   2100
cagaccgacg tggaacggat caaggacacc tacggcagaa cccagaacga ggatttcaag   2160
aaggccctga ccgacgccga caactccgtg aacaagctga ccaacaagct gcccgatctg   2220
tggcggaaga tcgagagcat caaccagcaa ctgctccctc tgggcaacat cagcgacaac   2280
atggacagaa tccgggaact gatccagcag gccagagatg ccgcctccaa agtggctgtg   2340
cccatgagat tcaacggcaa gagcggagtg gaagtgcggc tgcccaacga tctggaagat   2400
ctgaagggct ataccagcct gagcctgttc ctgcagaggc ccaacagcag agagaatggc   2460
ggcaccgaga atatgttcgt gatgtacctg ggaaacaagg acgccagccg ggactatatc   2520
ggaatggccg ttgtggacgg ccagctgacc tgcgtgtaca acctgggaga cagagaagct   2580
gaactgcagg tcgaccagat cctgaccaag agcgagacaa aagaggccgt gatggacaga   2640
gtgaagttcc agcggatcta ccagttcgcc cggctgaatt acaccaaggg cgccacaagc   2700
agcaagcccg aaacacctgg cgtgtacgac atggacggcc ggaactctaa cactctgctg   2760
aatctggacc ccgagaacgt ggtgttttac gtcggcggct accctcctga cttcaagctg   2820
cctagcagac tgagcttccc accttacaag ggctgcatcg agctggatga cctgaacgaa   2880
aacgtgctgt ccctgtacaa cttcaaaaag accttcaacc tgaacaccac cgaggtggaa   2940
ccctgcaggc gcagaaaaga ggaatccgac aagaactact tcgaaggcac cggctacgcc   3000
agagtgccta cacaacctca cgctcccatt cctaccttcg gccagaccat ccagacaacc   3060
gtggatagag gcctgctgtt cttcgccgag aacggcgaca gattcatctc cctgaatatc   3120
gaggatggca agctgatggt ccgatacaag ctgaatagcg agctgcccaa agaaagaggc   3180
gtgggcgacg ccatcaacaa cggcagggat cacagcatcc agatcaagat cggcaaactg   3240
cagaaacgga tgtggatcaa cgtggacgtg cagaacacca tcatcgacgg cgaggtgttc   3300
gacttcagca cctactatct cggcggaatc cctatcgcca tcagagagcg gttcaatatc   3360
agcacccctg ccttccgggg ctgcatgaag aacctgaaaa agaccagcgg cgtcgtgcgg   3420
ctgaatgata cagtgggcgt gaccaagaag tgcagcgagg actggaagct tgtgcggagc   3480
```

-continued

```
gccagttttt ctagaggcgg acagctgagc tttaccgacc tgggactgcc tcctaccgat   3540

catctgcagg caagcttcgg attccagacc ttccagccaa gcggaatcct gctggaccac   3600

cagacctgga ccagaaacct gcaagtgacc ctggaagatg gctacatcga actgagcacc   3660

agcgactctg gcggccctat ctttaagagc cctcagacct acatggatgg gctgctgcac   3720

tacgtgtccg tgatcagcga taacagcggc ctgagactgc tgatcgacga ccagctcctg   3780

cggaacagca agcggctgaa gcacatctcc agcagcagac agagtctgag actcggcggc   3840

agcaatttcg agggctgtat cagcaacgtg ttcgtgcagc gcctgagtct gtctccagaa   3900

gtgctggacc tgaccagcaa tagcctgaag agggatgtgt ctctcggcgg ctgctccctg   3960

aacaaacctc ctttcctgat gctgctgaag ggcagcaccc ggttcaacaa gaccaagacc   4020

tttcggatca atcagctgct ccaggacacc cctgtggcta gccctagaag cgtgaaagtg   4080

tggcaggacg cctgcagtcc cctgcctaaa acacaggcca atcacggggc tctgcagttc   4140

ggcgatatcc ccacaagcca tctgctgttt aagctgcccc aagagctgct caagcctcgg   4200

agccagttcg ctgtggatat gcagaccacc tcctccagag gactggtgtt tcacaccggc   4260

accaagaaca gcttcatggc cctgtacctg agcaaaggca ggctggtgtt tgccctgggc   4320

accgacggaa agaaactgcg gatcaagagc aaagagaagt gcaacgacgg caagtggcac   4380

accgtggtgt tcggacacga tggcgagaaa ggcagactcg tggtggatgg cctgagagcc   4440

agagagggat ctctgcctgg caactccacc atctccatca gagcccctgt gtatctgggc   4500

agccctccta gcggaaagcc taagagcctg cctaccaact ccttcgtggg ctgtctgaag   4560

aactttcagc tggacagcaa gcctctgtac acccctagca gcagctttgg cgtgtcctcc   4620

tgtctcggag gccctctgga aaagggcatc tacttctctg aggaaggcgg ccacgttgtc   4680

ctggctcatt ctgttctgct gggccccgag ttcaagctgg tgttctctat ccggcctaga   4740

agcctgaccg gcatcctgat tcacatcggc agccagcctg ggaagcacct gtgtgtgtat   4800

ctcgaggccg gcaaagtgac cgccagcatg gattctggtg ctggcggcac aagcacctcc   4860

gtgacaccta agcagagcct gtgtgatggc cagtggcaca gtgtggccgt gacaatcaag   4920

cagcacattc tgcacctgga actggacacc gacagcagct ataccgccgg acagatccca   4980

tttcctccag ccagcacaca agagcctctg caccttggag gcgcccctgc caatctgacc   5040

acactgagaa tccccgtgtg gaagtccttc ttcggctgcc tgcggaatat ccatgtgaac   5100

cacattccag tgcctgtgac agaggccctg gaagtgcagg gacccgtgtc tctgaatgga   5160

tgccccgatc agtga                                                    5175
```

```
<210> SEQ ID NO 45
<211> LENGTH: 3519
<212> TYPE: DNA
<213> ORGANISM: Homo sapiens

<400> SEQUENCE: 45

atgagaccat tcttcctctt gtgttttgcc ctgcctggcc tcctgcatgc ccaacaagcc     60

tgctcccgtg gggcctgcta tccacctgtt ggggacctgc ttgttgggag gacccggttt    120

ctccgagctt catctacctg tggactgacc aagcctgaga cctactgcac ccagtatggc    180

gagtggcaga tgaaatgctg caagtgtgac tccaggcagc ctcacaacta ctacagtcac    240

cgagtagaga atgtggcttc atcctccggc cccatgcgct ggtggcagtc acagaatgat    300

gtgaaccctg tctctctgca gctggacctg gacaggagat tccagcttca agaagtcatg    360

atggagttcc aggggcccat gcccgccggc atgctgattg agcgctcctc agacttcggt    420
```

-continued

```
aagacctggc gagtgtacca gtacctggct gccgactgca cctccacctt ccctcgggtc    480
cgccagggtc ggcctcagag ctggcaggat gttcggtgcc agtccctgcc tcagaggcct    540
aatgcacgcc taaatggggg gaaggtccaa cttaacctta tggatttagt gtctgggatt    600
ccagcaactc aaagtcaaaa aattcaagag gtgggggaga tcacaaactt gagagtcaat    660
ttcaccaggc tggcccctgt gccccaaagg ggctaccacc ctcccagcgc ctactatgct    720
gtgtcccagc tccgtctgca ggggagctgc ttctgtcacg gccatgctga tcgctgcgca    780
cccaagcctg gggcctctgc aggcccctcc accgctgtgc aggtccacga tgtctgtgtc    840
tgccagcaca acactgccgg cccaaattgt gagcgctgtg cacccttcta caacaaccgg    900
ccctggagac cggcggaggg ccaggacgcc catgaatgcc aaaggtgcga ctgcaatggg    960
cactcagaga catgtcactt tgaccccgct gtgtttgccg ccagccaggg ggcatatgga   1020
ggtgtgtgtg acaattgccg ggaccacacc gaaggcaaga actgtgagcg gtgtcagctg   1080
cactatttcc ggaaccggcg cccgggagct tccattcagg agacctgcat ctcctgcgag   1140
tgtgatccgg atggggcagt gccaggggct ccctgtgacc cagtgaccgg gcagtgtgtg   1200
tgcaaggagc atgtgcaggg agagcgctgt gacctatgca agccgggctt cactggactc   1260
acctacgcca acccgcaggg ctgccaccgc tgtgactgca acatcctggg gtcccggagg   1320
gacatgccgt gtgacgagga gagtgggcgc tgcctttgtc tgcccaacgt ggtgggtccc   1380
aaatgtgacc agtgtgctcc ctaccactgg aagctggcca gtggccaggg ctgtgaaccg   1440
tgtgcctgcg acccgcacaa ctccctcagc ccacagtgca accagttcac agggcagtgc   1500
ccctgtcggg aaggctttgg tggcctgatg tgcagcgctg cagccatccg ccagtgtcca   1560
gaccggacct atggagacgt ggccacagga tgccgagcct gtgactgtga tttccgggga   1620
acagagggcc cgggctgcga caaggcatca ggccgctgcc tctgccgccc tggcttgacc   1680
gggccccgct gtgaccagtg ccagcgaggc tactgtaatc gctacccggt gtgcgtggcc   1740
tgccaccctt gcttccagac ctatgatgcg gacctccggg agcaggccct gcgctttggt   1800
agactccgca atgccaccgc cagcctgtgg tcagggcctg ggctggagga ccgtggcctg   1860
gcctcccgga tcctagatgc aaagagtaag attgagcaga tccgagcagt tctcagcagc   1920
cccgcagtca cagagcagga ggtggctcag gtggccagtg ccatcctctc cctcaggcga   1980
actctccagg gcctgcagct ggatctgccc ctggaggagg agacgttgtc ccttccgaga   2040
gacctggaga gtcttgacag aagcttcaat ggtctcctta ctatgtatca gaggaagagg   2100
gagcagtttg aaaaaataag cagtgctgat ccttcaggag ccttccggat gctgagcaca   2160
gcctacgagc agtcagccca ggctgctcag caggtctccg acagctcgcg ccttttggac   2220
cagctcaggg acagccggag agaggcagag aggctggtgc ggcaggcggg aggaggagga   2280
ggcaccggca gccccaagct tgtggccctg aggctggaga tgtcttcgtt gcctgacctg   2340
acacccacct tcaacaagct ctgtggcaac tccaggcaga tggcttgcac cccaatatca   2400
tgccctggtg agctatgtcc ccaagacaat ggcacagcct gtggctcccg ctgcaggggt   2460
gtccttccca gggccggtgg ggccttcttg atggcggggc aggtggctga gcagctgcgg   2520
ggcttcaatg cccagctcca gcggaccagg cagatgatta gggcagccga ggaatctgcc   2580
tcacagattc aatccagtgc ccagcgcttg gagacccagg tgagcgccag ccgctcccag   2640
atggaggaag atgtcagacg cacacggctc ctaatccagc aggtccggga cttcctaaca   2700
gaccccgaca ctgatgcagc cactatccag gaggtcagcg aggccgtgct ggccctgtgg   2760
```

-continued

```
ctgcccacag actcagctac tgttctgcag aagatgaatg agatccaggc cattgcagcc   2820

aggctcccca acgtggactt ggtgctgtcc cagaccaagc aggacattgc gcgtgcccgc   2880

cggttgcagg ctgaggctga ggaagccagg agccgagccc atgcagtgga gggccaggtg   2940

gaagatgtgg ttgggaacct gcggcagggg acagtggcac tgcaggaagc tcaggacacc   3000

atgcaaggca ccagccgctc ccttcggctt atccaggaca gggttgctga ggttcagcag   3060

gtactgcggc cagcagaaaa gctggtgaca agcatgacca agcagctggg tgacttctgg   3120

acacggatgg aggagctccg ccaccaagcc cggcagcagg gggcagaggc agtccaggcc   3180

cagcagcttg cggaaggtgc cagcgagcag gcattgagtg cccaagaggg atttgagaga   3240

ataaaacaaa agtatgctga gttgaaggac cggttgggtc agagttccat gctgggtgag   3300

cagggtgccc ggatccagag tgtgaagaca gaggcagagg agctgtttgg ggagaccatg   3360

gagatgatgg acaggatgaa agacatggag ttggagctgc tgcggggcag ccaggccatc   3420

atgctgcgct cagcggacct gacaggactg gagaagcgtg tggagcagat ccgtgaccac   3480

atcaatgggc gcgtgctcta ctatgccacc tgcaagtga                          3519
```

<210> SEQ ID NO 46
<211> LENGTH: 3519
<212> TYPE: DNA
<213> ORGANISM: Artificial Sequence
<220> FEATURE:
<223> OTHER INFORMATION: Synthetic Construct

<400> SEQUENCE: 46

```
atgaggccct tcttcctgct gtgctttgcc ctgcctggac tgctgcatgc tcagcaggct     60

tgtagcagag gcgcctgcta tcctcctgtg ggcgatctgc ttgtgggcag aaccagattc    120

ctgcgggcca gctctacatg cggcctgaca aagcctgaga catactgcac ccagtacggc    180

gagtggcaga tgaagtgctg caagtgcgac agcagacagc cccacaacta ctacagccac    240

agagtggaaa acgtggccag cagcagcggc cctatgagat ggtggcagag ccagaacgac    300

gtgaaccccg ttagcctgca gctggacctg gacagacggt ttcagctgca agaagtgatg    360

atggaatttc agggccccat gcctgccggc atgctgatcg agagaagcag cgatttcggc    420

aagacctggc gggtgtacca gtatctggcc gccgattgca ccagcacatt ccccagagtt    480

agacagggca gaccccagag ctggcaggat gttcgttgtc agtctctgcc ccagcggcct    540

aacgctagac tgaatggcgg aaaggtgcag ctcaacctga tggacctggt gtctggcatc    600

cctgccacac agtcccagaa aatccaagaa gtgggcgaga tcaccaacct gagagtgaac    660

ttcacccggc tggctcccgt tcctcagaga ggatatcatc ctcctagcgc ctactacgcc    720

gtgtctcagc ttagactgca gggcagctgc ttctgtcacg gccacgctga tagatgcgcc    780

cctaaacctg gtgcctctgc cggaccttct acagccgtgc aagtgcacga tgtgtgcgtg    840

tgccagcaca ataccgccgg acctaactgc gagagatgtg cccctttcta caacaaccgg    900

ccttggaggc ctgccgaagg acaggatgct cacgagtgcc agagatgcga ctgcaacggc    960

cacagcgaga catgccactt tgaccctgcc gtgtttgccg cttctcaggg cgcttatggc   1020

ggcgtgtgtg acaactgcag agatcacacc gagggcaaga actgcgagcg ctgtcagctg   1080

cactacttcc ggaatagaag gccaggcgcc agcatccaag agacatgcat cagctgcgag   1140

tgcgatcccg atggtgctgt tcctggcgct ccttgtgatc ctgtgacagg ccagtgcgtg   1200

tgtaaagaac acgtgcaggg cgaaagatgc gacctgtgca agcctggctt taccggcctg   1260

acctacgcca atcctcaggg ctgccacaga tgtgattgca acatcctggg cagcagacgg   1320
```

-continued gacatgccct gtgatgaaga gtctggcaga tgcctgtgcc tgcctaatgt cgtgggcccc 1380
aagtgcgatc agtgtgcccc atatcactgg aagctggcct ctggccaggg atgcgaacct 1440
tgtgcctgcg atccccacaa cagcctgtct ccacagtgca accagttcac cggccagtgt 1500
ccttgcagag aaggctttgg cggcctgatg tgttctgccg ccgctatcag acagtgcccc 1560
gatagaacat atggcgacgt ggccacaggc tgcagagcct gcgattgtga cttccgggga 1620
acagaaggac ccggctgcga taaggccagc ggaagatgtc tgtgtcggcc tggactcaca 1680
ggccccagat gtgaccagtg tcagcggggc tactgcaaca gataccctgt gtgtgtggcc 1740
tgccatcctt gcttccagac ctacgacgcc gacctgagag aacaggccct gagattcggc 1800
agactgagaa atgccaccgc cagcctttgg agcggacctg gccttgaaga tagaggcctg 1860
gcctccagaa tcctggacgc caagtctaag atcgagcaga tcagagccgt gctgtctagc 1920
ccagccgtga ccgaacaaga ggtggcccaa gtggctagcg ccatcctgag cctgagaaga 1980
actctgcagg gactgcagct cgatctgccc ctggaagagg aaacactgag cctgcctaga 2040
gatctggaaa gcctggatcg gagcttcaac ggcctgctga caatgtacca gagaaagaga 2100
gagcagttcg agaagatcag cagcgccgat cctagcggcg ccttcagaat gctgagcaca 2160
gcctatgagc agagcgccca ggctgctcag caagtgtccg atagcagcag actgctggac 2220
cagctgcggg actctagaag agaagccgaa agacttgtgc ggcaggcagg cggcggaggt 2280
ggaacaggat ctcctaaact ggtggccctg cggctggaaa tgtcctctct gcctgatctg 2340
acccctacct tcaacaagct gtgcggcaac agccggcaga tggcctgcac acctattagc 2400
tgtcctggcg agctgtgccc tcaggataat ggaaccgcct gcggctccag atgtagaggc 2460
gttttgccaa gagccggcgg agcctttctg atggctggac aagttgccga gcagctgaga 2520
ggcttcaacg ctcagctgca gcggaccaga cagatgatta gagccgccga ggaaagcgcc 2580
agccagattc aatctagcgc ccagagactg gaaacccagg tgtccgccag cagatcccag 2640
atggaagaag atgtgcggcg gacaagactg ctgatccagc aagtgcggga cttcctgacc 2700
gatcctgata ccgatgccgc cacaatccaa gaggtgtccg aagctgttct ggcactgtgg 2760
ctgcctaccg atagcgctac agtgctgcag aagatgaacg agatccaggc aatcgccgcc 2820
agactgccca atgtggatct ggtgctgagc cagaccaagc aggatatcgc cagagctaga 2880
aggctgcagg ccgaggccga agaggcaaga tctagagccc atgccgtgga aggccaagtc 2940
gaggacgttg tgggcaatct gagacaggga accgtggctc tgcaagaggc ccaggataca 3000
atgcagggca ccagcagaag cctgcgcctg atccaggata gagtggccga agtgcagcag 3060
gtcctgaggc cagccgaaaa gctggtcacc agcatgacca aacagctggg cgatttctgg 3120
acgcgcatgg aagaactgag gcatcaggca agacagcagg gcgctgaagc agtgcaggct 3180
caacaacttg ccgagggcgc ttctgaacag gctctgtctg cccaagaggg cttcgagcgg 3240
atcaagcaga agtacgccga gctgaaggac agactgggcc agagttctat gctgggcgaa 3300
cagggcgcca gaattcagag cgtgaaaaca gaggccgagg aactgttcgg cgagacaatg 3360
gaaatgatgg accggatgaa ggacatggaa ctggaactgc tgaggggcag ccaggccatc 3420
atgctgagaa gtgccgatct gacaggcctg gaaaagagag tggaacagat ccgggaccac 3480
atcaacggcc gggtgctgta ctacgccaca tgcaagtaa 3519

<210> SEQ ID NO 47
<211> LENGTH: 3582
<212> TYPE: DNA

<213> ORGANISM: Homo sapiens

<400> SEQUENCE: 47

```
atgcctgcgc tctggctggg ctgctgcctc tgcttctcgc tcctcctgcc cgcagcccgg     60
gccacctcca ggagggaagt ctgtgattgc aatgggaagt ccaggcagtg tatctttgat    120
cgggaacttc acagacaaac tggtaatgga ttccgctgcc tcaactgcaa tgacaacact    180
gatggcattc actgcgagaa gtgcaagaat ggcttttacc ggcacagaga aagggaccgc    240
tgtttgccct gcaattgtaa ctccaaaggt tctcttagtg ctcgatgtga caactccgga    300
cggtgcagct gtaaaccagg tgtgacagga gccagatgcg accgatgtct gccaggcttc    360
cacatgctca cggatgcggg gtgcacccaa gaccagagac tgctagactc caagtgtgac    420
tgtgacccag ctggcatcgc agggccctgt gacgcgggcc gctgtgtctg caagccagct    480
gtcactggag aacgctgtga taggtgtcga tcaggttact ataatctgga tgggggggaac    540
cctgagggct gtacccagtg tttctgctat gggcattcag ccagctgccg cagctctgca    600
gaatacagtg tccataagat cacctctacc tttcatcaag atgttgatgg ctggaaggct    660
gtccaacgaa atgggtctcc tgcaaagctc caatggtcac agcgccatca agatgtgttt    720
agctcagccc aacgactaga ccctgtctat tttgtggctc ctgccaaatt tcttgggaat    780
caacaggtga gctatggtca aagcctgtcc tttgactacc gtgtggacag aggaggcaga    840
cacccatctg cccatgatgt gattctggaa ggtgctggtc tacggatcac agctcccttg    900
atgccacttg gcaagacact gccttgtggg ctcaccaaga cttacacatt caggttaaat    960
gagcatccaa gcaataattg gagcccccag ctgagttact ttgagtatcg aaggttactg   1020
cggaatctca cagccctccg catccgagct acatatggag aatacagtac tgggtacatt   1080
gacaatgtga ccctgatttc agcccgccct gtctctggag ccccagcacc ctgggttgaa   1140
cagtgtatat gtcctgttgg gtacaagggg caattctgcc aggattgtgc ttctggctac   1200
aagagagatt cagcgagact ggggcctttt ggcacctgta ttccttgtaa ctgtcaaggg   1260
ggagggggcct gtgatccaga cacaggagat tgttattcag gggatgagaa tcctgacatt   1320
gagtgtgctg actgcccaat tggtttctac aacgatccgc acgacccccg cagctgcaag   1380
ccatgtccct gtcataacgg gttcagctgc tcagtgatgc cggagacgga ggaggtggtg   1440
tgcaataact gccctcccgg ggtcaccggt gcccgctgtg agctctgtgc tgatggctac   1500
tttggggacc cctttggtga acatggccca gtgaggcctt gtcagccctg tcaatgcaac   1560
aacaatgtgg accccagtgc ctctgggaat tgtgaccggc tgacaggcag gtgtttgaag   1620
tgtatccaca acacagccgg catctactgc gaccagtgca aagcaggcta cttcggggac   1680
ccattggctc ccaacccagc agacaagtgt cgagcttgca actgtaaccc catgggctca   1740
gagcctgtag gatgtcgaag tgatggcacc tgtgtttgca agccaggatt tggtggcccc   1800
aactgtgagc atggagcatt cagctgtcca gcttgctata atcaagtgaa gattcagatg   1860
gatcagttta tgcagcagct tcagagaatg gaggccctga tttcaaaggc tcagggtggt   1920
gatggagtag tacctgatac agagctggaa ggcaggatgc agcaggctga gcaggccctt   1980
caggacattc tgagagatgc ccagatttca gaaggtgcta gcagatccct tggtctccag   2040
ttggccaagg tgaggagcca agagaacagc taccagagcc gcctggatga cctcaagatg   2100
actgtggaaa gagttcgggc tctgggaagt cagtaccaga accgagttcg ggatactcac   2160
aggctcatca ctcagatgca gctgagcctg gcagaaagtg aagcttcctt gggaaacact   2220
aacattcctg cctcagacca ctacgtgggg ccaaatggct ttaaaagtct ggctcaggag   2280
```

gccacaagat tagcagaaag ccacgttgag tcagccagta acatggagca actgacaagg 2340
gaaactgagg actattccaa acaagccctc tcactggtgc gcaaggccct gcatgaagga 2400
gtcggaagcg gaagcggtag cccggacggt gctgtggtgc aagggcttgt ggaaaaattg 2460
gagaaaacca agtccctggc ccagcagttg acaagggagg ccactcaagc ggaaattgaa 2520
gcagataggt cttatcagca cagtctccgc ctcctggatt cagtgtctcg gcttcaggga 2580
gtcagtgatc agtcctttca ggtggaagaa gcaaagagga tcaaacaaaa agcggattca 2640
ctctcaagcc tggtaaccag gcatatggat gagttcaagc gtacacagaa gaatctggga 2700
aactggaaag aagaagcaca gcagctctta cagaatggaa aaagtgggag agagaaatca 2760
gatcagctgc tttcccgtgc caatcttgct aaaagcagag cacaagaagc actgagtatg 2820
ggcaatgcca ctttttatga agttgagagc atccttaaaa acctcagaga gtttgacctg 2880
caggtggaca acagaaaagc agaagctgaa gaagccatga agagactctc ctacatcagc 2940
cagaaggttt cagatgccag tgacaagacc cagcaagcag aaagagccct ggggagcgct 3000
gctgctgatg cacagagggc aaagaatggg gccggggagg ccctggaaat ctccagtgag 3060
attgaacagg agattgggag tctgaacttg gaagccaatg tgacagcaga tggagccttg 3120
gccatggaaa agggactggc ctctctgaag agtgagatga gggaagtgga aggagagctg 3180
gaaaggaagg agctggagtt tgacacgaat atggatgcag tacagatggt gattacagaa 3240
gcccagaagg ttgataccag agccaagaac gctggggtta caatccaaga cacactcaac 3300
acattagacg gcctcctgca tctgatggac cagcctctca gtgtagatga agaggggctg 3360
gtcttactgg agcagaagct ttcccgagcc aagacccaga tcaacagcca actgcggccc 3420
atgatgtcag agctggaaga gagggcacgt cagcagaggg gccacctcca tttgctggag 3480
acaagcatag atgggattct ggctgatgtg aagaacttgg agaacattag ggacaacctg 3540
cccccaggct gctacaatac ccaggctctt gagcaacagt ga 3582

<210> SEQ ID NO 48
<211> LENGTH: 3582
<212> TYPE: DNA
<213> ORGANISM: Artificial Sequence
<220> FEATURE:
<223> OTHER INFORMATION: Synthetic Construct

<400> SEQUENCE: 48
atgcctgctc tgtggctggg ctgctgcctg tgttttagtc tgctgctgcc agccgccaga 60
gccacatcta gaagagaagt gtgcgactgc aacggcaaga gccggcagtg catcttcgac 120
agagagctgc acagacagac cggcaacggc ttcagatgcc tgaactgcaa cgacaacacc 180
gacggcatcc actgcgagaa gtgcaagaac ggcttctacc ggcaccgcga gagggataga 240
tgcctgcctt gcaactgcaa ctccaagggc agcctgagcg ccagatgcga caatagcggc 300
agatgtagct gcaagcctgg cgtgacaggc gctagatgcg atagatgtct ccccggcttc 360
cacatgctga ccgatgccgg atgtacccag gaccagagac tgctggacag caagtgcgat 420
tgcgaccctg ccggaattgc cggaccttgt gatgccggaa gatgcgtgtg taaacctgcc 480
gtgaccggcg agagatgtga cagatgtaga agcggctact acaacctgga cggcggcaat 540
cctgaaggct gcacccagtg cttttgctac ggccacagcg ccagctgtag aagcagcgcc 600
gaatactccg tgcacaagat caccagcacc ttccaccagg atgtggacgg atggaaggcc 660
gtgcagagaa atggctctcc tgccaagctg cagtggtccc agagacacca ggacgtgttc 720

-continued

```
agcagcgctc agagactgga ccccgtgtac tttgtggccc ctgccaagtt cctgggcaac     780
cagcaagtgt cttacggcca gagcctgagc ttcgactaca gagtggatag aggcggcaga     840
caccccagcg ctcacgatgt gattcttgaa ggcgccggac tgcggatcac agcccctctt     900
atgcctctgg gcaagaccct gccttgtggc ctgaccaaga cctacacctt ccggctgaat     960
gagcacccca gcaacaactg gtccccacag ctgagctact tcgagtacag acggctgctg    1020
cggaacctga cagccctgag aatcagagcc acctacggcg agtacagcac cggctacatc    1080
gacaacgtga ccctgatcag cgccagacct gtttctggtg ctcctgctcc ttgggtcgag    1140
cagtgtatct gtcccgtggg ctacaagggc cagttctgcc aggattgtgc cagcggctac    1200
aagagagact ctgccagact gggccccttc ggcacatgca tcccttgtaa ttgtcaaggc    1260
ggcggagcct gcgatcccga tacaggcgat tgctacagcg gcgacgagaa ccccgatatc    1320
gagtgcgccg attgtcccat cggcttttac aacgaccctc acgaccccag atcctgcaag    1380
ccatgtcctt gccacaatgg cttcagctgc agcgtgatgc ccgaaaccga agaggtcgtg    1440
tgcaacaatt gcccaccagg cgttacaggg gccagatgtg aactgtgtgc cgacggctac    1500
ttcggcgatc cttttggaga acacggaccc gtgcgacctt gccagccttg tcagtgcaac    1560
aacaacgtgg acccaagcgc cagcggcaac tgcgatagac tgacaggcag atgtctgaag    1620
tgcatccaca ataccgccgg gatctactgt gaccagtgca aggccggcta ttttggcgac    1680
cctctggctc ccaatcctgc cgataagtgc agagcctgca actgtaaccc tatgggctct    1740
gagcctgtgg gctgcagatc tgatggaacc tgcgtgtgca agccaggctt tggcggacct    1800
aattgtgaac acggcgcctt tagctgcccc gcctgctaca atcaagtgaa gatccagatg    1860
gaccagttca tgcagcagct gcagaggatg gaagccctga tctctaaagc ccaaggcgga    1920
gatggcgtgg tgcctgatac agagctggaa ggcagaatgc agcaggccga acaggccctg    1980
caggacattc tgagagatgc ccagattagc gagggcgcct ctagaagtct gggactgcag    2040
ctggctaaag tgcggagcca agagaacagc taccagagca gactggacga cctgaagatg    2100
accgtggaaa gagtcagagc cctgggcagc cagtaccaga acagagtgcg ggatacccac    2160
cggctgatca cccagatgca actgtctctg gccgagagcg aagccagcct gggcaatacc    2220
aatattcccg ccagcgacca ctacgtgggc cccaacggtt ttaagagcct ggctcaagag    2280
gccaccagac tggccgaaag ccatgtggaa agcgcctcca acatggaaca gctgacccgg    2340
gaaaccgagg actactctaa gcaggccctg agcctcgtca gaaaagccct gcatgaaggc    2400
gtcggcagcg gctctggatc tcctgatggt gctgtggtgc agggactcgt ggaaaagctg    2460
gaaaagacca aatctctggc ccagcagctg accagagaag ccacacaggc cgagatcgag    2520
gccgacagaa gctaccagca ctcactgagg ctgctggact ccgtgtctag actgcagggc    2580
gtgtccgacc agagcttcca ggtggaagag gccaagcgga tcaagcagaa ggccgatagc    2640
ctgagcagcc tggtcaccag acacatggac gagttcaagc ggacccagaa gaacctcggc    2700
aactggaaag aggaagccca gcaactgctg cagaacggca agtctggaag agagaagtct    2760
gaccagctgc tgagcagagc caacctggcc aagtctagag cccaagaggc cctgtctatg    2820
ggcaacgcca ccttctacga ggtggaatcc atcctgaaga acctgcgcga gttcgacctg    2880
caagtggaca acagaaaggc cgaggccgag gaagccatga agagactgag ctacatcagc    2940
cagaaagtgt ccgacgcctc cgacaagaca cagcaggcag aaagagcact gggatctgcc    3000
gcagccgatg ctcagagagc taaaaacggc gctggcgagg ccctggaaat cagctctgag    3060
atcgagcaag agatcggctc cctgaatctg gaagccaatg tgacagccga tggcgccctg    3120
```

-continued

```
gccatggaaa aaggactggc ctctctgaag tccgagatga gagaggtgga aggcgagctg   3180
gaacggaaag aactggaatt cgacaccaat atggacgctg tgcagatggt catcacagag   3240
gcccagaagg tggacaccag agccaaaaat gccggcgtga ccatccagga caccctgaat   3300
actctggacg gactgctgca cctgatggat cagcctctga gcgtggacga ggaaggactg   3360
gttctgctgg aacagaagct gagccgggcc aagactcaga tcaacagcca gctgaggccc   3420
atgatgagcg aactggaaga acgggccaga cagcagaggg gccatctgca tctgctcgaa   3480
accagcatcg atggcatcct ggccgacgtg aagaatctcg agaacatccg ggacaacctg   3540
ccacctggct gctacaacac acaggcactg gaacagcagt ga                      3582
```

<210> SEQ ID NO 49
<211> LENGTH: 3891
<212> TYPE: DNA
<213> ORGANISM: Clostridium botulinum

<400> SEQUENCE: 49

```
atgccatttg ttaataaaca atttaattat aaagatcctg taaatggtgt tgatattgct     60
tatataaaaa ttccaaatgc aggacaaatg caaccagtaa aagcttttaa aattcataat    120
aaaatatggg ttattccaga aagagataca tttacaaatc ctgaagaagg agatttaaat    180
ccaccaccag aagcaaaaca agttccagtt tcatattatg attcaacata tttaagtaca    240
gataatgaaa aagataatta tttaaaggga gttacaaaat tatttgagag aatttattca    300
actgatcttg gaagaatgtt gttaacatca atagtaaggg gaataccatt ttggggtgga    360
agtacaatag atacagaatt aaaagttatt gatactaatt gtattaatgt gatacaacca    420
gatggtagtt atagatcaga agaacttaat ctagtaataa taggaccctc agctgatatt    480
atacagtttg aatgtaaaag ctttggacat gaagttttga atcttacgcg aaatggttat    540
ggctctactc aatacattag atttagccca gattttacat ttggttttga ggagtcactt    600
gaagttgata caaatcctct tttaggtgca ggcaaatttg ctacagatcc agcagtaaca    660
ttagcacatg aacttataca tgctggacat agattatatg gaatagcaat taatccaaat    720
agggttttta aagtaaatac taatgcctat tatgaaatga gtgggttaga agtaagcttt    780
gaggaactta gaacatttgg gggacatgat gcaaagttta tagatagttt acaggaaaac    840
gaatttcgtc tatattatta taataagttt aaagatatag caagtacact taataaagct    900
aaatcaatag taggtactac tgcttcatta cagtatatga aaaatgtttt taaagagaaa    960
tatctcctat ctgaagatac atctggaaaa ttttcggtag ataaattaaa atttgataag   1020
ttatacaaaa tgttaacaga gatttacaca gaggataatt ttgttaagtt ttttaaagta   1080
cttaacagaa aaacatattt gaattttgat aaagccgtat ttaagataaa tatagtacct   1140
aaggtaaatt acacaatata tgatggattt aatttaagaa atacaaattt agcagcaaac   1200
tttaatggtc aaaatacaga aattaataat atgaatttta ctaaactaaa aaattttact   1260
ggattgtttg aattttataa gttgctatgt gtaagaggga taataacttc taaaactaaa   1320
tcattagata aaggatacaa taaggcatta aatgatttat gtatcaaagt taataattgg   1380
gacttgtttt ttagtccttc agaagataat tttactaatg atctaaataa aggagaagaa   1440
attacatctg atactaatat agaagcagca gaagaaaata ttagtttaga tttaatacaa   1500
caatattatt taacctttaa ttttgataat gaacctgaaa atatttcaat agaaaatctt   1560
tcaagtgaca ttataggcca attagaactt atgcctaata tagaaagatt tcctaatgga   1620
```

-continued

```
aaaaagtatg agttagataa atatactatg ttccattatc ttcgtgctca agaatttgaa   1680
catggtaaat ctaggattgc tttaacaaat tctgttaacg aagcattatt aaatcctagt   1740
cgtgtttata catttttttc ttcagactat gtaaagaaag ttaataaagc tacggaggca   1800
gctatgtttt taggctgggt agaacaatta gtatatgatt ttaccgatga aactagcgaa   1860
gtaagtacta cggataaaat tgcggatata actataatta ttccatatat aggacctgct   1920
ttaaatatag gtaatatgtt atataaagat gatttgtag gtgctttaat attttcagga   1980
gctgttattc tgttagaatt tataccagag attgcaatac ctgtattagg tacttttgca   2040
cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catatttaat gaattctatg   2400
atcccttatg gtgttaaacg gttagaagat tttgatgcta gtcttaaaga tgcattatta   2460
aagtatatat atgataatag aggaacttta attggtcaag tagatagatt aaaagataaa   2520
gttaataata cacttagtac agatatacct tttcagcttt ccaaatacgt agataatcaa   2580
agattattat ctacatttac tgaatatatt aagaatatta ttaatacttc tatattgaat   2640
ttaagatatg aaagtaatca tttaatagac ttatctaggt atgcatcaaa aataaatatt   2700
ggtagtaaag taaattttga tccaatagat aaaaatcaaa ttcaattatt taatttagaa   2760
agtagtaaaa ttgaggtaat tttaaaaaat gctattgtat ataatagtat gtatgaaaat   2820
tttagtacta gcttttggat aagaattcct aagtatttta acagtataag tctaaataat   2880
gaatatacaa taataaattg tatggaaaat aattcaggat ggaaagtatc acttaattat   2940
ggtgaaataa tctggacttt acaggatact caggaaataa aacaaagagt agtttttaaa   3000
tacagtcaaa tgattaatat atcagattat ataaacagat ggatttttgt aactatcact   3060
aataatagat taaataactc taaaatttat ataaatggaa gattaataga tcaaaaacca   3120
atttcaaatt taggtaatat tcatgctagt aataatataa tgtttaaatt agatggttgt   3180
agagatacac atagatatat ttggataaaa tattttaatc tttttgataa ggaattaaat   3240
gaaaaagaaa tcaaagattt atatgataat caatcaaatt caggtatttt aaaagacttt   3300
tggggtgatt atttacaata tgataaacca tactatatgt taaatttata tgatccaaat   3360
aaatatgtcg atgtaaataa tgtaggtatt agaggttata tgtatcttaa agggcctaga   3420
ggtagcgtaa tgactacaaa catttattta aattcaagtt tgtatagggg gacaaaattt   3480
attataaaaa aatatgcttc tggaaataaa gataatattg ttagaaataa tgatcgtgta   3540
tatattaatg tagtagttaa aaataaagaa tataggttag ctactaatgc atcacaggca   3600
ggcgtagaaa aaatactaag tgcattagaa atacctgatg taggaaatct aagtcaagta   3660
gtagtaatga agtcaaaaaa tgatcaagga ataacaaata aatgcaaaat gaatttacaa   3720
gataataatg ggaatgatat aggctttata ggatttcatc agtttaataa tatagctaaa   3780
ctagtagcaa gtaattggta taatagacaa atagaaagat ctagtaggac tttgggttgc   3840
tcatgggaat ttattcctgt agatgatgga tggggagaaa ggccactgta a            3891
```

<210> SEQ ID NO 50
<211> LENGTH: 3891

<212> TYPE: DNA
<213> ORGANISM: Artificial Sequence
<220> FEATURE:
<223> OTHER INFORMATION: Synthetic Construct

<400> SEQUENCE: 50
atgcccttcg tgaacaagca gttcaactac aaggaccccg tgaacggcgt ggacattgcc 60
tacatcaaga tccccaacgc cggccagatg cagcccgtga aggcctttaa gatccacaac 120
aagatctggg tcatccccga gcgggacacc ttcacaaatc ccgaggaagg cgacctgaat 180
cctccacctg aagccaaaca ggtgcccgtg tcctactacg acagcaccta cctgagcacc 240
gacaacgaga aggacaacta cctgaagggc gtgaccaagc tgttcgagcg gatctacagc 300
accgatctgg gcagaatgct gctgacctct atcgtgcggg gcatcccatt ttggggcggc 360
agcacaatcg acaccgagct gaaagtgatc gacaccaact gcatcaacgt gatccagcct 420
gacggcagct acagaagcga ggaactgaac ctggtcatca tcggccccag cgccgacatc 480
atccagttcg agtgcaagag cttcggccac gaggtgctga acctgaccag aaatggctac 540
ggcagcaccc agtacatccg gttcagcccc gatttcacct tcggcttcga ggaatccctg 600
gaagtggaca ccaatcctct gctcggagcc ggcaagtttg ccaccgatcc tgctgtgaca 660
ctggcccacg aactgattca cgccggacac agactgtacg gaatcgccat caatcccaac 720
cgggtgttca aagtgaacac caacgcctac tatgagatga gcggactgga agtgtccttt 780
gaggaactgc ggaccttcgg cggacacgac gccaagttta tcgacagcct gcaagagaac 840
gagttccggc tgtactacta caacaagttc aaggatatcg ccagcacgct gaacaaggcc 900
aagagcatcg tgggcacaac agccagcctg cagtacatga agaacgtttt caaagagaag 960
tacctgctga gcgaggacac cagcggcaag ttctccgtgg acaagctgaa gttcgacaag 1020
ctgtacaaga tgctgaccga gatctacacc gaggacaact tcgtgaagtt cttcaaggtg 1080
ctcaaccgca agacctacct caacttcgac aaggccgtgt tcaagatcaa catcgtgccc 1140
aaagtcaact acaccatcta cgacggcttc aacctgcgca acaccaacct ggccgccaac 1200
ttcaacggcc agaacaccga gatcaacaac atgaacttca ccaagctgaa aaacttcacc 1260
ggcctgttcg agttctataa gctgctgtgc gtgcgcggca tcatcaccag caagaccaag 1320
agcctggaca agggctataa caaggccctg aacgacctgt gcatcaaagt taacaactgg 1380
gacctgttct tcagccccag cgaggataat ttcaccaacg acctgaacaa aggcgaggaa 1440
atcaccagcg acaccaatat cgaggccgcc gaggaaaaca tcagcctgga cctgatccag 1500
cagtactacc tgaccttcaa tttcgataac gagcccgaga acatcagcat cgagaacctg 1560
agcagcgata tcatcggaca gctggaactg atgcccaaca tcgagagatt ccccaacggc 1620
aagaagtacg agctggacaa gtacaccatg ttccactacc tgcgggccca agagttcgag 1680
cacggcaagt ctagaatcgc cctgaccaac agcgtgaacg aggccctgct gaaccccagc 1740
agagtgtaca ccttcttcag cagcgactac gtgaagaaag tcaacaaggc tacagaggcc 1800
gccatgttcc tcggctgggt tgagcagctg gtgtacgact tcaccgacga gacaagcgag 1860
gtgtccacca ccgacaagat cgccgatatc accatcatca tcccttacat cggccctgct 1920
ctgaacatcg gcaacatgct gtataaggac gatttcgtgg gcgccctgat cttctctggc 1980
gccgtgattc tgctcgagtt catccctgag atcgctatcc ccgtgctggg cacatttgct 2040
ctggtgtctt atatcgccaa caaggtgctg acagtgcaga ccatcgacaa cgccctgagc 2100
aagcggaacg agaagtggga cgaagtgtac aagtacatcg tgaccaactg gctggccaaa 2160

```
gtgaataccc agatcgacct gattcggaag aagatgaagg aagccctcga gaaccaggcc   2220
gaggccacaa aggccatcat caactaccag tacaatcagt acacagagga agagaagaac   2280
aacatcaatt tcaacatcga cgacctgtcc tccaagctca acgagagcat caacaaagcc   2340
atgatcaata tcaacaagtt tctgaaccag tgcagcgtca gctacctgat gaacagcatg   2400
atcccctacg gcgtgaagcg gctggaagat ttcgatgcca gcctgaagga cgctctgctg   2460
aagtacatct acgataaccg gggcaccctg atcggccagg tggacagact gaaggacaaa   2520
gtgaacaata ccctgtccac cgacattccg tttcagctga gcaaatacgt ggacaaccag   2580
agactgctga gcacattcac cgagtatatc aagaatatca tcaacacctc catcctgaac   2640
ctccgctacg agagcaacca cctgatcgat ctgagcagat acgccagcaa gatcaatatt   2700
ggctctaaag tgaacttcga cccgatcgac aagaaccaga tccagctgtt caatctcgag   2760
tctagcaaga tcgaagtgat cctgaagaac gccatcgtgt acaactctat gtacgagaac   2820
ttctccacca gcttttggat cagaatcccc aagtacttca acagcatctc cctgaacaac   2880
gagtacacga tcatcaattg catggaaaac aactccggct ggaaagtgtc cctgaactac   2940
ggcgagatca tctggacact gcaggacacc caagagatca agcagagagt ggtgttcaag   3000
tactctcaga tgatcaacat tagcgactac atcaaccggt ggatcttcgt gaccatcacc   3060
aacaaccggc tgaacaactc caagatctac atcaatggcc ggctcatcga ccagaagcct   3120
atcagcaacc tgggaaacat ccacgcctcc aacaatatca tgttcaagct ggacggctgc   3180
cgggacaccc accggtatat ctggatcaag tactttaacc tgttcgacaa agagctgaac   3240
gagaaagaga ttaaggacct gtacgacaac cagtccaaca gcggcatcct gaaggatttc   3300
tggggcgact acctgcagta tgacaagccc tactacatgc tgaatctgta cgaccccaac   3360
aaatatgtgg acgtgaacaa cgtggggatc agaggctaca tgtacctgaa aggccccaga   3420
ggcagcgtga tgaccaccaa catctacctg aactccagcc tgtacagagg caccaagttc   3480
atcatcaaga agtatgcctc cggcaacaag gacaacattg tgcggaacaa cgaccgggtg   3540
tacattaacg tggtggtcaa gaacaaagag taccggctgg ccaccaatgc ctctcaggca   3600
ggcgtggaaa agatcctgag cgccctggaa atccccgacg tgggcaatct gtctcaggtg   3660
gtcgtgatga agtccaagaa cgaccagggc atcacaaaca agtgcaagat gaacctccag   3720
gacaacaacg gcaacgacat cggctttatc ggcttccacc agtttaacaa cattgccaag   3780
ctggtcgcca gcaactggta caaccggcag atcgagagaa gcagcagaac cctgggctgc   3840
agctgggagt ttatccctgt ggatgatggc tggggcgaaa gacccctgta a            3891
```

<210> SEQ ID NO 51
<211> LENGTH: 3876
<212> TYPE: DNA
<213> ORGANISM: Clostridium botulinum

<400> SEQUENCE: 51

```
atgccagtta caataaataa ttttaattat aatgatccta ttgataataa taatattatt     60
atgatggagc ctccatttgc gagaggtacg gggagatatt ataaagcttt taaaatcaca    120
gatcgtattt ggataatacc ggaaagatat acttttggat ataaacctga ggattttaat    180
aaaagttccg gtatttttaa tagagatgtt tgtgaatatt atgatccaga ttacttaaat    240
actaatgata aaaagaatat atttttacaa acaatgatca agttatttaa tagaatcaaa    300
tcaaaaccat tgggtgaaaa gttattagag atgattataa atggtatacc ttatcttgga    360
gatagacgtg ttccactcga agagtttaac acaaacattg ctagtgtaac tgttaataaa    420
```

-continued

```
ttaatcagta atccaggaga agtggagcga aaaaaaggta ttttcgcaaa tttaataata    480
tttggacctg ggccagtttt aaatgaaaat gagactatag atataggtat acaaaatcat    540
tttgcatcaa gggaaggctt cgggggtata atgcaaatga agttttgccc agaatatgta    600
agcgtattta ataatgttca agaaaacaaa ggcgcaagta tatttaatag acgtggatat    660
ttttcagatc cagccttgat attaatgcat gaacttatac atgttttaca tggattatat    720
ggcattaaag tagatgattt accaattgta ccaaatgaaa aaaaattttt tatgcaatct    780
acagatgcta tacaggcaga agaactatat acatttggag gacaagatcc cagcatcata    840
actccttcta cggataaaag tatctatgat aaagttttgc aaaattttag agggatagtt    900
gatagactta acaaggtttt agtttgcata tcagatccta acattaatat taatatatat    960
aaaaataaat ttaaagataa atataaattc gttgaagatt ctgagggaaa atatagtata   1020
gatgtagaaa gttttgataa attatataaa agcttaatgt ttggttttac agaaactaat   1080
atagcagaaa attataaaat aaaaactaga gcttcttatt ttagtgattc cttaccacca   1140
gtaaaaataa aaaatttatt agataatgaa atctatacta tagaggaagg gtttaatata   1200
tctgataaag atatggaaaa agaatataga ggtcagaata aagctataaa taaacaagct   1260
tatgaagaaa ttagcaagga gcatttggct gtatataaga tacaaatgtg taaaagtgtt   1320
aaagctccag gaatatgtat tgatgttgat aatgaagatt tgttctttat agctgataaa   1380
aatagttttt cagatgattt atctaaaaac gaaagaatag aatataatac acagagtaat   1440
tatatagaaa atgacttccc tataaatgaa ttaattttag atactgattt aataagtaaa   1500
atagaattac caagtgaaaa tacagaatca cttactgatt ttaatgtaga tgttccagta   1560
tatgaaaaac aacccgctat aaaaaaaatt tttacagatg aaaataccat ctttcaatat   1620
ttatactctc agacatttcc tctagatata agagatataa gtttaacatc ttcatttgat   1680
gatgcattat tattttctaa caaagtttat tcattttttt ctatggatta tattaaaact   1740
gctaataaag tggtagaagc aggattattt gcaggttggg tgaaacagat agtaaatgat   1800
tttgtaatcg aagctaataa aagcaatact atggataaaa ttgcagatat atctctaatt   1860
gttccttata taggattagc tttaaatgta ggaaatgaaa cagctaaagg aaattttgaa   1920
aatgcttttg agattgcagg agccagtatt ctactagaat ttataccaga acttttaata   1980
cctgtagttg gagccttttt attagaatca tatattgaca ataaaaataa aattattaaa   2040
acaatagata atgctttaac taaaagaaat gaaaaatgga gtgatatgta cggattaata   2100
gtagcgcaat ggctctcaac agttaatact caattttata caataaaaga gggaatgtat   2160
aaggctttaa attatcaagc acaagcattg gaagaaataa taaaatacag atataatata   2220
tattctgaaa aagaaaagtc aaatattaac atcgatttta atgatataaa ttctaaactt   2280
aatgagggta ttaaccaagc tatagataat ataaataatt ttataaatgg atgttctgta   2340
tcatatttaa tgaaaaaaat gattccatta gctgtagaaa aattactaga ctttgataat   2400
actctcaaaa aaaatttgtt aaattatata gatgaaaata aattatattt gattggaagt   2460
gcagaatatg aaaaatcaaa agtaaataaa tacttgaaaa ccattatgcc gtttgatctt   2520
tcaatatata ccaatgatac aatactaata gaaatgttta ataaatataa tagcgaaatt   2580
ttaaataata ttatcttaaa tttaagatat aaggataata atttaataga tttatcagga   2640
tatggggcaa aggtagaggt atatgatgga gtcgagctta atgataaaaa tcaatttaaa   2700
ttaactagtt cagcaaatag taagattaga gtgactcaaa atcagaatat catatttaat   2760
```

-continued

```
agtgtgttcc ttgattttag cgttagcttt tggataagaa tacctaaata taagaatgat   2820

ggtatacaaa attatattca taatgaatat acaataatta attgtatgaa aaataattcg   2880

ggctggaaaa tatctattag gggtaatagg ataatatgga ctttaattga tataaatgga   2940

aaaaccaaat cggtattttt tgaatataac ataagagaag atatatcaga gtatataaat   3000

agatggtttt ttgtaactat tactaataat ttgaataacg ctaaaattta tattaatggt   3060

aagctagaat caaatacaga tattaaagat ataagagaag ttattgctaa tggtgaaata   3120

atatttaaat tagatggtga tatagataga acacaattta tttggatgaa atatttcagt   3180

atttttaata cggaattaag tcaatcaaat attgaagaaa gatataaaat tcaatcatat   3240

agcgaatatt taaaagattt ttggggaaat cctttaatgt acaataaaga atattatatg   3300

tttaatgcgg ggaataaaaa ttcatatatt aaactaaaga aagattcacc tgtaggtgaa   3360

attttaacac gtagcaaata taatcaaaat tctaaatata taaattatag agatttatat   3420

attggagaaa aatttattat aagaagaaag tcaaattctc aatctataaa tgatgatata   3480

gttagaaaag aagattatat atatctagat ttttttaatt taaatcaaga gtggagagta   3540

tatacctata aatattttaa gaaagaggaa gaaaaattgt ttttagctcc tataagtgat   3600

tctgatgagt tttacaatac tatacaaata aaagaatatg atgaacagcc aacatatagt   3660

tgtcagttgc tttttaaaaa agatgaagaa agtactgatg agataggatt gattggtatt   3720

catcgtttct acgaatctgg aattgtattt gaagagtata aagattattt ttgtataagt   3780

aaatggtact taaaagaggt aaaaaggaaa ccatataatt taaaattggg atgtaattgg   3840

cagtttattc ctaaagatga agggtggact gaataa                              3876
```

<210> SEQ ID NO 52
<211> LENGTH: 3876
<212> TYPE: DNA
<213> ORGANISM: Artificial Sequence
<220> FEATURE:
<223> OTHER INFORMATION: Synthetic Construct

<400> SEQUENCE: 52

```
atgcccgtga ccatcaacaa cttcaactac aacgacccca tcgacaacaa caacatcatt     60

atgatggaac cgcctttcgc cagaggcaca ggccggtact acaaggcctt caagatcacc    120

gaccggatct ggatcatccc cgagagatac accttcggct acaagcccga ggacttcaac    180

aagagcagcg gcatcttcaa ccgggacgtg tgcgagtact acgaccccga ctacctgaac    240

accaacgaca agaagaacat cttcctgcag accatgatca agctgttcaa ccggatcaag    300

agcaagcccc tgggcgagaa gctgctggaa atgatcatca acggcatccc ttacctgggc    360

gacagaagag tgcccctgga agagttcaac accaatatcg ccagcgtgac cgtgaacaag    420

ctgatctcta accccggcga ggtggaacgg aagaagggca tcttcgccaa cctgatcatc    480

ttcggccctg gacctgtgct gaacgagaac gagacaatcg acatcggcat ccagaaccac    540

ttcgccagca gagaaggctt cggcggcatc atgcagatga agttctgccc cgagtacgtg    600

tccgtgttca acaacgtgca agagaacaag ggcgccagca tctttaacag acggggctac    660

ttcagcgacc ccgctctgat tctgatgcac gagctgatcc acgtgctgca cggcctgtat    720

ggcatcaagg tggacgacct gcctatcgtg cccaacgaga agaaattctt catgcagtcc    780

accgacgcca tccaggccga ggaactgtac acatttggcg gacaggaccc cagcatcatc    840

acccctagca ccgacaagag catctacgac aaggtgctgc agaatttccg ggcatcgtg     900

gaccggctga acaaagtgct cgtgtgcatc agcgatccca acatcaatat caacatctac    960
```

-continued

```
aagaacaagt tcaaggataa gtacaagttc gtcgaggaca gcgagggcaa gtacagcatc   1020
gacgtggaaa gcttcgacaa gctgtacaag agcctgatgt tcggcttcac cgagacaaat   1080
atcgccgaga actacaagat caagacccgg gccagctact tctccgactc tctgcctcct   1140
gtgaagatta agaacctgct ggacaacgag atctacacca tcgaggaagg cttcaacatc   1200
agcgacaagg acatggaaaa agagtaccgg ggccagaaca aggccattaa caagcaggcc   1260
tacgaggaaa tcagcaaaga acacctggcc gtgtacaaga ttcagatgtg caagagcgtg   1320
aaggcccctg gcatctgcat tgacgtggac aatgaggacc tgttctttat cgccgacaag   1380
aacagcttta gcgacgacct gagcaagaac gagcggatcg agtacaacac ccagagcaac   1440
tacatcgaga acgacttccc catcaacgaa ctgatcctgg acaccgacct gatcagcaag   1500
atcgagctgc ccagcgagaa caccgagagc ctgaccgact tcaatgtgga cgtgcccgtg   1560
tacgagaagc agcccgccat caagaagatc tttaccgacg agaataccat cttccagtac   1620
ctgtacagcc agacctttcc tctggacatc cgggacatca gcctgacctc cagcttcgat   1680
gatgccctgc tgttcagcaa caaggtctac agcttcttca gcatggacta catcaagacc   1740
gccaacaagg tggtggaagc cggcctgttt gccggctggg ttaagcagat cgtgaacgat   1800
ttcgtgatcg aggccaacaa gtccaacacc atggacaaga tcgccgatat ctccctgatc   1860
gtgccctaca tcggactggc cctgaacgtg ggaaacgaga cagccaaggg caacttcgag   1920
aatgccttcg agattgccgg cgctagcatc ctgctcgagt tcatccctga gctgctgatc   1980
cctgtcgtgg gcgcttttct gctggaatcc tacatcgata acaaaaacaa gatcatcaag   2040
acgatcgaca acgccctgac caagcggaac gagaagtgga gcgatatgta cggactgatc   2100
gtggcccagt ggctgagcac cgtgaatacc cagttttaca ccatcaaaga agggatgtac   2160
aaggccctga attaccaggc tcaggctctg gaagagatca ttaagtaccg ctacaatatc   2220
tacagcgaga aagagaagtc taacatcaac atcgacttca acgacatcaa cagcaagctc   2280
aacgagggca tcaaccaggc cattgacaac attaacaact ttatcaacgg ctgcagcgtg   2340
tcctacctga tgaagaagat gattcctctg gccgtggaaa agctgctcga cttcgacaat   2400
accctgaaga agaacctcct gaactacatt gacgagaaca agctctacct gatcggcagc   2460
gccgagtacg agaaaagcaa agtgaacaag tacctcaaga ccatcatgcc cttcgacctg   2520
tccatctaca caaacgacac catcctgatc gagatgttta acaagtacaa cagcgagatc   2580
ctgaacaata tcatcctgaa cctgcggtac aaggacaaca atctgatcga tctgagcggc   2640
tacggcgcca aggtggaagt gtatgatggc gtggaactga acgataagaa tcagttcaag   2700
ctgaccagca gcgccaactc caagatcaga gtgacccaga accagaacat tatcttcaac   2760
agcgtgttcc tggacttctc cgtgtccttc tggatcagaa tccccaagta caagaacgac   2820
ggcattcaga actacatcca caacgagtac acaatcatca actgtatgaa gaacaacagc   2880
ggctggaaga tcagcatccg gggcaacaga atcatctgga ccctgatcga catcaatggc   2940
aagacaaaga gcgtgttctt cgagtataac atccgcgagg acatctccga gtacatcaac   3000
cggtggttct tcgtgacaat caccaacaac ctgaacaacg ccaagatcta catcaacggg   3060
aagctcgaga gcaacaccga catcaaggat atccgggaag tgatcgccaa cggcgagatc   3120
atctttaagc tggacggcga catcgaccgg acacagttca tctggatgaa gtacttttcc   3180
atcttcaata ccgagctgag ccagagcaat atcgaagaga ggtacaagat ccagtcttac   3240
agcgagtacc tgaaggactt ctggggcaac cctctgatgt acaacaaaga atattacatg   3300
```

-continued

```
ttcaacgccg gcaacaagaa ctcttacatc aagctgaaga aagacagccc cgtgggagaa   3360

atcctgacca ggtctaagta caaccagaac tccaagtata tcaactaccg ggacctgtac   3420

atcggcgaga agttcatcat ccggcgcaag agcaacagcc agtccatcaa tgacgacatc   3480

gtgcggaaag aggactatat ctacctcgac ttcttcaacc tcaatcaaga gtggcgcgtg   3540

tacacctaca agtactttaa gaaagaggaa gagaagctgt tcctggctcc tatcagcgac   3600

tccgacgagt tctacaatac catccagatc aaagagtacg acgagcagcc cacctacagc   3660

tgccagctgc tgtttaagaa ggacgaggaa tccaccgatg agatcggcct gattggcatc   3720

caccggttct acgagagcgg catcgtgttc gaagagtaca aggattactt ctgcatcagc   3780

aagtggtatc tgaaagaagt gaagcggaag ccctacaatc tgaagctggg ctgcaactgg   3840

cagtttatcc ccaaggacga aggctggacc gagtga                             3876
```

<210> SEQ ID NO 53
<211> LENGTH: 2477
<212> TYPE: PRT
<213> ORGANISM: Homo sapiens

<400> SEQUENCE: 53

```
Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270
```

-continued

```
His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
```

-continued

```
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln Ile
    1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
                1045                1050                1055

Gln Pro Ala Ser Glu Tyr Thr Val Ser Leu Val Ala Ile Lys Gly Asn
            1060                1065                1070

Gln Glu Ser Pro Lys Ala Thr Gly Val Phe Thr Thr Leu Gln Pro Gly
        1075                1080                1085

Ser Ser Ile Pro Pro Tyr Asn Thr Glu Val Thr Glu Thr Thr Ile Val
    1090                1095                1100

Ile Thr Trp Thr Pro Ala Pro Arg Ile Gly Phe Lys Leu Gly Val Arg
1105                1110                1115                1120
```

```
Pro Ser Gln Gly Gly Glu Ala Pro Arg Glu Val Thr Ser Asp Ser Gly
                1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
        1155                1160                1165

Lys Val Val Thr Pro Leu Ser Pro Pro Thr Asn Leu His Leu Glu Ala
    1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
                1205                1210                1215

Gln Gly Asn Ser Leu Glu Glu Val Val His Ala Asp Gln Ser Ser Cys
            1220                1225                1230

Thr Phe Asp Asn Leu Ser Pro Gly Leu Glu Tyr Asn Val Ser Val Tyr
        1235                1240                1245

Thr Val Lys Asp Asp Lys Glu Ser Val Pro Ile Ser Asp Thr Ile Ile
    1250                1255                1260

Pro Glu Val Pro Gln Leu Thr Asp Leu Ser Phe Val Asp Ile Thr Asp
1265                1270                1275                1280

Ser Ser Ile Gly Leu Arg Trp Thr Pro Leu Asn Ser Ser Thr Ile Ile
                1285                1290                1295

Gly Tyr Arg Ile Thr Val Val Ala Ala Gly Glu Gly Ile Pro Ile Phe
            1300                1305                1310

Glu Asp Phe Val Asp Ser Ser Val Gly Tyr Tyr Thr Val Thr Gly Leu
        1315                1320                1325

Glu Pro Gly Ile Asp Tyr Asp Ile Ser Val Ile Thr Leu Ile Asn Gly
    1330                1335                1340

Gly Glu Ser Ala Pro Thr Thr Leu Thr Gln Gln Thr Ala Val Pro Pro
1345                1350                1355                1360

Pro Thr Asp Leu Arg Phe Thr Asn Ile Gly Pro Asp Thr Met Arg Val
                1365                1370                1375

Thr Trp Ala Pro Pro Pro Ser Ile Asp Leu Thr Asn Phe Leu Val Arg
            1380                1385                1390

Tyr Ser Pro Val Lys Asn Glu Glu Asp Val Ala Glu Leu Ser Ile Ser
        1395                1400                1405

Pro Ser Asp Asn Ala Val Val Leu Thr Asn Leu Leu Pro Gly Thr Glu
    1410                1415                1420

Tyr Val Val Ser Val Ser Ser Val Tyr Glu Gln His Glu Ser Thr Pro
1425                1430                1435                1440

Leu Arg Gly Arg Gln Lys Thr Gly Leu Asp Ser Pro Thr Gly Ile Asp
                1445                1450                1455

Phe Ser Asp Ile Thr Ala Asn Ser Phe Thr Val His Trp Ile Ala Pro
            1460                1465                1470

Arg Ala Thr Ile Thr Gly Tyr Arg Ile Arg His His Pro Glu His Phe
        1475                1480                1485

Ser Gly Arg Pro Arg Glu Asp Arg Val Pro His Ser Arg Asn Ser Ile
    1490                1495                1500

Thr Leu Thr Asn Leu Thr Pro Gly Thr Glu Tyr Val Val Ser Ile Val
1505                1510                1515                1520

Ala Leu Asn Gly Arg Glu Glu Ser Pro Leu Leu Ile Gly Gln Gln Ser
                1525                1530                1535
```

-continued

```
Thr Val Ser Asp Val Pro Arg Asp Leu Glu Val Val Ala Ala Thr Pro
            1540                1545                1550

Thr Ser Leu Leu Ile Ser Trp Asp Ala Pro Ala Val Thr Val Arg Tyr
        1555                1560                1565

Tyr Arg Ile Thr Tyr Gly Glu Thr Gly Gly Asn Ser Pro Val Gln Glu
    1570                1575                1580

Phe Thr Val Pro Gly Ser Lys Ser Thr Ala Thr Ile Ser Gly Leu Lys
1585                1590                1595                1600

Pro Gly Val Asp Tyr Thr Ile Thr Val Tyr Ala Val Thr Gly Arg Gly
                1605                1610                1615

Asp Ser Pro Ala Ser Ser Lys Pro Ile Ser Ile Asn Tyr Arg Thr Glu
            1620                1625                1630

Ile Asp Lys Pro Ser Gln Met Gln Val Thr Asp Val Gln Asp Asn Ser
        1635                1640                1645

Ile Ser Val Lys Trp Leu Pro Ser Ser Ser Pro Val Thr Gly Tyr Arg
    1650                1655                1660

Val Thr Thr Thr Pro Lys Asn Gly Pro Gly Pro Thr Lys Thr Lys Thr
1665                1670                1675                1680

Ala Gly Pro Asp Gln Thr Glu Met Thr Ile Glu Gly Leu Gln Pro Thr
                1685                1690                1695

Val Glu Tyr Val Val Ser Val Tyr Ala Gln Asn Pro Ser Gly Glu Ser
            1700                1705                1710

Gln Pro Leu Val Gln Thr Ala Val Thr Asn Ile Asp Arg Pro Lys Gly
        1715                1720                1725

Leu Ala Phe Thr Asp Val Asp Val Asp Ser Ile Lys Ile Ala Trp Glu
    1730                1735                1740

Ser Pro Gln Gly Gln Val Ser Arg Tyr Arg Val Thr Tyr Ser Ser Pro
1745                1750                1755                1760

Glu Asp Gly Ile His Glu Leu Phe Pro Ala Pro Asp Gly Glu Glu Asp
                1765                1770                1775

Thr Ala Glu Leu Gln Gly Leu Arg Pro Gly Ser Glu Tyr Thr Val Ser
            1780                1785                1790

Val Val Ala Leu His Asp Asp Met Glu Ser Gln Pro Leu Ile Gly Thr
        1795                1800                1805

Gln Ser Thr Ala Ile Pro Ala Pro Thr Asp Leu Lys Phe Thr Gln Val
    1810                1815                1820

Thr Pro Thr Ser Leu Ser Ala Gln Trp Thr Pro Pro Asn Val Gln Leu
1825                1830                1835                1840

Thr Gly Tyr Arg Val Arg Val Thr Pro Lys Glu Lys Thr Gly Pro Met
                1845                1850                1855

Lys Glu Ile Asn Leu Ala Pro Asp Ser Ser Ser Val Val Val Ser Gly
            1860                1865                1870

Leu Met Val Ala Thr Lys Tyr Glu Val Ser Val Tyr Ala Leu Lys Asp
        1875                1880                1885

Thr Leu Thr Ser Arg Pro Ala Gln Gly Val Val Thr Thr Leu Glu Asn
    1890                1895                1900

Val Ser Pro Pro Arg Arg Ala Arg Val Thr Asp Ala Thr Glu Thr Thr
1905                1910                1915                1920

Ile Thr Ile Ser Trp Arg Thr Lys Thr Glu Thr Ile Thr Gly Phe Gln
                1925                1930                1935

Val Asp Ala Val Pro Ala Asn Gly Gln Thr Pro Ile Gln Arg Thr Ile
            1940                1945                1950

Lys Pro Asp Val Arg Ser Tyr Thr Ile Thr Gly Leu Gln Pro Gly Thr
```

-continued

```
        1955                1960                1965

Asp Tyr Lys Ile Tyr Leu Tyr Thr Leu Asn Asp Asn Ala Arg Ser Ser
    1970                1975                1980

Pro Val Val Ile Asp Ala Ser Thr Ala Ile Asp Ala Pro Ser Asn Leu
1985                1990                1995                2000

Arg Phe Leu Ala Thr Thr Pro Asn Ser Leu Leu Val Ser Trp Gln Pro
                2005                2010                2015

Pro Arg Ala Arg Ile Thr Gly Tyr Ile Ile Lys Tyr Glu Lys Pro Gly
            2020                2025                2030

Ser Pro Pro Arg Glu Val Val Pro Arg Pro Arg Pro Gly Val Thr Glu
        2035                2040                2045

Ala Thr Ile Thr Gly Leu Glu Pro Gly Thr Glu Tyr Thr Ile Tyr Val
    2050                2055                2060

Ile Ala Leu Lys Asn Asn Gln Lys Ser Glu Pro Leu Ile Gly Arg Lys
2065                2070                2075                2080

Lys Thr Asp Glu Leu Pro Gln Leu Val Thr Leu Pro His Pro Asn Leu
                2085                2090                2095

His Gly Pro Glu Ile Leu Asp Val Pro Ser Thr Val Gln Lys Thr Pro
            2100                2105                2110

Phe Val Thr His Pro Gly Tyr Asp Thr Gly Asn Gly Ile Gln Leu Pro
        2115                2120                2125

Gly Thr Ser Gly Gln Gln Pro Ser Val Gly Gln Gln Met Ile Phe Glu
    2130                2135                2140

Glu His Gly Phe Arg Arg Thr Thr Pro Pro Thr Thr Ala Thr Pro Ile
2145                2150                2155                2160

Arg His Arg Pro Arg Pro Tyr Pro Pro Asn Val Gly Glu Glu Ile Gln
                2165                2170                2175

Ile Gly His Ile Pro Arg Glu Asp Val Asp Tyr His Leu Tyr Pro His
            2180                2185                2190

Gly Pro Gly Leu Asn Pro Asn Ala Ser Thr Gly Gln Glu Ala Leu Ser
        2195                2200                2205

Gln Thr Thr Ile Ser Trp Ala Pro Phe Gln Asp Thr Ser Glu Tyr Ile
    2210                2215                2220

Ile Ser Cys His Pro Val Gly Thr Asp Glu Glu Pro Leu Gln Phe Arg
2225                2230                2235                2240

Val Pro Gly Thr Ser Thr Ser Ala Thr Leu Thr Gly Leu Thr Arg Gly
                2245                2250                2255

Ala Thr Tyr Asn Ile Ile Val Glu Ala Leu Lys Asp Gln Gln Arg His
            2260                2265                2270

Lys Val Arg Glu Glu Val Val Thr Val Gly Asn Ser Val Asn Glu Gly
        2275                2280                2285

Leu Asn Gln Pro Thr Asp Asp Ser Cys Phe Asp Pro Tyr Thr Val Ser
    2290                2295                2300

His Tyr Ala Val Gly Asp Glu Trp Glu Arg Met Ser Glu Ser Gly Phe
2305                2310                2315                2320

Lys Leu Leu Cys Gln Cys Leu Gly Phe Gly Ser Gly His Phe Arg Cys
                2325                2330                2335

Asp Ser Ser Arg Trp Cys His Asp Asn Gly Val Asn Tyr Lys Ile Gly
            2340                2345                2350

Glu Lys Trp Asp Arg Gln Gly Glu Asn Gly Gln Met Met Ser Cys Thr
        2355                2360                2365

Cys Leu Gly Asn Gly Lys Gly Glu Phe Lys Cys Asp Pro His Glu Ala
    2370                2375                2380
```

```
Thr Cys Tyr Asp Asp Gly Lys Thr Tyr His Val Gly Glu Gln Trp Gln
2385                2390                2395                2400

Lys Glu Tyr Leu Gly Ala Ile Cys Ser Cys Thr Cys Phe Gly Gly Gln
                2405                2410                2415

Arg Gly Trp Arg Cys Asp Asn Cys Arg Arg Pro Gly Gly Glu Pro Ser
            2420                2425                2430

Pro Glu Gly Thr Thr Gly Gln Ser Tyr Asn Gln Tyr Ser Gln Arg Tyr
        2435                2440                2445

His Gln Arg Thr Asn Thr Asn Val Asn Cys Pro Ile Glu Cys Phe Met
    2450                2455                2460

Pro Leu Asp Val Gln Ala Asp Arg Glu Asp Ser Arg Glu
2465                2470                2475


<210> SEQ ID NO 54
<211> LENGTH: 786
<212> TYPE: PRT
<213> ORGANISM: Homo sapiens

<400> SEQUENCE: 54

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
        115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Ala Lys Phe Gly Ala Gly Ala Ala Gly
            260                 265                 270

Val Leu Pro Gly Val Gly Gly Ala Gly Val Pro Gly Val Pro Gly Ala
```

```
        275                 280                 285

Ile Pro Gly Ile Gly Gly Ile Ala Gly Val Gly Thr Pro Ala Ala Ala
    290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
        355                 360                 365

Ser Pro Glu Ala Ala Ala Lys Ala Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Gly Val Pro Gly Val Gly Gly Val
            420                 425                 430

Pro Gly Val Gly Ile Ser Pro Glu Ala Gln Ala Ala Ala Ala Ala Lys
        435                 440                 445

Ala Ala Lys Tyr Gly Ala Ala Gly Ala Gly Val Leu Gly Gly Leu Val
    450                 455                 460

Pro Gly Ala Pro Gly Ala Val Pro Gly Val Pro Gly Thr Gly Gly Val
465                 470                 475                 480

Pro Gly Val Gly Thr Pro Ala Ala Ala Ala Ala Lys Ala Ala Ala Lys
                485                 490                 495

Ala Ala Gln Phe Gly Leu Val Pro Gly Val Gly Val Ala Pro Gly Val
            500                 505                 510

Gly Val Ala Pro Gly Val Gly Val Ala Pro Gly Val Gly Leu Ala Pro
        515                 520                 525

Gly Val Gly Val Ala Pro Gly Val Gly Val Ala Pro Gly Val Gly Val
    530                 535                 540

Ala Pro Gly Ile Gly Pro Gly Gly Val Ala Ala Ala Ala Lys Ser Ala
545                 550                 555                 560

Ala Lys Val Ala Ala Lys Ala Gln Leu Arg Ala Ala Ala Gly Leu Gly
                565                 570                 575

Ala Gly Ile Pro Gly Leu Gly Val Gly Val Gly Val Pro Gly Leu Gly
            580                 585                 590

Val Gly Ala Gly Val Pro Gly Leu Gly Val Gly Ala Gly Val Pro Gly
        595                 600                 605

Phe Gly Ala Gly Ala Asp Glu Gly Val Arg Arg Ser Leu Ser Pro Glu
    610                 615                 620

Leu Arg Glu Gly Asp Pro Ser Ser Ser Gln His Leu Pro Ser Thr Pro
625                 630                 635                 640

Ser Ser Pro Arg Val Pro Gly Ala Leu Ala Ala Ala Lys Ala Ala Lys
                645                 650                 655

Tyr Gly Ala Ala Val Pro Gly Val Leu Gly Gly Leu Gly Ala Leu Gly
            660                 665                 670

Gly Val Gly Ile Pro Gly Gly Val Val Gly Ala Gly Pro Ala Ala Ala
        675                 680                 685

Ala Ala Ala Ala Lys Ala Ala Ala Lys Ala Ala Gln Phe Gly Leu Val
    690                 695                 700
```

```
Gly Ala Ala Gly Leu Gly Gly Leu Gly Val Gly Gly Leu Gly Val Pro
705                 710                 715                 720

Gly Val Gly Gly Leu Gly Gly Ile Pro Pro Ala Ala Ala Ala Lys Ala
                725                 730                 735

Ala Lys Tyr Gly Ala Ala Gly Leu Gly Gly Val Leu Gly Gly Ala Gly
            740                 745                 750

Gln Phe Pro Leu Gly Gly Val Ala Ala Arg Pro Gly Phe Gly Leu Ser
        755                 760                 765

Pro Ile Phe Pro Gly Gly Ala Cys Leu Gly Lys Ala Cys Gly Arg Lys
    770                 775                 780

Arg Lys
785


<210> SEQ ID NO 55
<211> LENGTH: 338
<212> TYPE: PRT
<213> ORGANISM: Homo sapiens

<400> SEQUENCE: 55

Met Ser Leu Ser Ala Phe Thr Leu Phe Leu Ala Leu Ile Gly Gly Thr
1               5                   10                  15

Ser Gly Gln Tyr Tyr Asp Tyr Asp Phe Pro Leu Ser Ile Tyr Gly Gln
            20                  25                  30

Ser Ser Pro Asn Cys Ala Pro Glu Cys Asn Cys Pro Glu Ser Tyr Pro
        35                  40                  45

Ser Ala Met Tyr Cys Asp Glu Leu Lys Leu Lys Ser Val Pro Met Val
    50                  55                  60

Pro Pro Gly Ile Lys Tyr Leu Tyr Leu Arg Asn Asn Gln Ile Asp His
65                  70                  75                  80

Ile Asp Glu Lys Ala Phe Glu Asn Val Thr Asp Leu Gln Trp Leu Ile
                85                  90                  95

Leu Asp His Asn Leu Leu Glu Asn Ser Lys Ile Lys Gly Arg Val Phe
            100                 105                 110

Ser Lys Leu Lys Gln Leu Lys Lys Leu His Ile Asn His Asn Asn Leu
        115                 120                 125

Thr Glu Ser Val Gly Pro Leu Pro Lys Ser Leu Glu Asp Leu Gln Leu
    130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
            180                 185                 190

Phe Asn Gln Ile Ala Arg Leu Pro Ser Gly Leu Pro Val Ser Leu Leu
        195                 200                 205

Thr Leu Tyr Leu Asp Asn Asn Lys Ile Ser Asn Ile Pro Asp Glu Tyr
    210                 215                 220

Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
            260                 265                 270

Asn Glu Asn Leu Glu Asn Tyr Tyr Leu Glu Val Asn Gln Leu Glu Lys
```

```
        275                 280                 285

Phe Asp Ile Lys Ser Phe Cys Lys Ile Leu Gly Pro Leu Ser Tyr Ser
    290                 295                 300

Lys Ile Lys His Leu Arg Leu Asp Gly Asn Arg Ile Ser Glu Thr Ser
305                 310                 315                 320

Leu Pro Pro Asp Met Tyr Glu Cys Leu Arg Val Ala Asn Glu Val Thr
                325                 330                 335

Leu Asn


<210> SEQ ID NO 56
<211> LENGTH: 478
<212> TYPE: PRT
<213> ORGANISM: Homo sapiens

<400> SEQUENCE: 56

Met Ala Pro Leu Arg Pro Leu Leu Ile Leu Ala Leu Leu Ala Trp Val
1               5                   10                  15

Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
        35                  40                  45

Ser Cys Cys Thr Asp Tyr Thr Ala Glu Cys Lys Pro Gln Val Thr Arg
    50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Glu Ala Pro Ala Pro Glu Val Gly
        115                 120                 125

Ala Ser Lys Pro Glu Gly Ile Asp Ser Arg Pro Glu Thr Leu His Pro
    130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
        195                 200                 205

Ala Phe Thr Arg Ile Asn Cys Gln Gly Lys Thr Tyr Leu Phe Lys Gly
    210                 215                 220

Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
    290                 295                 300

Phe Ala Met Met Gln Arg Asp Ser Trp Glu Asp Ile Phe Glu Leu Leu
```

305 310 315 320

Phe Trp Gly Arg Thr Ser Ala Gly Thr Arg Gln Pro Gln Phe Ile Ser
325 330 335

Arg Asp Trp His Gly Val Pro Gly Gln Val Asp Ala Ala Met Ala Gly
340 345 350

Arg Ile Tyr Ile Ser Gly Met Ala Pro Arg Pro Ser Leu Ala Lys Lys
355 360 365

Gln Arg Phe Arg His Arg Asn Arg Lys Gly Tyr Arg Ser Gln Arg Gly
370 375 380

His Ser Arg Gly Arg Asn Gln Asn Ser Arg Arg Pro Ser Arg Ala Thr
385 390 395 400

Trp Leu Ser Leu Phe Ser Ser Glu Glu Ser Asn Leu Gly Ala Asn Asn
405 410 415

Tyr Asp Asp Tyr Arg Met Asp Trp Leu Val Pro Ala Thr Cys Glu Pro
420 425 430

Ile Gln Ser Val Phe Phe Phe Ser Gly Asp Lys Tyr Tyr Arg Val Asn
435 440 445

Leu Arg Thr Arg Arg Val Asp Thr Val Asp Pro Pro Tyr Pro Arg Ser
450 455 460

Ile Ala Gln Tyr Trp Leu Gly Cys Pro Ala Pro Gly His Leu
465 470 475

<210> SEQ ID NO 57
<211> LENGTH: 1724
<212> TYPE: PRT
<213> ORGANISM: Homo sapiens

<400> SEQUENCE: 57

Met Pro Pro Ala Val Arg Arg Ser Ala Cys Ser Met Gly Trp Leu Trp
1 5 10 15

Ile Phe Gly Ala Ala Leu Gly Gln Cys Leu Gly Tyr Ser Ser Gln Gln
20 25 30

Gln Arg Val Pro Phe Leu Gln Pro Pro Gly Gln Ser Gln Leu Gln Ala
35 40 45

Ser Tyr Val Glu Phe Arg Pro Ser Gln Gly Cys Ser Pro Gly Tyr Tyr
50 55 60

Arg Asp His Lys Gly Leu Tyr Thr Gly Arg Cys Val Pro Cys Asn Cys
65 70 75 80

Asn Gly His Ser Asn Gln Cys Gln Asp Gly Ser Gly Ile Cys Val Asn
85 90 95

Cys Gln His Asn Thr Ala Gly Glu His Cys Glu Arg Cys Gln Glu Gly
100 105 110

Tyr Tyr Gly Asn Ala Val His Gly Ser Cys Arg Ala Cys Pro Cys Pro
115 120 125

His Thr Asn Ser Phe Ala Thr Gly Cys Val Val Asn Gly Gly Asp Val
130 135 140

Arg Cys Ser Cys Lys Ala Gly Tyr Thr Gly Thr Gln Cys Glu Arg Cys
145 150 155 160

Ala Pro Gly Tyr Phe Gly Asn Pro Gln Lys Phe Gly Gly Ser Cys Gln
165 170 175

Pro Cys Ser Cys Asn Ser Asn Gly Gln Leu Gly Ser Cys His Pro Leu
180 185 190

Thr Gly Asp Cys Ile Asn Gln Glu Pro Lys Asp Ser Ser Pro Ala Glu
195 200 205

```
Glu Cys Asp Asp Cys Asp Ser Cys Val Met Thr Leu Leu Asn Asp Leu
    210                 215                 220

Ala Thr Met Gly Glu Gln Leu Arg Leu Val Lys Ser Gln Leu Gln Gly
225                 230                 235                 240

Leu Ser Ala Ser Ala Gly Leu Leu Glu Gln Met Arg His Met Glu Thr
                245                 250                 255

Gln Ala Lys Asp Leu Arg Asn Gln Leu Leu Asn Tyr Arg Ser Ala Ile
            260                 265                 270

Ser Asn His Gly Ser Lys Ile Glu Gly Leu Glu Arg Glu Leu Thr Asp
        275                 280                 285

Leu Asn Gln Glu Phe Glu Thr Leu Gln Glu Lys Ala Gln Val Asn Ser
    290                 295                 300

Arg Lys Ala Gln Thr Leu Asn Asn Asn Val Asn Arg Ala Thr Gln Ser
305                 310                 315                 320

Ala Lys Glu Leu Asp Val Lys Ile Lys Asn Val Ile Arg Asn Val His
                325                 330                 335

Ile Leu Leu Lys Gln Ile Ser Gly Thr Asp Gly Glu Gly Asn Asn Val
            340                 345                 350

Pro Ser Gly Asp Phe Ser Arg Glu Trp Ala Glu Ala Gln Arg Met Met
        355                 360                 365

Arg Glu Leu Arg Asn Arg Asn Phe Gly Lys His Leu Arg Glu Ala Glu
    370                 375                 380

Ala Asp Lys Arg Glu Ser Gln Leu Leu Leu Asn Arg Ile Arg Thr Trp
385                 390                 395                 400

Gln Lys Thr His Gln Gly Glu Asn Asn Gly Leu Ala Asn Ser Ile Arg
                405                 410                 415

Asp Ser Leu Asn Glu Tyr Glu Ala Lys Leu Ser Asp Leu Arg Ala Arg
            420                 425                 430

Leu Gln Glu Ala Ala Ala Gln Ala Lys Gln Ala Asn Gly Leu Asn Gln
        435                 440                 445

Glu Asn Glu Arg Ala Leu Gly Ala Ile Gln Arg Gln Val Lys Glu Ile
    450                 455                 460

Asn Ser Leu Gln Ser Asp Phe Thr Lys Tyr Leu Thr Thr Ala Asp Ser
465                 470                 475                 480

Ser Leu Leu Gln Thr Asn Ile Ala Leu Gln Leu Met Glu Lys Ser Gln
                485                 490                 495

Lys Glu Tyr Glu Lys Leu Ala Ala Ser Leu Asn Glu Ala Arg Gln Glu
            500                 505                 510

Leu Ser Asp Lys Val Arg Glu Leu Ser Arg Ser Ala Gly Lys Thr Ser
        515                 520                 525

Leu Val Glu Glu Ala Glu Lys His Ala Arg Ser Leu Gln Glu Leu Ala
    530                 535                 540

Lys Gln Leu Glu Glu Ile Lys Arg Asn Ala Ser Gly Asp Glu Leu Val
545                 550                 555                 560

Arg Cys Ala Val Asp Ala Ala Thr Ala Tyr Glu Asn Ile Leu Asn Ala
                565                 570                 575

Ile Lys Ala Ala Glu Asp Ala Ala Asn Arg Ala Ala Ser Ala Ser Glu
            580                 585                 590

Ser Ala Leu Gln Thr Val Ile Lys Glu Asp Leu Pro Arg Lys Ala Lys
        595                 600                 605

Thr Leu Ser Ser Asn Ser Asp Lys Leu Leu Asn Glu Ala Lys Met Thr
    610                 615                 620

Gln Lys Lys Leu Lys Gln Glu Val Ser Pro Ala Leu Asn Asn Leu Gln
```

-continued

```
625                 630                 635                 640

Gln Thr Leu Asn Ile Val Thr Val Gln Lys Glu Val Ile Asp Thr Asn
                645                 650                 655

Leu Thr Thr Leu Arg Asp Gly Leu His Gly Ile Gln Arg Gly Asp Ile
            660                 665                 670

Asp Ala Met Ile Ser Ser Ala Lys Ser Met Val Arg Lys Ala Asn Asp
        675                 680                 685

Ile Thr Asp Glu Val Leu Asp Gly Leu Asn Pro Ile Gln Thr Asp Val
    690                 695                 700

Glu Arg Ile Lys Asp Thr Tyr Gly Arg Thr Gln Asn Glu Asp Phe Lys
705                 710                 715                 720

Lys Ala Leu Thr Asp Ala Asp Asn Ser Val Asn Lys Leu Thr Asn Lys
                725                 730                 735

Leu Pro Asp Leu Trp Arg Lys Ile Glu Ser Ile Asn Gln Gln Leu Leu
            740                 745                 750

Pro Leu Gly Asn Ile Ser Asp Asn Met Asp Arg Ile Arg Glu Leu Ile
        755                 760                 765

Gln Gln Ala Arg Asp Ala Ala Ser Lys Val Ala Val Pro Met Arg Phe
    770                 775                 780

Asn Gly Lys Ser Gly Val Glu Val Arg Leu Pro Asn Asp Leu Glu Asp
785                 790                 795                 800

Leu Lys Gly Tyr Thr Ser Leu Ser Leu Phe Leu Gln Arg Pro Asn Ser
                805                 810                 815

Arg Glu Asn Gly Gly Thr Glu Asn Met Phe Val Met Tyr Leu Gly Asn
            820                 825                 830

Lys Asp Ala Ser Arg Asp Tyr Ile Gly Met Ala Val Val Asp Gly Gln
        835                 840                 845

Leu Thr Cys Val Tyr Asn Leu Gly Asp Arg Glu Ala Glu Leu Gln Val
    850                 855                 860

Asp Gln Ile Leu Thr Lys Ser Glu Thr Lys Glu Ala Val Met Asp Arg
865                 870                 875                 880

Val Lys Phe Gln Arg Ile Tyr Gln Phe Ala Arg Leu Asn Tyr Thr Lys
                885                 890                 895

Gly Ala Thr Ser Ser Lys Pro Glu Thr Pro Gly Val Tyr Asp Met Asp
            900                 905                 910

Gly Arg Asn Ser Asn Thr Leu Leu Asn Leu Asp Pro Glu Asn Val Val
        915                 920                 925

Phe Tyr Val Gly Gly Tyr Pro Pro Asp Phe Lys Leu Pro Ser Arg Leu
    930                 935                 940

Ser Phe Pro Pro Tyr Lys Gly Cys Ile Glu Leu Asp Asp Leu Asn Glu
945                 950                 955                 960

Asn Val Leu Ser Leu Tyr Asn Phe Lys Lys Thr Phe Asn Leu Asn Thr
                965                 970                 975

Thr Glu Val Glu Pro Cys Arg Arg Arg Lys Glu Glu Ser Asp Lys Asn
            980                 985                 990

Tyr Phe Glu Gly Thr Gly Tyr Ala Arg Val Pro Thr Gln Pro His Ala
        995                 1000                1005

Pro Ile Pro Thr Phe Gly Gln Thr Ile Gln Thr Thr Val Asp Arg Gly
    1010                1015                1020

Leu Leu Phe Phe Ala Glu Asn Gly Asp Arg Phe Ile Ser Leu Asn Ile
1025                1030                1035                1040

Glu Asp Gly Lys Leu Met Val Arg Tyr Lys Leu Asn Ser Glu Leu Pro
                1045                1050                1055
```

-continued

```
Lys Glu Arg Gly Val Gly Asp Ala Ile Asn Asn Gly Arg Asp His Ser
            1060                1065                1070

Ile Gln Ile Lys Ile Gly Lys Leu Gln Lys Arg Met Trp Ile Asn Val
        1075                1080                1085

Asp Val Gln Asn Thr Ile Ile Asp Gly Glu Val Phe Asp Phe Ser Thr
    1090                1095                1100

Tyr Tyr Leu Gly Gly Ile Pro Ile Ala Ile Arg Glu Arg Phe Asn Ile
1105                1110                1115                1120

Ser Thr Pro Ala Phe Arg Gly Cys Met Lys Asn Leu Lys Lys Thr Ser
                1125                1130                1135

Gly Val Val Arg Leu Asn Asp Thr Val Gly Val Thr Lys Lys Cys Ser
            1140                1145                1150

Glu Asp Trp Lys Leu Val Arg Ser Ala Ser Phe Ser Arg Gly Gly Gln
        1155                1160                1165

Leu Ser Phe Thr Asp Leu Gly Leu Pro Pro Thr Asp His Leu Gln Ala
    1170                1175                1180

Ser Phe Gly Phe Gln Thr Phe Gln Pro Ser Gly Ile Leu Leu Asp His
1185                1190                1195                1200

Gln Thr Trp Thr Arg Asn Leu Gln Val Thr Leu Glu Asp Gly Tyr Ile
                1205                1210                1215

Glu Leu Ser Thr Ser Asp Ser Gly Gly Pro Ile Phe Lys Ser Pro Gln
            1220                1225                1230

Thr Tyr Met Asp Gly Leu Leu His Tyr Val Ser Val Ile Ser Asp Asn
        1235                1240                1245

Ser Gly Leu Arg Leu Leu Ile Asp Asp Gln Leu Leu Arg Asn Ser Lys
    1250                1255                1260

Arg Leu Lys His Ile Ser Ser Ser Arg Gln Ser Leu Arg Leu Gly Gly
1265                1270                1275                1280

Ser Asn Phe Glu Gly Cys Ile Ser Asn Val Phe Val Gln Arg Leu Ser
                1285                1290                1295

Leu Ser Pro Glu Val Leu Asp Leu Thr Ser Asn Ser Leu Lys Arg Asp
            1300                1305                1310

Val Ser Leu Gly Gly Cys Ser Leu Asn Lys Pro Pro Phe Leu Met Leu
        1315                1320                1325

Leu Lys Gly Ser Thr Arg Phe Asn Lys Thr Lys Thr Phe Arg Ile Asn
    1330                1335                1340

Gln Leu Leu Gln Asp Thr Pro Val Ala Ser Pro Arg Ser Val Lys Val
1345                1350                1355                1360

Trp Gln Asp Ala Cys Ser Pro Leu Pro Lys Thr Gln Ala Asn His Gly
                1365                1370                1375

Ala Leu Gln Phe Gly Asp Ile Pro Thr Ser His Leu Leu Phe Lys Leu
            1380                1385                1390

Pro Gln Glu Leu Leu Lys Pro Arg Ser Gln Phe Ala Val Asp Met Gln
        1395                1400                1405

Thr Thr Ser Ser Arg Gly Leu Val Phe His Thr Gly Thr Lys Asn Ser
    1410                1415                1420

Phe Met Ala Leu Tyr Leu Ser Lys Gly Arg Leu Val Phe Ala Leu Gly
1425                1430                1435                1440

Thr Asp Gly Lys Lys Leu Arg Ile Lys Ser Lys Glu Lys Cys Asn Asp
                1445                1450                1455

Gly Lys Trp His Thr Val Val Phe Gly His Asp Gly Glu Lys Gly Arg
            1460                1465                1470
```

```
Leu Val Val Asp Gly Leu Arg Ala Arg Glu Gly Ser Leu Pro Gly Asn
        1475                1480                1485

Ser Thr Ile Ser Ile Arg Ala Pro Val Tyr Leu Gly Ser Pro Pro Ser
    1490                1495                1500

Gly Lys Pro Lys Ser Leu Pro Thr Asn Ser Phe Val Gly Cys Leu Lys
1505                1510                1515                1520

Asn Phe Gln Leu Asp Ser Lys Pro Leu Tyr Thr Pro Ser Ser Ser Phe
                1525                1530                1535

Gly Val Ser Ser Cys Leu Gly Gly Pro Leu Glu Lys Gly Ile Tyr Phe
            1540                1545                1550

Ser Glu Glu Gly Gly His Val Val Leu Ala His Ser Val Leu Leu Gly
        1555                1560                1565

Pro Glu Phe Lys Leu Val Phe Ser Ile Arg Pro Arg Ser Leu Thr Gly
    1570                1575                1580

Ile Leu Ile His Ile Gly Ser Gln Pro Gly Lys His Leu Cys Val Tyr
1585                1590                1595                1600

Leu Glu Ala Gly Lys Val Thr Ala Ser Met Asp Ser Gly Ala Gly Gly
                1605                1610                1615

Thr Ser Thr Ser Val Thr Pro Lys Gln Ser Leu Cys Asp Gly Gln Trp
            1620                1625                1630

His Ser Val Ala Val Thr Ile Lys Gln His Ile Leu His Leu Glu Leu
        1635                1640                1645

Asp Thr Asp Ser Ser Tyr Thr Ala Gly Gln Ile Pro Phe Pro Pro Ala
    1650                1655                1660

Ser Thr Gln Glu Pro Leu His Leu Gly Gly Ala Pro Ala Asn Leu Thr
1665                1670                1675                1680

Thr Leu Arg Ile Pro Val Trp Lys Ser Phe Phe Gly Cys Leu Arg Asn
                1685                1690                1695

Ile His Val Asn His Ile Pro Val Pro Val Thr Glu Ala Leu Glu Val
            1700                1705                1710

Gln Gly Pro Val Ser Leu Asn Gly Cys Pro Asp Gln
        1715                1720


<210> SEQ ID NO 58
<211> LENGTH: 1172
<212> TYPE: PRT
<213> ORGANISM: Homo sapiens

<400> SEQUENCE: 58

Met Arg Pro Phe Phe Leu Leu Cys Phe Ala Leu Pro Gly Leu Leu His
1               5                   10                  15

Ala Gln Gln Ala Cys Ser Arg Gly Ala Cys Tyr Pro Pro Val Gly Asp
            20                  25                  30

Leu Leu Val Gly Arg Thr Arg Phe Leu Arg Ala Ser Ser Thr Cys Gly
        35                  40                  45

Leu Thr Lys Pro Glu Thr Tyr Cys Thr Gln Tyr Gly Glu Trp Gln Met
    50                  55                  60

Lys Cys Cys Lys Cys Asp Ser Arg Gln Pro His Asn Tyr Tyr Ser His
65                  70                  75                  80

Arg Val Glu Asn Val Ala Ser Ser Ser Gly Pro Met Arg Trp Trp Gln
                85                  90                  95

Ser Gln Asn Asp Val Asn Pro Val Ser Leu Gln Leu Asp Leu Asp Arg
            100                 105                 110

Arg Phe Gln Leu Gln Glu Val Met Met Glu Phe Gln Gly Pro Met Pro
        115                 120                 125
```

-continued

```
Ala Gly Met Leu Ile Glu Arg Ser Ser Asp Phe Gly Lys Thr Trp Arg
    130                 135                 140

Val Tyr Gln Tyr Leu Ala Ala Asp Cys Thr Ser Thr Phe Pro Arg Val
145                 150                 155                 160

Arg Gln Gly Arg Pro Gln Ser Trp Gln Asp Val Arg Cys Gln Ser Leu
                165                 170                 175

Pro Gln Arg Pro Asn Ala Arg Leu Asn Gly Gly Lys Val Gln Leu Asn
            180                 185                 190

Leu Met Asp Leu Val Ser Gly Ile Pro Ala Thr Gln Ser Gln Lys Ile
        195                 200                 205

Gln Glu Val Gly Glu Ile Thr Asn Leu Arg Val Asn Phe Thr Arg Leu
    210                 215                 220

Ala Pro Val Pro Gln Arg Gly Tyr His Pro Pro Ser Ala Tyr Tyr Ala
225                 230                 235                 240

Val Ser Gln Leu Arg Leu Gln Gly Ser Cys Phe Cys His Gly His Ala
                245                 250                 255

Asp Arg Cys Ala Pro Lys Pro Gly Ala Ser Ala Gly Pro Ser Thr Ala
            260                 265                 270

Val Gln Val His Asp Val Cys Val Cys Gln His Asn Thr Ala Gly Pro
        275                 280                 285

Asn Cys Glu Arg Cys Ala Pro Phe Tyr Asn Asn Arg Pro Trp Arg Pro
    290                 295                 300

Ala Glu Gly Gln Asp Ala His Glu Cys Gln Arg Cys Asp Cys Asn Gly
305                 310                 315                 320

His Ser Glu Thr Cys His Phe Asp Pro Ala Val Phe Ala Ala Ser Gln
                325                 330                 335

Gly Ala Tyr Gly Gly Val Cys Asp Asn Cys Arg Asp His Thr Glu Gly
            340                 345                 350

Lys Asn Cys Glu Arg Cys Gln Leu His Tyr Phe Arg Asn Arg Arg Pro
        355                 360                 365

Gly Ala Ser Ile Gln Glu Thr Cys Ile Ser Cys Glu Cys Asp Pro Asp
    370                 375                 380

Gly Ala Val Pro Gly Ala Pro Cys Asp Pro Val Thr Gly Gln Cys Val
385                 390                 395                 400

Cys Lys Glu His Val Gln Gly Glu Arg Cys Asp Leu Cys Lys Pro Gly
                405                 410                 415

Phe Thr Gly Leu Thr Tyr Ala Asn Pro Gln Gly Cys His Arg Cys Asp
            420                 425                 430

Cys Asn Ile Leu Gly Ser Arg Arg Asp Met Pro Cys Asp Glu Glu Ser
        435                 440                 445

Gly Arg Cys Leu Cys Leu Pro Asn Val Val Gly Pro Lys Cys Asp Gln
    450                 455                 460

Cys Ala Pro Tyr His Trp Lys Leu Ala Ser Gly Gln Gly Cys Glu Pro
465                 470                 475                 480

Cys Ala Cys Asp Pro His Asn Ser Leu Ser Pro Gln Cys Asn Gln Phe
                485                 490                 495

Thr Gly Gln Cys Pro Cys Arg Glu Gly Phe Gly Gly Leu Met Cys Ser
            500                 505                 510

Ala Ala Ala Ile Arg Gln Cys Pro Asp Arg Thr Tyr Gly Asp Val Ala
        515                 520                 525

Thr Gly Cys Arg Ala Cys Asp Cys Asp Phe Arg Gly Thr Glu Gly Pro
    530                 535                 540
```

-continued

```
Gly Cys Asp Lys Ala Ser Gly Arg Cys Leu Cys Arg Pro Gly Leu Thr
545                 550                 555                 560

Gly Pro Arg Cys Asp Gln Cys Gln Arg Gly Tyr Cys Asn Arg Tyr Pro
                565                 570                 575

Val Cys Val Ala Cys His Pro Cys Phe Gln Thr Tyr Asp Ala Asp Leu
            580                 585                 590

Arg Glu Gln Ala Leu Arg Phe Gly Arg Leu Arg Asn Ala Thr Ala Ser
        595                 600                 605

Leu Trp Ser Gly Pro Gly Leu Glu Asp Arg Gly Leu Ala Ser Arg Ile
    610                 615                 620

Leu Asp Ala Lys Ser Lys Ile Glu Gln Ile Arg Ala Val Leu Ser Ser
625                 630                 635                 640

Pro Ala Val Thr Glu Gln Glu Val Ala Gln Val Ala Ser Ala Ile Leu
                645                 650                 655

Ser Leu Arg Arg Thr Leu Gln Gly Leu Gln Leu Asp Leu Pro Leu Glu
            660                 665                 670

Glu Glu Thr Leu Ser Leu Pro Arg Asp Leu Glu Ser Leu Asp Arg Ser
        675                 680                 685

Phe Asn Gly Leu Leu Thr Met Tyr Gln Arg Lys Arg Glu Gln Phe Glu
    690                 695                 700

Lys Ile Ser Ser Ala Asp Pro Ser Gly Ala Phe Arg Met Leu Ser Thr
705                 710                 715                 720

Ala Tyr Glu Gln Ser Ala Gln Ala Ala Gln Gln Val Ser Asp Ser Ser
                725                 730                 735

Arg Leu Leu Asp Gln Leu Arg Asp Ser Arg Arg Glu Ala Glu Arg Leu
            740                 745                 750

Val Arg Gln Ala Gly Gly Gly Gly Gly Thr Gly Ser Pro Lys Leu Val
        755                 760                 765

Ala Leu Arg Leu Glu Met Ser Ser Leu Pro Asp Leu Thr Pro Thr Phe
    770                 775                 780

Asn Lys Leu Cys Gly Asn Ser Arg Gln Met Ala Cys Thr Pro Ile Ser
785                 790                 795                 800

Cys Pro Gly Glu Leu Cys Pro Gln Asp Asn Gly Thr Ala Cys Gly Ser
                805                 810                 815

Arg Cys Arg Gly Val Leu Pro Arg Ala Gly Gly Ala Phe Leu Met Ala
            820                 825                 830

Gly Gln Val Ala Glu Gln Leu Arg Gly Phe Asn Ala Gln Leu Gln Arg
        835                 840                 845

Thr Arg Gln Met Ile Arg Ala Ala Glu Glu Ser Ala Ser Gln Ile Gln
    850                 855                 860

Ser Ser Ala Gln Arg Leu Glu Thr Gln Val Ser Ala Ser Arg Ser Gln
865                 870                 875                 880

Met Glu Glu Asp Val Arg Arg Thr Arg Leu Leu Ile Gln Gln Val Arg
                885                 890                 895

Asp Phe Leu Thr Asp Pro Asp Thr Asp Ala Ala Thr Ile Gln Glu Val
            900                 905                 910

Ser Glu Ala Val Leu Ala Leu Trp Leu Pro Thr Asp Ser Ala Thr Val
        915                 920                 925

Leu Gln Lys Met Asn Glu Ile Gln Ala Ile Ala Ala Arg Leu Pro Asn
    930                 935                 940

Val Asp Leu Val Leu Ser Gln Thr Lys Gln Asp Ile Ala Arg Ala Arg
945                 950                 955                 960

Arg Leu Gln Ala Glu Ala Glu Glu Ala Arg Ser Arg Ala His Ala Val
```

```
                965                 970                 975

Glu Gly Gln Val Glu Asp Val Val Gly Asn Leu Arg Gln Gly Thr Val
            980                 985                 990

Ala Leu Gln Glu Ala Gln Asp Thr Met Gln Gly Thr Ser Arg Ser Leu
        995                 1000                1005

Arg Leu Ile Gln Asp Arg Val Ala Glu Val Gln Gln Val Leu Arg Pro
    1010                1015                1020

Ala Glu Lys Leu Val Thr Ser Met Thr Lys Gln Leu Gly Asp Phe Trp
1025                1030                1035                1040

Thr Arg Met Glu Glu Leu Arg His Gln Ala Arg Gln Gln Gly Ala Glu
                1045                1050                1055

Ala Val Gln Ala Gln Gln Leu Ala Glu Gly Ala Ser Glu Gln Ala Leu
            1060                1065                1070

Ser Ala Gln Glu Gly Phe Glu Arg Ile Lys Gln Lys Tyr Ala Glu Leu
        1075                1080                1085

Lys Asp Arg Leu Gly Gln Ser Ser Met Leu Gly Glu Gln Gly Ala Arg
    1090                1095                1100

Ile Gln Ser Val Lys Thr Glu Ala Glu Glu Leu Phe Gly Glu Thr Met
1105                1110                1115                1120

Glu Met Met Asp Arg Met Lys Asp Met Glu Leu Glu Leu Leu Arg Gly
                1125                1130                1135

Ser Gln Ala Ile Met Leu Arg Ser Ala Asp Leu Thr Gly Leu Glu Lys
            1140                1145                1150

Arg Val Glu Gln Ile Arg Asp His Ile Asn Gly Arg Val Leu Tyr Tyr
        1155                1160                1165

Ala Thr Cys Lys
    1170


<210> SEQ ID NO 59
<211> LENGTH: 1193
<212> TYPE: PRT
<213> ORGANISM: Homo sapiens

<400> SEQUENCE: 59

Met Pro Ala Leu Trp Leu Gly Cys Cys Leu Cys Phe Ser Leu Leu Leu
1               5                   10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160
```

-continued

```
Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg His Pro Ser Ala His Asp Val Ile
        275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
        355                 360                 365

Arg Pro Val Ser Gly Ala Pro Ala Pro Trp Val Glu Gln Cys Ile Cys
    370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
                405                 410                 415

Asn Cys Gln Gly Gly Gly Ala Cys Asp Pro Asp Thr Gly Asp Cys Tyr
            420                 425                 430

Ser Gly Asp Glu Asn Pro Asp Ile Glu Cys Ala Asp Cys Pro Ile Gly
        435                 440                 445

Phe Tyr Asn Asp Pro His Asp Pro Arg Ser Cys Lys Pro Cys Pro Cys
    450                 455                 460

His Asn Gly Phe Ser Cys Ser Val Met Pro Glu Thr Glu Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
            500                 505                 510

Pro Cys Gln Pro Cys Gln Cys Asn Asn Asn Val Asp Pro Ser Ala Ser
        515                 520                 525

Gly Asn Cys Asp Arg Leu Thr Gly Arg Cys Leu Lys Cys Ile His Asn
    530                 535                 540

Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
```

```
            580                 585                 590

Cys Lys Pro Gly Phe Gly Gly Pro Asn Cys Glu His Gly Ala Phe Ser
        595                 600                 605

Cys Pro Ala Cys Tyr Asn Gln Val Lys Ile Gln Met Asp Gln Phe Met
    610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
            660                 665                 670

Ala Ser Arg Ser Leu Gly Leu Gln Leu Ala Lys Val Arg Ser Gln Glu
        675                 680                 685

Asn Ser Tyr Gln Ser Arg Leu Asp Asp Leu Lys Met Thr Val Glu Arg
    690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735

Leu Gly Asn Thr Asn Ile Pro Ala Ser Asp His Tyr Val Gly Pro Asn
            740                 745                 750

Gly Phe Lys Ser Leu Ala Gln Glu Ala Thr Arg Leu Ala Glu Ser His
        755                 760                 765

Val Glu Ser Ala Ser Asn Met Glu Gln Leu Thr Arg Glu Thr Glu Asp
    770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
                805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
        835                 840                 845

Leu Arg Leu Leu Asp Ser Val Ser Arg Leu Gln Gly Val Ser Asp Gln
    850                 855                 860

Ser Phe Gln Val Glu Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
                885                 890                 895

Lys Asn Leu Gly Asn Trp Lys Glu Glu Ala Gln Gln Leu Leu Gln Asn
            900                 905                 910

Gly Lys Ser Gly Arg Glu Lys Ser Asp Gln Leu Leu Ser Arg Ala Asn
        915                 920                 925

Leu Ala Lys Ser Arg Ala Gln Glu Ala Leu Ser Met Gly Asn Ala Thr
    930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Glu Ala Met Lys Arg Leu
                965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala Ala Ala Asp Ala Gln Arg Ala Lys
        995                 1000                1005
```

```
Asn Gly Ala Gly Glu Ala Leu Glu Ile Ser Ser Glu Ile Glu Gln Glu
    1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
                1045                1050                1055

Glu Gly Glu Leu Glu Arg Lys Glu Leu Glu Phe Asp Thr Asn Met Asp
            1060                1065                1070

Ala Val Gln Met Val Ile Thr Glu Ala Gln Lys Val Asp Thr Arg Ala
        1075                1080                1085

Lys Asn Ala Gly Val Thr Ile Gln Asp Thr Leu Asn Thr Leu Asp Gly
    1090                1095                1100

Leu Leu His Leu Met Asp Gln Pro Leu Ser Val Asp Glu Glu Gly Leu
1105                1110                1115                1120

Val Leu Leu Glu Gln Lys Leu Ser Arg Ala Lys Thr Gln Ile Asn Ser
                1125                1130                1135

Gln Leu Arg Pro Met Met Ser Glu Leu Glu Glu Arg Ala Arg Gln Gln
            1140                1145                1150

Arg Gly His Leu His Leu Leu Glu Thr Ser Ile Asp Gly Ile Leu Ala
        1155                1160                1165

Asp Val Lys Asn Leu Glu Asn Ile Arg Asp Asn Leu Pro Pro Gly Cys
    1170                1175                1180

Tyr Asn Thr Gln Ala Leu Glu Gln Gln
1185                1190


<210> SEQ ID NO 60
<211> LENGTH: 1296
<212> TYPE: PRT
<213> ORGANISM: Clostridium botulinum

<400> SEQUENCE: 60

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
```

```
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605
```

```
Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Leu
    1010                1015                1020
```

-continued

```
Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295


<210> SEQ ID NO 61
<211> LENGTH: 1291
<212> TYPE: PRT
<213> ORGANISM: Clostridium botulinum

<400> SEQUENCE: 61

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110
```

```
Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525
```

```
Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
```

-continued

```
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
        995                 1000                1005

Asn Asn Leu Asn Asn Ala Lys Ile Tyr Ile Asn Gly Lys Leu Glu Ser
    1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
                1045                1050                1055

Lys Tyr Phe Ser Ile Phe Asn Thr Glu Leu Ser Gln Ser Asn Ile Glu
            1060                1065                1070

Glu Arg Tyr Lys Ile Gln Ser Tyr Ser Glu Tyr Leu Lys Asp Phe Trp
        1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
            1140                1145                1150

Ser Gln Ser Ile Asn Asp Asp Ile Val Arg Lys Glu Asp Tyr Ile Tyr
        1155                1160                1165

Leu Asp Phe Phe Asn Leu Asn Gln Glu Trp Arg Val Tyr Thr Tyr Lys
    1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
            1220                1225                1230

Asp Glu Ile Gly Leu Ile Gly Ile His Arg Phe Tyr Glu Ser Gly Ile
        1235                1240                1245

Val Phe Glu Glu Tyr Lys Asp Tyr Phe Cys Ile Ser Lys Trp Tyr Leu
    1250                1255                1260

Lys Glu Val Lys Arg Lys Pro Tyr Asn Leu Lys Leu Gly Cys Asn Trp
1265                1270                1275                1280

Gln Phe Ile Pro Lys Asp Glu Gly Trp Thr Glu
                1285                1290


<210> SEQ ID NO 62
<211> LENGTH: 2871
<212> TYPE: PRT
<213> ORGANISM: Homo sapiens

<400> SEQUENCE: 62

Met Arg Arg Gly Arg Leu Leu Glu Ile Ala Leu Gly Phe Thr Val Leu
1               5                   10                  15

Leu Ala Ser Tyr Thr Ser His Gly Ala Asp Ala Asn Leu Glu Ala Gly
            20                  25                  30
```

```
Asn Val Lys Glu Thr Arg Ala Ser Arg Ala Lys Arg Arg Gly Gly Gly
        35                  40                  45

Gly His Asp Ala Leu Lys Gly Pro Asn Val Cys Gly Ser Arg Tyr Asn
    50                  55                  60

Ala Tyr Cys Cys Pro Gly Trp Lys Thr Leu Pro Gly Gly Asn Gln Cys
65                  70                  75                  80

Ile Val Pro Ile Cys Arg His Ser Cys Gly Asp Gly Phe Cys Ser Arg
                85                  90                  95

Pro Asn Met Cys Thr Cys Pro Ser Gly Gln Ile Ala Pro Ser Cys Gly
            100                 105                 110

Ser Arg Ser Ile Gln His Cys Asn Ile Arg Cys Met Asn Gly Gly Ser
        115                 120                 125

Cys Ser Asp Asp His Cys Leu Cys Gln Lys Gly Tyr Ile Gly Thr His
    130                 135                 140

Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
                165                 170                 175

Cys Glu Arg Asp Tyr Arg Thr Gly Pro Cys Phe Thr Val Ile Ser Asn
            180                 185                 190

Gln Met Cys Gln Gly Gln Leu Ser Gly Ile Val Cys Thr Lys Thr Leu
        195                 200                 205

Cys Cys Ala Thr Val Gly Arg Ala Trp Gly His Pro Cys Glu Met Cys
    210                 215                 220

Pro Ala Gln Pro His Pro Cys Arg Arg Gly Phe Ile Pro Asn Ile Arg
225                 230                 235                 240

Thr Gly Ala Cys Gln Asp Val Asp Glu Cys Gln Ala Ile Pro Gly Leu
                245                 250                 255

Cys Gln Gly Gly Asn Cys Ile Asn Thr Val Gly Ser Phe Glu Cys Lys
            260                 265                 270

Cys Pro Ala Gly His Lys Leu Asn Glu Val Ser Gln Lys Cys Glu Asp
        275                 280                 285

Ile Asp Glu Cys Ser Thr Ile Pro Gly Ile Cys Glu Gly Gly Glu Cys
    290                 295                 300

Thr Asn Thr Val Ser Ser Tyr Phe Cys Lys Cys Pro Pro Gly Phe Tyr
305                 310                 315                 320

Thr Ser Pro Asp Gly Thr Arg Cys Ile Asp Val Arg Pro Gly Tyr Cys
                325                 330                 335

Tyr Thr Ala Leu Thr Asn Gly Arg Cys Ser Asn Gln Leu Pro Gln Ser
            340                 345                 350

Ile Thr Lys Met Gln Cys Cys Cys Asp Ala Gly Arg Cys Trp Ser Pro
        355                 360                 365

Gly Val Thr Val Ala Pro Glu Met Cys Pro Ile Arg Ala Thr Glu Asp
    370                 375                 380

Phe Asn Lys Leu Cys Ser Val Pro Met Val Ile Pro Gly Arg Pro Glu
385                 390                 395                 400

Tyr Pro Pro Pro Pro Leu Gly Pro Ile Pro Pro Val Leu Pro Val Pro
                405                 410                 415

Pro Gly Phe Pro Pro Gly Pro Gln Ile Pro Val Pro Arg Pro Pro Val
            420                 425                 430

Glu Tyr Leu Tyr Pro Ser Arg Glu Pro Pro Arg Val Leu Pro Val Asn
        435                 440                 445

Val Thr Asp Tyr Cys Gln Leu Val Arg Tyr Leu Cys Gln Asn Gly Arg
```

```
    450                 455                 460

Cys Ile Pro Thr Pro Gly Ser Tyr Arg Cys Glu Cys Asn Lys Gly Phe
465                 470                 475                 480

Gln Leu Asp Leu Arg Gly Glu Cys Ile Asp Val Asp Glu Cys Glu Lys
                485                 490                 495

Asn Pro Cys Ala Gly Gly Glu Cys Ile Asn Asn Gln Gly Ser Tyr Thr
            500                 505                 510

Cys Gln Cys Arg Ala Gly Tyr Gln Ser Thr Leu Thr Arg Thr Glu Cys
        515                 520                 525

Arg Asp Ile Asp Glu Cys Leu Gln Asn Gly Arg Ile Cys Asn Asn Gly
    530                 535                 540

Arg Cys Ile Asn Thr Asp Gly Ser Phe His Cys Val Cys Asn Ala Gly
545                 550                 555                 560

Phe His Val Thr Arg Asp Gly Lys Asn Cys Glu Asp Met Asp Glu Cys
                565                 570                 575

Ser Ile Arg Asn Met Cys Leu Asn Gly Met Cys Ile Asn Glu Asp Gly
            580                 585                 590

Ser Phe Lys Cys Ile Cys Lys Pro Gly Phe Gln Leu Ala Ser Asp Gly
        595                 600                 605

Arg Tyr Cys Lys Asp Ile Asn Glu Cys Glu Thr Pro Gly Ile Cys Met
    610                 615                 620

Asn Gly Arg Cys Val Asn Thr Asp Gly Ser Tyr Arg Cys Glu Cys Phe
625                 630                 635                 640

Pro Gly Leu Ala Val Gly Leu Asp Gly Arg Val Cys Val Asp Thr His
                645                 650                 655

Met Arg Ser Thr Cys Tyr Gly Gly Tyr Lys Arg Gly Gln Cys Ile Lys
            660                 665                 670

Pro Leu Phe Gly Ala Val Thr Lys Ser Glu Cys Cys Cys Ala Ser Thr
        675                 680                 685

Glu Tyr Ala Phe Gly Glu Pro Cys Gln Pro Cys Pro Ala Gln Asn Ser
    690                 695                 700

Ala Glu Tyr Gln Ala Leu Cys Ser Ser Gly Pro Gly Met Thr Ser Ala
705                 710                 715                 720

Gly Ser Asp Ile Asn Glu Cys Ala Leu Asp Pro Asp Ile Cys Pro Asn
                725                 730                 735

Gly Ile Cys Glu Asn Leu Arg Gly Thr Tyr Lys Cys Ile Cys Asn Ser
            740                 745                 750

Gly Tyr Glu Val Asp Ser Thr Gly Lys Asn Cys Val Asp Ile Asn Glu
        755                 760                 765

Cys Val Leu Asn Ser Leu Leu Cys Asp Asn Gly Gln Cys Arg Asn Thr
    770                 775                 780

Pro Gly Ser Phe Val Cys Thr Cys Pro Lys Gly Phe Ile Tyr Lys Pro
785                 790                 795                 800

Asp Leu Lys Thr Cys Glu Asp Ile Asp Glu Cys Glu Ser Ser Pro Cys
                805                 810                 815

Ile Asn Gly Val Cys Lys Asn Ser Pro Gly Ser Phe Ile Cys Glu Cys
            820                 825                 830

Ser Ser Glu Ser Thr Leu Asp Pro Thr Lys Thr Ile Cys Ile Glu Thr
        835                 840                 845

Ile Lys Gly Thr Cys Trp Gln Thr Val Ile Asp Gly Arg Cys Glu Ile
    850                 855                 860

Asn Ile Asn Gly Ala Thr Leu Lys Ser Gln Cys Cys Ser Ser Leu Gly
865                 870                 875                 880
```

-continued

```
Ala Ala Trp Gly Ser Pro Cys Thr Leu Cys Gln Val Asp Pro Ile Cys
                885                 890                 895

Gly Lys Gly Tyr Ser Arg Ile Lys Gly Thr Gln Cys Glu Asp Ile Asp
            900                 905                 910

Glu Cys Glu Val Phe Pro Gly Val Cys Lys Asn Gly Leu Cys Val Asn
        915                 920                 925

Thr Arg Gly Ser Phe Lys Cys Gln Cys Pro Ser Gly Met Thr Leu Asp
    930                 935                 940

Ala Thr Gly Arg Ile Cys Leu Asp Ile Arg Leu Glu Thr Cys Phe Leu
945                 950                 955                 960

Arg Tyr Glu Asp Glu Glu Cys Thr Leu Pro Ile Ala Gly Arg His Arg
                965                 970                 975

Met Asp Ala Cys Cys Cys Ser Val Gly Ala Ala Trp Gly Thr Glu Glu
            980                 985                 990

Cys Glu Glu Cys Pro Met Arg Asn Thr Pro Glu Tyr Glu Glu Leu Cys
        995                 1000                1005

Pro Arg Gly Pro Gly Phe Ala Thr Lys Glu Ile Thr Asn Gly Lys Pro
    1010                1015                1020

Phe Phe Lys Asp Ile Asn Glu Cys Lys Met Ile Pro Ser Leu Cys Thr
1025                1030                1035                1040

His Gly Lys Cys Arg Asn Thr Ile Gly Ser Phe Lys Cys Arg Cys Asp
                1045                1050                1055

Ser Gly Phe Ala Leu Asp Ser Glu Glu Arg Asn Cys Thr Asp Ile Asp
            1060                1065                1070

Glu Cys Arg Ile Ser Pro Asp Leu Cys Gly Arg Gly Gln Cys Val Asn
        1075                1080                1085

Thr Pro Gly Asp Phe Glu Cys Lys Cys Asp Glu Gly Tyr Glu Ser Gly
    1090                1095                1100

Phe Met Met Met Lys Asn Cys Met Asp Ile Asp Glu Cys Gln Arg Asp
1105                1110                1115                1120

Pro Leu Leu Cys Arg Gly Gly Val Cys His Asn Thr Glu Gly Ser Tyr
                1125                1130                1135

Arg Cys Glu Cys Pro Pro Gly His Gln Leu Ser Pro Asn Ile Ser Ala
            1140                1145                1150

Cys Ile Asp Ile Asn Glu Cys Glu Leu Ser Ala His Leu Cys Pro Asn
        1155                1160                1165

Gly Arg Cys Val Asn Leu Ile Gly Lys Tyr Gln Cys Ala Cys Asn Pro
    1170                1175                1180

Gly Tyr His Ser Thr Pro Asp Arg Leu Phe Cys Val Asp Ile Asp Glu
1185                1190                1195                1200

Cys Ser Ile Met Asn Gly Gly Cys Glu Thr Phe Cys Thr Asn Ser Glu
                1205                1210                1215

Gly Ser Tyr Glu Cys Ser Cys Gln Pro Gly Phe Ala Leu Met Pro Asp
            1220                1225                1230

Gln Arg Ser Cys Thr Asp Ile Asp Glu Cys Glu Asp Asn Pro Asn Ile
        1235                1240                1245

Cys Asp Gly Gly Gln Cys Thr Asn Ile Pro Gly Glu Tyr Arg Cys Leu
    1250                1255                1260

Cys Tyr Asp Gly Phe Met Ala Ser Glu Asp Met Lys Thr Cys Val Asp
1265                1270                1275                1280

Val Asn Glu Cys Asp Leu Asn Pro Asn Ile Cys Leu Ser Gly Thr Cys
                1285                1290                1295
```

-continued

```
Glu Asn Thr Lys Gly Ser Phe Ile Cys His Cys Asp Met Gly Tyr Ser
            1300                1305                1310

Gly Lys Lys Gly Lys Thr Gly Cys Thr Asp Ile Asn Glu Cys Glu Ile
        1315                1320                1325

Gly Ala His Asn Cys Gly Lys His Ala Val Cys Thr Asn Thr Ala Gly
    1330                1335                1340

Ser Phe Lys Cys Ser Cys Ser Pro Gly Trp Ile Gly Asp Gly Ile Lys
1345                1350                1355                1360

Cys Thr Asp Leu Asp Glu Cys Ser Asn Gly Thr His Met Cys Ser Gln
                1365                1370                1375

His Ala Asp Cys Lys Asn Thr Met Gly Ser Tyr Arg Cys Leu Cys Lys
            1380                1385                1390

Glu Gly Tyr Thr Gly Asp Gly Phe Thr Cys Thr Asp Leu Asp Glu Cys
        1395                1400                1405

Ser Glu Asn Leu Asn Leu Cys Gly Asn Gly Gln Cys Leu Asn Ala Pro
    1410                1415                1420

Gly Gly Tyr Arg Cys Glu Cys Asp Met Gly Phe Val Pro Ser Ala Asp
1425                1430                1435                1440

Gly Lys Ala Cys Glu Asp Ile Asp Glu Cys Ser Leu Pro Asn Ile Cys
                1445                1450                1455

Val Phe Gly Thr Cys His Asn Leu Pro Gly Leu Phe Arg Cys Glu Cys
            1460                1465                1470

Glu Ile Gly Tyr Glu Leu Asp Arg Ser Gly Gly Asn Cys Thr Asp Val
        1475                1480                1485

Asn Glu Cys Leu Asp Pro Thr Thr Cys Ile Ser Gly Asn Cys Val Asn
    1490                1495                1500

Thr Pro Gly Ser Tyr Ile Cys Asp Cys Pro Pro Asp Phe Glu Leu Asn
1505                1510                1515                1520

Pro Thr Arg Val Gly Cys Val Asp Thr Arg Ser Gly Asn Cys Tyr Leu
                1525                1530                1535

Asp Ile Arg Pro Arg Gly Asp Asn Gly Asp Thr Ala Cys Ser Asn Glu
            1540                1545                1550

Ile Gly Val Gly Val Ser Lys Ala Ser Cys Cys Cys Ser Leu Gly Lys
        1555                1560                1565

Ala Trp Gly Thr Pro Cys Glu Met Cys Pro Ala Val Asn Thr Ser Glu
    1570                1575                1580

Tyr Lys Ile Leu Cys Pro Gly Gly Glu Gly Phe Arg Pro Asn Pro Ile
1585                1590                1595                1600

Thr Val Ile Leu Glu Asp Ile Asp Glu Cys Gln Glu Leu Pro Gly Leu
                1605                1610                1615

Cys Gln Gly Gly Lys Cys Ile Asn Thr Phe Gly Ser Phe Gln Cys Arg
            1620                1625                1630

Cys Pro Thr Gly Tyr Tyr Leu Asn Glu Asp Thr Arg Val Cys Asp Asp
        1635                1640                1645

Val Asn Glu Cys Glu Thr Pro Gly Ile Cys Gly Pro Gly Thr Cys Tyr
    1650                1655                1660

Asn Thr Val Gly Asn Tyr Thr Cys Ile Cys Pro Pro Asp Tyr Met Gln
1665                1670                1675                1680

Val Asn Gly Gly Asn Asn Cys Met Asp Met Arg Arg Ser Leu Cys Tyr
                1685                1690                1695

Arg Asn Tyr Tyr Ala Asp Asn Gln Thr Cys Asp Gly Glu Leu Leu Phe
            1700                1705                1710

Asn Met Thr Lys Lys Met Cys Cys Cys Ser Tyr Asn Ile Gly Arg Ala
```

-continued

```
        1715                1720                1725

Trp Asn Lys Pro Cys Glu Gln Cys Pro Ile Pro Ser Thr Asp Glu Phe
    1730                1735                1740

Ala Thr Leu Cys Gly Ser Gln Arg Pro Gly Phe Val Ile Asp Ile Tyr
1745                1750                1755                1760

Thr Gly Leu Pro Val Asp Ile Asp Glu Cys Arg Glu Ile Pro Gly Val
                1765                1770                1775

Cys Glu Asn Gly Val Cys Ile Asn Met Val Gly Ser Phe Arg Cys Glu
            1780                1785                1790

Cys Pro Val Gly Phe Phe Tyr Asn Asp Lys Leu Leu Val Cys Glu Asp
        1795                1800                1805

Ile Asp Glu Cys Gln Asn Gly Pro Val Cys Gln Arg Asn Ala Glu Cys
    1810                1815                1820

Ile Asn Thr Ala Gly Ser Tyr Arg Cys Asp Cys Lys Pro Gly Tyr Arg
1825                1830                1835                1840

Phe Thr Ser Thr Gly Gln Cys Asn Asp Arg Asn Glu Cys Gln Glu Ile
                1845                1850                1855

Pro Asn Ile Cys Ser His Gly Gln Cys Ile Asp Thr Val Gly Ser Phe
            1860                1865                1870

Tyr Cys Leu Cys His Thr Gly Phe Lys Thr Asn Asp Asp Gln Thr Met
        1875                1880                1885

Cys Leu Asp Ile Asn Glu Cys Glu Arg Asp Ala Cys Gly Asn Gly Thr
    1890                1895                1900

Cys Arg Asn Thr Ile Gly Ser Phe Asn Cys Arg Cys Asn His Gly Phe
1905                1910                1915                1920

Ile Leu Ser His Asn Asn Asp Cys Ile Asp Val Asp Glu Cys Ala Ser
                1925                1930                1935

Gly Asn Gly Asn Leu Cys Arg Asn Gly Gln Cys Ile Asn Thr Val Gly
            1940                1945                1950

Ser Phe Gln Cys Gln Cys Asn Glu Gly Tyr Glu Val Ala Pro Asp Gly
        1955                1960                1965

Arg Thr Cys Val Asp Ile Asn Glu Cys Leu Leu Glu Pro Arg Lys Cys
    1970                1975                1980

Ala Pro Gly Thr Cys Gln Asn Leu Asp Gly Ser Tyr Arg Cys Ile Cys
1985                1990                1995                2000

Pro Pro Gly Tyr Ser Leu Gln Asn Glu Lys Cys Glu Asp Ile Asp Glu
                2005                2010                2015

Cys Val Glu Glu Pro Glu Ile Cys Ala Leu Gly Thr Cys Ser Asn Thr
            2020                2025                2030

Glu Gly Ser Phe Lys Cys Leu Cys Pro Glu Gly Phe Ser Leu Ser Ser
        2035                2040                2045

Ser Gly Arg Arg Cys Gln Asp Leu Arg Met Ser Tyr Cys Tyr Ala Lys
    2050                2055                2060

Phe Glu Gly Gly Lys Cys Ser Ser Pro Lys Ser Arg Asn His Ser Lys
2065                2070                2075                2080

Gln Glu Cys Cys Cys Ala Leu Lys Gly Glu Gly Trp Gly Asp Pro Cys
                2085                2090                2095

Glu Leu Cys Pro Thr Glu Pro Asp Glu Ala Phe Arg Gln Ile Cys Pro
            2100                2105                2110

Tyr Gly Ser Gly Ile Ile Val Gly Pro Asp Asp Ser Ala Val Asp Met
        2115                2120                2125

Asp Glu Cys Lys Glu Pro Asp Val Cys Lys His Gly Gln Cys Ile Asn
    2130                2135                2140
```

```
Thr Asp Gly Ser Tyr Arg Cys Glu Cys Pro Phe Gly Tyr Ile Leu Ala
2145                2150                2155                2160

Gly Asn Glu Cys Val Asp Thr Asp Glu Cys Ser Val Gly Asn Pro Cys
                2165                2170                2175

Gly Asn Gly Thr Cys Lys Asn Val Ile Gly Gly Phe Glu Cys Thr Cys
            2180                2185                2190

Glu Glu Gly Phe Glu Pro Gly Pro Met Met Thr Cys Glu Asp Ile Asn
        2195                2200                2205

Glu Cys Ala Gln Asn Pro Leu Leu Cys Ala Phe Arg Cys Val Asn Thr
    2210                2215                2220

Tyr Gly Ser Tyr Glu Cys Lys Cys Pro Val Gly Tyr Val Leu Arg Glu
2225                2230                2235                2240

Asp Arg Arg Met Cys Lys Asp Glu Asp Glu Cys Glu Glu Gly Lys His
                2245                2250                2255

Asp Cys Thr Glu Lys Gln Met Glu Cys Lys Asn Leu Ile Gly Thr Tyr
            2260                2265                2270

Met Cys Ile Cys Gly Pro Gly Tyr Gln Arg Arg Pro Asp Gly Glu Gly
        2275                2280                2285

Cys Val Asp Glu Asn Glu Cys Gln Thr Lys Pro Gly Ile Cys Glu Asn
    2290                2295                2300

Gly Arg Cys Leu Asn Thr Arg Gly Ser Tyr Thr Cys Glu Cys Asn Asp
2305                2310                2315                2320

Gly Phe Thr Ala Ser Pro Asn Gln Asp Glu Cys Leu Asp Asn Arg Glu
                2325                2330                2335

Gly Tyr Cys Phe Thr Glu Val Leu Gln Asn Met Cys Gln Ile Gly Ser
            2340                2345                2350

Ser Asn Arg Asn Pro Val Thr Lys Ser Glu Cys Cys Cys Asp Gly Gly
        2355                2360                2365

Arg Gly Trp Gly Pro His Cys Glu Ile Cys Pro Phe Gln Gly Thr Val
    2370                2375                2380

Ala Phe Lys Lys Leu Cys Pro His Gly Arg Gly Phe Met Thr Asn Gly
2385                2390                2395                2400

Ala Asp Ile Asp Glu Cys Lys Val Ile His Asp Val Cys Arg Asn Gly
                2405                2410                2415

Glu Cys Val Asn Asp Arg Gly Ser Tyr His Cys Ile Cys Lys Thr Gly
            2420                2425                2430

Tyr Thr Pro Asp Ile Thr Gly Thr Ser Cys Val Asp Leu Asn Glu Cys
        2435                2440                2445

Asn Gln Ala Pro Lys Pro Cys Asn Phe Ile Cys Lys Asn Thr Glu Gly
    2450                2455                2460

Ser Tyr Gln Cys Ser Cys Pro Lys Gly Tyr Ile Leu Gln Glu Asp Gly
2465                2470                2475                2480

Arg Ser Cys Lys Asp Leu Asp Glu Cys Ala Thr Lys Gln His Asn Cys
                2485                2490                2495

Gln Phe Leu Cys Val Asn Thr Ile Gly Gly Phe Thr Cys Lys Cys Pro
            2500                2505                2510

Pro Gly Phe Thr Gln His His Thr Ser Cys Ile Asp Asn Asn Glu Cys
        2515                2520                2525

Thr Ser Asp Ile Asn Leu Cys Gly Ser Lys Gly Ile Cys Gln Asn Thr
    2530                2535                2540

Pro Gly Ser Phe Thr Cys Glu Cys Gln Arg Gly Phe Ser Leu Asp Gln
2545                2550                2555                2560
```

```
Thr Gly Ser Ser Cys Glu Asp Val Asp Glu Cys Glu Gly Asn His Arg
                2565                2570                2575

Cys Gln His Gly Cys Gln Asn Ile Ile Gly Gly Tyr Arg Cys Ser Cys
            2580                2585                2590

Pro Gln Gly Tyr Leu Gln His Tyr Gln Trp Asn Gln Cys Val Asp Glu
        2595                2600                2605

Asn Glu Cys Leu Ser Ala His Ile Cys Gly Gly Ala Ser Cys His Asn
    2610                2615                2620

Thr Leu Gly Ser Tyr Lys Cys Met Cys Pro Ala Gly Phe Gln Tyr Glu
2625                2630                2635                2640

Gln Phe Ser Gly Gly Cys Gln Asp Ile Asn Glu Cys Gly Ser Ala Gln
                2645                2650                2655

Ala Pro Cys Ser Tyr Gly Cys Ser Asn Thr Glu Gly Gly Tyr Leu Cys
            2660                2665                2670

Gly Cys Pro Pro Gly Tyr Phe Arg Ile Gly Gln Gly His Cys Val Ser
        2675                2680                2685

Gly Met Gly Met Gly Arg Gly Asn Pro Glu Pro Pro Val Ser Gly Glu
    2690                2695                2700

Met Asp Asp Asn Ser Leu Ser Pro Glu Ala Cys Tyr Glu Cys Lys Ile
2705                2710                2715                2720

Asn Gly Tyr Pro Lys Arg Gly Arg Lys Arg Arg Ser Thr Asn Glu Thr
                2725                2730                2735

Asp Ala Ser Asn Ile Glu Asp Gln Ser Glu Thr Glu Ala Asn Val Ser
            2740                2745                2750

Leu Ala Ser Trp Asp Val Glu Lys Thr Ala Ile Phe Ala Phe Asn Ile
        2755                2760                2765

Ser His Val Ser Asn Lys Val Arg Ile Leu Glu Leu Leu Pro Ala Leu
    2770                2775                2780

Thr Thr Leu Thr Asn His Asn Arg Tyr Leu Ile Glu Ser Gly Asn Glu
2785                2790                2795                2800

Asp Gly Phe Phe Lys Ile Asn Gln Lys Glu Gly Ile Ser Tyr Leu His
                2805                2810                2815

Phe Thr Lys Lys Lys Pro Val Ala Gly Thr Tyr Ser Leu Gln Ile Ser
            2820                2825                2830

Ser Thr Pro Leu Tyr Lys Lys Lys Glu Leu Asn Gln Leu Glu Asp Lys
        2835                2840                2845

Tyr Asp Lys Asp Tyr Leu Ser Gly Glu Leu Gly Asp Asn Leu Lys Met
    2850                2855                2860

Lys Ile Gln Val Leu Leu His
2865                2870


<210> SEQ ID NO 63
<211> LENGTH: 2912
<212> TYPE: PRT
<213> ORGANISM: Homo sapiens

<400> SEQUENCE: 63

Met Gly Arg Arg Arg Arg Leu Cys Leu Gln Leu Tyr Phe Leu Trp Leu
1               5                   10                  15

Gly Cys Val Val Leu Trp Ala Gln Gly Thr Ala Gly Gln Pro Gln Pro
            20                  25                  30

Pro Pro Pro Lys Pro Pro Arg Pro Gln Pro Pro Pro Gln Gln Val Arg
        35                  40                  45

Ser Ala Thr Ala Gly Ser Glu Gly Gly Phe Leu Ala Pro Glu Tyr Arg
    50                  55                  60
```

```
Glu Glu Gly Ala Ala Val Ala Ser Arg Val Arg Arg Arg Gly Gln Gln
65                  70                  75                  80

Asp Val Leu Arg Gly Pro Asn Val Cys Gly Ser Arg Phe His Ser Tyr
                85                  90                  95

Cys Cys Pro Gly Trp Lys Thr Leu Pro Gly Gly Asn Gln Cys Ile Val
            100                 105                 110

Pro Ile Cys Arg Asn Ser Cys Gly Asp Gly Phe Cys Ser Arg Pro Asn
        115                 120                 125

Met Cys Thr Cys Ser Ser Gly Gln Ile Ser Ser Thr Cys Gly Ser Lys
    130                 135                 140

Ser Ile Gln Gln Cys Ser Val Arg Cys Met Asn Gly Gly Thr Cys Ala
145                 150                 155                 160

Asp Asp His Cys Gln Cys Gln Lys Gly Tyr Ile Gly Thr Tyr Cys Gly
                165                 170                 175

Gln Pro Val Cys Glu Asn Gly Cys Gln Asn Gly Gly Arg Cys Ile Gly
            180                 185                 190

Pro Asn Arg Cys Ala Cys Val Tyr Gly Phe Thr Gly Pro Gln Cys Glu
        195                 200                 205

Arg Asp Tyr Arg Thr Gly Pro Cys Phe Thr Gln Val Asn Asn Gln Met
    210                 215                 220

Cys Gln Gly Gln Leu Thr Gly Ile Val Cys Thr Lys Thr Leu Cys Cys
225                 230                 235                 240

Ala Thr Ile Gly Arg Ala Trp Gly His Pro Cys Glu Met Cys Pro Ala
                245                 250                 255

Gln Pro Gln Pro Cys Arg Arg Gly Phe Ile Pro Asn Ile Arg Thr Gly
            260                 265                 270

Ala Cys Gln Asp Val Asp Glu Cys Gln Ala Ile Pro Gly Ile Cys Gln
        275                 280                 285

Gly Gly Asn Cys Ile Asn Thr Val Gly Ser Phe Glu Cys Arg Cys Pro
    290                 295                 300

Ala Gly His Lys Gln Ser Glu Thr Thr Gln Lys Cys Glu Asp Ile Asp
305                 310                 315                 320

Glu Cys Ser Ile Ile Pro Gly Ile Cys Glu Thr Gly Glu Cys Ser Asn
                325                 330                 335

Thr Val Gly Ser Tyr Phe Cys Val Cys Pro Arg Gly Tyr Val Thr Ser
            340                 345                 350

Thr Asp Gly Ser Arg Cys Ile Asp Gln Arg Thr Gly Met Cys Phe Ser
        355                 360                 365

Gly Leu Val Asn Gly Arg Cys Ala Gln Glu Leu Pro Gly Arg Met Thr
    370                 375                 380

Lys Met Gln Cys Cys Cys Glu Pro Gly Arg Cys Trp Gly Ile Gly Thr
385                 390                 395                 400

Ile Pro Glu Ala Cys Pro Val Arg Gly Ser Glu Glu Tyr Arg Arg Leu
                405                 410                 415

Cys Met Asp Gly Leu Pro Met Gly Gly Ile Pro Gly Ser Ala Gly Ser
            420                 425                 430

Arg Pro Gly Gly Thr Gly Gly Asn Gly Phe Ala Pro Ser Gly Asn Gly
        435                 440                 445

Asn Gly Tyr Gly Pro Gly Gly Thr Gly Phe Ile Pro Ile Pro Gly Gly
    450                 455                 460

Asn Gly Phe Ser Pro Gly Val Gly Gly Ala Gly Val Gly Ala Gly Gly
465                 470                 475                 480
```

-continued

```
Gln Gly Pro Ile Ile Thr Gly Leu Thr Ile Leu Asn Gln Thr Ile Asp
                485                 490                 495

Ile Cys Lys His His Ala Asn Leu Cys Leu Asn Gly Arg Cys Ile Pro
            500                 505                 510

Thr Val Ser Ser Tyr Arg Cys Glu Cys Asn Met Gly Tyr Lys Gln Asp
        515                 520                 525

Ala Asn Gly Asp Cys Ile Asp Val Asp Glu Cys Thr Ser Asn Pro Cys
    530                 535                 540

Thr Asn Gly Asp Cys Val Asn Thr Pro Gly Ser Tyr Tyr Cys Lys Cys
545                 550                 555                 560

His Ala Gly Phe Gln Arg Thr Pro Thr Lys Gln Ala Cys Ile Asp Ile
                565                 570                 575

Asp Glu Cys Ile Gln Asn Gly Val Leu Cys Lys Asn Gly Arg Cys Val
            580                 585                 590

Asn Thr Asp Gly Ser Phe Gln Cys Ile Cys Asn Ala Gly Phe Glu Leu
        595                 600                 605

Thr Thr Asp Gly Lys Asn Cys Val Asp His Asp Glu Cys Thr Thr Thr
    610                 615                 620

Asn Met Cys Leu Asn Gly Met Cys Ile Asn Glu Asp Gly Ser Phe Lys
625                 630                 635                 640

Cys Ile Cys Lys Pro Gly Phe Val Leu Ala Pro Asn Gly Arg Tyr Cys
                645                 650                 655

Thr Asp Val Asp Glu Cys Gln Thr Pro Gly Ile Cys Met Asn Gly His
            660                 665                 670

Cys Ile Asn Ser Glu Gly Ser Phe Arg Cys Asp Cys Pro Pro Gly Leu
        675                 680                 685

Ala Val Gly Met Asp Gly Arg Val Cys Val Asp Thr His Met Arg Ser
    690                 695                 700

Thr Cys Tyr Gly Gly Ile Lys Lys Gly Val Cys Val Arg Pro Phe Pro
705                 710                 715                 720

Gly Ala Val Thr Lys Ser Glu Cys Cys Cys Ala Asn Pro Asp Tyr Gly
                725                 730                 735

Phe Gly Glu Pro Cys Gln Pro Cys Pro Ala Lys Asn Ser Ala Glu Phe
            740                 745                 750

His Gly Leu Cys Ser Ser Gly Val Gly Ile Thr Val Asp Gly Arg Asp
        755                 760                 765

Ile Asn Glu Cys Ala Leu Asp Pro Asp Ile Cys Ala Asn Gly Ile Cys
    770                 775                 780

Glu Asn Leu Arg Gly Ser Tyr Arg Cys Asn Cys Asn Ser Gly Tyr Glu
785                 790                 795                 800

Pro Asp Ala Ser Gly Arg Asn Cys Ile Asp Ile Asp Glu Cys Leu Val
                805                 810                 815

Asn Arg Leu Leu Cys Asp Asn Gly Leu Cys Arg Asn Thr Pro Gly Ser
            820                 825                 830

Tyr Ser Cys Thr Cys Pro Pro Gly Tyr Val Phe Arg Thr Glu Thr Glu
        835                 840                 845

Thr Cys Glu Asp Ile Asn Glu Cys Glu Ser Asn Pro Cys Val Asn Gly
    850                 855                 860

Ala Cys Arg Asn Asn Leu Gly Ser Phe Asn Cys Glu Cys Ser Pro Gly
865                 870                 875                 880

Ser Lys Leu Ser Ser Thr Gly Leu Ile Cys Ile Asp Ser Leu Lys Gly
                885                 890                 895

Thr Cys Trp Leu Asn Ile Gln Asp Ser Arg Cys Glu Val Asn Ile Asn
```

-continued

```
            900                 905                 910

Gly Ala Thr Leu Lys Ser Glu Cys Cys Ala Thr Leu Gly Ala Ala Trp
        915                 920                 925

Gly Ser Pro Cys Glu Arg Cys Glu Leu Asp Thr Ala Cys Pro Arg Gly
    930                 935                 940

Leu Ala Arg Ile Lys Gly Val Thr Cys Glu Asp Val Asn Glu Cys Glu
945                 950                 955                 960

Val Phe Pro Gly Val Cys Pro Asn Gly Arg Cys Val Asn Ser Lys Gly
                965                 970                 975

Ser Phe His Cys Glu Cys Pro Glu Gly Leu Thr Leu Asp Gly Thr Gly
            980                 985                 990

Arg Val Cys Leu Asp Ile Arg Met Glu Gln Cys Tyr Leu Lys Trp Asp
        995                 1000                1005

Glu Asp Glu Cys Ile His Pro Val Pro Gly Lys Phe Arg Met Asp Ala
    1010                1015                1020

Cys Cys Cys Ala Val Gly Ala Ala Trp Gly Thr Glu Cys Glu Glu Cys
1025                1030                1035                1040

Pro Lys Pro Gly Thr Lys Glu Tyr Glu Thr Leu Cys Pro Arg Gly Ala
                1045                1050                1055

Gly Phe Ala Asn Arg Gly Asp Val Leu Thr Gly Arg Pro Phe Tyr Lys
            1060                1065                1070

Asp Ile Asn Glu Cys Lys Ala Phe Pro Gly Met Cys Thr Tyr Gly Lys
        1075                1080                1085

Cys Arg Asn Thr Ile Gly Ser Phe Lys Cys Arg Cys Asn Ser Gly Phe
    1090                1095                1100

Ala Leu Asp Met Glu Glu Arg Asn Cys Thr Asp Ile Asp Glu Cys Arg
1105                1110                1115                1120

Ile Ser Pro Asp Leu Cys Gly Ser Gly Ile Cys Val Asn Thr Pro Gly
                1125                1130                1135

Ser Phe Glu Cys Glu Cys Phe Glu Gly Tyr Glu Ser Gly Phe Met Met
            1140                1145                1150

Met Lys Asn Cys Met Asp Ile Asp Glu Cys Glu Arg Asn Pro Leu Leu
        1155                1160                1165

Cys Arg Gly Gly Thr Cys Val Asn Thr Glu Gly Ser Phe Gln Cys Asp
    1170                1175                1180

Cys Pro Leu Gly His Glu Leu Ser Pro Ser Arg Glu Asp Cys Val Asp
1185                1190                1195                1200

Ile Asn Glu Cys Ser Leu Ser Asp Asn Leu Cys Arg Asn Gly Lys Cys
                1205                1210                1215

Val Asn Met Ile Gly Thr Tyr Gln Cys Ser Cys Asn Pro Gly Tyr Gln
            1220                1225                1230

Ala Thr Pro Asp Arg Gln Gly Cys Thr Asp Ile Asp Glu Cys Met Ile
        1235                1240                1245

Met Asn Gly Gly Cys Asp Thr Gln Cys Thr Asn Ser Glu Gly Ser Tyr
    1250                1255                1260

Glu Cys Ser Cys Ser Glu Gly Tyr Ala Leu Met Pro Asp Gly Arg Ser
1265                1270                1275                1280

Cys Ala Asp Ile Asp Glu Cys Glu Asn Asn Pro Asp Ile Cys Asp Gly
                1285                1290                1295

Gly Gln Cys Thr Asn Ile Pro Gly Glu Tyr Arg Cys Leu Cys Tyr Asp
            1300                1305                1310

Gly Phe Met Ala Ser Met Asp Met Lys Thr Cys Ile Asp Val Asn Glu
        1315                1320                1325
```

```
Cys Asp Leu Asn Ser Asn Ile Cys Met Phe Gly Glu Cys Glu Asn Thr
    1330                1335                1340

Lys Gly Ser Phe Ile Cys His Cys Gln Leu Gly Tyr Ser Val Lys Lys
1345                1350                1355                1360

Gly Thr Thr Gly Cys Thr Asp Val Asp Glu Cys Glu Ile Gly Ala His
                1365                1370                1375

Asn Cys Asp Met His Ala Ser Cys Leu Asn Ile Pro Gly Ser Phe Lys
            1380                1385                1390

Cys Ser Cys Arg Glu Gly Trp Ile Gly Asn Gly Ile Lys Cys Ile Asp
        1395                1400                1405

Leu Asp Glu Cys Ser Asn Gly Thr His Gln Cys Ser Ile Asn Ala Gln
    1410                1415                1420

Cys Val Asn Thr Pro Gly Ser Tyr Arg Cys Ala Cys Ser Glu Gly Phe
1425                1430                1435                1440

Thr Gly Asp Gly Phe Thr Cys Ser Asp Val Asp Glu Cys Ala Glu Asn
                1445                1450                1455

Ile Asn Leu Cys Glu Asn Gly Gln Cys Leu Asn Val Pro Gly Ala Tyr
            1460                1465                1470

Arg Cys Glu Cys Glu Met Gly Phe Thr Pro Ala Ser Asp Ser Arg Ser
        1475                1480                1485

Cys Gln Asp Ile Asp Glu Cys Ser Phe Gln Asn Ile Cys Val Phe Gly
    1490                1495                1500

Thr Cys Asn Asn Leu Pro Gly Met Phe His Cys Ile Cys Asp Asp Gly
1505                1510                1515                1520

Tyr Glu Leu Asp Arg Thr Gly Gly Asn Cys Thr Asp Ile Asp Glu Cys
                1525                1530                1535

Ala Asp Pro Ile Asn Cys Val Asn Gly Leu Cys Val Asn Thr Pro Gly
            1540                1545                1550

Arg Tyr Glu Cys Asn Cys Pro Pro Asp Phe Gln Leu Asn Pro Thr Gly
        1555                1560                1565

Val Gly Cys Val Asp Asn Arg Val Gly Asn Cys Tyr Leu Lys Phe Gly
    1570                1575                1580

Pro Arg Gly Asp Gly Ser Leu Ser Cys Asn Thr Glu Ile Gly Val Gly
1585                1590                1595                1600

Val Ser Arg Ser Ser Cys Cys Cys Ser Leu Gly Lys Ala Trp Gly Asn
                1605                1610                1615

Pro Cys Glu Thr Cys Pro Pro Val Asn Ser Thr Glu Tyr Tyr Thr Leu
            1620                1625                1630

Cys Pro Gly Gly Glu Gly Phe Arg Pro Asn Pro Ile Thr Ile Ile Leu
        1635                1640                1645

Glu Asp Ile Asp Glu Cys Gln Glu Leu Pro Gly Leu Cys Gln Gly Gly
    1650                1655                1660

Asn Cys Ile Asn Thr Phe Gly Ser Phe Gln Cys Glu Cys Pro Gln Gly
1665                1670                1675                1680

Tyr Tyr Leu Ser Glu Asp Thr Arg Ile Cys Glu Asp Ile Asp Glu Cys
                1685                1690                1695

Phe Ala His Pro Gly Val Cys Gly Pro Gly Thr Cys Tyr Asn Thr Leu
            1700                1705                1710

Gly Asn Tyr Thr Cys Ile Cys Pro Pro Glu Tyr Met Gln Val Asn Gly
        1715                1720                1725

Gly His Asn Cys Met Asp Met Arg Lys Ser Phe Cys Tyr Arg Ser Tyr
    1730                1735                1740
```

```
Asn Gly Thr Thr Cys Glu Asn Glu Leu Pro Phe Asn Val Thr Lys Arg
1745                1750                1755                1760

Met Cys Cys Cys Thr Tyr Asn Val Gly Lys Ala Trp Asn Lys Pro Cys
                1765                1770                1775

Glu Pro Cys Pro Thr Pro Gly Thr Ala Asp Phe Lys Thr Ile Cys Gly
            1780                1785                1790

Asn Ile Pro Gly Phe Thr Phe Asp Ile His Thr Gly Lys Ala Val Asp
        1795                1800                1805

Ile Asp Glu Cys Lys Glu Ile Pro Gly Ile Cys Ala Asn Gly Val Cys
    1810                1815                1820

Ile Asn Gln Ile Gly Ser Phe Arg Cys Glu Cys Pro Thr Gly Phe Ser
1825                1830                1835                1840

Tyr Asn Asp Leu Leu Leu Val Cys Glu Asp Ile Asp Glu Cys Ser Asn
                1845                1850                1855

Gly Asp Asn Leu Cys Gln Arg Asn Ala Asp Cys Ile Asn Ser Pro Gly
            1860                1865                1870

Ser Tyr Arg Cys Glu Cys Ala Ala Gly Phe Lys Leu Ser Pro Asn Gly
        1875                1880                1885

Ala Cys Val Asp Arg Asn Glu Cys Leu Glu Ile Pro Asn Val Cys Ser
    1890                1895                1900

His Gly Leu Cys Val Asp Leu Gln Gly Ser Tyr Gln Cys Ile Cys His
1905                1910                1915                1920

Asn Gly Phe Lys Ala Ser Gln Asp Gln Thr Met Cys Met Asp Val Asp
                1925                1930                1935

Glu Cys Glu Arg His Pro Cys Gly Asn Gly Thr Cys Lys Asn Thr Val
            1940                1945                1950

Gly Ser Tyr Asn Cys Leu Cys Tyr Pro Gly Phe Glu Leu Thr His Asn
        1955                1960                1965

Asn Asp Cys Leu Asp Ile Asp Glu Cys Ser Ser Phe Phe Gly Gln Val
    1970                1975                1980

Cys Arg Asn Gly Arg Cys Phe Asn Glu Ile Gly Ser Phe Lys Cys Leu
1985                1990                1995                2000

Cys Asn Glu Gly Tyr Glu Leu Thr Pro Asp Gly Lys Asn Cys Ile Asp
                2005                2010                2015

Thr Asn Glu Cys Val Ala Leu Pro Gly Ser Cys Ser Pro Gly Thr Cys
            2020                2025                2030

Gln Asn Leu Glu Gly Ser Phe Arg Cys Ile Cys Pro Pro Gly Tyr Glu
        2035                2040                2045

Val Lys Ser Glu Asn Cys Ile Asp Ile Asn Glu Cys Asp Glu Asp Pro
    2050                2055                2060

Asn Ile Cys Leu Phe Gly Ser Cys Thr Asn Thr Pro Gly Gly Phe Gln
2065                2070                2075                2080

Cys Leu Cys Pro Pro Gly Phe Val Leu Ser Asp Asn Gly Arg Arg Cys
                2085                2090                2095

Phe Asp Thr Arg Gln Ser Phe Cys Phe Thr Asn Phe Glu Asn Gly Lys
            2100                2105                2110

Cys Ser Val Pro Lys Ala Phe Asn Thr Thr Lys Ala Lys Cys Cys Cys
        2115                2120                2125

Ser Lys Met Pro Gly Glu Gly Trp Gly Asp Pro Cys Glu Leu Cys Pro
    2130                2135                2140

Lys Asp Asp Glu Val Ala Phe Gln Asp Leu Cys Pro Tyr Gly His Gly
2145                2150                2155                2160

Thr Val Pro Ser Leu His Asp Thr Arg Glu Asp Val Asn Glu Cys Leu
```

-continued

```
                2165                2170                2175

Glu Ser Pro Gly Ile Cys Ser Asn Gly Gln Cys Ile Asn Thr Asp Gly
            2180                2185                2190

Ser Phe Arg Cys Glu Cys Pro Met Gly Tyr Asn Leu Asp Tyr Thr Gly
        2195                2200                2205

Val Arg Cys Val Asp Thr Asp Glu Cys Ser Ile Gly Asn Pro Cys Gly
    2210                2215                2220

Asn Gly Thr Cys Thr Asn Val Ile Gly Ser Phe Glu Cys Asn Cys Asn
2225                2230                2235                2240

Glu Gly Phe Glu Pro Gly Pro Met Met Asn Cys Glu Asp Ile Asn Glu
                2245                2250                2255

Cys Ala Gln Asn Pro Leu Leu Cys Ala Phe Arg Cys Met Asn Thr Phe
            2260                2265                2270

Gly Ser Tyr Glu Cys Thr Cys Pro Ile Gly Tyr Ala Leu Arg Glu Asp
        2275                2280                2285

Gln Lys Met Cys Lys Asp Leu Asp Glu Cys Ala Glu Gly Leu His Asp
    2290                2295                2300

Cys Glu Ser Arg Gly Met Met Cys Lys Asn Leu Ile Gly Thr Phe Met
2305                2310                2315                2320

Cys Ile Cys Pro Pro Gly Met Ala Arg Arg Pro Asp Gly Glu Gly Cys
                2325                2330                2335

Val Asp Glu Asn Glu Cys Arg Thr Lys Pro Gly Ile Cys Glu Asn Gly
            2340                2345                2350

Arg Cys Val Asn Ile Ile Gly Ser Tyr Arg Cys Glu Cys Asn Glu Gly
        2355                2360                2365

Phe Gln Ser Ser Ser Ser Gly Thr Glu Cys Leu Asp Asn Arg Gln Gly
    2370                2375                2380

Leu Cys Phe Ala Glu Val Leu Gln Thr Ile Cys Gln Met Ala Ser Ser
2385                2390                2395                2400

Ser Arg Asn Leu Val Thr Lys Ser Glu Cys Cys Cys Asp Gly Gly Arg
                2405                2410                2415

Gly Trp Gly His Gln Cys Glu Leu Cys Pro Leu Pro Gly Thr Ala Gln
            2420                2425                2430

Tyr Lys Lys Ile Cys Pro His Gly Pro Gly Tyr Thr Thr Asp Gly Arg
        2435                2440                2445

Asp Ile Asp Glu Cys Lys Val Met Pro Asn Leu Cys Thr Asn Gly Gln
    2450                2455                2460

Cys Ile Asn Thr Met Gly Ser Phe Arg Cys Phe Cys Lys Val Gly Tyr
2465                2470                2475                2480

Thr Thr Asp Ile Ser Gly Thr Ser Cys Ile Asp Leu Asp Glu Cys Ser
                2485                2490                2495

Gln Ser Pro Lys Pro Cys Asn Tyr Ile Cys Lys Asn Thr Glu Gly Ser
            2500                2505                2510

Tyr Gln Cys Ser Cys Pro Arg Gly Tyr Val Leu Gln Glu Asp Gly Lys
        2515                2520                2525

Thr Cys Lys Asp Leu Asp Glu Cys Gln Thr Lys Gln His Asn Cys Gln
    2530                2535                2540

Phe Leu Cys Val Asn Thr Leu Gly Gly Phe Thr Cys Lys Cys Pro Pro
2545                2550                2555                2560

Gly Phe Thr Gln His His Thr Ala Cys Ile Asp Asn Asn Glu Cys Gly
                2565                2570                2575

Ser Gln Pro Ser Leu Cys Gly Ala Lys Gly Ile Cys Gln Asn Thr Pro
            2580                2585                2590
```

Gly Ser Phe Ser Cys Glu Cys Gln Arg Gly Phe Ser Leu Asp Ala Thr
2595 2600 2605

Gly Leu Asn Cys Glu Asp Val Asp Glu Cys Asp Gly Asn His Arg Cys
2610 2615 2620

Gln His Gly Cys Gln Asn Ile Leu Gly Gly Tyr Arg Cys Gly Cys Pro
2625 2630 2635 2640

Gln Gly Tyr Ile Gln His Tyr Gln Trp Asn Gln Cys Val Asp Glu Asn
2645 2650 2655

Glu Cys Ser Asn Pro Asn Ala Cys Gly Ser Ala Ser Cys Tyr Asn Thr
2660 2665 2670

Leu Gly Ser Tyr Lys Cys Ala Cys Pro Ser Gly Phe Ser Phe Asp Gln
2675 2680 2685

Phe Ser Ser Ala Cys His Asp Val Asn Glu Cys Ser Ser Ser Lys Asn
2690 2695 2700

Pro Cys Asn Tyr Gly Cys Ser Asn Thr Glu Gly Gly Tyr Leu Cys Gly
2705 2710 2715 2720

Cys Pro Pro Gly Tyr Tyr Arg Val Gly Gln Gly His Cys Val Ser Gly
2725 2730 2735

Met Gly Phe Asn Lys Gly Gln Tyr Leu Ser Leu Asp Thr Glu Val Asp
2740 2745 2750

Glu Glu Asn Ala Leu Ser Pro Glu Ala Cys Tyr Glu Cys Lys Ile Asn
2755 2760 2765

Gly Tyr Ser Lys Lys Asp Ser Arg Gln Lys Arg Ser Ile His Glu Pro
2770 2775 2780

Asp Pro Thr Ala Val Glu Gln Ile Ser Leu Glu Ser Val Asp Met Asp
2785 2790 2795 2800

Ser Pro Val Asn Met Lys Phe Asn Leu Ser His Leu Gly Ser Lys Glu
2805 2810 2815

His Ile Leu Glu Leu Arg Pro Ala Ile Gln Pro Leu Asn Asn His Ile
2820 2825 2830

Arg Tyr Val Ile Ser Gln Gly Asn Asp Asp Ser Val Phe Arg Ile His
2835 2840 2845

Gln Arg Asn Gly Leu Ser Tyr Leu His Thr Ala Lys Lys Lys Leu Met
2850 2855 2860

Pro Gly Thr Tyr Thr Leu Glu Ile Thr Ser Ile Pro Leu Tyr Lys Lys
2865 2870 2875 2880

Lys Glu Leu Lys Lys Leu Glu Glu Ser Asn Glu Asp Asp Tyr Leu Leu
2885 2890 2895

Gly Glu Leu Gly Glu Ala Leu Arg Met Arg Leu Gln Ile Gln Leu Tyr
2900 2905 2910

<210> SEQ ID NO 64
<211> LENGTH: 2809
<212> TYPE: PRT
<213> ORGANISM: Homo sapiens

<400> SEQUENCE: 64

Met Thr Leu Glu Gly Leu Tyr Leu Ala Arg Gly Pro Leu Ala Arg Leu
1 5 10 15

Leu Leu Ala Trp Ser Ala Leu Leu Cys Met Ala Gly Gly Gln Gly Arg
20 25 30

Trp Asp Gly Ala Leu Glu Ala Ala Gly Pro Gly Arg Val Arg Arg Arg
35 40 45

Gly Ser Pro Gly Ile Leu Gln Gly Pro Asn Val Cys Gly Ser Arg Phe

-continued

```
    50                  55                  60

His Ala Tyr Cys Cys Pro Gly Trp Arg Thr Phe Pro Gly Arg Ser Gln
65                  70                  75                  80

Cys Val Val Pro Ile Cys Arg Arg Ala Cys Gly Glu Gly Phe Cys Ser
                85                  90                  95

Gln Pro Asn Leu Cys Thr Cys Ala Asp Gly Thr Leu Ala Pro Ser Cys
            100                 105                 110

Gly Val Ser Arg Gly Ser Gly Cys Ser Val Ser Cys Met Asn Gly Gly
        115                 120                 125

Thr Cys Arg Gly Ala Ser Cys Leu Cys Gln Lys Gly Tyr Thr Gly Thr
    130                 135                 140

Val Cys Gly Gln Pro Ile Cys Asp Arg Gly Cys His Asn Gly Gly Arg
145                 150                 155                 160

Cys Ile Gly Pro Asn Arg Cys Ala Cys Val Tyr Gly Phe Met Gly Pro
                165                 170                 175

Gln Cys Glu Arg Asp Tyr Arg Thr Gly Pro Cys Phe Gly Gln Val Gly
            180                 185                 190

Pro Glu Gly Cys Gln His Gln Leu Thr Gly Leu Val Cys Thr Lys Ala
        195                 200                 205

Leu Cys Cys Ala Thr Val Gly Arg Ala Trp Gly Leu Pro Cys Glu Leu
    210                 215                 220

Cys Pro Ala Gln Pro His Pro Cys Arg Arg Gly Phe Ile Pro Asn Ile
225                 230                 235                 240

His Thr Gly Ala Cys Gln Asp Val Asp Glu Cys Gln Ala Val Pro Gly
                245                 250                 255

Leu Cys Gln Gly Gly Ser Cys Val Asn Met Val Gly Ser Phe His Cys
            260                 265                 270

Arg Cys Pro Val Gly His Arg Leu Ser Asp Ser Ser Ala Ala Cys Glu
        275                 280                 285

Asp Tyr Arg Ala Gly Ala Cys Phe Ser Val Leu Phe Gly Gly Arg Cys
    290                 295                 300

Ala Gly Asp Leu Ala Gly His Tyr Thr Arg Arg Gln Cys Cys Cys Asp
305                 310                 315                 320

Arg Gly Arg Cys Trp Ala Ala Gly Pro Val Pro Glu Leu Cys Pro Pro
                325                 330                 335

Arg Gly Ser Asn Glu Phe Gln Gln Leu Cys Ala Gln Arg Leu Pro Leu
            340                 345                 350

Leu Pro Gly His Pro Gly Leu Phe Pro Gly Leu Leu Gly Phe Gly Ser
        355                 360                 365

Asn Gly Met Gly Pro Pro Leu Gly Pro Ala Arg Leu Asn Pro His Gly
    370                 375                 380

Ser Asp Ala Arg Gly Ile Pro Ser Leu Gly Pro Gly Asn Ser Asn Ile
385                 390                 395                 400

Gly Thr Ala Thr Leu Asn Gln Thr Ile Asp Ile Cys Arg His Phe Thr
                405                 410                 415

Asn Leu Cys Leu Asn Gly Arg Cys Leu Pro Thr Pro Ser Ser Tyr Arg
            420                 425                 430

Cys Glu Cys Asn Val Gly Tyr Thr Gln Asp Val Arg Gly Glu Cys Ile
        435                 440                 445

Asp Val Asp Glu Cys Thr Ser Ser Pro Cys His His Gly Asp Cys Val
    450                 455                 460

Asn Ile Pro Gly Thr Tyr His Cys Arg Cys Tyr Pro Gly Phe Gln Ala
465                 470                 475                 480
```

-continued

```
Thr Pro Thr Arg Gln Ala Cys Val Asp Val Asp Glu Cys Ile Val Ser
                485                 490                 495

Gly Gly Leu Cys His Leu Gly Arg Cys Val Asn Thr Glu Gly Ser Phe
            500                 505                 510

Gln Cys Val Cys Asn Ala Gly Phe Glu Leu Ser Pro Asp Gly Lys Asn
        515                 520                 525

Cys Val Asp His Asn Glu Cys Ala Thr Ser Thr Met Cys Val Asn Gly
    530                 535                 540

Val Cys Leu Asn Glu Asp Gly Ser Phe Ser Cys Leu Cys Lys Pro Gly
545                 550                 555                 560

Phe Leu Leu Ala Pro Gly Gly His Tyr Cys Met Asp Ile Asp Glu Cys
                565                 570                 575

Gln Thr Pro Gly Ile Cys Val Asn Gly His Cys Thr Asn Thr Glu Gly
            580                 585                 590

Ser Phe Arg Cys Gln Cys Leu Gly Gly Leu Ala Val Gly Thr Asp Gly
        595                 600                 605

Arg Val Cys Val Asp Thr His Val Arg Ser Thr Cys Tyr Gly Ala Ile
    610                 615                 620

Glu Lys Gly Ser Cys Ala Arg Pro Phe Pro Gly Thr Val Thr Lys Ser
625                 630                 635                 640

Glu Cys Cys Cys Ala Asn Pro Asp His Gly Phe Gly Glu Pro Cys Gln
                645                 650                 655

Leu Cys Pro Ala Lys Asp Ser Ala Glu Phe Gln Ala Leu Cys Ser Ser
            660                 665                 670

Gly Leu Gly Ile Thr Thr Asp Gly Arg Asp Ile Asn Glu Cys Ala Leu
        675                 680                 685

Asp Pro Glu Val Cys Ala Asn Gly Val Cys Glu Asn Leu Arg Gly Ser
    690                 695                 700

Tyr Arg Cys Val Cys Asn Leu Gly Tyr Glu Ala Gly Ala Ser Gly Lys
705                 710                 715                 720

Asp Cys Thr Asp Val Asp Glu Cys Ala Leu Asn Ser Leu Leu Cys Asp
                725                 730                 735

Asn Gly Trp Cys Gln Asn Ser Pro Gly Ser Tyr Ser Cys Ser Cys Pro
            740                 745                 750

Pro Gly Phe His Phe Trp Gln Asp Thr Glu Ile Cys Lys Asp Val Asp
        755                 760                 765

Glu Cys Leu Ser Ser Pro Cys Val Ser Gly Val Cys Arg Asn Leu Ala
    770                 775                 780

Gly Ser Tyr Thr Cys Lys Cys Gly Pro Gly Ser Arg Leu Asp Pro Ser
785                 790                 795                 800

Gly Thr Phe Cys Leu Asp Ser Thr Lys Gly Thr Cys Trp Leu Lys Ile
                805                 810                 815

Gln Glu Ser Arg Cys Glu Val Asn Leu Gln Gly Ala Ser Leu Arg Ser
            820                 825                 830

Glu Cys Cys Ala Thr Leu Gly Ala Ala Trp Gly Ser Pro Cys Glu Arg
        835                 840                 845

Cys Glu Ile Asp Pro Ala Cys Ala Arg Gly Phe Ala Arg Met Thr Gly
    850                 855                 860

Val Thr Cys Asp Asp Val Asn Glu Cys Glu Ser Phe Pro Gly Val Cys
865                 870                 875                 880

Pro Asn Gly Arg Cys Val Asn Thr Ala Gly Ser Phe Arg Cys Glu Cys
                885                 890                 895
```

```
Pro Glu Gly Leu Met Leu Asp Ala Ser Gly Arg Leu Cys Val Asp Val
            900                 905                 910

Arg Leu Glu Pro Cys Phe Leu Arg Trp Asp Glu Asp Glu Cys Gly Val
        915                 920                 925

Thr Leu Pro Gly Lys Tyr Arg Met Asp Val Cys Cys Cys Ser Ile Gly
    930                 935                 940

Ala Val Trp Gly Val Glu Cys Glu Ala Cys Pro Asp Pro Glu Ser Leu
945                 950                 955                 960

Glu Phe Ala Ser Leu Cys Pro Arg Gly Leu Gly Phe Ala Ser Arg Asp
                965                 970                 975

Phe Leu Ser Gly Arg Pro Phe Tyr Lys Asp Val Asn Glu Cys Lys Val
            980                 985                 990

Phe Pro Gly Leu Cys Thr His Gly Thr Cys Arg Asn Thr Val Gly Ser
        995                 1000                1005

Phe His Cys Ala Cys Ala Gly Gly Phe Ala Leu Asp Ala Gln Glu Arg
    1010                1015                1020

Asn Cys Thr Asp Ile Asp Glu Cys Arg Ile Ser Pro Asp Leu Cys Gly
1025                1030                1035                1040

Gln Gly Thr Cys Val Asn Thr Pro Gly Ser Phe Glu Cys Glu Cys Phe
                1045                1050                1055

Pro Gly Tyr Glu Ser Gly Phe Met Leu Met Lys Asn Cys Met Asp Val
            1060                1065                1070

Asp Glu Cys Ala Arg Asp Pro Leu Leu Cys Arg Gly Gly Thr Cys Thr
        1075                1080                1085

Asn Thr Asp Gly Ser Tyr Lys Cys Gln Cys Pro Pro Gly His Glu Leu
    1090                1095                1100

Thr Ala Lys Gly Thr Ala Cys Glu Asp Ile Asp Glu Cys Ser Leu Ser
1105                1110                1115                1120

Asp Gly Leu Cys Pro His Gly Gln Cys Val Asn Val Ile Gly Ala Phe
                1125                1130                1135

Gln Cys Ser Cys His Ala Gly Phe Gln Ser Thr Pro Asp Arg Gln Gly
            1140                1145                1150

Cys Val Asp Ile Asn Glu Cys Arg Val Gln Asn Gly Gly Cys Asp Val
        1155                1160                1165

His Cys Ile Asn Thr Glu Gly Ser Tyr Arg Cys Ser Cys Gly Gln Gly
    1170                1175                1180

Tyr Ser Leu Met Pro Asp Gly Arg Ala Cys Ala Asp Val Asp Glu Cys
1185                1190                1195                1200

Glu Glu Asn Pro Arg Val Cys Asp Gln Gly His Cys Thr Asn Met Pro
                1205                1210                1215

Gly Gly His Arg Cys Leu Cys Tyr Asp Gly Phe Met Ala Thr Pro Asp
            1220                1225                1230

Met Arg Thr Cys Val Asp Val Asp Glu Cys Asp Leu Asn Pro His Ile
        1235                1240                1245

Cys Leu His Gly Asp Cys Glu Asn Thr Lys Gly Ser Phe Val Cys His
    1250                1255                1260

Cys Gln Leu Gly Tyr Met Val Arg Lys Gly Ala Thr Gly Cys Ser Asp
1265                1270                1275                1280

Val Asp Glu Cys Glu Val Gly Gly His Asn Cys Asp Ser His Ala Ser
                1285                1290                1295

Cys Leu Asn Ile Pro Gly Ser Phe Ser Cys Arg Cys Leu Pro Gly Trp
            1300                1305                1310

Val Gly Asp Gly Phe Glu Cys His Asp Leu Asp Glu Cys Val Ser Gln
```

-continued

```
        1315                1320                1325

Glu His Arg Cys Ser Pro Arg Gly Asp Cys Leu Asn Val Pro Gly Ser
    1330                1335                1340

Tyr Arg Cys Thr Cys Arg Gln Gly Phe Ala Gly Asp Gly Phe Phe Cys
1345                1350                1355                1360

Glu Asp Arg Asp Glu Cys Ala Glu Asn Val Asp Leu Cys Asp Asn Gly
                1365                1370                1375

Gln Cys Leu Asn Ala Pro Gly Gly Tyr Arg Cys Glu Cys Glu Met Gly
            1380                1385                1390

Phe Asp Pro Thr Glu Asp His Arg Ala Cys Gln Asp Val Asp Glu Cys
        1395                1400                1405

Ala Gln Gly Asn Leu Cys Ala Phe Gly Ser Cys Glu Asn Leu Pro Gly
    1410                1415                1420

Met Phe Arg Cys Ile Cys Asn Gly Gly Tyr Glu Leu Asp Arg Gly Gly
1425                1430                1435                1440

Gly Asn Cys Thr Asp Ile Asn Glu Cys Ala Asp Pro Val Asn Cys Ile
                1445                1450                1455

Asn Gly Val Cys Ile Asn Thr Pro Gly Ser Tyr Leu Cys Ser Cys Pro
            1460                1465                1470

Gln Asp Phe Glu Leu Asn Pro Ser Gly Val Gly Cys Val Asp Thr Arg
        1475                1480                1485

Ala Gly Asn Cys Phe Leu Glu Thr His Asp Arg Gly Asp Ser Gly Ile
    1490                1495                1500

Ser Cys Ser Ala Glu Ile Gly Val Gly Val Thr Arg Ala Ser Cys Cys
1505                1510                1515                1520

Cys Ser Leu Gly Arg Ala Trp Gly Asn Pro Cys Glu Leu Cys Pro Met
                1525                1530                1535

Ala Asn Thr Thr Glu Tyr Arg Thr Leu Cys Pro Gly Gly Glu Gly Phe
            1540                1545                1550

Gln Pro Asn Arg Ile Thr Val Ile Leu Glu Asp Ile Asp Glu Cys Gln
        1555                1560                1565

Glu Leu Pro Gly Leu Cys Gln Gly Gly Asp Cys Val Asn Thr Phe Gly
    1570                1575                1580

Ser Phe Gln Cys Glu Cys Pro Pro Gly Tyr His Leu Ser Glu His Thr
1585                1590                1595                1600

Arg Ile Cys Glu Asp Ile Asp Glu Cys Ser Thr His Ser Gly Ile Cys
                1605                1610                1615

Gly Pro Gly Thr Cys Tyr Asn Thr Leu Gly Asn Tyr Thr Cys Val Cys
            1620                1625                1630

Pro Ala Glu Tyr Leu Gln Val Asn Gly Gly Asn Asn Cys Met Asp Met
        1635                1640                1645

Arg Lys Ser Val Cys Phe Arg His Tyr Asn Gly Thr Cys Gln Asn Glu
    1650                1655                1660

Leu Ala Phe Asn Val Thr Arg Lys Met Cys Cys Cys Ser Tyr Asn Ile
1665                1670                1675                1680

Gly Gln Ala Trp Asn Arg Pro Cys Glu Ala Cys Pro Thr Pro Ile Ser
                1685                1690                1695

Pro Asp Tyr Gln Ile Leu Cys Gly Asn Gln Ala Pro Gly Phe Leu Thr
            1700                1705                1710

Asp Ile His Thr Gly Lys Pro Leu Asp Ile Asp Glu Cys Gly Glu Ile
        1715                1720                1725

Pro Ala Ile Cys Ala Asn Gly Ile Cys Ile Asn Gln Ile Gly Ser Phe
    1730                1735                1740
```

```
Arg Cys Glu Cys Pro Ala Gly Phe Asn Tyr Asn Ser Ile Leu Leu Ala
1745                1750                1755                1760

Cys Glu Asp Val Asp Glu Cys Gly Ser Arg Glu Ser Pro Cys Gln Gln
                1765                1770                1775

Asn Ala Asp Cys Ile Asn Ile Pro Gly Ser Tyr Arg Cys Lys Cys Thr
            1780                1785                1790

Arg Gly Tyr Lys Leu Ser Pro Gly Gly Ala Cys Val Gly Arg Asn Glu
        1795                1800                1805

Cys Arg Glu Ile Pro Asn Val Cys Ser His Gly Asp Cys Met Asp Thr
    1810                1815                1820

Glu Gly Ser Tyr Met Cys Leu Cys His Arg Gly Phe Gln Ala Ser Ala
1825                1830                1835                1840

Asp Gln Thr Leu Cys Met Asp Ile Asp Glu Cys Asp Arg Gln Pro Cys
                1845                1850                1855

Gly Asn Gly Thr Cys Lys Asn Ile Ile Gly Ser Tyr Asn Cys Leu Cys
            1860                1865                1870

Phe Pro Gly Phe Val Val Thr His Asn Gly Asp Cys Val Asp Phe Asp
        1875                1880                1885

Glu Cys Thr Thr Leu Val Gly Gln Val Cys Arg Phe Gly His Cys Leu
    1890                1895                1900

Asn Thr Ala Gly Ser Phe His Cys Leu Cys Gln Asp Gly Phe Glu Leu
1905                1910                1915                1920

Thr Ala Asp Gly Lys Asn Cys Val Asp Thr Asn Glu Cys Leu Ser Leu
                1925                1930                1935

Ala Gly Thr Cys Leu Pro Gly Thr Cys Gln Asn Leu Glu Gly Ser Phe
            1940                1945                1950

Arg Cys Ile Cys Pro Pro Gly Phe Gln Val Gln Ser Asp His Cys Ile
        1955                1960                1965

Asp Ile Asp Glu Cys Ser Glu Glu Pro Asn Leu Cys Leu Phe Gly Thr
    1970                1975                1980

Cys Thr Asn Ser Pro Gly Ser Phe Gln Cys Leu Cys Pro Pro Gly Phe
1985                1990                1995                2000

Val Leu Ser Asp Asn Gly His Arg Cys Phe Asp Thr Arg Gln Ser Phe
                2005                2010                2015

Cys Phe Thr Arg Phe Glu Ala Gly Lys Cys Ser Val Pro Lys Ala Phe
            2020                2025                2030

Asn Thr Thr Lys Thr Arg Cys Cys Cys Ser Lys Arg Pro Gly Glu Gly
        2035                2040                2045

Trp Gly Asp Pro Cys Glu Leu Cys Pro Gln Glu Gly Ser Ala Ala Phe
    2050                2055                2060

Gln Glu Leu Cys Pro Phe Gly His Gly Ala Val Pro Gly Pro Asp Asp
2065                2070                2075                2080

Ser Arg Glu Asp Val Asn Glu Cys Ala Glu Asn Pro Gly Val Cys Thr
                2085                2090                2095

Asn Gly Val Cys Val Asn Thr Asp Gly Ser Phe Arg Cys Glu Cys Pro
            2100                2105                2110

Phe Gly Tyr Ser Leu Asp Phe Thr Gly Ile Asn Cys Val Asp Thr Asp
        2115                2120                2125

Glu Cys Ser Val Gly His Pro Cys Gly Gln Gly Thr Cys Thr Asn Val
    2130                2135                2140

Ile Gly Gly Phe Glu Cys Ala Cys Ala Asp Gly Phe Glu Pro Gly Leu
2145                2150                2155                2160
```

```
Met Met Thr Cys Glu Asp Ile Asp Glu Cys Ser Leu Asn Pro Leu Leu
                2165                2170                2175

Cys Ala Phe Arg Cys His Asn Thr Glu Gly Ser Tyr Leu Cys Thr Cys
            2180                2185                2190

Pro Ala Gly Tyr Thr Leu Arg Glu Asp Gly Ala Met Cys Arg Asp Val
        2195                2200                2205

Asp Glu Cys Ala Asp Gly Gln Gln Asp Cys His Ala Arg Gly Met Glu
    2210                2215                2220

Cys Lys Asn Leu Ile Gly Thr Phe Ala Cys Val Cys Pro Pro Gly Met
2225                2230                2235                2240

Arg Pro Leu Pro Gly Ser Gly Glu Gly Cys Thr Asp Asp Asn Glu Cys
                2245                2250                2255

His Ala Gln Pro Asp Leu Cys Val Asn Gly Arg Cys Val Asn Thr Ala
            2260                2265                2270

Gly Ser Phe Arg Cys Asp Cys Asp Glu Gly Phe Gln Pro Ser Pro Thr
        2275                2280                2285

Leu Thr Glu Cys His Asp Ile Arg Gln Gly Pro Cys Phe Ala Glu Val
    2290                2295                2300

Leu Gln Thr Met Cys Arg Ser Leu Ser Ser Ser Ser Glu Ala Val Thr
2305                2310                2315                2320

Arg Ala Glu Cys Cys Cys Gly Gly Gly Arg Gly Trp Gly Pro Arg Cys
                2325                2330                2335

Glu Leu Cys Pro Leu Pro Gly Thr Ser Ala Tyr Arg Lys Leu Cys Pro
            2340                2345                2350

His Gly Ser Gly Tyr Thr Ala Glu Gly Arg Asp Val Asp Glu Cys Arg
        2355                2360                2365

Met Leu Ala His Leu Cys Ala His Gly Glu Cys Ile Asn Ser Leu Gly
    2370                2375                2380

Ser Phe Arg Cys His Cys Gln Ala Gly Tyr Thr Pro Asp Ala Thr Ala
2385                2390                2395                2400

Thr Thr Cys Leu Asp Met Asp Glu Cys Ser Gln Val Pro Lys Pro Cys
                2405                2410                2415

Thr Phe Leu Cys Lys Asn Thr Lys Gly Ser Phe Leu Cys Ser Cys Pro
            2420                2425                2430

Arg Gly Tyr Leu Leu Glu Glu Asp Gly Arg Thr Cys Lys Asp Leu Asp
        2435                2440                2445

Glu Cys Thr Ser Arg Gln His Asn Cys Gln Phe Leu Cys Val Asn Thr
    2450                2455                2460

Val Gly Ala Phe Thr Cys Arg Cys Pro Pro Gly Phe Thr Gln His His
2465                2470                2475                2480

Gln Ala Cys Phe Asp Asn Asp Glu Cys Ser Ala Gln Pro Gly Pro Cys
                2485                2490                2495

Gly Ala His Gly His Cys His Asn Thr Pro Gly Ser Phe Arg Cys Glu
            2500                2505                2510

Cys His Gln Gly Phe Thr Leu Val Ser Ser Gly His Gly Cys Glu Asp
        2515                2520                2525

Val Asn Glu Cys Asp Gly Pro His Arg Cys Gln His Gly Cys Gln Asn
    2530                2535                2540

Gln Leu Gly Gly Tyr Arg Cys Ser Cys Pro Gln Gly Phe Thr Gln His
2545                2550                2555                2560

Ser Gln Trp Ala Gln Cys Val Asp Glu Asn Glu Cys Ala Leu Ser Pro
                2565                2570                2575

Pro Thr Cys Gly Ser Ala Ser Cys Arg Asn Thr Leu Gly Gly Phe Arg
```

-continued

```
            2580                2585                2590

Cys Val Cys Pro Ser Gly Phe Asp Phe Asp Gln Ala Leu Gly Gly Cys
        2595                2600                2605

Gln Glu Val Asp Glu Cys Ala Gly Arg Arg Gly Pro Cys Ser Tyr Ser
    2610                2615                2620

Cys Ala Asn Thr Pro Gly Gly Phe Leu Cys Gly Cys Pro Gln Gly Tyr
2625                2630                2635                2640

Phe Arg Ala Gly Gln Gly His Cys Val Ser Gly Leu Gly Phe Ser Pro
                2645                2650                2655

Gly Pro Gln Asp Thr Pro Asp Lys Glu Glu Leu Leu Ser Ser Glu Ala
            2660                2665                2670

Cys Tyr Glu Cys Lys Ile Asn Gly Leu Ser Pro Arg Asp Arg Pro Arg
        2675                2680                2685

Arg Ser Ala His Arg Asp His Gln Val Asn Leu Ala Thr Leu Asp Ser
    2690                2695                2700

Glu Ala Leu Leu Thr Leu Gly Leu Asn Leu Ser His Leu Gly Arg Ala
2705                2710                2715                2720

Glu Arg Ile Leu Glu Leu Arg Pro Ala Leu Glu Gly Leu Glu Gly Arg
                2725                2730                2735

Ile Arg Tyr Val Ile Val Arg Gly Asn Glu Gln Gly Phe Phe Arg Met
            2740                2745                2750

His His Leu Arg Gly Val Ser Ser Leu Gln Leu Gly Arg Arg Arg Pro
        2755                2760                2765

Gly Pro Gly Thr Tyr Arg Leu Glu Val Val Ser His Met Ala Gly Pro
    2770                2775                2780

Trp Gly Val Gln Pro Glu Gly Gln Pro Gly Pro Trp Gly Gln Ala Leu
2785                2790                2795                2800

Arg Leu Lys Val Gln Leu Gln Leu Leu
                2805
```

UNITED STATES PATENT AND TRADEMARK OFFICE
CERTIFICATE OF CORRECTION

| | | |
|---|---|---|
| PATENT NO. | : 12,128,122 B2 | Page 1 of 1 |
| APPLICATION NO. | : 16/915695 | |
| DATED | : October 29, 2024 | |
| INVENTOR(S) | : Suma Krishnan et al. | |

It is certified that error appears in the above-identified patent and that said Letters Patent is hereby corrected as shown below:

On the Title Page

Column 1, item (54) Title, Line 3, After "AESTHETIC" insert -- APPLICATIONS --

In the Specification

Column 1, Title, Line 3, After "AESTHETIC" insert -- APPLICATIONS --

Signed and Sealed this
Eighth Day of April, 2025

Coke Morgan Stewart
*Acting Director of the United States Patent and Trademark Office*